US008158598B2

(12) United States Patent
Bhanot et al.

(10) Patent No.: US 8,158,598 B2
(45) Date of Patent: Apr. 17, 2012

(54) COMPOSITIONS AND THEIR USES DIRECTED TO PTPR ALPHA

(75) Inventors: Sanjay Bhanot, Carlsbad, CA (US); Susan F. Murray, Carlsbad, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 348 days.

(21) Appl. No.: 12/299,610

(22) PCT Filed: May 7, 2007

(86) PCT No.: PCT/US2007/068390
§ 371 (c)(1),
(2), (4) Date: Mar. 11, 2009

(87) PCT Pub. No.: WO2007/131232
PCT Pub. Date: Nov. 15, 2007

(65) Prior Publication Data
US 2010/0022619 A1 Jan. 28, 2010

Related U.S. Application Data

(60) Provisional application No. 60/798,246, filed on May 5, 2006.

(51) Int. Cl.
*A61K 31/70* (2006.01)
*C07H 21/04* (2006.01)
*C12Q 1/68* (2006.01)

(52) U.S. Cl. ............... 514/44 A; 536/23.1; 536/24.1; 536/24.5; 435/375; 435/377

(58) Field of Classification Search .................. None
See application file for complete search history.

(56) References Cited

U.S. PATENT DOCUMENTS

| | | | |
|---|---|---|---|
| 5,801,154 | A | 9/1998 | Baracchini et al. |
| 6,582,908 | B2 | 6/2003 | Fodor et al. |
| 2001/0053519 | A1 | 12/2001 | Fodor et al. |
| 2003/0228597 | A1 | 12/2003 | Cowsert et al. |
| 2004/0023904 | A1 | 2/2004 | Cowsert et al. |
| 2004/0023906 | A1 | 2/2004 | Dean et al. |
| 2007/0031844 | A1 | 2/2007 | Khvorova et al. |

FOREIGN PATENT DOCUMENTS

| | | |
|---|---|---|
| WO | WO 93/24510 | 12/1993 |
| WO | WO 94/01550 * | 1/1994 |
| WO | WO 94/26764 | 11/1994 |
| WO | WO 2004/011623 | 2/2004 |

OTHER PUBLICATIONS

Berger et al., "Universal bases for hybridization, replication and chain termination" Nucleic Acids Research (2000) 28(15):2911-2914.
Branch et al., "A good antisense molecule is hard to find," TIBS (1998) 23:45-50.
Cheng et al., "Coordinated action of protein tyrosine phosphatases in insulin signal transduction." Eur. J. Biochem. (2002) 269(4):1050-1059.
Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.
Crooke et al., "Basic Principles of Antisense Therapeutics" Antisense Research and Application (1998) Chapter 1:1-50.
Daum et al., "Multiple Forms of the Human Tyrosine Phosphatase RPTP-Alpha—Isozymes and Differences in Glycosylation" J. Biol. Chem. (1994) 269:10524-10528.
Gait et al., "Applications of Chemically Synthesized RNA" in RNA: Protein Interactions (1998) Ed. Smith.
Gallo et al., "2'-C-Methyluridine phosphoramidite: a new building block for the preparation of RNA analogues carrying the 2'-hydroxyl group" Tetrahedron (2001) 57:5707-5713.
Jirik et al., "Cloning and chromosomal assignment of a widely expressed human receptor-like protein-tyrosine phosphatase" FEBS Lett. (1990) 273:239-242.
Jirik et al., "The human protein-tyrosine phosphatase PTP.alpha./LRP gene (PTPA) is assigned to chromosome 20p13" Cytogenet. Cell Genet. (1992) 60:117-118.
Kaplan et al., "Cloning of three human tyrosine phosphatases reveals a multigene family of receptor-linked protein-tyrosine-phosphatases expressed in brain" PNAS USA (1990) 87:7000-7004.
Maher et al., "Comparative hybrid arrest by tandem antisense oligodeoxyribonucleotides or oligodeoxyribonucleoside methylphosphonates in a cell-free system" Nuc. Acid. Res. (1988) 16(8):3341-3358.
Moeller et al., "Selective Down-regulation of the Insulin Receptor Signal by Protein-tyrosine Phosphatases alpha and epsilon" J. Biol. Chem. (1995) 270:23126-23131.
New England Biolabs 1998/99 Catalog (cover page and pp. 121 and 284).
Reynolds et al., "Rational siRNA design for RNA interference" Nature Biotechnology (2004) 22(3):326-330.
Sanghvi et al., "Heterocyclic Base Modifications in Nucleic Acids and Their Applications in Antisense Oligonucleotides" Antisense Research and Applications (1993) pp. 273-288.
Scaringe, "RNA Oligonucleotide Synthesis va 5'-Sily1-2'-Orthoester Chemistry" Methods (2001) 23:206-217.
Woolf et al., "Specificity of antisense oligonucleotides in vivo" PNAS USA (1992) 89:7305-7309.
International Search Report for Application PCT/US2007/068390 dated Apr. 25, 2008.
Cong et al., "Overexpression of protein tyrosine phosphatase-alpha (PTP-alpha) but not PTP-kappa inhibits translocation of GLUT4 in rat adipose cells" Biochemical and Biophysical Research Communications (1999) 255(2):200-207.
Kapp et al., "The protein tyrosine phosphatase alpha modifies insulin secretion in INS-1E cells" Biochemical and Biophysical Research Communications (2003) 311(2):361-364.
Lacasa et al., "Interaction of the insulin receptor with the receptor-like protein tyrosine phosphatases PTPalpha and PTPepsilon in living cells" Molecular Pharmacology (2005) 67(4):1206-1213.
European Search Report for application EP 07797356.8 dated Oct. 27, 2010.

* cited by examiner

*Primary Examiner* — Sean McGarry
(74) *Attorney, Agent, or Firm* — Jones Day

(57) ABSTRACT

Disclosed herein are compounds, compositions and methods for modulating the expression of PTPR.alpha. in a cell, tissue or animal. Also provided are methods of target validation. Also provided are uses of disclosed compounds and compositions in the manufacture of a medicament for treatment of diseases and disorders. Also provided are methods for the prevention, amelioration and/or treatment of airway hyperresponsiveness and pulmonary inflammation by administration of antisense compounds targeted to PTPR.alpha.

20 Claims, 3 Drawing Sheets

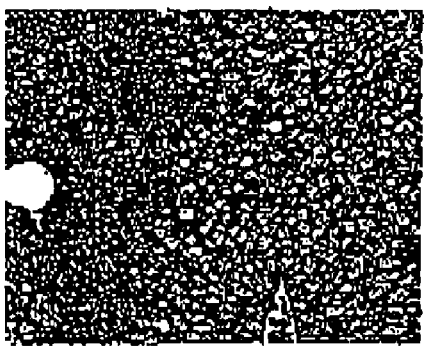
B) PTPR.alpha. shows improvement of steatosis compared with saline.
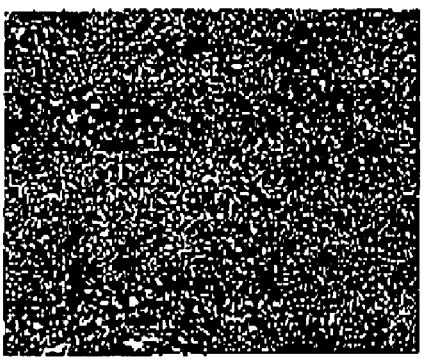
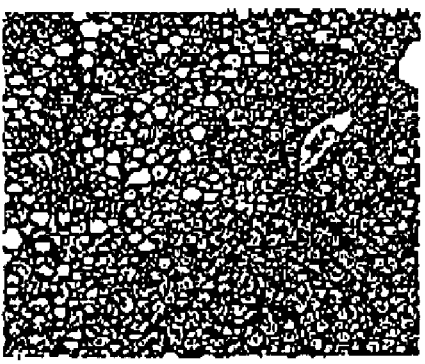
A) Saline-Moderate to severe steatosis.
Figures 1a and 1b

COMPOSITIONS AND THEIR USES DIRECTED TO PTPR ALPHA

CROSS-REFERENCE TO RELATED APPLICATIONS

This application is related to U.S. patent application Ser. No. 11/502,251, filed Aug. 9, 2006; which is a continuation-in-part of U.S. patent application Ser. No. 11/036,095, filed on Jan. 14, 2005, which is a continuation in part of U.S. patent application Ser. No. 10/210,556, filed on Jul. 31, 2002 now abandoned. The entire contents of these applications and patents are incorporated herein by reference in their entirety.

SEQUENCE LISTING

The present application is being filed along with a Sequence Listing in electronic format. The Sequence Listing is provided as a file entitled BIOL0084WOSEQ.TXT, created on May 7, 2007 which is 508 Kb in size. The information in the electronic format of the sequence listing is incorporated herein by reference in its entirety.

BACKGROUND OF THE INVENTION

The process of protein phosphorylation represents one course by which intracellular signals are propagated in a cellular response. Within the cell, proteins can be phosphorylated on serine, threonine or tyrosine residues and the extent of phosphorylation is regulated by the opposing action of phosphatases, which remove the phosphate moieties.

PTPR.alpha. (also known as protein tyrosine phosphatase receptor type alpha, LCA-related phosphatase; LRP, HLPR, HPTPA, PTPRA, PTPA, PTP-R alpha, PTPRL2 and RPTPA) is a widely expressed member of the family of receptor-like phosphatases. It was cloned from a human hepatoblastoma cell line (Jirik et al., FEBS Lett., 1990, 273, 239-242) and a brain stem cell line (Kaplan et al., Proc. Natl. Acad. Sci. U.S.A., 1990, 87, 7000-7004) and was mapped to chromosome 20p13, a chromosomal region involved in translocations and deletions in myeloid disorders and neoplasms (Jirik et al., Cytogenet. Cell Genet., 1992, 60, 117-118; Kaplan et al., Proc. Natl. Acad. Sci. U.S.A., 1990, 87, 7000-7004).

Kaplan et al. have presented evidence for the existence of two major PTPR.alpha. RNA transcripts of approximately 4.3 and 6.3 kb (Kaplan et al., Proc. Natl. Acad. Sci. U.S.A., 1990, 87, 7000-7004) whose proteins differ in a stretch of 9 amino acid residues situated in the external juxtamembrane segment (Daum et al., J. Biol. Chem., 1994, 269, 10524-10528). The larger of the two species appears to be more prevalent in fetal tissues, suggesting that the differential expression of the two transcripts is developmentally regulated and/or a result of alternative splicing mechanisms (Kaplan et al., Proc. Natl. Acad. Sci. U.S.A., 1990, 87, 7000-7004). Four additional variants have been subsequently identified.

PTPR.alpha. has been identified as a negative regulator of insulin receptor signaling indicating that it may play a key role in insulin action and in the pathophysiology of non-insulin-dependent diabetes (Moeller et al., J. Biol. Chem., 1995, 270, 23126-23131). However, the importance of PTPR.alpha.'s role in insulin signaling is considered unclear. (Cheng, A., et al., Eur. J. Biochem. (2002) 269:1050-1059).

There is a need in the art for compositions that modulate the activity of PTPR.alpha. and methods for their use as a treatment of prophylactic for diseases and conditions associated with alterations in plasma glucose and in insulin levels as well as insulin action, such as for type 2 diabetes.

SUMMARY OF THE INVENTION

Provided are antisense compounds, particularly oligomeric compounds, especially nucleic acid and nucleic acid-like oligomers, which are targeted to a nucleic acid encoding PTPR.alpha. Preferably, the antisense compounds are antisense oligonucleotides targeted to PTPR.alpha., particularly human PTPR.alpha., and are capable of modulating the expression of PTPR.alpha. Prefered compounds comprise at least an 8 nucleobase portion, preferably a 12 nucleobase portion, more preferably at least a 15 nucleobase portion, of the sequences listed in Table 3 or 4, or are at least 80% identical to the complement of validated target segments, or to the antisense oligonucleotide sequences listed in Table 3 or 4.

Provided are methods for modulating the expression of PTPR.alpha. in cells or tissues comprising contacting the cells with at least one antisense compound, as described, and analyzing the cells for indicators of a decrease in expression of PTPR.alpha. mRNA and/or protein by direct measurement of mRNA and/or protein levels, and/or indirect indicators of a disease or condition such as measuring plasma triglyceride levels, plasma glucose levels, plasma transaminase levels, plasma insulin levels, hepatic triglyceride levels or similar indicators of type 2 diabetes, fatty liver, obesity or metabolic syndrome.

Provided are methods for the prevention, amelioration, and/or treatment of type 2 diabetes, fatty liver disease or metabolic syndrome comprising administering at least one antisense compound of this invention to an individual in need of such intervention.

Provided are methods for using the antisense compounds disclosed herein to prepare a medicament for the prevention, amelioration, and/or treatment of a disease or condition, especially a those associated with at least one indicator of type 2 diabetes, fatty liver disease, obesity or metabolic syndrome.

Further Methods and Compositions are Provided as Follows:
1. An antisense compound of 15 to 35 nucleobases targeted to a nucleic acid molecule encoding human PTPR.alpha. wherein the nucleic acid molecule encoding human PTPR.alpha. is SEQ ID NO: 18 and wherein the antisense compound hybridizes with nucleotides 716 to 894, nucleotides 1063 to 1229, nucleotides 1818 to 2045, nucleotides 2328 to 2779, nucleotides 2982 to 3211, nucleotides 1210 to 1905 of SEQ ID NO: 18 or nucleotides 2860 to 2990 of SEQ ID NO: 11.
2. Any one of the antisense compounds described herein can be targeted to at least two or more nucleic acid molecules encoding human PTPR.alpha.
3. Any one of the antisense compounds described herein, wherein the compound is at least about 80% complementary to a target region of the nucleic acid encoding PTPR.alpha.
4. Any one of the antisense compounds described herein, wherein the compound optionally includes a complementary strand 15 to 35 nucleobases in length.
5. Any one of the antisense compounds described herein, wherein the compound is an antisense oligonucleotide.
6. Any one of the compounds described herein having at least one modified internucleoside linkage, sugar moiety, or nucleobase.
7. Any one of the compounds described herein comprising a chimeric oligonucleotide.

8. Any one of the compounds described herein wherein the modified internucleoside linkage comprises a phosphorothioate linkage.
9. Any one of the compounds described herein wherein the at least one modified sugar moiety comprises a 2'-MOE, a LNA, a 2'-OMe, an ENA, a 2'-F or combinations thereof.
10. Any one of the compounds described herein wherein the modified nucleobase comprises 5-methylcytosine.
11. A pharmaceutical composition comprising one or more compounds described herein and a pharmaceutically acceptable penetration enhancer, carrier, or diluent.
12. A method for the prevention, amelioration, or treatment of a disease or condition wherein indicators of the disease or condition comprise increased plasma glucose levels, increased plasma lipid levels, increased hepatic triglyceride levels, increased plasma transaminase levels, reduced hepatic function, reduced insulin sensitivity or combinations thereof comprising administration of one or more compounds described herein to an individual in need of such intervention.
13. The methods described herein wherein the disease or condition is fatty liver disease and wherein administration of compounds described herein results in a decrease in plasma lipid levels, a decrease in plasma transaminase levels, a decrease in hepatic triglyceride levels or combinations thereof.
14. The methods described herein wherein the disease or condition is type-2 diabetes and wherein administration of one or more compounds described herein results in a decrease in plasma glucose levels, an improvement in insulin sensitivity or combinations thereof.
15. The methods described herein wherein the disease or condition is metabolic syndrome and wherein administration of one or more compounds described herein results in a decrease in plasma glucose levels, a decrease in plasma lipid levels, a decrease in hepatic triglyceride levels, an improvement in insulin sensitivity, an improvement in hepatic function, a decrease in plasma transaminase levels or combinations thereof.
16. Use of an antisense compounds described herein in the manufacture of a medicament for the treatment, prevention or amelioration of a disease or condition wherein indicators of the disease or condition comprise increased plasma glucose levels, increased plasma lipid levels, increased hepatic triglyceride levels, increased plasma transaminase levels, reduced hepatic function, reduced insulin sensitivity or combinations thereof wherein the medicament reduces the expression of a nucleic acid molecule encoding PTPR.alpha.
17. The use of the compounds described herein wherein the disease or condition comprises type-2 diabetes, fatty liver, metabolic syndrome or combinations thereof.
18. The use of the compounds described herein wherein the antisense compounds optionally further comprises a complementary strand 15 to 35 nucleobases in length.
19. A method for lowering blood glucose levels in an animal in need thereof by administering one or more compounds provided herein.
20. A method for lowering triglyceride levels in an animal in need thereof by administering one or more compounds provided herein.
21. The method of lowering triglyceride levels wherein the triglyceride levels are lowered in the plasma.
22. The method of lowering triglyceride levels wherein the triglyceride levels are lowered in the liver.
23. The methods as provided wherein the animal suffers from type-2 diabetes, fatty liver disease, obesity, metabolic syndrome of combinations thereof.

BRIEF DESCRIPTION OF THE FIGURES

FIGS. 1a and 1b illustrate that administration of the disclosed antisense compounds is useful for clearing fat from the liver. FIG. 1a is an oil red stained liver section of an ob/ob mouse treated with saline and showing no clearing. FIG. 1b is an oil red stained liver section of an ob/ob mouse treated with an antisense inhibitor of PTPR.alpha and showing clearing of fat from the liver.

DETAILED DESCRIPTION OF THE INVENTION

Figure 2:
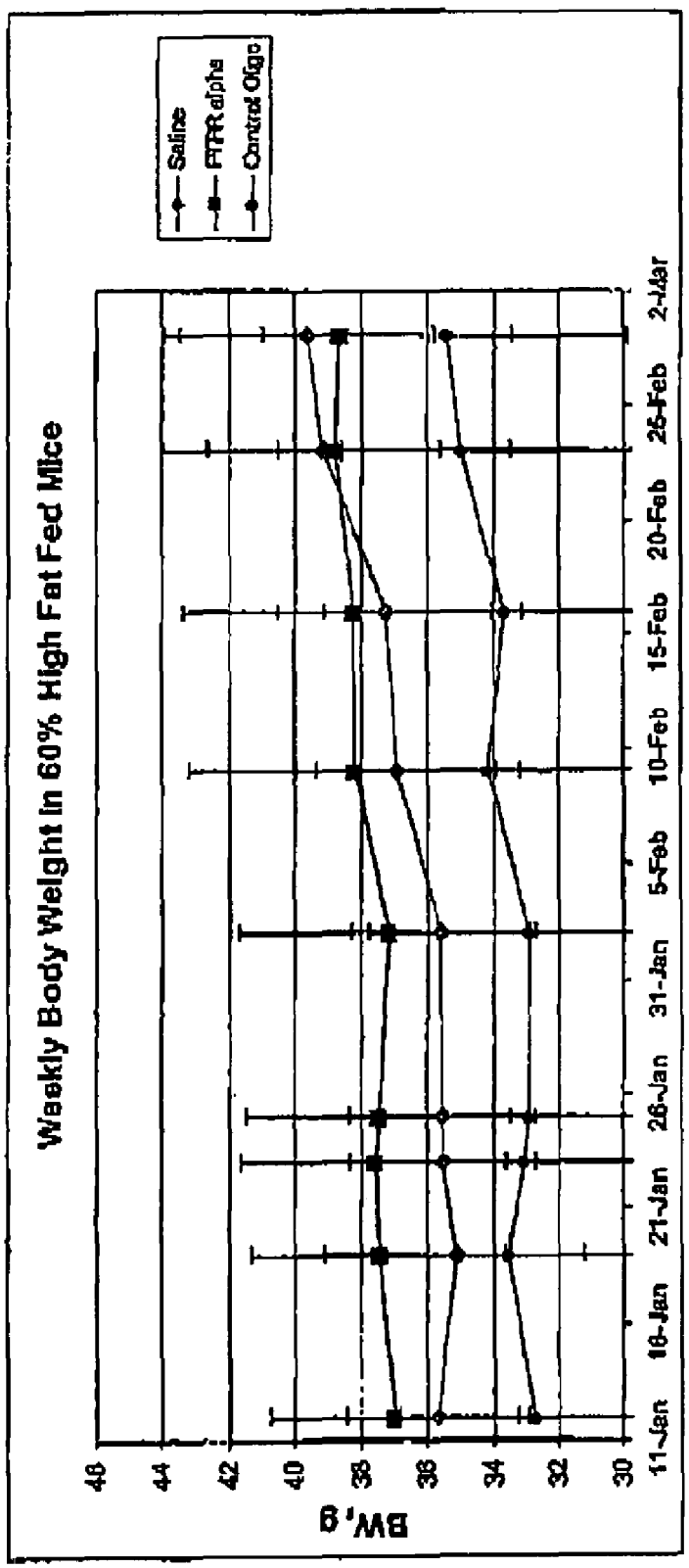
FIG. 2 is a graph illustrating weekly body weights for DIO mice receiving treatment oligo, control oligo or saline.

Provided are antisense compounds for the prevention, amelioration, and/or treatment of diseases or conditions associated with increases in plasma triglyceride levels, plasma glucose levels, plasma transaminase levels, plasma insulin levels hepatic triglyceride levels and further associated with PTPR.alpha activity. As used herein, the term "prevention" means to delay or forestall onset or development of a condition or disease for a period of time from hours to days, preferably weeks to months. As used herein, the term "amelioration" means a lessening of at least one indicator of the severity of a condition or disease. The severity of indicators may be determined by subjective or objective measures which are known to those skilled in the art. As used herein, "treatment" means to administer an antisense composition to effect an alteration or improvement of the disease or condition. Prevention, amelioration, and/or treatment may require administration of multiple doses at regular intervals, or prior to exposure to an agent to alter the course of the condition or disease. Moreover, a single agent may be used in a single individual for each prevention, amelioration, and treatment of a condition or disease sequentially, or concurrently.

Disclosed herein are antisense compounds, including antisense oligonucleotides and other antisense compounds for use in modulating the expression of nucleic acid molecules encoding PTPR.alpha. This is accomplished by providing antisense compounds that hybridize with one or more target nucleic acid molecules encoding PTPR.alpha. As used herein, the terms "target nucleic acid" and "nucleic acid molecule encoding PTPR.alpha." have been used for convenience to encompass RNA (including pre-mRNA and mRNA or portions thereof) transcribed from DNA encoding PTPR.alpha., and also cDNA derived from such RNA. In a preferred embodiment, the target nucleic acid is an mRNA encoding human PTPR.alpha.

Target Nucleic Acids

"Targeting" an antisense compound to a particular target nucleic acid molecule can be a multistep process. The process usually begins with the identification of a target nucleic acid whose expression is to be modulated. For example, the target nucleic acid can be a cellular gene (or mRNA transcribed from the gene) whose expression is associated with a particular disorder or disease state, or a nucleic acid molecule from an infectious agent. As disclosed herein, the target nucleic acid encodes PTPR.alpha.

Variants

It is also known in the art that alternative RNA transcripts can be produced from the same genomic region of DNA.

These alternative transcripts are generally known as "variants." More specifically, "pre-mRNA variants" are transcripts produced from the same genomic DNA that differ from other transcripts produced from the same genomic DNA in either their start or stop position and contain both intronic and exonic sequence. Variants can result in mRNA variants including, but not limited to, those with alternate splice junctions, or alternate initiation and termination codons. Variants in genomic and mRNA sequences can result in disease.

Target Names, Synonyms, Features

Accordingly, there are provided compositions and methods for modulating the expression of PTPR.alpha. Table 1 lists the GenBank accession numbers of sequences corresponding to nucleic acid molecules encoding PTPR.alpha. (nt=nucleotide), the date the version of the sequence was entered in GenBank, and the corresponding SEQ ID NO in the instant application, when assigned, each of which is incorporated herein by reference.

TABLE 1

Gene Targets

| Species | Genbank # | Genbank Date | SEQ ID NO |
|---|---|---|---|
| human | NM_080841.1 | Jan. 31, 2002 | SEQ ID NO: 4 |
| human | M34668.1 | Apr. 27, 1993 | SEQ ID NO: 18 |
| human | a consensus sequence constructed from GenBank accession numbers AL161656.15 and AL121905.23 | | SEQ ID NO: 19 |
| human | X54890.1 | Apr. 21, 1993 | SEQ ID NO: 20 |
| human | X53364.1 | Apr. 21, 1993 | SEQ ID NO: 21 |
| human | AF121183.1 | May 24, 1999 | SEQ ID NO: 22 |
| human | the complement of GenBank accession number BE168541.1 | Jan. 21, 2000 | SEQ ID NO: 23 |
| human | the complement of GenBank accession number AW024120.1 | Sept. 13, 1999 | SEQ ID NO: 24 |
| human | the complement of GenBank accession number AA903762.1 | Apr. 9, 1998 | SEQ ID NO: 25 |
| human | the complement of GenBank accession number AI674319.1 | May 19, 1999 | SEQ ID NO: 26 |
| human | residues 2749000-2925000 of GenBank accession number NT_011387.6 | Oct. 17, 2001 | SEQ ID NO: 27 |
| mouse | NM_008980.1 | Jan. 6, 2000 | SEQ ID NO: 11 |
| mouse | AW323517.1 | Jan. 26, 2000 | SEQ ID NO: 93 |
| mouse | L13686.1 | Jun. 12, 1993 | SEQ ID NO: 94 |
| mouse | L13668.1 | Jun. 12, 1993 | SEQ ID NO: 95 |
| mouse | L13670.1 | Jun. 12, 1993 | SEQ ID NO: 96 |
| mouse | L13672.1 | Jun. 12, 1993 | SEQ ID NO: 97 |
| mouse | L13674.1 | Jun. 12, 1993 | SEQ ID NO: 98 |
| mouse | L13675.1 | Jun. 12, 1993 | SEQ ID NO: 99 |
| mouse | L13676.1 | Jun. 12, 1993 | SEQ ID NO: 100 |
| mouse | L13608.1 | Jun. 12, 1993 | SEQ ID NO: 101 |
| mouse | BE372094.1 | Jul. 21, 2000 | SEQ ID NO: 102 |

Modulation of Target Expression

Modulation of expression of a target nucleic acid can be achieved through alteration of any number of nucleic acid (DNA or RNA) functions. "Modulation" or "Modulation of Expression" means a perturbation of function, for example, either an increase (stimulation or induction) or a decrease (inhibition or reduction) in expression of the target mRNA. As another example, modulation of expression can include perturbing splice site selection of pre-mRNA processing. "Expression" includes all the functions by which a gene's coded information is converted into structures present and operating in a cell. These structures include the products of transcription and translation. The functions of RNA to be modulated can include translocation functions, which include, but are not limited to, translocation of the RNA to a site of protein translation, translocation of the RNA to sites within the cell which are distant from the site of RNA synthesis, and translation of protein from the RNA. RNA processing functions that can be modulated include, but are not limited to, splicing of the RNA to yield one or more RNA species, capping of the RNA, 3' maturation of the RNA and catalytic activity or complex formation involving the RNA which may be engaged in or facilitated by the RNA. Modulation of expression can result in the increased level of one or more nucleic acid species or the decreased level of one or more nucleic acid species, either temporally or by net steady state level. One result of such interference with target nucleic acid function is modulation of the expression of PTPR.alpha. Thus, in one embodiment, modulation of expression can mean increase or decrease in target RNA or protein levels. In another embodiment modulation of expression can mean an increase or decrease of one or more RNA splice products, or a change in the ratio of two or more splice products.

The effect of antisense compounds on target nucleic acid expression can be tested in any of a variety of cell types provided that the target nucleic acid is present at measurable levels and can be routinely determined using, for example, PCR or Northern blot analysis. Cell lines are derived from both normal tissues and cell types and from cells associated with various disorders (e.g. hyperproliferative disorders). Cell lines derived from multiple tissues and species can be obtained from American Type Culture Collection (ATCC, Manassas, Va.) and other public sources. Primary cells, or those cells which are isolated from an animal and not subjected to continuous culture, can be prepared according to methods known in the art, or obtained from various commercial suppliers. Additionally, primary cells include those obtained from donor human subjects in a clinical setting (i.e. blood donors, surgical patients). These techniques are well known to those skilled in the art.

Assaying Modulation of Expression

Modulation of PTPR.alpha. expression can be assayed in a variety of ways known in the art. PTPR.alpha. mRNA levels can be quantitated by, e.g., Northern blot analysis, competitive polymerase chain reaction (PCR), or real-time PCR. RNA analysis can be performed on total cellular RNA or poly(A)+mRNA by methods known in the art. Methods of RNA isolation are taught in, for example, Ausubel, F. M. et al., *Current Protocols in Molecular Biology*, Volume 1, pp. 4.1.1-4.2.9 and 4.5.1-4.5.3, John Wiley & Sons, Inc., 1993.

Northern blot analysis is routine in the art and is taught in, for example, Ausubel, F. M. et al., *Current Protocols in Molecular Biology*, Volume 1, pp. 4.2.1-4.2.9, John Wiley & Sons, Inc., 1996. Real-time quantitative (PCR) can be conveniently accomplished using the commercially available ABI PRISM™ 7700 Sequence Detection System, available from PE-Applied Biosystems, Foster City, Calif. and used according to manufacturer's instructions. The method of analysis of modulation of RNA levels is not a limitation of the instant invention.

Levels of a protein encoded by PTPR.alpha. can be quantitated in a variety of ways well known in the art, such as immunoprecipitation, Western blot analysis (immunoblotting), ELISA or fluorescence-activated cell sorting (FACS). Antibodies directed to a protein encoded by PTPR.alpha. can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al., *Current Protocols in Molecular Biology*, Volume 2, pp. 11.12.1-11.12.9, John Wiley & Sons, Inc., 1997. Preparation of monoclonal antibodies is taught in, for example, Ausubel, F. M. et al., *Current Protocols in Molecular Biology*, Volume 2, pp. 11.4.1-11.11.5, John Wiley & Sons, Inc., 1997.

Immunoprecipitation methods are standard in the art and can be found at, for example, Ausubel, F. M. et al., *Current Protocols in Molecular Biology*, Volume 2, pp. 10.16.1-10.16.11, John Wiley & Sons, Inc., 1998. Western blot (immunoblot) analysis is standard in the art and can be found at, for example, Ausubel, F. M. et al., *Current Protocols in Molecular Biology*, Volume 2, pp. 10.8.1-10.8.21, John Wiley & Sons, Inc., 1997.

Active Target Segments

The locations on the target nucleic acid defined by having one or more active antisense compounds targeted thereto are referred to as "active target segments." There may be substantial variation in activity (e.g., as defined by percent inhibition) of the antisense compounds within an active target segment. Active antisense compounds are those that are determined to modulate the expression of their target RNA. Preferably, active antisense compounds inhibit expression of their target RNA at least about 50%, more preferably at least about 70% and most preferably at least about 80%. In a more preferred embodiment, the level of inhibition required to define an active antisense compound is defined based on the results from the screen used to define the active target segments. Those skilled in the art understand that the percent inhibition by an antisense compound on a target mRNA will vary between assays due to factors relating to assay conditions.

Hybridization

As used herein, "hybridization" means the pairing of complementary strands of antisense compounds to their target sequence. While not limited to a particular mechanism, the most common mechanism of pairing involves hydrogen bonding, which may be Watson-Crick, Hoogsteen or reversed Hoogsteen hydrogen bonding, between complementary nucleoside or nucleotide bases (nucleobases). For example, the natural base adenine is complementary to the natural nucleobases thymidine and uracil which pair through the formation of hydrogen bonds. The natural base guanine is complementary to the natural base 5-methyl cytosine and the artificial base known as a G-clamp. Hybridization can occur under varying circumstances.

An antisense compound is specifically hybridizable when there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

As used herein, "stringent hybridization conditions" or "stringent conditions" refers to conditions under which an antisense compound will hybridize to its target sequence, but to a minimal number of other sequences. Stringent conditions are sequence-dependent and will be different in different circumstances, and "stringent conditions" under which antisense compounds hybridize to a target sequence are determined by the nature and composition of the antisense compounds and the assays in which they are being investigated.

Complementarity

"Complementarity," as used herein, refers to the capacity for precise pairing between two nucleobases on either two oligomeric compound strands or an antisense compound with its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be a complementary position. The antisense compound and the further DNA or RNA are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the antisense compound and a target nucleic acid.

Identity

Antisense compounds, or a portion thereof, may have a defined percent identity to a SEQ ID NO, or a compound having a specific Isis number. As used herein, a sequence is identical to the sequence disclosed herein if it has the same nucleobase pairing ability. For example, a RNA which contains uracil in place of thymidine in the disclosed sequences would be considered identical as they both pair with adenine. Similarly, a G-clamp modified heterocyclic base would be considered identical to a cytosine or a 5-Me cytosine in the sequences of the instant application as it pairs with a guanine. This identity may be over the entire length of the oligomeric compound, or in a portion of the antisense compound (e.g., nucleobases 1-20 of a 27-mer may be compared to a 20-mer to determine percent identity of the oligomeric compound to the SEQ ID NO.) It is understood by those skilled in the art that an antisense compound need not have an identical sequence to those described herein to function similarly to the antisense compound described herein. Shortened versions of antisense compound taught herein, or non-identical versions of the antisense compound taught herein fall within the scope of this disclosure. Non-identical versions are those wherein each base does not have the same pairing activity as the antisense compounds disclosed herein. Bases do not have the same pairing activity by being shorter or having at least one abasic site. Alternatively, a non-identical version can include at least one base replaced with a different base with different pairing activity (e.g., G can be replaced by C, A, or T). Percent identity is calculated according to the number of bases that have identical base pairing corresponding to the SEQ ID NO or antisense compound to which it is being compared. The non-identical bases may be adjacent to each other, dispersed through out the oligonucleotide, or both.

For example, a 16-mer having the same sequence as nucleobases 2-17 of a 20-mer is 80% identical to the 20-mer. Alternatively, a 20-mer containing four nucleobases not identical to the 20-mer is also 80% identical to the 20-mer. A 14-mer having the same sequence as nucleobases 1-14 of an 18-mer is 78% identical to the 18-mer. Such calculations are well within the ability of those skilled in the art.

The percent identity is based on the percent of nucleobases in the original sequence present in a portion of the modified sequence. Therefore, a 30 nucleobase antisense compound comprising the full sequence of the complement of a 20 nucleobase active target segment would have a portion of 100% identity with the complement of the 20 nucleobase active target segment, while further comprising an additional 10 nucleobase portion. The complement of an active target segment may constitute a single portion. In a preferred embodiment, the oligonucleotides are at least about 80%, more preferably at least about 85%, even more preferably at least about 90%, most preferably at least 95% identical to at least a portion of the complement of the active target segments presented herein.

It is well known by those skilled in the art that it is possible to increase or decrease the length of an antisense compound and/or introduce mismatch bases without eliminating activity. For example, in Woolf et al. (Proc. Natl. Acad. Sci. USA 89:7305-7309, 1992, incorporated herein by reference), a series of ASOs 13-25 nucleobases in length were tested for their ability to induce cleavage of a target RNA. ASOs 25 nucleobases in length with 8 or 11 mismatch bases near the ends of the ASOs were able to direct specific cleavage of the target mRNA, albeit to a lesser extent than the ASOs that contained no mismatches. Similarly, target specific cleavage was achieved using a 13 nucleobase ASOs, including those with 1 or 3 mismatches. Maher and Dolnick (Nuc. Acid. Res. 16:3341-3358,1988, incorporated herein by reference) tested a series of tandem 14 nucleobase ASOs, and a 28 and 42 nucleobase ASOs comprised of the sequence of two or three of the tandem ASOs, respectively, for their ability to arrest translation of human DHFR in a rabbit reticulocyte assay. Each of the three 14 nucleobase ASOs alone were able to inhibit translation, albeit at a more modest level than the 28 or 42 nucleobase ASOs. Antisense compounds having a contiguous nucleobase composition that is shorter or longer or that comprises mismatches are contemplated in this invention so long as the antisense oligonucleotide activity is maintained.

Therapeutics

Antisense compounds can be used to modulate the expression of PTPR.alpha. in an animal, such as a human. In one non-limiting embodiment, the methods comprise the step of administering to said animal in need of therapy for a disease or condition associated with, increased plasma glucose levels, increased plasma lipid levels, increased hepatic triglyceride levels, increased plasma transaminase levels, reduced hepatic function, reduced insulin sensitivity or combinations thereof, an effective amount of an antisense compound that inhibits expression of PTPR.alpha. A disease or condition associated with PTPR.alpha. includes, but is not limited to, increased plasma glucose levels, increased plasma lipid levels, increased hepatic triglyceride levels, increased plasma transaminase levels, reduced hepatic function, reduced insulin sensitivity or combinations thereof. In one embodiment, the antisense compounds effectively inhibit the levels or function of PTPR.alpha. RNA. Because reduction in PTPR.alpha. mRNA levels can lead to alteration in PTPR.alpha. protein products of expression as well, such resultant alterations can also be measured. Antisense compounds that effectively inhibit the level or function of PTPR.alpha. RNA or protein products of expression are considered an active antisense compounds. In one embodiment, the antisense compounds inhibit the expression of PTPR.alpha. causing a reduction of RNA by at least 10%, by at least 20%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100%.

For example, the reduction of the expression of PTPR.alpha. can be measured in a bodily fluid, tissue or organ of the animal. Methods of obtaining samples for analysis, such as body fluids (e.g., plasma), tissues (e.g., biopsy), or organs, and methods of preparation of the samples to allow for analysis are well known to those skilled in the art. Methods for analysis of RNA and protein levels are discussed above and are well known to those skilled in the art. The effects of treatment can be assessed by measuring biomarkers associated with the PTPR.alpha. expression in the aforementioned fluids, tissues or organs, collected from an animal contacted with one or more compounds, by routine clinical methods known in the art. These biomarkers include but are not limited to: liver transaminases, body weight, organ weight, percent fat, lipids, non-esterified fatty acids, glucose, insulin and other markers of diabetes, fatty liver and metabolic syndrome.

The antisense compounds can be utilized in pharmaceutical compositions by adding an effective amount of a compound to a suitable pharmaceutically acceptable diluent or carrier. Acceptable carriers and diluents are well known to those skilled in the art. Selection of a diluent or carrier is based on a number of factors, including, but not limited to, the solubility of the compound and the desired route of administration. Such considerations are well understood by those skilled in the art. In one aspect, the compounds inhibit the expression of PTPR.alpha. The antisense compounds can also be used in the manufacture of a medicament for the treatment of diseases and conditions related to PTPR.alpha. expression.

Methods whereby bodily fluids, organs or tissues are contacted with an effective amount of one or more of the antisense compounds or compositions are also contemplated. Bodily fluids, organs or tissues can be contacted with one or more of the compounds disclosed herein resulting in modulation of PTPR.alpha. expression in the cells of bodily fluids, organs or tissues.

Thus, provided herein is the use of an isolated single- or double-stranded antisense compound targeted to PTPR.alpha. in the manufacture of a medicament for the treatment of a disease or disorder by means of the method described above. In a preferred embodiment, the antisense compound is a single stranded antisense compound.

Kits, Research Reagents, and Diagnostics

The antisense compounds disclosed herein can be utilized for diagnostics, and as research reagents and kits. Furthermore, antisense compounds, which are able to inhibit gene expression with specificity, are often used by those of ordinary skill to elucidate the function of particular genes or to distinguish between functions of various members of a biological pathway.

For use in kits and diagnostics, the antisense compounds, either alone or in combination with other compounds or therapeutics, can be used as tools in differential and/or combinatorial analyses to elucidate expression patterns of a portion or the entire complement of genes expressed within cells and tissues. Methods of gene expression analysis are well known to those skilled in the art.

Compounds

The term "oligomeric compound" refers to a polymeric structure capable of hybridizing to a region of a nucleic acid molecule. Generally, oligomeric compounds comprise a plurality of monomeric subunits linked together by internucleoside linking groups and/or internucleoside linkage mimetics. Each of the monomeric subunits comprises a sugar, abasic sugar, modified sugar, or a sugar mimetic, and except for the abasic sugar includes a nucleobase, modified nucleobase or a nucleobase mimetic. Preferred monomeric subunits comprise nucleosides and modified nucleosides.

An "antisense compound" or "antisense oligomeric compound" refers to an oligomeric compound that is at least partially complementary to the region of a target nucleic acid molecule to which it hybridizes and which modulates (increases or decreases) its expression. This term includes oligonucleotides, oligonucleosides, oligonucleotide analogs, oligonucleotide mimetics, antisense compounds, antisense oligomeric compounds, and chimeric combinations of these. Consequently, while all antisense compounds can be said to be oligomeric compounds, not all oligomeric compounds are antisense compounds. An "antisense oligonucleotide" is an antisense compound that is a nucleic acid-based oligomer. An antisense oligonucleotide can, in some cases, include one or more chemical modifications to the sugar, base, and/or internucleoside linkages. Nonlimiting examples of antisense compounds include primers, probes, antisense compounds, antisense oligonucleotides, external guide sequence (EGS) oligonucleotides, alternate splicers, and siRNAs. As such, these compounds can be introduced in the form of single-stranded, double-stranded, circular, branched or hairpins and can contain structural elements such as internal or terminal bulges or loops. Antisense double-stranded compounds can be two strands hybridized to form double-stranded compounds or a single strand with sufficient self complementarity to allow for hybridization and formation of a fully or partially double-stranded compound. The compounds are not auto-catalytic. As used herein, "auto-catalytic" means a compound has the ability to promote cleavage of the target RNA in the absence of accessory factors, e.g. proteins.

In one embodiment, the antisense compound comprises a single stranded oligonucleotide. In some embodiments the antisense compound contains chemical modifications. In a preferred embodiment, the antisense compound is a single stranded, chimeric oligonucleotide wherein the modifications of sugars, bases, and internucleoside linkages are independently selected.

The antisense compounds disclosed herein may comprise an antisense compound from about 12 to about 35 nucleobases (i.e. from about 12 to about 35 linked nucleosides). In other words, a single-stranded compound comprises from about 12 to about 35 nucleobases, and a double-stranded antisense compound (such as a siRNA, for example) comprises two strands, each of which is independently from about 12 to about 35 nucleobases. This includes oligonucleotides 15 to 35 and 16 to 35 nucleobases in length. Contained within the antisense compounds (whether single or double stranded and on at least one strand) are antisense portions. The "antisense portion" is that part of the antisense compound that is designed to work by one of the aforementioned antisense mechanisms. One of ordinary skill in the art will appreciate that about 12 to about 35 nucleobases includes 12, 13, 14, 15, 16, 17, 18, 19, 20, 21, 22, 23, 24, 25, 26, 27, 28, 29, 30, 31, 32, 33, 34, or 35 nucleobases.

Antisense compounds about 12 to 35 nucleobases in length, preferably about 15 to 35 nucleobases in length, comprising a complementary stretch of at least 8, preferably at least 12, more preferably at least 15 consecutive nucleobases selected from within the active target regions, are considered to be suitable antisense compounds as well.

Modifications can be made to the antisense compounds and may include conjugate groups attached to one of the termini, selected nucleobase positions, sugar positions or to one of the internucleoside linkages. Possible modifications include, but are not limited to, 2'-fluoro (2'-F), 2'-OMethyl (2'-OMe), 2'-Methoxy ethoxy (2'-MOE) sugar modifications, inverted abasic caps, deoxynucleobases, and bicyclice nucleobase analogs such as locked nucleic acids (including LNA) and ENA.

In one embodiment, double-stranded antisense compounds encompass short interfering RNAs (siRNAs). As used herein, the term "siRNA" is defined as a double-stranded compound having a first and second strand, each strand having a central portion and two independent terminal portions. The central portion of the first strand is complementary to the central portion of the second strand, allowing hybridization of the strands. The terminal portions are independently, optionally complementary to the corresponding terminal portion of the complementary strand. The ends of the strands may be modified by the addition of one or more natural or modified nucleobases to form an overhang Each strand of the siRNA duplex may be from about 12 to about 35 nucleobases. In a preferred embodiment, each strand of the siRNA duplex is about 17 to about 25 nucleobases. The two strands may be fully complementary (i.e., form a blunt ended compound), or include a 5' or 3' overhang on one or both strands. Double-stranded compounds can be made to include chemical modifications as discussed herein.

Chemical Modifications

As is known in the art, a nucleoside is a base-sugar combination. The base portion of the nucleoside is normally a heterocyclic base (sometimes referred to as a "nucleobase" or simply a "base"). The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. In forming oligonucleotides, the phosphate groups covalently link adjacent nucleosides to one another to form a linear polymeric compound. Within oligonucleotides, the phosphate groups are commonly referred to as forming the internucleoside backbone of the oligonucleotide. The normal linkage or backbone of RNA and DNA is a 3' to 5' phosphodiester linkage. It is often preferable to include chemical modifications in oligonucleotides to alter their activity. Chemical modifications can alter oligonucleotide activity by, for example: increasing affinity of an antisense oligonucleotide for its target RNA, increasing nuclease resistance, and/or altering the pharmacokinetics of the oligonucleotide. The use of chemistries that increase the affinity of an oligonucleotide for its target can allow for the use of shorter oligonucleotide compounds.

The term "nucleobase" or "heterocyclic base moiety" as used herein, refers to the heterocyclic base portion of a nucleoside. In general, a nucleobase is any group that contains one or more atom or groups of atoms capable of hydrogen bonding to a base of another nucleic acid. In addition to "unmodified" or "natural" nucleobases such as the purine nucleobases adenine (A) and guanine (G), and the pyrimidine nucleobases thymine (T), cytosine (C) and uracil (U), many modified nucleobases or nucleobase mimetics known to those skilled in the art are amenable to the disclosed antisense compounds. The terms modified nucleobase and nucleobase mimetic can overlap but generally a modified nucleobase refers to a nucleobase that is fairly similar in structure to the parent nucleobase, such as for example a 7-deaza purine or a 5-methyl cytosine, whereas a nucleobase mimetic would include more complicated structures, such as for example a tricyclic phenoxazine nucleobase mimetic. Methods for preparation of the above noted modified nucleobases are well known to those skilled in the art.

Antisense compounds disclosed herein may also contain one or more nucleosides having modified sugar moieties. The furanosyl sugar ring of a nucleoside can be modified in a number of ways including, but not limited to, addition of a substituent group, bridging of two non-geminal ring atoms to form a bicyclic nucleic acid (BNA) and substitution of an atom or group such as —S—, —N(R)— or —C(R.sub.1)

($R_2$) for the ring oxygen at the 4'-position. Modified sugar moieties are well known and can be used to alter, typically increase, the affinity of the antisense compound for its target and/or increase nuclease resistance. A representative list of preferred modified sugars includes but is not limited to bicyclic modified sugars (BNA's), including LNA and ENA (4'-(CH$_2$)$_2$-O-2' bridge); and substituted sugars, especially 2'-substituted sugars having a 2'-F, 2'-OCH$_3$ or a 2'-O(CH$_2$)$_2$-OCH$_3$ substituent group. Sugars can also be replaced with sugar mimetic groups among others. Methods for the preparations of modified sugars are well known to those skilled in the art.

Also included are internucleoside linking groups that link the nucleosides or otherwise modified monomer units together thereby forming an antisense compound. The two main classes of internucleoside linking groups are defined by the presence or absence of a phosphorus atom. Representative phosphorus containing internucleoside linkages include, but are not limited to, phosphodiesters, phosphotriesters, methylphosphonates, phosphoramidate, and phosphorothioates. Representative non-phosphorus containing internucleoside linking groups include, but are not limited to, methylenemethylimino (—CH$_2$-N(CH$_3$)—O—CH$_2$-), thiodiester (—O—C(O)—S—), thionocarbamate (—O—C(O)(NH)—S—); siloxane (—O—Si(H)2-O—); and N,N'-dimethylhydrazine (—CH$_2$-N(CH$_3$)—N(CH$_3$)-). Antisense compounds having non-phosphorus internucleoside linking groups are referred to as oligonucleosides. Modified internucleoside linkages, compared to natural phosphodiester linkages, can be used to alter, typically increase, nuclease resistance of the antisense compound. Internucleoside linkages having a chiral atom can be prepared racemic, chiral, or as a mixture. Representative chiral internucleoside linkages include, but are not limited to, alkylphosphonates and phosphorothioates. Methods of preparation of phosphorous-containing and non-phosphorous-containing linkages are well known to those skilled in the art.

As used herein the term "mimetic" refers to groups that are substituted for a sugar, a nucleobase, and/ or internucleoside linkage. Generally, a mimetic is used in place of the sugar or sugar-internucleoside linkage combination, and the nucleobase is maintained for hybridization to a selected target. Representative examples of a sugar mimetic include, but are not limited to, cyclohexenyl or morpholino. Representative examples of a mimetic for a sugar-internucleoside linkage combination include, but are not limited to, peptide nucleic acids (PNA) and morpholino groups linked by uncharged achiral linkages. In some instances a mimetic is used in place of the nucleobase. Representative nucleobase mimetics are well known in the art and include, but are not limited to, tricyclic phenoxazine analogs and universal bases (Berger et al., Nuc Acid Res. 2000, 28:2911-14, incorporated herein by reference). Methods of synthesis of sugar, nucleoside and nucleobase mimetics are well known to those skilled in the art.

As used herein the term "nucleoside" includes, nucleosides, abasic nucleosides, modified nucleosides, and nucleosides having mimetic bases and/or sugar groups.

The term "oligonucleotide" refers to an oligomeric compound which is an oligomer or polymer of ribonucleic acid (RNA) or deoxyribonucleic acid (DNA). This term includes oligonucleotides composed of naturally- and non-naturally-occurring nucleobases, sugars and covalent internucleoside linkages, possibly further including non-nucleic acid conjugates.

Compounds having reactive phosphorus groups are used for forming internucleoside linkages including for example phosphodiester and phosphorothioate internucleoside linkages. Methods of preparation and/or purification of precursors or antisense compounds are not a limitation of the compositions or methods disclosed herein. Methods for synthesis and purification of DNA, RNA, and the antisense compounds are well known to those skilled in the art.

As used herein the term "chimeric antisense compound" refers to an antisense compound, having at least one sugar, nucleobase and/or internucleoside linkage that is differentially modified as compared to the other sugars, nucleobases and internucleoside linkages within the same oligomeric compound. The remainder of the sugars, nucleobases and internucleoside linkages can be independently modified or unmodified. In general a chimeric oligomeric compound will have modified nucleosides that can be in isolated positions or grouped together in regions that will define a particular motif. Any combination of modifications and or mimetic groups can comprise a chimeric oligomeric compound.

Chimeric oligomeric compounds typically contain at least one region modified so as to confer increased resistance to nuclease degradation, increased cellular uptake, and/or increased binding affinity for the target nucleic acid. An additional region of the oligomeric compound may serve as a substrate for enzymes capable of cleaving RNA:DNA or RNA:RNA hybrids. By way of example, RNase H is a cellular endonuclease that cleaves the RNA strand of an RNA:DNA duplex. Activation of RNase H, therefore, results in cleavage of the RNA target, thereby greatly enhancing the efficiency of inhibition of gene expression. Consequently, comparable results can often be obtained with shorter oligomeric compounds when chimeras are used, compared to for example phosphorothioate deoxyoligonucleotides hybridizing to the same target region. Cleavage of the RNA target can be routinely detected by gel electrophoresis and, if necessary, associated nucleic acid hybridization techniques known in the art.

Certain chimeric as well as non-chimeric oligomeric compounds can be further described as having a particular motif. As used herein, the term "motif" refers to the orientation of modified sugar moieties and/or sugar mimetic groups in an antisense compound relative to like or differentially modified or unmodified nucleosides. As used herein, the terms "sugars", "sugar moieties" and "sugar mimetic groups" are used interchangeably. Such motifs include, but are not limited to, gapped motifs, alternating motifs, fully modified motifs, hemimer motifs, blockmer motifs, and positionally modified motifs. The sequence and the structure of the nucleobases and type of internucleoside linkage is not a factor in determining the motif of an antisense compound.

As used herein, the term "gapped motif" refers to an antisense compound comprising a contiguous sequence of nucleosides that is divided into 3 regions, an internal region (gap) flanked by two external regions (wings). The regions are differentiated from each other at least by having differentially modified sugar groups that comprise the nucleosides. In some embodiments, each modified region is uniformly modified (e.g. the modified sugar groups in a given region are identical); however, other motifs can be applied to regions. For example, the wings in a gapmer could have an alternating motif. The nucleosides located in the gap of a gapped antisense compound have sugar moieties that are different than the modified sugar moieties in each of the wings.

As used herein, the term "alternating motif" refers to an antisense compound comprising a contiguous sequence of nucleosides comprising two differentially sugar modified nucleosides that alternate for essentially the entire sequence of the antisense compound, or for essentially the entire sequence of a region of an antisense compound.

As used herein, the term "fully modified motif" refers to an antisense compound comprising a contiguous sequence of nucleosides wherein essentially each nucleoside is a sugar modified nucleoside having uniform modification.

As used herein, the term "hemimer motif" refers to a sequence of nucleosides that have uniform sugar moieties (identical sugars, modified or unmodified) and wherein one of the 5'-end or the 3'-end has a sequence of from 2 to 12 nucleosides that are sugar modified nucleosides that are different from the other nucleosides in the hemimer modified antisense compound.

As used herein, the term "blockmer motif" refers to a sequence of nucleosides that have uniform sugars (identical sugars, modified or unmodified) that is internally interrupted by a block of sugar modified nucleosides that are uniformly modified and wherein the modification is different from the other nucleosides. Methods of preparation of chimeric oligonucleotide compounds are well known to those skilled in the art.

As used herein, the term "positionally modified motif" comprises all other motifs. Methods of preparation of positionally modified oligonucleotide compounds are well known to those skilled in the art.

The compounds described herein contain one or more asymmetric centers and thus give rise to enantiomers, diastereomers, and other stereoisomeric configurations that may be defined, in terms of absolute stereochemistry, as (R) or (S), alpha or beta, or as (D) or (L) such as for amino acids et al. All such possible isomers, as well as their racemic and optically pure forms, are included herein.

In one aspect, antisense compounds are modified by covalent attachment of one or more conjugate groups. Conjugate groups may be attached by reversible or irreversible attachments. Conjugate groups may be attached directly to antisense compounds or by use of a linker. Linkers may be mono- or bifunctional linkers. Such attachment methods and linkers are well known to those skilled in the art. In general, conjugate groups are attached to antisense compounds to modify one or more properties. Such considerations are well known to those skilled in the art.

Oligomer Synthesis

Oligomerization of modified and unmodified nucleosides can be routinely performed according to literature procedures for DNA (Protocols for Oligonucleotides and Analogs, Ed. Agrawal (1993), Humana Press) and/or RNA (Scaringe, Methods (2001), 23, 206-217. Gait et al., Applications of Chemically synthesized RNA in RNA: Protein Interactions, Ed. Smith (1998), 1-36. Gallo et al., Tetrahedron (2001), 57, 5707-5713).

Antisense compounds can be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives. The invention is not limited by the method of antisense compound synthesis.

Oligomer Purification and Analysis

Methods of oligonucleotide purification and analysis are known to those skilled in the art. Analysis methods include capillary electrophoresis (CE) and electrospray-mass spectroscopy. Such synthesis and analysis methods can be performed in multi-well plates. The method of the invention is not limited by the method of oligomer purification.

Salts, Prodrugs and Bioequivalents

The antisense compounds disclosed herein may comprise any pharmaceutically acceptable salts, esters, or salts of such esters, or any other functional chemical equivalent which, upon administration to an animal including a human, is capable of providing (directly or indirectly) the biologically active metabolite or residue thereof. Accordingly, for example, the disclosure is also drawn to prodrugs and pharmaceutically acceptable salts of the antisense compounds, pharmaceutically acceptable salts of such prodrugs, and other bioequivalents.

The term "prodrug" indicates a therapeutic agent that is prepared in an inactive or less active form that is converted to an active form (i.e., drug) within the body or cells thereof by the action of endogenous enzymes, chemicals, and/or conditions. In particular, prodrug versions of the oligonucleotides are prepared as SATE ((S-acetyl-2-thioethyl)phosphate) derivatives according to the methods disclosed in WO 93/24510 or WO 94/26764. Prodrugs can also include antisense compounds wherein one or both ends comprise nucleobases that are cleaved (e.g., by incorporating phosphodiester backbone linkages at the ends) to produce the active compound.

The term "pharmaceutically acceptable salts" refers to physiologically and pharmaceutically acceptable salts of the compounds: i.e., salts that retain the desired biological activity of the parent compound and do not impart undesired toxicological effects thereto. Sodium salts of antisense oligonucleotides are useful and are well accepted for therapeutic administration to humans. In another embodiment, sodium salts of dsRNA compounds are also provided.

Formulations

The antisense compounds may also be admixed, encapsulated, conjugated or otherwise associated with other molecules, molecule structures or mixtures of compounds.

Also included are pharmaceutical compositions and formulations which include the antisense compounds. The pharmaceutical compositions may be administered in a number of ways depending upon whether local or systemic treatment is desired and upon the area to be treated The pharmaceutical formulations, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers, finely divided solid carriers, or both, and then, if necessary, shaping the product (e.g., into a specific particle size for delivery).

A "pharmaceutical carrier" or "excipient" can be a pharmaceutically acceptable solvent, suspending agent or any other pharmacologically inert vehicle for delivering one or more nucleic acids to an animal and are known in the art. The excipient may be liquid or solid and is selected, with the planned manner of administration in mind, so as to provide for the desired bulk, consistency, etc., when combined with a nucleic acid and the other components of a given pharmaceutical composition.

Combinations

Pharmaceutical compositions may comprise two or more antisense compounds. In another related embodiment, pharmaceutical compositions may comprise one or more antisense compounds, particularly oligonucleotides, targeted to a first nucleic acid and one or more additional antisense compounds targeted to a second nucleic acid target. Alternatively, pharmaceutical compositions may comprise two or more antisense compounds targeted to different regions of the same nucleic acid target. Two or more combined compounds may be used together or sequentially. Pharmaceutical compositions may comprise an antisense compound combined with other non-antisense compound therapeutic agents.

Nonlimiting Disclosure and Incorporation by Reference

While certain compounds, compositions and are being described herein with specificity in accordance with certain embodiments, the following examples serve only as illustrations and not as limitations. Each of the references, GenBank accession numbers, and the like recited in the present application is incorporated herein by reference in its entirety.

EXAMPLE 1

Cell Types and Transfection Methods

Example 1—Cell types—The effect of oligomeric compounds on target nucleic acid expression was tested in one or more of the following cell types.

T-24 cells: The human transitional cell bladder carcinoma cell line T-24 was obtained from the American Type Culture Collection (ATCC) (Manassas, Va.). T-24 cells were routinely cultured in complete McCoy's 5A basal media (Invitrogen Corporation, Carlsbad, Calif.) supplemented with 10% fetal calf serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence. Cells were seeded into 96-well plates (Falcon-Primaria #353872) at a density of 7000 cells/well for use in RT-PCR analysis.

b.END cells: The mouse brain endothelial cell line b.END was obtained from Dr. Werner Risau at the Max Plank Institute (Bad Nauheim, Germany). b.END cells were routinely cultured in DMEM, high glucose (Gibco/Life Technologies, Gaithersburg, Md.) supplemented with 10% fetal calf serum (Gibco/Life Technologies, Gaithersburg, Md.). Cells were routinely passaged by trypsinization and dilution when they reached 90% confluence. Cells were seeded into 96-well plates (Falcon-Primaria #3872) at a density of 3000 cells/well for use in RT-PCR analysis.

For Northern blotting or other analysis, cells may be seeded onto 100 mm or other standard tissue culture plates and treated similarly, using appropriate volumes of medium and oligonucleotide.

NHDF cells: Human neonatal dermal fibroblast (NHDF) were obtained from the Clonetics Corporation (Walkersville, Md.). NHDFs were routinely maintained in Fibroblast Growth Medium (Clonetics Corporation, Walkersville, Md.) supplemented as recommended by the supplier. Cells were maintained for up to 10 passages as recommended by the supplier.

HEK cells: Human embryonic keratinocytes (HEK) were obtained from the Clonetics Corporation (Walkersville, Md.). HEKs were routinely maintained in Keratinocyte Growth Medium (Clonetics Corporation, Walkersville, Md.) formulated as recommended by the supplier. Cells were routinely maintained for up to 10 passages as recommended by the supplier.

Treatment with oligomeric compounds: When cells reach appropriate confluency, they are treated with oligonucleotide using a transfection method as described.

Lipofectin™ When cells reached 65-75% confluency, they were treated with oligonucleotide. Oligonucleotide was mixed with LIPOFECTIN™ Invitrogen Life Technologies, Carlsbad, Calif.) in Opti-MEM™-1 reduced serum medium (Invitrogen Life Technologies, Carlsbad, Calif.) to achieve the desired concentration of oligonucleotide and a LIPOFECTIN™ concentration of 2.5 or 3.micro.g/mL per 100 nM oligonucleotide. This transfection mixture was incubated at room temperature for approximately 0.5 hours. For cells grown in 96-well plates, wells were washed once with 100 .micro.L OPTI-MEM™-1 and then treated with 130 .micro.L of the transfection mixture. Cells grown in 24-well plates or other standard tissue culture plates are treated similarly, using appropriate volumes of medium and oligonucleotide. Cells are treated and data are obtained in duplicate or triplicate. After approximately 4-7 hours of treatment at 37.deg.C., the medium containing the transfection mixture was replaced with fresh culture medium. Cells were harvested 16-24 hours after oligonucleotide treatment.

Control Oligonucleotides

Control oligonucleotides are used to determine the optimal oligomeric compound concentration for a particular cell line. Furthermore, when oligomeric compounds are tested in oligomeric compound screening experiments or phenotypic assays, control oligonucleotides are tested in parallel.

The concentration of oligonucleotide used varies from cell line to cell line. To determine the optimal oligonucleotide concentration for a particular cell line, the cells are treated with a positive control oligonucleotide at a range of concentrations. The concentration of positive control oligonucleotide that results in 80% inhibition of the target mRNA is then utilized as the screening concentration for new oligonucleotides in subsequent experiments for that cell line. If 80% inhibition is not achieved, the lowest concentration of positive control oligonucleotide that results in 60% inhibition of the target mRNA is then utilized as the oligonucleotide screening concentration in subsequent experiments for that cell line. If 60% inhibition is not achieved, that particular cell line is deemed as unsuitable for oligonucleotide transfection experiments. The concentrations of antisense oligonucleotides used herein are from 50 nM to 300 nM when the antisense oligonucleotide is transfected using a liposome reagent and 1 µM to 40 µM when the antisense oligonucleotide is transfected by electroporation.

EXAMPLE 2

Real-time Quantitative PCR Analysis of PTPR.alpha. mRNA Levels

Quantitation of PTPR.alpha. mRNA levels was accomplished by real-time quantitative PCR using the ABI PRISM™ 7600, 7700, or 7900 Sequence Detection System (PE-Applied Biosystems, Foster City, Calif.) according to manufacturer's instructions.

Prior to quantitative PCR analysis, primer-probe sets specific to the PTPR.alpha. being measured were evaluated for their ability to be "multiplexed" with a GAPDH amplification reaction. After isolation the RNA is subjected to sequential reverse transcriptase (RT) reaction and real-time PCR, both of which are performed in the same well. RT and PCR reagents were obtained from Invitrogen Life Technologies (Carlsbad, Calif.). RT, real-time PCR was carried out in the same by adding 20 .micro.L PCR cocktail (2.5× PCR buffer minus MgCl.sub.2, 6.6 mM MgCl.sub.2, 375. micro.M each of dATP, dCTP, dCTP and dGTP, 375 nM each of forward primer and reverse primer, 125 nM of probe, 4 Units RNase inhibitor, 1.25 Units PLATINUM® Taq, 5 Units MuLV reverse transcriptase, and 2.5× ROX dye) to 96-well plates containing 30 .micro.L total RNA solution (20-200 ng). The RT reaction was carried out by incubation for 30 minutes at 48.deg.C. Following a 10 minute incubation at 95.deg.C. to activate the PLATINUM® Taq, 40 cycles of a two-step PCR protocol were carried out: 95.deg.C. for 15 seconds (denaturation) followed by 60.deg.C. for 1.5 minutes (annealing/extension).

Gene target quantities obtained by RT, real-time PCR were normalized using either the expression level of GAPDH, a gene whose expression is constant, or by quantifying total RNA using RiboGreen™ (Molecular Probes, Inc. Eugene, Oreg.). GAPDH expression was quantified by RT, real-time PCR, by being run simultaneously with the target, multiplexing, or separately. Total RNA was quantified using RiboGreen™ RNA quantification reagent (Molecular Probes, Inc. Eugene, Oreg.).

170 .micro.L of RiboGreen™ working reagent (RiboGreen™ reagent diluted 1:350 in 10 mM Tris-HCl, 1 mM EDTA, pH 7.5) was pipetted into a 96-well plate containing 30 .micro.L purified cellular RNA. The plate was read in a CytoFluor 4000 (PE Applied Biosystems) with excitation at 485 nm and emission at 530 nm.

The GAPDH PCR probes have JOE covalently linked to the 5' end and TAMRA or MGB covalently linked to the 3' end, where JOE is the fluorescent reporter dye and TAMRA or MGB is the quencher dye. In some cell types, primers and probe designed to a GAPDH sequence from a different species are used to measure GAPDH expression. For example, a human GAPDH primer and probe set is used to measure GAPDH expression in monkey-derived cells and cell lines.

Probes and primers for use in real-time PCR were designed to hybridize to target-specific sequences. The primers and probes and the target nucleic acid sequences to which they hybridize are presented in Table 2. The target-specific PCR probes have FAM covalently linked to the 5' end and TAMRA or MGB covalently linked to the 3' end, where FAM is the fluorescent dye and TAMRA or MGB is the quencher dye.

TABLE 2

PTPR.alpha.-specific primers and probes for use in real-time PCR

| Species | Target SEQ ID NO | Sequence Description | Sequence 5' to 3') | SEQ ID NO |
|---|---|---|---|---|
| Human | 4 | Fwd Primer | GGTGGACTACACAGTACGAAGTTC | 5 |
| Human | 4 | Rev Primer | GATGAGGCGCTGTGGCTTT | 6 |
| Human | 4 | Probe | FAM-CATCCAGCAGGTGGGCGACATG-TAMRA | 7 |
| Mouse | 11 | Fwd Primer | GATATAATGAAATCCTCAGCCTGGA | 12 |
| Mouse | 11 | Rev Primer | GAATGAGTCTTAGGTTTATCTTCTTTAGGAA | 13 |

TABLE 2-continued

PTPR.alpha.-specific primers and probes for use in real-time PCR

| Species | Target SEQ ID NO | Sequence Description | Sequence 5' to 3') | SEQ ID NO |
|---|---|---|---|---|
| Mouse | 11 | Probe | FAM-TGGGCCAGATTGTTCCTTGCTTCAAAT-TAMRA | 14 |

EXAMPLE 3

Antisense Inhibition of Human PTPR.alpha. Expression by Oligomeric Compounds

Accordingly, a series of oligonucleotides were designed to target different regions of the human PTPR.alpha. RNA, using published sequences (GenBank accession number NM_080841.1, representing a human PTPR.alpha. variant herein designated hPTPRA-3, incorporated herein as SEQ ID NO: 4; GenBank accession number M34668.1, representing the main mRNA of human PTPR.alpha., herein designated hPTPRA, incorporated herein as SEQ ID NO: 18; a consensus sequence constructed from GenBank accession numbers AL161656.15 and AL121905.23, representing a genomic sequence of human PTPR.alpha., incorporated herein as SEQ ID NO: 19; GenBank accession number X54890.1, representing a human PTPR.alpha. variant herein designated hPTPRA-4, incorporated herein as SEQ ID NO: 20; GenBank accession number X53364.1, representing a human PTPR.alpha. variant herein designated hPTPRA-5, incorporated herein as SEQ ID NO: 21; GenBank accession number AF121183.1, representing a 5'-extension of SEQ ID NO: 18, incorporated herein as SEQ ID NO: 22; the complement of GenBank accession number BE168541.1, representing a 5'-extenstion of SEQ ID NO: 22 incorporated herein as SEQ ID NO: 23; the complement of GenBank accession number AW024120.1, representing a 5'-extension of SEQ ID NO: 20, incorporated herein as SEQ ID NO: 24; the complement of GenBank accession number AA903762.1, representing a 3'-extension of SEQ ID NO: 18, incorporated herein as SEQ ID NO: 25; the complement of GenBank accession number AI674319.1, representing a variant of human PTPR.alpha. herein designated hPTPRA-7, incorporated herein as SEQ ID NO: 26, and residues 2749000-2925000 of GenBank accession number NT_011387.6, representing a genomic sequence of human PRPTA, incorporated herein as SEQ ID NO: 27). The oligonucleotides are shown in Table 3. "Target site" indicates the first (5'-most) nucleotide number on the particular target sequence to which the oligonucleotide binds. All compounds in Table 3 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE) nucleotides. The internucleoside (backbone) linkages are phosphorothioate (P=S) throughout the oligonucleotide. All cytidine residues are 5-methylcytidines. The compounds were analyzed for their effect on human PTPR.alpha. mRNA levels by quantitative real-time PCR as described in other examples herein. Data are averages from two experiments in which T-24 cells were treated with the antisense oligonucleotides. The positive control for each data point is identified in the table by sequence ID number. If present, "N.D." indicates "no data".

TABLE 3

Inhibition of human PTPR.alpha. mRNA levels
by chimeric phosphorothioate oligonucleotides
having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 147239 | Coding | 27 | 101612 | ttggtgccacagaaagagaa | 83 | 28 | 2 |
| 147240 | Coding | 27 | 101621 | ggctgaatgttggtgccaca | 82 | 29 | 2 |
| 147244 | Coding | 27 | 123433 | agggccaccatcaccgcaat | 72 | 30 | 2 |
| 147246 | Coding | 27 | 123448 | actagcagagaggacagggc | 83 | 31 | 2 |
| 147247 | Coding | 4 | 706 | cttaaaccttaacatgtaca | 62 | 32 | 2 |
| 147252 | Coding | 27 | 141723 | acaggtggcctggataggac | 91 | 33 | 2 |
| 147253 | Coding | 27 | 141728 | gcctcacaggtggcctggat | 81 | 34 | 2 |
| 147256 | Coding | 27 | 144039 | ttgatgtaatcagaatctgg | 94 | 35 | 2 |
| 147259 | Coding | 27 | 158044 | cgtactgtgtagtccaccag | 95 | 36 | 2 |
| 147260 | Coding | 4 | 1338 | cccacctgctggatgcagaa | 98 | 37 | 2 |
| 147262 | Coding | 27 | 158737 | ggaactgagtgatgaggcgc | 89 | 38 | 2 |
| 147263 | Coding | 27 | 158815 | aggccttcaccttcttgagg | 87 | 39 | 2 |
| 147267 | Coding | 27 | 161150 | agataatgctccagaagggc | 66 | 40 | 2 |
| 147269 | Coding | 27 | 163359 | cgcatcttgtcattctggat | 87 | 41 | 2 |
| 147270 | Coding | 27 | 163783 | actggaatgatcactctgtt | 90 | 42 | 2 |
| 147272 | Coding | 27 | 164391 | tggagaagagggccctggct | 89 | 43 | 2 |
| 147273 | Coding | 27 | 164429 | tccactcccagatcattcgc | 78 | 44 | 2 |
| 147274 | Coding | 4 | 2104 | ggcacacttctcctggcctc | 80 | 45 | 2 |
| 147275 | Intron: Exon Junction | 27 | 172236 | tactgggcacacttctcctg | 77 | 46 | 2 |
| 147276 | Intron: Exon Junction | 27 | 172246 | agatggccagtactgggcac | 93 | 47 | 2 |
| 147278 | Coding | 27 | 172302 | cattcctcctccttcttcag | 78 | 48 | 2 |
| 147279 | Coding | 27 | 172336 | ggtgaccaggaggtctcgga | 75 | 49 | 2 |
| 147280 | Coding | 27 | 172341 | gtgttggtgaccaggaggtc | 84 | 50 | 2 |
| 147281 | Coding | 4 | 2223 | ttctccctggtgttggtgac | 71 | 51 | 2 |
| 147282 | Coding | 27 | 172462 | tggaagtggaactgccggat | 66 | 52 | 2 |
| 147283 | Coding | 27 | 173896 | agccgcaggctcttgacagt | 70 | 53 | 2 |
| 147285 | Coding | 27 | 174766 | acttgaagttggcataatct | 74 | 54 | 2 |
| 147288 | Coding | 27 | 174875 | ttctaaaacagttataagat | 65 | 55 | 2 |
| 147291 | Coding | 27 | 174937 | agtgctaacacatttacata | 35 | 56 | 2 |
| 147297 | Coding | 27 | 175134 | agagctctgagaactttgtg | 78 | 57 | 2 |
| 194483 | 5'UTR | 18 | 20 | acctgctcccctgagcgtgt | 47 | 58 | 2 |
| 194484 | 5'UTR | 18 | 470 | gtgtcatgtagagacaggtc | 22 | 59 | 2 |
| 194485 | Start Codon | 18 | 685 | ggaatccatgcttgttagct | 52 | 60 | 2 |

TABLE 3-continued

Inhibition of human PTPR.alpha. mRNA levels
by chimeric phosphorothioate oligonucleotides
having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 194486 | Coding | 18 | 716 | gaccactgccgagcagaaca | 91 | 61 | 2 |
| 194487 | Coding | 18 | 1063 | tgctgcggtgctggaattcc | 82 | 62 | 2 |
| 194488 | Coding | 18 | 2026 | acctgtacgccctacacctg | 84 | 63 | 2 |
| 194489 | Stop Codon | 18 | 3094 | tgttgccgcttacttgaagt | 83 | 64 | 2 |
| 194490 | 3'UTR | 18 | 3338 | aatttctcggctgaggattt | 63 | 65 | 2 |
| 194491 | Exon: Intron Junction | 19 | 2575 | tgggccaaaccttggctgca | 7 | 66 | 2 |
| 194492 | Exon: Intron Junction | 19 | 11234 | gaacactcacagagtcgggc | 81 | 67 | 2 |
| 194493 | Intron | 19 | 30977 | cataatatattaagtacagc | 1 | 68 | 2 |
| 194494 | Intron: Exon Junction | 19 | 60678 | gttgtgtcacctgcaacaaa | 66 | 69 | 2 |
| 194495 | Intron | 19 | 85496 | cagtacttactagcttcttt | 85 | 70 | 2 |
| 194496 | Intron: Exon Junction | 19 | 93080 | tgaagaagtcctagaacacc | 57 | 71 | 2 |
| 194497 | Intron: Exon Junction | 19 | 101743 | ccatgcttatctggaaaata | 72 | 72 | 2 |
| 194498 | Exon: Intron Junction | 19 | 124321 | gtaggctcaccttaacatgt | 68 | 73 | 2 |
| 194499 | Intron: Exon Junction | 19 | 125366 | gacaggtcatgcacaccctg | 86 | 74 | 2 |
| 194500 | Intron: Exon Junction | 19 | 125503 | tttcttaaacctaatgagaa | 94 | 75 | 2 |
| 194501 | Exon: Intron Junction | 19 | 125577 | aatgccttacccacatcctc | 52 | 76 | 2 |
| 194502 | Intron | 19 | 127990 | caggctggtttcgaactcct | 87 | 77 | 2 |
| 194503 | Intron | 19 | 132617 | ttaaagccaaatttcttttc | 76 | 78 | 2 |
| 194504 | Intron | 19 | 151456 | gcccagccccaaagtgcttc | 92 | 79 | 2 |
| 194505 | 5'UTR | 20 | 49 | gttgtgtcacagagtcgggc | 6 | 80 | 2 |
| 194506 | Coding | 20 | 592 | ggtgtctcatctgaaggagg | 91 | 81 | 2 |
| 194507 | 5'UTR | 21 | 73 | tgaagaagtctagcttcttt | 9 | 82 | 2 |
| 194508 | Start Codon | 21 | 165 | atccatgcttatcaccaggg | 31 | 83 | 2 |
| 194509 | 5'UTR | 22 | 51 | ggctcgagccacatccccat | 13 | 84 | 2 |
| 194510 | 5'UTR | 22 | 148 | acaccttgatggccagctcc | 35 | 85 | 2 |
| 194511 | 5'UTR | 23 | 115 | agcagcacctggatggtgag | 36 | 86 | 2 |

TABLE 3-continued

Inhibition of human PTPR.alpha. mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 194512 | 5'UTR | 23 | 218 | ccagtgggccaggatcctgc | 46 | 87 | 2 |
| 194513 | 5'UTR | 24 | 20 | gttcattgctgttcagagac | 14 | 88 | 2 |
| 194514 | 5'UTR | 24 | 183 | cctcgcctccatggcgaggg | 39 | 89 | 2 |
| 194515 | 3'UTR | 25 | 115 | cccatgatatcagtggtggg | 69 | 90 | 2 |
| 194516 | 3'UTR | 25 | 190 | ctcagggagtcaaagctttt | 49 | 91 | 2 |
| 194517 | Exon: Exon Junction | 26 | 197 | gggctccacatcctcagtgc | 86 | 92 | 2 |

As shown in Table 3, SEQ ID NOS: 28, 29, 30, 31, 32, 33, 34, 35, 36, 37, 38, 39, 40, 41, 42, 43, 44, 45, 46, 47, 48, 49, 50, 51, 52, 53, 54, 55, 57, 60, 61, 62, 63, 64, 65, 67, 69, 70, 71, 72, 73, 74, 75, 76, 77, 78, 79, 81, 90 and 92 demonstrated at least 50% inhibition of human PTPR.alpha. expression in this assay and are therefore preferred. The target sites to which these preferred sequences are complementary are herein referred to as "preferred target sites" and are therefore preferred sites for targeting by antisense compounds. These preferred target sites are shown in Table 5.

EXAMPLE 4

Antisense Inhibition of Mouse PTPR.alpha. Expression by Oligomeric Compounds

Accordingly, a second series of oligonucleotides were designed to target different regions of the mouse PTPR.alpha. RNA, using published sequences (GenBank accession number NM_008980.1, representing a variant of mouse PTPR.alpha. herein designated mPTPRA-2, incorporated herein as SEQ ID NO: 11; GenBank accession number AW323517.1, representing a 5'-extension of SEQ ID NO: 11, incorporated herein as SEQ ID NO: 93; GenBank accession numbers L13686.1, L13668.1, L13670.1, L13672.1, L13674.1, L13675.1, L13676.1 and L13608.1, representing partial genomic sequences of mouse PTPR.alpha., incorporated herein as SEQ ID NOs: 94, 95, 96, 97, 98, 99, 100 and 101 respectively; and GenBank accession number BE372094.1, representing the main mRNA of mouse PTPR.alpha., herein designated mPTPRA, incorporated herein as SEQ ID NO: 102). The oligonucleotides are shown in Table 4. "Target site" indicates the first (5'-most) nucleotide number on the particular target sequence to which the oligonucleotide binds. All compounds in Table 4 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE) nucleotides. It is expected that antisense oligonucleotides with mismatches or varying nucleotide lengths will have similar profiles to those described herein. The internucleoside (backbone) linkages are phosphorothioate (P=S) throughout the oligonucleotide. All cytidine residues are 5-methylcytidines. The compounds were analyzed for their effect on mouse PTPR.alpha. mRNA levels by quantitative real-time PCR as described in other examples herein. Data are averages from two experiments. The positive control for each data point is identified in the table by sequence ID number. If present, "N.D." indicates "no data".

TABLE 4

Inhibition of mouse PTPR.alpha. mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 147237 | Start Codon | 11 | 17 | caggaatccatgctgaccga | 77 | 103 | 1 |
| 147238 | Start Codon | 11 | 25 | gaatgaaccaggaatccatg | 1 | 104 | 1 |
| 147241 | Coding | 11 | 376 | tcccctccagggttctgtt | 1 | 105 | 1 |
| 147242 | Coding | 11 | 407 | gtttctggagtggttgctgc | 54 | 106 | 1 |
| 147243 | Coding | 11 | 445 | tcaccgcaataattggtgtc | 49 | 107 | 1 |
| 147245 | Coding | 11 | 460 | aggacagggccaccatcacc | 73 | 108 | 1 |

TABLE 4-continued

Inhibition of mouse PTPR.alpha. mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 147248 | Coding | 11 | 519 | gtatttcttaaaccttaaca | 25 | 109 | 1 |
| 147249 | Coding | 11 | 531 | cccagcttgcttgtatttct | 73 | 110 | 1 |
| 147250 | Coding | 11 | 665 | tcctcttccagcttgtccac | 52 | 111 | 1 |
| 147251 | Coding | 11 | 735 | aggacaagcagggagagcgt | 57 | 112 | 1 |
| 147254 | Coding | 11 | 876 | tctttctaacaatggagtgg | 4 | 113 | 1 |
| 147255 | Coding | 11 | 926 | gagtggtcatctgagagaca | 0 | 114 | 1 |
| 147257 | Coding | 11 | 1040 | tcttttggtccttgtgcagc | 39 | 115 | 1 |
| 147258 | Coding | 11 | 1177 | tcccataggtccagcagcct. | 83 | 116 | 1 |
| 147261 | Coding | 11 | 1258 | cgtcgcccacctgctggatg | 71 | 117 | 1 |
| 147264 | Coding | 11 | 1385 | tgagggttacaggccttcac | 52 | 118 | 1 |
| 147265 | Coding | 11 | 1489 | ctttgcgttccgaatgcatc | 52 | 119 | 1 |
| 147266 | Coding | 11 | 1523 | gcccggatccggctcacaaa | 0 | 120 | 1 |
| 147268 | Coding | 11 | 1711 | aagttaatttcttaaactcc | 14 | 121 | 1 |
| 147271 | Coding | 11 | 1903 | tggcaatgtaggagtctttc | 56 | 122 | 1 |
| 147277 | Coding | 11 | 2039 | ccatcagatggccagtactg | 27 | 123 | 1 |
| 147284 | Coding | 11 | 2430 | atactgttccagtgtctgga | 38 | 124 | 1 |
| 147286 | Stop Codon | 11 | 2504 | gtcacctgtcacttgaagtt | 63 | 125 | 1 |
| 147287 | 3'UTR | 11 | 2585 | aagatatatacaattttggg | 0 | 126 | 1 |
| 147289 | 3'UTR | 11 | 2606 | tgccatttctaaaacagtta | 66 | 127 | 1 |
| 147290 | 3'UTR | 11 | 2627 | aacaggtaatagaagcctat | 66 | 128 | 1 |
| 147292 | 3'UTR | 11 | 2670 | aggactatcagtgctaacac | 75 | 129 | 1 |
| 147293 | 3'UTR | 11 | 2763 | gcaaggaacaatctggccca | 96 | 130 | 1 |
| 147294 | 3'UTR | 11 | 2788 | tcttctttaggaaaagatat | 37 | 131 | 1 |
| 147295 | 3'UTR | 11 | 2805 | aatgagtcttaggtttatct | 48 | 132 | 1 |
| 147296 | 3'UTR | 11 | 2830 | ttttagttggcactgagcta | 40 | 133 | 1 |
| 147298 | 3'UTR | 11 | 2860 | cctcaagagctctgagaact | 78 | 134 | 1 |
| 147299 | 3'UTR | 11 | 2867 | accatttcctcaagagctct | 76 | 135 | 1 |
| 147300 | 3'UTR | 11 | 2971 | tgcctgaggtggctgatctt | 55 | 136 | 1 |
| 147301 | 3'UTR | 11 | 3024 | ctgacgatccctgctgtggt | 60 | 137 | 1 |
| 147302 | 3'UTR | 11 | 3039 | aagagtgtttattacctgac | 35 | 138 | 1 |
| 147303 | 5'UTR | 93 | 28 | atgcccccgcgagtccctgt | 71 | 139 | 1 |
| 147304 | 5'UTR | 93 | 93 | gaagcggcagagagaggact | 35 | 140 | 1 |
| 147305 | Intron | 94 | 2 | agagtggtcatctgcaaaca | 15 | 141 | 1 |
| 147306 | Intron: Exon Junction | 95 | 1 | cacatttacactacaatgaa | 14 | 142 | 1 |

TABLE 4-continued

Inhibition of mouse PTPR.alpha. mRNA levels
by chimeric phosphorothioate oligonucleotides
having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 147307 | Intron: Exon Junction | 96 | 1 | tacacctgcactgtagccag | 49 | 143 | 1 |
| 147308 | Intron: Exon Junction | 97 | 3 | tgaagttaatttctgaatga | 0 | 144 | 1 |
| 147309 | Exon: Intron Junction | 98 | 136 | ttgaactcacctggcctctc | 61 | 145 | 1 |
| 147310 | Exon: Intron Junction | 99 | 122 | ctcaccctggtgttggtgac | 18 | 146 | 1 |
| 147311 | Intron: Exon Junction | 100 | 1 | tcttgttctcctttggaaga | 19 | 147 | 1 |
| 147312 | 3'UTR | 101 | 138 | ataagactgctctgcccaag | 65 | 148 | 1 |
| 147313 | 3'UTR | 101 | 167 | taggaacaacccaggagagc | 58 | 149 | 1 |
| 147314 | Exon: Intron Junction | 102 | 633 | tagagtgttcttagggcagg | 28 | 150 | 1 |

As shown in Table 4, SEQ ID NOs 103, 106, 108, 110, 111, 112, 116, 117, 118, 119, 122, 125, 127, 128, 129, 130, 134, 135, 136, 137, 139, 145, 148 and 149 demonstrated at least 50% inhibition of mouse PTPR.alpha. expression in this experiment and are therefore preferred. The target sites to which these preferred sequences are complementary are herein referred to as "preferred target sites" and are therefore preferred sites for targeting antisense oligonucleotides. These preferred target sites are shown in Table 5. Moreover, nucleotides 2860 to 2990 of SEQ ID NO: 11 form a region wherein the screened oligonucleotides inhibited expression of PTPR.alpha. by an average of about 70%, and thus is designated as an active target segment (active target segment E).

TABLE 5

Sequence and position of preferred
target sites identified in PTPR.alpha..

| SITEID | TARGET SEQ ID NO | TARGET SITE | SEQUENCE | REV COMP OF SEQ ID | ACTIVE IN | SEQ ID NO |
|---|---|---|---|---|---|---|
| 62483 | 27 | 101612 | ttctctttctgtggcaccaa | 28 | H. sapiens | 151 |
| 62484 | 27 | 101621 | tgtggcaccaacattcagcc | 29 | H. sapiens | 152 |
| 62488 | 27 | 123433 | attgcggtgatggtggccct | 30 | H. sapiens | 153 |
| 62490 | 27 | 123448 | gccctgtcctctctgctagt | 31 | H. sapiens | 154 |
| 62491 | 4 | 706 | tgtacatgttaaggtttaag | 32 | H. sapiens | 155 |
| 62496 | 27 | 141723 | gtcctatccaggccacctgt | 33 | H. sapiens | 156 |
| 62497 | 27 | 141728 | atccaggccacctgtgaggc | 34 | H. sapiens | 157 |
| 62500 | 27 | 144039 | ccagattctgattacatcaa | 35 | H. sapiens | 158 |
| 62503 | 27 | 158044 | ctggtggactacacagtacg | 36 | H. sapiens | 159 |
| 62504 | 4 | 1338 | ttctgcatccagcaggtggg | 37 | H. sapiens | 160 |
| 62506 | 27 | 158737 | gcgcctcatcactcagttcc | 38 | H. sapiens | 161 |
| 62507 | 27 | 158815 | cctcaagaaggtgaaggcct | 39 | H. sapiens | 162 |

TABLE 5-continued

Sequence and position of preferred
target sites identified in PTPR.alpha..

| SITEID | TARGET SEQ ID NO | TARGET SITE SEQUENCE | REV COMP OF SEQ ID | ACTIVE IN | SEQ ID NO |
|---|---|---|---|---|---|
| 62511 | 27 | 161150 gcccttctggagcattatct | 40 | H. sapiens | 163 |
| 62513 | 27 | 163359 atccagaatgacaagatgcg | 41 | H. sapiens | 164 |
| 62514 | 27 | 163783 aacagagtgatcattccagt | 42 | H. sapiens | 165 |
| 62516 | 27 | 164391 agccagggccctcttctcca | 43 | H. sapiens | 166 |
| 62517 | 27 | 164429 gcgaatgatctgggagtgga | 44 | H. sapiens | 167 |
| 62518 | 4 | 2104 gaggccaggagaagtgtgcc | 45 | H. sapiens | 168 |
| 62519 | 27 | 172236 caggagaagtgtgcccagta | 46 | H. sapiens | 169 |
| 62520 | 27 | 172246 gtgcccagtactggccatct | 47 | H. sapiens | 170 |
| 62522 | 27 | 172302 ctgaagaaggaggaggaatg | 48 | H. sapiens | 171 |
| 62523 | 27 | 172336 tccgagacctcctggtcacc | 49 | H. sapiens | 172 |
| 62524 | 27 | 172341 gacctcctggtcaccaacac | 50 | H. sapiens | 173 |
| 62525 | 4 | 2223 gtcaccaacaccagggagaa | 51 | H. sapiens | 174 |
| 62526 | 27 | 172462 atccggcagttccacttcca | 52 | H. sapiens | 175 |
| 62527 | 27 | 173896 actgtcaagagcctgcggct | 53 | H. sapiens | 176 |
| 62529 | 27 | 174766 agattatgccaacttcaagt | 54 | H. sapiens | 177 |
| 62532 | 27 | 174875 atcttataactgttttagaa | 55 | H. sapiens | 178 |
| 62541 | 27 | 175134 cacaaagttctcagagctct | 57 | H. sapiens | 179 |
| 112597 | 18 | 685 agctaacaagcatggattcc | 60 | H. sapiens | 180 |
| 112598 | 18 | 716 tgttctgctcggcagtggtc | 61 | H. sapiens | 181 |
| 112599 | 18 | 1063 ggaattccagcaccgcagca | 62 | H. sapiens | 182 |
| 112600 | 18 | 2026 caggtgtagggcgtacaggt | 63 | H. sapiens | 183 |
| 112601 | 18 | 3094 acttcaagtaagcggcaaca | 64 | H. sapiens | 184 |
| 112602 | 18 | 3338 aaatcctcagccgagaaatt | 65 | H. sapiens | 185 |
| 112604 | 19 | 11234 gcccgactctgtgagtgttc | 67 | H. sapiens | 186 |
| 112606 | 19 | 60678 tttgttgcaggtgacacaac | 69 | H. sapiens | 187 |
| 112607 | 19 | 85496 aaagaagctagtaagtactg | 70 | H. sapiens | 188 |
| 112608 | 19 | 93080 ggtgttctaggacttcttca | 71 | H. sapiens | 189 |
| 112609 | 19 | 101743 tattttccagataagcatgg | 72 | H. sapiens | 190 |
| 112610 | 19 | 124321 acatgttaaggtgagcctac | 73 | H. sapiens | 191 |
| 112611 | 19 | 125366 cagggtgtgcatgacctgtc | 74 | H. sapiens | 192 |
| 112612 | 19 | 125503 ttctcattaggtttaagaaa | 75 | H. sapiens | 193 |
| 112613 | 19 | 125577 gaggatgtgggtaaggcatt | 76 | H. sapiens | 194 |
| 112614 | 19 | 127990 aggagttcgaaaccagcctg | 77 | H. sapiens | 195 |
| 112615 | 19 | 132617 gaaaagaaatttggctttaa | 78 | H. sapiens | 196 |
| 112616 | 19 | 151456 gaagcactttgggctgggc | 79 | H. sapiens | 197 |
| 112618 | 20 | 592 cctccttcagatgagacacc | 81 | H. sapiens | 198 |

TABLE 5-continued

Sequence and position of preferred
target sites identified in PTPR.alpha..

| SITEID | TARGET SEQ ID NO | TARGET SITE | SEQUENCE | REV COMP OF SEQ ID | ACTIVE IN | SEQ ID NO |
|---|---|---|---|---|---|---|
| 112627 | 25 | 115 | cccaccactgatatcatggg | 90 | H. sapiens | 199 |
| 112629 | 26 | 197 | gcactgaggatgtggagccc | 92 | H. sapiens | 200 |
| 62481 | 11 | 17 | tcggtcagcatggattcctg | 103 | M. musculus | 201 |
| 62486 | 11 | 407 | gcagcaaccactccagaaac | 106 | M. musculus | 202 |
| 62489 | 11 | 460 | ggtgatggtggccctgtcct | 108 | M. musculus | 203 |
| 62493 | 11 | 531 | agaaatacaagcaagctggg | 110 | M. musculus | 204 |
| 62494 | 11 | 665 | gtggacaagctggaagagga | 111 | M. musculus | 205 |
| 62495 | 11 | 735 | acgctctccctgcttgtcct | 112 | N. musculus | 206 |
| 62502 | 11 | 1177 | aggctgctggacctatggga | 116 | M. musculus | 207 |
| 62505 | 11 | 1258 | catccagcaggtgggcgacg | 117 | M. musculus | 208 |
| 62508 | 11 | 1385 | gtgaaggcctgtaaccctca | 118 | M. musculus | 209 |
| 62509 | 11 | 1489 | gatgcattcggaacgcaaag | 119 | M. musculus | 210 |
| 62515 | 11 | 1903 | gaaagactcctacattgcca | 122 | M. musculus | 211 |
| 62530 | 11 | 2504 | aacttcaagtgacaggtgac | 125 | M. musculus | 212 |
| 62533 | 11 | 2606 | taactgttttagaaatggca | 127 | M. musculus | 213 |
| 62534 | 11 | 2627 | ataggcttctattacctgtt | 128 | M. musculus | 214 |
| 62536 | 11 | 2670 | gtgttagcactgatagtcct | 129 | M. musculus | 215 |
| 62537 | 11 | 2763 | tgggccagattgttccttgc | 130 | M. musculus | 216 |
| 62542 | 11 | 2860 | agttctcagagctcttgagg | 134 | M. musculus | 217 |
| 62543 | 11 | 2867 | agagctcttgaggaaatggt | 135 | M. musculus | 218 |
| 62544 | 11 | 2971 | aagatcagccacctcaggca | 136 | M. musculus | 219 |
| 62545 | 11 | 3024 | accacagcagggatcgtcag | 137 | M. musculus | 220 |
| 62547 | 93 | 28 | acagggactcgcggggcat | 139 | M. musculus | 221 |
| 62553 | 98 | 136 | gagaggccaggtgagttcaa | 145 | M. musculus | 222 |
| 62556 | 101 | 138 | cttgggcagagcagtcttat | 148 | M. musculus | 223 |
| 62557 | 101 | 167 | gctctcctggttgttccta | 149 | M. musculus | 224 |

As these "preferred target regions" have been found by experimentation to be open to, and accessible for, hybridization with the antisense compounds, one of skill in the art will recognize or be able to ascertain, using no more than routine experimentation, further embodiments encompassing other compounds that specifically hybridize to these sites and consequently inhibit the expression of PTPR.alpha.

In one embodiment, the "preferred target region" may be employed in screening candidate antisense compounds. "Candidate antisense compounds" are those that inhibit the expression of a nucleic acid molecule encoding PTPR.alpha. and which comprise at least an 8-nucleobase portion which is complementary to a preferred target region. The method comprises the steps of contacting a preferred target region of a nucleic acid molecule encoding PTPR.alpha. with one or more candidate antisense compounds, and selecting for one or more candidate antisense compounds which inhibit the expression of a nucleic acid molecule encoding PTPR.alpha. Once it is shown that the candidate antisense compound or compounds are capable of inhibiting the expression of a nucleic acid molecule encoding PTPR.alpha., the candidate antisense compound may be employed as an antisense compound as described herein.

Accordingly, antisense compounds include ribozymes, external guide sequence (EGS) oligonucleotides (oligozymes), and other short catalytic RNAs or catalytic oligonucleotides which hybridize to the target nucleic acid and modulate its expression.

EXAMPLE 5

Targeting of Individual Oligonucleotides to Specific Variants of Human PTPR.alpha.

In some instances it is advantageous to selectively inhibit the expression of one or more variants of PTPR.alpha. Consequently, there are provided oligonucleotides that selectively target, hybridize to, and specifically inhibit one or more, but fewer than all of the variants of human PTPR.alpha. A summary of the target sites of the PTPR.alpha. main mRNA and variants is shown in Table 6 and includes GenBank accession number NM_080841.1, representing hPTPRA-3, incorporated herein as SEQ ID NO: 4; GenBank accession number M34668.1, representing hPTPR.alpha. main mRNA, incorporated herein as SEQ ID NO: 18; GenBank accession number X54890.1, representing hPTPRA-4, incorporated herein as SEQ ID NO: 20; GenBank accession number X53364.1, representing hPTPRA-5, incorporated herein as SEQ ID NO: 21; the complement of GenBank accession number AI674319.1, representing hPTPRA-7, incorporated herein as SEQ ID NO: 26; GenBank accession number NM_002836.1 (entered Mar. 24, 1999), representing hPTPRA-1, incorporated herein as SEQ ID NO: 225; GenBank accession number NM_080840.1 (entered Jan. 31, 2002), representing hPTPRA-2, incorporated herein as SEQ ID NO: 226; and GenBank accession number X54130.1 (entered Apr. 21, 1993), representing hPTPRA-6, incorporated herein as SEQ ID NO: 227.

TABLE 6

Targeting of individual oligonucleotides to specific variants of human PTPR.alpha.

| ISIS # | OLIGO SEQ ID NO. | TARGET SITE | VARIANT | VARIANT SEQ ID NO. |
|---|---|---|---|---|
| 147239 | 28 | 389 | hPTPRA-3 | 4 |
| 147239 | 28 | 866 | hPTPRA | 18 |
| 147239 | 28 | 357 | hPTPRA-4 | 20 |
| 147239 | 28 | 349 | hPTPR-5 | 21 |
| 147239 | 28 | 857 | hPTPRA-1 | 225 |
| 147239 | 28 | 520 | hPTPRA-2 | 226 |
| 147239 | 28 | 201 | hPTPRA-6 | 227 |
| 147240 | 29 | 398 | hPTPRA-3 | 4 |
| 147240 | 29 | 875 | hPTPRA | 18 |
| 147240 | 29 | 366 | hPTPRA-4 | 20 |
| 147240 | 29 | 358 | hPTPR-5 | 21 |
| 147240 | 29 | 866 | hPTPRA-1 | 225 |
| 147240 | 29 | 529 | hPTPRA-2 | 226 |
| 147240 | 29 | 210 | hPTPRA-6 | 227 |
| 147244 | 30 | 648 | hPTPRA-3 | 4 |
| 147244 | 30 | 1152 | hPTPRA | 18 |
| 147244 | 30 | 616 | hPTPRA-4 | 20 |
| 147244 | 30 | 608 | hPTPR-5 | 21 |
| 147244 | 30 | 1143 | hPTPRA-1 | 225 |
| 147244 | 30 | 779 | hPTPRA-2 | 226 |
| 147244 | 30 | 460 | hPTPRA-6 | 227 |
| 147246 | 31 | 663 | hPTPRA-3 | 4 |
| 147246 | 31 | 1167 | hPTPRA | 18 |
| 147246 | 31 | 631 | hPTPRA-4 | 20 |
| 147246 | 31 | 623 | hPTPR-5 | 21 |
| 147246 | 31 | 1158 | hPTPRA-1 | 225 |
| 147246 | 31 | 794 | hPTPRA-2 | 226 |
| 147246 | 31 | 475 | hPTPRA-6 | 227 |
| 147247 | 32 | 706 | hPTPRA-3 | 4 |
| 147247 | 32 | 1210 | hPTPRA | 18 |
| 147247 | 32 | 674 | hPTPRA-4 | 20 |
| 147247 | 32 | 666 | hPTPR-5 | 21 |
| 147247 | 32 | 1201 | hPTPRA-1 | 225 |
| 147247 | 32 | 837 | hPTPRA-2 | 226 |
| 147247 | 32 | 518 | hPTPRA-6 | 227 |
| 147259 | 36 | 1818 | hPTPRA | 18 |
| 147259 | 36 | 1282 | hPTPRA-4 | 20 |
| 147259 | 36 | 1274 | hPTPR-5 | 21 |
| 147259 | 36 | 1809 | hPTPRA-1 | 225 |
| 147259 | 36 | 1445 | hPTPRA-2 | 226 |
| 147259 | 36 | 1126 | hPTPRA-6 | 227 |
| 147260 | 37 | 1338 | hPTPRA-3 | 4 |
| 147260 | 37 | 1842 | hPTPRA | 18 |
| 147260 | 37 | 1306 | hPTPRA-4 | 20 |
| 147260 | 37 | 1298 | hPTPR-5 | 21 |
| 147260 | 37 | 1833 | hPTPRA-1 | 225 |
| 147260 | 37 | 1469 | hPTPRA-2 | 226 |
| 147260 | 37 | 1150 | hPTPRA-6 | 227 |
| 147262 | 38 | 1382 | hPTPRA-3 | 4 |
| 147262 | 38 | 1886 | hPTPRA | 18 |
| 147262 | 38 | 1350 | hPTPRA-4 | 20 |
| 147262 | 38 | 1342 | hPTPR-5 | 21 |
| 147262 | 38 | 1877 | hPTPRA-1 | 225 |
| 147262 | 38 | 1513 | hPTPRA-2 | 226 |
| 147262 | 38 | 1194 | hPTPRA-6 | 227 |
| 147263 | 39 | 1460 | hPTPRA-3 | 4 |
| 147263 | 39 | 1964 | hPTPRA | 18 |
| 147263 | 39 | 1428 | hPTPRA-4 | 20 |
| 147263 | 39 | 1420 | hPTPR-5 | 21 |
| 147263 | 39 | 1955 | hPTPRA-1 | 225 |
| 147263 | 39 | 1591 | hPTPRA-2 | 226 |
| 147263 | 39 | 1272 | hPTPRA-6 | 227 |
| 147267 | 40 | 1680 | hPTPRA-3 | 4 |
| 147267 | 40 | 2184 | hPTPRA | 18 |
| 147267 | 40 | 1648 | hPTPRA-4 | 20 |
| 147267 | 40 | 1640 | hPTPR-5 | 21 |
| 147267 | 40 | 2175 | hPTPRA-1 | 225 |
| 147267 | 40 | 1811 | hPTPRA-2 | 226 |
| 147267 | 40 | 1492 | hPTPRA-6 | 227 |
| 147269 | 41 | 1824 | hPTPRA-3 | 4 |
| 147269 | 41 | 2328 | hPTPRA | 18 |
| 147269 | 41 | 1792 | hPTPRA-4 | 20 |
| 147269 | 41 | 1784 | hPTPR-5 | 21 |
| 147269 | 41 | 2319 | hPTPRA-1 | 225 |
| 147269 | 41 | 1955 | hPTPRA-2 | 226 |
| 147269 | 41 | 1636 | hPTPRA-6 | 227 |
| 147270 | 42 | 1908 | hPTPRA-3 | 4 |
| 147270 | 42 | 2412 | hPTPRA | 18 |
| 147270 | 42 | 1876 | hPTPRA-4 | 20 |
| 147270 | 42 | 1868 | hPTPR-5 | 21 |
| 147270 | 42 | 2403 | hPTPRA-1 | 225 |
| 147270 | 42 | 2039 | hPTPRA-2 | 226 |
| 147270 | 42 | 1720 | hPTPRA-6 | 227 |
| 147272 | 43 | 2007 | hPTPRA-3 | 4 |
| 147272 | 43 | 2511 | hPTPRA | 18 |
| 147272 | 43 | 1975 | hPTPRA-4 | 20 |
| 147272 | 43 | 1967 | hPTPR-5 | 21 |
| 147272 | 43 | 2502 | hPTPRA-1 | 225 |
| 147272 | 43 | 2138 | hPTPRA-2 | 226 |
| 147272 | 43 | 1819 | hPTPRA-6 | 227 |
| 147273 | 44 | 2045 | hPTPRA-3 | 4 |
| 147273 | 44 | 2549 | hPTPRA | 18 |
| 147273 | 44 | 2013 | hPTPRA-4 | 20 |
| 147273 | 44 | 2005 | hPTPR-5 | 21 |
| 147273 | 44 | 2540 | hPTPRA-1 | 225 |
| 147273 | 44 | 2176 | hPTPRA-2 | 226 |
| 147273 | 44 | 1857 | hPTPRA-6 | 227 |
| 147274 | 45 | 2104 | hPTPRA-3 | 4 |
| 147274 | 45 | 2608 | hPTPRA | 18 |
| 147274 | 45 | 2072 | hPTPRA-4 | 20 |
| 147274 | 45 | 2064 | hPTPR-5 | 21 |
| 147274 | 45 | 2599 | hPTPRA-1 | 225 |
| 147274 | 45 | 2235 | hPTPRA-2 | 226 |
| 147274 | 45 | 1916 | hPTPRA-6 | 227 |
| 147275 | 46 | 2109 | hPTPRA-3 | 4 |
| 147275 | 46 | 2613 | hPTPRA | 18 |
| 147275 | 46 | 2077 | hPTPRA-4 | 20 |
| 147275 | 46 | 2069 | hPTPR-5 | 21 |
| 147275 | 46 | 2604 | hPTPRA-1 | 225 |
| 147275 | 46 | 2240 | hPTPRA-2 | 226 |

TABLE 6-continued

Targeting of individual oligonucleotides to specific variants of human PTPR.alpha.

| ISIS # | OLIGO SEQ ID NO. | TARGET SITE | VARIANT | VARIANT SEQ ID NO. |
|---|---|---|---|---|
| 147275 | 46 | 1921 | hPTPRA-6 | 227 |
| 147276 | 47 | 2119 | hPTPRA-3 | 4 |
| 147276 | 47 | 2623 | hPTPRA | 18 |
| 147276 | 47 | 2087 | hPTPRA-4 | 20 |
| 147276 | 47 | 2079 | hPTPR-5 | 21 |
| 147276 | 47 | 2614 | hPTPRA-1 | 225 |
| 147276 | 47 | 2250 | hPTPRA-2 | 226 |
| 147276 | 47 | 1931 | hPTPRA-6 | 227 |
| 147278 | 48 | 2175 | hPTPRA-3 | 4 |
| 147278 | 48 | 2679 | hPTPRA | 18 |
| 147278 | 48 | 2143 | hPTPRA-4 | 20 |
| 147278 | 48 | 2135 | hPTPR-5 | 21 |
| 147278 | 48 | 2670 | hPTPRA-1 | 225 |
| 147278 | 48 | 2306 | hPTPRA-2 | 226 |
| 147278 | 48 | 1987 | hPTPRA-6 | 227 |
| 147279 | 49 | 2209 | hPTPRA-3 | 4 |
| 147279 | 49 | 2713 | hPTPRA | 18 |
| 147279 | 49 | 2177 | hPTPRA-4 | 20 |
| 147279 | 49 | 2169 | hPTPR-5 | 21 |
| 147279 | 49 | 2704 | hPTPRA-1 | 225 |
| 147279 | 49 | 2340 | hPTPRA-2 | 226 |
| 147279 | 49 | 2021 | hPTPRA-6 | 227 |
| 147280 | 50 | 2214 | hPTPRA-3 | 4 |
| 147280 | 50 | 2718 | hPTPRA | 18 |
| 147280 | 50 | 2182 | hPTPRA-4 | 20 |
| 147280 | 50 | 2174 | hPTPR-5 | 21 |
| 147280 | 50 | 2709 | hPTPRA-1 | 225 |
| 147280 | 50 | 2345 | hPTPRA-2 | 226 |
| 147280 | 50 | 2026 | hPTPRA-6 | 227 |
| 147281 | 51 | 2223 | hPTPRA-3 | 4 |
| 147281 | 51 | 2727 | hPTPRA | 18 |
| 147281 | 51 | 2191 | hPTPRA-4 | 20 |
| 147281 | 51 | 2183 | hPTPR-5 | 21 |
| 147281 | 51 | 2718 | hPTPRA-1 | 225 |
| 147281 | 51 | 2354 | hPTPRA-2 | 226 |
| 147281 | 51 | 2035 | hPTPRA-6 | 227 |
| 147282 | 52 | 2256 | hPTPRA-3 | 4 |
| 147282 | 52 | 2760 | hPTPRA | 18 |
| 147282 | 52 | 2224 | hPTPRA-4 | 20 |
| 147282 | 52 | 2216 | hPTPR-5 | 21 |
| 147282 | 52 | 2751 | hPTPRA-1 | 225 |
| 147282 | 52 | 2387 | hPTPRA-2 | 226 |
| 147282 | 52 | 2068 | hPTPRA-6 | 227 |
| 147283 | 53 | 2478 | hPTPRA-3 | 4 |
| 147283 | 53 | 2982 | hPTPRA | 18 |
| 147283 | 53 | 2446 | hPTPRA-4 | 20 |
| 147283 | 53 | 2438 | hPTPR-5 | 21 |
| 147283 | 53 | 2973 | hPTPRA-1 | 225 |
| 147283 | 53 | 2609 | hPTPRA-2 | 226 |
| 147283 | 53 | 2290 | hPTPRA-6 | 227 |
| 147285 | 54 | 2579 | hPTPRA-3 | 4 |
| 147285 | 54 | 3083 | hPTPRA | 18 |
| 147285 | 54 | 2547 | hPTPRA-4 | 20 |
| 147285 | 54 | 2539 | hPTPR-5 | 21 |
| 147285 | 54 | 3074 | hPTPRA-1 | 225 |
| 147285 | 54 | 2710 | hPTPRA-2 | 226 |
| 147285 | 60 | 2391 | hPTPRA-6 | 227 |
| 147288 | 55 | 2688 | hPTPRA-3 | 4 |
| 147288 | 55 | 3192 | hPTPRA | 18 |
| 147288 | 55 | 2655 | hPTPRA-4 | 20 |
| 147288 | 55 | 3183 | hPTPRA-1 | 225 |
| 147288 | 55 | 2819 | hPTPRA-2 | 226 |
| 147291 | 56 | 2750 | hPTPRA-3 | 4 |
| 147291 | 56 | 3254 | hPTPRA | 18 |
| 147291 | 56 | 2717 | hPTPRA-4 | 20 |
| 147291 | 56 | 3245 | hPTPRA-1 | 225 |
| 147291 | 56 | 2881 | hPTPRA-2 | 226 |
| 147297 | 57 | 2947 | hPTPRA-3 | 4 |
| 147297 | 57 | 3451 | hPTPRA | 18 |
| 147297 | 57 | 3442 | hPTPRA-1 | 225 |
| 147297 | 57 | 3078 | hPTPRA-2 | 226 |
| 194483 | 58 | 20 | hPTPRA | 18 |
| 194484 | 59 | 470 | hPTPRA | 18 |
| 194484 | 59 | 461 | hPTPRA-1 | 225 |
| 194485 | 60 | 685 | hPTPRA | 18 |
| 194486 | 61 | 239 | hPTPRA-3 | 4 |
| 194486 | 61 | 716 | hPTPRA | 18 |
| 194486 | 61 | 207 | hPTPRA-4 | 20 |
| 194486 | 61 | 199 | hPTPR-5 | 21 |
| 194486 | 61 | 707 | hPTPRA-1 | 225 |
| 194486 | 61 | 370 | hPTPRA-2 | 226 |
| 194486 | 61 | 51 | hPTPRA-6 | 227 |
| 194487 | 62 | 586 | hPTPRA-3 | 4 |
| 194487 | 62 | 1063 | hPTPRA | 18 |
| 194487 | 62 | 554 | hPTPRA-4 | 20 |
| 194487 | 62 | 546 | hPTPR-5 | 21 |
| 194487 | 62 | 1054 | hPTPRA-1 | 225 |
| 194487 | 62 | 717 | hPTPRA-2 | 226 |
| 194487 | 62 | 398 | hPTPRA-6 | 227 |
| 194488 | 63 | 1522 | hPTPRA-3 | 4 |
| 194488 | 63 | 2026 | hPTPRA | 18 |
| 194488 | 63 | 1490 | hPTPRA-4 | 20 |
| 194488 | 63 | 1482 | hPTPR-5 | 21 |
| 194488 | 63 | 2017 | hPTPRA-1 | 225 |
| 194488 | 63 | 1653 | hPTPRA-2 | 226 |
| 194488 | 63 | 1334 | hPTPRA-6 | 227 |
| 194489 | 64 | 2590 | hPTPRA-3 | 4 |
| 194489 | 64 | 3094 | hPTPRA | 18 |
| 194489 | 64 | 2558 | hPTPRA-4 | 20 |
| 194489 | 64 | 3085 | hPTPRA-1 | 225 |
| 194489 | 64 | 2721 | hPTPRA-2 | 226 |
| 194489 | 64 | 2402 | hPTPRA-6 | 227 |
| 194490 | 65 | 2834 | hPTPRA-3 | 4 |
| 194490 | 65 | 3338 | hPTPRA | 18 |
| 194490 | 65 | 3329 | hPTPRA-1 | 225 |
| 194490 | 65 | 2965 | hPTPRA-2 | 226 |
| 194500 | 75 | 128 | hPTPRA-7 | 26 |
| 194505 | 80 | 49 | hPTPRA-4 | 20 |
| 194505 | 80 | 212 | hPTPRA-2 | 226 |
| 194506 | 81 | 624 | hPTPRA-3 | 4 |
| 194506 | 81 | 592 | hPTPRA-4 | 20 |
| 194506 | 81 | 584 | hPTPR-5 | 21 |
| 194506 | 81 | 755 | hPTPRA-2 | 226 |
| 194506 | 81 | 436 | hPTPRA-6 | 227 |
| 194507 | 82 | 113 | hPTPRA-3 | 4 |
| 194507 | 82 | 73 | hPTPR-5 | 21 |
| 194508 | 83 | 205 | hPTPRA-3 | 4 |
| 194508 | 83 | 165 | hPTPR-5 | 21 |
| 194514 | 89 | 64 | hPTPRA-2 | 226 |
| 194515 | 90 | 3043 | hPTPRA-3 | 4 |
| 194515 | 90 | 3547 | hPTPRA | 18 |
| 194515 | 90 | 3538 | hPTPRA-1 | 225 |
| 194515 | 90 | 3174 | hPTPRA-2 | 226 |
| 194517 | 92 | 778 | hPTPRA-3 | 4 |
| 194517 | 92 | 1282 | hPTPRA | 18 |
| 194517 | 92 | 738 | hPTPR-5 | 21 |
| 194517 | 92 | 197 | hPTPRA-7 | 26 |
| 194517 | 92 | 1273 | hPTPRA-1 | 225 |
| 194517 | 92 | 909 | hPTPRA-2 | 226 |
| 194517 | 92 | 590 | hPTPRA-6 | 227 |

Human PTPR.alpha. mRNA sequences from Table 1 were aligned and the screened human oligos were determined to have a complementary sequence to a common PTPR.alpha. mRNA, specifically (SEQ ID NO: 18). Antisense compounds targeting SEQ ID NO: 18 are shown in Table 6b. The antisense compounds were then grouped according to activity and active target segments were determined. An active target segment is used herein to describe a region of the PTPR.alpha. mRNA that has one or more active antisense compounds targeted thereto. Each of the following active target segment was targeted by multiple, active antisense oligonucleotides. These regions include nucleotides 716 to 894, nucleotides 1063 to 1229, nucleotides 1818 to 2045 and nucleotides 2328 to 2779 of SEQ ID NO: 18. Each of the oligonucleotides tested within each of these regions inhibited expression of human PTPR.alpha. by at least 60% in this assay. In active target segment A (nucleotides 716 to 894) the screened oligonucleotides inhibited expression of PTPR.alpha. by an average of about 85%. In active target segment B (nucleotides 1063 to 1229) the screened oligonucleotides inhibited expression of PTPR.alpha. by an average of about 75%. In active target segment C (nucleotides 1818 to 2045) the screened oligonucleotides inhibited expression of PTPR.alpha. by an average of about 90%. In active target segment D (nucleotides 2328 to 2779) the screened oligonucleotides inhibited expression of PTPR.alpha. by an average of about 80%. In active target segment F (nucleotides 1210-1905) the screened oligonucleotides inhibited expression of PTPR.alpha. by an average of about 87%. In active target segment G (nucleotides 2982-3211) the screened oligonucleotides inhibited expression of PTPR.alpha. by an average of about 73%. Identification of these regions allows for the design of antisense oligonucleotides that modulate the expression of PTPR.alpha.

TABLE 6b

Exemplary human PTPR.alpha. oligos targeting SEQ ID NO: 18

| ISIS No: | Target Site | Start Codon | Stop Codon | Length | Oligo SEQ ID NO: |
|---|---|---|---|---|---|
| 194483 | 112595 | 20 | 39 | 20 | 58 |
| 194484 | 112596 | 470 | 489 | 20 | 59 |
| 194485 | 112597 | 685 | 704 | 20 | 60 |
| 194486 | 112598 | 716 | 735 | 20 | 61 |
| 147239 | 62483 | 866 | 885 | 20 | 28 |
| 147240 | 62484 | 875 | 894 | 20 | 29 |
| 194487 | 112599 | 1063 | 1082 | 20 | 62 |
| 147244 | 62488 | 1152 | 1171 | 20 | 30 |
| 147246 | 62490 | 1167 | 1186 | 20 | 31 |
| 147247 | 62491 | 1210 | 1229 | 20 | 32 |
| 147252 | 62496 | 1447 | 1466 | 20 | 33 |
| 147253 | 62497 | 1452 | 1471 | 20 | 34 |
| 147256 | 62500 | 1566 | 1585 | 20 | 35 |
| 147259 | 62503 | 1818 | 1837 | 20 | 36 |
| 147260 | 62504 | 1842 | 1861 | 20 | 37 |
| 147262 | 62506 | 1886 | 1905 | 20 | 38 |
| 147263 | 62507 | 1964 | 1983 | 20 | 39 |
| 194488 | 112600 | 2026 | 2045 | 20 | 63 |
| 147267 | 62511 | 2184 | 2203 | 20 | 40 |
| 147269 | 62513 | 2328 | 2347 | 20 | 41 |
| 147270 | 62514 | 2412 | 2431 | 20 | 42 |
| 147272 | 62516 | 2511 | 2530 | 20 | 43 |
| 147273 | 62517 | 2549 | 2568 | 20 | 44 |
| 147274 | 62518 | 2608 | 2627 | 20 | 45 |
| 147275 | 62519 | 2613 | 2632 | 20 | 46 |
| 147276 | 62520 | 2623 | 2642 | 20 | 47 |
| 147278 | 62522 | 2679 | 2698 | 20 | 48 |
| 147279 | 62523 | 2713 | 2732 | 20 | 49 |
| 147280 | 62524 | 2718 | 2737 | 20 | 50 |
| 147281 | 62525 | 2727 | 2746 | 20 | 51 |
| 147282 | 62526 | 2760 | 2779 | 20 | 52 |
| 147283 | 62527 | 2982 | 3001 | 20 | 53 |
| 147285 | 62529 | 3083 | 3102 | 20 | 54 |
| 194489 | 112601 | 3094 | 3113 | 20 | 64 |
| 147288 | 62532 | 3192 | 3211 | 20 | 55 |
| 147291 | 62535 | 3254 | 3273 | 20 | 56 |
| 194490 | 112602 | 3338 | 3357 | 20 | 65 |
| 147297 | 62541 | 3451 | 3470 | 20 | 57 |

EXAMPLE 6

Targeting of Individual Oligonucleotides to Specific Variants of Mouse PTPR.alpha.

It is advantageous to selectively inhibit the expression of one or more variants of PTPR.alpha. Oligonucleotides are provided that selectively target, hybridize to, and specifically inhibit one or more, but fewer than all of the variants of mouse PTPR.alpha. A summary of the target sites of the PTPR.alpha. main mRNA and variants is shown in Table 7 and includes GenBank accession number NM_008980.1, representing mPTPRA-2, incorporated herein as SEQ ID NO: 11 and GenBank accession number BE372094.1, representing mPTPR.alpha. main mRNA, incorporated herein as SEQ ID NO: 102.

TABLE 7

Targeting of individual oligonucleotides to specific variants of mouse PTPR.alpha.

| ISIS # | OLIGO SEQ ID NO. | TARGET SITE | VARIANT | VARIANT SEQ ID NO. |
|---|---|---|---|---|
| 147237 | 103 | 17 | mPTPRA-2 | 11 |
| 147238 | 104 | 25 | mPTPRA-2 | 11 |
| 147254 | 113 | 876 | mPTPRA-2 | 11 |
| 147255 | 114 | 926 | mPTPRA-2 | 11 |
| 147257 | 115 | 1040 | mPTPRA-2 | 11 |
| 147258 | 116 | 1177 | mPTPRA-2 | 11 |
| 147261 | 117 | 1258 | mPTPRA-2 | 11 |
| 147264 | 118 | 1385 | mPTPRA-2 | 11 |
| 147265 | 119 | 1489 | mPTPRA-2 | 11 |
| 147266 | 120 | 1523 | mPTPRA-2 | 11 |
| 147268 | 121 | 1711 | mPTPRA-2 | 11 |
| 147271 | 122 | 1903 | mPTPRA-2 | 11 |
| 147277 | 123 | 2039 | mPTPRA-2 | 11 |
| 147284 | 124 | 2430 | mPTPRA-2 | 11 |
| 147286 | 125 | 2504 | mPTPRA-2 | 11 |
| 147287 | 126 | 2585 | mPTPRA-2 | 11 |
| 147289 | 127 | 2606 | mPTPRA-2 | 11 |
| 147290 | 128 | 2627 | mPTPRA-2 | 11 |
| 147292 | 129 | 2670 | mPTPRA-2 | 11 |
| 147293 | 130 | 2763 | mPTPRA-2 | 11 |
| 147294 | 131 | 2788 | mPTPRA-2 | 11 |
| 147295 | 132 | 2805 | mPTPRA-2 | 11 |
| 147296 | 133 | 2830 | mPTPRA-2 | 11 |
| 147298 | 134 | 2860 | mPTPRA-2 | 11 |
| 147299 | 135 | 2867 | mPTPRA-2 | 11 |
| 147300 | 136 | 2971 | mPTPRA-2 | 11 |
| 147301 | 137 | 3024 | mPTPRA-2 | 11 |
| 147302 | 138 | 3039 | mPTPRA-2 | 11 |
| 147314 | 150 | 633 | mPTPRA | 102 |

EXAMPLE 7

Effect of Antisense Inhibitors of PTPR.alpha. in ob/ob Mice: a Model of Obesity and Diabetes ob/ob mice are used as a model of obesity and of type-2 diabetes. These mice have a deficiency in the Leptin hormone produced by fat that regulates appetite. Deficiencies in this hormone in both humans and non-human animals lead to obesity. The ob/ob mice have a mutation in the leptin gene which results in obesity and hyperglycemia. ob/ob mice have higher circulating levels of insulin and are less hyperglycemic than db/db mice, which harbor a mutation in the leptin receptor. ISIS 147299 (SEQ ID NO: 135) was tested in the ob/ob model of obesity and diabetes.

Male C57B1/6J-Lep ob/ob mice (Jackson Laboratory, Bar Harbor, Me.) were fed a diet with a fat content of 10-15% and were subcutaneously injected with ISIS 147299 at a dose of 25 mg/kg two times per week for 4 weeks. The mice received a final dose at 12.5 mg/kg at day 30. Saline-injected animals served as controls. After the treatment period, mice were sacrificed and target levels were evaluated in liver and fat. RNA isolation and target mRNA expression level quantitation were performed as described by other examples herein.

Animals treated with ISIS 147299 on average showed about a 75% reduction in liver PTPR.alpha. mRNA levels (n=5), and on average about a 50% reduction in fat PTPR.alpha. (n=5) compared to saline controls.

To assess the physiological effects resulting from inhibition of PTPR.alpha. mRNA, the ob/ob mice were further evaluated throughout the treatment period and at the end of the treatment period for body weight, percent fat from body weight, organ weight, chemistries, including serum transaminase, cholesterol, triglycerides and non-esterified fatty acids, liver triglycerides, plasma glucose levels, fed plasma insulin levels and glucose tolerance. Triglycerides, lipoproteins, cholesterol and transaminases were measured by routine clinical analyzer instruments (e.g. Olympus Clinical Analyzer, Melville, N.Y.). Serum free fatty acids were measured using a Wako Chemicals kit for non-esterified free fatty acids (Richmond, Va.). Serum apolipoproteins were measured using apolipoprotein-specific ELISA or by protein immunoblot with apolipoprotein-specific antibodies. Tissue triglyceride levels were measured using a Triglyceride GPO Assay from Roche Diagnostics (Indianapolis, Ind.). Liver triglyceride levels were used to assess hepatic steatosis, or clearing of lipids from the liver. Hepatic steatosis was also assessed by routine histological analysis of frozen liver tissue sections stained with oil red O stain.

The effects of target inhibition on glucose and insulin metabolism were evaluated in the ob/ob mice treated with the oligomeric compounds. Plasma glucose was measured at the start of the treatment and after 2 weeks, 3 weeks and 4.5 weeks of treatment. Mice were sacrificed at day 33 and plasma glucose was measured. (Table 8) Plasma insulin is similarly measured at the beginning of the treatment, and at 2 weeks, at 3 weeks and at 4.5 weeks of treatment. (Table 9)

TABLE 8

Fed Plasma Glucose Levels

| | Base Line | Wk 2 | Wk 3 | Week 4.5 Sacrifice |
|---|---|---|---|---|
| Saline (sem) | 406.6 mg/dl (24.29) | 419.9 mg/dl (23.60) | 394.0 mg/dl (36.00) | 516.4 mg/dl (42.37) |
| PTPR.alpha. antisense oligo (sem) | 403.3 mg/dl (25.85) | 376.7 mg/dl (24.80) | 330.0 mg/dl (19.49) | 295.7 mg/dl (22.17) |

TABLE 9

Fed Plasma Insulin Levels

| | Wk 0 | Wk 2 | Wk 3 | Wk 4.5 |
|---|---|---|---|---|
| Saline (sem) | 21.29 ng/ml (2.08) | 35.19 ng/ml (3.78) | 29.41 ng/ml (3.19) | 18.7 ng/ml (6.96) |
| PTPR.alpha. antisense oligo (sem) | 21.57 ng/ml (1.66) | 31.37 ng/ml (3.22) | 25.08 ng/ml (3.00) | 15.2 ng/ml (2.34) |

In ob/ob mice treated with ISIS 147299, fed plasma glucose levels were approximately 403.3 mg/dl at base line, 376.7 mg/dl at week 2, 330.0 mg/dl at week 3 and 295.7 mg/dl at sacrifice. Fed plasma insulin levels were approximately 21.57 ng/ml at baseline, 31.37 at week 2, 25.08 at week 3 and 15.2 at week 4.5. Compared to saline control animals, plasma glucose levels are reduced in animals following treatment with an antisense oligonucleotide that inhibit PTPR.alpha.

Plasma lipids in ob/ob mice were also measured throughout the treatment period and at the end of the treatment period. Table 10. Cholesterol levels were approximately 179.3 mg/dl at baseline, 240.3 mg/dl after 2 weeks, 242.9 mg.dl after 3 weeks and 247.3 mg/dl at sacrifice for the ice receiving an antisense inhibitor of PTPR.alpha. There was no significant change in plasma cholesterol levels for mice receiving an antisense inhibitor of PTPR.alpha. Triglycerides were approximately 165.7 mg/dl at base line, 107.9 mg/dl after 2 weeks, 87.4 mg/dl after 3 weeks and 88.9 mg/dl at sacrifice for ISIS 147299-treated mice. For mice receiving treatment with an antisense inhibitor of PTPR.alpha. there was a decrease in fed plasma triglyceride levels.

TABLE 10

Plasma Lipid Levels in ob/ob mice

| | Base Line | Wk 2 | Wk 3 | Wk 4.5 Sacrifice |
|---|---|---|---|---|
| Cholesterol (sem) | | | | |
| Saline | 174.6 mg/dL (4.40) | 209.7 mg/dL (9.28) | 218.3 mg/dL (8.86) | 258.0 mg/dL (5.07) |
| PTPR.alpha. antisense oligo | 179.3 mg/dL (4.19) | 240.3 mg/dL (6.01) | 242.9 mg/dL (7.48) | 247.3 mg/dL (10.87) |
| Triglycerides (sem) | | | | |
| Saline | 136.6 mg/dL (10.98) | 132.0 mg/dL (7.54) | 129.7 mg/dL (9.33) | 119.3 mg/dL (3.09) |
| PTPR.alpha. antisense oligo | 165.7 mg/dL (17.17) | 107.9 mg/dL (14.70) | 87.4 mg/dL (5.04) | 88.9 mg/dL (4.03) |

Treatment of the ob/ob mice with ISIS 147299 decreased hepatic triglyceride levels and improved hepatic function. Liver triglycerides were approximately 109.71 mg/g after 4.5 weeks of treatment. (Table 11) Oil Red-O staining of liver sections showed a marked clearing of lipid deposits for the treated group compared to control. (FIGS. 1a and 1b.) Plasma transaminase levels were reduced in the mice receiving treatment compared to those receiving saline. Plasma Alanine Aminotransferase (ALT) levels were approximately 86.3 IU/L at baseline, 244.1 after 2 weeks, 258.3 IU/l after 3 weeks and 137.7 IU/L at sacrifice for the treated group. Plasma Aspartate Aminotransferase (AST) levels were approximately 71.1 IU/L at base line, 128.4 IU/L after 2 weeks, 144.0 IU/L after 3 weeks and 134.4 IU/L at sacrifice following treatment. Fasted transaminase levels were determined after 4 weeks of treatment and were approximately 246.9 IU/L for ALT and 139.1 for AST. Table 12. These values show that treatment with an antisense inhibitor of PTPR.alpha. reduced hepatic and plasma triglyceride levels and improved hepatic function compared to the saline control group.

TABLE 11

Liver Triglyceride Levels

| | mg/g (sem) |
|---|---|
| Saline | 151.26 (11.11) |
| PTPR.alpha. antisense oligo | 109.71 (6.24) |

TABLE 12

Plasma Transaminase Levels

|  | Base Line | Wk 2 | Wk 3 | Wk 4 Fasted | Wk 4.5 Sacrifice |
|---|---|---|---|---|---|
| ALT (sem) | | | | | |
| Saline | 90.6 IU/L (6.51) | 147.6 IU/L (9.08) | 209.7 IU/L (14.71) | 189.7 IU/L (15.26) | 209.4 IU/L (20.65) |
| PTPR.alpha. antisense oligo | 86.3 IU/L (3.19) | 244.1 IU/L (23.14) | 258.3 IU/L (27.97) | 246.9 IU/L (26.73) | 137.7 IU/L (14.75) |
| AST (sem) | | | | | |
| Saline | 73.4 IU/L (4.50) | 112.3 IU/L (7.79) | 164.9 IU/L (11.63) | 176.3 IU/L (11.44) | 218.6 IU/L (26.21) |
| PTPR.alpha. antisense oligo | 71.1 IU/L (2.01) | 128.4 IU/L (11.65) | 144.0 IU/L (15.12) | 139.1 IU/L (16.14) | 134.4 IU/L (9.28) |

No changes in body weight, fat content, plasma cholesterol or plasma free fatty acid levels were observed for mice receiving treatment with ISIS 147299 compared to saline controls.

These results indicate that antisense inhibition of PTPR.alpha. expression improves plasma glucose levels, glucose tolerance and plasma and hepatic triglycerides levels in the ob/ob mouse model of diabetes and obesity. Consequently, antisense inhibitors of PTPR.alpha. are useful for preventing, ameliorating or treating conditions and disorders associated with these factors.

EXAMPLE 8

Effect of Antisense Inhibitors of PTPR.alpha. on Diet-induced Obesity in Mice

Antisense inhibitors of PTPR.alpha. expression are expected to reduce obesity or weight gain. This is tested in the high fat diet (HFD) model, also known as the DIO (diet-induced obesity) model.

Four week old male C57bl/6 mice were fed a high fat diet (60% kCal) ad libitum beginning at 4 weeks of age and continuing for 10 weeks. After the 10 weeks the mice were maintained on the diet as described and were treated with either an antisense inhibitor of PTPR.alpha., a control oligonucleotide having similar chemistry to the treatment oligonucleotide but not having a sequence that is complementary to the target mRNA, or saline. During this feeding schedule, animals were weighed at regular intervals and body weight and percent fat measurements were determined. At sacrifice, organ weights were determined as well.

Figure 3:
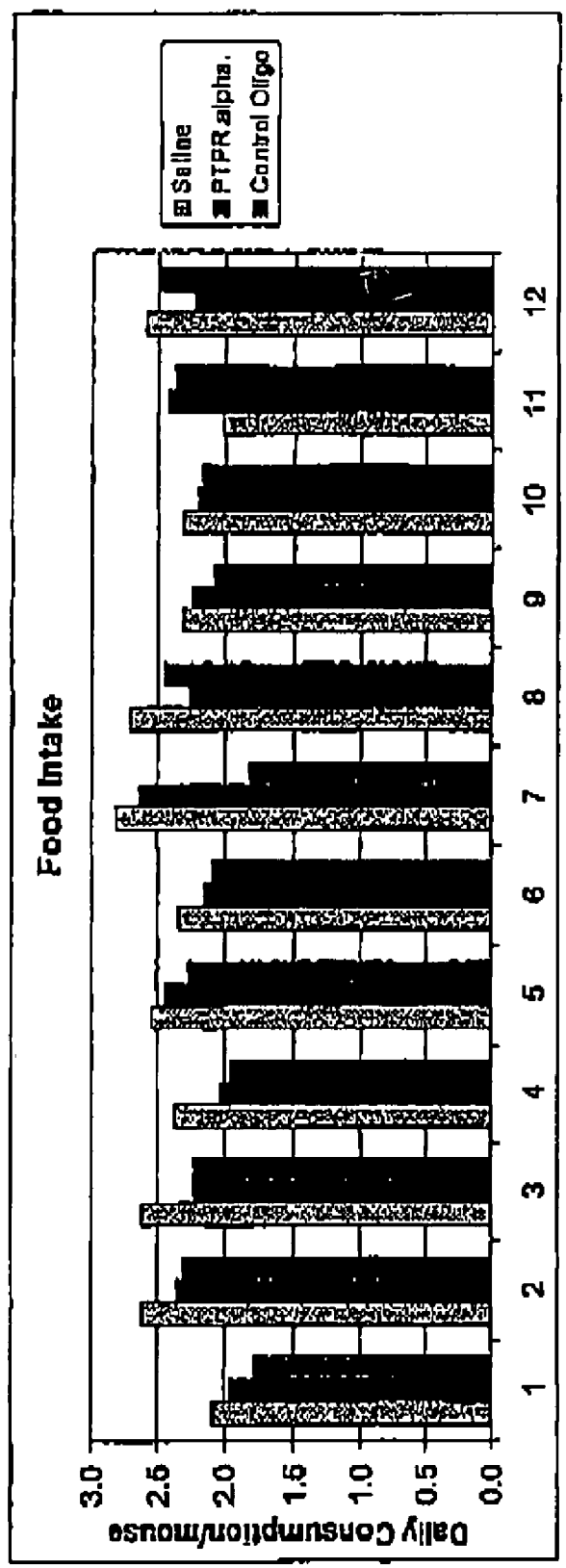
FIG. 3 is a graph illustrating food intake for DIO receiving treatment oligo, control oligo or saline.

Mice in the treatment group received 25 mg/kg of ISIS 147299 (SEQ ID NO: 135) twice a week by subcutaneous injection. Control group mice received a same treatment routine except using saline or, 25 mg/kg of control oligonucleotide that is not an antisense inhibitor of PTPR.alpha (CCT-TCCCTGAAGGTTCCTCC-SEQ ID NO: 228). A further control group received no treatment and was fed normal chow. Food consumption was determined for mice in each of the groups. Mice treated with the antisense PTPR.alpha. inhibitor had reduced body weight gains and reduced food consumption. FIGS. 2 and 3. There were no differences in organ weight and percent fat between the groups.

Blood was drawn weekly and transaminase levels, plasmid glucose levels, NEFA levels, and plasma lipid levels were determined. There was a decrease in plasma lipid levels for the mice receiving an antisense inhibitor of PTPR.alpha. After five weeks of treatment plasma triglyceride levels for mice receiving an antisense inhibitor of PTPR.alpha. were 59.9 IU/l (sem=3.57) compared to 75.9 IU/L (sem=2.20) for saline, 77.2 IU/L (sem=4.81) for control oligo and 91.80 IU/L (sem=5.92) for normal chow.

Insulin levels are presented in Table 13. For mice treated with an antisense inhibitor of PTPR.alpha. fed plasma insulin levels were approximately 2.66 ng/ml at base line, 2.96 ng/ml after 2 weeks, 2.71 ng/ml after 3 weeks and 1.95 ng/ml after 5 weeks. At week four fasted insulin levels were approximately 0.58 ng/ml for the mice receiving treatment with an antisense inhibitor of PTPR.alpha.

TABLE 13

Insulin Levels in DIO mice

| ng/ml (sem) | BL | Wk 2 | Wk 3 | Fasted Wk 4 | Wk 5 |
|---|---|---|---|---|---|
| Saline | 2.63 (0.30) | 3.91 (0.40) | 5.07 (0.73) | 1.75 (0.47) | 6.97 (1.03) |
| PTPR.alpha. | 2.66 (0.29) | 2.96 (0.27) | 2.71 (0.36) | 0.58 (0.15) | 1.95 (0.18) |
| Control Oligo | 2.53 (0.56) | 2.23 (0.46) | 2.01 (0.46) | 0.63 (0.16) | 2.42 (0.57) |
| Normal Chow | 0.96 (0.20) | 1.10 (0.31) | 1.37 (0.43) | 0.57 (0.17) | 1.28 (0.24) |

At day 41 of the treatment period the DIO mice were given an insulin tolerance test. Insulin tolerance tests are a good measure of insulin sensitivity. Mice were fasted for 3 hours and then received 0.35 U/kg of humilin (Lilly, Indianapolis, Ind.) via gavage of a 0.1 U/ml solution in saline. Blood glucose was measured at time point 0 and at 15, 20 or 30 minute intervals for up to 2 hours. Glucose levels are measured using a YSI glucose analyzer (YSI Scientific, Yellow Springs, Ohio). Results of the insulin tolerance test are shown in Table 14.

TABLE 14

Glucose During Insulin Tolerance Test in DIO Mice

| mg/dL (sem) | 0 | 30 | 60 | 90 | 120 |
|---|---|---|---|---|---|
| Saline | 194.4 (7.20) | 175.3 (9.13) | 182.9 (7.60) | 216.7 (11.68) | 242.9 (13.72) |
| PTPR.alpha. | 179.7 (7.18) | 142.0 (8.91) | 149.3 (11.36) | 165.3 (12.38) | 200.1 (12.35) |
| Control Oligo | 161.8 (6.61) | 121.0 (11.84) | 126.8 (6.34) | 150.8 (10.71) | 186.0 (12.29) |
| Normal Chow | 106.6 (20.56) | 100.8 (18.50) | 113.2 (22.18) | 125.0 (23.58) | 127.4 (24.27) |

Insulin levels were reduced for the animals receiving ISIS 147299 antisense inhibitor to PTPR.alpha. In addition, there was a reduction in plasma glucose levels seen during the insulin tolerance test for animals receiving ISIS 147229. A similar decrease was seen with control oligo, but not in the groups receiving saline.

The results from the ob/ob mouse studies and the DIO mouse studies indicate that antisense inhibition of PTPR.alpha. results in a reduction of plasma glucose levels and triglyceride levels in the plasma and liver. Antisense inhibition of PTPR.alpha. may provide a therapeutic strategy for conditions and diseases associated with these factors, such as type II diabetes, fatty liver disease and metabolic syndrome.

What is claimed is:

1. A method for the prevention, amelioration, or treatment of a disease or condition wherein indicators of the disease or condition comprise increased plasma glucose levels, increased plasma lipid levels, increased hepatic triglyceride levels, increased plasma transaminase levels, reduced hepatic function, reduced insulin sensitivity or combinations thereof comprising administering an antisense compound 12 to 35 linked nucleosides in length targeted to a nucleic acid molecule encoding human PTPR alpha to an individual in need of such intervention, wherein plasma glucose levels, plasma lipid levels, hepatic triglyceride levels or plasma transaminase levels are decreased, hepatic function or insulin sensitivity is improved or combinations thereof.

2. The method of claim 1 wherein the disease or condition is fatty liver disease and wherein administration of the compound results in a decrease in plasma lipid levels, a decrease in plasma transaminase levels, a decrease in hepatic triglyceride levels or combinations thereof.

3. The method of claim 1 wherein the disease or condition is type-2 diabetes and wherein administration of the compound results in a decrease in plasma glucose levels, an improvement in insulin sensitivity or combinations thereof.

4. The method of claim 1 wherein the disease or condition is metabolic syndrome and wherein administration of the compound results in a decrease in plasma glucose levels, a decrease in plasma lipid levels, a decrease in hepatic triglyceride levels, an improvement in insulin sensitivity, an improvement in hepatic function, a decrease in plasma transaminase levels or combinations thereof.

5. The method of claim 1 wherein the disease or condition comprises type-2 diabetes, fatty liver, metabolic syndrome or combinations thereof.

6. The method of claim 1 wherein the antisense compound optionally further comprises a complementary strand 15 to 35 nucleobases in length.

7. A method for lowering blood glucose levels in an animal in need thereof by administering an antisense compound 12 to 35 nucleosides in length targeted to a nucleic acid molecule encoding human PTPR alpha.

8. A method for lowering triglyceride levels in an animal in need thereof by administering an antisense compound 12 to 35 nucleosides in length targeted to a nucleic acid molecule encoding human PTPR alpha.

9. The method of claim 8 wherein the triglyceride levels are lowered in the plasma.

10. The method of claim 8 wherein the triglyceride levels are lowered in the liver.

11. The method of claim 7, 8, 9 or 10 wherein the animal suffers from type-2 diabetes, fatty liver disease, obesity, metabolic syndrome of combinations thereof.

12. The method of claim 1, wherein the compound is at least 80% complementary to a target region of the nucleic acid encoding PTPRalpha.

13. The method of claim 1, wherein the compound optionally includes a complementary strand 15 to 35 nucleobases in length.

14. The method of claim 1, wherein the compound is an antisense oligonucleotide.

15. The compound of claim 14, wherein the compound has at least one modified internucleoside linkage, sugar moiety, or nucleobase.

16. The compound of claim 14, wherein the compound comprises a chimeric oligonucleotide.

17. The compound of claim 15, wherein the modified internucleoside linkage comprises a phosphorothioate linkage.

18. The compound of claim 15, wherein the at least one modified sugar moiety comprises a 2'-MOE, a LNA, a 2'-OMe, an ENA, a 2'-F or combinations thereof.

19. The compound of claim 15, wherein the modified nucleobase comprises 5-methylcytosine.

20. The method of claim 12, wherein the compound is administered in a pharmaceutical composition comprising the compound and a pharmaceutically acceptable penetration enhancer, carrier, or diluent.

* * * * *

```
                        SEQUENCE LISTING

<160> NUMBER OF SEQ ID NOS: 228

<210> SEQ ID NO 1

<400> SEQUENCE: 1

000

<210> SEQ ID NO 2

<400> SEQUENCE: 2

000

<210> SEQ ID NO 3

<400> SEQUENCE: 3

000

<210> SEQ ID NO 4
<211> LENGTH: 3148
<212> TYPE: DNA
<213> ORGANISM: H. sapiens

<400> SEQUENCE: 4
gtgacacaac taaaaaaaaa caaaggtatt tatggaattc cactgagtgg taatggatga      60
tgcagttcaa ataactaagg acacatgttc aaagagcata attaactttt taaaagaagc     120
tagacttctt cagaagcttg ccagtttttc aagctgattt ctctcactgg caactcttca     180
gagtgctgtt cctactccac cctcccctgg tgataagcat ggattcctgg ttcattcttg     240
ttctgctcgg cagtggtctg atatgtgtca gtgccaacaa tgctaccaca gttgcacctt     300
ctgtaggaat tacaagatta attaactcat caacggcaga accagttaaa gaagaggcca     360
aaacttcaaa tccaacttct tcactaactt ctctttctgt ggcaccaaca ttcagcccaa     420
atataactct gggacccacc tatttaacca ctgtcaattc ttcagactct gacaatggga     480
ccacaagaac agcaagcacc aattctatag gcattacaat ttcaccaaat ggaacgtggc     540
ttccagataa ccagttcacg gatgccagaa cagaaccctg ggaggggaat tccagcaccg     600
cagcaaccac tccagaaact ttccctcctt cagatgagac accaattatt gcggtgatgg     660
tggccctgtc ctctctgcta gtgatcgtgt ttattatcat agttttgtac atgttaaggt     720
```

```
ttaagaaata caagcaagct gggagccatt ccaattcttt ccgcttatcc aacggccgca    780
ctgaggatgt ggagcccag agtgtgccac ttctggccag atccccaagc accaacagga     840
aatacccacc cctgcccgtg acaagctgg aagaggaaat taaccggaga atggcagacg     900
acaataagct cttcagggag gaattcaacg ctctccctgc atgtcctatc caggccacct    960
gtgaggctgc ttccaaggag gaaacaagg aaaaaaatcg atatgtaaac atcttgcctt    1020
atgaccactc tagagtccac ctgacaccgg ttgaaggggt tccagattct gattacatca    1080
atgcttcatt catcaacggt taccaagaaa agaacaaatt cattgctgca caaggaccaa    1140
aagaagaaac ggtgaatgat ttctggcgga tgatctggga acaaaacaca gccaccatcg    1200
tcatggttac caacctgaag gagagaaagg agtgcaagtg cgcccagtac tggccagacc    1260
aaggctgctg gacctatggg aatattcggg tgtctgtaga ggatgtgact gtcctggtgg    1320
actacacagt acggaagttc tgcatccagc aggtgggcga catgaccaac agaaagccac    1380
agcgcctcat cactcagttc cactttacca gctggccaga ctttggggtg ccttttaccc    1440
cgatcggcat gctcaagttc ctcaagaagg tgaaggcctg taaccctcag tatgcagggg    1500
ccatcgtggt ccactgcagt gcaggtgtag ggcgtacagg tacctttgtc gtcattgatg    1560
ccatgctgga catgatgcat acagaacgga aggtggacgt gtatggcttt gtgagccgga    1620
tccgggcaca gcgctgccag atggtgcaaa ccgatatgca gtatgtcttc atataccaag    1680
cccttctgga gcattatctc tatggagata cagaactgga agtgacctct ctagaaaccc    1740
acctgcagaa aatttacaac aaaatcccag ggaccagcaa caatggatta gaggaggagt    1800
ttaagaagtt aacatcaatc aaaatccaga atgacaagat gcggactgga aaccttccag    1860
ccaacatgaa gaagaaccgt gttttacaga tcattcccata tgaattcaac agagtgatca    1920
ttccagttaa gcggggcgaa gagaatacag actatgtgaa cgcatccttt attgatggct    1980
accggcagaa ggactcctat atcgccagcc agggccctct tctccacaca attgaggact    2040
tctggcgaat gatctgggag tggaaatcct gctctatcgt gatgctaaca gaactggagg    2100
agagaggcca ggagaagtgt gcccagtact ggccatctga tggactggtg tcctatggag    2160
atattacagt ggaactgaag aaggaggagg aatgtgagag ctacaccgtc cgagacctcc    2220
tggtcaccaa caccagggag aataagagcc ggcagatccg gcagttccac ttccatggct    2280
ggcctgaagt gggcatcccc agtgacggaa agggcatgat cagcatcatc gccgccgtgc    2340
agaagcagca gcagcagtca gggaaccacc ccatcaccgt gcactgcagc gccggggcag    2400
gaaggacggg gaccttctgt gccctgagca ccgtcctgga gcgtgtgaaa gcagagggga    2460
ttttggatgt cttccagact gtcaagagcc tgcggctaca gaggccacac atggtccaga    2520
cactggaaca gtatgagttc tgctacaagg tggtgcagga gtatattgat gcattctcag    2580
attatgccaa cttcaagtaa gcggcaacaa gggtccgtgg accaggagga ttgcctttaa    2640
tattttgtaa tattctgttt tgttaatata ccccaaattg tgtatatatc ttataactgt    2700
tttagaaatt ggtacatagg cttctattac ctattaggtg gaaattttat atgtaaatgt    2760
gttagcactg atagtccttt ttccaatgtt ttattgggga attaaatagt gtgatgtttg    2820
gattgatatc gtgaaatcct cagccgagaa attgggctgg attgtgcttt ggttaataca    2880
tctttcccta aagaagataa acacaaaatc cattccaggt agctcggcac caactaagaa    2940
aaaaagcaca aagttctcag agctctcgag gaaagtggtt gtccccgtac caccatgcac    3000
tgtaaatatc cctccctct ctccctggtc cctcccca tccccaccac tgatatcatg       3060
gggagtaata ggaccagagc ggtatctctg gcaccacact agggactatc aggtaataaa    3120
```

-continued

```
agctttgact ccctgaaaaa aaaaaaaa                                         3148
```

<210> SEQ ID NO 5
<211> LENGTH: 25
<212> TYPE: DNA
<213> ORGANISM: Artificial Sequence
<220> FEATURE:
<223> OTHER INFORMATION: PCR Primer

<400> SEQUENCE: 5

```
ggtggactac acagtacgga agttc                                              25
```

<210> SEQ ID NO 6
<211> LENGTH: 19
<212> TYPE: DNA
<213> ORGANISM: Artificial Sequence
<220> FEATURE:
<223> OTHER INFORMATION: PCR Primer

<400> SEQUENCE: 6

```
gatgaggcgc tgtggcttt                                                     19
```

<210> SEQ ID NO 7
<211> LENGTH: 22
<212> TYPE: DNA
<213> ORGANISM: Artificial Sequence
<220> FEATURE:
<223> OTHER INFORMATION: PCR Probe

<400> SEQUENCE: 7

```
catccagcag gtgggcgaca tg                                                 22
```

<210> SEQ ID NO 8

<400> SEQUENCE: 8

000

<210> SEQ ID NO 9

<400> SEQUENCE: 9

000

<210> SEQ ID NO 10

<400> SEQUENCE: 10

000

<210> SEQ ID NO 11
<211> LENGTH: 3070
<212> TYPE: DNA
<213> ORGANISM: M. musculus

<400> SEQUENCE: 11

```
ccgcccagcg ccgggctcgg tcagcatgga ttcctggttc attcttgtcc tgtttggcag         60
tggtctaata catgttagtg ccaacaatgc tactacagtt tcaccttctt taggaacgac        120
aagattaatt aaaacatcaa aacagaatt ggctaaggaa gagaataaaa cctcaaattc         180
aacctcttca gtaatttctc tttctgtggc accaacattc agcccaaacc tgactctgga        240
gcccacctat gtgactactg ttaattcttc acactctgac aatgggacca ggagggcagc        300
cagcacggaa tctggaggca ctaccatttc cccgaacgga agctggctta ttgagaacca        360
```

```
gttcacggat gccataacag aaccctggga ggggaactcc agcactgcag caaccactcc      420
agaaaccttc cccccggcag atgagacacc aattattgcg gtgatggtgg ccctgtcctc      480
tctgctagta atcgtgttta ttatcatagt tctgtacatg ttaaggttta agaaatacaa      540
gcaagctggg agtcattcca actctttccg cctgtcaaat ggccgcacgg aggatgtgga      600
gccccaaagt gtaccacttc tggccaggtc cccaagcacc aacaggaagt acccaccact      660
gcctgtggac aagctggaag aggagattaa ccggagaatg gctgatgaca ataagatctt      720
cagagaagaa ttcaacgctc tccctgcttg tcctatccag gccacctgtg aggctgcctc      780
caaggaagaa aacaaggaaa aaaccgcta tgtaaacatc ctgccctttc tctctttagc      840
tgtgagcaag gatgcagtga agcactgaa caaaaccact ccattgttag aaagaaggtt      900
tattgggaaa tcaaactcca gaggctgtct ctcagatgac cactctagag tgcacctgac      960
acctgttgaa ggggtcccag attctgatta catcaacgct tcattcatta atggctacca     1020
ggaaaagaac aaattcatcg ctgcacaagg accaaaagaa gaaacagtga atgacttctg     1080
gagaatgata tgggaacaaa acacagctac tattgtcatg gtgaccaacc tgaaggagag     1140
aaaggagtgt aaatgtgccc aatactggcc agaccaaggc tgctggacct atgggaatgt     1200
ccgtgtgtct gtcgaggatg tgactgttct ggtggactac acagtacgga aattctgcat     1260
ccagcaggtg ggcgacgtga ccaacaggaa accacagcgc ctcatcactc agttccactt     1320
caccagctgg ccagactttg gggtgccttt caccccaatt ggcatgctca agttcctcaa     1380
gaaggtgaag gcctgtaacc ctcagtacgc aggggctatc gtggtccact gcagtgcagg     1440
tgtagggcgc actggcacct tgttgtcat cgatgccatg ctggacatga tgcattcgga     1500
acgcaaagtg gatgtatacg ggtttgtgag ccggatccgg gcccagcgct gccagatggt     1560
acagacagac atgcagtacg tcttcatata ccaggccctt ctggagcatt atctgtatgg     1620
ggacacagaa ctggaagtga cttctctaga aacccaccta caaaaatttt ataacaagat     1680
cccagggacg agcaacaacg ggttagagga ggagtttaag aaattaactt caatcaaaat     1740
ccagaatgac aagatgcgca cgggaaacct tccagccaac atgaagaaga ccgggttttt     1800
acagatcatt ccatatgaat ttaacagagt gatcattcca gtcaaacgag gcgaagagaa     1860
cacagactat gtgaacgcat cctttcattga tggatccggg cagaaagact cctacattgc     1920
cagccagggc cctcttctcc acacgattga ggacttctgg cgaatgatct gggagtggaa     1980
gtcctgttct atcgtaatgc tgacagaact ggaagagaga ggccaggaga agtgtgccca     2040
gtactggcca tctgatggcc tggtgtccta tggagacatc acagttgagc tgaagaagga     2100
ggaggaatgt gaaagctaca ctgtccgaga cctcctggtc accaacacca gggagaacaa     2160
gagtcggcaa atccggcagt tccacttcca cggctggcct gaggtgggca tcccagcga     2220 cggcaagggc atgatcaaca tcattgcagc agtgcagaag cagcagcagc agtcggggaa     2280
ccatcccatc actgtgcact gcagtgccgg ggcaggacgg acaggaacct tctgtgcctt     2340
gagcacagtc ctggaacgtg tgaaagcaga aggaatttta gatgtcttcc aaactgtcaa     2400
gagcctgcgg ctgcagaggc cacacatggt ccagacactg gaacagtatg aattctgcta     2460
caaggtggta caggagtaca ttgacgcctt ttcagattat gccaacttca gtgacaggt     2520 gacaaggccc acagacagga gaattgcctt taatattttg taatattctg tttttgttaa     2580
tatacccaaa attgtatata tcttataact gttttagaaa tggcacatag gcttctatta     2640
cctgttaggt ggagattttg tatgtaaatg tgttagcact gatagtcctt ttccagtgtt     2700
ttattgggaa attaaatagt gtgatatttg ggttgatata atgaaatcct cagcctggaa     2760
```

-continued

```
actgggccag attgttcctt gcttcaaata tcttttccta aagaagataa acctaagact    2820
cattccaggt agctcagtgc caactaaaac aaagcacaaa gttctcagag ctcttgagga    2880
aatggttgtc tccctgtccc caggcaggcc tcttcccctc cctgtcctgt aaatatccct    2940
cccctctcca gtccaccctc atctcccacc aagatcagcc acctcaggca tggggagtaa    3000
tgagaccaga gcgcctctct ggcaccacag cagggatcgt caggtaataa acactcttga    3060
ttccctgagg                                                          3070
```

<210> SEQ ID NO 12
<211> LENGTH: 25
<212> TYPE: DNA
<213> ORGANISM: Artificial Sequence
<220> FEATURE:
<223> OTHER INFORMATION: PCR Primer

<400> SEQUENCE: 12

```
gatataatga aatcctcagc ctgga                                         25
```

<210> SEQ ID NO 13
<211> LENGTH: 31
<212> TYPE: DNA
<213> ORGANISM: Artificial Sequence
<220> FEATURE:
<223> OTHER INFORMATION: PCR Primer

<400> SEQUENCE: 13

```
gaatgagtct taggtttatc ttctttagga a                                  31
```

<210> SEQ ID NO 14
<211> LENGTH: 27
<212> TYPE: DNA
<213> ORGANISM: Artificial Sequence
<220> FEATURE:
<223> OTHER INFORMATION: PCR Probe

<400> SEQUENCE: 14

```
tgggccagat tgttccttgc ttcaaat                                       27
```

<210> SEQ ID NO 15

<400> SEQUENCE: 15

000

<210> SEQ ID NO 16

<400> SEQUENCE: 16

000

<210> SEQ ID NO 17

<400> SEQUENCE: 17

000

<210> SEQ ID NO 18
<211> LENGTH: 3615
<212> TYPE: DNA
<213> ORGANISM: H. sapiens

<400> SEQUENCE: 18

```
gaattcgggg gagtaagaga cacgctcagg ggagcaggta cccccttctcc taaagatgaa    60 gaggagcaaa ctggcactaa gcaaggccat cgagagcggg gacactgacc tggtgttcac   120
```

```
ggtgttgctg cacctgaaga acgagctgaa ccgaggagat tttttcatga cccttcggaa    180
tcagcccatg gccctcagtt tgtaccgaca gttctgtaag catcaggagc tagagacgct    240
gaaggacctt tacaatcagg atgacaatca ccaggaattg ggcagcttcc acatccgagc    300
cagctatgct gcagaagagc gtattgaggg gcgagtagca gctctgcaga cagccgccga    360
tgccttctac aaggccaaga atgagtttgc agccaaggct acagaggatc aaatgcggct    420
cctacggctg cagcggcgcc tagaagacga gctgggggc cagttcctag acctgtctct    480
acatgacaca gttaccaccc tcattcttgg cggtcacaac aagcgtgcag agcagctggc    540
acgtgacttc cgcatccctg acaagaggtg acacaactaa aaaaaaacaa aggtatttat    600
ggaattccac tgagtggtaa tggatgatgc agttcaaata actaaggaca catgttcaaa    660
gagcataatt aacttttta aagaagctaa caagcatgga ttcctggttc attcttgttc    720
tgctcggcag tggtctgata tgtgtcagtg ccaacaatgc taccacagtt gcaccttctg    780
taggaattac aagattaatt aactcatcaa cggcagaacc agttaaagaa gaggccaaaa    840
cttcaaatcc aacttcttca ctaacttctc tttctgtggc accaacattc agcccaaata    900
taactctggg acccacctat ttaaccactg tcaattcttc agactctgac aatgggacca    960
caagaacagc aagcaccaat tctataggca ttacaatttc accaaatgga acgtggcttc   1020
cagataacca gttcacggat gccagaacag aaccctggga ggggaattcc agcaccgcag   1080
caaccactcc agaaactttc cctccttcag gtaattctga ctcgaaggac agaagagatg   1140
agacaccaat tattgcggtg atggtggccc tgtcctctct gctagtgatc gtgtttatta   1200
tcatagtttt gtacatgtta aggtttaaga aatacaagca agctgggagc cattccaatt   1260
ctttccgctt atccaacggc cgcactgagg atgtggagcc ccagagtgtg ccacttctgg   1320
ccagatcccc aagcaccaac aggaaatacc caccccctgcc cgtggacaag ctggaagagg   1380
aaattaaccg gagaatggca gacgacaata agctcttcag ggaggaattc aacgctctcc   1440
ctgcatgtcc tatccaggcc acctgtgagg ctgcttccaa ggaggaaaac aaggaaaaaa   1500
atcgatatgt aaacatcttg ccttatgacc actctagagt ccacctgaca ccggttgaag   1560
gggttccaga ttctgattac atcaatgctt cattcatcaa cggttaccaa gaaaagaaca   1620
aattcattgc tgcacaagga ccaaaagaag aaacggtgaa tgatttctgg cggatgatct   1680
gggaacaaaa cacagccacc atcgtcatgg ttaccaacct gaaggagaga aaggagtgca   1740
agtgcgccca gtactggcca gaccaaggct gctggaccta tgggaatatt cgggtgtctg   1800
tagaggatgt gactgtcctg gtggactaca cagtacggaa gttctgcatc cagcaggtgg   1860
gcgacatgac caacagaaag ccacagcgcc tcatcactca gttccacttt accagctggc   1920
cagactttgg ggtgcctttt acccgatcg gcatgctcaa gttcctcaag aaggtgaagg   1980
cctgtaaccc tcagtatgca ggggccatcg tggtccactg cagtgcaggt gtagggcgta   2040
caggtacctt tgtcgtcatt gatgccatgc tggacatgat gcatacagaa cggaaggtgg   2100
acgtgtatgg ctttgtgagc cggatccggg cacagcgctg ccagatggtg caaaccgata   2160
tgcagtatgt cttcatatac caagcccttc tggagcatta tctctatgga gatacagaac   2220
tggaagtgac ctctctagaa acccacctgc agaaaattta caacaaaatc ccagggacca   2280
gcaacaatgg attagaggag gagtttaaga agttaacatc aatcaaaatc cagaatgaca   2340
agatgcggac tggaaacctt ccagccaaca tgaagaagaa ccgtgtttta cagatcattc   2400
catatgaatt caacagagtg atcattccag ttaagcgggg cgaagagaat acagactatg   2460
tgaacgcatc ctttattgat ggctaccggc agaaggactc ctatatcgcc agccagggcc   2520
```

```
ctcttctcca cacaattgag gacttctggc gaatgatctg ggagtggaaa tcctgctcta      2580
tcgtgatgct aacagaactg gaggagagag gccaggagaa gtgtgcccag tactggccat      2640
ctgatggact ggtgtcctat ggagatatta cagtggaact gaagaaggag gaggaatgtg      2700
agagctacac cgtccgagac ctcctggtca ccaacaccag ggagaataag agccggcaga      2760
tccggcagtt ccacttccat ggctggcctg aagtgggcat ccccagtgac ggaaagggca      2820
tgatcagcat catcgccgcc gtgcagaagc agcagcagca gtcagggaac cacccccatca      2880 ccgtgcactg cagcgccggg gcaggaagga cggggacctt ctgtgccctg agcaccgtcc      2940
tggagcgtgt gaaagcagag gggattttgg atgtcttcca gactgtcaag agcctgcggc      3000
tacagaggcc acacatggtc cagacactgg aacagtatga gttctgctac aaggtggtgc      3060
aggagtatat tgatgcattc tcagattatg ccaacttcaa gtaagcggca acaagggtcc      3120
gtggaccagg aggattgcct ttaatatttt gtaatattct gttttgttaa tatccccaa       3180 attgtgtata tatcttataa ctgttttaga aattggtaca taggcttcta ttacctatta      3240
ggtggaaatt ttatatgtaa atgtgttagc actgatagtc cttttccaa tgttttattg       3300 gggaattaaa tagtgtgatg tttggattga tatcgtgaaa tcctcagccg agaaattggg      3360
ctggattgcg ctttggttaa tacatctttc cctaaagaag ataaacacaa aatccattcc     3420
aggtagctcg gcaccaacta agaaaaaaag cacaaagttc tcagagctct cgaggaaagt      3480
ggttgtcccc gtaccaccat gcactgtaaa tatccctccc ctctctccct ggtcccctcc      3540
cccatcccca ccactgatat catggggagt aataggacca gagcggtatc tctggcacca      3600
cactagcccg aattc                                                       3615

<210> SEQ ID NO 19
<211> LENGTH: 186739
<212> TYPE: DNA
<213> ORGANISM: H. sapiens

<400> SEQUENCE: 19
cagctcctcc aacccagctt atttgaacca caacccagaa tggttagggg ccagatgtgg        60
gagtgttctc tgtcatgatg ccctggctct ggactgctcc ccaccagaaa gagagccaga       120
aggcggacga gtacctgcgg gagatccagg agctgggcca gctgacccag gccgtgcagc       180
agtgcattga ggctgcagga catgagcacc agccagacat gcagaagagt ctgctcaggg       240
ttggcctgga tggccgggcc ggggagggtg gggctgggag ggggtgggat gggcagcagg       300
gaagctctct cctatcgccc tctggctctt ctcaggccgc ctccttcgga aagtgtttcc       360
tggacagatt tccacccgac agcttcgtgc acatgtgtca ggacctgcgt gtgctcaatg       420
ctgttcggga ctatcacatc gggatcccgc tcacctatag ccagtatccc tgtgcacgcc       480
agaagggtac cctacagcca gggtggcag gggaagggc tggagatgcg tctgcaggta       540
cctggcaagc ggggcttatt ctccaactgg atccttaacc gaggaaaata cagatataag      600
cagctcacca tccaggtgct gctgacagg tagggtaagc ccaagggtgc agtgagcggg       660
ctgtcagggg ggtgggcatt acagccttgg gtggggtctt atggtcactg ctcctgacct      720
atctaggatg tgggaggcct gatgtgcagg ctgaggccac tctgctccct ttctcctcca      780
cctcactcct tgtatccttt acccaccggg tctaccaggc tcgtgttgcg gagactttac      840
cccctggcca tccagatatg cgagtacttg cgccttcctg aagtacaggg cgtcagcagg      900
atcctggccc actgggcctg ctacaaggca aggatgtggg atgggatcca agggcattta      960
gaggattcca ggccctggtg aggtggagga aatagaaagt gtagaactgc gctgggcacg     1020
```

```
gtggctcatg cctgtaatcc caacactttg ggaggctgag gcgggcgaat cacctgaggt    1080
caggtattcg agactagcct ggctaacatg gtgaaacccc gtctctacta aaaatacaaa    1140
attagccggg cacggtggcg catgcctgta atcccagcta cccggaggc tgaggcagga     1200 gaattgcttt cacctgggag gcagaggttg cagtgagctg agattgcact gctgcactcc    1260
agcctgggcg acagagcaag actctgtctc aaaaaaaaag aaagaagtgg cgggggcgga   1320
ggaggaggga aagagagaga aagaagaaag agagaaagaa agaaagaaga aggaagggag   1380
ggaggaaggg aactgaaggg gtgggtccta agggcttgca ggagtggaga gtgaggaatg    1440
gcatccagat gtttgtgaca ccccgcatcc cttgcaggtg caacagaagg atgtctcaga   1500
tgaggatgtg gctcgagcca ttaaccagaa gctggggac acgcctggtg tctcttactc    1560
cgacattgct gcacgagcct atggttgtgg ccgcacggag ctggccatca aggtgtgggt    1620
gcccagccct ccacagacac tctgatgtgg ttgttcaggg cccccatgcc agctccttct    1680
ctctgtgcct tccttctcac ctcacagctg ctggagtatg agccacgctc aggggagcag   1740 gtacccettc tcctaaagat gaagaggagc aaactggcac taagcaaggc catcgagagc   1800
ggggacactg acctgggtga gggcaaggct gggggggcccc tgggctaagt gggagcctgg   1860
ctggaattcc cactccacct tactctcctg cagtgttcac ggtgttgctg cacctgaaga    1920
acgagctgaa ccgaggagat ttttcatga cccttcggaa tcagcccatg ccctcagtt     1980 tgtaccgaca ggtgtgtgta gtgggcaggg ttgtggtgta gccttctgag cacttgagtt   2040
ggccttgctg actgattgcc tgcctgtggc cccagttctg taagcatcag gagctagaga   2100
cgctgaagga cctttacaat caggatgaca atcaccagga attgggcagc ttccacatcc    2160
gagccagcta tgctgcagaa gaggtctgag atccatgggg cgtgtgggc gtgtgggca     2220 tgtgggctgg ggctgttggt ccggttcctt caggaatcta ggccttcgtg ttgggtgcac   2280
actccatctg gtcctcactg tgagggagac tctgacgtga ggccaggatg ggggttagtg   2340
tcagaggagc tagccatccc tctaggacat cagagtggtg cacctagcag gcaaggctga   2400
ccctggcgac cctgggcaca gggatggggg agaagactgt agcctgggtg aggagggcga   2460
gggtcctgca tgctgtgagt tcaggccttc cttcttgtct ttatagcgta ttgaggggcg    2520
agtagcagct ctgcagacag ccgccgatgc cttctacaag gccaagaatg agtttgcagc   2580
caaggtttgg cccaccttt tccaagagcc tcctcgtctc ctggtcttcc ctcctggtcc    2640
ctcatcccca tcatgcctca ttatccgggt ccccaggcta cagaggatca aatgcggctc   2700
ctacggctgc agcggcgcct agaagacgag ctgggggcc agttcctaga cctgtctcta    2760
catgacacag ttaccaccct cattcttggc ggtcacaaca agcgtgcaga gcagctggca   2820
cgtgacttcc gcatccctga caagaggtag gtgagggccc aggctgcatg tgggtcccag   2880
gaccacctgc ctctcctgca acacctccaa gcccagcttt cctgcaggct ctggtggctg   2940
aagctgactg ccctggcaga tttggaagat tgggaagagc tagagaagtt ttccaagagc   3000
aagaaatcac ccattggcta cctggtgagg caggtcctc cctccagccc acttccagtg    3060
agggtagtct tcgggagaga gggctaggca gggagacaga taggatggcc cgttcatgct    3120
cctgttcagc tgcccgcata gttagcgagt gcttcctgta tacacatttg tgggcaggca   3180
tcatctgctg tgttgggtgc actggaggat gggtccaagt ttgcctgcag atgttacggg    3240
gagagagaat gagctgcttt ccccaggag ggccacaggg ggcactatgt gctagaggga     3300
aagtcttgtc tgaggagggt ggagggggca caggagggt gcatatggga ggcagtggag    3360
atactgaggg ctgttttctg tggtgggtag ttcagaggtg tatagggcag gtttgagaat   3420
```

```
gtcaatcaca agagaacaca ggaaatgtga gggctggtgg caggaacgcc tgttgcaagg    3480
ggtaatggtg ggtggtagag cagaagcgtg gaaataattg gtctcaagtc tctgacagag    3540 cttttggttta ggtgatttct gccctaagaa tgttgagatc acaactgtct gtgcatgggg    3600
gttgggggat tatatgtact gacgggtgta tacatataga atatatatgg acgatgtatg    3660
cattgcgcct ctgctcgtaa gagagaggac aggagggctg tgcattacct tctccctcca    3720
cccgcttcct ctcctccaag ccttttgtgg agatctgcat gaaacaacat aacaaatacg    3780
aagccaagaa gtatgcttcc cgcgtgggtc ccgagcagaa ggtcaaggct ttgcttcttg    3840
ttgggtgcgt caactgaggg cctgtgggtg ctgggtggct gagctgtggg ctggtgagag    3900
gcagggtttg tgcccttgag cagccccaac accacctcct ctcttgctca aaccacagcg    3960
atgtggctca ggctgcagat gtggccatcg aacaccggaa tgaggctgag ctgagcctcg    4020
tattgtccca ctgcacggga gccacagatg gggccacagc tgacaagatt caacgggcca    4080
gggcacaagc ccagaagaag tgaggagtcc atcctgtaca tctcaagcaa ggggttcctc    4140
ccctagcacc tgggcttggc agaagggcca tagttcatcc agctcctccc ctagagcaat    4200
gctgaggagc gggggcatgg tagcagggct gtctggtttt aaataaagtt ggaacacttc    4260
acagtgcttg tcttacacag tccagcctaa gcaaaggcaa gctcaagaca ggatcctcca    4320
gacaccacag caaaactcca tgtgttccgt tgtgttggga ccggaggtgg gggcttctcc    4380
agccatactc gcaagaaacg tgtcctctcc acagttacca aggaaagctt tctctatctc    4440
acagctccta ggaagattat agggagagat ggcacaaaac ttaagcacca gctcaccaag    4500
aacatactgt aaagcattct gtgtgtgtgc gtgtaaacac gcaagaacca cgctaaacac    4560
ttttgctgcc tgtacttcct ttattcctcg tgacagccct gtgaggtaac atcaccccac    4620
tttacagaaa ggagattgag gaccagggag ttcgataata acaaatatgt ggcaaaacag    4680
ggatttgaaa ccccgggcca agtgcaagct ggaactggaa tcgggccctc tgtgagaagg    4740
gagcctgagg caaggcccca atttgcactg cagtggtgat tggaggacta atgagaagtg    4800
tgtggcctgc gggccatagg ggtcagggg tggtggcctt tggaactctt gcccactgaa    4860
ctgtggtgag caattccaag ttgtctctgg gccaaataga aaggaggat ggaagatttc    4920 aattctgcca aaaagaacca tgaacaccag acccgcaatc agtaggagta cccgcggggc    4980
cctctgctct ctctatctag ccttccgttg gcactccagt gcacccctc tgctctccct    5040 gtctagccct ccgttggcac tccagtgcac ccctctgct ctccctatct agccttccct    5100
tggcactcca gtgcaccttg gcttcatgcc cagggcccca cccaacactg agggcattgc    5160
cttttccttt gtcgccccca ctttgtctac aaggaggaaa ccacagccag agggagtgca    5220
ggcctcactg gagcttcagg cctctcccta tttaacaccc ctagggccga ccatgctttt    5280
agaaagacag tgagagactc agggcctgag aaggtatttc ttttttttcct tttcctacct    5340 gacttgtaaa tgaaagtttg tgaaagtcct tcaaggagat ataagtcaaa tggtaaaata    5400
actatcatgc tcgccattca ttatgtgggt caagaatttg gacaggttgt aacagggatg    5460
gtttgtgtct gtttcatagt gtctgaggca tcagctggaa gactaaaagg ttgatagcta    5520
ggggctgaaa tcatgtgaaa gcttgctaac tcacacactt ggtgagtgac gctggttctt    5580
cactgggacc ttagctgggg tggtctgcca gaacacctgc aacatggtgg ctgggtccca    5640
aggacaagca tcccaagagg gtgccaggta gaatctggac tgccttccta acctagattt    5700
ggaagttacg tggtgtcaca tctgctagag tatttgtcac agcagtaata caggcccacc    5760
ccaccaattt caaggggaaa tagactccac ctcttttttt tttttttttt tttgcgtggt    5820
```

```
agagatgggg tctcgggggt ctccttatgt tgcccaagct ggttttaaac tcctgagctc   5880
aagcagtcct ccctcctcag catctcaaag tgctggggtt acagcatgaa ccactgaacc   5940
tggcctggac tccacctcct gatagggagt agcaaagttc tggaaatact gtggctaggt   6000
tttggaatca caatctggca cagcccatca gctttcccgt ttggaatcag cagacaagag   6060
gaaaggaaat aatccccaat gctgggctca tcattctggg cttttttttt tttttttttt   6120
tttttttttt tgtcccagt cttggcccca caattcctca ctgccctggt agctctttga    6180
tgcctttaaa aaatgttttc ccagcttttc gagttctcaa tgaaaaagga ttgctatcaa   6240
acaacccagt tttcctctct ggaaagggag gcttgaccag tgcttttaga atgtacacaa   6300
tacaaaaccc acatctccaa agtaacatac agtatattta ctcataggct atgtaaacaa   6360
acactgtaca tatgaagttt tagaaatatg tgagaaataa cttttaactg atgacaaatg   6420
tatatcaaca gtgatttcaa ctttataaaa ggtgtgtgtg catgtagaga agcattggaa   6480
ttgtctatgg ggagagttgc tttaaaaagg cagttttgta tacttttttg taaagttaat   6540
cactgatttg cccccacct ccacagttta ttataaaaac tttcaaacat acagccaggt    6600 agaataatt ttacagtgaa catttgtgta actaccactg gattctacca ttagcatctt    6660
actatatcac acatctgttc atctatccat tcctctatgt caatccatcg tattttcat    6720 atatttcaaa gtaagttgca gacatcagta cacctccccc taaatacttc agtatgcatt   6780
tcaataacta gagttcattt ttggtttgca attttttttt tcttttcagg caaaatctac   6840
atacattgca atccacagat cttaaatgta attttctaag ttttgacaga tgtataagcc   6900
tatgaattgt gacatttaaa aaccagaact gggatttttct ttttttcaaat ccttgcttac  6960 tcaattgaaa ttagtgtgag atgccttctg ccctgagcag tttgtacagc aggcctatgc   7020
ctacatgggt gggcagggcc aagtttcgtc aatgtatga cgctaggatt ggggctagga    7080
actaggactg tgtagctgga ggcaaagaat ctgggaacat ttcttcttgt atcagtggta   7140
gccagtgcag ggagaatcag ggcaaaggct gggcgcagtg gctcatgcct gtaattccag   7200
cactttggga ggcttaggtg ggtggatcac ctggggtcag gagtttgaga ccagcctggc   7260
caacatggtg aaaccctgtc tctagtaaaa atacaaaaaa attagctggg ggtggtggcg   7320
ggtcctgtaa tcccagctac ttgggaggct gaggcaggag aatcgcttga ttgcttgaac   7380
ccaggaggtg gaggttgcag tgagctgaaa tggcgccatt gcactccagc ctgggcaatg   7440
agtgaaactc tgtcttaaaa atatatatat atatatcgag caaaggctcc tacaactcac   7500
cttctcaggg taaggggctg tatgtccagt ctcttagata caaagttcca gtgaaagact   7560
cttggggttg gccaggcgca gtggttcacc cctgtaatcc cagcattttg ggaggctgag   7620
gcaggcagat cgcctgaggt caggagttca agaccagcct ggccaacatg gtgaaaccct   7680
gtctctacta aaaatacaaa attagccagg cgtggtggcg catgcctgta atcccagcta   7740
ctcgggaggc tgaggcagga gaatcgcttg aacccgggag gcagaggttg cagtgagccg   7800
agatcgtgcc attgcactca agcctgggca acaagagcaa aaactccgtc tcaaaaaaaa   7860
gaaaaaaaaa actcgggttt gaacagtgtg gcctgcaaag ggacttggct ctcatttact   7920
tcacctttct atcttattgc cttgctttat tttcatttca gcatttagga aattttcttg   7980
ttcttttgtt tattgtctgt gttcctatcc agaatgtaag ctcctgagag cagaggcctc   8040
ttctgtcctc ttctgtctta ttccctgctg tgtccagcac atggtctgca ctcaataagt   8100
atttgttgcg agaatgactc attgttccat ttactagaag gggaaggag gccccgagag    8160 gggaaatgac ttgcctaaag aaacaggagt cctttccccc catcctccag ctctcctgat   8220
```

```
cctctccttt gctcataaac cctgtgactg ttggggcacc tgtggggtgg ctgcgaaatg    8280
cctacctgta ggtatgtgct cctgtgggtt gggactaatg caggactagg agtaggaggg    8340
ctctgcagtc ccccatttgg gtaggcttgg gcacaggaaa ctgcctcctt tcccttcctc    8400
agttctcttc tcttccagga taacccttta ctctgtgatg atgatgggcg agggagctca    8460
ggacactctg ggagccaagt aggatggagg gctgggcagg tctctacagg caggcagctg    8520 aggaggggc tctgtcttct tccaatggaa acagcatctg tgtggttgct gagctgaacc    8580
ctccttccca gggtctccag ggtctgtagt tctccttggt ctgtagttct gtcacccctg    8640
tgcacacccc acaaatgctt tgaccatagt gcagctgtct catggggaga gaaagaactt    8700
tcatttcctg agaatgggtt acttgccaag ctgaacatgc ctaattctca atacagccct    8760
gggaagttcc aggaagagtt gcagagggag gctcaggtca cccagcacat ggtgggctg     8820 gaaaccccgg gctctttgac taccacgccc aacaacaatt tttccaagtg tggtcatatc    8880 caaaggggt ccttcagata atctcaaaga tgaacactta ctgcaatcac tatttcagtt     8940
atattaaaaa tataagtagc atgtcaaccc cttctagggt aatacaaata aaaagtaaaa    9000
aaaaactaat caacaaaaag aaacatatta agaaataata gtgtaaatta gatataaggc    9060
aaaagtaagc tggtgggtt tggttctaga gcatagggct gctatcccag ctactgaggt     9120
acctcctgcg tttgcagtca ttacttgtta ggggtttca cactttgact tcctgcttt      9180 cacttttcca ttcggtgttg cgggatagat tgagtttgga cttaaggga tatgtgaatg     9240 ttgggcgtgg ggaaggatcc accctcactg gggtctgagc gttaggagag taggcgtgtg    9300
gactctgggc cttgggctg gagtgtctat tggtcagagg tgtcgggttc ggccatttca     9360
ccctcacctc taggctggcc ctgctgagag ggagagagag tcacaactcc cactcaagga    9420
gagacttccc tgctggggag gggacggcct gaggcccgcc ccacccatat tcccaggccc    9480
tggctctggt tagcatggac taacttattc cacaatacgg aggagtgggg cacagagtcc    9540
ctaactggcg ccccaacaga aggcggtggt ggggaccgga gatggtagga ctggagatgg    9600
taggggctgc tgatgtgagc ccacaatacg gaggagtggg gcacagagtc cctaactggc    9660
gccccaacag aaggcggtgg tggggaccgg agatggtagg actggagatg gtgggggctg    9720
ctgggagccc cttttgcgcc gcagtgtttc ctgccatgaa gagttgccgc cggtcacaac    9780
ccttccccgg gggcgccccg aatgtgggac tccttccggc ctggggtgcg tgaggggac     9840 tcagggttg cccggtctgg aggagagact cgccgccacc taccccggga accgcagact     9900
ctgggtctgg gataaagcgt cccctacccg caagctcggt ttgtgcgcta ctgtgcaatc    9960
tgtcttttgc ctgcagacgc ccagccgctc gccctgcgcg ggtctcggaa tgtccagggg   10020
tccctactgg ggatcacaac ccggcgaaat gtcgcatttg ccaccaccta tctcgactgc   10080
gtaatcggct ttcagccgca gacgctcagg tcctgcagca cccgcgggga tccgtgtagg   10140
aacctgctgc cgctggatgg actgagcgat tgcttcgcgg gtgtcacgca ccagacgccg   10200
tgccgggagc gccgggaagg gggtacgcgc cccaaccccg gccggggag gccgcactct    10260 ggctcctctc tgcgttttga gcctcccctc ccccgccagg cgtatcgcaa aaggcacctc   10320
catcgcagag caccatgtgt tgtgcttcta ctcagctcgg tggcgagcgg ggccccagca   10380
tgcgcatctg gaaagcgggg gagattaccc tggagctcgg gtggggacgg cgtgggctga   10440
cttgatataa gacgacaccc acggagccaa atccgttcta gggacttggc aggttcctct   10500
cccctcccca gtgagatccgt cgttctttgc agcaattagg ggaggaaaa aaaagaccca   10560 cagtatcacg tttggagagg gttaggaaga tggctctcga gttgcaggcc gccctggtgg   10620
```

```
ctagacattg gtgtagtttg tgcctggcct cggtttcctg atctgtaaac tgggaagaag    10680
gcccaagtca tgaggcctgt gactgtagaa tggctgaagg cactggtgca ctcgcagccg    10740
gtccttccgg ggtccagctt cccgaaggac tgggcagccc cggggcgaac ccctctggag    10800
ctaccaggag aacgtgcgac cgggttcggc gccccagccg gcaagtgagc gcccagcgga    10860
gcgcaagggc ggggcccgcg cgggccgag acgcccgttc gctgtcggcc aaccagcgcc     10920
tgtctctgaa cagccaatga acacgcgtct tacagccaag gcgggtcgg gagcgaggct     10980 gcggcgagtg cggcgctgac agagacgcgc gcgcgcgcga tcgcgctcgg accccggccg    11040
ctgccgccat cactgtcgcc cgcccagtcg cccctcagcc gcttcccctc gccatggagg    11100
cgaggccgcc gccgccgccg cggggctcgg agccgcgggc cgggcggcgg ccctgagggc    11160
tagtggcggc ccgaaacgcc gccgcggagc cgaggcggag ccgctgtcct cgtcccagc    11220 ggtcccgccc aacgcccgac tctgtgagtg ttcgcggccg ctgcgccggg gtgggctccg    11280 gaaggggag cggctcccgg gggcggtggg aggggtcccg ggccacagcc cagagcccgg    11340
agcccgaagc cctaagccat cttttccggg tagaagcctg cgggcgcctg caggttgatt    11400
gtgcatcctt gcgggtccgt cgcggggagg gggtccccgg aaacgtgccg gcccgagtgc    11460
cgacccctcg cgactgccca ggaactttgc atgcgtcctt ctgggaccag gccagggcac    11520
tgccagagtt gattctcaga gaagaaactt agaacggcga aacagaatt tgctcaggtc     11580 catttaatgg gaggaaagag gaaaactctt ggcatgagaa aatttgcttt tgcagtgacc    11640
aacttttctt tcccttcaag tccacctccc tcggtccccc ggcccgtctc ccaggccct     11700 ctccttgccg ccctctccca actgttgagg ctgtttaaga agggaaataa gggctgagag    11760
ctgcccagaa ttcagaatag gccaattgag aacgcaggtc ccctcccttt ttactttcgg    11820
taaataaaaa attttttttg aaaaaattag ttactaatta tatctcctga agattaaaaa    11880
aaaaaaatag cagagcagag tcctgtcttg agggtttcgt ttttatttt gagatcactg     11940 atgatatttg taagacagga aaagaagaat gtgcaaatcc accctctgca gggtgaacgc    12000
catcagaagc ctttgctcag gagagggatt ccggctctag aaccagtcca catcaccctg    12060
gagatggctt cgtttgccac ctgctagctg tgcaggcagc ctgagaaaca aagatggtg     12120 ggcgagagga ggactgacta ggaaagggcg aacatcttcc tgcctggcca ctccctttcag   12180 aaacagatct gatgctgtca cttgtttact taaaaactcc ctcgcttttc tttttcccat    12240
gggatgaatg aagcctaaaa tgccttatca ggtcatacaa agcccttgac aatcttgcct    12300
caatttactc ctttactttt agcctaatcg gatcctccaa ttctccttcc cctcatcccg    12360
cttgctggct agtattcaga gctgcttgac tgcccctca catgttggga tgttttgtt     12420 ttatgtgatc ctctttcttc cccacctta cctgccaagc tccacttttt cttttaaagt     12480
tcttctcatt tgagaagctt cttgcgggca ggagctgtgt cttgcccacc tttctatctc    12540
ccgtggtggg agaatcctcc aagttgtctt gtagattctt tccaatctct tctctcttat    12600
gcctaggctc tgtttatttc ccggtatcca cttcccaaga gattttttcg tgttttgaag   12660
gcctgcttgg agtacatgcc caggactttt agtatttctg attcccggct tccccatgtc   12720
catcccaccc agcccccata agcagtcagc aggtgggaac tggtaggtcc catatcccac   12780
tggcctccaa aaaactgtct ctgaaagact aaaagccctt cagtctcttt tcacctctgc   12840
ctgctcaaag tgacctggct gataccgtgc attgtaaggc atggtgggat cccgggcct    12900 gttctctgtt tagccactta acatctgggt gaaatacaga accagaaaaa ccaccctct    12960 gacttcagta cattcatgtg tcttccctt gccaggtgaa ttgcttggga tacaaaagtg    13020
```

```
aggaagtcag tccttaacct ttgaggaact cagagtctaa tgtaggacag gtggatataa   13080
atacatcaca ggtgctataa gattgtgata ataataatag ctattttta tttgccttgt    13140 gacaagctat gtaatgtttt ccatgaattc cctcagtctt ttcaacagtc ataaagggc    13200 ttattcctac tctacagggt tggaaactga ggccaaacag tgggcaaatg agggaatagt   13260
caagatttga attttggccg tgtatttgca gagcctctgc caggctgtgt agggagcatc   13320
ccctgcctgg gtgatttggg aaagctttcc tgggacgggg gggccttcgg atcatgaagg   13380
atgcatagga gtttgcgcgt ggtggactgc acacataggc aagagggagc agcacaagca   13440
aacttggtgg tggaaggaat ccactgtcct tggggaggag ggaagaggtt aatcatagct   13500
ggatcaggta aggacaatgg agagctacta gaggatttaa aggaggtcag ggacttgggc   13560
tgaaagaatt ttggaaagat catttggggg caatataggg ccaaatgcag atgcccctgc   13620
aatataggag gcactggttg ggtctgacag aggtagagtc acagcctctt agacccagag   13680
gaaggtgtag agagaatcct gctcaatttt gggaaaagat aattaatgca gatgagagaa   13740
aaattcaaaa gttctagcaa tacaaaagag tatatagaga aaaatgtccc tcctaccctg   13800
gccccaagtc tcctgtctcc ctaacctcct ccccagagat ggctgaagtt ttcagtttat   13860
atggccttcc atagacactg ttgctttata aatatgtgcc tgcttatcca tactcctccc   13920
accatgggac gtaccactca caccttactg ggtttttta cttaacatat ttaggaaatc    13980
attctattat caacatatat agagagttat ttgttctttc tgttgacatg cttttactta   14040
tttagttgta tggctgtact gtaacatctt tgggttaaat atttgtttcc aggttcttct   14100
cttacagcaa tgaatgtcct tgtacatact gtgttatgtg ctcatttgca aagttatctg   14160
aacaatatgc ttttagaagt agaattactg ggtcaaggga tatgtctgca ttttttgattt   14220 gcagacatgg agccaaactg ccacccgttt ctgggggggtt gtaccaattt atcctctccc   14280
ccaaagtgta tagctggata gatgatcttt ggagaattca ggaggatcaa ctacgatgct   14340 tttttcagcta ttatatgcct acttttcctc cacaaatcct cccccaccct atgcgattct   14400
agccagtttc tttgaattta cagagggaga tgttgaggct cagaaggata aaagtaactt   14460
gtgcaggatg atcagtgcgg gtggtggtgg gtgttttgtt ttgtattttt gcacccctca   14520
tgtttgtatt tgccagcacc tttcattgga ggtgctcagt gtcagtttgt aaacattatt   14580
gcattatttt tctccatttt cacatggaaa aaaatgagat gcaggggaag tttgagttat   14640
gagagggaaa ctggccaaat atagaatctt gtcattttac ttccagtgca ataataaatg   14700
tttccaaatg acaaagctga agagatgttt tttgtttgtt tgtttgtttg tttgtttttt   14760
gagatggagt tttgctcttg ttgcccaggc tggaatgcaa tggcgctatc ttggctcacg   14820
caacttttgc ctcctgggtt caagcgattc tcctgcctca gcctcccgag tagctgggat   14880
tacaggcatg tgtcactgta cctggctaat tttgtatttt tagtaaagac ggggtttctc   14940
catgttggta aggctggtct tgaactcctg acctcaggtg atccgctggt cttggcctcc   15000
caaagtcctg ggattacaag catgagccac cgtgcccggt gaagaaatgg ttttttagtg   15060
agtctgagta caacaaaaat agcaataata taacactaac ttaataaaac tgaacagcag   15120
gcccaaaaat agcccaacat taaaatttat tttaatgtat tctctatgga aaagagaatc   15180
cattaaatgt aaaactattt attttactct aaattcacat ccatttgtgt cagtgtacaa   15240
gacataattt ttatagtagc agtcagtaca tatagaatat gattttgaa ttcttcaata    15300 gcataaaata ttttatattt actcatttaa gtatttgttc atttaaaatc acaggctggg   15360
tgcggtggct cacgcctgta atcccagcac tttgggaggc tgaggcaggt ggatcatgag   15420
```

```
gtcaagagat caagaccatc ctggccaaca tggtgaaacc ccatctctac taaaaataca   15480
aaaattagct gggtgtggtg gcgcgtgcct gtaatcccag ctactcggga ggctgaggca   15540
tgagaatcac ttgaacccag gaggcggaag ttgcagtgag ccaagatctt gccactgtac   15600
tccagcctgg cgacagagcg agactccgtc tcaaaaaaaa gaaaaaaaaa atcacagtat   15660
agtattccat gcatcgacag ctgtagtttt ttttaaattt gttttgtttt ttttgagaca   15720
gggtctcact ctgccaccct ggctggagtg cagtggcatg atcacagctc actgcagcct   15780
tgacctcctg ggctaaatga tcttcccatc tcagccacct gaatagctgg gactgcacag   15840
gtctgtgcca ccacgaccag ctaattttt tattttttgt agagacattt ttatgttgcc   15900
caggctagtc ttgaactcct ggactcaagt gatccacccg ccttggcctc ccaaagtgct   15960
gggattacag gtgtgagcca ccactctcag ccaacagctg tagttggtgc aatccttttt   16020
attcttttat ttttttctac cttttttgcta ttataaatgg tacttttata ccccttgttc   16080
aaatacttct tttggattat ttccttggac tcttactccc aacctgggct caccaagtca   16140
gaggatacag tttcggtgcc taattgcaat ctggaaaggt tgaactagtt ccagcacta   16200 tcagcaattt atggggccat ttcttgacaa cccatctagt gctattacaa agaaatgtaa   16260
tgataccttg aattaggttt aatttacatt gctttggaaa aagagaccag tagctgattt   16320
agattttttg aaagaagtac agtgctgtga tatagattat ctccaagatt tatgtaactg   16380
aagccaactt gtggttgaag aaagatttgg ttgatgagat tgaaatattg tggaagttta   16440
gaataggatc atagcagtat aaaatataag gctagatgct gttcagttgg aaataccagg   16500
cattgtgccg gaagctgggg acaccccaga gtaacataga tgtgatgtct gtcctcatga   16560
cacttttagg ttagtgcagt agacagacat taaaatcacc tatggtaatt atagatgtga   16620
tgaaagggga agaatagggt gtcgggagtg tcagagaagt tcagcagcta aacaacattt   16680
gcagttaaac atttgtgaag gccctgagct gagaagggat ttggtagctc agggcagcgc   16740
ttcgctaact tgaatgtgct catgaaccat ctgggaatct tgttaaaatg ccaagtcctg   16800
aatcagtagg tttggggtgg gacttgggat tctgtgttac taaccagctc ctgggtgagg   16860
cagatgctgc tggtgggtgg atcacacttg gtgtagcaag gcctaattga gagcttggtg   16920
agcacctaaa actggctgac catggtgagc aggaaggggc aggtggcttg cagtgacaga   16980
gtaattctct gcctaggctg cactttagat tcacctgggg aacttagaaa aatcagggtt   17040
gcaaatgccc cacccgcagc cattttaatt taattggtct cagttggggc ctgagaatgt   17100
gtatacagtc atgcacagta taacgatgtt tccatcaagg agagactgca tatgccacag   17160
tggtcccata agattataat ccataatttt actatacctt ttctattttt agatatgttt   17220
aaatacacaa atactcactg tgttagttac ttacagtatt cagtacagta acatgctgta   17280
caggtttgta gcctaggagc agtaggctat acaatatagc ctagatacgt agcaagctgt   17340
accatctcat tttgtgtaag tacctttat gatgtttgca gaattatgaa atcacatcag   17400
gactcatcct cagaatgtgt tccattgtta agtgatgcat acctgtatat atattttaac   17460
tccccaggtg attctaatgt gtagccaggc ttgagaacta gagactaagg acagtgttga   17520
gactagagaa tggcaaggag cagagttgag ggtcctgtat ggcatgcaag gattttggac   17580
tctatcctga aggcagagct aaatcttga aggattttta agcaggagag tgaactgatc   17640
tgatttgcaa ttgttaaaaa gttcactgtg gctgtagtcc agagcagtag ttttcaaatt   17700
gaggtagata agatgatcca ggggaactgg aagaaaattt agaacttttt attgttttta   17760
tctaaaagat aagataaaac atttaattta ggaattgtct ctggcatctt cttgggtcta   17820
```

```
taggtcaaac agttaatgtg ttaactgtag aactttgggt gtcctgaagg aagagactga   17880
attctgcagt gagcagagac atatttatac atttgttctc catgtattgc aacatgttgt   17940
taacagttta tattaaccag ttctcattga actagccttt acaaaatgga catgcagaga   18000
aaccagtgat caaagaaaat actaataata caagcacaag caaacaagtt gtcagagctg   18060
acacttgtcc aactcctgtg atgaattctt ggtgagctat tcaaataagt cagctcttac   18120
taaattggaa agtatcagga aatttataag aaacatgaac tttcgtgctc tgtcattaat   18180
aggaatcttg ctttaagatt cctttaatc gtatgtagaa cccagctgca cggtggctca   18240
cacccataat cccactgttt tgggagcctg aggtgcagga ggccaggagc tcaagacaaa   18300
cctgggcaac atagcgagac cccatctcta ccaaaaataa aaattagcc gtgtggtgtc   18360 acgtgcctgt agtcccactt acttgggagg ctgaggcaga ggattgcttg aacccaggag   18420
ttcaaggctg cattgagcca tgattgcacc actgtactcc agcctggggg acagagggag   18480
actctgtgtc tcaaaaaaaa aaagaggagg accgggcata gtgggtcaca cctgtaatcc   18540
cagcactttg ggaggtcagg gtgggtggat cacaaggtca agagatcgag accatcctgg   18600
ccaacacagt gaaaccccat ctctactaaa aatacaagaa ttcgccgggc gtggtggcgt   18660
gtgcctctgg gtaatttcag ctactcggga ggctgaggca ggagaatcct ctgagcccag   18720
gaggcggagt ttgcagtgag ccgagatctc gccactgcac tcaagcctgg gtgacagagc   18780
aagactctgt ctccaaaaaa aaaaaagtat gtaaaacctt gagatattaa ataataaaat   18840
atgaggctgt caccagtatg aagacatttg aaaaccaaaa atttggaaca taaaaagaac   18900
ctctacattt tttttgcagt gatgtttaaa gataaaggat attccatcag atgctttaca   18960
aaattttgct aacttcaatt attaaaattt atattttgag ggttttttgc ttttaagaga   19020
cagggtctca ctctgttgcc caggctggag tacagtggca caatgatagc tcactgcagc   19080
attgaactcc tgggctcaag cgatcttccc accttggcct tccaaagctc tgggactaca   19140
catgtgaacc accatgcctg gccagttttt aagtttattg ttcttataaa agacaaaatg   19200
gggccgggtg cagtggctca tgcatgtaat cccagcactt tgggaggccg aagtggacgg   19260
atcacttgag gtcaggagtt tgaaaccagc ctggccaaca tggcaaaacc ctgtctctac   19320
taaaaacaca gaaattagcc aggtatggtg gcacacctg tagtcccagc tactcgggag   19380
gctgaggcag gagaatcgct tgaacctggg aggcggagat tgcagtgagc tgaggttgcg   19440
ccgctgtact ccagcctggg agacagagcg agactgtttc aggggaaaaa aagaaaaaag   19500
acaaaaaaac acataccctt ggcagattct tcctgcccca cccccaaaag gcccacttaa   19560
acaaaaaatg gactgatgta ctacatggaa ataattttg tcaggaaatc aaaatactgt   19620
tggaagatgt atagaaaaca ttgctgaata tgtgaacaaa caatattaga acaaattttg   19680
cagtgtggga agtttggtat acggttataa aagtacagaa gcttctagca tgtctcagta   19740
tcgctagata ctcttttttt tcttttcttt ctttctttct ttttttttt ttgagacagt   19800 tttgttctgt cacccaggct ggagtgcagt ggcaccatca tggttcactg cagcattgac   19860
ctcccagtct caagtgatca tcctacctca gcctctcaag tagccaggac cacaggcatg   19920
caccaccata cctatttttt ttatttttta tttttaggag agatgaggtc tcactatgtt   19980
tcccaggctg gccttgaact cctggctcaa gcaatccacc tgccaaaaga ccttccaaag   20040
tgctgggatt acaggcatga gccaccgtgc caactgtgcc aggcctagat tacctttaa   20100 tagttacatc caagaataag gaccacttct tttgtgagct actggaagaa agttgtactg   20160
gagaagacat attttaata gtaaatgatt gccttcataa gaacattact atatggaata   20220
```

```
atagactgaa tgtaaattaa tggaacagct gctttgactg aacaaaagaa tgaaattcat    20280
tcattacttc tctatgggca ggctgttgag tccacttatt tgttaattat cttgtggtag    20340
agttgttgat gagttttgca ttttttcttt ttaaaaaaat gccaacttt tgttatggta     20400 agtggctaca gtttgagtaa tcctaatatg aaatccaaaa ggcttccaaa tccaacactt    20460
tttttttttt ttttttttt tgagacaggt tctcactctg tatgtagccc aggctggagc     20520
gcagtggcat gatcatggct cattgcagcc ttgacctcct gggctcgggt gatcctccca    20580
cctcagcctc ctgagtagct gggactacag gcatgcacca ccatgcccag ctaattttgc    20640
aaccagtagg aataatgcaa atagtacaaa atctgaaaaa tacctaaatc tgaaacactt    20700
ctggtcccaa gcatttcaga taaggaatac tcaacctgaa cctagcaaat atcatttgaa    20760
aaaataatat cttaatctgt ctcttcaagt aaaagtatta tttaaatagt gagtgaaaaa    20820
ggaactactt ctttcttag aaagaaatgt gcaggccggg cgcggtggct cacgcctgta     20880
atcccagcac tttgggaggc cgaggcgggc ggatcacgag gtcaggagat cgagaccatc    20940
ctggctaaca cggtgaaacc ccgtctccac taaaaataca aaaaattagc cgggcgtggt    21000
ggcgggcgcc tgtagtccca gctactcggg aggctgaggc aggagaatgg cgtgaacccg    21060
ggaggcggag cttgcagtga gccgagatcg cgccactgca ctccagcctg ggcgacagag    21120
cgagactccg tctcaaaaaa aaaaaaaaa aaaaaaaaa agaaagaaat gtgcaatggt      21180
agagcgtttt cctcgttgga atttttttta catgtaatca ttataagcta taacttacat    21240
attataaaat tctcctttt aaaatgtaca gttctgtggt ttttgtata tgcatagagt      21300 tgtgcagctt ttgccactgt ctagtttaag aacatttcat caccccaaaa gagaccctgc    21360
acccattagc ctcacttccc attctctcct ccctccagtc cctggcaact actaatcttc    21420
ctgtttcttt ggatttgcct attctggaca tttcatataa atgaaatcat acaatatgtg    21480 acctttgta gctggcttct tttacttagc ataatgtttc tggggttcat tcatgttgta     21540
tcatgtatca gtacttcatt ccttcttatg gctgaataat aatccattat attgatatac    21600
gacatttggc taactggttc atcaattgat gaacatttat ttgtttctac ttttggctt    21660 tatgaataat gctgctgtga acattcatgt ataaattt gtgtagtcat aggtttaat      21720 ttctcttggg tatatatata cctaggagta ggattgctgg gttaaacggt gactaacttt   21780 gagggctgt caaactgttt tgtaaagtga ctacccattc ccagtagcaa ctcacaaagg     21840
ttccagcagc aatacaatag gggtccagtt tctcccagca atgcttaggg gtcccaatgt    21900
ctcccatctt tgccaacatt tgttactctc tttttgatta tagccatctt agtgggtgtg    21960
aagttgtatc tcattgtggt ttttatttgc atttccatga tgatttatga tgtgcatctt    22020
ttcatgtgct gttggccgtt tatgtatgtt ctttggggaa atgtctgttc agatacttgg    22080
ctcattttaa aatttagtta ttgctctttt tattattaag ttacttatat atttttagat    22140
ataagtccca tatcagatat acgatctgta aatatttttt cccatctgtg ggttgtgtgt    22200
tcagctgttt gcgtggacat atccttttgg gtagatctag gagtggaact gctgagtcaa    22260
atggtaactc tctggttttt tttgttttt ttgttttttt ttttttttga gacggagtct     22320
cgctctgtcg cccaggctgg agtgcagtga cacgattttg gctcactgca agctctgcct    22380
cccaggttca tgccattctc ctgcctcagc ctcccgagta gctgggacta caggcgcccc    22440
ccaccacatc cagctaattt tttgtatttt tagtagagat gggatttcac agtgttagcc    22500
aggatggtct cgacctcgtg atccgcccgc ctcggcctcc caaagtgctg ggattacagg    22560
cacaagccac tgcgcccggt ttgaggaacc actgactttg ttgaggaaca gaaagaacgc    22620
```

```
ctgcaccttt ttacaatccc agcagcagtg tatgagtgta tcagtttctc catatccttg   22680
tcaacacttg ttgttttttt taactgtagc catcctagta ggtgtaaagt ggtattgcat   22740
tatgttttaa tttgcatttc cttaatgact catgatctga ctgtgatttt gttgcatcta   22800
taaaattctc ataatttgac acatgaaaac cttagaaaca attttgtaac ctaataaaaa   22860
tctccaaatg tgtttctaaa acatttccca gatgatctaa tgaagtaaag aatctaggca   22920
ttggtcacca gtggctgtta aaaccattag ggaactttat aataaaggga tcagtgtgac   22980
aatcttctga tcaatcataa catctctaaa attgggacaa ccaaatctta tattctttct   23040
atgtgatact aggaagaaca tatcattcat gaaatagtct tgcttgcccc aacaaacaga   23100
gtcaaacctt cctctgatta gtgtagatct gattactggt ttataggata taattggcaa   23160
atttagaatg tgaaaaatat ataggacaaa tgaacccat ttacttcaaa tgaatggcaa   23220 gaaaaaaaa gtacacgaac tgctacagat taaaaagac ttgaggctgg gcgtggtggc   23280
ccacgcctgt aatcccagca ctttgggagg ccaaggtggg tggatcatga ggtcaggagt   23340
tcgagaacag cctgaccaac atggtgaaac cccgtctcta ctaaaaatac aaaaattagc   23400
tgggcgtggt ggcacgcacc tataatccca gctactcggg aggctgaggc aggagaattg   23460
cttgaaccca ggaggcggag gttgcagtga gatcatgcca ccacactcca gtgtgggcga   23520
cagagcaaga ctctgtcttg aaaaaataa aaaagacttg aatgaaacat attaattgaa   23580
cataagtata gatcttgttt agatcctgtt tcatgcaaac caactgtaaa aagttattta   23640
tgagcccatt gggagtaatt taaatttgaa aaccacttgt atattagatg atttttaaac   23700
aattttaatt tttttaaaggt tattatagta gtatggttac attaaaaaga aagactcctt   23760
tctcttacag ataggtactg aagtattttg gatgaaatga tgttgatatc tggaatttgc   23820
tttaaaataa ttcagcatgt ttggaggatt acagacgaga caagaattgc catacgttga   23880
taattattga agctggataa taggtatata agggtttatt atagtatttt ctctactgtt   23940
gtatatgttt gagaattccc atagtaaaaa attaaagag aaaccactgt aagggaagag   24000
ttttagtgga tttcatgtcc atttgttaga aatagaaaaa tgtggccagg cacggtgact   24060
cacacctgta atcccagcac tttgggaggc cgaggcgggc ggatcacctg aggttgggag   24120
ttcgagacca gcctgaccaa catggagaaa cccccgtctc tactaaaaaa aaaaaaaaaa   24180
tacaaaatta gcctggcatg gtggtgcata cctgtaatcc cagctactcg ggaggctgag   24240
gcaggagact tgctttaacc tgggaggtgg aggttgccct gagccgagat cgcaccattg   24300
tactccagcc tgggcaacaa gagtgaaact ctgtctcaaa aaaaaaaag gaaaagaaaa   24360 aaaagaaaaa gaaataaaaa aatgtagtat ctttgattaa ttttcaaaag tatatcacag   24420
aagatagata tttgctagcc atatttaaaa ggaaatattt gtataatggg ggtgaaaaaa   24480
tgattatcac agtttagtaa acacagccat agtgcttctt cctttggatt catgtttctt   24540
tttggttatg atagcattaa aacttggaat caggctttta aattgctcta taatatatta   24600
aaatgagatt tttcaaacat aatgagaaat atttaatcat atggattgca ctaaatatt   24660 tttaagatgg gttttacatt actattttaa ttgatggaag taccattatt gtgatcatta   24720
tgtatttcat ttgaaatgtt ttgtagtatt tataggtatt agtacctgtg ttctgtttat   24780
aaatgaacat gtgttgggga tgtatactct tatttattgg tggatgtgca gtaaaaggtt   24840
tgtttgtgga gaacggactg gcagggtat agagacttat ttgatgttta ttagagcaaa   24900
tgtggccagt gatgatggtg ttctggattg gcttagggtg ggaggagtgg tgataggggat   24960 ggagatacat ggacaagtat gatttaagca gtagaggcat tagggttcta gatttctggc   25020
```

```
tttttggaag agatgattgc tagttaatga actgagcttt tgtgtgtggg aagaagttga    25080
aacctggccc ctgtgaattg tgcaagtagt tcttaaatat tgattgacaa atagcttaac    25140
gagcaactaa ttttcaaata ttggttgaca agtggcttat tacaatattg taaatgcatt    25200
gatactacca ttagtaaaga gaatgtcttc ctttgataat gttagcagca ctgttaccag    25260
agcagtgtgg gatagttcca ggactttcac tgtctaaaag gaactggagg cccaagcttt    25320 tacgggata cttctgctct cctggttccc atgtcccag tgatgtgaat gtccctgact       25380
cagtgcctct gctcacgctg tctgtgagat cactgccttc cagtgcctct tacctcttgg    25440
gcctgcccac tttgttaaca gggacagatt tcacagtgat ttccagccag tatttctctc    25500
tccccagttt ggggtgttag ctagaatggt ccctcaaagc cctcaaacac ggatgagaaa    25560
tagaagaagc tcagggagac tatacctggg ctaggttctt gctaccagct ggtggaagac    25620
aaagaaaacc ccttttcttc ctgtatttca tgcccagtga gcagtagtgc catcagcagc    25680
agttgtgaac ccctaaatca gtgattctca atatgactga catggtgggg aagacgtaag    25740
tttgaaaatg cattttcagg ctaggtgtgg tggctcacac ctgtaatcct agcactttcg    25800
gaggccaaca tgggaggatc acttgagccc aggagttcga ccagcctg ggcaacatag      25860 tgagaccctg cttctacaga aaaataaaag ctagccaggt gtaatggcat gcacccatag    25920
tcctagctac ttgggaggct gaggtgggag gattgcttaa gcccaggaga tcaaggctgc    25980
agtgaacata ccacagcact ccagcctggg cagcagagtg agacccctgt ctcaaaaga    26040 aaaagcattt aaaaaaaaaa aaggtttgtt agtgtttgtc tcaaaatttt gcttaattta    26100
aaattatgta tatatttgaa taatatgtgt ccatgttaat agttctaaaa gtatatatag    26160
tatatatagt aaaaggtagt tttctctccc cctgcctttc agctttccct ttccataggc    26220
atccacaagt actatgagca atacttgtga aaccatgctg aaatactaca tgctcataaa    26280
atgtaagtta cttaagtttg gtatttcaag taacaataag ggaagatagg agagttttat    26340
gtttatcaaa aggggtgaat gttatagcag attgagatga gatgttctta cctttgggtg    26400
ggatcttaag tggagctcaa ttcggttttcc ccaatgttag tgggagagat tacttaaacc    26460
atccatactt atccagttgt acttggtaag ttttcaaagg ttctactttg aagagggctt    26520
ttgttgagca agtagtggtt aatagagcag ctcagttaca tgtgtaagtt ttttgatgtg    26580
ggaaaagggc ttttgtatac agaaggacta ttttaaaatt atttgggctt taaattaaca    26640
tgtattaaag tggtaaattt aaaacccagt tttcttttag tcttgttatt gtacttgtaa    26700
gcataggcat tttgtataga aataagaata gtaattttca cctgcttgtc aattaagtta    26760
atataaattt aacagattta attgctccag gccccttact tagtgaatta aatttcctta    26820
gatgtttaaa atacatttac acagtcagtc tgtcaggcac agtcagtcct tgacaggtca    26880
gagttaccac cttaaacaga aacttcttaa gctcttgggc aatctgtgat actaagaaat    26940
taaatttgta aatgtagtaa aacaggtttt ggttaagact tccagtgctt ttcattagct    27000
gaatctgaat taccaacatt taaaaaacac ataccctaaa cttaacgcaa aagtactact    27060
agtaccatga gtttgatata ccatacctca ttttattgct catgtctttt ctttctggga    27120
ttgtgatgcc acttacccaa ttaaggagga cagttttatc atctcagaaa gccatggtta    27180
tcagattaaa aatacagaat catgatacag ttattattgg tcagagattt gagactggga    27240
aagggaacta aggggtctgt gtttccagga taattctact caagagatgc tgtgcctttc    27300
cttatgttaa gagtcctgaa tgtggcatca aaggggaat ccatgttcag agtttgtttt      27360
gcaacccccc ataccttttt ttgagacagg atcttggtag gttgcccatg ctggtgtgca    27420
```

```
gtggtgcaat catggctcac tgcagccttg acctcctggg ctcaagtgat cctcccgcct   27480
cagcctcctg agtaagtagc tgggaccaca gatgtacgtc atcatgccca gctaattttt   27540
tgattttttt ttttttttttg tagagatgag gcctcactat gagcctagga tgatctcaaa   27600
ttcctggcct caaacagtcc tcccgcctca gcctgcccaa gtgctgggat tacaggcata   27660
agccaccatg cctggccttt tcttcaaaaa taacccttca atcaattttt ttttcctgg    27720 tcaaattgga ttttgtgttt cttttatata ttccttgtca ggccctacag ttatttaat    27780 tttgggtgtt ggatagacta gggttcatat tccatgcctg ccatgctttt tgtgaacttg   27840
ggcaaaatag ttagctcttc tgagactcac ttttgtcacc tagtaaatgg gttcagctgt   27900
agtactctat gtatttgttt gttttaagca ttagatagtg cgtggtaaat gcttagcaca   27960
gttcttagca catagtaaat ctttaataaa tgttagaaaa tataatgatc ttgattctct   28020
gtcttccctc cctagtagtt gatttggggc acagtgtagc attatttgaa ttatcacaga   28080
ataacttttt acctttctga ttttaacagg ggagagtgtg taaaggatgg gagagggaag   28140
agagaaaaaa gctgagtaaa tgtgatcaac tttacagtct ttattccctg aactatcttt   28200
ccctgagtta tgtgacacat tctccttgtt ttcctctttc tatctttgtg ccactcctc    28260 agttccctag gcccctcttc tttgaccact ccttgtttga gttaccaaag attccatctc   28320
tggccttctt gtgttgattc tacacgttct tcctggaagc acatgtccat ggtttcagct   28380
tccttgctaa ttaggagaaa ctttgtcctc agaacccatc tggattacag ccaacagcct   28440
actggtctcc attgggctat ctcccaggta cctataacag tctcagaact gactcatctt   28500
ccttttcagc gtgttatttt tataatctct atcttgatga atggcacaac acagtgaccc   28560
aaactggaaa cttgaatgtt gttcatctgg ttggtgatct gttcctaact gttttacatc   28620
tgtaacattt ctcaaatttg cctatttttcc accatttctc ctatccctta attcaggctg   28680
cttctcacct agatgactgc tgcaggttcc cttgttgtct actcattatt agtttctcat   28740
tccaagtcat tgattagatg gctgccaaaa gtgatctctt taacttccca actttagatt   28800
ctgtgaataa aatccaaact ccttaacaga gcaggccctc atgatccaac tcctcttaac   28860
gttggtagcc ttatcttttc tctgagccca ctgccgcttg atccttggtg gtgctgtgct   28920 cttcttgct ctctgtcttt ggttggactg cccacctccc tccttcttac ttgacattat    28980
aatttatcag atagagatca gctcctccag tcagcatttc cttactgact actccaagtc   29040
tgacccagtg tagattctgt gcttatatct gtcaagtcac ttattgtatg ataattcata   29100
cacttatatg ataattcaca cattggcatg tgtagattaa acatttatag tctcagaagg   29160
atcctgatag tccaaaaggt atagtaatgc agttgtctct tagtatcttc aggtgattga   29220
ttccaggatc cccccccatgg agatcaaaat ccagggatac tcaggtgcct tatataaaat   29280
ggcatatttg catgtaacct atgcacatcc tcctgtgtac tttataggcc ctaaataatc   29340
tccagattac ctatatggct aaaacaatgc aaatactatg taaatagctg ttatactgta   29400 ttttttaagtt tgtttcttat tttatggttt tatttgttta ttttttttgat ctgtggatgt   29460 gcaacccaca gatagagagg gtcaactggg ccgggcgcgg tggctcacac ccgtaatccc   29520
agcactttgg gaggctgggg tgggaggatt gcctgaggtt aggagctcga gaccagcctg   29580
gccaatatgg tgaaaccgtg tctctactaa aaatacaaaa attagccagg catggtggca   29640
ggtgcctgta atcctagcta ctctggaggc tgaggcagga caattgcttg aacctgggag   29700
ttgaaggttg cagtgagcca agatcctgcc atagcactcc agcctgggca acagaatgag   29760
actctgtctc aaaaaaaaaa aaaaaaaaaa agaagagagg gccaactgta tgtaatttac   29820
```

```
tgaagcatgg attcacatta tagatggtcc ctgatttatg atggttcaac ttatgatttt   29880
tatactatga tggtgggaaa gctggtgtga tatacgtatt cagtagaaat tgtacttcca   29940
attttgaaat ttgatctttt cccaggctag tgatatgcag tgtgacaatt tctcatggtg   30000
ctgggcagaa gcattgaccc acacctccca gtcagccatg tgatcaggag ggtaaatgag   30060
tatactccat ggtgtactgt gttgccaggt gattctgctc aactgtatgc taatgtgagt   30120
gttctgaaca catttaaggt aggctaggct aactatggca ttcggtaggt aaagtgtgtt   30180
aaatgcattt cctacttaaa cgatattttc agtttatggt gggtatattg aatatagcc    30240 ccattgtagg gcaaggagca tctttattta cccagttgag tttagtggca gcagaactaa   30300
gttcggttta gctgttcagt gagccaagcc tcacttagca tctaattctg tcttttatttt  30360 ctgctttaga taggccacag ctctcctgaa gggattaaga ctttctgtgt gaaaaatggt   30420
attcagaagg aagccagcat taattctgtt tttatacatt tatgaagatt tgaaggaatt   30480
tcactgtcaa ttctgtctta attgtattct gtataataaa tcataatggt atccaacggc   30540
tcttgaaagg tttggttttt gtgaacattt ctttgaatgt caaagttgta ttagtttgtt   30600
tctcaattaa actgggtgct ctttgagggc agggatttat gggacttgtt tgttttgcag   30660
ttttatatct ccagctgcta atgcagtgcc tggtttgtag taggaatgag agatttactc   30720
caatagaacc atactaaaga tcttacactt atggattaca gttgatagct ttgtagagtg   30780
aactggtatt ccctttaaat gagacgacat gacctgagta taaagtataa tcaactacat   30840
gactccagca agaataccat gtgtccctca gatagcatag ctggcagatg gagttatgca   30900
catcaactgg acatttaaga cagctggaga tttcttacat ttagatgaca gtttagatta   30960
gaaatattta atcttagctg tacttaatat attatgtagc tatatgatac atcatgtata   31020
tatggtatat catatatatc atatatttaa tcacatttaa tccttagcta tattttcatc   31080
cccaaaatgg tatatggatc tgttttatt gtcagctggt tatttattgt tgcttatcca    31140
tggctcatga aaatcttcat gttacttggg aaatctttca ctctgccttt tgaaggacag   31200
cccagaacca tttccttctt ggcacatgac cttctaaccc agtgaccaaa gagtatgtaa   31260
aagcatggta cacactgctt ttgaagatta cgtgtgtcta ttctagatgt gtcttatttc   31320
ttgcagatat attgcctaca aagatttga tatatatata tacagtagac tatactatat    31380
aattaatatt tataccagat attaaatata taagcattct actagaacta agttaagaa    31440 tttgaaatag tctcatgtga gtaattaaaa taacaatagc atcttttttca agaaagtttt  31500 ttttaatatg gtggagataa tgacatggaa aaaagtagtt aattattttt ggtattcccg   31560
tatttcatca gtaggttgcc atagaacata atagttatat aatcaaacag cagaataatt   31620
ttatatgagg tttattgata cagaaatgtt tggttcagtg tttgtcttcc agttttgcag   31680
attttctttt cgattttaaa actggagaat acattaaaac cagaaacttt cagcctctat   31740
aatgccctca aaactcagca ggttttgaaa atgcctcttc cttctcttct cctccccata   31800
atcctgctta tttttggcat taagtgagtc aggggttcca aacccaaata cgttttcaa    31860 ggctatgtag tcagtgtgaa tgagagaagt aaatctgttg ggtcctgtgc cacactggag   31920
tttccaaggc tggtctaaat gagttcaact tcagtttttt tgtgtttttt tagagatgga   31980
gtcttgctgt gttgcttgag ctggtcttga actcccgggc tcaagtgatc ttccagcctt   32040
ggcctcccaa ggtgctagaa ttataggcat gagccactgt gctggccaat tttttttttt   32100
ttagcccact gtgctaccag tttgtgatct tcactttaac tgtgaaagga ctgtcaaaga   32160
ttgtacgtat aagatttagt ttgagagcca ggcctggtgg ctcatgcctg taatcccagc   32220
```

```
actttgggag gctgaggcgg gtggatcacg aggtcaggag atcaagacca tcttggctaa   32280
cacggtgaaa ccccgtctct actaaaaata caaataaatt ggccaggcgt ggtgacgggc   32340
gcctgtagtc ccagctactc gggaggctga acaggagaa tggggtgaac ccggaggcg     32400 gagcttgcag tgagcagaga tcacgtcact gcactccagc ctgggcgaca gagcgagact   32460
ccttcaccca aaaaaaaaaa aaaaagtag tttgtctttc tctttgaaac tgaattcatt    32520
aaacaaaagc ctaaataact atactattac ttgttattta tttatttatt tattttagac   32580
agagtcttga tctgtcagca ggctggagtg cagtggtata atcttggctc actgcaacct   32640
ctgcctccca ggttcaagtg attctcgtgc ctcagcctcc tgagtagttg ggactacagg   32700
catgcgtcac cacacccagc taatttttgt attttggta gagatggggc ttcaccatat    32760
tggccaggct ggtctagaac tcctgacctc aagtgatcca cccacctcag cctcccaaag   32820
tgcataagtg ctgggattac aggtgtgagc caccacaccc agcctactac atattctttt   32880
agacccagct gaaatatcac gtaattgctg aaggctcctg aactcttcca gatcaggat    32940 tgatttcct cattttaaga ttgtcatgac aactgtagta ttgataactg tattttattt    33000
tatttatttt tttttgagac agagtgttgc tctgtcaccc aggctggagt gcaatggcac   33060
gatcctggct cactgcaaac ttagcctcct gcgttcaagc aattctcgtg cctcagcctc   33120
ccaagtagct gggattacag atgtgcacca ccaaacacct ggaattagtc tggctaattt   33180
ttgaagtttt agtggagatg gggtttcccc atcttggcca ggctgttctc gaactcctgc   33240
ctcaagtgat ccacctgcct tggccttcca aagtgctggg attacaggtg tgagctaccg   33300
cacccggctt attaccaat ttttaatgtt cagcacaact tgatcatgat gtacaatgtc    33360
ttttttatgt tatgtgttga tggagtcaaa ttaccgatat tttggttcag tttttttcaat  33420 aagagatcag gctatttct gatttcatt ctgttttttt ctttgatctg tatgtatta     33480 taagtgtctc ttattttcaa ataggttttt tctagttatc tttttgtaac ggatttatag   33540
attatacatt gtggttaaag aatatggtct ataggctggg cacggtggct cacacctgta   33600
atcccagcac tttgggaggc tgaggcaggg ggatcacttg aggtcatgag ttcaagacca   33660
gcctggccaa catggtgaaa ccctgtctct actaaaaata caaaaaaat ttagccgggc    33720 atggtggtgg gtgcctgtaa tcccagctac tagggaggct gaggcaggag aatcgcttga   33780
acccgggagg tggaggttgc agtgagccga gatagtgcca ctgcaatcca gcctgtgcaa   33840
cagagggaga ctccgtctca aaacaaaaa caaaaaacaa acgaaaacac acacacgcaa    33900
agaatacggc ctacatgcac tttcagtcct ttggaaattg ttggtattta tttgccatt    33960 ggcctagttt acccagattc cacaggttgt taatgttgta caattgcgtc ttctcttct    34020 cacttcaccc atctatgtaa tttttctgaa tcatttgaga aataagttgc aaacataatg   34080
ctgtattacc cataaatcag ggtgtgtttc ctgaaaacaa ggatactctc ctataaaatc   34140
aggaaataaa tattgatata atactgccat ctgattcaca gaccctactc aaatttcact   34200
gatcttccaa ttatgtcttt tatagcaaaa acaaaacaac agaaaccaac aaaattccct   34260
caagaaaaca aaagcagaaa aacttccctt tccccttcac ttatttctga ttcagggacc   34320
attcaggatt atgccttgcg tttagttgtc atgtctgttc agtctctttt aatctagaat   34380
agttctcagt ctttccttat tttcagtgat cctaatattt ttgaagagta gagaattatt   34440
ttgtagcaag tcccacaatt tgggttagtc tgatgtttcc ttttgaatag atttaggtta   34500
tgcatttgtg gcaggaatac caagacacg atattatgtt cttctcactg catcgtatca    34560
agaggttcat gtcaatttgt ccaattactg gttatgttta attttaccac ttggttaaga   34620
```

```
tgttggctgg caagtttttg taaaattagt ttagaggtat ttcatactta ctggttagta    34680
agtaataatg cattttgtgg ggtgatgctt tgagactata taaatagctt atttctcatc    34740 aaattttttgc ttgctagttt taccatccat tggtgatttg tgcctgaatc agttattata   34800
gtggttgcta gatggtaaat ttaaaaaatt tcattatttc ttctgaattc atcacttggc    34860
atttcttttt tttttttttt tttttgaga cggagtctcg ctttgtcacc caggctggag     34920
tgcaatggcg tgatctcgtc tcactgcaac ctctgcctcc caggttcacg tgattctgcc    34980
acctcaccct cccaagtagc tggggttaca ggcacccgcc atcatgccct actaattttt    35040 gtattttttag ttgagatggg gtttcaccat gttggctagg ctggtcttga actcttgacc   35100
tcagatgatc tgcccacctt ggcctcccaa agtgctggga tcacaggctt gagccaccgt    35160
gcccagccaa tcacttgcta tttcactcta aggaaaagct ttctctctct ggttttgtc    35220 tttgttttg tttgtttaaa aatctttaa acatatgagc acagcctcat tgattcttat     35280
tttgttcctt tttcatgtat tttttgatat tcaaattgtc ccaaatttgg ccagtgggaa   35340 cccctttcagg ctggctcctg tgtccttttt ccatgtcctc atcattcttt ttttttttt    35400 ttttttttg agacagagtt ttgctcttgt tgcccaggct ggggtgcaat ggcgtgctct    35460
ttgttcactg caacctccac ctcccaggtt caagcgatcc tcctgcctca gccacccaag   35520
tagctgggat tgtaggcacc tgccaccaca cctggctaat tttctatttt tgtttttat    35580 ttttttatt ttttgagacg gagtcttgct ccgtcgccca ggctggagtg cagtggcgcg    35640
atctcggctc actgcaagct ccgcctctcg ggttcacgcc attctcctgt ctcagcctcc   35700
aggcatgcgc caccatgccc ggctaatttt tttgtatttt tagtagagac ggggtttcac   35760
tgtgttagcc aggatggtct cgatctcctg accttgtgat ccgcccacct cggcctccca   35820
aagtgctggg attacaggcg tgagccaccg cgcctggcaa ttttctatt tttagtggag    35880 acaggatttc accatgttgg tcaggctggt ctcgaactcc tgacctcagg tgatccgccc   35940
gccttggctt cccaaagtgc tgagattata ggcatgagcc accacgcctg gtcatgtccc   36000
catcattctt tgatcacttt ttttcttact ttttggaata taagattttt ctgtgggctg    36060
ggcgaggtgg ctcacgccta taatcctagc actctgggag gccgaggctg gtgggtcacc   36120
tgaggtctgg agttcgagac cagcctggcc aacatagtga aaccttgtct ctactaaaaa   36180
tataaaaatt agccgggcat agtggcacac acctgtagtc ccagctgcta gggaggctga    36240
ggcaggagaa ttgcttgaac ccgggaggcg gaggttgcag tgagctgaga ttgcgccact   36300
gcactccagc ctggatgaca gggcgagact ccgtctcaaa aaaaaaaat ttctgggctc    36360 atctttactt ttgttatctc agtcgtggaa tcaataattt tatcagggaa ccctggttcc   36420
ttttattagt gaatgtactt agaaaataaa atatgtgcac tactagatat gttctttcta   36480
ttggggtgtt cttccttta ggctctatgt gaggagagaa ctagaatatt gttttaaaat    36540
gtaccaggta atcccagcac tttggtaggc tgaggcaggc aaggctggca gatcacttga   36600
gatcaggagt tcgagaccag cttggccaac atgatgaaac ccatctcta ccaaaaaaca    36660 caaaaagtag ccaggcgtgg tgacacgcac ctatagtcct agctagagtg agatagagtg    36720
agaccctgac ttaaaaaat aaacaaataa ataaaatata ctggaattta atttataggt    36780
atgaatgaca cagagaggcc aatattattg aaaatgtgtt actcacagtt cttctgaaac   36840
agcaggcgca ccatactatg caggaccaca tggggaagca ccagggtggg tcaggaggca   36900
gaaggaacca gaggaaagga tgggtgagtt tttttttgt taaagtgcta gaaagttgtt   36960
aggtgggaca tcccctattg agcagaaaga gaaacacaaa tgttgagatt tgtggttgga   37020
```

```
cggtttgtaa tatgattttt gtgtagcctc aaaaacacag agatggtatg aatgtaaaca   37080
actttggtcg ttaatttggc ccatcctttc aagatgccaa atcatcaatt acagaatatc   37140
aagaatgatt ataggtat gtatgcatgt ctatacatac atatatacat ctgtatcttc     37200
ctgtaaataa tgaaagccat ggtttcattc caatactctt aattctagtc caacacaata   37260
gggtttcttc tggtgtttcc cttttctgac attgaaaaat ctgaggccag cacagtggc    37320 tcttgcctgt aatcccagca ctttgggagg ccaaggcagg tagatcactt aaggtcagtt   37380
gctcgagacc agcctggcca acatgatgaa accccatctc tactaaaagt acaaaagtta   37440
gccaggtgtt gtagtagtgg tcgcctgtaa tctcagctac tcgggaggct gaggcaggag   37500
aatcgtttga acccaggagg tgggggctgc agtgagctga gatagcgcca ctgcactcta   37560
gcctgggcga cagagtgaga ctccatctca aaaacaaaac aaaacaaaac gaaaaatctg   37620
cctctccttt tttttttca ttcattcatt aattctttag atgggtctt gccctgtcac     37680 ccaggcggta gcgcagtgac acgattatag ctcactgttg cctcaagcca tcctctcgcc   37740
tcagactcct gagtatctgg gaccatacag gcacgtgcca ctgtgcttgg ctctcacatt   37800 gtcctttta ctcaccttcc tgttggtgac aatctcctga ctatgtaggc catttttcttg   37860 cccccagccc cactgaatga gctggctgat cactccttca agttccatga gccattgtta   37920
catacaggta gtactcagtt tgcttggttt tgatattcat aaatttccat tgctgtggtt   37980
taattaaata atgccagtcc tcaaatagca gttaatgaaa tacaaaatat aacctgtgat   38040
caagaaaagc ttctcaggtg ggcgtggtgg ctcatgcctg taatcccagc actttgggag   38100
gccggggcgg gtggatcacc tgaggtcagg agttcgagac cagcctgacc aacatggtga   38160
aaccccatct ctactaaaaa tacaaaaaat tagctgggcg tggtggcagg tgcctgtaat   38220
cccagctact ttggaggctg aggcaggaga attgcttgaa ctcaggaggc ataggttgca   38280
gtgacccaag atcaagccat tgcactccag cctgagcaac aagagcgaaa ctccatctca   38340 aaaaaaaaa aaaatagctt ctccaaaatt ttaaaattt accctgaccc tgaaatagtt    38400
gattgttccc tccctagaca tcattcagtt ggagctagcc taattttgtt tttttttgttt  38460 tgttttgttt tgagatggag tcttgctctg ttgcccaggc tagagtgcag tggcgcgatc   38520
tcggctcact gtgacctctg cctcctggtt caagtgattc tcctgcctca gcctccagag   38580
tagctgggat tacaggcgcg cgacaccaca cctcgctaat ttttgtattt ttggtagaga   38640
cagggtttca ccatcttggc cagactggcc tcgaactcct gaccttgtga tccacctgct   38700
tcggcctccc aaattgctgg gattacaggc atgagccacc gcacccagcc ttttttttc    38760 ccttgaggag aattacagtc tgcactgctc tcagctgaac tttacacagc ttttacattt   38820
ccctctgtca gttcctcttg taatggtggg tgggtagctg aagggaggat atgtacaata   38880
atgtattttt agttcctttg aacagagagg ttgcttcagc cattgctatt gatggcagga   38940
agtatattta tagctccagg gaaggagggg tagtacgact gctggtttaa gaaaacctgg   39000
gagattgtat ttaatatatg ttgttaaaac tcatttgtac tttattgtaa gttcttgcct   39060
tagaaatgca gctgagatga atgaacctgt tacttatgtt atattgttac ttatgttata   39120
tatgttatat gtattattgt aagtatattg actctgctcc ctaatttgga aaaatcttcc   39180
gttttgaaat tttacaatat acaataccta aaacaaagag tacttctaga gcatacagga   39240
tgtatgtgga gaattcaggt gttagcatgc aattgaacag taaagatact gactagcagt   39300
ataaatatcg tccccattta gatattttat tcataaagtt cttgttggtg tagcttttat   39360
tgtgattttt tcttttttttt ttttggatac agagtctcgc tctgtcaccc aggctagagt   39420
```

```
gcagtggcgc agtcttagct cactgcaacc tctgcctccc aggttcaagt gattctcctg   39480
cctcagcctc ccgagaacct gggactacag gtgagcatta ccacactggc taatttttat   39540 attttttagta gagatggggt ttcaccatgt tggtcaggct ggtctcgagc tcctgacctc   39600
aggtgatgca cttccctcgg cctcccaaag tgcagggatt acaggtgtga gccactgcgc   39660
ctggccaatt gtgatttttt taaagattga aaccaaaata ttttatacag atcataagat   39720
attcttggta aacactaagc acctcataac tttaccacaa ttttgattgc acaactttca   39780
cctgtggtta tcatgtgcaa tgggcacatt caacacaaat caaattattc tgaagcttgc   39840
tttctttctt ttttccctac tcccttctt aattgagggg agcaaaaagt tggtttccag   39900
ggatatgtct tctctcttat gctggtccca gattgatgca gtcatggaaa ctaggcagta   39960
aactcattct tggcagctgc cggcactggt ctgattcttt cttttaaaag catgagattc   40020
tttaataaca catattggaa agattgatgc caagtgattc caggtcatcc tagaggaggc   40080 tgggaacat tgttgaatag atttaaatga ttcagttaag tgagtgatt aacccaaggt   40140 ttgtgtctaa tttaaacagg acctataaaa tatagaacaa ttggtttgtt tcttttttag   40200
aatattgaag attagatttt aatttgagaa ttttactaat ttgagggttt tatttttgt    40260 ttttaagcgt tcaaaatgtt gaattgtaga tatgctgagt tttataatga gcacaatgaa   40320 ggttttcaa ctggcccgtt aaagccaacc cactaatgaa atgaaaatat gaatatat      40380 gactccataa tatttcatgg attttgaagc tgggctgcct gggttcaaat cccatctctg   40440 ctacttttg ggtacgtaac cttgtgccag ttacttaacc tctctgtgcc tcagtttctt    40500
catctgcaaa atgggagata gtgcagtttg agtgttccta atctgaaatc tgaaatgctc    40560
caaaatctga aactttttga atgcctacat gactgctcaa aggaaatgct tattccatgg    40620
agcatttgga tttcggattt ttgggttaag aatgctcaat tggtaagtaa gtgtaatgca    40680
aatattccaa catcttttaaa aacctgaaat ccaaaccacg tctggttcca agcatttgg    40740 ataagggata ctcaacctgt aaataatgtc tgtttcatgg ggttgtgatg tggagtaagt   40800
gagcaaagtt gtgtaatgtg cctagcttat agggaacact tagcaaatgt tggctattcc    40860
atttatatat aagaaataga attattggct gggtgtagtg gctgatgcct gtaatcatag    40920
tgctttggga ggctaaggtg ggggattgct taaggctagg agttcaagac cagcctgggc    40980
aacatagcaa gactctgact ctgcaaaaaa attcacaaat tagttgggcg cggtggttat    41040
atgcctgtag cccttgctac tcaggaggct gaagcaggag gatcgcttga gcccaggaat    41100
ttgaggctgt ggtgagccat gataatgcca ctacactcca gcttgggcaa tagagtgaga    41160
ccccaactta aaaaaagaa agaattattg atgggattgt aaaggctgaa tattaaataa     41220
attcagagga ggttttttacg gaacttattt gtgaaatatt tttaaaggaa ggaaggcatg    41280
tttgttttag gttataagaa gatggcagat ttaggaagct cctccctact ccagatgaat    41340
aagccatctg ttttctatc ccttttaagg atttgcttgg tgggtttcca taactttttt     41400
ttttttgaga ctggatcttt tacccaccca ggctggcggg cagtggcgca atcatggctc    41460
actgcaactt caatctcctg ggctccagca gtcctcccgc ctcagtctct cttgagtagc    41520
taggaccaca gacgcgtgcc accatgccca gccaattttt atttattttt ttgtgtgtgt    41580
ggagataggg tctttctatg atgccccggc tggtcttgaa ctcctgggct caagtgatct    41640
tgctttggcc ttataaagtg ctgggattac agttatgagc catggcgccc agtctatgta    41700
ttcttacaaa attaaattca tgttaagtgc tacactagca gaattttaa aattttaaa     41760 tgatgcacaa atagagaaga gagagtgcaa attaacgaga aataggcaag actaatttga    41820
```

```
agaaaactat gaagctttac tgaaggattt ttttaaagat ataaaatgct ggccaggcgc   41880
ggtggctcat gcctataatc ccagcacttt gggaggccga ggtgggcgga tcgtgaggtc   41940
aggagatcga gaccatcctg gccaacatgg tgaaactccg tctctactaa aatacaaaaa   42000
attagccggg catggtagcg gatgcctgcg gtcccagcta ctcgggaggc tgagctggaa   42060
gaatcacttg aacccaggag gcagagttgc agtgagccga gatcacacca ctgcattcta   42120
gcctggctag agagcaagac tccgtctcaa aaaaaaaaa aaaaaagaa taggcaaata    42180 actagagaaa aatagtccag aaacagacct gaatatatat aggaatttag aatatgaaag   42240
tgtcagtgtg taggaaggag tgaaatgaaa aagaaagaa aaaggaata tgttgaaagt    42300 ggcattcaga aatcagggag aaaatgatcg attactaaga atgatcctgt aacagtgggc   42360
tgtttgggga aaaatacgta aagatttcta atttagacta tattcaaata atcaccaaat   42420
tatatagagc agggataccc aacctccagg ccacagacca tcctgttagg aactgggcca   42480
cacagcagga tatgaacttt aggccaggga acattacacc tgagctctgc ctcctgtcag   42540
atcagcagca gcattagatt ttcataggag cacaaaccct actgcgaact gtacactcca   42600
gggatctagg ttgtgtgctc cttatgagaa tctaatgcct gatgatctga ggtgttgcag   42660
cttcatccca aaatctgaaa ccatatcctc caccctcca tttcatagaa aaattgtctt    42720
ccacaaaact ggtccctggg tgccaaaaag attggagacc gctgataata gagtatatat   42780
aatcaaatta cagaaataac cacactctat tcttcctcta gaatatactg aatgtttcct   42840
aagaaaagtt gaacactcat ggctggttgg ctgctctcta gcatcttg ccttcgtctc     42900 tcactagttg aatttacac ttccaggggt cagtatgttt gttccaaatc tgcttatgcc    42960
agttacattg agtactgtaa ttttataatt taattaaaca ttaactaatg aaatatgact   43020
gcaaaaagta gttgttttta ggaaaattaa gttgtagatc ttgaacaaat tggataaata   43080
caaatcccct tttcccctt tcaccaaatt actgtcttac taattgtggg cgtgaatatt    43140
ttgaaagatt gggggtggaa atcataaaat tcttttttt tttttttttt ttttgctct     43200 tgtttcccag gctagagtgc aatggtgtgg tctcagctca ccacaacctc tgcctcctgg   43260
gttcaaatga ttctcctgtc tcagcctgcc gaatagctgg gattacaggc atgcgccacc   43320
acacctggct actttttgt attttagta gagacatagt ttctccatgt tggtcaggct    43380
ggtctcgaac tcctgacctc aggtgatcca cccgcctcgg cctcccaaag tgctggtatt   43440
acaggtgtga gccaccacac ctgacctcgt aaaattctta aacgatctat actcagttgt   43500
cttacagttg cctagattct tgttccattt aaagaaactg aaatttgaaa tcacaaatgt   43560
ggattatgga tatgatgggt tatggatatg atatatttgt aatgaatatg caagagagaa   43620
catttgaaac attaattagt agaaatgtac ttaaagaaga ggccttggtt ttttaccgta   43680
atattggcag gtgacatgta tttgttttga gtaaaaatca aatatttcag ttacattttt   43740
aaaattacct gatatactgt acttttcat gtaaccagtc agccctgagt cctatttgtg    43800
ttagataagt ttttaccaat cccgaaagga gatagaggac aagcttttat atgcttcggc   43860
tgaagaaaac ctttctccaa agaagtaatt atctgatcct cctataaagg gccagatagt   43920
aaatatttta gattttgcag gctgaagtag aatcaagggt aatacgtacg ttctgatata   43980
acaagagaga aaacaaattt tgagaaattt cttaattgat taaattcaaa ataataaaca   44040
caatttattg aaatacaggt atactaatga gaagaatgga gttcttttcg gagtgataac   44100
attttcttaa ttggagttca gagttagtgc ttcctattca ataaataatc atcaaaattg   44160
attgcaagta tttatctatt aatgcaggtc tgtaatgagg ttttatatat ttcatctttg   44220
```

```
acatgtcttc acacatacat gtcaaataat tgataccagc ccataaacat atgattttaa   44280
ttgagcatat taataactca ggaagcattt atagaattag gttttctta taacatttac    44340
cttttagtat attattcatt gctgcttaat tacttccaat ggaaggttag acagaagctc   44400
cacaattgca ctgttaaata gatactgaaa tatagatatt tccttgtgca ttaaggtcct   44460
aaaaattatt ctggaaatgt agtgtgagct aagaaactat atccactgca aatttgtttg   44520
ggaatggaga tctcacttct tgttttaact tttgatagca tgtaaagtgt ataaagcagc   44580
tcaacgttgc ttatgattca aaagttagtt gtctaaataa caacagttta agtttcatat   44640
ataagtgttg ttctgtcctg taattttaag ttgaatttac tattataaaa ttagcaaaag   44700
ctaattctca aagccattta ttgtttgatc atagtgtctg aaagcagtct tattgttgtg   44760
aaaaatttca atctcagttc caagctgaaa agaaaaaaaa aaaagcatga taaaacttta   44820
gtacagctca gccgtcaaac tgctgtgtgc ctgggcaagt caggttattc agcttctgtt   44880
tctgacaatg gttaagccca tggcagtgaa tgaaattcac cattaacatg gttggtttaa   44940
taattcatga taaattcaga tattttttcat agaatatcta ttgataaaaa acatgaataa   45000
ccaccttaca ttttcacgtt ttataaatca cccaactaag ccttttttctg cttcacacat   45060
attttttacca ttatcaatga taacgtatct gagattccac tttaggttat atggaattag  45120
tactttttca ccttcttgtt tgtagttgtt caacacagac tattcataga agctaattct   45180
tcagttgttt taaacttggc actgactcct tgaataaaca tctgaacagt gttgtaacat   45240
ctatcaaact cattcaaaag agatggaaat ctacttaacc tcaattgcct tggttttttt   45300
tttaaacaga ttattgatct tgctcctaat attttcgact tttagagcaa atgattttgt   45360
tgaaaggcta atagtctttt tttcttttta aattatctta tattaaattt aaaaaataat   45420
ttttttgtta cctgtctgga gaaagcctag agaaaggcta attaatactc ttaaacaagt   45480
ttattttctc tggatacatt tcttcagctt cttcatgatt taattcactt atcactagaa   45540
tattacttt cttgctttgc taacaaatga gctacttaga aacttccctc ctttacaaac    45600
tttctattcc ttaccttccc tccttgctgt aatgaaatat tccactttaa attttcaaat   45660
ttttctgacc attgctttcc tgtgaatcgg aaatactgtg atcggtcctt agtttggtaa   45720
cattgatgta ttttgaattc ttttagcaca gacagacagt tgactccttg aacaacgcag   45780
tttcaaactg cacaggtcca attatatgag aattttttt caataaatac aatcagcagt    45840
ttatacatat acaaccaaac gtggatcaaa aatacgttat ttgaggaaac ccccagatac   45900
agaacagtga aattttttgta tcctctgggc cactgtggga cttgagtgtg catagatttt  45960
ggtatccacg gttgatccac agataccaag ggatgaccgt agagtcattg cataataaac   46020
aaaatgcttc cctatcttgt cttgataaaa taatgcatac cctccactgt gccttaaaag   46080
catgacattc aggctgggtg tggtggctca cacttgtaat cccagcactt ttggaggcca   46140
gggtgggagg attgcttgag cccaggagtt caagaccagc cttggcaaca tagtgagagt   46200
ccatctctag ttttaaaaaa atacaaaatt aaaaaaaatg aaaaacatga cattcaaagt   46260
gcatttgttt ttgtttcgac atgatggtta tgcactaata actaatgata gttatgtact   46320
aataaaatgt caaaataata acgactttta gttactgata acagttatgc attaataaaa   46380
aataaaatgt cacagtatga caatatgcat gtgtggcacc aaacatgctg ttgagttata   46440
actttgtgac tgtgatttgt gggatactga gcagcagtgg aaagctatat aagccactcc   46500
actctgccag tcagtacagt ggctgattac caattatgga taaccagaac acatcaaaaa   46560
gcagttcaac aaggatcaga ataataacat gtaagtacca tttattaagt agttatgtgt   46620
```

```
aaggcactgt gtcagactgt ataatgtaca ttatttaacc ttcaaaagat tgagagggaa    46680
gatcccttga gtctgggagg tcgaggttgc agttagctgt gattgcacca ctgcactcta    46740
gcctgagtga tggagcgaaa tcctgtctca aaaaacaaaa caaaacaaaa caggcctggt    46800
gcggtggctc atgcttgtaa atcccagcac tttgggaggc tgaggctgag gtcaggagtt    46860
tgagaccagc tgggccaaca tggcgaaacc acgtctctac taaaaataca gaaattagtt    46920
ggtgtggtgg ctcacaccta aatcccagc tactcgggag gctgaggcag gagaattgct     46980
tcaacccagg aggcggaggt tgcagtgagc caagatcatg ccactgcact ccagcctgga    47040
tgagagtgag actccatctc aaaaaaaac caaaacaaaa caaacgaaaa ctacaaaaga     47100
ttgtctgaag ccagccacag acaatagtaa atgaatgagt gcagctacat tctttcttat    47160
ttatggatgc agaagtttga atttcatata attttttccgt ttcacttata tataaattat   47220
atattatata ttacataata tataatatat attataagat aatataatat atattagata    47280
atatatataa tataagataa tatatattag ataatatata taatataaga taatatatat    47340
tatataatat aattaaaata tattaattat aatatataat atatgacata tatatgttat    47400
atattgttat atataaatatg tgtaattata tattataata tatgatatat ataataatcta  47460 tcatatatca tatatataat ctatcatata tcatatataa tctatcatat atcatatcat    47520
atataatata tatcatatca tatataatat atatgatgta tagtatatat gatatataac    47580
atatatataa tatatgatgt atagtatata tgatatataa catcatatat actatacgtc    47640
atatataata tgacgtatag tatatatgat atatgatata tatactatat tgtatatgat    47700 ataataatatg tattgtatat tatatataat atatatataa ggcacagtgg agggtatgca   47760
ttatatataa tatgtattat atattttata tattataata tatattttat ataataatata  47820 ttttgtatat tatatatttt atatataata tattttgtat attatatatt ttatatataa   47880
tatattttgt atattatata atatataaaa tgtatattat ataaagtaa agtatatatt    47940 atatataatt tttatatata cttttttttt ttttttttt ttagactgga tcttgctctg    48000
tcacccaggc tggaatggag tggctgggac tacaggtgtg tgctatcatg cccagctagt    48060 ttttttttg tttttttttt gtttttttta attttttttt tttttttaag acggagtctc    48120
gctgtcaccc aggctggagt gcagtgacat gatctcggct cactgcaagc tccgcctccc    48180
gggttcacac cattctcctg cctcagcctc ccaagtagct gggactacag gcacccacca   48240
cacgtccagc taattttttg tattttagt agagacgggg tttcactgtg ttagccagga    48300
tggtctcgat ctccggacct catgatccac ctgccttggc ctcccaaagt gctgggatca    48360
caggtgtgag ccaccgcacc cggcctactt tttatttaa ctttttttt ttttttgta     48420 gagatgtggt ctcactgtgt tgcccaggct ggtctcaatc tcctggggtc aaacagtgct    48480
cctgcctcgg cttcccaaaa tgttggtatt acaggtatga gccactttgc ctggctatct   48540
tataaataat tttgatgtta ggaattttta gttgcttta tttttatttt tgttgttta     48600 aatatttatt aatagaagca agggtggat aaatcttcta gatcaaactc ttccttaaaa    48660
tagttctgct tttggtagga ttccagattt tcctagtttt gttaagtgtt tctaatgatg    48720
tttggcatag gtgttaactt catgggcctg ttgtatacaa accaatttt ttcttgctct    48780 gagtgaacag taacagaacc tggtaggtga gtcacactga tactgcattc actgaagtta    48840
ctaagctgaa tgataagaga tgagaatcct ttgcatttgt attcaaatca agagttgtag    48900
aatttgaaat tcctgttttg atgaactatg tgaagcatgc tgtcattctt ctctgctagt    48960
ctatgttgat gatgtcatta aactagtctt tgacttttag ttcttggctt aaaatattgg    49020
```

```
aatgattata taataaatag gtttatttca tgtggaaaag gaataatgtg tttgccctga   49080
aatagtctga tctgatcagg aggatattat gctgagcatg gctggaaata aatttgtagc   49140
accaattaaa tacactgtag cagctctgag agggaataaa agtaaaatat aaatagtaaa   49200
tatgagagaa agtgactatg ggatctaact atgtaagagc agggtgggag tatgggtaga   49260
tacgtacatg cccectagat tttaggaaag catatttcaa gaagtagaga agacatggat   49320
atcaatcagt ggaaatcgta tactaaaacg gaagtcagtg aaaaaaaaag actgctctca   49380
aactaaagat agatggttgc ttctaatagg taggtattca gattcgatta agaaattaga   49440
aggccgggca tggggactca ggcctataat cccagtactt gggaggtca tggtgggcag    49500 atcacttgag cccaggagtt cgagacaagc ctgggcaacc tggtgaaacc ccatctccac   49560
aaaaaatacc aaaattaatt agcagggtgt agaggcacat gtctgtattc ccagctactc   49620
aggaggctga agtgagagaa tcacttgagc ctgggaggtt gaggctacag tgagccgaga   49680
tcacaccatt gcactccagc ctgggtgaca gagtaagacc ctatctcaaa aaacaaattt   49740
tgaaaatata cagaagtata gaaaactga agtaatttaa tttgtgttaa aatctgtttg    49800
gtattaaaac taatgtttgg ccgggcatgg tggctcacgc ctattaatta tcctagcact   49860
ttgggaggcc gaggcaagtg gattgcttga gctcaggagt tcaagaccag cctgggcaac   49920
gtggcgaaac tccgtctcta caaaaaatac aaaaattagc tgggcatggt ggctcacgcc   49980
cgtagtccca gctcctttgc aggctgaggc aggaggatca cttaagtcca ggaggtggag   50040
gttgaagtga gctgagatcg cacctctgca ctccagcctg ggtgacagag tgagaccctg   50100
tctcaaaaac agacaacgac aaaaaacct aatgttttat gaaaaagctc tttaattttt     50160
cgtgaccaaa ctgctattct ctagacctac actgtccaaa atgatagcca ttagccatgt   50220
gtgctactgt gttggacagc acgtatttag aacatttcca acatcacaaa agttctattg   50280
cagaatgcta tgaaaatgag atacactttc attagaaaag ctagtaaaaa taagtagggg   50340
taatggggta cttttgactat ccagaaatttt tactaaggaa gaattagatt tttataatac   50400
tgggacatta gtgtgcactt ttttttgtcgt aattgcattt tgtttttat tttgaaataa     50460 atacatgtac agaaaaattg caagaatagt tacagagtct tttcgctccc tgaaccatta   50520
gagagtgagc cccatcagcc ccaaatactt taatgagcat taaatctgga gtttggccgg   50580
gcacggtggc tcacgcctgt aatcccagca ctttaggatg acgaggtggg cagatcattt   50640
gaggtcagga gtttgagacc agcttggcca acatgatgaa aacctgtctc cactaaaaat   50700
acaaaaaaat gagccgagct tggtggtgca cacctgtaat cccagctact caggaggctg   50760
aggcatgaga atcacttgaa cctaggaggc ggaggttgca gtgagctgag attgtgtcac   50820
tgcattccag cctgggtgac agagtgagac cctgtctcca aaataaaat aaaataaatc      50880 tggagtttaa taccagtaca gtactaccag cttatcttca ggccccattc gagttattct   50940
agttgtcccc aaaaggtgaa ggatccagtt taaaatcaca cattgcattt agttgtcatg   51000
tctgtctttg acttgatcgc cttgacactt ttgaagatta caggctcatt attttgagga   51060
agtcattaac atggacctga tgtttcttca tctttagatt cagattatgc atttttatcag   51120 aattgccaca taaattgtgc tgtgttctta ttttatccat ccaggtacta cataatttcc   51180
atgtgtccca tttttcttga tgttaacctt ggtcacttga ttaagattgt gtctgccagt    51240
tttctctacc atacatttaa ctatttttc ctttataatc agtatttat gaggaggagg      51300 aggaggtact ttgagacaat gtaagtatcc cattcctcat caaactttca ccttctagtt   51360
ttagcaccca ttgaaatttt tttgctggat tattggtatg atggctgcca aatgatgatt   51420
```

```
ttctaatttc atcatccctt ctacatccat tcattgacat ttcattgaaa ggaaaaactg    51480
ttttcttccc atttatttaa cttatatcaa tatggactta cggattcata ttttattcaa    51540
taagttatct attagtgtac tttggtactt tgatgctgag tttgtcccag atttggtcag    51600 tggaaccct gtcaagctgg cttctgtatc cttttgacat tgtcctatca ttctttgatc     51660
actttcctct ttctgggacc agatatgatc aaagcccttc ttatactttt cctgccctac    51720
ctctggaatc atttcaccaa ggtaccctgg ttccctttat tgaagaatgt atttagaggt    51780
taggtctgga cagtagatgg cattgttcca ctgaggtgtc actgctccta gactttctca    51840
gcagacagag ctagagcata tatgcatgta tatacataca caaacataca tccacacaca    51900
tagactcatt ttttattttc ttgctctgtg tgtgtgtgtg tgtgtgtgtg tgtgtgtgtg    51960
tactgtgagt tcacactggt acctagtacc tcaacacctc agagttcatt ttattttttct   52020 tccttttgt atttgtaact cccttctctg acagagaaac tgggcccag ttttcttaa       52080 tatattacta tttacttaat tgatcaatcc ccttgaatgt gcccagtctt tccttcctt     52140 atcagatcat gtgcatgcta accttgctca gccccaccta atggttttta gactgaatta    52200
tttggagacg aaaaaagtac ggttgatgct cattagtcac agatttttt tatttgcaaa     52260 ttcacctact tgctaaaatt tatgtgtaac cccaaaatct gtactcgtag cacttttatg    52320
gtcattcatg aacacgtaca gaagggtaaa acatttgagt cgctattggg taacgtgtat    52380
tcctaggtga ggccaagcaa ggcagtctac tgccttcttc tttgagtcct catactataa    52440
atagttgtcc cttttgcagt ttacttagcg ccacatattt tgcattttga cttcttttac    52500
ttagcatgtg ttttcaagtt ccatccatgt ttatagcatg tatcagtact tcattcttct    52560
tctttttttt ttttaaagag ttggggggtct cactgtgttg caggctggaa tacagtggct   52620
attcacatag gccatcatag catgctgtag cctcaaactt tcactgggct caagtaatcc    52680
tcccacctca gcctcccaag tagctgagat tagaggtgtg ggccactgta ccaggttcct    52740 tccttttctaa ggctgaataa tagttcattg tatgtataat accacatttt gtttatctat   52800
tcatccaata atgggcattt aggttatttc caccatttgg ctatcttttg aaaatctttt    52860
catgtgcttg ttggccatta gtatatattc tttggagaaa tgtctcttaa attctttgcc    52920 tatttttaa attgggggga agttgtcttt ttttgttact gaattgtaag agttctttat    52980
tctgataact agacccttat cagatacatg atatctgatt aacacatagt ttcttgcatc    53040
ccataggttg tctttcaaaa ttttgacgaa ttccaatttg tcagttttgt tgcttatgat    53100
ttttagtgtc atatctaaga atccattttc aaattcagtg tcatgaagat ttacctatgt    53160
tttcttctaa gaattttata gttttagacc aagcgcggtg gctcatgcct gtaatcctag    53220
cactttgaga ggctgagaca ggcggattgc ctgagctcag gatttcaaga tcagcctcag    53280
caagatggtg cccatctcta ctcaaataca aaaaattagc ctatggcgtg tgcctgttca    53340
gctactcggg aagttgaggc aggaaaatta cttgaaccat ggaggcagag gttgcagtga    53400
gccgagattg catcactgca ctccagcctg ggcacagag cgaaactatg tttccaaaaa     53460
aataataaca ataattttat agttgtagct ttttaagttt ttaatccact ttgatttttt    53520
tgttttgttt tgttttttga cagggtct tgctctgtgc tgcaggctgg agtgcagtag      53580
agcagtcttg gctcactgca gccttgacct cctgggctca agctatcctc ccacctcagc    53640
ctcccaagta gttgggatca caggcttgtg ccaccatgcc tggctaattt ttgtatttt    53700 tctagagatg gggtttcact attattgcct aggctggtct taaactcctg ggctcaagta    53760
atccatgccc accttggcgt cccaaagtgc tgggattaca ggcgtgagcc accactttca    53820
```

```
gtcccaagtt aatttttata tatggtatga ggtaaggatt cattcttttg catgtgaata   53880
tccagttgtc ccagtgccat tgttgaaga gcctgttctt tccccattga atgttgtctt   53940
agcactcttt ccaaaaatta gttgaccata gggcatggtg gctcatgctt ataatccaag   54000
agctttggaa ggcccagatg aaaagattac ttaaggccag tatttcatca ccagccagcc   54060
atggtggtgt gtgcttctgg gagggtgagg cagaaagatg gcttgagctc gggtgttgaa   54120
ggctgcagtg agctctgatt gtgccactgc actccagcct gggtgacaga gtgagacact   54180
gtctctaaaa aatagaataa taaaaatcag ttgactatag attttgtggat ttatttctga   54240 actcatttaa aactattcca ttgatctata tatcactcct tataccatta ccacacagct   54300
ttggttaccg gtgctttgca ataagttttg aaatcaggaa gtatgagttc tccaactttg   54360
ttcttccttt tcaagattgt tttggccatt cggagtccct tgcaattcca tataaatttt   54420
aggatcagtt ttttttatttc tttttttttt tttttttgaga cagagtctcc ctctattgcc   54480
caggctggag tgcagtggcg tggtcttggc tcactgcaac ctccatctcc caggttcaag   54540
caattctcct gcctcagcct cccgagtagc tgggattaca ggcacacacc atccgcccaa   54600
ctaaattttg tattttagt agagatgggg tttcagcatg ttggccaggc tggtctcgaa   54660
ctcctgaccc ccaagtgatc cgccggcctc ggcctcccaa agtgctggga ttacagacat   54720
gaaagctttt ttatttttga aaaataaat aaataaataa agacataaga tgtctttcca   54780
tttatttagg gtctccttgt tcttggaggt agattttctc tgatctattt tcattgagac   54840
cttgggcctt aagagagcca caatttcatg agagattatt tctctggagc ccttcctacc   54900
cttctcctat ttcctgtctc ctttcctccc ttgttattca aaagtcttaa caaatgctcc   54960
tgggcccaat acagaggtca gctcacactt ccagccttag ctttggttca cttttttgctt   55020 tcttgccact ggtagttttc cctcctctct taagaactta gctaagcttt tcaaaggatg   55080
tttgcattta tccaacattt ctagattttg gtagctggag agttttaata atttctaga   55140 ttgctgtttt actagattag aaaaagatag agctgggtgt agtggcacat gcctgtaatc   55200
ccagctactc cagaggctga agtgggagga ttgcttgagc ctgggagtta gaccaacctg   55260
ggcaacatag tgagacctat ctcaaaaaaa aaagtaagac tttagggcgc agtgtaatcc   55320
cagcactttt ggagaccgag gcgggtggat ctcgaggtca ggagttcaag acaagcctgg   55380
ccaagattgt gaaacccccgt ttctactaaa aatacaaaac ttagctgggc agagtggcag   55440
gcgcctgtaa tcccagctac tctggaggct gaagaagaga atcacttgaa cccgggtggc   55500
agaggtttca gtgagccgag attgcaccac tgcactccag cctgggcgat agagtgagac   55560
tctgtctcaa aaaaaaaaaa aaaaaaaag acagtgtttt ttaaagatgg agtttagtat   55620
acagaaatat tgggtgtcag gcaaagtatt aattactttg tacgtattct cttttccttc   55680
ttttttttaa aacgagacag ggtgaccagg ctaaactctg actgttgggc tcaagtgatc   55740
ctgccttagc ctctggagta gctgggcatt acaggcacat gccactgtgc ccggctacat   55800
actcacttat aaaactctat ttttaaatga cagctcctct ttacaaaata gatcaggaga   55860
gcgattttcc tgtctgcttc ctgaggaagc aaaaaggcag aaacatggtg agcagcaaga   55920
ccagtggttg ccgtagtaag catgggactt cctatgaatg gctctgttaa cagtagggga   55980
tggtaatgtt ctttgatttg tggactctgt ttgatttgtg gacaaggttt tatttcctgt   56040
ctttggggta ggagggtctg ccatatccac aaattggctc ttcccatttg ttgtattcat   56100
ttagttagac catgattgga aagcctcact ggctgtgcac attgcaccat acttaggaat   56160
atatgacggt tatacatttc aaacagggct ttaaaacctt ccattcagct cctttttggat   56220
```

```
aaagctcttt tcctcatgtg gttgttgaca tacatgaatt ataggctttg tttagctagt   56280
gggtaagagc agattttgga gtcatgtaca cctgggtttg agtttcagtc ttgccatgta   56340
ccagttgttt gtggacaagt tatttattaa taactactct gtaccatagt ttcttcattg   56400
gtagtatctt caaaatgaag tatctatttc ctgtgctgtt ttgaaggtaa ccttaaataa   56460
tgtgcattgt acaatttgat acagtgtctg cacgtagta aatactttaa tatataatac   56520
ctgtttttat tctgatcctt gttgagctgc tgcttttga tgtgttgatt atatataatt   56580
ggtaatcatc cattttactg acatcttcca agatttgacc aagttgattg tctcaaattt   56640
ccaagcagaa aaagtaccca gaaaacagaa attaagcagt tattaaagaa tcgaatagca   56700
atgatcatta cgacttgtgc ttaataagaa atgtgggcca tgtctgcctg agcctttatt   56760
taatgcattt taaaatttgc tgggtttttt cctcccttta aaccttacta tcaggttcag   56820
taataagtta aactaaaaag aaacggatgc cttagaataa agaaagattc aaattaatag   56880
gatatataat ggcctttcat ggtggtggaa tttctgtgtg ttttgaacta agggaaagac   56940
ttaaaggaag attgcctaca gtgtactgga cactttgcta ggctctgtgg atattatcaa   57000
gacacagtcc ttaccctcaa ggatcttttt atttttcttt tagagacggg atcttgccct   57060
gccacccagg ctggagtgca gtagcaaaat catagttcac tgcaacctcc actcactctc   57120
aaggatctta ctctcagctg ggggaggcca taaacagtta aagtagctta ctctcagctg   57180
ggggaggcca taaacagtta aagagttaat gattgactct agggctaagg gaaagaaagt   57240
aattgggtca actaggattt ctagcttggc aaggggtag acctggattg gcaaactaca   57300
acccaatgcc agttttgca tagcccacaa actacaaatg tttcttacat ctttgagtgg   57360
ttggaaaaat atcaaaagaa gaatactatt ttgtaacgtg gaaattatat aaaattaaca   57420
tttacatgtt cataaataag gtttttattag aatatagcta tgctgaaact acatatctat   57480
gactgctttt ttgtcacaac agcagagatg agtaattgtg acaaaggctg tttggcctgc   57540
agagccaaac atttactgtg tggctctttta cagaaaaagt ttgctaactc aatgagtagg   57600
tggtaatttt tatccattga aacaagcaat taaggaagaa cagatacagg agaagataac   57660
atttctgtga gtgttgatta tttgaatcag aggtacttgt gaatatgcag gtctagaagg   57720
caagggaatt tataggtttg gagtttggaa agagcttgag gctggaaatg gatgtgggag   57780
gaaaggagga gatcaagaag actggatgga ggagtgcaat ttttagccct gtctgcacat   57840
tggaatcacc tgtagtgctt aaaaccaaac aaaaccagac agacatttcc aggaacccaa   57900
ccccaactcc ctcttttccca agattatgat gcacctgagc tggacttggg caccagaatt   57960
ttttgaaagc tcccccagca actctaatgt gcagccactg gtacagagtg agaagattgg   58020
aagatgggac accaggaaca ccaacattta agggatagtt ctaggtgctt ctgctgagga   58080
gaggaaattc tgagggagtg atgatgggaa tttagggtg gtcagatcct gtaatttgag   58140
atcattgttg actgatgaat caagagcagt ttctgtagag gccaggtgag ggtgtatgtc   58200
agaggcccct ggtttgaggt gggagagtat gaactattga gaatattgac cgggaggaaa   58260 gggggggaaag tgatggctgg gatgggggc attgggaatg tagtttgttc tagagaggtt   58320
tttttaagat gttaaagcct tgaggctatt tatgtgctga gggagtgagt actcagaaag   58380
aaagcctgga atgcagtat cagatgccac cattcagttt tcatgatgga gtgaaggct   58440 agattttgaa tagttcttgg aataatctta atattgtaac cttttggaa ctgtttgctt   58500 aatgtgcttt cttcatttag gtgcattaca ttgtacctgg aaagagaaat ggacccaggc   58560
attgagaagc aaggccaaca actctgcttt gcttgcccgg ttactgtcgt tctgtctggg   58620
```

```
acattggtct catctctgaa agcaggaggg caaactgaat gggctctgta gtctcttcta    58680
aaagttttta gtttaaacta ttaatagtac aactttgatt taacaaatga ggaagctgag    58740
cttacgagat gtctgtgaag cccattgtct gatcttttat ttccttagta cctgggaatg    58800
cgcttttttt tttttttttt tttgaagaac accaacagtt gttcacccct ccttgaattt    58860
gggtacactg tatatacaga gtataccaat ttagcctgcc attagaacat gtcttcacga    58920
gcaaaatcta gtataaagtc ttactttaat attttcttta ttatgtataa ataatagatg    58980
gttgttatgg aatactggat agtacaaaag tttagaattt ttaacatttt ggtttatttta   59040
ttgggactct tttttccccc cagtgattct tgtttctcca acaatgtgaa tgcgcactcc    59100
attcagtgtg aacgtgaatg ttaatttatg tgccagctgg attctacagg aagcagacac    59160
agatggggtt ggaggggcaa agggcttatt agaggagtaa tgcctgtgaa gaaagggga     59220
acggaacatg tttgggtata gggagccatc agactgcagt gcacacctga cgaagtctct    59280
gcccacccag attgcctgat agaggaatac cacaagaggg agaaatggct aggctcttgt    59340
actaccactt tgcacagtca ttgactagag atagatcttt gatcaatgta gagattttca    59400
gccttggcat tgttgacatt tgggactgga tactttgtta taggggttg tcctgtgatt     59460
tgtaagatgc ttagcagcat cctaggcctc tatcccctag atgccagtag cccagcctcc    59520
ctgctattag ttgtgacagt caaaactatc tttagacact gccatatgtt ccctagggaa    59580
gggcctaatg gtatataaac aaccctatgg tggcatagtc caagttttgg gacagggagg    59640
agtgttctat actacccctta ctggaaagac ctatgagcta ttcagaaatc tgaactattt    59700
aagatggagc tttgttctgt ggctcctgga attttaagca caccctgtg aaacatcttg     59760
ttaggatata ctccactctc caaaacaatc cataatgttt aaatagggct gttttattga    59820
ttgattgatt gattgattga gatggagtct cactctgttg cccaggctgg agtacactgt    59880
cacgatctcg gctcactgca acctcccccct cctgggttca agcaattctc ctgcctcagc    59940
ctcccaagta actgggatta cagacaccca ccaccgtgcc tggctaattt ttgtattttt    60000
ggtagagacg ggggtttcacc atgttggcca ggctggtctc gaactcctga cttctcaggt    60060
gatccgcctg cctcggcctc ccaaagtgct gggattatag gcatgagcca ccgcacctgg    60120
ccttatttt cttttgaga tggagtctga ctttgtcgcc tgagctggag tgcagtggcg    60180
cgatctgggc tcactgcagc ctctgcctcc cgggttcaag caattctacc tcagcctcct    60240
gaacagctga gattagagat gcgtgccacc atgcccagct aattttttgta ttttttagtag   60300
atgcaggatt tcagcatgtt ggctaggctg gtctcaaact cctgacctca gtgatccac     60360
ccacctcggc ctcccaaagt gctgggatta caggcatgag ccaccgctcc tggctatttt   60420
cttttgagac tgggtctcat tctgttccca ggctggagtg cagtggcaca atctcagctc    60480
actgaaaact ccaccttctg ggctcaagca gtcctccac ctcagcctgc taagtagctg    60540
ggattatagg catgtgccac cctgcctggc tacttttgt ggagatggga ttttgcatgt    60600
tgcctaggct gggcttgaat tcctaagcta gaacaatctg ctcagggatg ttgtatatttt   60660
ctaaaggtat ttttccttt gttgcaggtg acacaactaa aaaaaaacaa aggtatttat     60720
ggaattccac tgagtggtaa tggatgatgc agttcaaata actaaggtaa gagaaataaa    60780
accagaactg tgaggaggct tttgccagcc aagtagtgtc cttaaataaa gctaacatca    60840
catgctttcc tgcttcattt cgtttctaag ctgtaagagt agcttatttt tttattatta    60900
taaacattgt aattatcctt taagatactt cttaacctga ttatgaatca gaatcacttg    60960
aagagctttt tttttttaaa aaaaagacc aaagtcaggc tgggcatggt ggatcacgcc     61020
```

```
tgtaatccca gcactttggg aggccgaggc gggcagatca cttgaggtca ggagttcaag    61080
accagcctgg ccaacatggt gaaacccat ctctaccaaa aatacaaaaa ttagccagat    61140
gtggtggcat gtgcctgtaa tcccagctac tcgggaggct gaagcaggag gatcccttga    61200
acccaggaga cagaggttgc agtgagctga gatcgcacac tgcattccat tctgggcacc    61260
aaagaatgaa actccttctc aaaaaaataa aaataaaaag accaaagtta atgcc ctgcc    61320 agcattgaat taaagcttct tgagtagatc acagatgatc tccaagtttt ttaagtggga    61380
atgtaaacca actctatagt tttagaaaac tctttggcaa tatctgcaaa acatacacgt    61440
atctaataac ccaggaattt caattctagg tatccacctt tgagaaatga aaatatatg    61500 tctacacaaa agtgcacata caaatgttca ctgcagcttt atgtattata gccagaaaaa    61560
ctgtaaccca atcaggtgtc caaaaacagg agaatagtta aacaaattgt gatatatggt    61620
caggtgtggt ggcttacacc tgtaatctaa gcacttggga ggctaaggcg ggcagatcag    61680
ttgaccagcc tggtcaacat ggtgaaaccc catctctact aaaattacaa aaatgagctg    61740
agtgtggtgg ctcacgcctg taatcccagc tactcaggag gctaagacag gagaatggct    61800
tgaagccagg aggcagaagt tgcagtgagg tgagatcacg cccctgcact ccatccaatc    61860
tgggcaacag ggcgagacta tgtatcaaca acaacaaaaa attgacatac actattgata    61920
acatggaatt ttattcagta atagaaagga acaaactacc agtagacatg acaacatgga    61980
tgaatctcgt agataaaagg ttgagtgaaa gaaaccagat ggacaagaaa agtagatgt    62040 agcagaatta ccgagtaaaa ctaaactaca gtgataaagg tcatatccct acttcctctg    62100
acaggaggtg ggaggttgtg actggaaaga ggtatgagag agcctctgca gcaccgaaaa    62160
ggtgttttgt tttgttttt gagactgagt cttgctatgt caccaggctg gagtgcagtg    62220
gtgtgatctc agctcactgc aacctccgct tcctgggttc aagcaattct cctgcctcag    62280
cttcccaagt agctgggatt acagacacg gccaccacgc ccagctaatt tttgtatttt    62340
taatagagac agagtttcac catgttggcc aggatggtct cgattgccca acctcatgat    62400
ccgcctgcct ctgcctccca aagtgctggg attacaggca tgagccaccg cgccggcct    62460 gaaaaggttt tacatcttaa tgtgttcata tacatacttt tctcatggta aaatatatat    62520
aagattaaat ttatcatttt aactactttt aaagtataca attcattggc attaagtaca    62580
ttcctgttgt gcagccatca ccactgtcca tctccaaaac ttttcatct ccccaaactg    62640 aaactccata tccattaaac actaactccc catttcctcc tccccagct gctggcaacc    62700 attctacctt ctgtctctat gaatttgact ataatagtta cctcgtataa gtggaatcat    62760
atttgtcatt tgacatctgg tttgtttcac ataggtttat ttcacaaagg tatcttgttt    62820
atttcacata ggatgacctt gttttcaagt catccatgtt gtagcatata tcagaattta    62880
cattttatgg ttgaataata ttctgttgta tgtttatacc actttatgtg tatccattca    62940
ttcactgatg gacacttggg ctgcttccac cttttggctg ttgtgactaa tggtgctatg    63000
aacatgggtg taggctgagt gtggtggctc acgcctgtaa tcccagcact tgggaggcc    63060 gaggcaggcg gatcacttga ggtcaggagt tcaagaccag cttggacaac atggcaaaac    63120
cccatttcta ccaaaaatgc aaaaattagc caggcatggt gctgcatgcc tgtaattccc    63180
agctacttgg gaggctgagg caggagaatc gcttgaacct aggaggtaga ggttgcagtg    63240
agcccagatg tgtgctactgc actccagcct gggtgacaga gtgaggctgt ctcaattgaa    63300 aaacaaaaa caaaaacaaa aaaaacaca tggatgtaca aacatctgtt cgagtccctg    63360
cttttagttc ttttgagtat attcttagaa gtaaaattac tggatcatat ggtaactcca    63420
```

```
tgtttcattt tttgaggaat caccatgctg tttttcacag tactgcatca ttttatattc   63480
ccaccagcaa tgcacaaggg cttcaatttc tttacattct gcttttgggt gacctccata   63540
attctaaatt atatgtatat gctgtttctt cttaattctt ttattaataa aaaagacaac   63600
ataattcttt gcctctccag tgtgaaaaaa tgggaattta ccttacacta tcccccatt    63660 taatatttgt attatttcct gttctgctgc tgtttattag tttcctcaga cttctgtaac   63720
aaaactccat gaactgggtg gcttaaacaa tagaaattta ttgtctcaga gttttggagg   63780
ctagaagtct tgcgggctgt gcgggagaat ctgttctatg attttcttct agcttctggt   63840
agcctcaggc atcccttaca ttgtagatgg cattctctct gtatcttcag attgtcttcc   63900
ctctatgcat atctgtctct tgtgtccaaa tttccttttt caaataagt gcgctagtca    63960 ttggattagg gaccacccta atgagctcat ctcaacttga tcatatgcaa aaatcctctt   64020
tctaaataag ttcacattca caggaactga gtaggggtt acaatttaa catcttttag     64080 gggacacaat tcagtctggg tgacagaaca aatctctgtc tcaaaaacaa aacaaaacaa   64140
acccataaag tgattacatt tctaactttc ggaagtactc ttcaacctcc ttttttagg    64200 ttaattttca gcactctttc cttctttctt cctttccttt ttccttttcc tttttttttt   64260
tttttttttt ttttactttt tatttttttg agacagagtc ttggtctgtc gctcaggctg   64320
gagtacagtg gtgtgatctt ggctcactgc aacctctgcc tcctaggctg aagtgatttt   64380
cctgcctcag cctcccaagt agctgggatt acaggcaccc gccaccacgc ccggctaatt   64440
tttgtatttt tagtagagcc aggttttcac cttgttggcc aagctggtct caaacttctg   64500
gcctcaagtg atccgcccgc ctcggcctcc caaagtgctg ggattacagg catatgccac   64560
cacacctggc taattttgt attttagta gagacagggt ttcacctgtt ggatctcctg     64620
acctcatgat cgcccctcctc agcctcccaa agtgctggga ttacagtcgt gagtgccgcg   64680
cccacttaat atttatgtta ttatagctaa gtaaatattg ttcactgtca ggccaggcag   64740
cattttctgg gttttattt ctttctctgt aggttcaatg tcatagaccc tgggctattc    64800
aaatgagaaa atgaagaaaa agtgaattct ctctctgaaa ctatcagttg cttccaatca   64860
tgtctttata ttttatattt gaaccgtaac tttctcataa aattttctcc ctggagtttc   64920
taattttctt gtctatttgc ctgttattat agtttcactt ttcaccaaga tctcaatcat   64980
acactccagc ctgtcaaggc tagttcaaac catacactgt ggcccaaatt taggctagtc   65040
gtacactcca atccgagacc agtgggcact gttttttagg ctgtctacac agtcatattg   65100 gtatttcct tactggtttt tctttgacgg gggtgcaggg gaggttgggt ccactgatct     65160
tggatatcag tctttctttg tatttgtttt ttaaatctta ctagaggcta ggggcatgg    65220 tggctcatgc ctgtaacccc agcactttgg gaggctgagg caggtggatc acttgaggcc   65280
aggagttcaa gaccagcctg gccaacacgg caaaaccctg tctctactaa aaatacaaaa   65340
attagccagg cgtggtggtg ggtgcctgta atcctagcta gtcgggaggc tgaggcagga   65400
gaattgcttg aacccgggtg gtggaggttg cagtgagcca agatcatacc attgcactgc   65460
agcctaggcg acagagtgag actccatctc agtcaatcaa tcagtcaatc aatctatctt   65520
accagagttc attctcaagt cacttactga gagaaaggt acctggcaga taaattttga     65580
ctctttctgg tatccgtttt ttgttgttgt tgttgttgtt gtttgtttgt tttggagacg   65640
gagtctcgct ctgttgccca ggctggagtg cagtggcgcg atcttggctc actgcaagct   65700
tcgcctccca ggttcatgcc attctcctgc ctcagcctcc taagtagctg ggactatagg   65760
cgcctgtcac cacgcctggc taatttttg tatttttagt agagatggag tttcactgtg    65820
```

```
ttagctgatc tgccctcctt ggcctcccaa agtgctggga ttacaggcgt gagccaccgt    65880
acccagcctc tggtgtctgt ttttaagacc ctcatgttgg agtgatggtt tggttgacta    65940
tagaattcta ggttgcctat tattttttcct caaaactttg aagtcattgc tccatttctt    66000
ctgacatccc ttgttgttca tgagaaatag aaagtttcat ataggaaatt aattttcctt    66060
cttttctgga agcttttatg ttctatatag tctggaattc catagaggtg tacttggtgg    66120
gccccttaat agatctgcag actcatagct ctccattttt tggttctttt ctgtcagcag    66180
ctttctgata ttgagcttcc tgggttgttc atataatgtt cttatctatt ctgtcctttt    66240
taaaaactct ttgcttttgg ttgttttcct ggagattgtc ataactttat ctcctaatct    66300
ttttttctct cttttttttt ttttttttga cagggtct  caccctgtgg  cccagactgg    66360
agttcagtgg tgccatcaca gctcactgca gcctcgagct cccaggttca agcaatcctc    66420
ccacctcagc tttccaagta gctggaacta taggcatgcg ctactacacc cagctaattt    66480 ttttatttt tagtagtgac agggtctcac tgtgttgccc tggctggtct caaactcctg    66540
agctcaagtg atccttctgc ctctggggac tacaggagta tgccaccaca cctggctaat    66600
ttttgtattt tttagtagag acaggggtttc accatgttgc caggctggtc ttgaactcct    66660
aggctcaagc gatccacctg cctcagcctc ccaaagtgct gggattacag gtgtgagcca    66720
ccacacctgg cctgctgttt tttctttttac tgtttcttaa actagtcttc tccccgcttt    66780
cttttcctgt atgaacgtta atagttgacc acagcattgg ccctgtaata ctcttttgtt    66840 ctttgtatt cttcagtttt atttagcctc tgttgtgtgt tcacacattc ctttttattt    66900
gcttgatgtg tgtcccatcc cttcttttga acactgtgtg gtcattaatg agagtgtggt    66960
aggattttat gtactgatat ttaagaaaat gaccataaaa tgttcttgga gatggtcttt    67020
aaagaccggg catggtagct catgtttgta atcttagtac tttgggtggc tgaggcagga    67080
ggattgcttg agctcaggag tttgagacca gcctgggaaa catggggaga tcccatctct    67140
acaaaaaatg cacaaattac ccaggcgtgg tagtacatgc ccgtggtccc agctattcca    67200
gagcctgaag tgggaggatt gcttgagccc aggagctcga ggctgcagta agccatgttt    67260
gcaccactgc actccagcct gagtaacaga acaagaccct gtctcaaaga aaggaaaaaa    67320 aaatttaag tagttgatta aaagaggtct ttagggtggg ctctaatttg atgtgactgg    67380
tgtccttgta agaaaaggaa atttgtacac gcagacatca gaaacaaata cacagaggaa    67440
tgaccaggtg aggatacagt aagatggtgg ccatctgcag gccaaggaga gaggtctcat    67500
aggaaaccaa acttgctgac actttcatct tggacttcta gcctgtacag ctgtgagaaa    67560 ataaattct gttgttgaac ccaccgagtc tgtgatactt ttatggcagc cctaccaaat    67620
gaatatagac atttaagaag gcttggtgca ttgcagcatt tggtaaatta ttatgcattt    67680
cgttgtattg tgcatgtagt gccattactg agaatagcag gatggatggg aagcatcgag    67740
acaaagtaaa atacgagctg gccactaaca tatggtatga ttttgtggta ggtgaaaaaa    67800
ggattccaga agtagagtgc ttatgaaaga aaagctcagt agtgtaagaa ttttacacca    67860
gtttgacttt aacagagagt gagttcaaca gtgaaagatg aggttgcaaa tgtagtttgg    67920
ggacccatat taatttcctg gtgctgccca aacaaagtac cataaactcg gtggctaaag    67980
acagcagaaa tatattgtct ggcagttctg gagcccaaa gtcaaggtgt tggcagtgtt    68040
ggttccttct tggggggaat ctgtcccatg catctctcct tagcttccaa gagcccctg    68100 tgttatttgg attgtaaatg atcactcaaa tcctctttct tcaattggca ttttcctgt    68160 ctgttttcac atgattatct tcttataagg acaccagtca tattggatta ggggcccaca    68220
```

```
gtactccaga atgacctcat ctttatttaa ctaattacat cttcaacgac cctatttcca   68280
aataaggtca catcctatgg tactggggat taggacttca tatcttttt ggggaggcat   68340 agttcaaccc ataacagggg ccaaactgtg aagcatttcc tatatatcaa tccagatatt   68400
ttcaaatcta ttgtttattc agtgggaaac cattgaaaac tttgagcagg atgaatctaa   68460
cactttagga agactccttg gggatggggt tggagagatg ttagctgcac tggaagtcag   68520
tagaccagag tctggaccac tgggagtctg gaccagatca atgttatgga aaaccaggat   68580
tctggggctc ccactcaaga tatcccaaac ccaaatcttc agactggaga cccaggactg   68640 tttttttaaaa gctccctctc tctccctgtg agtcagatga tttagcctag cttggatgta   68700
acactgggtg tgaggtgata gaggcatgaa atggggttggt ggttatgcaa gtagaaagac   68760
cagagagaac ctgggaaaag agacatttcg aaaaagtagt atgtaaactg gcaccggaga   68820
gtctgagaca gtggtggaat ccttaacaga aataaagatg tctagagaat aaattgggtt   68880
taaagggaag gtaattaatt tggtttacag tgtaaggtga tagacagtca gcaggcactt   68940
ggagaatggt gatgtatgtt cagaagtgag ataatggagg tgataatcaa aacccttgt   69000 tttgatttga gcctttgtgt gggagaaagg atatggcgag aagaacagaa gatcaggaag   69060
ccaatactgt agaccctcat tccctagccc ctgaaacaaa tggatttgac ttctctgtca   69120
tgacacctgg aacaaatgtg gcattgctta cttacttcct ttgccatgaa ctcagtgaag   69180
gcagggacgg gtcttggctt gtgtgtgtgt gtgtgtgtgt gtgtgtgtaa gagactgggt   69240
ctcattctgt tacccaggca tgagtgccat ggcataatca tagctcactg cagcctcaaa   69300
cgaacctcct ccctcaggcc tcctgagttg ctgggactac aggcatgcac caatggccct   69360 ggcttttaa aggccatcat ctagcacagt gcctggcttt tcaatggaag tctgttgaat   69420
gactgactga ctgaccgact tggaaaatga acacatcaac ttgagaataa gaactttaac   69480
ttttttcttc cttgcatccc ctaacattta atccaatgcc tggtccttaa taggacccaa   69540
ataaaatttt gatgtgtgaa tggtagaaga aaagctaaaa ttgagtagtc attgtgtcaa   69600
agagaaccag gaaacagaga agcttttgag aataagttga ccataacatg tcaaatgcaa   69660
gtcaaggaga atgaaaactg agggcaggaa ttagatttaa tcaggaggtt atttgtagat   69720
ttgagaacga aggatttaag aacataatga ggttgttaag ggagaatgaa ggaattaaga   69780
tcataatgag gttgttaagt agaggtggaa agtgaggaaa tgaaagccaa gtacatctta   69840
tacaagttta gtagtaatga ggaaaagaga agctcataga gttaaagctc taaaaatctg   69900
tttagaacat ccgtgtctat ttgtaaacaa aggggtatga gggttaggga tggaaaaatg   69960
gaaagtacca gaaggaaatg cataaatttta ggggaaagat ctcaaatggg atcaagaaca   70020
tgggcagtag ccttaaaaag gatgagggaa tctcttcctc tagtctaaaa agggagaata   70080
gaggctctat agaggagaga gaggtcatgt cctcttgtca gccatctgct cagagggagc   70140
ttgggctgct gtgctagaaa ctgacatagg aaactgacaa aggaaggata tgttttctgc   70200
acagcactga ggagtgtgat actcctaagc agtagttggc agcctgagat aggaatggtg   70260
gaaccagatg gtaagtataa tccaggaatc aggatggcac tttctgtaga ttaggagtt    70320 gtaggctggg ggtgtacttt tattcactct tctctgattc agaggttta taattttcac   70380 taacatcatt aaaacaata ttggatgcct actacctgtt ggttttatt ttaatcttgg   70440 gaaaaaaag taaagctac tatcctgagg tttctggttt tattggggag atagatcata   70500
tatgtaaaaa gcaagtttag caaatggcac atggcattat agactaagtc ccaaatcagt   70560
agattacata aatgtcagag agattacaat tatagcagta cactttgagg ttcttttccc   70620
```

```
cttagcttat gaacatttaa attttgtcac ttttataaat acatgcctat ttgagaggta    70680
agaaaagtac catgttgctt taatttgctt ttctttgtta gcaaagatga attttttcag    70740
ttgtttatca ttattttact ttttatgaat tgcctattca tagcttttat ccatctttcc    70800
atggttgtgt ttgtacttac taatttgtaa atacctcatt taataaggtt atttaacctt    70860
ttgcctgtaa cattttgcaa atgttttttc tagcttgttt tttggggttc tttcttttgg    70920
ttggttggtt ggttggttgg ttggttgggt ttttttttg agacagatca tcactctgtt    70980
acccaggctg gaatgcagtg gtgccatctc tgctcactgc aacctccacc ttctggggtc    71040
aaatgattct tgtgtctcag cctcccaagt agctgggatt acaggcgcac gccaccacgc    71100
ccagctaatt tttataattt ttgtagagat ggggtttcac gatgttggct agggtggtct    71160
caaaactcct gacctcaagt gatttgcctc cctcagcctc ccaaagtgct gggattacag    71220
atgcagccac catggccagc ttttctagt ttttttaatt taaacatttt ctttcagatt    71280
tcttattttg atttattttc agtttatgat gttttgttga cacataagag tttaaatatc    71340
ttatgtatta gaaactatta aatatttctt tttaatattt aggaaggcta cctcagcctg    71400
agaacagaca aatattttca aatgttttct tcaaattgtt ttatagttta ttggtactta    71460
tttacattcc attgtattat tgttatttat atacttaaaa cttttaaacca ttttggaata    71520 ttgcatgaaa tagagaccta attttgctg agtagttcag cagtttctag tactgtttac    71580
taaataatct atgaaaattt tctgcggatt cctaaatgat tttgtccagg ctggagtaca    71640
gtggcacaat catggctcac tgcggcatct acctccccag gctcaggtga ttgtcccacc    71700
tcagcctctc aagtagctgg gactacagaa gtgccactac acccagctaa ttttttgcatt    71760 tttttgtaga gactatattt caccatgttg ctgagcctgg tcttgaactc ctgggctcaa    71820
gcgacctgcc cacttcggcc tcccaaagta ctaggattac aaggcatgag ccaccgggta    71880 tttttttatca tattcccaat acttatgtat acagacttcc ttgtttataa atctgtatct    71940
gtaccattgc cacatattat tgtattaata taatctcata gtgcaaatac ttgttcatta    72000
tttgttttaa ataatgccta gactacactc acctatttgt atatgtgaac ttttttttaaa    72060 acatttatt ttttaataat ttaagactca gaaagctgca gtagtacagg ttcccaggta    72120
tgcttcaccc aagggctttc aattagaacc tttttttttt tttttttttt tgagatggag    72180
tctcgctctg tcaccaggct ggagtgcagt ggcgccatct cagcacactg caacctctga    72240
ctccctgatt cgagcaattc tcctgtctca gcctcccgag tagctggaat tacaggcata    72300
cgccaccaca cccagctaat ttttgtattt ttagtcaaga cggtgtttcg ccatgttggt    72360
caggctgatc tcaaactcct gacctcaggt gatctgcttg ccttagcctc ccaaagtgct    72420
gggattagag tggtgagcca ctgtgcccgg cccctgaaat caccttttct gtaatgctac    72480
tttgttcaat aaaaataaca tattaatatc cttttttaaaa atacatacaa tatattgtta    72540
ttaactgtag tcaccatgat gtacaataga tctcttgaac ttattcctcc taactgaatt    72600
ttgtgtcctt tgttcagtat ttccccaatt cccctaccca ccaacctcta gtaaccacca    72660
ttttactctc tatttctatg aattcaactt tttacattcc acgtgtaagt gagatcatgt    72720
gatatttgtc tttctatgtc tggcttattt cgtttaacat aatgtcctcc aggtttatcc    72780
atgttatcac aaatgacaga atttattctt ttttaaggc tgaatagtgt tccattgtgt    72840
atgtatgcca cattttcttt caccattcat ccatcaatga atgaaaacac ttaggttgat    72900
ttcatatctt agctattgtg aataatgctg caatgaacat agtagtacag atatctcttc    72960 aacatacccca tattagttat atcctttaga tatatatcca ataggggaa ttactgaatc    73020
```

```
atatagtagt tctatttaaa tttttttttg tttttttaatt ttgtttgttt agagacaggg    73080
tctcgctgtg tctccaaggc tgtagcacag ttctgcaatc ataactcact gtaagctcaa    73140
gtgatctact tcagcttcgc tactacaggc acatgccact atagtcagct aatttttaaa    73200
aattgtttgt agagtccagg tgtggtggct cacgcctgta atcccagcaa tttgggaggc    73260
ctaggcgggt ggatcacctg aagtcaggag tttgacacta gcctgactgc catggtaaaa    73320
ccccatctct actaaaaata caaaaaaatt agccgggcgt ggctgtgcat gcctatgatc    73380
ccagctactt gggaggctga gaggcaggag aatcacttga acccgggagg cagaggttgc    73440
agtaagccaa gatctcgcca ttgcactcca gcctgggcga caagagtgaa aatccaactc    73500
aaaaaaaaaa aaaatcgttt gtagagacag ggtctcacaa tattgaccag tctggtctca    73560
aactcctggc ttcaggcagt cttcctgtct tggcctccca aagtgctgac attatagcca    73620
tgagcccctg cacccagcct tattttttaat tttttgagga acctccatac atgttttcca    73680
taatggctgt acttatttac cttctcacct tattgtataa tggtgcatat ctcagaatgt    73740
gtccttactg agtgacacat aactatattt gaagtaagtt tcttatagat agcatatagt    73800
tgggtctttt cttttctttt tttaatagag acagggtctt gctatgttgc ccaggctggt    73860
tttgaactcc tgggctcaag cagtatgcct gcctgggcct cccaaagtgt tggtattata    73920
ggcatgagcc accatgcctg gcctaggtct ttttttttg agacagggtc tcacttttgt    73980
cacccaagct ggagtgccgt ggtgcaatca tggctcactg cagcctcaac ctcctaggct    74040
caatcagccc tccacctcag cctcctgagt agctgggatt acagatgcat gccatcatgc    74100
ctggctaatt tttgttttgt ttgggg tttt tttggtagag acagggtttt gccatgttgc    74160
ccaggctggt ctcgaagtct tgggctgaag tgatccacct accttggtct cccaaagtgc    74220
tgggattaca agcgtaaacc attacacgtg gtctagttgg gttctttttt aaaagaatca    74280
gttctactaa tttcttttcg ttggtatgta taaaccattt atatttaata taattattga    74340
tactttggat ttaaatttgc cattttttgtt tcattcatta tttttgttct tctgtttccc    74400 cttttcctgtt ttacagtggg ttccttgaac atttttttaat atttcatttt gagtgtatct    74460
ctttataaag tttttttgtgt gattgctcta ggaatatata tgtagataac ttattacagt    74520 ctattaaatat caactttta ccaccttaag tagaatgtag ttagttttag tagaaggaat    74580
cttttagttc cttctacctt tcttcttctt tttttttttt tttgagacgg agtcttgctc    74640
tgtcatcagg ttggagtgca gtggcgtgat ctcagctcat tgcaatctcc acctcccggg    74700
ttcaagccat tctcctgcct cagcccctcc gagtagctgg gattacaggt gcatgccacc    74760
acacccagct aattttttgta tttttagtag agatgaggtt tcaccatgtt ggccaggatg    74820
gtctcgattt cctgacctcg tgatctgccg gcctcagcct cccaaagtgc tgggattaca    74880
ggcatgagcc attgtgcctg gcacaccttc cttctttatg gtacagttgt cttaaatatt    74940
acctctacat acaaggagaa ccacttcagg gactgctata atttttactt tcaaccatca    75000
aacataatct ttaaaactca agagaagaat tgcttaatta gtgtatgtat gtgtgtctgt    75060
atatgaataa acatatatat atgcataaca tatatatgga tatatgcata tatagacaca    75120
cacacaccct ttccattgct tttttcttac ttctatttga ggttttcttc tgttatcatt    75180
tacttccttt ctgatagagt ttcttagcc attcttttca aagctgatct gttggtgaca    75240
catttttagt tttgttcatc tgccagtatt tgtatttcat ttttatttct gaaggatatt    75300
ttcactgtct atagaatttt agcttgatag ttattttctt tcagcatttg aaaaatattg    75360
tatccatcct tgtggtttcc atggttcctg atgaaaaatc tgttgtcttt caaattgtta    75420
```

```
ttctcctatg agtgatatgt tgtttctctc taattgattt caggacttTT ctttagtttt    75480
tagaagtttg attctgtaag tttatatcta aatctgaggc tgagtgtggt ggctcatgcc    75540
cataatccca acactttgag aggccaaggt aagaggattt cgtgagtcca ggagtttgag    75600
accagcctgg acaacatagt gagacccCac ctctaaaaca gatagataga tagttgattt    75660
tgttttTgTT ttttccTTTT tttgagacgg agtcttgctg tgtcacccag gctggagggc    75720
agtggctcga tcttggttca ctacaacctc cgcctcctgg gttcaagcaa ttctcctgcg    75780
tcagccaccc aagtagctgg gattacaggc accCgccacc acaccCaact cattttttgt    75840
atttttagta cagatggggt ttcaccatgt tggccaagct ggtctcgaac tcctgacctc    75900
aggtgatccc cctgcctcag cctcccaaaa tgctgggatt acagatgcga gccaccgtac    75960
ccagtagaca gttTttagcc attatttctt aaatttTTTT tTTtcatctc tccatTcatt    76020
ctcttactct tgggaccctg atagcatgaa tgttagatct ttgttattat cccacaggac    76080
tttgaaactg tgttcatttc tTttcaatct actttctctc ttgtacagac tggatgattt    76140
ccattcattt aagttactA attgtttcct ttatcatTTT tcTTTtgctg ttgagcccat    76200
ccagtgggtc ttTTtaattt cagaaattTT attttTaaaa attccatttg gtactccTTa    76260
tgtcttctat atgctgagtg tttataatgt cttgtttgag cagtttcatg agcgctgttt    76320
taaattcttt tcaaataatt ccaaaatcta tattatcttg gtattgtcat ctgttgattg    76380
ccttTTTTca ttcaagttga gatTTTcatg ttcctggtat aatgagtaat gttggattgc    76440
atcctagcac ttgaaatatt gtgctatgag attctggttc ctgtttaaat ttTTatattt    76500
aacagtcaac ctgtttaggt ttagaacaca taccctgtcc cactttTgtc gactgtggtt    76560
cagttttcag tcttgttTTA ctcttatggt ctgtgctacc gaaaggccag tctgaaattt    76620
aggtgttatt ccggagcagt gtTcagttct tatgccTTTT gctgtgttgt ttctggtcat    76680
ttttacacat gggttgctca gaggcactTT taggatttca tacacagatt cagagaattc    76740
atttctctag ctctctcctc accataatcc tTTcccaatt ctgtagtTTT gctgggatta    76800
ggactccatc tggttattcc agggtagaga aagatgagTT cacccacatt ctctgcagct    76860
gtaacatgga gaagagggga aaggcgtgcc acctcatTat ggcagagTTg tgttggaagg    76920
cagaatgctg ttcacaatTT ctgggccaca gtgtctggtg aggaaaagga ggggtacctc    76980
ctcccctTTT ttagtttgcc tggtcaaaat gtTTTTgtct gctgagctgc ccctTTccca    77040
gttctttacc tagagagggc aggctTTTct tggcactTTc ttgtctgtgc ttactggatc    77100
tttcagattg tggcttcaga gcttgggcta ggacatatta gaagttaaac caaaccaaac    77160
aaaaagtag ggagcttcct gttgggtcag tcctcatgtc ccctggtccc tagccaatct    77220
accTTctTTT ttctactTTT cagaatTTTT ctgtcacTTg tgtcatgaat ttcatctaga    77280
atgTTcggTT ataatcggtg ggaagggctg ggcgcggtgg ctgacgccta caatcccagc    77340
actTtgggag gccaaggcga gcggatcacc tgaggtgagg agttcgagac cagcctggcc    77400
aacatggtga aaccccgtct ctactaaaaa tacaaaaaaa attagccggg catggtgggg    77460
gacgcctgta atcccagcta cttgggaggc tcagatagga gaatcgtTTg aacccaggag    77520
gtggaggTTg cagtgagctg agatcgcgcc actgcgctcc agcctgggca agaagagcaa    77580
aactccatct caaacaaaaa caaaacaaa acaaatcag tgggaggaat agggtggaat    77640
atgcTTactc catcTTTtcc tgaactgtaa atccctgctg caatTTtaaa ttatgaactt    77700
tagTTccagT agTTTTTTTT aacctatgta cgtagtcTTT caaatacaaa taacagTTaa    77760
ggggtTTTcc cccaataatt atatcTTgTT ttcTTTTctT ttcTTTTTTT tTTTTTTaaa    77820
```

-continued

```
gagaccgggt ctcgctgtat cgcctaggct ggacttgaac tcctgtgctc aggcaatcct   77880
cctccctcag ccttccaagt atctgggact acaggcatat accccatac ctagctgttt    77940 tcttatccca ttatctactt ttagaacaag gattggcaaa ctataatctg tttcccatat   78000
ccagctcact gcttattttg gtatggcaga caagctcaga ataggttttc cttttttttg   78060
gagacaggtc tcactttgtc actgaggctg gagtgcattg gtgtaaacac agctcacttc   78120
agcctcgacc tcccaggctc atgggatcct cctgtctcag agagaaaaag agagagagaa   78180
aaaaagaaat tatatgaaat tcaaatttca gcgttttatt agaatatgcc atgttcattt   78240
gtttatatat tgtctgtggc tgccttcatg gtacgacagc agagttgagt agttgaagca   78300
gagacttaat tgccagccct ttttccagat gatttgtaaa tcctagaagt gaaaccattg   78360
tccctttctt gtcctgcttt agtgatactg atatttcaag atacataatt ttcttgggtg   78420
aaagtttctt ttgtttctgg tttctaggta tttgtgagat atttctctca caaacgtgt    78480 tcttttcttc tggttttttt ttgggggttt ttttttgtttc tttggttttt tgagacagtc   78540
tcgctctgtc acccaggctg gagttcagtg gcgcgatctc aactcactgc aacctctgcc   78600
tcctgggttc aagcagttct cctgcctcgg cctcccagt agctgggatt acaggtgcct    78660
gcaatcacgc caggctaatt tttgtatttt tagtagagat ggggtttcac catgttggcc   78720
aggctggtct tgaactcctg acctcaggtg atctgccctc cttggcctcc caagtgctg    78780 ggattacagg catgagccac tacgccttgt ctcttttcct ctgttatctg acttactgga   78840
tggcatctgt taggtaaatc agaaaccaaa gaggagtagc attcagcact ccctgtcacc   78900
ccaagagcaa atctattatc acccctgtg cagtttactt cctgaatatc tccttccttg    78960
taacactttt gtgtctccac cagtaacttc taactggact gtccacatcc agtgctatat   79020
tctctacacc cagctaaatg aagtgttcat tccaaaatgc agggcaggga ggtcactgtc   79080
atgcttctgt tcttcaaagg cttcttaatg cttatgggac aaagaaaaat caccttgtg    79140 tggccctacc ctgtatacat ctccagcttc ctggcacctg ctcccccta ctctttatac    79200 ttcagacacg gtggcttctt tcagaccctg ctcctgccct ttctgaggtt acggactggc   79260
atggagttcc ctgccctcct taatgcctcc ctgattcctg ttcatcttct acttgtcagc   79320
tcaggaatca gtgccttagg gaggccttgg ctgagctccc tgactaggtc aaattttctt   79380
cttctatagg ctcttagagt cctataattc tcttttccat cacttctcct atttgtctgt   79440
gaggtgattt gtttaatgtc agttttctgc tactagactg taagcttcat gaagataggg   79500
attctgttag aatttgttca ctatttctag tagaaggaac agggcctagc acatagtaaa   79560
tactgagtaa gcgggttatt tccccaatga ttgcctttt aaagaaaacc agttctgtaa    79620
accagcattc atcaggctta tcatatggct tttatattt tgaattattt ttgtgaggat    79680
ttttattaat atgttttcca ataatggacc atggttaaat ttttgaagta agccttactt   79740
gatcaggttg tggtataatt ataacatatg ctgctttttc tttgctagga ttttaagatt   79800
ttgcagttaa agttatttc tttttgtgt gctttgtcag atttttgacat cagtgttata    79860 ctagtatttt catggcttat tttattccat tctttatttt tcaactttc tatatcctta    79920 agcttaaaaa tgtctctttt aaacagcata taattgaggg cttttattat taggctttat   79980 aattttttgta ttttaattgg aacatttagt ttgtttaata tagttaatat attctttgct  80040
ttctattttc ctcaaagatt tgaatagaac aaaaggctga cctcccccaa gcaagaggga   80100
attctctggc agtctgcctt tgcacttgaa atgcaactcc tccctgaatc tccagcctgc   80160
cagcctcttc tattatgagt caattcctta aaataattct atatgatata tatttaatat   80220
```

```
aattaatata taatgtggct actacctagt agaattaatg tatacttaat atgacatata    80280
atataattac agtagtacct tcttatctgg gggaagcatt atattccaag accoccagtg    80340 gatgcctaaa accacagata tatattttcc tatacataca tagctgtgat aaagtttaat    80400
ttataaatta ggcacagtaa aaaattaaca ataactaata ataaaataca atacttataa    80460
taatatgcca gcatgttcct ttttctcttt tttcttgctt tttggattga tagacttttt    80520
tactatccta gcttttttcc ctcttgccaa gttatagacc ctgttctttt agtggttacc    80580
ctacagatta caacacatag cctgcatgta taggaatgaa atacagttta cgtagggttc    80640
agtaccatct gtggtttcag gcatctactg ggagtcttgg aacatatccc cccacccccc    80700
ccccagataa gggggtagta ctgaaattat attaaatata tgcttattat attaaatatt    80760
agtcatatat tacatacata ttatatagat ttattttaag ggattgattc acagtggggg    80820
aggctagcag gctggagacc caggaaggaa ctgcacttca agttcaaggg tagtctgctg    80880
gagaattccc tcttgcgtgg ggaaggtcag ccttttgtgc tattcagacc ttcagttgta    80940
tggatgaagc ccacctacat tatggagggc aaccttctgt actcaagagt ccattgattt    81000
aaatgtaaat ctcatccaaa aaaccccctc acagaaatat ccagaataac ctttaaccaa    81060
atatctggac actgtggtgt ggcccaacca aattaacaat cacaagtcta ctctttatca    81120
acttggcacc catacacatc tccttaaacc attattaatc tccaaataaa gacagtaaca    81180
aagtcatact tctgcttagc atgaaagaac tatcttgcat gtagccgaaa acacactatt    81240
cctttctcta aaagaggatg cagattattt ggttgatgtt tactcttctt gatatcctgc    81300
aacttaaatt ctaaagttta agaaaaagtt aatacttaag tattatgatc agctgttaat    81360
ctaatttttt ttgacgaaaa tattttcgta tccattttct attgctgcct agcaaaacat    81420
ccccaaattt aatattttaa agcaacaacc atcaaaaatt ggctcacaat tctgtgaata    81480
tcaatcaatg ctgggtagct gtttggttcc tctactggtc tttttttttt tttttttttt    81540
agacagggtc tcactctgcc acccaggctg gagtgcagtg gcatgatctc ggctcactgt    81600
aacctccgcc tcccaggctc aagcaattgt cctgtctcaa ccttctgagt agctgggatt    81660
acagacacac accactacca cctggctaat tttttttattt ttagtagata tagggtttca    81720
ccatgttggc caggctggtc tcgaactcct cacctcaaat gatccacctg cctcggcctc    81780
ccaaagtgct gggattacag gcgtgagcca ccatgcctgg cccctctgct ggtcttgatt    81840
gaagtcattc atgcaactgt aatcatctaa tggttcatct gggactgaga ttgtctcaag    81900
cacatgtctg gcagttggtg tcacttgttg attgggcctc tctcttaacg taaggaagtg    81960
agccaaagct tctcacatta tgacagcagt gttcccatag agccaaatga cagctgtaag    82020
ttctcttgag gtatcaactt ggaagacaca ccattacttc tgcatttat tggtttaagc     82080 aagtcacagg gccaactcaa attaaaggaa tggagaaata aacttcacct gttgatagga    82140
gtggcagtgt ctcactgtaa aaggcatgtg tacaaggatg ggattttacg tagccatctt    82200
tgcaaacagt ctaccacagt gtctttttc ctttcgagtg cttaaaaaaa ttgtttttaa     82260
ataattattt ggttttcaga aatttcacta ttgtgtatct agacacagat ttcctttta    82320 tttatctgtt tgggggtgt ttagggcttc ttggatctgt ggtttgatgt ttttcctcag     82380
ttttggagaa ttttcagcct tcgtctgttc ttcgaatatt tcttctgttc catttctccc    82440
tttccgcttt tctgaaactg aaattacatg taggttagat catttcattg tatcctttat    82500
acctcttacc ttctctttgg tattttttta taaatctttt tgcttctctc tgcttcattc    82560
tagatacttc cttttgacct atttaccagc tcactaattc tctcttcagg tatattttac    82620
```

```
ctgttcttaa atttatccat taagatcttt ttttcagatc tgctattaca tttttatacc   82680
attcttgact aaaattctta atgctacagg actgttcttc ttgtctgttt cttactgatt   82740
ctcatgttgc cttttatgg actagacact gtagttttaa aattatttat agaaatgacc    82800
tgagacctat gatatatttt tcaagagagg atttacgttt gtttctagct ttgcctagga   82860
gtcttcaatc atttaattc agtttcaggg actgatttgc ttttaagcag ggctgtagtc    82920
cctacagggg tggtcaactt catttcacta cctaatatac ctattatgtg tggagtactt   82980
tgctagatgt tgggtaggtc ttgtgagcag agcagacctc tctttggtct gtatggagca   83040
cggagcttga ttataattgg caggtgtgtg tgtgtgtgtg tgtgtgtgtg tgtaaataaa   83100
taaatattta tttatttatt tattataggc cgggtacagt ggcttacacc tgtaatccca   83160
gcactttatg aagtcaaggc aggtggatca cttgaggtca ggagtttgag gccagccttg   83220
ccaacatggt gaaaccctgt ctcttctgaa aatacaaaaa ttagccagac gtggtggcag   83280
gtgcctgtaa tcccagctac tcgagaggct gcggcatgac agtcactcaa gcccgggagg   83340
tagaggttgc agtgagctga gattgtgcca ctgtaatcca gcctgggtga cagagtgaga   83400
ctccatctca atatatatat gcgtgtgtgt atatatatat atctatatct ttaagataga   83460
tatatttata tagctaagta attaataaat atattaagtt ctatgaaagc aatgagtagg   83520
ctgctatggt tgtgaatatt tggactacac aggggataag aatgggtcta ccataattag   83580
cagggacagg ttttgtttaa gccaaaaact aagagggctt agaacagaaa ccgccaggca   83640
gaagcagtta ccagtgtgaa gactagatga caaccaaaaa agtatgtggg aggagggagg   83700
ggaggttgcg cagtggggag ttgagattga cttagaactg tattaatgag ctttccccc    83760 aaccccatt tttctcccat ttaccttcag aaaaattagt gatttggcta ccagtgaatc    83820
taggctccag gtgtagctct gtagttttgg actagttacc taattcttca ttcacaacaa   83880
aacagaagga gagaggaaaa agagagcaaa catggaattg ggatgggaag taagagagca   83940
catgaggaga gagactatgt caagtttctt cgtattcctt ttttaattac agaagaaaag   84000
atgggataaa aatattccat cttatttctc tgtttaaaag aaagagtagg ccgggcatgg   84060
tggctcacac ctgtaatccc agcactttgg gaggctgagg caggcggatc acaaggtcag   84120
gagtttgaca ccagcctgac caacatggtg aaaccccatc tctactaaaa ttacaaaaat   84180
tagccgggcg tggtggcgca tgcctgtaat cccagctact gggaggctg aggcaggaga   84240 atcgcttgaa cccgggaggc agaggttgca gtgagccgag atcacgccac tgcactccag   84300
cctgggcaac agagcgagac tccttctcag aaaaaaaaaa aataataata ataaaataaa   84360
taaaagaaag agtaaatgaa tcaaaatgaa gagaagccat tttatctgcc tcctggatga   84420
agagtttcat tgatgaacct gaaatgtttt ggttaacatg agaaaggagg gtgagaagat   84480
gcctgagatg tgagctcctt gaggacagga gctgctttct ctctccagcc tggcacaaga   84540
caaggaactt agttgaatga atgagcaaat aagtggttct ctgctttgaa ggaacttgga   84600
ctgtcattac cttgcaaatc aggtttacca tttatttgct ttatataagt tccagaaaga   84660
aactatttcc tctcataata ttactaccct aaacttctgg tctgatctat ggattgtaga   84720
gcttaaattt cctcaaaccc caacagtcag agattgttac accaagataa atagcatatt   84780
tctcagcgcc ttgtattttc tgtctttggc cacagacctt aggacttagg ctgatatttg   84840
agaaggaaaa actggaattt agtagaatta tacttcctgt atcttaattt ccaactctt    84900 atataaggtt tgcttttct agagagagac taatctggaa tgagaatgaa ttctcatcag    84960
taaaggcaaa gctttaagtg ggtcatctga ctttgctttt gtgctctaca ttcaccctgc   85020
```

```
tcataaaagg tcctttcatg agttttctag gctttcatca ctgccagcgt ctccacaggc    85080
attgtgaaag tattaaactt cctaccctcc cccatgcttg tctcatggac tctttcgtag    85140
agtgcacagt ggactgtgtt tagctcagca ggaactcttt gcaaacactg aatacatgaa    85200 caaccccct  ggaaagataa gagatttcag tattgcttgg tgtcatagcc gcagaagtta    85260
gtgtctgcca gtatctgatg aatatggtga cttgcagcct aattttgtg  aaattatgag    85320 gccaaagttt aagaagtgtt catgttaaag ttacttatat ataaatttg  cctatcgata    85380 atttctgtca ataggaggtt gatgaatgct tcacataacc tagatactcc taattaactg    85440 tttttattt  ctttttttct aggacacatg ttcaaagagc ataattaact ttttaaaaga    85500
agctagtaag tactgaaata gtttttaag  tttttctac  aagaatagag gaagaaagga    85560
aacatggaat tctgaagggc tacttagcaa gctgcttatg gcataatctg gggtggggt     85620 gcatagtaaa ggatttgcat tttactgaga ccgatacatg tcaagggaat ggtatttaaa    85680
attagtgata tgtgttgatt tttcaaggac tatagcccat caactacaat aggctccaaa    85740
aaattctggt gaaattagct tcttggagcc ttccagttta cctactatgt tattcccact    85800 ataaatatt  ctcaactttt ggggttttag ccacttaagt ttttttatttt ctctaatgtc    85860 tctagtatct gctttagttt cctgtcaatg ctagactctg tggttcagca gttcatccat    85920
tctcttccca gtactcaacc tcgttgctta tagtttcatt acattcatct agcaaaacct    85980
taattctgta tgtttgccat accattagtg cttagagcat tttttcagaa aagaatcctg    86040 gaaaatgga  tcttatctca cctgggccct caggactgct gggctgcctg gtgtcagcac    86100
ttcccgccat tttctatagc accagtatta ttcttaatac tttaaaaaac caccaggcac    86160
ggtggctcac gcctggaatc ccagcacttt gggaggccaa ggtgggcgga tcacaaggtc    86220
aggagatcaa gaccatcctg gctaacacag tgaaaccctg tctgtactaa aatagaaaa     86280 aaattagctg ggcgtggtgg cgggcacctg tagtcccagc tgctggggag gctgaggcag    86340
gagaatggcg tgaacccggg aggcggagct tgcagtgagc cgagattgca ccactgcact    86400
ccagcctggg tgacagagcg agactccgtc tcaaaaaaaa aaagtaaata aaataaaaa     86460 accatatccc actatctccc ccttctctct ttgcctgtga tcttgctgca tacttatggg    86520
gaaatcttta agatgtcaga tttcagttct ctcactttc  tacaacttct cccacttttg    86580
cctttcttat gtaccttccc ttccttccca tctgattcct tatcagtatt tacacatgat    86640
tagttcttgc ctaacctaat agacccttc  ttgagtgcaa atcagtggct atttttgcta    86700
gggtataaaa attcctatc  taatcacctt gacaaagtta ccctgttatt tccaataact    86760
tacttcctat ggattcttgt agatttctt  tttttttttt ttaatttttt tattttcaga    86820
tgttttctcg ctttgtcacc atgcctggcc taaattctcg taggttttct atgtaaacaa    86880
tcagattttc tgcaagtatt agtctccttt ctaattgtta taattttaat ttcttttttct   86940 ttttaaaatt tttcgtagag acaaggtttt gctatgttgt ccagcctggt cttgaactcc    87000
tgggctcaag caatcctccc atctcagcct cccaaagtgc cattacagtg gcatgagcca    87060
ctgtgcctgg ccaaatttct tttcttgttg cgaaggcaga cttttcatac aatactgaat    87120
agaagtgata gtagattact ttatttctga ttttcaaagg aatgctttcc gtttctctct    87180
gttgaagata attgcgtatt gttttttttt ttaaatagta acttttatca ggttaaggaa    87240
ggtttcttct atttctattt aaaaggattt tttaaaatct tgaattcata tgttttttatc   87300 taatgcattt tctacatcag ttgaaatggt tgtatgaact cttttaatat gggtgaatta    87360
tatttataga ttttatgtta aaatatcctt gtatatcttg gataaactca actggatcat    87420
```

```
gatttatctt ttttatatgc tagattcaat ttgttgatac tttgttatga tttttgaata    87480
tatattattg tgtaaaagtg agcctgtgat tttctttctt gtaatgtttc tgtccagttt    87540
tggtgcctgg ttttgctctc tccttagaat gagctgggaa ctagtcactc ttgttttctc    87600
acctataata gcatctgggt ccagtgtttt ttatgtggga caaatttgaa cttgtggtca    87660
acctctttaa ttgtaagaat attcaggtct tttgttcttc ctgggctagt ttttttattct   87720 ttttctagag attcgttcat ttttcttagt tttatttgcc tataattgtg gataatctgt    87780
tttttatctg ctacttctgt aattatttcc acatttgatt tataatatta acttgtgggc    87840
caggcgtcgt ggctcacacc tgtaatccca gcactttggg aggccgaggc gggcggatca    87900
cgaggtcaag agatcgagac catcctggcc atcatggtga acccctgtct ctactaaaaa    87960
tacaaaaaaa aaaattagcc gggcgtggtg gcaggcacct gtagtcccag ctactcagaa    88020
ggctgaggca ggagaatggc gtgaacccag gaggcggagg ttgcagtgag ccgagatcgc    88080
accactgcac tccagcctgg gcgacagagc gagactccat ctcaaaaaaa aaaaaaattt    88140
acttgtgtct tctcttttta cctgtttgtt aatttatcaa ataactactt ttggctttgt    88200
ttcattttta ttatacaata aaatgaaatt cttttcattg tatttctttt cattgattat    88260
tcctataatt cttaaacaac tttataattg atgtaacaat aacctgtaca catttaaagt    88320
gtaaaattta ttcattttg atccatgtat atagcaggga aatatcacca caacaagagt    88380
gtgaacatat aatctctccc caaagttttc ttgtgtcttt tataatcact gcctcttgcc    88440
cctgcccact ccctcatcct taagcaacca ttggtctgtt ttctgccact atagattaga    88500
ttgtattttc tagagttttta tacaagtgaa atcatgtagt atagtattaa ccatgtgttt    88560
gtttgtttgt ttgtttctttt cttctttct tttttttta gacggagtct cgctttgtca    88620
cccaggctaa agtgcagtgg ggcgatctcg gcttactgcc agctccgact ccggggttca    88680
caccattctc ctacctctgc ctcccgagta gctgggactc caggcgtgcc cgccaccacg    88740
cccagctagt ttttgtattt ttagtagaga cggggtttca ccatgttagc caggatggtc    88800
tcgatctcct gacctcgtga tccgcccacc tcagcctccc aaagcgctgg gattacaggc    88860
aggagccact gcgcccagca actatgtgtt tctgatcctt tgtcagggct agccaattcc    88920
tagagacagt gaataactca ctcataatct agctgcctcc tttatgtcgc tctcatagga    88980
ctttgacacc tctctgctac aatccacctg ccctgttcat ttcaagatca ggtaccagga    89040
aactcgggac atccctatgc tgcagaactc actgaaatta ttcaaactag ccagtcctaa    89100
acatgcttac cctgccttgc ccattccttc cgctgaaacc acataaaggc tcttgcccat    89160
gttttcatcc cattccattg acctccttac tgacccctagc tagtgcttcc tcatgtggcc    89220
cctgcatggc atggtgtgca ccttcctctt cggaactgcg agtaactgtc ttgtcagcgg    89280
caatcatctt gtgatctgtt ggcctcatca tatttgaata acaataaaat ctgttttaag    89340
gctgggcgcg gtggctcatg cctgtaatcc cagcactttg ggaggccaag gcaggcggat    89400
cacgaggtca agagattgag gtgaaacccc ctctctacta aaagtagaaa aattagctgg    89460
gcatggtggt gcgtgcctgt aatcccagct actcaggaga ctgaggcagg gaatctcttg    89520
aacccaggag gcagaggttg cggtgagcca agattgcacc acggcactcc agcctggtga    89580
cagagcgaga ctccatctca aaaaagaaa aaaaaaaac tgtcaaatga tactccaaaa    89640
tggttgtacc attttatatt tgcaacaaca atgtctgagg gtactgattg ctccatatcc    89700
ttgacagcac ttggtatagc tgatctttta attttagtca ctttagtggg catatactgg    89760
tattttatgt tttactttttt attttcctaa tgattaatag tttgcagcat ctttcatgtg    89820
```

```
cttatttccc tttcatatat cttctttgat aaaaatatct gttcaaatat tttgcccatt   89880
attttgttgg aatacttatt ttcttactgt tgagctttga gagttcttta tatatctgga   89940
taccaatcct ttgtcagata tattttttgc aaaatttttt cccagcctgt gatttagttt   90000
gttattctca tgtcttttaa aaaaaattgt agttaaaata tacacataat acaaaattta   90060
acattttaac tctttgtaag tatacagttt tgtggtatta agcatagtca cattgttgtg   90120
caaccatcac cgccatccat ctctggaact ttttcatcct ccctgactga aattctgtac   90180
ccatttaaac actaacttct cattcccct tactccagcc cctggcaacc atcgttctgt    90240
tttccttctc tatgagtttg actgctctaa gtacttcata taagtggagt catacaatat   90300
tttcattttg tgactggctt attagtataa tgtcttcaag tttcatccat gtggtagcat   90360
gtgtcagaat ttccttcctt tttaaggcta acattccatc ctatgtatat accacatttt   90420
atccattcat ctgttgatgg acatttaagt tgcttcctcc ttttggctat tgtgaataat   90480
gctgctgtga atgttgttgt ataaatatct gttcgagttc ctgctttcaa ttcttttgag   90540
tatgttccca aaagtagaat tgctgggtca tatgttaata ctgtatttag tttttttgagg  90600 aattgccata ctgatttcta tagtagtggt accatttaca ttccaaccag cagtgttcag   90660
ggttccaatt tgttaacatt cttgccaacc cttgttgttt tctggatttt ttttattttg   90720 gggttttta ttttatttat ttattttttt tttgaggcag agtctcactc tgtcacccag     90780
gctgaagtgt agtggcgcaa tctcggctca ctgcaacctc tgcccccgg gttcaagcga    90840 ttctcctgcc tcagcctccg agtagctggg actacaggcg cgcgttacca cgcctggcta   90900 atttttttgta tttttagtag aggtgggtt tcactgtgtt aatcaggatg gtctcgatct    90960
ccggaccttg tgattcaccc gcctcagcct cccgaagtgc tgggattaca ggcgtgagcc   91020
actatgcctg gccatttttt attttttaaac aatagccatc ctaatgggta tgaaataggt   91080
tttttggtgt tttgttttt ttttttgaga cagaatcttg ctgtgttgcc ctggctggag     91140
tgtagtgacg tgatctcggc tcacctcaac ctccgtctcc tgggttcaag cacttctcct   91200
gcctcagact tccaagtggc tgggactaca ggcgcccgcc accacaccca gctagttttt   91260 gtattttag tagagatggg gtttcactgt gttggccagg ctggtccacg atccatccac     91320
cttggcctcc caaagtgttg ggattacagg ggtgagccac catgcacagc cagggttttg   91380
ttttgttttg tttttactat tttttttttt ttttagagac aagctgtctc ccaagctgta    91440
gtgcagtggc accattcgta tctcactgta acctcaaact cctggaccca agcaatcctc   91500
ctgcctcagc cttccatgta gctacgtcta caggcatgtg ccaccatacc cggctaactt   91560
tttttttttt tttttttttg agagttttgc tcttgttgcc caggctggag tgcaatggca   91620
tgatcttggc tcactgcaac ctcctcttcc tgggttcaag tgattttcct gcctcagcct   91680
cctgagtagc tgggattaca ggcgcccgcc accacgcctg gctaattttt tgtattttta   91740
gtagagatgg ggtttcacca tgttggccag gctgggctcg aactcctgac ctcaggtgat   91800
ccacccacct tgacctccca aagggctggg attacaggcg tgcgccacca cacctggccc   91860
ccagctaact tttaaatgta ttttgtagag atgaggtctc actgtgttgg ccaggctggt   91920
cttgaacttc tgagctcaag tcattctccc acctcggcct cccaaagtgc tgggattaca   91980
ggcatgagcc accacacctg gccccttgc ccatttaaa aattaggttg ttttgttgt       92040 tgttgagttg taggagctct ttgtatattc tgcatttcgg ttccttattg gatatgtgat   92100
tggcatacat ttttccccat ccatggattg cttttcatt ctgttatagt atccttgatt    92160
cacagaagtt tttaatattg atgaggtcct gcttagtctg tgttttgttt tgttgcttgt   92220
```

```
gcttttggtg ttatatccaa gaaattttg ccaaatccaa agtcatgaag ctttgccctc    92280
tgtttccttc tgagttttat agttttagga cttaaattta ggttttcgac ccattttag    92340 ttaattttg caagtggtat aagggagggg tccagcgtta ttgtttcacg tgtagatata    92400
cagttttctg agtaccattt gatgaaaagg ctgtccattg aattgctttt gcaacttta    92460 tttgggcata tttatgtgag tctgttactg gttctatatt ttactccatt gatctatgtg    92520
tctattcctc tgctaatact gtcttaaata tggtagctat atagtaagcc ttaacactga    92580
gtagatagat ttctcccctt ttttgttct ttttcaaaat tgtcactggt ttgttttat     92640 tttttacttt atgcagataa tctgtactat actttggttt catgtatcaa gtagtttgtt    92700
ccaagttgtg ctttaagcag aacaaataaa ttttcatatt gttctttgtg ttaatctgca    92760
atataaacct ataccaaatt ctattttgtg tatttgttta ttgtagtaat ctgactgact    92820
cttttgcctc cagactcatc tctttcaagg tccccaactg aatcttgttt taggtggaac    92880
ttagaagcag tagaagttaa gaatctattt cacagcctta gtagtctagt ttcattctct    92940
atataatgtt gtctatgcaa gtgagctgct ctccagtgcc ttagtttcac taatgttggg    93000
gaaggtctct tctcttgttt tggacttctc tatcacattg cctttctcaa gagaagacat    93060
ataatgaaag ttgatatctg gtgttctagg acttcttcag aagcttgcca gttttcaag    93120 ctgatttctc tcactggcaa ctcttcagag tgctgttcct actccaccct ccctggtgg    93180 tatgtatcag ttttctactc atcagcaccc acctactcct gcctactgtg tttctcagat    93240
gtctgctgcc tggctagctc attgctgctt ttgtcactca tagagctgtc ttcttccctt    93300
tttttggctt tctgcctgac ttccagggca gctgctctgt cattgcctgt ctgccattct    93360
gtcttttttc cccctacccc ccacagatac aacatctact ctaataccac acattctcca    93420
tgttcaaact aacctcatca ctttccccac cacattcccc aaaactggtc atcctccagc    93480
ttatagcatt gcagttcact gaagttagac atctgggcct tgcttacctc caacatctca    93540
ttagccttcg attctacccc tataaatcct cttctcagtc tcctttagat attcctgccc    93600
tgctgtgaga tccatctggt ttattggcta gattacttca gaaagcttca gtcagtgacc    93660
ctccttactt caaaccccac cagttgatcc ttcactctgc catcagtcat tgcttctaaa    93720
atctaaattg ttccatttaa ccttgctgtg ataaaacctt tggtagttct tcagtgtgtt    93780
cagtggtaag ttaaaacttt cactgtaatg tacaggcccc ttcatgatat gatcgctgcc    93840
tcctcgagcc tcattgtgtg catttcccg ccccacccct tcctcaccca ccctagtctt    93900
tcatgtctgc cattttttaca ttcatttagc agatatttat tgaagccccc tgtgatgtcc    93960
ttacctaggt ctttcttgtt gccaggacca gacaggcttt ttcaagcttc caagtcatct    94020
cagtttgaaa gactatgtct gacccttgtc ttggccaatt actctttatc cttccaagtt    94080
caatgattgt cccactgcac tccaaccaga gtgagagagc aagaccctgt ctcagtaaat    94140
aaaaataaat aaataaataa ataaataaat aaataaatca gccataattt atttaatcat    94200
gtctctctcc cccattgata gacgttaagg gtatttccag tattcttctc ttgaaaacaa    94260
tgctacattg aataaccttg tacatgggtc actttgaaag tatggatatg tatccgtgga    94320
ataagttccc agaagtggaa ttgtgtcaga ggggttgtgc atttgtaatt ctgatgaata    94380
tttatagatt atatgagagt acctgtttac tcaaactctt gccaatgcag cattatcaaa    94440 gtttttatg ttcgccagtg tgatagatta aaaatggta tctcagccag gcgcagtggc    94500
tcacgcctgt aatcccagca ctttgggagg ctgaggcggg cagatcacgg ggtcaggaga    94560
tcgagaccat cctggccaac acagtgaaac cctgtctcta ctaaaaatac aaaaaattat    94620
```

```
ccaggcgtgg tggcgggcac ctgtagtccc agctactcgg aaggctgagg caggagaatg   94680
gcatgaacct gggaggcgga gcttgcactg agccgagatc gcgccacaac attcgagcct   94740
gggcgacaga gcgagactcc gtctcaaata ataaaaaaaa aagatggtat ctcagcattg   94800
atttctttga tcatcagtga ggttgagcat cttttcatag atttaagaga actgtatggt   94860
tttttgtgag ttatgtttca tatcgtttac ccattttact tttaggctgg aagcagctgt   94920
tttagtggaa tggtggaaca agaagccaga ttgccatgga gagacaactc tttctagaga   94980
tttggctatg aagcagagta gagacaatga tagctgaagg attgatgtag atgcaaagaa   95040
atttttcatc ttctttgaaa acttaattgt gttaaaaact ggtatgaaag ggaggggtta   95100
aagctagaga tggtggtaga aaaaaatgca gggttcctaa aggactgaga ttcctggatg   95160
gaatttcagg gaagggaaa atttctggat atagtgactg gggagttaag ggtgtctagt   95220
ccaatggctt ttattttctt ggaagggtag gcaaggccaa cagccacatg tgtgggagga   95280
gatggttaga ggggagagga ggtttgaagg caccgctatg gagaattgga gagagctaag   95340
gaaagacaga aagactgcag aaagtgctta gggttccact gaagcggaaa tagtgatttg   95400
tagtgataca acccttatga gttatttgat ttttttttt ttttaagcag catctggcag   95460
tccaagtata gggctgacag tttgggattt tctttccat gttggtgtaa aagaagaaca   95520
gtgtagtgaa ggaagttagg acaaaagaat gattgaactg acaccaagtt ttcttgattt   95580
ggtagaaaag gaaataaaga tagagcagag atattgaaaa gaattagaga ggggttcaag   95640
agactgaagg cctgggtgag gtcagagagc aggtgtggta gacataacag agagaactac   95700
aaggatagaa agtgtggttg gagagtggga aggcaagatt tattcagtat gggggctttt   95760
ctgggtgatg acagcatctg gagtacagcc attgtcgtga gtggcccaag tgtagcagag   95820
ataaagcgtt gttggagtga aggaagtcaa ggaactgaga ggctggccta gatggggatt   95880
ttggttgtca tccatgagga tattgaagtc atccaggaga atagcaggcc tgggggacag   95940
gaaggaaact gagccactta cagtgtcttc agtgatagga aagcacaggg caaaaagctt   96000
tcaagaacag ggactgttaa gccgggtaca gtggctcaca cctataatcc tagcattttg   96060
ggaggccaag gcgggtggat cacttgaggt caggagttca agaccagcct ggccaacatg   96120
gtgaaacccc atctctacta aaaaaaaaaa aaaaaaaaaa aaaaagaaa tacaaaaatt   96180 agccaggcat ggtggcacgc gcctgtaatc ccagctactt gggaggctga ggcaggagaa   96240
ttgcttgaac ctaggaggcg gaggtggcag tgagcctaga tcacaccact gtactccagc   96300
ctgggcaaca gagcgagact gtatcaaaaa aaaaaaaaaa aaaaagaac agggactgtt   96360 agagcaggct ccaggagaaa tgctttgcat atggcattct tgaggagtga ggaggacctc   96420
aaccctactt cctgaaatgg agctctgaga tgttggagta gaaatttgga aaccagagag   96480
agaagtaagg atagtgttgt tgcaaatgca ttgtatatgg ggggtcggga agtcacagga   96540
gtttgcctca aagtctttct cggagacgga tgaggttttc actgtgattt tcctggtcgt   96600
ggtctatgga tatagtacct gttagtgaca tggatcttct taacttctga tgtgtctttt   96660
cctccctagt gtacgcatac caattctctc cacagcttcc atcaccatgc atttgttctt   96720
ttcccttgtt cttgtattac ctttctggaa aggaatttt attgtaggct aattgttact   96780
cccaccagta tttaaccact ggatatttca tatgattgat ctcttctgat ttggaaaata   96840
aaaatgtaat ctcattatat tcatttgatt agtggggaca gtcaacactt ctttgtgtat   96900
tttcttagct gttcgttttt ctcgtctgta aattatctgt ttaggtcctt cagatttttc   96960
aaaattggac tgttatgttt tcagtattgt tatgagttct tgtttcaatt atttatgaca   97020
```

```
gttcattttc ttttttaaaa tagacttttt ttttcttaga gaaataagaa aaaataaaaa    97080
ttaaaataga ctttgtgttt tagagagttt caggttcaca gcaaaattga tcaaaaagta    97140
tggagagttc cggccaggcg cggtggctca cacctgtaat cccagcactt tggaaggcca    97200
aggtgggcag atcacaaggt caggagttta agaccagcct ggccaatatg atgaaacccc    97260
atgtctacta acaatacaca aattagctgg gtgtggtggt gcacacctgt aactgtacct    97320
actcaggagg ctgaggcaga agaatctctt gaacctggga ggtggaggtt acagtgagcc    97380
acagtcatgc ccctgcactc cagcctgggc aacagagtga gactccgtcc taaaaaaaga    97440
aagaaagaaa atatagagca ttcctaaata ccacctgtcc ccaacacctg cacagcctcc    97500
tcattatcca catcctacac cactgtggta cctttgttgc aattgatgga ccaacattga    97560
ctcctcatta tcacccaagc tttggtgttg tacattctgt agatttggac aaatgtataa    97620
tgacatgtgt ctaccattgt agtatcatac agaagaattt gactgccctg acagtcctct    97680
gctccacctg cttactcctc tctcccttt cctaactgca caaccactga tttttttttt    97740 tttttttga cggagtct cactctgtcc cccaggccgg agtgcagtgg cgccatcttg    97800
ggtcactgca agctccacct cccgggttca tgccattctc ctgcctcagc ctcccgagta    97860
gctgggacta caggtgcccg ccaccacatc cggctaattt tttgtatttg tagtagagac    97920
ggggtttcac catgttagcc aggatggtct cgatctcctg acctcgtgat ccgcccacct    97980
cggcctccca agctgggat tacaggcatg agccaccacg ccctaccttt ttttttaaaaa    98040 acaaggtctt gctctgtcac ccaggcctga gtgcagtgat gatcactcct cactgaagcg    98100
tcgacctccc aggctcaagt gatcctccca cctcagcctc taaatagct gagactacac    98160 acacacacca ccatgcccag ctaagttttg tattttttat agaaatgtgg tcttgctgtg    98220
ttgtccaggc tggtcttgaa ctcctgagct caagcaattt gcctgccttg gcctctcaag    98280
gtgttgggat tacaggcatg agtcaccgca cctggccttt tttattttct tttttttttt    98340
ttaaccagtg atcttttact gtctccatgg ttttcacat tggcttctgt cacttagtaa    98400
tatatgttta agtttcttct acgtatttc atgtttttag cttatttctt tttagcagtg    98460
agtaatattt cattgtctgg atgtgccatc acttatttat ccattcgcct gctgaaggat    98520
atcttgattc ctcccagtcg tggcaattat aaataaagtt gctgtaaaca tccatgtgca    98580 ggttttttt aagtggcata agttttcatc tcatttggtt aaataccaag gagcacaatt    98640
gctggatcat atggtaagag cttatttatt ttttgagag actaccaagc tgccttccaa    98700
agtggatgta ccattttgca ttcccaccag cagtgaatga gagttcctgc tgctccatat    98760
tcttacaaac atgtagtatt gtcaaatgtt ttggattta aaaccaaaat ccattttcat    98820
agatgtgtag tggtatcccg ttttaatttg caattaccta atgacttgat gttctgtgtc    98880
ttttcagatg cttatttgcc gtactgttta tcttctttgg tgaggtgtct cttcaggtct    98940
tttgcccatt tttaatctgg ttgttatttt tcttgttgag tttaagaatt ctctgtcctt    99000
tgtcagatct atcttttgca aatatttct cctagtctgt ggcttatcct ctgattctct    99060
tggcattgtc tttcacagag tagacatttt atattttaat gaagtccaga ctatcaatta    99120
tgttctcatg gatcatgcct ttgatgttat atctaaaaag ttctcgccat acccaaagtc    99180
atctagattt tctcctgtta tcttcttggc atttatagt cttatgattg atatttaggt    99240
ctatgattca tttttagtta aattttgtg aaagataata aggtctgata tggattaatt    99300
tttctatatg tagctgtccc tttccagtat catttgttga aaagactatc ttgctccatt    99360
ttattgcctt tgctcctttg tcagttgact atatttatgt gggtctgttt atgatctctg    99420
```

```
ttccgttcca ttgatctgtt tgccttttct tttgctaata ccacagtctt aattaccata   99480
gctttaaagt aagtcttgaa gtccaatagc attaatcttt gactcttctt taatattgag   99540
ttgccccttc agaatcttaa tgtctctcca tgtaaacttt agaatcagca tttttatatt   99600
cacaaaataa cttgctgaga ttatgattga gattgcattg aatctatagg cttatttggg   99660
aataactgac atcttgacaa tattgagtct tcctgtccat aaacattatt tatgatgggc   99720
ttcttcttta tgtttaggag cttttgtttt ttctgtcaga tattccactt ctacctttat   99780
gatttcttaa ttgccttta tgcttagaaa gttttcctc atcctgagct cacatattca     99840
tttattttct tttaaaatgt gttttcaagc atttaatttt taaacctatg tggaatttat   99900
tttggtatat ggaatgaggt ggtggtctaa ctccctcctc tcaaatatgt agttattttt   99960
cccaaaacca ttttctatta atttatcaag aatagacatg tatacatata catatataat  100020
agtcagcctt ccacttgttg tttgacccct gtgaaggaaa ttgtatgagt ttccaatttt  100080
ggattaggct caggtagtaa ttgagctggg ttctgccaga gatccatgtt aattcactat  100140
ccaaacagag ttataaaatg taagttttat gaaaatctaa cagtatatca ctggtttaat  100200
gatcacagcc taggaagaat ggggaaattg tcaaaatctt ctgtggatgc acctgaaggc  100260
cactgctgaa cccatttccc tgctaggcac ggctgctggt accagggca aactcctgga   100320 gtatatatga accacctaca tctccttctc ttcccccct accttgaga ttttcatgtg     100380 tcccttaagg atgtgtgtcc tacttccctt ggagagtcac taccacattg aacactttag  100440
actgtgagtc ctgtgaagat ggggctcatg agtgtattgc tccccagttg tttctctagc  100500
actagctcag tatagggcat aaaaatctga atggatgaac aaaccactat tactggtggg  100560
gacatgctac tatcttacat ggttcgaggt ggaataaagg ttgagaacag ctatataatg  100620
tgttccttga agggcagcag tacatcagtg caatcagcct accttctcca tacttctcac  100680
tctgaaaact gtaaagctgc acctagcaat caacttggga gctttaaaag ggactgctcc  100740
ctagctctca cccacaaagc tgtagtctag cacaggtgac ttttttaaaa agttttttg   100800 gtccagatgt gatgactcac gcctgtaatc ccagcacttc gggaggctga ggctgggagg  100860
tcacctgggg tcaggagttt gagaccagcg tgaccaacat ggagaaaccc catctctact  100920
aaaaatttgc cgggcatggt ggcacatgcc tctaatctca gctactcggg aggctgaggc  100980
aggagaattg cttgaacccg ggaggcggag gttgccgtga gccaagatca caccattgca  101040
ctccagcccg ggcgacagtg caagactccg tctcaaaaaa aataaaaaa ggagtcctat   101100 taagacttat ttttacaggt tggatatctc taatcccaaa atctgaaatg ctccaaaatt  101160
tgaaactttt tgagcgcaga catgatgctc aaaaaaatgc tcactgggac attttggatt  101220
tcaaaatttg gattagggac taggtgtggg agctcacacc tgtaatcata gcactttggg  101280
aagttgaagc aagaggatca gttgaaccca agagtttgag agcagcctag acaacatagt  101340
gagacgccgt ctctacagaa aattttaaaa attagccagg catcgtagta catgcctata  101400
gtcccagcta ctcaggaggc tgagacagaa ggatcacttg agtccaggag gtagaggctg  101460
cactgagcta tgatcataac cactgtctcc atcctgggca acagagcaag acctatctc   101520 ttaaaaaaaa tctgaaacac tgctagtcct caagataagg gatagtcagt ctttataaag  101580
actcaattag ttattggata tctgaggaag catgcatatc aggctcccaa aagatcattg  101640
gtttaggcac acattttaat agcttggaaa tccagaatac tcttctggtg accagctcag  101700
acatagtcct gataatatag gacctcatct aacatgactc cctatttttcc agataagcat  101760 ggattcctgg ttcattcttg ttctgctcgg cagtggtctg atatgtgtca gtgccaacaa  101820
```

```
tgctaccaca ggtaaattgt catttgataa ggctgctatt tgaaatgaaa ttttgctttc   101880
acatttaatg agccacattt gaaaaccgag atggtatttg aagaaaggaa tataaaaatt   101940
ttattcaaag tgatggtaaa ataggtgtct tcagaaatct tggaattgaa tgctcagcat   102000
tgtttttcat acatacataa ctgctttaaa taaatcaaag agattatgtg ttctttcctg   102060
aaaagtaaaa taaattgttg acatttacaa ctctatatat ggtttctgag gaactaagtg   102120
aagaatcttg tgtctttctc ccttaaaccg tagtcctttg gaggaggtag gaaaggtcca   102180
gcatgagata aaaacgtagg gggtgggtgg tgttgagggg gattggtctt tgcttggtct   102240
ccatatgttt gagagtttat taaggcttgc tgctttgtgt ctcacagctt tttagcctca   102300
cattcttcat gtgctatttc cttgttttt ggtgtttgta gttgcacctt ctgtaggaat   102360
tacaagatta attaactcat caacggcaga accagttaaa gaagaggcca aaacttcaaa   102420
tccaacttct tcactaactt ctctttctgt ggcaccaaca ttcagcccaa atataactct   102480
gggacccacc tatttaacca ctgtcaattc ttcagactct gacaatggga ccacaagaac   102540
agcaagcacc aattctatag gcattacaat ttcaccaaat ggaacgtggc ttccagataa   102600
ccagttcacg gatgccagaa cagaaccctg ggaggggaat tccagcaccg cagcaaccac   102660
tccagaaact ttccctcctt caggtactag agatgattct gtttgttctt ttgctctttg   102720
agtttagtct tcctttatt atcttgtttg tgttttctag ccttaaaatt tcttcaaata   102780
agtaaaattg ctcaagtgaa gtaatgaaac ctgtatgtgg aattttgg ttagcatgag   102840 tgaagaggaa agaagaaaga ttctggagaa tatctttctg ctaggtggga tcctggttag   102900
attgagagga cttaaatgtg tttaaaggta gagaagaagg cttaaaaaga caagagaaat   102960
agaggagctc attgacgatg caagagactg aagatgaaaa gatacagaga atgagtaata   103020
agattaggtt tggaaaggga gggatccgtg gagaccatgg aaaggagaat gggtattgat   103080
gtccatgaca gttagatgtg agatacagag aatgagtaat aagattaggt ttggaaaggg   103140
agggatccat ggagaccatg gaaaggagaa tggacattga tgtccatgac agttagatat   103200
ggagtggcag gccagtggcc aggggtggca tcaggctctg ggaaatggtt acattgcagt   103260
gccagttgtt cagggcctca ggttgaagca gtagtcccaa ggagaaaatc agagacgtgg   103320
atctgagacc agggcaggta agacaagttt ctgacctctt tgaaccttag gtaccttgtc   103380
tgtaaaagag gattagagat accctcaaag ggcttctatg aggagtaaag gaaataatca   103440
ttacctgatt gctatgtaac tgtcatccct tttctagcaa aaatcactct ttcctcttct   103500
gtgttcccag ttagatggtg agtgccccta agcagaatca catctcgctc atgtggaaca   103560
ttcaggaact gtttgctcag ttgattctca tttgttacta cagatgatat cttttactgc   103620
gccttataac tcagacccct cacctgccag cttttcccca tattttctac cgtaaagaca   103680
agacagcatt tgcagttaag agcacagtct tcagtgccac actgagtttg aatcccagct   103740
cttccataaa ccagccatgt ttatggcata gctggcttac tttatctctc tacctcggtt   103800
tgttcatctg tgaaacaaga atgagtgata gtaatagttc ttacctcata gaggagatat   103860
taggattaaa caagttaata tgggtaaagc acttataaag gtgcctacac atggtaagca   103920
ctatttttaa gtgtgagctg ttagtattgt tgtggttatt gctctgatag ttaccagtaa   103980
aatatatgaa ggtaccttta atgcagatgg catcccacta ttcttgatga gataggggac   104040
tgcagacaaa taatgtctga tacttgcttt gtgctttaga gttaatgtag ttttgtcata   104100
gttattactg tgtgctaggc atcgtactaa gagttttcta gaataatcct atgaattaag   104160
ttctatttta tgttttatag gtgaaagtat tttacaatga tgaaaccata atttgtggaa   104220
```

```
tgtttttcag tgtacaggtc atgacacaat tcatgaaatc actttagcag gccaccacta   104280
gttgtttgtt ttgttttatt ttaatggatg atccagttcc atgtttattc ttttaatgtt   104340
acatacaatt ttttgaaatt ttagtaacaa cataaaatgt tgggttgtgg ccattgctta   104400
gggagaaagg caggataact tgtacaaact gtatgagtga atggaaaagg tggagactgt   104460
aacacaggcc tgactgactg aacagcccat gttctattgt gtactgtctt tcatttaaca   104520
gttctgtgac atgaccatgg ataatcatct ccttttaaca gatgcttgat ttcagactgt   104580
atatagaggt taaatgattt gttttagatc tcaaggctga caaattaggc ctatttctca   104640
cttttgcggt ctttccactc tgcttgtagg aacttagtt ttccataaac tgacttaggt    104700
ccaaattgtg ccacagctaa gaatctagtt attgtacatt taacacagtt cacgtcatag   104760
gaggctgaga ctatgtttct ctagtggcgt ttattcaaga tgagtaaaac acaagaaacc   104820
attatcgcac atgggaattt catagtctta aaccccacat cccacttatc accaccattt   104880
accagtcctc ctgtaacagt tacaatttt tattaaatca gtatttgatg tatattattg     104940
taattatgaa atattcattg ctgagctata agtataaatg gattgttttt cttgtacagt   105000
tttttttctg gatttaatac ttaccttatt ttttgtttat ttagttttct atttagtcag   105060
gccaggcaca ctggctaaca cctgtaatcc cagcactttg ggaggccaag gtggacagat   105120
cacttgagct caagagtttg agaccagcct ggggaacatg gtgaaacccc atctctacaa   105180
aaaatacaaa aattagctgg gcatgggtgc atgtgcttgt agtcccagct actcaggagc   105240
ctgaggtggg aggattgctt aagcccagga ggttgaggct gcagtgagct gtgttcatac   105300
cactgcactc cagcctgggt gacaaagcga gaccatgtct caaaaaagtt attgctactc   105360
aattcttacc atgctctcca gagcctctca aaacagcttt ctacaaagtg agatctgtta   105420
gataatctat ttcttttta cctctagaaa ttcctcctga gccctccatt gtcttattcc      105480
agtctaggct tgtcgatctc tagggctact acacagatac atcagcctga gatttccctt   105540
ctctgtcatt ctgggaattc cccttgctgc tgcttcctga cttccatatt gtcttccttt   105600
ttgtcttctc atcattcggt agattcctga gaaaaggggt ccatgggagg caaattgcat   105660
ccttacatat ctaaaaatat ctttagggct gtgcatagaa tttgaggaat attttttccc   105720
cagaattttt aaagtaatgc cctaactgac acctgtttac caggtttgga ggattttact   105780
gctatcttaa tccctaattg tttgtatgct ttctaggatc ttctctttat catcagtatc   105840
ctgaaatttc acagagatgt atcttgatgt gggtctttt cgttcattat tatggatact     105900
taataggccc tttagagcct tgatcttgca tttctgaaaa ttttctccca tttctttgaa   105960
accttctccc cctcttcctt tttttttttt ctcaaattct taatatttgg atattggatg   106020
tatcctgaat taattccttta atctttaaaa ttttccttt ctgttgatct ttgctttgag     106080 tcttttctc cttttaaaaa taaacaaagg ccagctaggc acagtggctt atatctgtaa     106140
ttccagcact tgggaggct gaagcaggag gatcgcttaa gcccgggagt ttgagaccag     106200
cctaagcatc gcagcaaaac ctcatctcta caaatgattt agaaattagc agggcctaat   106260
ggctcatgcc tgtggtccca gctactcagg gctgaggcag gaggattact tgaggcctgg   106320
cagttgaggc tgctgcagtg agctgtgatc gcaccaccgt actccagtct gggcaacaga   106380
gggagacctc atctcaaaaa taataggcc tggtgtggtg gctcactcct gtaatcccag      106440
cactttggga ggccaaggca ggtggatcac ttgaagccag gagctcaaga ccagcctagc   106500
cgacatggca aaccctctg tctacctact aaaaataaaa aaattagtca acgtgttgg        106560 catatacttg taatcccagc tacttgggag gctgagacat gagaattgct tgaacctggg   106620
```

```
aggtggaggt tgcagtgagt caagtccctg cactatagcc tggggaacag agtgagaccc  106680
gagactctat ctcaaaaaaa aaaaatcagt gacaagtaaa aaggtagaat acctttttt   106740 ttttctttga dacagtctca ccctgtcgcc cagtctggag tgcaatggcg cagtctcggc  106800
atactgcaaa ctctgccttc agggttcaaa caattctcct gcctcagcct cctgagtagc  106860
tgggattaca catgcccacc accacaccca gctgtttttt gtattttag  tagagacagg   106920 tttcaccatg ttggccatgc tggtctcgaa ctcctgacct catgatccac ctgccccggc  106980
ctcccaaagt gctggtatta caggcgtgag ccactgcgcc cagcctagaa tacctttta   107040 aaataaataa ataggccggg cgcggcggct catgcctgta atcccagcac tttgggaggc  107100
tgaggcgggc agatcacgag gtcaggagat caagaccctc ctggctaaca tggtgtaaat  107160
aaataggccg ggcgcggcgg ctcatgcctg taatcccagc actttgggag gctgaggcgg  107220
gcagatcacg aggtcaggag atcaagaccc tcctggctaa catggtgaaa ccccatctct  107280 actaaaaat  acaaaaaaaa attagctggg cgtggtggca ggtgcctgta gtcccagcta  107340
ctctggaggc tgaggcagga gaatggcgtg aacccaggag gtggagcttg cagtgagccg  107400
agattgcgcc actacactcc agcctgggca acagagcaag actctctctc taaataaata  107460 ataataaat  aaataactcc ttttacaaaa gcatatatat tcattttttc catttataat  107520 ataataata  gatatgctga gttgatttct gcatattgct ttttcagtta ccctatcata  107580
cttgctcttt gttttagtaa agagctgctg tattgaagga tataccttaa tctctttatc  107640
cagtttcccc atcagtggac actaagattg ttttcagagt actcttataa acaatacagt  107700
ttgtcatttc agacacatat gagaatatta gcaggatgaa ttattttaag tctgcattta  107760
taaatttatg gatattgcca catttacctc tgctaggaag tctattccta ttaacaatat  107820
gtcaaagtgc ctattttct  aaactctctt cagtgtggtg aattgttaaa cttggggatc  107880
tctgccaatc tgacaggtga aaaataacat ctcagtgtaa gtttaatttg cattttgctg  107940
agattgagca attttgtgta atttaaaaga tcatttattt ttctgagcat tctctgttga  108000 tattcttac  ccattttat  tagagtgtca aggttttcct gactcgtttg tagatgttct  108060
ttgtacgttt gggaaatgag tcctttgcct atggtaaaac tgcaaatgtt gttccctagg  108120
tggtcatcta gattttctgc attgcagaag atatcattag ctattttta  tttttttaat  108180 ttaaatattt ctcagtttag gttttctagg aattgggtca tatctaggaa ggctttcctt  108240
actccaagat tataaaaata attttcttct ggacttctat ggtttcgtgt gtgtgtgtgt  108300
gtgtgtacac gcacttaagt ctgtctcgaa tttattctga tgcagagtga gctatggatc  108360 tgttttccc  caaatatcta acttgtccca ataccccta  ataatttat  tttcctcatt  108420 gatttgaaat gccacctatc ttatatattg aattcagata tttatttacc tcttcatatg  108480
tatttgagta tttgggaaca ttcattttat tttctattaa tctttttctc tgtccatgtg  108540
caaagcctca ctgtctcaat aattgtaact ttgtaaagta tttaatatcc agtaaaatga  108600
gtcattcctt gttaatttta tttttcagaa ttttgttagc aattcttatt ataaacatta  108660
gaattaactt gtctagcagg aaaaaagtt  tgtattgatc atgttaaata cgtagattaa  108720
cagagaaaat ggcatcttac agatgttgag tctaactatc caagaatgca atatattcca  108780
ttttctgaag tcttttttt  ttaaatcttc tgttttgta  attataaatg gagcattttc  108840
ttccatcaga tcttctaact ggctgctgtt ggggatatga aggctactga ttttgtaga   108900 gacatttgt  actggccacc ttaaactctc ttagtattgg aagtaatttt cttcattaat  108960
ttttatggct tcaagtcatc tcatctgcat atatcttcca aatttttaga actttctttt  109020
```

```
tcttctgttt aatcgcattg atgaatacct ccagaacaaa gttaagcagc tggtaaatgc 109080
agacagcatt ctcttgtatc tgacactaag gaggacactt tcagtggttt ttcattatac 109140
gtggtactga ctcttgagtt gagataaaca tattttattg tgttcaggat ttaatgagcg 109200
tttatgttag gaatgggtgt taaattttgc cagttgcctg ttcaggatca atgagaaaga 109260
tctgaatgat ttttttttctc ttttggtctg tttctatggt ggattctatt cctaggtttg 109320
tttgtttgtt tgtttatttt gagatggagt ctgttaccag gctggagtgc agtggcgcca 109380
tctcagctca ctgcaacctc cacctcgcgg gttcaagtga ttcccctgcc tcagcctccg 109440
agtagctggg actacaggca cgcaccacca tgcccggcta atttttttgta ttttagtaga 109500 gacgtggttt caccatgttg gccaacctgg tctcgaactc ctgacccat gatcctgcct 109560 cagcctccca aagtgctggg attataggtg tgagccactc gcccctgcca gttttttattt 109620 attcatttttt tagagacagg gtcttgctct gaattaattc tttaatcttc ttaattttttc 109680 tttttctgttg acctttgctt tgctttaagt cttttccttt gagtcatcca ggctgaagta 109740
cagtggcacg atcatggctc actgtaacct tgaactccca gacttaagca aaccccacct 109800
cagacttctg agtagctaag gactataggc gcatgtcacc acgcccagct aattttttaaa 109860 ttttctcaga aacagggact cactgtgttg cccagactgg tcatgaactc ctggcctcaa 109920
gcagtcctca gccttagcct tccaaagcac tgggattata ggcatgagcc aaggccgcc 109980 aaacatattg tatcgttcct gtaacaagct gttgcagtct atttgatatt atttcttatt 110040 ttttttcattt agaattttct ctgtctagat attctcaaat tatctctaaa tgagattgat 110100
ctatgttttt cctttgtgtg tgtattcttt ttgataagtt ttagttttta gtgttttgtt 110160
ttgctacatg gaaaggattt gaaagtttac actaaaaaat atgcttttttt tttttaagac 110220 aggcttttttc actgttgcct agtgctggag tgcagtggca tgatctcggc tcattgcggc 110280
ctgcacctcc tgggctcagg tgatcctctc acctcagcct cccaagtagc tgggattaca 110340
ggtgtgttcc accatgccca gctaattttt tgtattttttt tgtagagatg gggtttcgcc 110400
atgttgccca ggctggtctt gaactcctgg gctcacatga ttctcctgtc ttagcctccc 110460
aaagtgctag gattacaggt gtgagccacc acatctggcc atttcattca tgtttttcaaa 110520 tgtatttgaa tgaggaaaag ttctccccttg tgattattta ttataatagc ctacagagct 110580
attaattttt aaattttgtt tactttatgt ctccttttttt tttttgttta ggctgaataa 110640
ccatttattt cataggttta ttgcctttttt tcttccaaag aacttgctat tgtgcattta 110700
tagtcctttt atgtttacgt tttctatttc attgattttt actttctacc ttctttagat 110760
ttattttgtt cttttttctat cttcttgaat tgagtgtgct ttaattgcat tctttccagt 110820
taattaacat atttagtgct gtgaattttg aacaagcaca gctttagcca catcccatag 110880
gtgtttctat aggcagttgt attaggatgc gctataagct gctctgacaa agataccaaa 110940
attcagtgac ttaaataaga ccaaagtgtc tttctctccc cagttacatt ccagaggtag 111000
acagggcctt cgtctcagta gggaccaaat tcctttcctc ttgtggccct gccatcctaa 111060
caatattgcc cttatctgtt tggttagaga tagttctcac cattgggttc tagttccaac 111120
cactgcgaag gacaaacaaa gggaataggg gccatttctc ttccaaaaga tgtgacctgg 111180
aagttactca cattgcttta gctcacatcc cgttggctag aattcatcac atgaccacac 111240
ctagcacaaa ggagtctcaa atatagtctg ccaggagagc ttggtgctca gctaaaaaac 111300
aaaggttctg tatcaaggca agaagagaaa gagactgatc tgagggggagg agagttggca 111360 ggttctgtca caaaacttct cgtcattgtt atttttaagg tattttttcca ttttgggttt 111420
```

```
tttgtttgtc tgattttttt ttttttttttt gagatggagt ctcgctctgt tgcccaggct   111480
ggagtgcagt ggcgtgatct ctgctcaccg caagctctgc ctcctggttc acgccattct   111540
cctgcctcag cctcccaagt agctgggact acaggcgtac accaccacgc ctggctaatt   111600
ttttttttgt atttttatta gagacagggt ttcactgtgt tacccaggat ggtctcattc   111660
tcctgacttt gtgatctgcc cacttcggcc tcccaaagtg ttaggattac aggcgtgagc   111720
caccgcgccc ggccgtctgt tgattttttg agatggaatc tcactctgcc ccccttctgg   111780
agtacagtgg tgtgatcttg ggtcactgca acctctaccc tcccaggttt aagcaattct   111840
tgtgcctcag cctcccaaag tgctgggatt aaagacgtga gccactgtgc ccagcccatt   111900
ttggttttga tttttttttt tctttgaaat agagtctcgc tctgttacct aggctggagt   111960
acagtggcat gatctcggct cactgcaacc tcccctcct gggttcaagt gattctcgtg    112020
cctcagcctc caagtagct gggattatag gcacccacca ccacgcccag ctaatttgtt    112080 ttgtatttt agtagagacg gggttttacc atgttggcca ggctggtctc gaactcctga    112140
cctcaggtga tccactgcac ccggcctcat tttggttttg atttttattt tcaaatgttt    112200
tcttactttg tcaatttcta attttattgc attgggacaa aagaatattg tactcttttct  112260 actgttgggg tttataaggg ctgtggatat ttcactcgcc tttgaaaaga aggttttctc   112320
tgttagtctg tagagtttgg tatgtaccaa ttagatttta ttacttatca ttttggtctt    112380
ttgtatcctt acttaatttt gtcctcttga attttaatgg agcaaaagac ataaagtcct   112440
ctaataacat gcgttctgtt tgcattctca tactttttat gaatattgat gctgcactat   112500
ttgtgtaccc agggagaagg ccagaccact gtccaaagtt tagtgaatct gggcagcctt    112560
gtttcccagt tgttggagga tgcctcatgg aggaaagcat tcctaatcct ggagcttgtt   112620
ttgttgtact ctaattgaat tgtaatgtgt ttctttaacc tgaatgaatg tttctatttt   112680
ttacttatta cacaggtaat tctgactcga aggacagaag aggtgagctg ctcaccttat   112740
atctgttgtt ccttttacac agtgtacagt attcatttat ttcctctgct cacagtctgt   112800
ggtaaccgtg tgcatctgtg gctgtgttgt tgtttactt tcccttaagt tatttccatg    112860
ttaatctcat ggagaagagc aatagaaaca agtactgtat tcagtatgtt ttttaatata   112920
gactatggat tctaacagct atgatgtatt ttaacaagta acaaaatata tcttactttg   112980
acatgtcact ttgttaacat acttttttgg tgatattagg tcataatttc tataccatta   113040
gttacttctg atttctaggc cacagttccc tttaaatatt ctttgtgttg ttttttcccct  113100 agtgtataaa atgtcaaccc tttgtggctt tatatggatt ttatggattt tcagccctta   113160
aatgtaaagt ctctatggcc tgagatgttg tgtctgtggt ttaagctgga ctgctgagtc   113220
cctggtcact agagagtagg gggacatggg tacttgtctg cagaagtgtg gcacattttg   113280
cctagaatga cagtaaggct gctatcaaag agcatgagag aaagagaaag agatcatcta   113340
acattctaag aagtgattat tacatttgag ttttaaaaat gttactattc gaagcagtgt   113400
ttttatcata attttctatt ttatcaaatc agacttgagt ttttttttctg attctgttat    113460 ttaaccatac acaattttcc ctgtgtaatt aagtaatgga acacttggag gcatatgaag   113520
tcccactaag tagggagcat ttgagtcaga aaagtgggta ctctcttcct ttatgtgatg    113580
tccatctgcc attgtatttg gtaaggaata gtgaggtgtt accatactgt gtacagattt    113640
ccctcacttt tccacctctc actttcctaa acttgggaac taaacattgg attaatacag   113700
tgtctttgct gttcagattc acttgccaga ttttatcaaa tgtagactta aataggtttt   113760
attgtgatag atatttactt gctccctaaa actgctctct taaccagcct tacaataaag   113820
```

```
tcaaaagtca aagtggtagg cttcaagatg aaacataaga tctgttgact ccttcctcta  113880
tttagtatat attttcataa tattcagcct tttcttgccc cagatatcat atctatttta  113940
cctacccaat atttaagtag tttccatgtt gtgattaaga aaacaaaatt accataatta  114000
cctagattat tgctaattgt gacatatgta aagtctatta atgtaataaa tctcctttct  114060
taagtcaaaa ataattttg tgtaattcca aacaggaaac tgaaaaggca taggtattct  114120
cagcagtctc taaagtccca aaatctaatg gcaattttac cagagcagat ctttagaagt  114180
attgctataa atttggatat cccattctaa ttttaagcca aatgcttttt gagaaataag  114240
ccagctgttt ggaaatgctt gtattataat cggtttgata agcagttatg tcttatgcag  114300
atgaattagg ggctacctgt ttttatgcac tggtctttgg ggtgcttttg aacagtagtg  114360
tctgatgttt taattgtcaa agcaaaaaga aatgagaggg agggcaactt ttcttcctct  114420
tctgaagtcc aggaaactgg ttattttctc atgcatatta tttttaaaata tattccagcc  114480 aggtgcagtg gctcacgcct gtaatcccag cactttggga ggccaaggcg ggtggatcac  114540
aaggtcagga gttcaagacc agcctgacca atatgataaa accccatctc tactaaaaat  114600
acaaaaatta gccgggcgtg gtggtgtgcg cctgtaatcc cagctactcg ggaggctgag  114660
tcaggagaat tgcttgaacc tgggaggcag aggttgcagt gagccaagat cgcgctcttg  114720
gctgcgatcc agactgcact ccagcctggg tgacagagca agactctgtc tcaaaaaaaa  114780 aaaaaaaat cagactctta atatttgtaa agaagtagtc cttgagctac tacttaagtc  114840
tagaaagagt tgatattctt gttttaagag tgttagggca cttttgggagg ctgaggcagg  114900 tggatcactt gagcccagga gttccagacc agcctgagca atatggggaa accttgtctc  114960
tactaaaaat acaaaaatta accaggcatg tggtacgtac ctgtagtccc agccacttgg  115020
gacgctgagg tgggaggatc acctgagccc aggaaatgga ggttgcagtg agccaagatt  115080
gcgtgactgt actctagcct gggcaacaga gcaagactct gtctcaaaaa aaaaagggc  115140 ggggattatc atagtgccat tattattatg agtttatgat ggctttctct aagcaccttt  115200
tacattcggc atttattcag tacctattaa gcatcaagga gtccagaaaa aattttatat  115260
ataaatatat ataaaatatg taaatatata tatgcatatg cttccctatc tcaggaagga  115320
aatatgtgaa catcaggaac cgaagtctac tcagttacat gccattggat atatcacaca  115380
aagtgctgag ggaactcaga aggctcatta tatctgggga gtgggaagga ggcacagaga  115440
tgtgctttgg gaagtttaaa ttaaaatagc aaatgggaa aatgaagaca caccagacag  115500
ggcacaagca aagagacatg aaagagtaag tcatgtgttt gaggatctgt gcgcagttga  115560
catgtgtgag gtgtggggag tgatcagagg tggcctcaac agaatgggtg tggtggtcca  115620
ctgagttcag gagttggagc atctcctgaa gatgatggtg agtaaggaag taacatagtc  115680
agattttggt tttagaaaga tattccagag gacttagggg agatagatgg acaatagaaa  115740
tttaggtttc tgaataattt ggctcaaaac aacggtgatt gggctcaacc cagtggttag  115800
attctagagg caatccaatg aatattgctg ttttagagc caataggaaa catttaaaac  115860
aacattacaa ccttgccttt gagagctgat aaatacttgt accaaaaagt gtggcaatag  115920
gtaaatgggc cataggaact ggggctatag gactatggct attcctttac tgactagttt  115980
gtagttgacc agtgtgtgtc tgaagtcctt aagtcactca cctgtttaga ggtgagccct  116040
tcaattaata tggccctttg ttttcaagga aagaagttat agcaagtagg tatctgttgt  116100
cccgggacac cattttagtg gttttcattt tcatgcttgc tccctggcct gaatctgaaa  116160
agtaaaactt tgctggaatg aagttggggt tgaaacagtt tcggtttgta accatactgt  116220
```

```
ctctgtctca tctactcagc tctgcctttg taatgtaaaa gcagccatag atggtatgta   116280
aatgaatgaa catggccatg ttctgatagc attttattta caaaaacagg cagtgggcta   116340
aatttgggct atagtttgcc gacccctctt ctaggcaaag aactgcctga gcgtaggaag   116400
ctggactgag gttctctgct agtgtgtgaa cttgtggatg ccaaagccaa tctcttccct   116460
tcatgtcaga cactttgcaa atgttacctc ttttagatct cccattaact ctaaaaggtg   116520
gagggtgcta ttatgcttcc atttcataca ttgttctaag agattatcac actactagta   116580
agttaggata gtaggaattt gaacttcagg tctgtcagac cctaaaaccc catgccctgg   116640
aaatggtttt ctaaggctgg cctgtggttc gttggttgat ttcaattaga atttaagaat   116700
tttttcagaa tacatctagg tgtaaagatt tttttgtcaa tattactcca caaactagat   116760
tatttctttt ggcctgataa ctcaggaact ttcttgtatt acttctctcc cttcttactg   116820
gtttcttctt tggactctcc tgttgcacag gtattggatc tcctggacct atccagttcc   116880
tttcttttct atgctgtcat attttcatc tcttattgct ctgtgttctg ggagcttcca   116940
ggacagttgc tctttcacac aactaatttg gttttcagtt atatcagttc tcctatttag   117000
cctttctttt tttggaggca gggctggggc agactcatgc tctgtcgccc aggctggagt   117060
gcagtggcct gatcacagct cactgcagcc ttgacctctg ggactcaagc gatcctccag   117120
cctcagcctc ccgggtagct gggactatag gcatatgcca ccatgcccag ctaatcaggt   117180
gtttgtttgt ttgtttggta gagacagact accagagtct cgctaagttg cccaggctgg   117240
tctcaaactc ctggcctcaa gcagtcctcc caccctggcc tcccaaagtg ttgggcttac   117300
aggcatgagc caccgtgccc ggccctgtta agcctttcta tctagatttt ttccctccta   117360
atcatgttgg tgtttttttg tttgttttca tttttgtttt gttttgtttt gagacggagt   117420
tttgctcttg ttgcccaagc tggtgtgcaa tggcacgatc tcggttcacc gcaacctctg   117480
ccttccaggt tcaaacgatt ctcctgcctc agccccaga gtagctggga ttacaggcat   117540
gtgccaccac acctggctaa ttttgtattt ttagtagaga tggggtttct ctatgttggt   117600
caggctgctc ttaaactacc aacctcaggt gatctgcctg cctcggcctc ccaaagtgtt   117660
gggattacag gcgtgagcca ccatgcccgg ccagttttta aagaactcct tcttactact   117720
cagattactc cttttaaat agtggctttt aaaaaatatc aatgtaggct gggcacagtg   117780
gctcacacct ataatcccag cactttggga ggctgaggca ggctgatcac ctgaggtcag   117840
gagttcaaga ccaggctggc caacatagtg aaaccctgtc tctactaaaa atacaaaact   117900
tagccaggcc tgcagttcca gctactaggg aggctaaggt gtgaggatcg ctcgaaccag   117960
gaggccgttg cagtgaacca agatcacgcc agtgcacttc agcctgggtg acggagtgag   118020
actccgtctc gagaaaagaa aaaaaaacgc aatgcagcag tggctcacgc acataatcat   118080
agcattttgg gaggccaagg caagaagatc acttgagacc aagagttcaa gaccagcctg   118140
ggcaacaaca agacccccctc cccccatctc tacaaaaaat ttaagaaaaa aatttttttt   118200
aaatcaatat ggcatcctgt tgcacaaatt gcagtatatt ttgaaagatt tattctgttt   118260
cttttgtcac ctccatttcc cagggctact gttgctctgt ttgagctatg ccctggacca   118320
ttgagtggct tagactgtgc tcacaatagg tgtcccttca tcccttcaga agacaaacat   118380
ggacatacgt cctaaaccag gaaggggttc agtgatggct caggaaaatc ggggcagggt   118440
gcagttatcc tctaggcgag ctgccgtttt cttttcctt tcctctcttg tggttgccta   118500
gaattagctt gggcactact atggtttttt tctgtctgca ggccccagga gaccttctgt   118560
ggacccaata tacttaacaa tcatatgcag tgtagacctg ctctggtgtc aattctaacc   118620
```

```
aaaacaaaaa aaaagcattt atgagacact cagggaaatt caagcagtaa ctgaataata   118680
ttagatgata ctaaggaatt agtgttactt tttaaattgg ataatagtat tatgtttatg   118740
ttaagaatct tgatctcttg gtgatacata cctaagtaat tgcatttgaa atgctaggtc   118800
tcggatttgc cttaaaagaa ttcagttaga atggcgtgag tatagaccag tggttcctta   118860 ctggggcta tttcccccac aaaggcattt agcaatgctt ggagatactt ttggtcatca    118920
aaattgggaa tttgctacag acatctaata attagaggct agggatattg ttaaatgtcc   118980
tacagtgcac atgacagacc cacataacag agaattgtat agcccaaaat gtcattagtg   119040
tgacgttgag aaaatatata tgcagcatat gttttgtaaa aaagaagccc ttaccagtct   119100
ctgtgacaaa ctctctactc tgtgtagagc actgttttc cagctgagtc tagatgggaa    119160
gccccgcttg tcatttgggc tgtgggtgta ctggtgctgg gttggcaggc ctttgcttaa   119220
gtaccatcct ggtacctcaa ggtccacttt caaccccagt cccaattccc tctgagcttg   119280
aggtgtttcc aggcccaaac tggtagaact agtacttagt tttcagctgg aggctctttg   119340
gctctgtttg atctcttgga catcgagtct ggtctgtttt gcttccaga aatctctcaa    119400 agattctgat ctacatatgc caccgtttgc tgcctttcag atatgctgtt gattcattag   119460
tatttttata tttcttctac catgtcagtg tgctttgggg gaagatgaag taaattcatg   119520
gatttagccc agtgtcttaa gccaaaggtg cctaattact ttcttcttct tctttttttt   119580 ttttttttg aggcagagtc tcgctccgtc acccaggctg gagtgcagtg gcacgatctt    119640
ggctcactga aacctccgcc tcctgggtac aagcgattct cctgcctcag cctcctgagt   119700
agctgggacc agaggggtgt gccaccacac ccgctaattt tgtattttta gcagagacgg   119760
ggtttcacca tattggccag gctggtcttg aactcctgac cttgtgatcc acccgcctcg   119820
gcctcccaaa gtgctgggat gtgcctaatt actttcttat aatacctgat atactgcccc   119880
ctgttgttgg aatttaacaa agacatttag tgataaatta ctatttttt ttgttctttg    119940 gctcaacgta atccattgtt tgttttgtgc ctgttatgtg tgagaccctg tgctaggttt   120000
taggtgtaca gtgagaatga agcagacatg taatccttgc tcttgtggaa tttatgctat   120060
aaaggaggga tattcattaa tcaacaaagt caaatatgta attataaagt gtgagaggta   120120
ttatcaagga aaataataag gtccttgcct tacaaaaata gtataggaaa taacagcaat   120180
tttttttttt tttttgagac agagtctcgc tctattgccc aggctgaagt gcagtggcgc   120240
aatctcggct cactacaacc tctgcccccc aggttcaagc gattctcctg cctcagcctc   120300
ctaagtagct gagattacag gcatgtgcca ccacacctgg ctaattttt ttgtattttt    120360 agtagagatg gggtttcacc atgttggcca agctggtctc gaattcttga cctcatgatc   120420
tgcccacctc ggcttcccaa agtgctggga ttgcaggcgt gagccactgt gcctggccgt   120480
aacagctaaa atgaagtaca cactgtgtgc tagttactgt gccaacaact ttacatgaaa   120540
gatctcattt aatacgcaga ataacttatt tcagaaatga ggaaactgag acttatgatc   120600
ctaatttagt attaggaagt cagagaagac ctgtgtggga aaagtgacac acagagaacc   120660
agacaagtag gagataacca ggcaaagaac agagagaggc tgtgtaaagc agaaggaata   120720
acatgctcaa aggcctgagg atgaatgaat gaaagcatgg aaggacacca gtggctgaaa   120780
ttgagtgagc aaggaaagag tgcaagagat agggcaggta ggggctaaat cgaggggtt    120840 gttagagtcc aggataagga gattagattt cattctgagg catgagaaac tgttggaggg   120900
ttttacctaa gagtgggaca caacctgagt tgctttccta gagatcactc tgctttgtgg   120960
agaatggatt ggcaggggca gaggcttact gtgatccagg tgagagagga tggaggttgg   121020
```

```
gactacactg gtggcaataa aaaaaatgca aaaaaaaaaa aaaaaaaagg cagacagatt   121080
tgaagtttta gatatatctc caaaatatat tatttgcagc tgtgctagat atagaagata   121140
agtgtgagga agaaatcaag ggggtttcca catttcttac ttgagcaaca gggtgggttg   121200
gagtactagc tactgaatgg tgagggaaag gttttaaaca cagaaagctt gtgttgccta   121260
tgaaatttaa agtggaggtg gcaaataggc agttgagaat ctggaactca gaaagaggt   121320 ctgatcaagc aaagcaactg tgggaattgc tagcatggca tttatattta cagtcatctc   121380
tctgatcaga ttaactagat atagagaaga gtgccaagga cagagccctg aggaattccc   121440
acatttagag atctggtgtt ggaagaggaa cagatagtga gggaaactga gatgggcaga   121500
cgagatagaa ggaaaatcag aggagtgttt cgttgtggaa agctaagaga ggaaagtgct   121560
tcagagagga aggagtgatc agccagtctg aacactcatt ttaaggtgag agccacatac   121620
cacagtatgt ttgaaactta ccattaacaa agaagcgtca tgtaatgtct tccatctcta   121680
aaaacaaaac caaaaaaaac ccatctgtcc acctcactca catctccctc catctgtcat   121740
tcctttcctc tgcatccctt aatgttaaaa gtccccacga aaggacccag tgtctcactg   121800
tcctttttct atctttattt cactccattt aggcttctc acccatattc aactgaaaat   121860
actcttggaa aggtcaccag tagccaccgt cttgtcaaat ctggtttcac ttctctgtct   121920
catccttctt aagtctgtag gcagtatttg attgaattga ttgctccctc cttgaaaaac   121980
tctgctcttg gcttctatga cactacattc ttagattaac ctctcacctc atggctactg   122040
cttatgggtc agtttagctt ttaacagaat gtaaatccag ttatatatct cctctgttca   122100
aagcccttcg atgacatagt gtttctcatc acactcagaa ttaaatccac aatcattaca   122160
atggactccc aagtcctaag tctgctggct tttgcccacc tctctggcat cttatattga   122220
actggccttt gtgctgtttc ttgaacctgc caagctcctg agagctacca tgcttgctgt   122280
tcccagtgtc tagaaagctc ttcacccaga tctttgcgtg gttcacttca cgttatttag   122340
agctctgctt gtatattact tcctcagaga gaccttccca gaccactgta tcactgctcc   122400
ccaacctgtc actttctctc tccccaccct gcttttttatt cctcatagca cttgtccctg   122460
tctaaaatta agtattgact tgtttataaa cagtgtcttc cttcctcccc acagaatgga   122520
agctttctat cacttgtctc cttgaacact tctctgttcc tagtgtctca aacaatggca   122580
tgcaattgct ggcccacaga tatttgaatg aatgctgcta aaaggttgaa tcagatgagg   122640
atgggaatgt tcctgttgga tttggcaata tgccatttgt tggtgttctg gctgagcagt   122700
ttaaacagag cactgagggt gggagtcagg gcaaatagat taaggagaac ctgaaggtaa   122760
ggaattagac aagacgaatt agacaactgt gtttcggaaa gtcagctgag aagagagacg   122820
cgaggctggt ggtagctggg ggagggtaaa tgaggtcaag aagacaagtc tttgagttga   122880
cagcagtgga tgtaatccag agcacacatg acaggatgga agagacttgt cttcccttt   122940 agcaggtagg aaaatggtga agatagttac caagccactc tgatggtgta gttcatggag   123000
tcgggtggag ggtgagagtg gaggcggatg agtcagtgcc tggccagctg catgagaaaa   123060
caaggctagg tattgggtga aagggagcca ggccctgtgg aatgaggtgg gattgccatg   123120
tcttcaaacc agatgttgcc atggttgggg tcctggcaaa aggtgactaa gggagcaggg   123180
tgtgaaagaa ggaaaaaaga agcaaccagc agttttgtta catggtggct gaggatctaa   123240
taatgtctcc ttgttttatt ttattttat ttagctggtc tcaaattcct ggcctcaagc   123300
aatccttcta cctcagcctc ccaaagtgct gggataggca tgagccgcca cacccagctg   123360
tctccttgtt tgtttgtttg tttgtttgtt tgtttgtttg tttgttttga gacagggtct   123420
```

-continued

```
tgctctgttg cccagggtgg agtgtagtgt acaggcccgg ctcactgtaa tctccatctc 123480
ctaagctcca gtgatcctcc tacctcagcc tcctgagtag ctgggactat aggcgcacat 123540
caccacaccg gctattttt taatttttag tagagatgga gttttaccct gttgccaggc 123600
tggtctcgaa taccttggct caagcaatcc acccgctttg tcctcctaaa atgctaggat 123660
tacaggcatg agccattgtg ccctacttgt ctccttgttt taattaggaa cagtattctc 123720
tgtgcccgga aaccatttgg gtttatgata ggaaaactgt cttttccct tcctctccca 123780 tcttcctcta gatggaaccc attgaggctg agagagtgta cagtgttggc cctgcatacc 123840
taacttgcca tcagaattga atgtgttcat gcctccagat attccagtgc ttttatgtg 123900 ctaagtactg ttttaggctc aaaggatata gcagtgagta aaacaaagtg tctgcctta 123960 aacagctttt attctaatgc agggagacag agtaaataaa tgtatgatag tcagagatgg 124020
ggtgagcatg tcatcctggg ccccatgctc tctccccacc tcacctcaat agccctggca 124080
tggcagtggg aggtgcacac tcatactttc ttctctgttt ccatttcctg gcatctgcag 124140
aaggactgaa tgagctcttc ctcttcaggg tgttgccctg aatggctgac ttaagccctc 124200
cattgcacaa cacagtaatg acttgttctg ttgtcttgat ttcagatgag acaccaatta 124260
ttgcggtgat ggtggccctg tcctctctgc tagtgatcgt gtttattatc atagttttgt 124320
acatgttaag gtgagcctac taacacttca cattctctta gattctgttt caatatccca 124380
gtgtcccaat gaacccacac agtccagtag acagtaggat atacacaatg aataggatag 124440
agggggaatg acccatgata gtgctaaaat tgaagttcta cttagaaatt atttaaaagc 124500
tctacatagt cttccttaag tcctaagccc tccctctttc ttccatctgt ccaagcccag 124560
tctcccaact ccagtgcaag ctaaagccca gaatggtagt ttggaggttg aggtaagaaa 124620
ccgcagtttg ttattagtga caggtgttac aggatctcta ggtctagccc tgctgaagca 124680
acccctaaaa gggcccagt aagattacat gctcaacaaa agcctactgt atttctggct 124740
ggggctttgt ccccagaccc ttctgggacc cctggccctg gcatgttgag ttgagccatg 124800
tgagttgtga gttacaggat ccctctttct aaccttcttt cagggtcctc tagacgttac 124860
cactcaagca gaagcaagga aggggaaccc aagggagaga agagggtggt gcatttattc 124920
tcttcctgct aaagctactg ccctgactaa ttggatttag ccctgcctta tctttggcct 124980
aaccaaagat gttctgtgct ccctctgttc ttctgcaggg ataaagagag aggaatcatg 125040 tgcccctat aatttgtcat gtgtctctat cattctgcag gagacttgtg gccaggactg 125100
tgtccaccca atccaaagct ctgggcttct ccctgggtct cccaggctac actgaggaaa 125160
taccaagatt tttgtttgat atatattgtc tgtctccccc agctgtattc cacccactca 125220
ccctctctct acctggtgtg gctgtgctct gcagtgagcc acatgagcct gaatatactg 125280
ttggggttcc ctggttggat tccagtgtgc caagggtaaa caggagtatc ccgaggtact 125340
cggtcacccc agcatgctgc tgcctcaggg tgtgcatgac ctgtctctaa aaagcccga 125400 ttatttttaa aggcgattta gaaaggctga attgatgagc aggaatacag aggtgtgatt 125460
tgcctctccc acctctgtgc tccattcttc actgtgatca ttttctcatt aggtttaaga 125520
aatacaagca agctgggagc cattccaatt cttcgcgctt atccaacggc cgcactgagg 125580
atgtgggtaa ggcattcctt aatgtcatgg ggaaccttca caaggaagga aatcaagaaa 125640
ttaggagttt ctccatcctt ttaaaagaat aagacaataa aaagaggaaa aaagatttt 125700 gaagaaaaca gtcctagttc ttacaggctt ggtccatgag gtagacccc gtttagcctc 125760 cagaagaggg gctaggttct cagggtacct gactgacctt ctcccttgtg tactgcagag 125820
```

```
ccccagagtg tgccacttct ggccagatcc ccaagcacca acaggaaata cccacccctg   125880
cccgtggaca agctggaaga ggaaattaac cggagaatgg cagacgacaa taagctcttc   125940
agggaggaat tcaacgtgag tactttgttg aggctggtgt atcagcaggg aagaaggcag   126000
acctaaagtc agacctttca gatctttgga gtcatgaagt aaaaaatggg cttttaatgt   126060
ttaagaggtg agaaatgttt taccaagttt atctgactcc ctgtatgatc atggatagga   126120
aatgaagtga gatttgcctc acctccctaa tctacccatc cattcagtca tcatcacatc   126180
tcttacttct tttgtttaat aaatacttag caagcatcta atatttgtca ggtaatattc   126240
tagttgccag tgatatgatg aggagcagaa acagatccaa tccctattct caaggaactc   126300
actgtccagg agggaaacct cacaaacaag aacaaatata actgtgtaag ttcaaacagc   126360
agtacagcac atgaaggact ggtgcatatt tgtaggcatc catattaaga ggttgccttt   126420
ttgagtctag agcaggggtg tcagtgttta aagtagacag tgggatagat cagtgtggga   126480
aatgacgacc atgggagact gcagagcaca ggtctcatct tgagtattta gattcacatt   126540
ttttataatt cccacaagga agcagaatat gttttaatc caccagttgg tgatcctagc   126600
ctaccagttc tgatcccaga tcagaagagc ttctggccag cacggtgact cacgcctgta   126660
atcccaacac tttgggaggc tgaggcgggc acatcacgag gtcaagagat agagaccatc   126720
ctggctgact tggtgaaacc ctgtctctac taaaaataca aaaattagct gggcgtggtg   126780
gcatgtgcct gtagtcccag ctactcagga ggctgaggca ggagaatcgc ttgaacccag   126840
gaggcggagg ttgcagtgag ccaaggtcac gccactgcac tctgacctgg cgacagagcg   126900
agactccatc tcaaaaaaac aagagcttcc tcgaataaat gatattttaa ttgatacctc   126960
atcataggca agggtggtgg ggacagggga ttggggagcc ttccagccac tggaaatagc   127020
aggagaattg tcaggagtga gtgtgctgaa ggagggcaca cccagaacat gacagggctg   127080
tgtgcagctg aagaccagag cttcaaagga ggataagagg tgaaactagt gtggccagac   127140
cacagacctt gcagatagtc atgagagaag tggcaagcca tagagcagcc agatttacat   127200
cttgaaaaaa tgactcagct gggcacggtg gctcacgcct gtaatcccag cactttggga   127260
ggccaaggcg gcggatcac aaggtcagga gatcgagacc atcctggcta acacagtgaa    127320
accctgtctc tactaaaaat acaaaaaatt agctgggcat ggtggtgggc acctatagtt   127380
gcagctactc tggaggctga ggcaggagaa tggtcagaac ccgggaggcg gagcttgcag   127440
tgagccgaga tcatgctact gcactgcagc ctgggcaaca gagggagacc ccatctcaaa   127500 aaaagaaaa aatgactctg gcttctgtaa ggagaatagc ccatgggcag accagaatag    127560
ttgcgggaat acagttaggg gttacaggtg ttaatatcag aagtgctagt agattgacct   127620
aatgtcatga ctaggaaatg ggggatggat ttaaggacac agaggagcag ttccagagtt   127680
ggtaaataca tcagctgggg cattgctaaa ccatcagttt ccttcacaac tttccactaa   127740
gccatgtgtc agctttgcct tataggctgg ctccttttt atcagtggga aaaatttcc    127800 caaaagcttc tggagacttc tcttgtcaca tgctccttct taaaccggtc gtgagcaagg   127860
gagaaaataa ggttactgtg gttggctgag actagtccag attactcctg ggtcaaggcc   127920
aggcatgcta gctcacacct ataatcccaa cactttgaga ggctgaggca ggcagattgc   127980
cttgatcaca ggagttcgaa accagcctga gcaacatggt gaaacccat ctctacaaca    128040 acaacaacaa caaatacaa aaattagctg agcatagtgg tacatgcctg cagtctcagc    128100
tacttgggag atgaggtggg agtatcgctt gagcctgcgg ggtggaggtt gcagtgagtc   128160
agattcactc cactgcaccc cagcctggac aacagagcca gatcctgtct caagaaaaaa   128220
```

```
ttttttttag atattcatgt gggatatgga tggataacct cacagaatag gaggtctggt    128280
aaaggaggaa tggttattgg gtcagtgggt caccattcat atctgctcca tgacagaagg    128340
gcttaggggg agtggtgagt gatgtcagat ttgcattttg agaaaataac taactacaat    128400
atagagaata gataaaaggg agaggcaaga gttgaagtgg gagaccattt accaggcaag    128460
agttaacaga atagcttgga cccttttttgg gggctattgg aaaaatagca ccatttaatg    128520
ttcattattg attgataaga tttaccacat cctgccaggc acagtggctc acacctgtaa    128580
tcccagcact ttgggaggcc aagccaggca gatcacctga gccaggagt tcaagactag    128640 cctggctaac atgggcaat cccatcccat ctctactaaa aatacaaaaa ttagccaggc    128700
gtggtggcac gtgcctgtaa tcccagctac ttggaagtct gaggctgagg caggagaatt    128760
gcttgaacct gggaggcgga ggttgcagtg agccaaggtc gtgccattgc actccagcct    128820
gggcgacaag agtgaaactc catctcaaaa aaaaaaaaa aaatttacc acatctcaca    128880 agacagcact ccagcctcag taccatagct ggatctgtgc taggcattgt actgttttgt    128940
aatctataat gccaactgct tctgggtgat ggggtatgtg atcccattac tatactttt    129000 ttctgacaaa ttagttcttt tcttttcca taacattaaa tttacataag catgaaacga    129060
attatttgtt tggaggtaat attccctgag actccatggt aaggtatttc agtaaatccc    129120
tggatggtga tggtattcct ggaggcatga caggtaaatt cggatagata ttgtggtgag    129180
agccatttgc tgtgctacca tggcaaccgt gttcacgagc tcattgggcc agcactaggg    129240
tagtgaggga aagggctgac catcatcacc tgggtttcta gcaatgagtg ccatcttgtg    129300
agcattcaca tggaacataa atattttctt tcttgtgcta gttatccact acccagcgat    129360
tggtttagat cctgacttcc agtgagataa gtggtgtgat aatttgcttg aagttctctt    129420
cactaggaga atttctcttt tatacacatt caaagccatc acttaagtag tatacccat    129480 agcagtctac ttccagccca gcatgggcca gcatgtttca ccaagcagtt tatataccag    129540
gccggacttt ttcttcttca gttaactgtt gatgtcaata ggaagtcaga agtatctatt    129600
gcggcagtgg gttgtgtggt aggcatttta tagagatcac ttccagctga aatgggatt    129660 ctgctgggca tgtccaaatc tatggctaat tgaatctcat aatacctagt ttacgagacc    129720
ggcccggtgg ctcatgcctg taatccctgc actttgagag gctgagttgg acagatcacc    129780
tgaggtcaga agttcaagac cagcctggcc aacatggtga aaccccgtct ctactaaaaa    129840
tacaaaaatt agccaggcat ggtggcaaat gcctgtaatc ccagctactc gggaggttga    129900
ggcaggagaa tcgcttgaac ccgggaggca gaggttgcat tgagccgaga ccacgccatt    129960
gcactgtagc ctgggcgaca agagcgaaac tccatctcaa aaaacaaaa caaacaaaaa    130020 aacccctagt ttacgatggg gagttgaagt catttggata cctgtctgtg atcaggcttg    130080
cagtctctac cctagagccc agtactaggc taggagcatg gtcttaccaa taggatcatg    130140
gtcttatatc catatccaaa tattacgatt cttctgttta ccttactaca aacactctag    130200
agctccatac aatctaccag agcttatttc tctgtggcct ggatcagcag gagcactttc    130260
tcttttcaga tcactcaata aattggtcag aggctgggca cagtggctca tgcctttaat    130320
cctcgcactt tgggagatga ggcaggcaga ttgctttgag tccaggagct caagaccagc    130380
ctgggcaaca tggcgaaagc ctgcctcttc aaaaaattag ctgggcatgg tggtatgcac    130440
ccgtagttcc agctactggg gaggctgagg tggggtattg cttgagccta ggagtttgag    130500
gctgcagtga gctgtgattg caccactgca ctgcagcctg tgtgacagag caagatcttg    130560
tctctatgta ggtaggtagg tagattgatt gattgatcag atggattaga tggattaaat    130620
```

```
tgagagatca gagttggatg caaggataag gtatctgctg tctccaaaac tcaaaatggc  130680
ccagcaagca ttgctcctct tgttagcag gagagggtg gtggggcaag gggcaacaag  130740 ttgtcttta tgttggagga gataccctga cgtgctgcag gcctttgact ttcagaaaat  130800
ttggctgagg tggcaggcca ctgtatttt atgtctgaca tgtacatcta agatacataa  130860
cttcctgctt ttcatgtctc acattgatgt cattagcata gttgtcaagg taatgtcctg  130920
tgaaacagac aaaatcttga tgaaccagat cacaacacag aaaggtcaag atgatttatc  130980
actgaggctg ctcttgccat gagcaagaaa aactgcttca agtagtccac acaacttaaa  131040
aagaacacac acttacccct agcagtagtc taggtaccag gagttatatg ttaatctgca  131100
gaaagtagag tacgtctgga aaagtaactg caaatctgca aagtcttctg tagcacttaa  131160
gatcctgcgg ttcacatgga gacttcgcct tttgctaaag agatcactgc tctaggagct  131220
tacatttgct ctttctgtga tggttcttat ccagtgggct agggaatctg tgtgtctttg  131280
ggcattacct aatggccaat gttattgaaa atcaaggtgg cacagaggga ggtctagcca  131340
acttcacaga gccgggagca tctagtttct ttccctccct tttggaggcc ctgacagaca  131400
ggcaggcagg cagacagaca gatcgacaga caggtaagat agattagata gattaatagg  131460
tcctaatgtg aagccacctc aggccaaaat tccttccatc agctggcctg caaaggctcc  131520
gttctaacta gcatatctta gcgacattct gagttcctag caagtagcta cctcaaggcc  131580
aggacctagc agaccccaaa agatgcattt ccctttacct agtacagttg ccatggcaaa  131640
tatctgcaga ttattaagaa aagatgagga gggaggttta taatatatgt gtgttaatgc  131700
gctgtggcag ggttcctcct tacagatgcc tggcctccct gttattgaag ggttctgggt  131760
ctgaaatgac ccaggcctac gagttggatg agggggcccc ctctctagca tggtggtcta  131820
gtaggctgcc taaactgacc tggaaagcta cttccgttt ccattactgg gagcttcaca  131880
atgaattatt cacagccata aacgtctgat catggtctcc aacagtcttt ctagcccact  131940
tagatcagga atcccatttt gaaatagtcc cttccactag catctcacgc tgctgaggac  132000
agccaggaaa gcacttctga aagattccag tgctttcctc accagtgtat agcctcagca  132060
aggcatgtga tgtggatccc atcaagggca tactgaaggt gtcagtagaa ggctgagcct  132120
ttagagtcca tatgccactc tggtctcctc tactttgtgc ccaggttttt ctggcttttc  132180
attatcacct cactaaatcc agcattcagt ccaggtttcc actggcgagc ctagctcaac  132240
attaaaacca tggccagtta cctgagctgt tacactacct gcagaagttc ttttgaccat  132300
accataatta gaaatttggc tttatccagg ctgggcacaa tggctcatgc ctgtaatccc  132360
agaactttgg gaggctgagg caggcagatc acttgaggtc aggagtttga gaccagcctg  132420
accaacatgc tgaaaccctg tctctactaa aaatacaaaa attagccggg catggtggtg  132480
agtgcctgta atcccagcta ctcgggaggc tgaggcagga gaatcgcttg aacccgggag  132540
gcagaggttg cagtgagcca agattgcacc actgctctcc agcctggggg acagaacaag  132600
actccatctc aaaaagaaa agaaatttgg ctttaaccaa gtcatactct cccttccttg  132660
ttataacgtc tccaaaatct atatcaacaa ttgttcctat catttgtaat gatccagctc  132720
agtgaattcc tgtagtttct tctggatatt tattagctct ttactttttt tccccgctg  132780 tagagacggg tcttgttgt gttgcccagg ctggtcttga actcctgatc tcaagcagtc  132840
ctcccacctt ggtctcccag agtgctggga ttacaggcat gagctactgt gcctggccag  132900
cattttactt ttctaccta tttatgcatt ttaccctcag gtcatgttat gcttgcattc  132960
tggtaatgtg tgggcaatgc aggctgggtt gtggggcagt tttcatcatg acagcaagat  133020
```

```
gcagtagaga gcataataga gattttgga aattaacttt ctttgggtcc tctctttat    133080 catcatttct gttgtctcac ttaaagcctt atctttctca tgagcaaccc aggaaagatg  133140
tgaattctgt ggcattaaaa ttcagcaact cgcaaaattt ggaaaccta acatttcact   133200 tagcaaaata catatatagt aatgtaaagg ccctgagtct tgggttttca tttcaaggtg  133260
agcatttgat attggagctg ggttatttct tgttttgttc tctaatattg tcagaagtaa  133320
tcctactcct tggtttcaac atttccctc tccttttaat tgggacaccc ctactcgttt   133380
accaccagct tgaacacatc acaggtaatt gcaagcaata actaaaatag tagttgtgca  133440
gctatgaact gtgagcagct tgctctttcc catcctggca attggttgtc agtttctttc  133500
cttccatctg aacccagtaa catcacccac gtttccccta gcagtctctc aactacaacc  133560
cactctgata gtaattgcta atcagttaa ggtcctctag ttaaaagcaa gagaagtcac    133620
ctcaactaaa ttaagcaaaa acaaacagaa ctattgattt gggaagacac tggaggagct   133680
ggcagaatca gaaggtaagt tggagtacca agtctcaggt agagccgacc ttggtggctt   133740 tggggcccctt ctagggaagc ccctgcttct tcctagttt caaaatcctg ggagagaatc   133800
tgattggctc agtatcagtc aggtatgact gtgtttggat cagtcagccc tgggagagaa   133860
gaggagaaat aacacatagg gcaaacaaac caatttgtgt ctactgtcat agaataatat   133920 tttagtaac catcagatgg ggaaggcctt tctaagctac ttagaagatt tagatgccag     133980
aatggaaaag tttgaaagat agcaaatata ttaaaatgtg aaacatcttt gtgacaaatg   134040
atgtcgtaaa aaagtggcca actgggagaa tctatttgcc ataggtagac aaagaatgtt   134100
ccagaatata caaacctgtg agtaaaaggt aaacaatcca gtcaagaaac tggcaattta   134160
cagaagaaat acagatggtc tataaagata tgaaaagaag atcaactata tctagtaatc  134220
agggaaatac agattaaagc taaccattat tttggaccta tcagatttga aaatttaaaa  134280
agctttatat caaatgtgga caaaagtatg gggctgcaga gacttacagg tgggggagtt  134340
taaattggta ttgcattgga gggatgattc tggcagtacc aatcattatt taaatgtttg  134400
agttttctga ccaagcttct gagattctta acagaaaaag ccatgtacaa agatgtttat  134460
gacagcatta tttataatag caaagaagat aaaaacgcaa atatctgtca aatagaatgg  134520
ccagatgatt tcttatatcc attatgatat tctatactat cattaaaata aatgtgttca  134580
catagatctc taagttatat tgttatgtga gaaaacatat gtgggataat ttcatttttg  134640
ttttcaaaaa tatgtatatc tgtgtgtgtt tgggtatgtt aatgcttttt tttttaagtc  134700
tgaaagacta caaattgtca acagtggctg cctacaaggg ggctggaaga gaggagagac  134760 ataatagggga actttgtttt ctactaaatt atttgactta aaacaagcat attcttttta  134820 taatatttt aaagcagatt tttttgaata tgggaaataa atctaatgga cttagtttgc    134880
ttcgatggat atataacatc tagaataaag aagttcctat gcctagtttg aactgtgtca   134940
ggagtcttgt ggtcaggtct ctataaaaag ggatatcacc aaatgggatg ttgttctgga   135000
gagaaactgg accatggggg tgaataacta aaggaacaac actcatagga catgacagct   135060
gttttcagat atgtgacagg ctaaaaggag actgtagcat ttccgtgaat gcccacctga   135120
ttagaagttc taggctgtgg ctttcatcct aattacaagc tggagctttt tgttcacca    135180 gcatttgtct ttctaggaat cattgaattt attcaaaaga aatactttga aaaccactc    135240 agaagccccc attttcaggg aaaattgagg tctttaaggc attatcaagg tttaaaaaga   135300
aacaaaaaga taaattgtg ttagcttctg gctgggtgca gttgttcatg cctgtaatct    135360
agcactttgg gaagccaatg cgggaagatt gaggccagga gtttaagacc agcctaggca   135420
```

```
atgtagcaag accttatctc tacaaaacaa ttttttttaa ttagccaggc gtgatggcac    135480
atgcctgtag ttctagctac tcagggggct gaggtgggag aatcatttga gcccaacact    135540
tggaggctac agtgtgagct atagtgctaa ctttatagag ctgcaggagc tacagtgagc    135600
tacagtgatc accgcactgc cctccagcct cctggctacc agagtgagac tctgtctcaa    135660
aaaaaaaaaa aaaaaaaggc ttagctcctg agaggaatgg gataggagag aaagaaaaga    135720
gggaaagagg tgaagccagt gaaatagtca gaatctgtgc gatgtgagat gtgaccttcc    135780
tcaggacctc acatctctta gattgccagg tgaagaaggc atgtgtgtgt cactagtgat    135840
gggactgagt gtggcatctg agttgagatg ggtgaaatcg cctctacatt gatgagttgt    135900
cccaaaataa gtgaatcaga gtcacagtcc tgtgggaatt agcaggaact gtgacaaggg    135960
ctttggaatt ccactgtcca gagagttggg agtttgcgtt ttgcaagggg cagaaaagat    136020
gcccgctgac atctgggttt tacattgctt agtacgaggg aaatgcaaaa gaaattgtgt    136080
gtctgggtgt tgggtcgttt taaacagaac tgttccaaga cctaccttgg aaggtagtaa    136140
atttcccatc actctagtgt tcagtcactg gtgactattg ggtgagagta ttgaaaggag    136200
attcagactt aaaagtgaat gagattcaga cctgtactgg agatctaggc aagaaaagaa    136260
aggtataagg attgcaaagg aagggacaaa atataaattt ttcacagacc aaatactgtc    136320
ttcagaaaaa cccacagatt catcagacat attatagaat taatatgaca tattatatta    136380
tagaattaat aaatatgaca tatttataat ttattatata tgacatattt ataattaata    136440
aatatgacat tatagaatta atatgacata ttatagaatt aatattcatc agacatatta    136500
tggaattagc aaggttgcta gatacagaag cagcataaaa atttaatgca tttctataca    136560
taggccacaa acagaaaacc taataatacc ttttaaaagg tgccaattac aatagcatcc    136620
aaatgtaaag tacctaggaa tggatttaac aatttagaga aaattattaa aatgtttgaa    136680
gacattaaag gaaaatagct taaattagtg aagagatagg atcaatggat taggaggctc    136740
aattttgtaa agatgtcaat tctcccccaa gatatataga ttcaatgcaa ttccaataaa    136800
aatcccaaca ggtttttttg tggaacttga caagctgatt ctaaaattta tatggaggag    136860
aaaagattca agaatagcca agacattcct gaagaagaag aacaaggtga ggagacctgc    136920
cttaccagat ataaagagat tataaaattt tagtaattaa gacagttttg tattggcact    136980
gggatagaca gatcgaccag tggaatgaaa taaagagccc agaagcagat ccatttgtaa    137040
gtggaaacct atttatgaca gaaatgctct tgcagtttgg gtggggaaaa gatggtcttc    137100
acaataaata gtgcctggga ccattggtaa ccctgtggga ataaatgaaa ttgaatgctt    137160
gtcacatatc aaacacaaaa accaattcca gttgctgtaa acactgaaat ttaaaggaca    137220
aaaatgataa aatgtagaga tcataatgta gtaaaatata cttctgatct cacagtagga    137280
aaggatttct taagacttaa aatgttgata aaagggaaga ttgatgaatt tacatgaaaa    137340
tgcaaaacct ctgttcataa atgataccat aaagaagatg aaagggaagg ccacaacctt    137400
ggtaaaagat aacacaggta actgataaag gaagagtatc cagaatatat aaagaacttc    137460
tacaaattgt taagaaaata agtaggctgg gcgcagtggt tcatgcctgt aatcccagca    137520
ctttgggagg ctgaggtagg cggatcacaa ggtcaggagt tcgagaccag cctggccaac    137580
acggtgagac cctgtctcta caaaaaaata caaaaaaaat tagccaggtg tggtggcggg    137640
cgcctgtaat cccagctaca ggggaggctg aggaaggaga attgcttgaa cacaggaggt    137700
ggaggctgca gtgagccaag attgcgccac tgcactccag tctgggtgac agaacaagac    137760 tccatttga aaaaaataat ccagtaggac aacggggaaa ccacttgact aggtacttca    137820
```

```
cggaagagga aactcttttg accagtatgc tatggaaaga tgatgaacct cattaataat   137880
cagagaaatg taaatcagtt aacacaaagt ctgacagtag caaatgttga taagcatacg   137940
gaactggaac actacattgc tggtgggagt ataaattagt acaacttctt tgaaaaacaa   138000
tttggcctta tctggtaagg ttaaagatac ctatacctga aattcttgca catatgcaca   138060
agaaagatac aaaaatgtgt ctcaaagcag gacctttaac tgtaaacaac ccaaatattc   138120
atcagtagta gaatggataa gtaaatttta acaccgtctc aaatggagca ctacaaagta   138180
gctgaagtta gcagccagga tgaatcttag gaacgtaatg ttgagccaaa gaaaaaagca   138240
actcaccact taatcatgat tccattttcc tcaaaaacta gactagcaat aataatacat   138300
tgttttggat gtaaaaaata tgagatacaa ataaaggaat gtaatgataa ttataaaact   138360
tcaggtttac cagtgagagg ggaaggaaga ggatataagg agaggagccc aaagagagct   138420
tctaagttaa attatgtgat ggatactttt taaaaaataa atatcaacaa atgtgaaaaa   138480
aaaatttttt tttaaccgac atgtctttaa aaaatgaatg agtacttagc cttggttcca   138540
gttaaggctt aaacaagaga tgaaacggtc ttcgatgcca cctagtgttt ctagagagtt   138600
taacatttta tagacttctg ctctagctgc tccttcctag ctctgtgagc taggtttttc   138660
agagtagaaa ccaaaaggag taggattcac cttgttttca tccgtgacgc aggctcttca   138720
ttctgaacct ttgcatctag cgctgtgttc tccaggcaa gccctttctt ctctcttgtt   138780
aaacaatggc tcctgtttct tcctgactct ttttaggagc cttagtccac ctggagacct   138840
agttttttctt tatcatgact gagggagcta gggatgctga tagggctgtg agatgtagtc   138900
tttgttattc ctgacatttt tgtattgaag actgttttca agagtcttgc tgtccctacg   138960
tctgttctac attttagaga agggatgcac aggaaaacta gtgcctctgg attagccatc   139020
agggcttaaa aaactgacat ctcatcctgc cctgtacttg ggtggaaacc tgtggaaatc   139080
ttatgtgaag gaagagaatg caaactgtgg gtgaactgag aaattctgat ctaaaataat   139140
ggtctctact gcgtgtgtaa gagtccagcc caggaaaatc ttttcttcct tttgtggtat   139200
tcacagcata gggtcagggg taattgcctc tgttagtaaa ataacatgca gaacctccag   139260
ggttttaatc tgaaaggaaa tctcttgagt aggtgagggc agatggattt tgaggtccta   139320
atttccctat ctttgggtct ttcactttaa tttctcctat cactgtcatg ctggtttcca   139380
gtaaatatat ttgctccttt cttaaagctc ttgcttccca gcctgggcaa catagcaaga   139440
tccacctcta caaaaataaa aattaaaaaa ttagccaggc atggtggtgc tgtgcctgta   139500
gtcccagtta ctcaggaggc tgaggcagta ggatacctcc agcccaggag ttcaaggctg   139560
caatgagcta tgatggcgcc actgcactcc agcctgggtg acagagcgag accctgtctc   139620
caaaaaaaaa caacaaaaaa ctcttgcttc catctgacaa aaaattggtt ccctttgggt   139680
tggcatttcc tttattcagt ctttttttaa attattatca aagacagaaa cgttcattct   139740
tcatttctgc ctcttgctct tcccagtcca cttttgcctt cattccatct ccaaatgtag   139800
taatttttt tttttttttt ttttgagaca gagttttgct ctttctgccc aggctggagt   139860
gcaatggcgc agtcttggct cactgcaacc tccatctccc gggttcaagc agttctccta   139920
cctcagcctc ccaagtagct ggggttacag gcatgtgcca ccatacctgg ctaattttt   139980
gtattttag tagagatggg gtttcaccat gttggtcagc tggtctcgaa caccagacct   140040
caaatgatcc acccgcctcg gcctcccaaa gtgctgggat tacaggcgtg agccaccgcg   140100
cctggcccaa atgtagtaat tctaattcca gaatatgtct caaatgcatc catttccttg   140160
tatcatcatt tttccatgct tctcttcttg ctcctctcta gtccattttc catacaataa   140220
```

```
caagtaattc tttaacatgg aaaatggatc acactttaaa aaccttcaat gatttcctta 140280
tgcacttaac ataaaatttg aactccctat tcaaggacct acctggaaat ggatgatctg 140340
actttgccag gctcatctct tcctacttcc tcctgccatc cccatcaacc tcaccttctg 140400
cgtgatacct gcactgattt tcggttcctc acacaaccaa gccttcttcc acctctgggt 140460
taccacagat gctgttctct gtgtctggaa tactattttc tatactcatc cttcctcaga 140520
gagacccacc tgtaatccaa atttggtgct ttctgatact tcatctctag tagcattctg 140580
ttctttgatt gcattcatca tggtatataa ttatatatgt atttgtttta tttgtttaat 140640
gtctgctttt cacccacaag tttatattgt ccttgagggc gagaactgca cttatatttg 140700
attccccact ctttgctctg tatctagccc agtgcctggt aggtacaaaa tatatatttg 140760
ttgaaagaat gaatgaaaag taatgcatga attgttcctc tactgctgaa tactacggtt 140820
gttctcagtt ttgggtcatt ctaaataatg atgaagtaaa taattaggac ataaagatttt 140880
ttatttccta agggtatgtt ctcaaaattg aagttgctag gccaaaaagt attttttgaaa 140940
agttttttta aggctcataa aatgtaattt ccaagtcact tactcggaat tagtgttgga 141000
atttttaaagt gcctcccttt ttgctttctt gtttgttttt atagtgtcag agtctcactg 141060
tgtcactcag gctggagtgc agtggtataa tcatggcctt gaactcctgg gctgaagtgt 141120
tcctcccacc tcagccttct gagtagctgg gactacaggc atgcaccacc atacctggct 141180
atttttttt ttttttttt tttaatgta gagacgaggt cttgctgtgt tgcccaggct 141240
ggtctcaaac ttctggcctc aagtagtcct cccacctcta cctcccaaag tgctgggatt 141300
acaggcatga gccaccacac ccagctcctt ttttcatcct taattttgaa tatatgaaac 141360
atacaagagg agaacagatc aaataataaa atttagcttc ccactctgat aaaactcatt 141420
tatttgaata cttattcttt gctacacatg agattatttc cttatgtggc agatgttgtt 141480
gttccaattt tatgtatta tttattattt attttgaga cggagtctcg ctctgtcgcc 141540
taggctggag tacaatggcg tgatcttggc tcactgcaac ctccacctcc caggttcaag 141600
cgattctcct gcctcagcct cctgagtagc tggggttaca ggtgtgcacc accatacccca 141660
gctaattgtt gtcttttttag tagagacagg gtttcgcctt gttagccagg ctggtctcga 141720
actcctgacc tcaggtgatc cacccgcctc agcctcccaa agtgctggga ttacaggcgt 141780
gagccacttc acccggcccc aattttacag atgaggaaac tggacctaga aattttaaca 141840
gatgtgctca agttcataca aacacagact atctcatgtc agatcattgt gtgataacct 141900
ccctgcacta actaatctac atttgctcca gaactgctgc aaatttaatg tcacctcacc 141960
caaatcttct gcttcttaac tgctgcatct atatgaatgc cctcccaccc acccaccagt 142020
ccttgcttcc ttgccacatg atgctagagg ctggggtgcc atgccccctt agatccctag 142080
gaagagatta aatcagctgg ccatccagaa ccttcctgtg tggttcactc tgagatgcat 142140
gtcatctttg tgtggtggta attagcatga ggataaatgg cccattcctt caggtatgtc 142200
cccattccaa tttacaaggg taggcccttt tggcccagta tcataacaac aggctgctaa 142260
ccacatagta atcatggaaa gagcatgcta tacttacata acagaaaggg cattctgccc 142320
cctgaggatt cttgtgttgt tgaactctaa ggagcttgtg gctgtttcgg gggagaggag 142380
cattctctgt gttaggctgc aggtattcac ctgggcccat gttttttcccc ccaggaaaag 142440
gtagaacatg ctaccaggtc agggtttggt gcagcagttt gcatgtttga tgtttatccc 142500
tgctaataat tcctctaatt tctcttaacc tttcaggctc tccctgcatg tcctatccag 142560
gccacctgtg aggctgcttc caaggaggaa aacaaggaaa aaaatcgata tgtaaacatc 142620
```

```
ttgccttgtg agtgtcttta gtgtttcttg ggatgtaacc tgaaattaca tctctggagg  142680
gattttctga agatggaaag aatcttgcaa ttgggcacag cagggtgaat aacaagagtg  142740
cgttcatggc agtactcagt ggctcatacc tgtaatccca gaactttgga aggccaaggt  142800
gggagaatct cttgagccca ggagtttgaa actagcctgg gcaatatagt gagacctcat  142860
ctctacaaaa accttaaaaa attagccagg catggtggtg tgtgtctgtc gtcccagcta  142920
ctcaggaggc tgaggtagga ggatcccttg agcccagggg ggcagaggtt gcagtgaccc  142980
aagatcgtgt cactgcattc tagcctgggt gacagggcaa gaccgtgtct caaaaaaata  143040
aagtaaaaga aatgaaataa ataataataa ataagataaa taaataagag taggttgaag  143100
actttgggct gaaagagcct ttatggatcc cacatactca gagtcaatta ggatgatcca  143160
ggaggatttt tgtgtcaggc ctaaagtttc taggaggtcc tggagaacag cttcactagg  143220
atcaggcagg aagcaggggg taatggtggt ggtagagatg gttttttgtg gtattcattg  143280
aaagaaattc taatgcagag ttctctgtat aaacccttcc cagagttagc cattgctaat  143340
cagttgatcc ataagctaac agacattttt ctagtccatt ggtatccaga atgggatatg  143400
cataatttaa tgagatatga gaggaagatg tttgaacctc acttgatttt tatatttgct  143460
tttcaaaaaa aaaaaattcc taatcctcag aacctgtgaa aatgtttttt ttttaatttt  143520
ttgtagagat ggtcttgctg tgttgccttg gctgatctca aactcctggc ctcaaacagt  143580
cctcctgctt tggtctccca agtgttggga ttacaagcat gagccagtga gcccagccag  143640
tatatttgcc ttttaaaaat tcatccttt aaatttttta tttcatttat tttttagag  143700 acagggccac ccaagctggg gtgcaatgat gtgatcatag atatgtatcc tcgaattcct  143760
gggctcaagt aatcctcctg ccacagcctg ctgagtaact agaactacag gtgcatctac  143820
catgcctggc tgattatttt ttagacacag ggtcttgctg tgttacccag cctggtctca  143880
aactcttggc ctcaagcagt cctcccactt tgacctccca agaattggg attacgtgca  143940 tgagccacca catctagacc ctaaaaattt tatatttcag ggtatatcat acattagcat  144000
atgtgcataa tttatcaata aatgagcatg tattagagat gcctgctcac attttataa  144060 gtgaagtatg gaaccaaaaa attaggacca ctacactatg catttacaga tacttttgtc  144120
tttttctttt ttcttctcg ctctgtcacc caggctggag tgcagtggca cgatcttggc  144180
tcactgcagg ctctacctcc tgggttcaag ccatttttcct gcttcagcct cccaagtagc  144240
tgggactacc tataggcaca tgccaccaca cccagctaat tttgtatttt tagtagagac  144300
ggagtttcac catgttggcc aggctggtct ggaactcctg acctcaagtg atgcaccgcc  144360
tctgcctcct gaagtgctag gattataggc gtgacccacc atgctcggcc ttgtcttctt  144420
atttatgtgc acatgttgga ggaggggat gtgtgtatgt gtgtgggtgt gggtatgtgt  144480
atatataata catatttttt aatatgattg gtatactgta cacatttctc tcttttaata  144540
gtatatattg tcagttcatc tgtcaagaaa cttctttttt tctcaactac ttagtattcc  144600
acattgtaga tgcatcttaa tttatttaac tagtcccta atgatactta aggtattccc  144660 aatttttgc tgttatactg ttggagttat attgttggag tggcatcttt atacaagcgt  144720
gagtctgtgc acataggcac agatgtctca actgtcctgg ttgcgtcagg ttctgtgaga  144780
aataaatttt gattttactg aaatattgtt ggtttgtttc ctagatgacc actctagagt  144840
ccacctgaca ccggttgaag gggttccaga ttctgattac atcaatgctt cattcatcaa  144900
cgtaaggatc gggtgctttc cctgtcactt ccctgcctga ccattgccac tatctgttgg  144960
ctcctcccca gctgtgtgtt aggagaaata tttgtcattt catgtttttcc ctgacaagtc  145020
```

```
tggttttttt aagtgactga attttttttt aaggtcagtc aaatagtttt aatcattttc   145080
tatatttacc ctgtcgtcat tccctatggt ttcccatgta gaaatctgtg tctaaatatg   145140
tattttgtga taagagtcag tgaatccttt attgagctga ttctaattac aaacaaaagc   145200
aggccttgcc ctcaacagta aaaataaggg agaacaggac aagaatacct gacatgacac   145260
cagctatatt atatatgtgt gtgtatgtat atatgtgtgt gtgtgtgtct gtgtgtgtgt   145320
atatatatat atatatgact atctggttag ccatatatga accaaggcct gagggaagag   145380
ctgatactaa gaggaggttt ttaaagatga tttagagaat gtttatagaa cagtctgtat   145440
gagagatttg aggttttttgt ttggttggtt ttgtctttgg cagtagcctg aaaaaacaca   145500
taaagagtta agaatatgtt ttataggttt gggggaagca tcctgtagag agagtgaatt   145560
tgaacagaaa aaagagagag ggaaagctgg caaaagcaag tctgactcct gatgcaaaat   145620
gcatgagaag actggataaa atttccactt gcatgtttat agcagcatta atcctaaaag   145680
ccaggtggga gcactccaag tgtccattga cggatgagtg aataaattaa atgtggtaca   145740
tgcatacagt ggaatgttat tcagcccttta aaaggaagga aattctaata catgctacaa   145800 catgatgaa cctggaagac atcatggtaa gtgaaataag ccagtcacaa aaggacaaat   145860
attgtatgat tctacatata gaatataaac tatatataca tatgtagagt agtcaaattc   145920
acagggacag aaagtagaat agtggttgct gggggaggga ggaatgagga gtgggtacag   145980
agtttcatct ggggaagatg aaaaagttct gtagacggat ggtggtgatg gttgcacgac   146040
agcgtgaata tacttaatgc tacagaactg tacacttaaa atggctaaaa tcagccgggc   146100
acggtggcac acctgtaatc tcagcacttt gggaggccaa ggcggtggat cacttgaggt   146160
cagaagtttg agaccagcct gaccaagatg gtgaaacctc atctctacta aaaaaaaaa   146220 aaaaacaaaa aaaaaaaaaa caacttagcc gggcgtggtg gcaggcgcct gtaatcccag   146280
ctacttggga gattgaggca gagaattgct tgaacccggg aggcggaggt tgcagtgagc   146340
cgagatggcg ccactgcact ccagcctggg cgacagggtg agactgtctc aaaaaaaaag   146400
aagagtcaaa atggctaaaa tcgtaaattt tatgttgtat tttaccacaa gaaaaaaaaa   146460
ggacactgat ggagagatta gtgtgaacat aagaagggct gtttcttcct ctgagagtga   146520
agataaagga gaggacagaa tggatagaga cgactcgtag gtgtgggtaa agcaagttga   146580
ggcaactcac ccgtgtgctc atggttgtgt actgaacaaa tgagatggga ctgtgacatg   146640
agagcttcga aagtttagaa cagcttctga ggtccctgag aaaaggatac caaagagaga   146700
aagcaaagga catgtctagt gggatgtcat tgatgggggt gggggtgct gagttgtgtg   146760 atttttttt tcttcatctg caccctggga ttggtggtaa atgcagagga catgtggtac   146820
tcagacaaaa gggaaggtca gtggctgctt caagtagtca gccaagggct tcagtttcag   146880
tagaaaagaa aagcgttagg aagttgttag gaataaacaa ctattcctaa ggtggtagga   146940
ttgaggaact ggagatcttg agaaagtgaa agaacaggag gttgtgtcca aaaaataggc   147000
tattagatgg acttcaaaaa tggggcagtc cgggcattct cactggagtg aatttgctga   147060
agttcctgta tgtatgttta acattaatgg ttacatgttt gtagttttaa ggaaagggac   147120
cctgactaga caaataattg ttgtagtcga taaggaaaat ggagaaaggc tagtaatcag   147180
caggaattcc tagaacttac atcgaagatc atgatgaaga gattaggtgg aataggttga   147240
ctttaatgtt atgcagaaga gaagagcaag atcagttagt gtgtccagct gcgggtaaga   147300
gaatactcaa ctaaaagttg tctagatggg aacattttt tttttctgg agacagtctc   147360 accccgacac ccaggctgga ttgcactggt acgatcttgg cttactacga cctctgcctc   147420
```

```
ccgggctcaa gcgattctca tgccttagcc tccctagtag ccaggattac agacatgtgc  147480
caccatgccc agctaatttt ttgtattttt agtagagacg gtgttttgct atgctggcca  147540
ggctggtctt gaactctgag cctcaagtga tccacctgcc tctgcctccc aaagtgctgg  147600
gattacaggc gtgagccacc gtgcccagct ggaacattta tttgtctcat atactgtgaa  147660
agcaaatgga gaccagttct tgagttggct gattccatgg gtcagtgaca tacttacaaa  147720
accaggtgct tccatctttc tactcagtta tccttagccc tgtcaacagt ctcatggcca  147780
caagatggct gcagcagtcc caagcattcc tcataaacac agcatccagc cgggtgcggt  147840
ggctcacgcc tgtaatccca gcactttggg aggccgaggc gggcggatca caaggtcagg  147900
agatcgagac catcctggct aacacggtga accccgtctc tactaaaaa tacaaaaaat  147960 tagtcgggcg tggtggcggg cacctgtagt cccagctact gggaggctg aggcaggaga  148020 acggcgtgaa cctgggaggc ggagcttgca gtgagccgag atcacgccac cgcactccag  148080
cctgggcgac agagcgagac tctgtctcaa aaaaataaa taataaaaa ataaaaaaaa  148140 taaacacagc atccagcaca gaagaggaac atatctgcct atgcttttct ctctgttagg  148200
gagcaaggct tttcacggaa tcctccccac caccctgtcc tcaggaccag caggccagga  148260
ttggatcaca tgttcacatc cctctctaat cactggctag acattgaga atgatcatga  148320 tttaccccctc tgagcctggg gaatgggcac cttccaagcc agtgaaaggt taatgtccaa  148380
acaaaattgt ggctctaatg gcaaagaaga aagggaggaa tggatttgag ttagtaacca  148440
gcagcatctg ccaccgtaac cagtttggtc ccttcccaca ttgaaggtga aaactgacaa  148500
aagttaattg tatgttaagg ctgttaagca gctgagatgg ggatctcttc atggtaatgg  148560
cacagtagaa agaaacagcc ttatcccttg accatgttta tttagagctt acactagggc  148620
attccataat gccttgatgg ttattagaca gttattagta ggcagagttt acatgaagag  148680
ggttaaatgg gggaccttat gaactcagtg aaggaacaaa agcagggaaa aacctgtggt  148740
taaccataag tgggaagcag ggattaaaga tttggatttc acagtttatt aaactcagtc  148800 aacattttt gagcacctgc tgtgtgccaa gcactgtggg taggcttaaa ggttacagag  148860
gtaagatgta atccctcata tactacacag gtagttaggt tgtttcctgt aatgtgctac  148920
gtgtgcaaag gaggtattgc caggttctgt ggagttatga gaaaaaacat tcagcccagc  148980
ctggtaaccc agtagagctc attattgaag agtgagtcag agttcaggag aagaaagttg  149040
ggcagaaact tcaaagcaaa ggagaaacat gagcaaagtc acagagacta gaaacagcag  149100
tcttaggtta taaggtataa gatgggaagt ggtgggaaat gagacttgat cttgaaaggt  149160
agtggatgtc aagtgtgtcc attggagttc ttacttgcag actatagagt gtacttttca  149220
tccactcttt taagcagaaa ggggtttatt ataagatact gggtacctta acaaaacctg  149280
gggaagagcc agtgagccaa gctcagatgc tgctcagcaa agagcagagc agctatagat  149340
ctatgcagca tgtgactgtc atagtgaaac ctctgcacag tgctgcagaa gaactggatg  149400
cttctactac cgtgcttgcc caaagaccag atttctagca cagtcgttat ctcatgttgc  149460
tcatttctac cccaagtctt gtgtgggagc atctgctagg aagaagctag gtctcgtgga  149520
ttgctgagct gctagggagt ctgggaaatg tagctgtaag atagtcaagc tagaagggag  149580
caggagtggg tactaagtga accacctaat agtgtctgcc agttttcagt acagctgagc  149640
ggttttgatg aatttatcta ggccgtgggg taccattgaa aagtgttcaa ggcagggagt  149700
agtgtgacca catttacata ttgatcactg gggctatcat gtacaacatg gatttaggag  149760
gggccaattg ggggctattg caatagcagg tagatcacaa atgatgaggg ttgacaagga  149820
```

```
agcggcgaca aagtgaaaac tacgtggagg tagaatttag caggaattgg tggttgattt   149880
atatatgaga gagtagaggg tgatatatcc atgtagatgt atccagcata cagttggtca   149940
tatctagagc tgtggacttg gaagtaataa aggagtgggc caagaacaga gcccttgggc   150000
ccacagcccc tgccaggcac attgaacagg tgctcatggg tgagatggaa ggagaccaag   150060
agaagagagc atctgagaag gcaaagataa agcatggctc aggaagtgtt tggcagtgaa   150120
gagggttatg tgcagattag agatcagtgg gaaagaggaa cagattttct ttggacttag   150180
tgtgtagggc agcatccttt gctgaagcaa attcagaggc cgtttgttgc atccttttg    150240 tgggctgcta gttaacactt atcaaaccct tttttttccc taacattgag gtataatata   150300
tataacataa aattcaccca ttttaagtga gaattcagtg attttttggt aagtttacca    150360
agttatgcag ccatcaccat aaatgtctta gaacattttc taacaacttt attgagatgt   150420
aattcaaata ccatgtattt cacccagagt ttacaattca gtgtttttt aagtatattc     150480 acatataact gcagcccatc accaattta gaacattgtc atcccctcaa aagaagaacc    150540
ttacactcta gctgttgccc ccttagtttt agaacacatt gctcacccca aaaagaacct   150600
cagtgtctaa atacaattaa tctccattct caccccccgg ccatcactta acttttgcg    150660 tagagaactg agaccacaca catggatctt gaagggaact aggcaccatg gagtagtggt   150720
gaaaggccta ggaaagtggg gtctgtagtt tgggaaacac ataggtcagc taacctaaca   150780
ctgttcacag gaggagatga aacagaggca gtggcacagt tggcaggtgg gcttccagcc   150840
tagagcctta ggagaaacca gtttccttac tcatttttag atgtctaaga atatatagga   150900
tttttttttt ttttgagac ggaatttcac tcttgttgcc caggctggag tgcaatggcg     150960
cgatctcact acaacctctg catccggggt tcaagcaatt ctcctgcctc agcctcccaa   151020
gtagctgaga ttacaggcat gcaccaccac acctgctaat tttgtatttt tagtagagat   151080
ggggtttctc catgttggtc atgctggcct caaactccct acctcaggtg atctgcccac   151140
ctcggcctcc caaagtgttg ggattagagg catgagccac cgcgcccagc ctagaatata   151200
taggatcttt agacgtgttt cttttagag gtaggaatgt agctaccacc tagagcccac    151260
tgagattcag ctttcagaat ctagagacat ctcaggagcc agggagccac atttcatctt   151320
tcccttgaac agaacacaag atcagtggct ttgcttcatt ctcattactc tgtattagtt   151380
aagcagtgcc gccacatcac tgtacaagca tgttttcagg aaggcatatg acgcactcct   151440
ggtaagatgg ggcaggaagc actttggggc tgggccttcc aaccaggtgt tcaggctgtt   151500
cagggcccgc atgctgcaat gagaatttag cagtgactcc tcatggagca ggaatatgat   151560
gcgcttaacg tattcttaag gacttctcag ttttaattat aagtttagta atataagcag   151620
aatttaacat ccagaattaa ggctatttcc atttccattc tctaataaat aaaaacattt   151680
gttgaaactt aaattgctct tctcaatgaa aactttaaca agtcttttgt tgctgactaa   151740
acatatccat ctctgaggcc taaagctttc tccttctgtg ttgggcagca accctgccct   151800
gcccttgttt gaactgaaat tgaaagtggc tcctcagacc aggcacggtg gctcacacct   151860
gtaatcccag tactttggga ggccaaggtg ggcggatcat ctgagttcag gaattcgaga   151920
gcagcgtggc caacatggtg aaaccccatc tctaattttt gtaaaaatac aaaaattagc   151980
cggccgtgat ggctcatgct tgtgatccca gctccttggg aagctgaggc aggagaatca   152040
cttgaacccg ggagcagaag gttgccgtga gccaagatcg caccactgca ctccagcctg   152100
ggtgacagag caagactccg tctcaaaaaa aaaagaaag tggctcctca gatttaggcc     152160
acttcttata tttggccact gccttgcagc cttgtagttc acattgccac cctggtgttg   152220
```

```
gtgtgacatg gtgtcccatc cctgaagctg cctcccttgt tactcacctt attgctgtct 152280
gagaaaggaa atgggtgatt cacaatcctt aaatcaagtg gctttctctt acctagaact 152340
tctgaattga acatacattt aaacaatgac gttgaaaaga tgtataactg gagcaataaa 152400
gactgaaaaa gaaagctgcg gccagttgtt agttttccg aggctcctta tctgttgagt 152460
ggcaccccag gctcccttgc tcttgtcccc cactgcctgt gatagagaag cctcttgtta 152520
aacactggga gctacttcac cacactcaca ggctattccc agaaagattt tgcacctggg 152580
taaagcatcc ttgagaaaat aacctgtttt cttcccaga gtgaacccag cttcatccct 152640
ggaaccacca catatgcttt tcccctggtg ggttcttaac ctgttaacac tgaaatctac 152700
attgttagct gctgataaag catcagaaac atggtctaat ctgggagtca gtatttggat 152760
ttcttttttc tttctttctt tttctttttt tttttttttt ggagatggag tcttgctctg 152820
tcaccaaggc tggagtgcag tggcgcaatc ttggcttggc tcagtgcaac ctccacctcc 152880
caggttcaag caattctctt gccttagcca ccctagtagc tggaattaca ggagtgcacc 152940
accacgcccg gctaattttt gtattttagt agagatgggg tttcaccatg ttggccccat 153000
gctctcacac tcttgacctt agatgatccg cccaccttgg cctctcaaag ttctgggatt 153060
acaggtgtga gctaccacgc ctggcctgga tttcttattc tagtatttat taataattca 153120
atttgagaag actacctaga ctatttgagt tttgtaatct ctaattccta gctctaaagc 153180
taatcccttg tgaatatcta gactggaaat ccccgttaag tacctgcaca ttttcaggtt 153240
ttgttaactg gttggagtca gactggagaa tttcatttct attcattttt ggttttctct 153300
ttctttttct ttccttcccc acccccagg gctaccaaga aagaacaaa ttcattgctg 153360 cacaaggtaa agtaatgaca acttttttct gttagattta accatgatca cataatgggt 153420 ttggttttt tctcccaaat gctgagtgga ttaaccagaa tgctgtagct tttctgtact 153480
ttttaccacc tgaaagaatt ataatccatt atacaggttt acagctaaca gccttcatct 153540
tgatgactta gtatccaggg atccattaaa agaagtcttt tgtgtatgt atattaaaaa 153600 gactggaaaa ggctgtatac acaaaacaca gtctaataag gccctctgtc cttggggcta 153660 gttaaccta ggttccagcc aggctgctca gagtttgaat taggaatcag tttccagaga 153720
ggatcagcca cctcacaggg tccaggctgg ttctcccca gctcatgggc ctgagcctca 153780
ccattattca cagatagttg gtctaggaac cctcagatca gggacccagc accatgtcct 153840
ttatgtgttc tacacacatt tccaggcctg ctgttctaac aactgtcttc actctttgaa 153900
ccctagcaaa aatatctgga tgtttgcagc attaaaaagt aattgaggcc gggcagggtg 153960
gctcatgcct gtaatcctaa cactttggga ggccaagaca ggaggatcgt ttgagcccag 154020
gagttcaaga tcagcctggg caacatagtg aaaccccgtc tctactaaaa attagccagg 154080
cgtggtggca cacacctgtg atcccagcta cttgggaggc tgaggcacaa gaatcacatg 154140
aacccgggag ccagaggttg cagtgagctg agattgcact actgtactcc agcctgggtg 154200
acagagtgag actttgtctc aagaaaaaga gtcattaggg actacaagat ttataaaaac 154260
aaagttctcc tccctttctct tttcacttttt ttagtctaat gccctgggg caaccatttt 154320 tatctattgg cttcttatga tagatgacat catctgatcc ccttacagag cacctccccc 154380
tcagtcagac agacgtgtac ccacatatcc tccccattct cccagaagag tcaaatcaca 154440
atttggggtt aaggtattta ttattattat gagtttacaa atattcacag ccgaaacaca 154500
cagtattatg ttatttttg tatagttttt ttccccttc ttttttagtc attgtgtttt 154560
ttatatacct actactgatt ttcctcccaa actctttacc agaagtatat atcttctctc 154620
```

```
agtaccttta gatacatgag gtttaattt tttatcttgg gatccttcta gaatcttctt   154680
tcttcagttg cattgtggat tggttgctct ctatcctctg gcagagttat cattctaaga   154740
ccagtaccct gggaattccg ttagcctctc tgctgtgttg gatctcattt attttcctct   154800
gtttgcctct cattttgtt tagaatttc tagtgactt ccgaaaaagg ttatatggga   154860
ggtaaatttt gaattctagc ctgaacaagt catccaacct ttctggggct gatgacaccc   154920
acctcagagc ataataggaa ggagtaaatg ccatatgaag cacttagctc actgtcaggt   154980
ccataatgta ggtattctgt gagcagtcat gatttctaat tcccaactgt aatatccttg   155040
ggagacatca ttcgtgttct gtttatattt ttgacagcct tccacccagc cccatccttg   155100
tgcagtgcct ggcacataca tggtagaaac atggaaaata ctcaattagt aacggggtgg   155160
atggatacat gggttagata tttagctggg gacatttggg cacaagcttc caaaagtcag   155220
gaatggatgt tcccagcctc ccagcatctt tcttcttggt gtatattctc ttcattttg   155280 ctgttggcta ctttaggacc aaaagaagaa acggtgaatg atttctggcg gatgatctgg   155340
gaacaaaaca cagccaccat cgtcatggtt accaacctga aggagagaaa ggaggtaagt   155400
ggaaaaattg gatgtgaaca gcagaaggat cactctgcat ataagctctg agtttaagcc   155460
tggctgtcta tcctttgtgg gtgctgtacc agtagttcat ccagaaagac acaggctgaa   155520
gtctatcaga ctttgctatg gcctggaagc cccagatatg aacctcaggt gtgtgcctag   155580
agcacattcc ctgtatttgg tagtcaaaca actcaccctg gttccagaac agcctgaaag   155640
agactgactt gggccatcag ctaaggaaaa gccacagagg ggttttttt gttgttgttt   155700 tgttttgttt tgttttgttt ttttattgat cattcttggg tgtttctcat agaggggat   155760 ttggcagggt cacaggacaa tagtggaggg aaggtcagca gataaacaag tgaacaaagg   155820
tctctggttt tcctaggcag aggaccctgc ggccttctgc agtgtttgtg tccctgggta   155880
cttgagatta gggagtggtg atgactctta acgagcctgc tgccttcaag catctgttta   155940
acaaagcaca tcttgcaccg cccttaatcc attcaaccct gagtggatac agcacatgtt   156000
tcagagagca cagggttggg ggtaaggtca cagatctaca ggatcccaag gcagaagatt   156060
ttttcttagt atagaacaaa atgaaaagtc tcccatgtct acttctttcc acacagacac   156120
ggcaaccatc cgatttctca atcttttccc cacctttccc ccctttctat tccacaaaac   156180
cgccattgtc atcatggccc gttctcaatg agctgctggg cacacctccc agacggggtg   156240
gtggccgggc agaggggctc ctcacttccc agtaggggcg gccgggcaga ggcgcccctc   156300
acctcccgga cagggcggct ggccgggcgg ggggctgatc cccccacctc cctcccggac   156360
ggggtggctg gccgggcaga ggggctcctc acttcccagt aggggcggcc gggcagaggc   156420
gcccctcacc tcccggacgg ggcggctggc cgggcagggg gctgatcccc caacctccct   156480
cccgacaggg gcagctggcc gggcggggg gctgaccccc ccacctcccg gacggggcgg   156540
ctggccgggc agagggctc ctcacttccc agtaggggcg gccgggcaga ggcgcccctc   156600
acctcctgga cggggcggct ggccgggcgg ggggctgatc cccaacctc cctcccggac   156660 ggggcggccg gccgggcgtg gggctgaccc ccccacctcc ctcccggacg gggcggctgg   156720
ccgggcgggg ggctgacccc cccacctccc tcccggacga ggtggctgcc gggcagagac   156780
gctcctcact tcccagacgg ggtggctgct gggcggaggg gctcctcact tctcagaccg   156840
ggcggctgct gggcggaggg gctcctcact tctcagacgg ggcggttgcc aggcagaggg   156900
tctcctcact tctcagacgg ggcggccagg cagagatgct cctcacatcc cggacggggc   156960
ggcagggcag aggtgctccc cacatctcag acgatgggcg gccgggcaga gacgctcctc   157020
```

```
acttcctaga tgggatggcg gccgggcaga gactctcctc actttccaga ctgggcagcc   157080
aggcagaggg gctcctcaca tcccagacga tgggcggccg ggcagagacg ctcctcactt   157140
cccagacggg gtggcggctg ggcagaggct gcaatctcgg cgctttggga ggccaaagca   157200
ggctgctggg aggtggaggt tgtagcgagc caagatcacg ccactgcact ccagcctggg   157260
caccattgag cactgagtga acagactcc gtctgcaatc ccggcacctc ggaggccga    157320 ggctggcaga tcacttgcgg ttaggagctg gagaccagcc cggccaacac agcgaaaccc   157380
cgtctccacc aaaaaaatac gaaaaccagt caggcgtggc ggcgcgcgcc tgcaatcgca   157440
ggcactcggc aggctgaggc aggagaatca ggcagggagg ttgcagtgag ccgagatggc   157500
agcagtaccg tccagcttcg gctcggcatc ggagggagac cgtggaaaga gagggagagg   157560
gagaccgtgg ggagagggag agggagagct gttttgtttt gtttttttgag acggagtctc   157620 gctctgtcgc ccaggctgaa gggcagtggt gccatctcgg ctcactgcaa gctccgcctc   157680
ccgggttcac accattcttc tgcctcagcc tcccgagtac caccgccac cacgcccagc   157740 taatttttg tgttttttt agtagagacg gggtttcact gtgttaggca ggatggtctc   157800
gatctcctga cctcgtgatc cacccacctc ggcctcccaa agtgctggga ttataggcgt   157860
gagccaccac gcccggccca cagaggagct ttttccct ggtttctcta gttccttatt   157920
tccctggttt tctgccccac ctgctgaggc ctttggtata tcctggatca gcagaggag    157980 ctttatgaac tgagaccctg caagccaaag ggaatttgag gccttggcct aatcctggag   158040
gcagcctcct aactgggcct tttccttttg tggctaccaa gtgcatgcct ggcctaacca   158100
gctctatcac tgggccacag ccagagccaa ttctgggtcc tggggtcgag ccccagcgag   158160
gaatacctat ttgttaccgt gtttctcaag gatggccctt gagtcacctt gatcctaggg   158220
tatcgggtgt catgatcaac agctccacag tggcatggga agacagtgct agggctgggc   158280
tttaggttag tttcctccaa ccaaacctct tgctcttgga agctatccaa agctcaggca   158340
acagaaaaag ctctaggcct ctcatggcag gtttacagtc tgcatcagtc taccctggtg   158400
gccccctcat agcagactgc tggttcgagg ggttcaaaca ggctttctcc tagagcatga   158460
cctgaaatgt tgtgaaagtg cagattttgt aggtaagatg gcttcagatt cgccctgaac   158520
caagggagtg tgggtgggaa acattgagaa gtatggggct agggctgtgt gtaagttagg   158580
agactgtgct caataggatg gcggctaagg aacttgagaa aagggcaaat ttgaataagt   158640
aagtgtgcaa ctgactgaga tagagaagag gtcaaaggc cttctggggg acttaatct     158700 gggctttgtg ggctcttcct tccaggccct ttgcatctgc catgggcagg aggtctaagg   158760
tcagggaatg tatgtctttt tctttccagt gcaagtgcgc ccagtactgg ccagaccaag   158820
gctgctggac ctatgggaat attcgggtgt ctgtagagga tgtgactgtc ctggtggact   158880
acacagtacg gaagttctgc atccagcagg tagtgtctcc tctgtccttt ctcagttctt   158940
atgttggatc tgctgaccag taagagggaa caggctggat catcccgctg tggtcaggag   159000
ttgctgagta tgcagtatgt gaattctgaa accagatatc cggctcagg ggaacttgtc    159060 tgtcaaagct aaaggagcag tattttcatg actggtgaaa aattacctgt tgagatgaag   159120
tctgatcatt tagatatgac caagcactgt ggaaagggag catggggagg cagtgcagtc   159180
tcctaggtgc ttgactcacc tttctcctcc tttcctactc caaagactcc tgacatcaag   159240
gatgtgatgg gcctgcccct ggccctccag gcaaccctgg agacctgagc aaaggtcacc   159300
ttcagccaag gggcagtgtg gtactgcgaa aagaggactt agctgggagc actgcatttt   159360
agttctgacc ctgccactga ctagttgtga gaccttgtgt ctgtggttaa ctaactcccc   159420
```

```
tgggtacact tacttttcca ttgtcactga caaccacagc tgtcaccttc cctccctgg    159480 tactgcccac ccttgggtat cagggccaac acacaggatc tcctcacttc acaggtgggc   159540
gacatgacca acagaaagcc acagcgcctc atcactcagt tccactttac cagctggcca   159600
gactttgggg tgccttttac cccgatcggc atgctcaagt tcctcaagaa ggtgaaggcc   159660
tgtaaccctc agtatgcagg ggccatcgtg gtccactgca ggtcagtgtg gcctgaccct   159720
tgtaccccca cccccacatt tcgccccat ggccagagca ggggaacagc acaagggccc    159780
tggctgagga ggctggcaca gagtagatga cctactgggg caccagcgca acagccagag   159840
actccaagtt ctagtgcagg gtggagaata tgacttgagg aaggagggta gggcagtcct   159900
ccaagattag gagttgggag accctgctat gaagccaaaa gactgggtca agtgctggcc   159960
atgtattttt gcagccttcg gacccttcta gctggaggtc aggattcagg acatactgga   160020
gttgttggct cctggagagc cccagctcta ccccattcag aattaggatt tagaccctga   160080
aggaagagcc cctgcctgtg ttgccccctcc ctatctgctc ccacaaggca ggctggccat   160140
ccctataacc ccctgctctc tggctacagt gcaggtgtag ggcgtacagg tacctttgtc   160200
gtcattgatg ccatgctgga catgatgcat acagaacgga aggtggacgt gtatggcttt   160260
gtgagccgga tccgggcaca gcgctgccag atggtgcaaa ccgatgtgag tgatctgtgg   160320
gtcaggtgag ggtgggggggt tccaggacta aaacatctgc ccacattgag gattcactca   160380
gtctcacagg ttattgtaaa tgattactat agagtgtgat tgtgggggaa agaaagatag   160440
atcacactgt taccgtgtct atgtagaaaa aggaagacac gagaaactcc attttgttct   160500
gtactaagaa aaattcttct gccttgagat gctgttaatc tgtaacccta gccccaaccc   160560
tgtgctcgca gaaacatgtg ctgtattgac tcaaggttta atggatttag ggctgtgcag   160620
gatgtgcttt gttaaaaatg tgtttgcagg cagtatgctt ggtaaaagtc atcgccgttc   160680
tccagtctca agcacccagg gacacaatgc actgcggaag gccgcaggga cctctgccca   160740
agaaagcctg ggtgttgtcc aaagtttctc cccactgaga tagcctgaga tatgccctcg   160800
tgggaaggga agggtctgtg ctgaggagga ttagtgaaag aggaaggctt ctttggagtt   160860
aagataagag gaaggcatct gtctcctgct cgtccctggg aatggaatgt cttggtgtaa   160920
aacccgatcg tacattctat ttactgagat aggagaaaac cgccttatgg ctggaggtga   160980
gatatgctgg cggcaatact gctctttact gcactgagat gtttgtgtaa agtcagacat   161040
aaatctggcc tacgtgcaca tcaaggcaca gcacctttcc ttaaacttat ttatgacaca   161100
gagtcctttg ctcacatgtt tttctgctga ccctctgccc accattaccc tatagtcctg   161160
ccacatcccc ttagccgaga tagtagagat agtgatcaat aaatactgag ggaactcaga   161220
gacgagtgct ggcgcatgtc ctccgtatgc tgagcaccgg tccctggcc cactgttctt    161280 tctctatact ttgtctctgt gtcttctttc tttcctcagt ctctcgtccc acctgacgag   161340
aaacatccac aggtgtggag gggctagccc ctttcatgtg atgaagggct cttataaatt   161400
atgtattcaa agaaatcgag cacagaggag gttgtggttt catgcctggg agagtcagga   161460
aggcagatga caggttactg gacttcaaag attagggaac aggcagctga aagagccagt   161520
gcccagagac atgatgaagc tcggccacat ctgggagcag cagtgagatt ggctctgcag   161580
ttggggcata gcaccaggag ggaggcaggg accagactat cacgggcttt gggtgtctcc   161640
agtttctgac agccccttca gactattaaa tctgcactct cagaatgaac aggaattgag   161700
tttgtccttc tctccaggcg tccaccaccc ccaagataga cctggaccct tcttcccaag   161760
taaagcaccc ccacagggac tcctgcattt caagtcccac ttcactaaat tgggataata   161820
```

```
agagggagtc cttttattcc tgctaggatc aaaggagaaa tggactggag tgaagtgggg   161880
gtgggaacag gtgatctggc atgagaacta tgttgtatgt aaccaagaac ttctgtgtca   161940
ttcatgtttc agatgcagta tgtcttcata taccaagccc ttctggagca ttatctctat   162000
ggagatacag aactggaagt gacctctcta gaaacccacc tgcagaaaat ttacaacaaa   162060
atcccaggga ccagcaacaa tggattagag gaggagttta aggtgagttg gagctggata   162120
acctccttca gattgaagga tccttgtaat ctggggaaca tgggatgcct gactgtgcat   162180
ttgccaacag taaatcccct tgtgaggcat gccagtggtt aaggagatgg tcctttcctc   162240
gtactctggt aactctcaac tcatcctgca cgttggaatc actttggttg tgttagagta   162300
gggagaagca ggcaacagta ttttaaggcc cctagccctc cgaggtgatt atgatacaca   162360
gcaagagcag ttttttctgt aagagccaga taataaatat tttaggcttt gcagcccaca   162420
tggtttctat ccagctactt agtgctgtct ttgtaacaca aaggcagcca taaccaatag   162480
gtaaatataa tgagtgtggc tgtttttataa aactttattt gcaggcagca ggcagcaggc   162540
cagatttggc ctctggacct tagatcactg atagctccta tatgccacta gacaatggtt   162600
ctcaacacac ctaaggcata tgtcacactg tcatcagtaa aagtgctctc ccaggctggg   162660
cacagtggct cacgcctgta atcacagcac tttgggaggc tgagacaggt ggatcatgag   162720
gtcaggagtt ccagaccagc ctggccaata tggtgaaacc ccgtctctac taaaaataca   162780
aaaagtagcc aggcatgatg gcacatgcct gtagtcccag ctactcagga ggctgaggcg   162840
agagaattgc ttgaacccgg aaggcagagg ttgcagtgag ccgaaatcat gccactgcac   162900
tccagcctgg gcgacagagc gagactccat ctcaaaaaaa aaaaaaaaaa aagtgctttc   162960
tcagaagcag gagattctgg gttggggtgg ggaggaccac ttagagaagt tcttctcaaa   163020
tatagcatgt gcacagattt cttgggatc ctgtcaagat gtgggttctg ccaggcacgg   163080
tggctaatgc ctgtaatccc agcactttgg gaggccaagt caggcagatc acctgagctc   163140
aggagttcaa gaccagcctg accaacacgg agaaactctg tctctattaa aaatacaaaa   163200
ttagccaggc atggtggcac atgcctgtaa tcccagctac ttgggaggct gaggcaggag   163260
aatcacttga acccaggagg cagagattgc agtgagctga gattgtgcca ctgcactcca   163320
gcctgggtga cagagcaaga ctctgtctca aaaaaaaaaa aaaaaagat attaggttct   163380 gattcagcag gtatgagtta gagcttgaga ttctgcattt cttttttct tttctttttt   163440 tttgagatgg agtttcactc ttgtcacccg ggctggggtg caatggcgcg atctcagctc   163500
actgcaacct ctgcctcccg ggttcaaggg attcttctgt ctcagcctcc taagtagctg   163560
ggtctacagg cacgtgccac tacccccggc taattttag tagagacagg gtttcaccat   163620
gttggccatg cgggtctcaa actcctaacc tcagttgatt gcccaccttg gcctcccaaa   163680
gtgctgggat tacaggcatg agccaccacg cccggcttga gattctgcat ttctaataag   163740
gtgaagccaa cgctgctggt gtatgggcta cactttgagt agcaaatgtc aagaaggagc   163800
ctcaatcggg aagggaggat gcaattctga ataagttttt ttgaagagcc ttaggcagcc   163860
tctgggggtg gaactgcaga gtggacacac tccctcctac gatgctggaa tcccttgctc   163920
caggatcaca aaattccaag ccaggagaat ctcaagagag tccacaggag cctggaaggt   163980
agcatttccc aaacagtctc ttggcttcag ggttccagct gaacatatgg gaacagaggt   164040
cagggccctg gtgagaagag cagtatggag ccagagtggc ctggaggtgc aggccaaggg   164100
acaggcataa tcttgtcaag ttcagttact gggatcagta atgtttcccc tccccttccc   164160
aattcagaag ttaacatcaa tcaaaatcca gaatgacaag atgcggactg gaaaccttcc   164220
```

```
agccaacatg aagaagaacc gtgttttaca gatcattcca tgtaagagcc ctcccgccac 164280
tccaaagcct tattgcccca tccctcaatt ccctccaccc cttccatttc tcaggtacta 164340
gttaatgatt ggcgtataga caagaatcat ggcattgcct cttgttgcac ccacttaaca 164400
acatggcgtt gccttttgtt gcaccttagt ggcttctgga aataacgtaa aagccaaagg 164460
ctttctccct aatgagctag aacagacat gtccttgccc agctgggatt ctgtctgccc 164520
agggcctgag gtgggagcaa tgcaaggaga gggagaggac aaatgatatt ggctagccat 164580
aagccgctat tcttcttaca gatgaattca acagagtgat cattccagtt aagcggggcg 164640
aagagaatac agactatgtg aacgcatcct ttattgatgt aagtggtggg tgtgacccct 164700
gagcccccaa cacccgtgg agattcagcc agcacttgca gtgcctccct cccatacctg 164760
ctggggagga tcatgtttga atcagtcaac aaatagtgaa ttgatactca cccacccact 164820
caccctgtgc attaggtctg tccagctcca tagagcagaa ggtgggggaa aacagatggc 164880
atgcagtagt ataatacctg gaagaaaaag ttcacagagc agaccacagc caagaggaac 164940
ctggctgccc cctgatcttt cccattcctg ccctcttcat cctagctcta atccctgttc 165000
cacttccctg tctcttacag aaagcaacca gcttgtcaga tagggtttcg tccttggcca 165060
caggggagct ctgcatgggc tgagtttgcc tccgagcagt ccccattccc ttctagtggt 165120
ctgtcttctc cactagtccc tctgtgatta aaccatctca cccttgcaat taacctggcc 165180
tgtgcagggc taccggcaga aggactccta tatcgccagc cagggccctc ttctccacac 165240
aattgaggac ttctggcgaa tgatctggga gtggaaatcc tgctctatcg tgatgctaac 165300
agaactggag gagagaggcc aggtgagttc aaaaggtcct gggtggtgag agacagagac 165360
agcatgaaaa gatgtgtgtg taaatgggga cgttgggaag gcaagaaggt gtttggacct 165420
tgtctttgac ttatacggtc caaagagtac gtttgcatag tataagtaca tacttaaagg 165480
tatataaata catatgcatt tccaggattg cccagcccgt tggtgtctaa gcagtcatta 165540
gcttctccca agactagaaa agcaatgtga tctgagcctc catgttattc ccagacagct 165600
cacacccttg cactttctcc tgaatacagt cccctagcc tagcctttgc acagtgcccc 165660
aggcgggggg ggcaccctct ccttcccagt gccccaggca gggcagatag gtcaaggttc 165720
tgaggtggac ccaatatgag tgtccctaag aagggattgc ctcattgctg actacataaa 165780
ataaagcagt agaatttgag aaattataca aacaagaaac ttacagtcta atattcagta 165840
ataaggaaat cttttaaaga aaaaagccct caggtctatt aaaaagcaga gctgtccgga 165900
aactcatact aaaaagggac actagcagtc ccctaggtca acttcctctc agtataggaa 165960
acctcctaat attgttcctg agtcagaatc atacagcctc tactaagcac attcaatctc 166020
agggatatct ccctcacccc ccacattatg gggggaccca gtctgtgttc tgacaatgct 166080 tattcttttta aaaattattt ctgttgaggt tgcacattgc agcaaatgag cggttcacta 166140
tgtctggggt gtcacttagc agggatgaga atctagagaa tgggcctgga gagaagctag 166200
caaggcctgg tgagaaaatt ccttctaagc cacagtgaag agtttggtct tcctaaagca 166260
attgaagagc ccttgacaac atcccatttg tgttttttaa aaaatccctc tggcagcagt 166320
gagaaggact cattagaaat gcgaaagctg tggcagtaat gctggtggcc tggactcggg 166380
tggtgagagg gtgctgtccc agaaagggtg aagtgaggag gaattaagga tggcacccac 166440
tcatgactca ttgaatttat agtcaaacat ttaaaataca agtatgttt tacattagtt 166500 gtctcaagtc actagttgtt ccccatctgt acttgtgtta actttggtac aaggctttac 166560
acatattttc tcaccctgat gtttcattac atcaggattt tttttttttt tttggttttg 166620
```

```
tttgtttgtt tgtttgtttg agagagggtc tcactttgtc acccaggctg gagtgcagtg   166680
gcacgatctt ggctcactgc agcctcaacc tcccaggttc aagtgatcct cccacatagc   166740
cctccaagta gctaggacta aaggcacgtg ccaccatgcc cagctagttt ttgtatttt    166800 ttgtagagac agggtttcac catgttgccc aggctggtct tgaactcctg ggctcaattg   166860
atccacccac ctggttgacc caaagtgcta ggattacagg tttgaaccac cttgcccggc   166920
atttttttca attttgatca gtcatttaac tcattagcta ttcttcctag acttgtatca   166980
tgtacctaat caacagacat actttgtagg tcttcatcat cttttttttt tttttttttg   167040
agacggagtc tctgtcaccc aggctggagt gcagtggcac aatatgggct cattgcaacc   167100
tctgcctccc aggttctggc aattctcctg ccacagcctc cctagtaact gggattaaag   167160
acacccacca tcatgcctgg ctaattttg taggcacggg gtttcaccat gttggccagg   167220
cttgtctcaa actcctgacc tcaggttatc tgcctgactc agcctcccaa agtgctggga   167280
ttacaggcgt gagccactgc gcccagtgtc ttcatcatca ttaataacaa tactgatgag   167340
gtgggaggtt cggttaaggt gcttggcttt gcactcaagg aagcacacac ctgagtaaca   167400
aaagctgttt aggaaatgag ccactgtgtt ctcaggagct aggtgcctgt tcctgccgtc   167460
tctgatcagt cgtgatggaa cctgcagatc agaccagggc cctacctgtg gttccttctg   167520 caccctgcc cttcagatct gtgatgggca ggaccaaaga gcaggccgaa gagctggaac   167580
cacgagcaca aggaccatct cggcccactg ccctgtgata aaatgtggcc cagtgaacat   167640
ctccgcctct gtccagtcag atgcaggctc ttccatcctt gaaaaggacc tagtgagagt   167700
aaagggcagg gggcaggaag catttcatgt gtgtggcggt ggggagaaga gtcgtgcgca   167760
cacaaattct gctgcctgtt gagtgaggcc tctccctctg ccttccactg tagcttatgc   167820
tctgtcttcc taggccagtg aagcagacag tagtgcttgc cctcaaaagc ttctgagtgg   167880
attggaacag gatgttagtg atgttctta caaggcctca ctggccccca agttcacttt    167940
ctgttccatt catgttgtca agtgtagctc ccagaagtaa ttaacgcact aagcctaaat   168000
gatgcaatga aaggtgccta cacttataca gtgacactac catcctcacc tacaatatta   168060
agttcccaga gaaaaaaatt cgatcccata atataaattc tgtacttaca aattaaaatc   168120
tcgaaggaat taaaaatttt taattatctc cctctgcttt tttttttttt tttttttttt   168180
ttttgagatg gagtctcact ctgtccacca gactggagtg cagtggcaca atctcagctc   168240
gctgcaacct ccacctccag ggttcaagtg attctcccac ctcagcctcc cgagtagctg   168300
ggattacagg catgcactac catgcccagc taatttccat agtagagaca gggtttcgtc   168360
atgttggcca tgctggtctc aaactcctga ccccaagtga tccgcccgcc ttagcctccc   168420
agagtgctaa gattacaggc atgagccatt gcgcctggcc tccttctgct ctatttaat    168480 caaaagggtc caccaggatg cctgggttcc ctcagcagct gcagcttgga ccatcatcag   168540
cctgggcaga cagagcagtg ccaggaactc ccatgctggg tcaaccctag gcctagccca   168600
accctaggcc tcatcctgct tctctaaagc atagtgaaac ctgatagcat tagtcttcac   168660
aaagctgtgt gtccccatca ccatgtccgc cttagacctc ataagagaca taagacataa   168720
gagacttcat gctatctggt ggaaagacaa agtaggagaa aagacagaaa accttccctg   168780
tttcacttct ttaagatgct attatctaga ggccgtaacg tgaacacaca aatctgagat   168840
gaaactccag tccccagctt ttcttctact ggtcttgaat ccccattccc catcttctgt   168900
ccctcaccca ctgatgactt taacacctgg cttactgctc cttttgagcc cctgttcctg   168960
actctgcttt tggaggcatc agtcaccatg tggatgatcc atctatcctc aatctttcta   169020
```

```
ttcctcagct tcctcagcca cctgatccca tggtcaagtc accatctgcc ctgtatctgc   169080
actgcccttg gaatctcaac aaggcatccg ccctgtttac tgcctccttc ctcccacctc   169140
agtattctct tttattccag tcattttgt  cttcatcaag tccttagagt tattgatgcc    169200
tccactttct caacatcagt cacaccgaac atgtcctcac cttcctcctt actctgtgtg   169260
tttttgagtt ctgtttttga gcgtttgagt tttctgattt gagttttgt  ggtatgtcat    169320 tattacctt  ccttattccc tcatgctttc ttactttcat agcaaactct ctagtaaaac    169380
ccagttatat gcctctatct gatatagcaa acatcactgg gcaaaaacac aaaacagtgc   169440
caaatgctct cacactgaac tcatgaccac aaatctcata gaggtaattg gtgccaccta   169500
gcaatgctat tgctctttct tttcttcctg aaacctccag catctgctct tgcctgtccc   169560
atcatactca caccttagct tgtgacctgg cctcattctt ctccaagaaa tcagacaaga   169620
acactgtcat cctcccaccc ccaaacaacc agcctcttca aatctgtacc aactctattc   169680
tctcttgtta cagtggaaaa gggtttctgc atctctcaat ccacctgtcc actgtgctct   169740
tggccccatt ccgtcctgcc tgctcaggga tgttgctgct ataaccatct tctctcccac   169800
ctccatcagc agttcccctc tttaaccact actctcatca gcctatacat gttacatttc   169860
ctatctttta aaacaaaaa  atctgctaat ctcactttcc cttccaccta ctatcctatt    169920
tctctgcacc ccttcccagc aaaactcctt taaagagttg gctttcggcc gggcgcggtg   169980
gctcacgcct gtaatcccag cactttggga ggccaaggtg gcggatcac  aaagtcagga    170040 gatcgagacc agcctggcca acatggcaaa accccatctc tactaaaaat acaaaaatta   170100
gctgggcgcg atggtgcatg cctgtgatcc cagctactcg ggaggctgag gcaggagaat   170160
cgtttgaacc agggagctga aggttgcaat gagccaagat cgcgccactg cattccagcc   170220
tggtggcaga gtgagactcc atctcaaaaa aaaaaaaaa  agagttggct ttctccctgc    170280
aagttctctg ttcgctctgt tccttccagg cttggcccca ctgggactgc tttagtcaag   170340
atcaccagtg actgtcctct tgccaaatcc aaaggtcatt tctcttttct gattttttt     170400 tttttgtcct tacagcagca tttgaaagag tcagtacctc cctcctcttc ctcagaacac   170460
ttacttccgt agcatcaccc cactcactaa cctggcagct cctttgttat ttctttgtga   170520
cctcctcctc taaaacattg gagtatacta gactcgggcg ctagcccact ctgttttctt   170580
ttgacacact agcccttcag gatctcagcc agtcctatgg ctttaagtac aacccatatg   170640
ccagggatcc tcaatctgcg tctctaggcc agtcacctgt ccccctccc  aatgtgggct    170700 cctgatttcc tccttccccc gacaccagtc caccccactc ttagccatct aaataaatag   170760
taccaccttc tgcccagttg ctcatgtcta aaatccggga gttaccttcc ttcctcccct   170820
ctcctcaccc ctcacatcca gtctgccact gagtcctgat acaggcagag cctccccact   170880
tttctccagc gtaactgctg tcatctgaac aagccctcgt ctctcactgc ttgcccgtgg   170940
gactgtgggc atgactcata tgcgcagcct cgtctgcagt ggcctggcaa ctggtcctcc   171000
tgctctcatc ctaacccact tttagttttt caaatggcag ctgctggtcc ttttgaaaat   171060
ataaatcatt gtcactcctt gtcttacaaa tcctgtttga ggcaggtgc  ggcagctcac    171120 gcctgtaatc ccagcacttt ggaggccga  ggcgggtgga tcacctgagg tcgggagttc    171180
gagaccagcc tgaccaacat ggagaaaccc cgtctctact aaaatacaa  aattagcggg    171240 catggtgatg catgcctgta atctcagcta ctggggaggc tgaggcagga gaatcacttg   171300
aacccgggag ccgaggttg  cagtgagcca agatcgcgcc attgcactcc agcgtgggca    171360
ataagagtga agctccatct caaaaaaaa  aaaaaaaaa  atcctctttg gtcttccaga    171420
```

-continued

```
gatcttgaga gaaaatccgc ccatgtatac aaaatttaga gacttttgat cagatgtggt  171480
ggctcacgcc tgtgtaatcc taccactttg ggaggctgag gcaggtggat cacctgaggt  171540
caagagtttg agaccagcct ggccgacatg gtgaaacct gtctctacta aaaatacaaa   171600
aattagctag gcatggtggc gcacacttgt agtcccagct acttgggagt ctggggtggg   171660
agaatcactt gaaactggga ggcggaggct gcagtaagtc aagatcatgc cactgcactc   171720
cagcctgggc gacagagcaa gactctctca aaaagaaaa aaaaaatgag actcttagtg    171780
ttgataccta gtccctagac ttgatatgta tttctgtctg agagatcatg ctcaattcct   171840
ccagcacaca cacactgtgg ctcacaccca tggggacctt atggttctga tggttttaaa   171900
ggcccagtct tcatcccagc tgagacactg tgtaaagcag tgttgagaag gcactgtggt   171960
agcaaaatcc attccaccca ccagtgccat aaaaactaat ataatgcctg atcgaggtga   172020
gccttaatga gaattttttt ttttttttgg ctgttctggt tgaagagagg cccagggcac    172080
cgatccctga ggcatcccca gggcttctag agaacatggg tggaaaagca ctagtccagg   172140
gcatgttctt gattcaacac tttaataatc atgattttat ttggactgtg agactattca   172200
caatttcttt ttctacttaa tttttttcca aatctttcaa tgacattata tgtatggttg   172260
agaattttc aattgccagt agtgaagaat ctcagatctt accccaaat tctctaaaga     172320
aatgggcagc ataactgtgt gatgttatat ttatgtattt atgccttggc ttgttctgca   172380
gacattgaac aaattcattt accagatact gagagcctac catgtgccag gcattgtgca   172440
aggtgtgggg aatacagaga tgaaaagaga cgcagccact cccacaagga gctgtagagg   172500
gaagtgagcc aggtgcaagc aaagacagac agtagaccac ctcctgctca ctagcaagga   172560
cagaaaggcg agtgctagca acttgaaggt accttgcaga tcaaagagat aaaggtaaaa   172620
gggagaaagg atactgtggc ctgggcggtg gtgaagccca tggctgtgtg ggaatgtgaa   172680
ttggttctga ttttctgaat tagcagtctg gcggatgtaa gcagcattaa atatgaaaac   172740
accccatggg agaaaagaa aggaattgga acaaagattt tcactcgtcc tcctctccct     172800
gcagccacca agtattggat accctgtgag cctgtagtca gagtcctta cagacccgg     172860
cagtgttta gatggtctct ggtgaggatc ggaggttaat tggaatgatg tgatataatg   172920
atcctgcaag ttttcaatac cttggggacg aagcgtatca gcgtaagagg tggctgtact   172980
gagaggggtc aggctgctcg tgggcagtgc tgcttctaca catgtggtac tctgagctcc   173040
tcacctctcc aacctgtctc tccaggagaa gtgtgcccag tactggccat ctgatggact   173100
ggtgtcctat ggagatatta cagtggaact gaagaaggag gaggaatgtg agagctacac   173160
cgtccgagac ctcctggtca ccaacaccag ggtaagatgg gtcgtgggtg gactctgccc   173220
acaggaaaag cagggttacc cctgcctccc tgatccccctt ttttccaaag gagaataaga  173280
gccggcagat ccggcagttc cacttccatg gctggcctga gtgggcatc cccagtgacg    173340
gaaagggcat gatcagcatc atcgccgccg tgcagaagca gcagcagcag tcagggaacc   173400
accccatcac cgtgcactgc aggtatggct cacccttgcc ctcagcggga gagagaaagc   173460
gaggaggggc agataggga agctgatgac catgggtcag actgaagaaa gccatacaag    173520
agcaagatat tggtgagcac atagtagttg agattgatgc caagacagga ttggatgcta   173580
agagagagga ccttggagct tgaacttggc acaataagtg ctaggggact aatgttcaga   173640
tagtgggcag gagagcagca ggggagactg gcagtggaga ccccggttgt gctatgaaca   173700
gagggtgaaa gagaagagga gtcaagggtg tctcccaggt tgagcctgg gttggtgtga    173760
ccagcagaag agagacagta aagaggtttg tttgagggga aaagttgaat tttgtatggg   173820
```

```
gcatgttgct ggaggttacg ttttagaaaa aatgcactcc tttacttaga atcctaacaa  173880
cagcttacaa ggcccaatat gttctgaggg gtccctggcc agggccggga gaggatggtg  173940
tgcaccatgg gctggctctg agcacactcc tgccatgggc ctgagatgcc agtttcccag  174000
gcagccacag ggctttgccc aagccttccc tgagtaccct gccagaactc ccactcctct  174060
tttctctttc cttaccacac atcttcttgt ctggggacat tgctaaaccc cacagtccct  174120
gcctcagagt aggcactcag tgtctggtga gtgaatcagc tgatgacatt gaatagggggg  174180 atattgtcaa ggtcagagtc tggattccgt ggatttggga agaaagtgaa agacatggaa  174240
aggaatcagc agatacacac cagtgtaggg agtggggttt gtcagaaaaa gggaaagaca  174300
ggactagagc tagttctaac tgagcgaaca gcaggtcaga acaacctagg ccagcatgtg  174360
caggtggaca gcaatggctc tgtgctggtg gggtgtgagt gaaggtcgtc ccccacggtc  174420
caacaggtga gtccctccac agcacatggg gccatgcagg aagggcacag ggtacactgc  174480
ctcccgaccc agaaccccctc caggctgtg ggtccacagg gcaaaggcga gcaccagctg  174540
cctgccccca cctcttctgc cactcaccac tgtcactcac cccccttgcac agagggccat  174600 cacaggtgtg gtaaatgtgt ctgctctgtt gcagcgccgg ggcaggaagg acggggacct  174660
tctgtgccct gagcaccgtc ctggagcgtg tgaaagcaga ggggattttg gatgtcttcc  174720
agactgtcaa gagcctgcgg ctacagaggc cacacatggt ccagacactg gtatgctgcc  174780
cacatatttg tccctgccac cacaccacct gcagcccttc tctcagggag gaggctcttc  174840
agaggggccc acccagtagt cagaagactg tctaaacaca gacctgccct tgccctccca  174900
aggtgcccca aatacacagg aaacattggg aggcaggatg gcagcaatgg gagcatagcc  174960
cctgttgcca gaggttgggc caggttagaa ggggtgtctg ggtgccccac agggctcatc  175020
tgtacttctc tgtgggtctt gggtaaggaa gatccatgaa gagtacctgc ctttgggctt  175080 gggctcccctg ttaagaggtc tgactttaat aagccgcaca tccacagagg ttttcctgaa  175140
tcccatggag ctagaaatgt ttggggggta aagaaaagtg aatgttagga ggtttgggag  175200
acgaggttct gagagccagg gtgcatgcta gcctggcagc catggtaagc gtgggccatg  175260
ctcagctgca ctgtctccca gcccagcaca tgcctgtctg acctctgtgg ggcctgggtc  175320
agctctggtc agctctgctt gtagaaggtc tgctgcattc agcccggaag gggaatgctg  175380
tcagaactct ggcaggcaga tcagagctca ggtgaaagtt caaaaacatt cagttcctct  175440
tgattttcca tcttcaacaa aaaatgagt ctgttaggaa ttacaggtac tgtgtgttct  175500
tcagtaaccc tgacttttc cctacctttc actctccagg aacagtatga gttctgctac  175560 aagtggtgc aggagtatat tgatgcattc tcagattatg ccaacttcaa gtaagcggca  175620
acaagggtcc gtggaccagg aggattgcct ttaatatttt gtaatattct gttttgttaa  175680 tacccccaa attgtgtata tatcttataa ctgttttaga aattggtaca taggcttcta  175740
ttacctatta ggtggaaatt ttatatgtaa atgtgttagc actgatagtc cttttttccaa  175800 tgttttattg gggaattaaa tagtgtgatg tttggattga tatcgtgaaa tcctcagccg  175860
agaaattggg ctggattgtg ctttggttaa tacatctttc cctaaagaag ataaacacaa  175920
aatccattcc aggtagctcg gcaccaacta agaaaaaaag cacaaagttc tcagagctct  175980
cgaggaaagt ggttgtcccc gtaccaccat gcactgtaaa tatccctccc ctctctccct  176040
ggtcccctcc cccatcccca ccactgatat catggggagt aataggacca gagcggtatc  176100
tctggcacca cactagggac tatcaggtaa taaaagcttt gactccctga ggaaatgtct  176160
ctccctttgt ctgggggtgg ggcagccata caggctgggg ctctcctcgg ctgttcatgg  176220
```

```
ccctcctgtt gctgttctct ctgagttatc tgagagaggc cacagtcccc cagctcctcc   176280
tgtccaccaa acacagccct tccagttctt aggtgatctc caggaccctc ctttcattcc   176340
cagcacatct ttggtttagt ggtcctggcc agcctccctc cctaggaagg tggccaggtc   176400
ctcactgagt ctccttaagg acaggggcac aggggagact agagctggct cagctttggg   176460
ctgaggccag tctgacctct ccagtctgtg gtgctttgct acaaaactgt ctggattgtg   176520
tcaccctatc taggataaat ctttatgtcc acatatattg tgttgaattg ttcccatttt   176580 cttctcatacg tgtcctcatt tctgggacag tgtgaatgtt tctcagatct agaagtcaga   176640
tggtgggagt cttagatccg aacttggttt tgagtgacat gttagacaaa agtgttgaac   176700
ttttgtttct taaagaagct ggatgttcat ttatgtctcc cgtaacagtc tgtgctgtcc   176760
agagacccag tatccttagg atattattct catcctcatg gttgaagctg ggtcactgcc   176820
atgtccataa tccaccctga ggaaagagca tggagagcca gcagcttcat ttctaaggac   176880
aggaagccaa atctgcactt ttcacttcca ctcataatcc accccgcatt ccactcatca   176940
gcttcacaag taggttttca cctggtcata gctatgccta actacaggga gtgctgggga   177000
agtgtgatct tttgttgggg gcacactggg agagtgggtc tgtccactgc ctcccagcct   177060
cagagcagct caccacagga gcaggagagt gaactcgtgg ctgtggctgt caggcagggc   177120 cttctcttgag agccagcgca ggcctgggct cctcagaggc ttctggagtg agagatggca   177180
cctcagcctg gcccatggag gcatgttcag ggatcagcac tactgtgctt cttggaggag   177240
gtgggacttg agctggaccc atgggaggct ggaaatttag atgagtgaaa aggaggaaag   177300
gcgaagtaga gccacattac agagggcctc agagtccaga taaagcagtt aacatgtagt   177360
ggctccagga gggaagcctg tctgtgcacc acatacccag gatgtttgtg ggaaggaagg   177420
agatgtgcgg aagggaccca ggagacctgc aggaggcaag ggctgcaaca gacccctct    177480 ggaagtttac aggaggtgag tgtgagtcat tagagacatt cagttctgta ggaactaacg   177540
aactcccaag aggcagtaaa cttaaaactc agcagtctcg ataagtatgg ataaattagg   177600
caaagacaga ttctgaggaa tttctggtga ggggtgccaa gtttgggag cagcccctgg    177660 ctccttgcaa gctacccttc agtgctctgt gtgaccaagt ccaagtcgat gcaggagggc   177720
aggcactggg tcagcaagcc actcagtgaa tgtgcaggtg aggccgttca taggcgcttg   177780
tgtgcctccc agcaggctgc ctgccattgc cagggctggc cttcagcagg gtgcgccacc   177840
atggcctgag tggttttctg ctgaagtccg tgctgatttg gccagtggat aggcatcacc   177900
tgggtgcaaa accattgtct ccaggtagga atgacctcag ctgtttgctc cgtgtctcgc   177960
tcagcctgta gatgtgtccc tcatcccttc atgcctccct cttcactcct cttttacttt   178020
ctactcgggg cttgcatgtt tacaagagag gtgaacccaa cagaaactag tataggccaa   178080
aaggaaaatg tgctgaagct cacacagcac agtcgtgtgg aaaagcagc agtgactgct    178140 tcatccagtg ccccttcccac agccagtcag ttgcgaccca aggggcttag ggtaggagtg   178200
tttctccata ggggaagagt aacagcctgc acccaccaca cacccaaagc cctacatcct   178260
gccacactga gacctcactt catttgggcg ggtccctcct gggttgcagt ttccttcatt   178320
gctcccctgt cccaaatact caagtctctc tcattaaaaa taaagagcag gccaggtgca   178380
gtggctcaca cctgtaatcc cacactttgg gaggccaagg cgggtggatc acttgagccc   178440
aggattcgag accaacctgg gcaacatgac aagatcctgt ctctacaaaa aataacaaaa   178500
atcatctggg catggaggca cacgcctgta gtcccagcta cttgggaggc tgaggtgaa    178560 ggatcacctg agcccatgag gtggaggcta cagtgagctg tgatcatgcc actgcactcc   178620
```

```
agcctgggtc aaagagtgag accctgtctc aaaaaaaaaa aaaaataggc cgggcacagt 178680
ggctaatgcc tataatccca gcactttggg aggccaaggc ggacggatca cctgaggtca 178740
ggagttcgag accagcctgg ccaacatggt gaaaccatct ctactaaaaa tacaaaaatt 178800
agccgggcgt ggtggcacgt gcctgtaatc ccagctaccg gggaggctga ggcaagagaa 178860
ttgctggaac ctgggaggca gaaactgcag tgagctgaga tcacgccact gcactccagc 178920
ctggatgaca gcgagactcc atctcaaaaa aaaaaaaga aaagaaaaa gaattaatta 178980 attaattaaa taaagagcat gtctcccacc ccaggcctaa gttcttccct ctatgagaga 179040
ctacttgcag aaacctgtgt tctcactctt cccccttcct cacttcattc ccacacattt 179100
cttttccatc cctgcgcacc aaggtcacct tggtgctaaa caccagggac ccatggtctc 179160
ttcccctttg tgtcacaggc tgtcctctgc ctcttatcct cacccttag ctgctcctcc 179220 actgtctcct ctctcagagg tcaggattct ggatctgtct ctgtggaccc tcagctctcc 179280
tccaatccca agtcccccgc atcctggtcg catgtcaggg tggtccagag atgcctgcct 179340
cccactgccc acacccaggg gcccgccctc cttctctca accttcccac atactctggc 179400
cccatggatc cacggcagtt cctgctggcc cttctccatt tgttcctta tgctgcaccc 179460 ctctgctgcc actccctgcg tccgtgactc cagctcactc gtctctgtcc ttcacccagg 179520
ccgcctgctc agggttttgtg cctctctgtg ctcctgcagc acctgagtgt ttattcacct 179580
ctgaacctct gctttcccac ctgagtacac gcagctcctg gctgcagtga cttcatatcc 179640
tgaggactgg agctccgtgg tgaacagatg gctttctatg ttctaatgag agggatacaa 179700
gagttccaca gttctagtct ggaaaggacc aaacatttct taaaagctaa gtatgttgcc 179760
ggaaaaaaaa gggagcagag cttcccag gaagcttggc tctggtttag atttttcagg 179820
aaaagccgga atcaaattac agaataaata aaggcaacca tccccttttt aaaggtacac 179880
cagccttggt gcatctttga agaaagcatt ctgtaaaccc caaccagaac taaactagta 179940
cgtcgaactc agattcattt tcactaaacc acaagcaaat gtttccctaa aaatcaccca 180000
gttaacaaag tccgcatatt taagccaaaa caatttaact gaacaaatgg ccacacgtt 180060 gatttccggt ccctgctaat aagtcagtct ggaagttcac aggtgtgccc atcctgcctt 180120
ggctgctgaa gtccaggtgt ctagggctga ctgatgccca ttatgcctcc cctccccat 180180 ctttgtcaca ggatttgacg caccagctct ccaaatgacc ctggccctcc catttgctgt 180240
tcagcccaag tgcggagatt ggctatgaac cctgtaaaca ggcctctgac ccccagaggc 180300
tgatggctgg ccaaggaaag ctgagctgct gacgcagact gggaagcaag agcccacttc 180360
cagcagccca ggctagctgt gtccaaatcc atgactgggg aggggttaga gccttgaggg 180420
acaaaattat tctacctacc tagggagact gcactggccc aacagctggg ccccatctca 180480
tgggcccgct tcttcgccag gagagaagcc actccgggt aggtactgcc ccacccaaac 180540
ccagccatct ggagtgaccc agccctggtt cccaggtgtg tggatgtgaa ttgtcccacc 180600
caacccactc tacagtgagc aaacggaagc cctctgggag agtggtcaca gcctccctg 180660 tacctctgaa cagcctgcca ggctccctac tcttaggctt ccactgtcca ccaggaaag 180720 ccctgagctg ggagttgggg agccccagg cattgcccct gcccaggaca caattctctt 180780
ttgggatcag ggaaggctgt gagggctttc taggtctcaa gatcaggagc ttgaagatgc 180840
agcctgggaa gtgggaaggt gagaccagga cataggccag cctaaagcaa gagtcctggg 180900
cctgaaggct cctgggaagg tggtggggag ggagcatgtg tcggtggcct cagggcagca 180960
gctgcctggt gaatgttcat ggactggatg ctctgggaag cgggttgggt ggtgagcttc 181020
```

```
tctcttcccc tctgaagacg tcactggagt ctgggggtgg agctgcctgg tctataaatc    181080
ctggggccat caggctaggg tcctgcagct gcctgaagga gccatctcat ccacagctct    181140
tccttggtga gtggggagcc ttccctaagg gctaggacac ctggaccaag tttcatcctg    181200
ggcgtatggt gtgctgctcc tcttccccat tcccaggtgc ctccacccct gaaccatgcc    181260
agagaagtcc ccttttcctc tcctctcccc aacagctcta ccatctattc ttgtgcttgt    181320
tgcccctggc atgggaggga taaggggtag aagcacttgc ccccatcaat accactcatc    181380
cattccacat ccccaactac tatggaagag atacagcagg ccacggagaa aagggcagaa    181440
ggcctgcaac tctggttccc tagcactggt gctccaaaca cgcctacatt gagaactccc    181500
ctgaccatcc atctatcctc ccatccattg gcctgaattc aggtctctgt tcccctccaa    181560
ctttcttcca cttctggaaa ctccttgaag gaaagatgga tggacctgga caagtgggag    181620
ggccctcaga gctggcaagg caggtagcct ctgtgcccca ggctcaggga aaggctcgt    181680 cccctggagc atcatcccct gctgggccag gatcccccag gatctggacc cctgtatgct    181740
tgggatgagg agcggtggca gagagggaag ggcataagga gataccaaag ctgcccctga    181800
gatgccagtt ttccaaagtg gccctggagg aagtagggggg atgtgggggt gaggtaagtc    181860
tccttgaatg ctgtaccctg tccattagag cagccatggc cagctccagg cgaggcctcc    181920
tgctcctgct gctgctgact gcccaccttg gaccctcaga ggctcagcac tggtcccatg    181980
gctggtaccc tggaggaaag cgagccctca gctcagccca ggatcccag aatgcccta    182040 ggcccccagg tgggtgtctc ccagcctcat ggggaggaag aaagtgatgg ccgggggctc    182100
ccccacccct ctggagcctg aggtcggggt agggaggaca gcatcagttc ccttctaagg    182160
aagggccctg gacactgcag caggcagccc agtccagact gcccatggcc tcccaagtga    182220
tgccctggct cccctggacg acagcatgcc ctgggagggc aggaccacgg cccagtggtc    182280
ccttcacagg aagcgacacc tggcacggac actgctggtg agtagggtga gaggtccca    182340 gcatcaagac cagccactgg tcatcagagg ccattgtggc ttagggttgg gtgctgggag    182400
ggtggggaga atgaaacacc actgagatgc ccctgccac agcaccccca gccatttctc    182460
agtgccccta ctgcacacag cagggtgctg tctgctatcc ttcctatttc ccaggaggat    182520
tctagacaat ttacaaagca cttgggttaa agaccaaagt cactagtaga ctagaaggag    182580
ataattgttc tataagacag tggtggccat gggatcccac aggcatcctg acaagccaat    182640
gactgtcttg aggtggacag accccaggcc agtggaaaga ggtgagggat gcaacctcac    182700
tcaaacagac aacagggcca agaggaccag gtggtgactg acatgtgcac taggaacatc    182760
tcagggactg cagagctccc caagaccata gcagaagaca ggcgtgggga atggtttgc    182820 tactgttttg caaatcaaac atttacagtg catcaggaga gcccggtaac taaagaagaa    182880
agtggttagt tcctatgagg caatgtctta ccgcctgatt tgtgtgtatg tgctgaggtt    182940
tctatgcgtc aggcttgttt agggtggaca agagggcatg cccaagggag ctggagatcc    183000
ccacactagc tggatcctca ggcttctacg ggaggcgggg ggcgtcctgc tgtgggaggc    183060
cacatgggga ctgggggga cgagagggga gagaaccagg aagatggcag ctcggcggtt    183120
acgagaccag tgtcctgaga catgaccgcc acctctccct ccgcagaccg cagcccgaga    183180
gccccgcccc gccccgccat cctccaataa agtgtgaggt tctccgaagc tgttgcgtcg    183240
agttctgtcc ttcgtcccct ccctgtcttc cccgctgaga cccttccctg cgtgggggct    183300
ggagggacgc gggtccggcc ccgcgggcgg gagtaactaa gggatggccc cgggccctgg    183360
cgggaaggcc gggccagagc ctgggggcgg gatgcggacg tccgcagggt cgccgcttcg    183420
```

```
gttccagagg ccacacggcc gggcggggcg tgagggacag cccgaggact acaggtccca    183480
aggttccccg cgccgcttcc ggggcacggt ggcgtcccgg caccgcggcc gcagtgagga    183540
gactcggcca tgctacgcgc gctgagccgc ctgggcgcgg gaccccgtg caggcccgg    183600 gcccctctgg tgctgccagc gcgcggccgc aagacccgcc acgacccgct ggccaaatcc    183660
aagatcgagc gagtgaacat gccgcccgcg gtggaccctg cggagttctt cgtgctgatg    183720
gagcgttacc agcactaccg ccagaccgtg cgcgccctca ggtgtgcggc cggggggagg    183780
tggccgcccg cgcgcgctgg tgacggtggg agtgggcgga gagggtgctg attcctggcg    183840
cgtctgcacc caggatggag ttcgtgtccg aggtgcagag gaaggtgcac gaggcccgag    183900
ccggggttct ggcggagcgc aaggccctga aggacgccgc cgagcaccgc gagctgatgg    183960
cctggaacca ggcggagaac cggcggctgc acagctgcg gtgcgtgggg cgggaggcgg    184020
ggcggggcgg cgcggcctgg ccggcctggg agaagcccgg gccccgctca gcctcggccc    184080 tttgacccctc acaggatagc gaggctgcgg caggaggagc gggagcagga gcagcggcag    184140
gcgttggagc aggcccgcaa ggccgaagag gtgcaggcct gggcgcagcg caaggagcgg    184200
gaagtgctgc agctgcaggt gggcaacgtc tccggagggt gggactccag ccggggcgc    184260 ggcttgcggg gcactgggaa ttctgggcac cgcgacgcgg gcgctggcta tgtgcagaga    184320
cttacagttg gcaggtccgg atttggagag gagagtgcca gtcaggcgca aagacccgga    184380
ggtgagcgga gtaattggac agtgttcagg tacctagcag gtctgtggga gggaccctgc    184440
gttccacaaa gaggttgtat tttgcataac aggtgatgaa gccatgaagg ttaagtatt    184500 tcaggctagg attagcaggt gtgcgactta aaagcaggga gaccacttag gagtaatgca    184560
gtgagaatgg atgaggcttg atttaaagta tagaagggtg gctgggagcg gtggttcacg    184620
cctgtaatcc cagtactatg ggaggccgaa gcgggcgtat cacttgaggt cgggagttcg    184680
agtccagcct ggccaagccc cgtctctcct aaaaatacaa aaattagccg ggcgtggtgt    184740
gcgccagtaa tcgcagctac tcgggaggct gaggcatgag aatcgcttga acccaggagg    184800
cagaggttgc agtgagccga gatggcgcca ctgcactcca tcctgggcga cagtgagact    184860
ccgtctcaaa ataaataaat aaataaataa ataaagtaat gggggaagg atgagttaga    184920 gtgattcaga ggggaccact gagggacgga tttcacctac caggacgtga gattttcata    184980
gctggcactc ggggctatgg ctgaagtgtc tgagaaaaga ggaacgtgga aaagcaacct    185040
gatatcactc cactgggagg ccagaggggc tctcaaatag gacctgggtt ccaggcatgc    185100
ttccccaggg agagcaggag ctgctttctc agtggggtga gaggccagca ggctgggtgg    185160
gctggctggc atgtgcccaa ggctcctgtt cagctgggct tttctctccc gataggaaga    185220
ggtgaaaaac ttcatcaccc gagagaacct ggaggcacgg gtggaagcag cattggactc    185280
ccggaagaac tacaactggg ccatcaccag agaggggctg gtggtcaggc cacaacgcag    185340
ggactcctag gggcccagta aggacagtgc ccgccaggga ccatgtatgt atcatggcgg    185400
aagagttggc cctgacctgg aataaagcag ttggtgttgc ttatgaggaa ggttcagcct    185460
tatccagcac agccttcacg ttttgccctc tgctgtcacc acttggtcag aaacttccaa    185520
acgcagtgcc ctgttctgcc ggtgtgtaca gcctcagcgc accaggagac cctagagtgg    185580
tttccatctc acagagaatc agacagggcc acagccccct caggcagcca ggtcatctga    185640
gtatcattaa gagtagtgat gggaagatta cagtctgagg gccaaacgtg cctgcttcct    185700 gttttttgtaa ataaagtttt gttggaacac agccacaccc actcattgac ttcttttttac    185760 tacagtggca aaggtgagta gttgcaacag agaccatatg aatcccaaag actaaaatct    185820
```

```
ttaactttt  acaggaaaag  tgtagtgatc  tctcatctgg  agctttagga  ctctagcctg    185880
tgtcacccag  gacctgagcc  acaagctaac  cattggccag  gcgcctgcct  ctgctctata    185940
ctgtgctttg  ctggccagag  tctggtgtat  ccaagaccca  gaaggcaaag  aggagacccc    186000
atttttttct  gggttccaca  aagaggttgt  attttgcctt  acaggtaatg  aagccatgaa    186060
gaattaaata  ttctaggcta  ggattagcag  gtgtgtgact  taaaagcagg  gaggccatta    186120
ggagtgggtc  tctccaccca  tggcctcagt  gacctacatt  tgccctggca  ttgccattgc    186180
ccttgggcca  cccagcagat  ggctgctggc  aggggagaca  tggttgacca  agattttatg    186240
aggttagtgt  ggcttagcaa  gcacttggac  caacctctat  gggtactggg  actacctgtg    186300
atgatgaaga  gagtatatag  atccatagtc  cctgttcaga  tgcaggccct  caagcagtgt    186360
ctgggatgag  ctggaggaat  gtttctcaac  cagagcagct  tccgtttgct  gccatgcaca    186420
tgaactccag  cttctctcca  tgtctcccac  ttctttgcag  ggaaggccta  gggaccccca    186480
agaaatgaaa  acctttttt   ttctttcttt  tttttttgag  acagagtctc  actatgttgc    186540
ccaggctgga  gtgcagtggc  acgatcttgc  tcactgcaag  ctctgcctcc  cgggttcacg    186600
ccattctcct  gcctcagcct  cccaagtagc  tgggactaca  ggcgtctgcc  aacacgcctg    186660
gctaattttt  tatatttta   gtagagacgt  agtttcactg  tgttagtcag  gatggtctcg    186720
atctcctgac  ctcgtgatc                                                    186739

<210> SEQ ID NO 20
<211> LENGTH: 31737
<212> TYPE: DNA
<213> ORGANISM: H. sapiens

<400> SEQUENCE: 20
tataatgccc  tcaaaactca  gcaggttttg  aaaatgcctc  ttccttctct  tctcctcccc      60
ataatcctgc  ttattttgg   cattaagtga  gtcagggtt   ccaaacccaa  atacgttttt     120
caaggctatg  tagtcagtgt  gaatgagaga  agtaaatctg  ttgggtcctg  tgccacactg     180
gagtttccaa  ggctggtcta  aatgagttca  acttcagttt  ttttgtgttt  ttttagagat     240
ggagtcttgc  tgtgttgctt  gagctggtct  tgaactcccg  ggctcaagtg  atcttccagc     300
cttggcctcc  caaggtgcta  gaattatagg  catgagccac  tgtgctggcc  aatttttttt     360
tttttagccc  actgtgctac  cagtttgtga  tcttcacttt  aactgtgaaa  ggactgtcaa     420
agattgtacg  tataagattt  agtttgagag  ccaggcctgg  tggctcatgc  ctgtaatccc     480
agcactttgg  gaggctgagg  cgggtggatc  acgaggtcag  gagatcaaga  ccatcttggc     540
taacacggtg  aaaccccgtc  tctactaaaa  atacaaataa  attggccagg  cgtggtgacg     600
ggcgcctgta  gtcccagcta  ctcgggaggc  tgagacagga  gaatggggtg  aacccgggag     660
gcggagcttg  cagtgagcag  agatcacgtc  actgcactcc  agcctgggcg  acagagcgag     720
actccttcac  ccaaaaaaaa  aaaaaaaag   tagtttgtct  ttctctttga  aactgaattc     780
attaaacaaa  agcctaaata  actatactat  tacttgttat  ttatttattt  attattta      840 gacagagtct  tgatctgtca  gcaggctgga  gtgcagtggt  ataatcttgg  ctcactgcaa     900
cctctgcctc  ccaggttcaa  gtgattctcg  tgcctcagcc  tcctgagtag  ttgggactac     960
aggcatgcgt  caccacaccc  agctaatttt  tgtatttttg  gtagagatgg  ggcttcacca    1020
tattggccag  gctggtctag  aactcctgac  ctcaagtgat  ccacccacct  cagcctccca    1080
aagtgcataa  gtgctgggat  tacaggtgtg  agccaccaca  cccagcctac  tacatattct    1140
tttagaccca  gctgaaatat  cacgtaattg  ctgaaggctc  ctgaactctt  ccagatcagg    1200
```

```
gattgatttt cctcatttta agattgtcat gacaactgta gtattgataa ctgtatttta    1260
ttttatttta tttttttttga gacagagtgt tgctctgtca cccaggctgg agtgcaatgg   1320
cacgatcctg gctcactgca aacttagcct cctgcgttca agcaattctc gtgcctcagc   1380
ctcccaagta gctgggatta cagatgtgca ccaccaaaca cctggaatta gtctggctaa   1440
tttttgaagt tttagtggag atggggtttc cccatcttgg ccaggctgtt ctcgaactcc   1500
tgcctcaagt gatccacctg ccttggcctt ccaaagtgct gggattacag gtgtgagcta   1560
ccgcacccgg cttattaacc aattttaat gttcagcaca acttgatcat gatgtacaat    1620
gtctttttta tgttatgtgt tgatggagtc aaattaccga tattttggtt cagttttttc   1680
aataagagat caggctattt tctgattttc attctgtttt tttctttgat ctgtatgtat   1740
ttataagtgt ctcttatttt caaataggtt ttttctagtt atctttttgt aacggattta   1800
tagattatac attgtggtta aagaatatgg tctataggct gggcacggtg gctcacacct   1860
gtaatcccag cactttggga ggctgaggca gggggatcac ttgaggtcat gagttcaaga   1920
ccagcctggc caacatggtg aaaccctgtc tctactaaaa atacaaaaaa aatttagccg   1980
ggcatggtgg tgggtgcctg taatcccagc tactagggag gctgaggcag gagaatcgct   2040
tgaacccggg aggtggaggt tgcagtgagc cgagatagtg ccactgcaat ccagcctgtg   2100
caacagaggg agactccgtc tcaaaaacaa aaacaaaaaa caaacgaaaa cacacacacg   2160
caaagaatac ggcctacatg cactttcagt cctttggaaa ttgttggtat ttatttgcca   2220
tttggcctag tttacccaga ttccacaggt tgttaatgtt gtacaattgc gtcttctctt   2280
tctcacttca cccatctatg taattttttct gaatcatttg agaaataagt tgcaaacata   2340
atgctgtatt acccataaat cagggtgtgt ttcctgaaaa caaggatact ctcctataaa   2400
atcaggaaat aaatattgat ataatactgc catctgattc acagaccta ctcaaatttc     2460 actgatcttc caattatgtc ttttatagca aaaacaaaac aacagaaacc aacaaaattc   2520
cctcaagaaa acaaaagcag aaaaacttcc ctttccccctt cacttatttc tgattcaggg   2580
accattcagg attatgcctt gcgtttagtt gtcatgtctg ttcagtctct tttaatctag   2640
aatagttctc agtctttcct tattttcagt gatcctaata ttttttgaaga gtagagaatt   2700 attttgtagc aagtcccaca atttgggtta gtctgatgtt tccttttgaa tagatttagg   2760
ttatgcattt gtggcaggaa taccaaagac acgatattat gttcttctca ctgcatcgta   2820
tcaagaggtt catgtcaatt tgtccaatta ctggttatgt ttaattttac cacttggtta   2880
agatgttggc tggcaagttt ttgtaaaatt agtttagagg tatttcatac ttactggtta   2940
gtaagtaata atgcattttg tggggtgatg ctttgagact atataaatag cttatttctc   3000
atcaaatttt tgcttgctag ttttaccatc cattggtgat ttgtgcctga atcagttatt   3060
atagtggttg ctagatggta aatttaaaaa atttcattat ttcttctgaa ttcatcactt   3120
ggcatttctt tttttttttt tttttttttg agacggagtc tcgctttgtc acccaggctg   3180
gagtgcaatg gcgtgatctc gtctcactgc aacctctgcc tcccaggttc acgtgattct   3240
gccacctcac cctcccaagt agctgggtt acaggcaccc gccatcatgc cctactaatt    3300
tttgtatttt tagttgagat ggggtttcac catgttggct aggctggtct tgaactcttg   3360
acctcagatg atctgcccac cttggcctcc caaagtgctg ggatcacagg cttgagccac   3420
cgtgcccagc caatcacttg ctatttcact ctaaggaaaa gctttctctc tctggttttt   3480
gtctttgttt ttgtttgttt aaaaatcttt taaacatatg agcacagcct cattgattct   3540
tattttgttc ctttttcatg tatttttttga tattcaaatt gtcccaaatt tggccagtgg   3600
```

```
gaacccttc   aggctggctc  ctgtgtcctt  tttccatgtc  ctcatcattc  ttttttttt    3660 tttttttttt  ttgagacaga  gttttgctct  tgttgcccag  gctggggtgc  aatggcgtgc   3720
tctttgttca  ctgcaacctc  cacctcccag  gttcaagcga  tcctcctgcc  tcagccaccc   3780
aagtagctgg  gattgtaggc  acctgccacc  acacctggct  aattttttcta ttttttgtttt  3840 tatttttttt  attttttgag  acggagtctt  gctccgtcgc  ccaggctgga  gtgcagtggc   3900
gcgatctcgg  ctcactgcaa  gctccgcctc  tcgggttcac  gccattctcc  tgtctcagcc   3960
tccaggcatg  cgccaccatg  cccggctaat  ttttttgtat  ttttagtaga  acgggggttt   4020
cactgtgtta  gccaggatgg  tctcgatctc  ctgaccttgt  gatccgccca  cctcggcctc   4080
ccaaagtgct  gggattacag  gcgtgagcca  ccgcgcctgg  caattttttct attttttagtg  4140 gagacaggat  ttcaccatgt  tggtcaggct  ggtctcgaac  tcctgacctc  aggtgatccg   4200
cccgccttgg  cttcccaaag  tgctgagatt  ataggcatga  gccaccacgc  ctggtcatgt   4260
ccccatcatt  ctttgatcac  ttttttttctt actttttgga  ataataagat  ttctgtggg    4320 ctgggcgagg  tggctcacgc  ctataatcct  agcactctgg  gaggccgagg  ctggtgggtc   4380
acctgaggtc  tggagttcga  gaccagcctg  gccaacatag  tgaaaccttg  tctctactaa   4440
aaatataaaa  attagccggg  catagtggca  cacacctgta  gtcccagctg  ctagggaggc   4500
tgaggcagga  gaattgcttg  aacccgggag  gcggaggttg  cagtgagctg  agattgcgcc   4560
actgcactcc  agcctggatg  acagggcgag  actccgtctc  aaaaaaaaaa  aatttctggg   4620
ctcatcttta  cttttgttat  ctcagtcgtg  gaatcaataa  ttttatcagg  gaaccctggt   4680 tcctttatt   agtgaatgta  cttagaaaat  aaaatatgtg  cactactaga  tatgttcttt   4740
ctattggggt  gttcttcctt  ttaggctcta  tgtgaggaga  gaactagaat  attgttttaa   4800
aatgtaccag  gtaatcccag  cactttggta  ggctgaggca  ggcaaggctg  gcagatcact   4860
tgagatcagg  agttcgagac  cagcttggcc  aacatgatga  aacccccatct ctaccaaaaa   4920 acacaaaaag  tagccaggcg  tggtgacacg  cacctatagt  cctagctaga  gtgagataga   4980
gtgagaccct  gacttaaaaa  aataaacaaa  taaataaaat  atactggaat  ttaatttata   5040
ggtatgaatg  acacagagag  gccaatatta  ttgaaaatgt  gttactcaca  gttcttctga   5100
aacagcaggc  gcaccatact  atgcaggacc  acatggggaa  gcaccagggt  gggtcaggag   5160
gcagaaggaa  ccagaggaaa  ggatgggtga  gttttttttt  tgttaaagtg  ctagaaagtt   5220
gttaggtggg  acatccccta  ttgagcagaa  agagaaacac  aaatgttgag  atttgtggtt   5280
ggacggtttg  taatatgatt  tttgtgtagc  ctcaaaaaca  cagagatggt  atgaatgtaa   5340
acaactttgg  tcgttaattt  ggcccatcct  ttcaagatgc  caaatcatca  attacagaat   5400
atcaagaatg  attatatagg  tatgtatgca  tgtctataca  tacatatata  catctgtatc   5460
ttcctgtaaa  taatgaaagc  catggttca   ttccaatact  cttaattcta  gtccaacaca   5520
atagggtttc  ttctggtgtt  tcccttttct  gacattgaaa  aatctgaggc  caggcacagt   5580
ggctcttgcc  tgtaatccca  gcactttggg  aggccaaggc  aggtagatca  cttaaggtca   5640
gttgctcgag  accagcctgg  ccaacatgat  gaaaccccat  ctctactaaa  agtacaaaag   5700
ttagccaggt  gttgtagtag  tggtcgcctg  taatctcagc  tactcgggag  gctgaggcag   5760
gagaatcgtt  tgaacccagg  aggtggggc   tgcagtgagc  tgagatagcg  ccactgcact   5820
ctagcctggg  cgacagagtg  agactccatc  tcaaaaacaa  acaaaacaa   aacgaaaat    5880 ctgcctctcc  tttttttttt  tcattcattc  attaattctt  tagatggggt  cttgccctgt   5940
cacccaggcg  gtagcgcagt  gacacgatta  tagctcactg  ttgcctcaag  ccatcctctc   6000
```

```
gcctcagact cctgagtatc tgggaccata caggcacgtg ccactgtgct tggctctcac   6060
attgtccttt ttactcacct tcctgttggt gacaatctcc tgactatgta ggccattttc   6120
ttgcccccag ccccactgaa tgagctggct gatcactcct tcaagttcca tgagccattg   6180
ttacatacag gtagtactca gtttgcttgg ttttgatatt cataaatttc cattgctgtg   6240
gtttaattaa ataatgccag tcctcaaata gcagttaatg aaatacaaaa tataaacctgt  6300 gatcaagaaa agcttctcag gtgggcgtgg tggctcatgc ctgtaatccc agcactttgg   6360
gaggccgggg cggtggatc  acctgaggtc aggagttcga gaccagcctg accaacatgg   6420
tgaaacccca tctctactaa aaatacaaaa aattagctgg gcgtggtggc aggtgcctgt   6480
aatcccagct actttggagg ctgaggcagg agaattgctt gaactcagga ggcataggtt   6540
gcagtgaccc aagatcaagc cattgcactc cagcctgagc aacaagagcg aaactccatc   6600
tcaaaaaaaa aaaaaaatag cttctccaaa attttaaaaa tttaccctga ccctgaaata   6660
gttgattgtt ccctccctag acatcattca gttggagcta gcctaatttt gttttttttg   6720
ttttgttttg ttttgagatg gagtcttgct ctgttgccca ggctagagtg cagtggcgcg   6780
atctcggctc actgtgacct ctgcctcctg gttcaagtga ttctcctgcc tcagcctcca   6840
gagtagctgg gattacaggc gcgcgacacc acacctcgct aattttttgta tttttggtag   6900 agacagggtt tcaccatctt ggccagactg gcctcgaact cctgaccttg tgatccacct   6960
gcttcggcct cccaaattgc tgggattaca ggcatgagcc accgcaccca gccttttttt   7020
ttcccttgag gagaattaca gtctgcactg ctctcagctg aacttacac  agcttttaca   7080 tttccctctg tcagttcctc ttgtaatggt gggtgggtag ctgaagggag gatatgtaca   7140
ataatgtatt tttagttcct ttgaacagag aggttgcttc agccattgct attgatggca   7200
ggaagtatat ttatagctcc agggaaggag gggtagtacg actgctggtt taagaaaacc   7260
tgggagattg tatttaatat atgttgttaa aactcatttg tacttattg  taagttcttg   7320 ccttagaaat gcagctgaga tgaatgaacc tgttacttat gttatattgt tacttatgtt   7380
atatatgtta tatgtattat tgtaagtata ttgactctgc tccctaatttt ggaaaaatct   7440 tccgttttga aattttacaa tatacaatac ctaaaacaaa gagtacttct agagcataca   7500
ggatgtatgt ggagaattca ggtgttagca tgcaattgaa cagtaaagat actgactagc   7560
agtataaata tcgtccccat ttagatattt tattcataaa gttcttgttg gtgtagcttt   7620
tattgtgatt ttttctttt  ttttttttgga tacagagtct cgctctgtca cccaggctag   7680
agtgcagtgg cgcagtctta gctcactgca acctctgcct cccaggttca gtgattctc   7740 ctgcctcagc ctcccgagaa cctgggacta caggtgagca ttaccacact ggctaatttt   7800
tatattttta gtagagatgg ggtttcacca tgttggtcag gctggtctcg agctcctgac   7860
ctcaggtgat gcacttccct cggcctccca aagtgcaggg attacaggtg tgagccactg   7920
cgcctggcca attgtgattt ttttaaagat tgaaaccaaa atatttata  cagatcataa   7980 gatattcttg gtaaacacta agcacctcat aactttacca caattttgat tgcacaactt   8040
tcacctgtgg ttatcatgtg caatgggcac attcaacaca aatcaaatta ttctgaagct   8100
tgctttcttt cttttttccc tactcccttt cttaattgag gggagcaaaa agttggtttc   8160
cagggatatg tcttctctct tatgctggtc ccagattgat gcagtcatgg aaactaggca   8220
gtaaactcat tcttggcagc tgccggcact ggtctgattc tttcttttaa aagcatgaga   8280
ttctttaata acacatattg gaaagattga tgccaagtga ttccaggtca tcctagagga   8340
ggcttgggaa cattgttgaa tagatttaaa tgattcagtt aagtgagtga tttaacccaa   8400
```

```
ggtttgtgtc taatttaaac aggacctata aaatatagaa caattggttt gtttcttttt    8460
tagaatattg aagattagat tttaatttga gaattttact aatttgaggg ttttatttt     8520
tgttttttaag cgttcaaaat gttgaattgt agatatgctg agtttttataa tgagcacaat  8580
gaaggttttt caactggccc gttaaagcca acccactaat gaaatgaaaa tatgaaatat   8640
tatgactcca taatatttca tggattttga agctgggctg cctgggttca aatcccatct   8700
ctgctacttt ttgggtacgt aaccttgtgc cagttactta acctctctgt gcctcagttt   8760
cttcatctgc aaaatgggag atagtgcagt ttgagtgttc ctaatctgaa atctgaaatg   8820
ctccaaaatc tgaaactttt tgaatgccta catgactgct caaaggaaat gcttattcca   8880
tggagcattt ggatttcgga ttttgggtt aagaatgctc aattggtaag taagtgtaat    8940
gcaaatattc caacatcttt aaaaacctga atccaaacc acgtctggtt ccaagcattt    9000
tggataaggg atactcaacc tgtaaataat gtctgtttca tggggttgtg atgtggagta   9060
agtgagcaaa gttgtgtaat gtgcctagct tataggaac acttagcaaa tgttggctat    9120
tccattata tataagaaat agaattattg gctgggtgta gtggctgatg cctgtaatca    9180
tagtgctttg ggaggctaag gtgggggatt gcttaaggct aggagttcaa gaccagcctg   9240
ggcaacatag caagactctg actctgcaaa aaaattcaca aattagttgg gcgcggtggt   9300
tatatgcctg tagcccttgc tactcaggag gctgaagcag gaggatcgct tgagcccagg   9360
aatttgaggc tgtggtgagc catgataatg ccactacact ccagcttggg caatagagtg   9420
agaccccaac ttaaaaaaaa gaaagaatta ttgatgggat tgtaaaggct gaatattaaa   9480
taaattcaga ggaggttttt acggaactta ttttgtgaaat atttttaaag gaaggaaggc   9540
atgtttgttt taggtttata agagatggca gatttaggaa gctcctccct actccagatg   9600
aataagccat ctgttttctt atccctttta aggatttgct tggtgggttt ccataacttt   9660
ttttttttg agactggatc ttttacccac ccaggctggc gggcagtggc gcaatcatgg   9720
ctcactgcaa cttcaatctc ctgggctcca gcagtcctcc cgcctcagtc tctcttgagt   9780
agctaggacc acagacgcgt gccaccatgc ccagccaatt tttatttatt tttttgtgtg   9840
tgtggagata gggtctttct atgatgcccc ggctggtctt gaactcctgg gctcaagtga   9900
tcttgctttg gccttataaa gtgctgggat tacagttatg agccatggcg cccagtctat   9960
gtattcttac aaaattaaat tcatgttaag tgctacacta gcagaatttt taaaatttt   10020
aaatgatgca caaatagaga agagagagtg caaattaacg agaaataggc aagactaatt  10080
tgaagaaaac tatgaagctt tactgaagga ttttttttaaa gatataaaat gctggccagg  10140
cgcggtggct catgcctata atcccagcac tttgggaggc cgaggtgggc ggatcgtgag   10200
gtcaggagat cgagaccatc ctggccaaca tggtgaaact ccgtctctac taaaatacaa   10260
aaaattagcc gggcatggta gcggatgcct gcggtcccag ctactcggga ggctgagctg   10320
gaagaatcac ttgaacccag gaggcagagt tgcagtgagc cgagatcaca ccactgcatt   10380
ctagcctggc tagagagcaa gactccgtct caaaaaaaaa aaaaaaaaaa gaataggcaa   10440
ataactagag aaaaatagtc cagaaacaga cctgaatata tataggaatt tagaaatatga  10500
aagtgtcagt gtgtaggaag gagtgaaatg aaaaaagaaa gaaaaaagga atatgttgaa   10560
agtggcattc agaaatcagg gagaaaatga tcgattacta agaatgatcc tgtaacagtg   10620
ggctgttttgg ggaaaaatac gtaaagattt ctaatttaga ctatattcaa ataatcacca  10680
aattatatag agcagggata cccaacctcc aggccacaga ccatcctgtt aggaactggg   10740
ccacacagca ggatatgaac tttaggccag ggaacattac acctgagctc tgcctcctgt   10800
```

```
cagatcagca gcagcattag attttcatag gagcacaaac cctactgcga actgtacact   10860
ccagggatct aggttgtgtg ctccttatga gaatctaatg cctgatgatc tgaggtgttg   10920
cagcttcatc ccaaaatctg aaaccatatc ctccacccct ccatttcata gaaaaattgt   10980
cttccacaaa actggtccct gggtgccaaa aagattggag accgctgata atagagtata   11040
tataatcaaa ttacagaaat aaccacactc tattcttcct ctagaatata ctgaatgttt   11100
cctaagaaaa gttgaacact catggctggt tggctgctct ctagcacatc ttgccttcgt   11160
ctctcactag ttgaatttta cacttccagg ggtcagtatg tttgttccaa atctgcttat   11220
gccagttaca tttagtactg taatttata atttaattaa acattaacta atgaaatatg    11280
actgcaaaaa gtagttgttt ttaggaaaat taagttgtag atcttgaaca aattggataa   11340
atacaaatcc ccttttcccc ttttcaccaa attactgtct tactaattgt gggcgtgaat   11400
attttgaaag attgggggtg gaaatcataa aattctttt tttttttttt ttttttttgc    11460
tcttgtttcc caggctagag tgcaatggtg tggtctcagc tcaccacaac ctctgcctcc   11520
tgggttcaaa tgattctcct gtctcagcct gccgaatagc tgggattaca ggcatgcgcc   11580
accacacctg gctactttt tgtattttta gtagagacat agtttctcca tgttggtcag    11640
gctggtctcg aactcctgac ctcaggtgat ccacccgcct cggcctccca agtgctggt    11700 attacaggtg tgagccacca cacctgacct cgtaaaattc ttaaacgatc tatactcagt   11760
tgtcttacag ttgcctagat tcttgttcca tttaagaaaa ctgaaatttg aaatcacaaa   11820
tgtggattat ggatatgatg ggttatggat atgatatatt tgtaatgaat atgcaagaga   11880
gaacatttga acattaatt agtagaaatg tacttaaga agaggccttg gttttttacc     11940
gtaatattgg caggtgacat gtatttgttt tgagtaaaaa tcaaatattt cagttacatt   12000
tttaaaatta cctgatatac tgtacttttt catgtaacca gtcagccctg agtcctattt   12060
gtgttagata agttttacc aatcccagaa ggagatagag acaagctttt tatatgcttc    12120
ggctgaagaa aacctttctc caaagaagta attatctgat cctcctataa agggccagat   12180
agtaaatatt ttagattttg caggctgaag tagaatcaag ggtaatacgt acgttctgat   12240
ataacaagag agaaaacaaa ttttgagaaa tttcttaatt gattaaattc aaaataataa   12300
acacaattta ttgaaataca ggtatactaa tgagaagaat ggagttcttt tcggagtgat   12360
aacattttct taattggagt tcagagttag tgcttcctat tcaataaata atcatcaaaa   12420
ttgattgcaa gtatttatct attaatgcag gtctgtaatg aggttttata tatttcatct   12480
ttgacatgtc ttcacacata catgtcaaat aattgatacc agcccataaa catatgattt   12540
taattgagca tattaataac tcaggaagca tttatagaat taggttttc ttataacatt    12600 tacctttag tatattattc attgctgctt aattacttcc aatggaaggt tagacagaag    12660
ctccacaatt gcactgttaa atagatactg aaatatagat atttccttgt gcattaaggt   12720
cctaaaaatt attctggaaa tgtagtgtga gctaagaaac tatatccact gcaaatttgt   12780
ttgggaatgg agatctcact tcttgtttta acttttgata gcatgtaaag tgtataaagc   12840
agctcaacgt tgcttatgat tcaaaagtta gttgtctaaa taacaacagt ttaagtttca   12900
tatataagtg ttgttctgtc ctgtaatttt aagttgaatt tactattata aaattagcaa   12960
aagctaattc tcaaagccat ttattgtttg atcatagtgt ctgaaagcag tcttattgtt   13020
gtgaaaaatt tcaatctcag ttccaagctg aaaagaaaaa aaaaaagca tgataaaact    13080 ttagtacagc tcagccgtca aactgctgtg tgcctgggca agtcaggtta ttcagcttct   13140
gtttctgaca atggttaagc ccatggcagt gaatgaaatt caccattaac atggttggtt   13200
```

```
taataattca tgataaattc agatatttt catagaatat ctattgataa aaaacatgaa  13260
taaccacctt acattttcac gttttataaa tcacccaact aagccttttt ctgcttcaca  13320
catatttta ccattatcaa tgataacgta tctgagattc cactttaggt tatatggaat  13380
tagtactttt tcaccttctt gtttgtagtt gttcaacaca gactattcat agaagctaat  13440
tcttcagttg ttttaaactt ggcactgact ccttgaataa acatctgaac agtgttgtaa  13500
catctatcaa actcattcaa aagagatgga aatctactta acctcaattg ccttggtttt  13560
tttttaaac agattattga tcttgctcct aatattttcg acttttagag caaatgattt  13620
tgttgaaagg ctaatagtct ttttttcttt ttaaattatc ttatattaaa tttaaaaaat  13680
aatttttg ttacctgtct ggagaaagcc tagagaaagg ctaattaata ctcttaaaca  13740
agtttattt ctctggatac atttcttcag cttcttcatg atttaattca cttatcacta  13800
gaatattact tttcttgctt tgctaacaaa tgagctactt agaaacttcc ctcctttaca  13860
aactttctat tccttacctt ccctccttgc tgtaatgaaa tattccactt taaattca  13920
aattttctg accattgctt tcctgtgaat cggaaatact gtgatcggtc cttagtttgg  13980
taacattgat gtattttgaa ttcttttagc acagacagac agttgactcc ttgaacaacg  14040
cagtttcaaa ctgcacaggt ccaattatat gagaattt tttcaataaa tacaatcagc  14100
agtttataca tatacaacca aacgtggatc aaaaatacgt tatttgagga aacccccaga  14160
tacagaacag tgaaattttt gtatcctctg gccactgtg ggacttgagt gtgcatagat  14220
tttggtatcc acgttgatc cacagatacc aagggatgac cgtagagtca ttgcataata  14280
aacaaaatgc ttccctatct tgtcttgata aaataatgca taccctccac tgtgccttaa  14340
aagcatgaca ttcaggctgg gtgtggtggc tcacacttgt aatcccagca cttttggagg  14400
ccagggtggg aggattgctt gagcccagga gttcaagacc agccttggca acatagtgag  14460
agtccatctc tagtttaaa aaatacaaa attaaaaaa atgaaaaaca tgacattcaa  14520
agtgcatttg ttttgttc gacatgatgg ttatgcacta ataactaatg atagttatgt  14580
actaataaaa tgtcaaaata taacgactt ttagttactg ataacagtta tgcattaata  14640
aaaaataaaa tgtcacagta tgacaatatg catgtgtggc accaaacatg ctgttgagtt  14700
ataactttgt gactgtgatt tgtgggatac tgagcagcag tggaaagcta taagccac  14760
tccactctgc cagtcagtac agtggctgat taccaattat ggataaccag aacacatcaa  14820
aaagcagttc aacaaggatc agaataataa catgtaagta ccatttatta agtagttatg  14880
tgtaaggcac tgtgtcagac tgtataatgt acattattta accttcaaaa gattgagagg  14940
gaagatccct tgagtctggg aggtcgaggt tgcagttagc tgtgattgca ccactgcact  15000
ctagcctgag tgatggagcg aaatcctgtc tcaaaaaca aaacaaaaca aaacaggcct  15060
ggtgcggtgg ctcatgcttg taaatcccag cactttggga ggctgaggct gaggtcagga  15120
gtttgagacc agctgggcca acatggcgaa accacgtctc tactaaaaat acagaaatta  15180
gttggtgtgg tggctcacac ctataatccc agctactcgg gaggctgagg caggagaatt  15240
gcttcaaccc aggaggcgga ggttgcagtg agccaagatc atgccactgc actccagcct  15300
ggatgagagt gagactccat ctccaaaaaa aaccaaaaca aaacaaacga aaactacaaa  15360
agattgtctg aagccagcca cagacaatag taaatgaatg agtgcagcta cattctttct  15420
tatttatgga tgcagaagtt tgaatttcat ataatttc cgtttcactt atatataaat  15480
tatatattat atattacata atatatata tatattaaa gataatataa tatatattag  15540
ataatatata taatataaga taatatatat tagataatat atataatata agataatata  15600
```

```
tattatataa taaattaaa atatattaat tataatatat aatatatgac atatatatgt    15660
tatatattgt tatatataat atgtgtaatt atatattata atatatgata tatatataat    15720
ctatcatata tcatatatat aatctatcat atatcatata taatctatca tatatcatat    15780
catatataat atatatcata tcatatataa tatatatgat gtatagtata tatgatatat    15840
aacatatata taatatatga tgtatagtat atatgatata taacatcata tatactatac    15900
gtcatatata atatgacgta tagtatatat gatatatgat atatatacta tattgtatat    15960
gatatataat atgtattgta tattatatat aatatatata taaggcacag tggagggtat    16020
gcattatata taatatgtat tatatatttt atatattata atatatattt tatatataat    16080
atattttgta tattatatat tttatatata atatatttg tatattatat atttatata     16140 taatatattt tgtatattat ataatatata aaatgtatat tatatataag taaagtatat    16200
attatatata atttttatat atacttttt ttttttttt tttttagact ggatcttgct      16260
ctgtcaccca ggctggaatg gagtggctgg gactacaggt gtgtgctatc atgcccagct    16320
agtttttttt ttgtttttt tttgtttttt ttaattttt tttttttt aagacggagt        16380 ctcgctgtca cccaggctgg agtgcagtga catgatctcg gctcactgca agctccgcct    16440
cccgggttca caccattctc ctgcctcagc ctcccaagta gctgggacta caggcaccca    16500
ccacacgtcc agctaatttt ttgtattttt agtagagacg gggtttcact gtgttagcca    16560
ggatggtctc gatctccgga cctcatgatc cacctgcctt ggcctcccaa agtgctggga    16620
tcacaggtgt gagccaccgc acccggccta ctttttatt taacttttt tttttttt        16680 gtagagatgt ggtctcactg tgttgcccag gctggtctca atctcctggg gtcaaacagt    16740
gctcctgcct cggcttccca aaatgttggt attacaggta tgagccactt tgcctggcta    16800
tcttataaat aattttgatg ttaggaattt ttagttgctt ttatttat tttgttgtt        16860 ttaaatattt attaatagaa gcaaggggtg gataaatctt ctagatcaaa ctcttcctta    16920
aaatagttct gcttttggta ggattccaga ttttcctagt tttgttaagt gtttctaatg    16980
atgtttggca taggtgttaa cttcatgggc ctgttgtata caaaccaatt ttttcttgc     17040 tctgagtgaa cagtaacaga acctggtagg tgagtcacac tgatactgca ttcactgaag    17100
ttactaagct gaatgataag agatgagaat cctttgcatt tgtattcaaa tcaagagttg    17160
tagaatttga aattcctgtt ttgatgaact atgtgaagca tgctgtcatt cttctctgct    17220
agtctatgtt gatgatgtca ttaaactagt cttttgacttt tagttcttgg cttaaaatat   17280
tggaatgatt atataataaa taggtttatt tcatgtggaa aaggaataat gtgtttgccc    17340
tgaaatagtc tgatctgatc aggaggatat tatgctgagc atggctggaa ataaatttgt    17400
agcaccaatt aaatacactg tagcagctct gagagggaat aaaagtaaaa tataaatagt    17460
aaatatgaga gaaagtgact atgggatcta actatgtaag agcagggtgg gagtatgggt    17520
agatacgtac atgccccta gattttagga aagcatattt caagaagtag agaagacatg      17580
gatatcaatc agtggaaatc gtatactaaa acggaagtca gtgaaaaaaa aagactgctc    17640
tcaaactaaa gatagatggt tgcttctaat aggtaggtat tcagattcga ttaagaaatt    17700
agaaggccgg gcatgggac tcaggcctat aatcccagta ctttgggagg tcatggtggg     17760
cagatcactt gagcccagga gttcgagaca agcctgggca acctggtgaa acccatctc     17820 cacaaaaaat accaaaatta attagcaggg tgtagaggca catgtctgta ttcccagcta    17880
ctcaggaggc tgaagtgaga gaatcacttg agcctgggag gttgaggcta cagtgagccg    17940
agatcacacc attgcactcc agcctgggtg acagagtaag accctatctc aaaaaacaaa    18000
```

```
ttttgaaaat atacagaagt atagaaaaac tgaagtaatt taatttgtgt taaaatctgt    18060
ttggtattaa aactaatgtt tggccgggca tggtggctca cgcctattaa ttatcctagc    18120
actttgggag gccgaggcaa gtggattgct tgagctcagg agttcaagac cagcctgggc    18180
aacgtggcga aactccgtct ctacaaaaaa tacaaaaatt agctgggcat ggtggctcac    18240
gcccgtagtc ccagctcctt tgcaggctga ggcaggagga tcacttaagt ccaggaggtg    18300
gaggttgaag tgagctgaga tcgcacctct gcactccagc ctgggtgaca gagtgagacc    18360
ctgtctcaaa aacagacaac gacaaaaaac cctaatgttt tatgaaaaag ctctttaatt    18420
tttcgtgacc aaactgctat tctctagacc tacactgtcc aaaatgatag ccattagcca    18480
tgtgtgctac tgtgttggac agcacgtatt tagaacattt ccaacatcac aaaagttcta    18540
ttgcagaatg ctatgaaaat gagatacact ttcattagaa aagctagtaa aaataagtag    18600
gggtaatggg gtactttgac tatccagaaa ttttactaag gaagaattag atttttataa    18660
tactgggaca ttagtgtgca cttttttttgt cgtaattgca ttttgttttt tattttgaaa    18720
taaatacatg tacagaaaaa ttgcaagaat agttacagag tcttttcgct ccctgaacca    18780
ttagagagtg agccccatca gccccaaata ctttaatgag cattaaatct ggagtttggc    18840
cgggcacggt ggctcacgcc tgtaatccca gcactttagg atgacgaggt gggcagatca    18900
tttgaggtca ggagtttgag accagcttgg ccaacatgat gaaaacctgt ctccactaaa    18960
aatacaaaaa aatgagccga gcttggtggt gcacacctgt aatcccagct actcaggagg    19020
ctgaggcatg agaatcactt gaacctagga ggcggaggtt gcagtgagct gagattgtgt    19080
cactgcattc cagcctgggt gacagagtga gaccctgtct ccaaaaataa aataaaataa    19140
atctggagtt taataccagt acagtactac cagcttatct tcaggcccca ttcgagttat    19200
tctagttgtc cccaaaaggt gaaggatcca gtttaaaatc acacattgca tttagttgtc    19260
atgtctgtct ttgacttgat cgccttgaca cttttgaaga ttacaggctc attattttga    19320
ggaagtcatt aacatggacc tgatgtttct tcatctttag attcagatta tgcatttat    19380 cagaattgcc acataaattg tgctgtgttc ttattttatc catccaggta ctacataatt    19440
tccatgtgtc ccattttttct tgatgttaac cttggtcact tgattaagat tgtgtctgcc    19500
agttttctct accatacatt taactatttt ttcctttata atcagtattt tatgaggagg    19560
aggaggaggt actttgagac aatgtaagta tcccattcct catcaaactt tcaccttcta    19620
gttttagcac ccattgaaat ttttttgctg gattattggt atgatggctg ccaaatgatg    19680
attttctaat ttcatcatcc cttctacatc cattcattga catttcattg aaaggaaaaa    19740 ctgtttttctt cccatttatt taacttatat caatatggac ttacggattc atattttatt    19800
caataagtta tctattagtg tactttggta ctttgatgct gagtttgtcc cagatttggt    19860
cagtggaaac cctgtcaagc tggcttctgt atccttttga cattgtccta tcattctttg    19920
atcactttcc tctttctggg accagatatg atcaaagccc ttcttatact tttcctgccc    19980
tacctctgga atcatttcac caaggtaccc tggttccctt tattgaagaa tgtatttaga    20040
ggttaggtct ggacagtaga tggcattgtt ccactgaggt gtcactgctc ctagactttc    20100
tcagcagaca gagctagagc atatatgcat gtatatacat acacaaacat acatccacac    20160
acatagactc attttttttat ttcttgctct gtgtgtgtgt gtgtgtgtgt gtgtgtgtgt    20220
gtgtactgtg agttcacact ggtacctagt acctcaacac ctcagagttc attttatttt    20280
tcttcctttt tgtatttgta actcccttct ctgacagaga aactgggccc cagttttct    20340 taatatatta ctatttactt aattgatcaa tccccttgaa tgtgcccagt ctttcctttc    20400
```

```
cttatcagat catgtgcatg ctaaccttgc tcagccccac ctaatggttt ttagactgaa    20460
ttatttggag acgaaaaaag tacggttgat gctcattagt cacagatttt ttttatttgc    20520
aaattcacct acttgctaaa atttatgtgt aaccccaaaa tctgtactcg tagcactttt    20580
atggtcattc atgaacacgt acagaagggt aaaacatttg agtcgctatt gggtaacgtg    20640
tattcctagg tgaggccaag caaggcagtc tactgccttc ttctttgagt cctcatacta    20700
taaatagttg tccctttgc agtttactta gcgccacata ttttgcattt tgacttcttt    20760
tacttagcat gtgttttcaa gttccatcca tgtttatagc atgtatcagt acttcattct    20820
tcttcttttt tttttttaaa gagttggggg tctcactgtg ttgcaggctg aatacagtg    20880 gctattcaca taggccatca tagcatgctg tagcctcaaa ctttcactgg gctcaagtaa    20940
tcctcccacc tcagcctccc aagtagctga gattagaggt gtgggccact gtaccaggtt    21000
ccttcctttc taaggctgaa taatagttca ttgtatgtat aataccacat tttgtttatc    21060
tattcatcca ataatgggca tttaggttat ttccaccatt tggctatctt ttgaaaatct    21120
tttcatgtgc ttgttggcca ttagtatata ttctttggag aaatgtctct taaattcttt    21180 gcctatttt taaattgggg ggaagttgtc tttttttgtt actgaattgt aagagttctt    21240
tattctgata actagaccct tatcagatac atgatatctg attaacacat agtttcttgc    21300
atcccatagg ttgtctttca aaattttgac gaattccaat ttgtcagttt tgttgcttat    21360 gattttagt gtcatatcta agaatccatt ttcaaattca gtgtcatgaa gatttaccta    21420
tgttttcttc taagaatttt atagttttag accaagcgcg gtggctcatg cctgtaatcc    21480
tagcactttg agaggctgag acaggcggat tgcctgagct caggatttca agatcagcct    21540
cagcaagatg gtgcccatct ctactcaaat acaaaaaatt agcctatggc gtgtgcctgt    21600
tcagctactc gggaagttga ggcaggaaaa ttacttgaac catggaggca gaggttgcag    21660
tgagccgaga ttgcatcact gcactccagc ctgggccaca gagcgaaact atgtttccaa    21720
aaaaataata acaataattt tatagttgta gcttttaag tttttaatcc actttgattt    21780
ttttgttttg ttttgttttt tgagacaggg tcttgctctg tgctgcaggc tggagtgcag    21840
tagagcagtc ttggctcact gcagccttga cctcctgggc tcaagctatc ctcccacctc    21900
agcctcccaa gtagtgggga tcacaggctt gtgccaccat gcctggctaa ttttgtatt    21960 ttttctagag atggggtttc actattattg cctaggctgg tcttaaactc ctgggctcaa    22020
gtaatccatg cccaccttgg cgtcccaaag tgctgggatt acaggcgtga gccaccactt    22080
tcagtcccaa gttaattttt atatatggta tgaggtaagg attcattctt ttgcatgtga    22140
atatccagtt gtcccagtgc catttgttga agagcctgtt cttttcccat tgaatgttgt    22200
cttagcactc tttccaaaaa ttagttgacc atagggcatg gtggctcatg cttataatcc    22260
aagagctttg gaaggcccag atgaaaagat tacttaaggc cagtatttca tcaccagcca    22320
gccatggtgg tgtgtgcttc tgggaggggtg aggcagaaag atggcttgag ctcgggtgtt    22380
gaaggctgca gtgagctctg attgtgccac tgcactccag cctgggtgac agagtgagac    22440
actgtctcta aaaatagaa taataaaaat cagttgacta tagatttgtg gatttatttc    22500
tgaactcatt taaaactatt ccattgatct atatatcact ccttatacca ttaccacaca    22560
gctttggtta ccggtgcttt gcaataagtt ttgaaatcag gaagtatgag ttctccaact    22620
ttgttcttcc ttttcaagat tgttttggcc attcggagtc ccttgcaatt ccatataaat    22680
tttaggatca gttttttat ttctttttt tttttttg agacagagtc tccctctatt    22740
gcccaggctg gagtgcagtg gcgtggtctt ggctcactgc aacctccatc tcccaggttc    22800
```

```
aagcaattct cctgcctcag cctcccgagt agctgggatt acaggcacac accatccgcc  22860
caactaaatt ttgtattttt agtagagatg gggtttcagc atgttggcca ggctggtctc  22920
gaactcctga cccccaagtg atccgccggc ctcggcctcc caaagtgctg ggattacaga  22980
catgaaagct ttttatttt tgaaaaaata aataaataaa taaagacata agatgtcttt  23040
ccatttattt agggtctcct tgttcttgga ggtagatttt ctctgatcta ttttcattga  23100
gaccttgggc cttaagagag ccacaatttc atgagagatt atttctctgg agcccttcct  23160
acccttctcc tatttcctgt ctcctttcct cccttgttat tcaaaagtct taacaaatgc  23220
tcctgggccc aatacagagg tcagctcaca cttccagcct tagctttggt tcacttttg   23280 ctttcttgcc actggtagtt ttccctcctc tcttaagaac ttagctaagc ttttcaaagg  23340
atgtttgcat ttatccaaca tttctagatt ttggtagctg gagagtttta ataattttct  23400
agattgctgt tttactagat tagaaaaaga tagagctggg tgtagtggca catgcctgta  23460
atcccagcta ctccagaggc tgaagtggga ggattgcttg agcctgggag ttagaccaac  23520
ctgggcaaca tagtgagacc tatctcaaaa aaaaaagtaa gactttaggg cgcagtgtaa  23580
tcccagcact tttggagacc gaggcgggtg gatctcgagg tcaggagttc aagacaagcc  23640
tggccaagat tgtgaaaccc cgtttctact aaaaatacaa aacttagctg ggcagagtgg  23700
caggcgcctg taatcccagc tactctggag gctgaagaag agaatcactt gaacccgggt  23760
ggcagaggtt tcagtgagcc gagattgcac cactgcactc cagcctgggc gatagagtga  23820
gactctgtct caaaaaaaaa aaaaaaaaa agacagtgt ttttaaaga tggagtttag  23880 tatacagaaa tattgggtgt caggcaaagt attaattact ttgtacgtat tctcttttcc  23940 ttctttttt taaaacgaga cagggtgacc aggctaaact ctgactgttg ggctcaagtg  24000
atcctgcctt agcctctgga gtagctgggc attacaggca catgccactg tgcccggcta  24060
catactcact tataaaactc tatttttaaa tgacagctcc tctttacaaa atagatcagg  24120
agagcgattt tcctgtctgc ttcctgagga agcaaaaagg cagaaacatg gtgagcagca  24180
agaccagtgg ttgccgtagt aagcatggga cttcctatga atggctctgt taacagtagg  24240
ggatggtaat gttctttgat ttgtggactc tgtttgattt gtggacaagg ttttatttcc  24300
tgtctttggg gtaggagggt ctgccatatc cacaaattgg ctcttcccat tgttgtatt   24360 catttagtta gaccatgatt ggaaagcctc actggctgtg cacattgcac catacttagg  24420
aatatatgac ggttatacat ttcaaacagg gctttaaaac cttccattca gctccttttg  24480
gataaagctc ttttcctcat gtggttgttg acatacatga attataggct ttgtttagct  24540
agtgggtaag agcagatttt ggagtcatgt acacctgggt ttgagtttca gtcttgccat  24600
gtaccagttg tttgtggaca agttatttat taataactac tctgtaccat agtttcttca  24660
ttggtagtat cttcaaaatg aagtatctat ttcctgtgct gttttgaagg taaccttaaa  24720
taatgtgcat tgtacaattt gatacagtgt ctgacacgta gtaaatactt taatatataa  24780
tacctgtttt tattctgatc cttgttgagc tgctgctttt tgatgtgttg attatatata  24840
attggtaatc atccatttta ctgacatctt ccaagatttg accaagttga ttgtctcaaa  24900
tttccaagca gaaaaagtac ccagaaaaca gaaattaagc agttattaaa gaatcgaata  24960
gcaatgatca ttacgacttg tgcttaataa gaaatgtggg ccatgtctgc ctgagccttt  25020
atttaatgca ttttaaaatt tgctgggttt tttcctccct ttaaacctta ctatcaggtt  25080
cagtaataag ttaaactaaa aagaaacgga tgccttagaa taaagaaaga ttcaaattaa  25140
taggatatat aatggccttt catggtggtg gaatttctgt gtgttttgaa ctaagggaaa  25200
```

```
gacttaaagg aagattgcct acagtgtact ggacactttg ctaggctctg tggatattat    25260
caagacacag tccttaccct caaggatctt tttatttttc ttttagagac gggatcttgc    25320
cctgccaccc aggctggagt gcagtagcaa aatcatagtt cactgcaacc tccactcact    25380
ctcaaggatc ttactctcag ctgggggagg ccataaacag ttaaagtagc ttactctcag    25440
ctgggggagg ccataaacag ttaaagagtt aatgattgac tctagggcta agggaaagaa    25500
agtaattggg tcaactagga tttctagctt ggcaaggggg tagacctgga ttggcaaact    25560
acaacccaat gccagttttt gcatagccca caaactacaa atgtttctta catctttgag    25620
tggttggaaa aatatcaaaa gaagaatact attttgtaac gtggaaatta tataaaatta    25680
acatttacat gttcataaat aaggttttat tagaatatag ctatgctgaa actacatatc    25740
tatgactgct tttttgtcac aacagcagag atgagtaatt gtgacaaagg ctgtttggcc    25800
tgcagagcca aacatttact gtgtggctct ttacagaaaa agtttgctaa ctcaatgagt    25860
aggtggtaat ttttatccat tgaaacaagc aattaaggaa gaacagatac aggagaagat    25920
aacatttctg tgagtgttga ttatttgaat cagaggtact tgtgaatatg caggtctaga    25980
aggcaaggga atttataggt ttggagtttg gaaagagctt gaggctggaa atggatgtgg    26040
gaggaaagga ggagatcaag aagactggat ggaggagtgc aattttttagc cctgtctgca    26100 cattggaatc acctgtagtg cttaaaacca aacaaaacca gacagacatt tccaggaacc    26160 caacccaac tccctctttc ccaagattat gatgcacctg agctggactt gggcaccaga    26220
attttttgaa agctcccca gcaactctaa tgtgcagcca ctggtacaga gtgagaagat    26280
tggaagatgg gacaccagga acaccaacat ttaagggata gttctaggtg cttctgctga    26340
ggagaggaaa ttctgaggga gtgatgatgg gaattttagg gtggtcagat cctgtaatt    26400 gagatcattg ttgactgatg aatcaagagc agtttctgta gaggccaggt gagggtgtat    26460
gtcagaggcc cctggtttga ggtgggagag tatgaactat tgagaatatt gaccgggagg    26520 aaaggggga aagtgatggc tgggatgggg ggcattggga atgtagtttg ttctagagag    26580 gttttttaa gatgttaaag ccttgaggct atttatgtgc tgagggagtg agtactcaga    26640
aagaaagcct ggaatggcag tatcagatgc caccattcag ttttcatgat ggagtgaagg    26700
gctagatttt gaatagttct tggaataatc ttaatattgt aacctttttg gaactgtttg    26760
cttaatgtgc tttcttcatt taggtgcatt acattgtacc tggaaagaga aatggaccca    26820
ggcattgaga agcaaggcca acaactctgc tttgcttgcc cggttactgt cgttctgtct    26880
gggacattgg tctcatctct gaaagcagga gggcaaactg aatgggctct gtagtctctt    26940
ctaaaagttt ttagtttaaa ctattaatag tacaactttg atttaacaaa tgaggaagct    27000
gagcttacga gatgtctgtg aagcccattg tctgatcttt tatttcctta gtacctggga    27060
atgcgctttt tttttttttt tttttgaag aacaccaaca gttgttcacc cttccttgaa    27120
tttgggtaca ctgtatatac agagtatacc aatttagcct gccattagaa catgtcttca    27180
cgagcaaaat ctagtataaa gtcttacttt aatatttct ttattatgta taaataatag    27240
atggttgtta tggaatactg gatagtacaa agtttagaa ttttaacat tttggtttat    27300 ttattgggac tctttttcc ccccagtgat tcttgtttct ccaacaatgt gaatgcgcac    27360
tccattcagt gtgaacgtga atgttaattt atgtgccagc tggattctac aggaagcaga    27420
cacagatggg gttggagggg caaagggctt attagaggag taatgcctgt gaagaaaagg    27480 ggaacgaac atgtttgggt ataggagcc atcagactgc agtgcacacc tgacgaagtc    27540
tctgcccacc cagattgcct gatagaggaa taccacaaga ggtagaaatg gctaggctct    27600
```

```
tgtactacca ctttgcacag tcattgacta gagatagatc tttgatcaat gtagagattt    27660
tcagccttgg cattgttgac atttgggact ggatactttg ttataggggg ttgtcctgtg    27720
atttgtaaga tgcttagcag catcctaggc ctctatcccc tagatgccag tagcccagcc    27780
tccctgctat tagttgtgac agtcaaaact atctttagac actgccatat gttccctagg    27840
gaagggccta atggtatata aacaacccta tggtggcata gtccaagttt tgggacaggg    27900
aggagtgttc tatactaccc ttactggaaa gacctatgag ctattcagaa atctgaacta    27960
tttaagatgg agctttgttc tgtggctcct ggaattttaa gcacacccct gtgaaacatc    28020
ttgttaggat atactccact ctccaaaaca atccataatg tttaaatagg ctgtttttat    28080
tgattgattg attgattgat tgagatggag tctcactctg ttgcccaggc tggagtacac    28140
tgtcacgatc tcggctcact gcaacctccc cctcctgggt tcaagcaatt ctcctgcctc    28200
agcctcccaa gtaactggga ttacagacac ccaccaccgt gcctggctaa ttttgtatt    28260 tttggtagag acggggtttc accatgttgg ccaggctggt ctcgaactcc tgacttctca    28320
ggtgatccgc ctgcctcggc ctcccaaagt gctgggatta taggcatgag ccaccgcacc    28380
tggccttatt tttcttttg agatggagtc tgactttgtc gcctgagctg gagtgcagtg    28440
gcgcgatctg ggctcactgc agcctctgcc tcccgggttc aagcaattct acctcagcct    28500
cctgaacagc tgagattaga gatgcgtgcc accatgccca gctaattttt gtatttttag    28560
tagatgcagg atttcagcat gttggctagg ctggtctcaa actcctgacc tcaagtgatc    28620
cacccacctc ggcctcccaa agtgctggga ttacaggcat gagccaccgc tcctggctat    28680
tttcttttga gactgggtct cattctgttc ccaggctgga gtgcagtggc acaatctcag    28740
ctcactggaa actccacctt ctgggctcaa gcagtcctcc cacctcagcc tgctaagtag    28800
ctgggattat aggcatgtgc caccctgcct ggctactttt tgtggagatg ggattttgca    28860
tgttgcctag gctgggcttg aattcctaag ctagaacaat ctgctcaggg atgttgtata    28920
tttctaaagg tattttttcct tttgttgcag gtgacacaac taaaaaaaaa caaaggtatt    28980
tatgaaattc cactgagtgg taatggatga tgcagttcaa ataactaagg taagagaaat    29040
aaaaccagaa ctgtgaggag cttttgcca gccaagtagt gtccttaaat aaagctaaca    29100
tcacatgctt tcctgcttca tttcgtttct aagctgtaag agtagcttat ttttttatta    29160
ttataaacat tgtaattatc ctttaagata cttcttaacc tgattatgaa tcagaatcac    29220
ttgaagagct tttttttttt aaaaaaaag accaaagtca ggctgggcat ggtggatcac    29280
gcctgtaatc ccagcacttt gggaggccga ggcgggcaga tcacttgagg tcaggagttc    29340
aagaccagcc tggccaacat ggtgaaaccc catctctacc aaaaatacaa aaattagcca    29400
gatgtggtgg catgtgcctg taatcccagc tactcgggag gctgaagcag gaggatccct    29460
tgaacccagg agacagaggt tgcagtgagc tgagatcgca cactgcattc cattctgggc    29520
accaaagaat gaaactcctt ctcaaaaaaa taaaaataaa aagaccaaag ttaatgccct    29580
gccagcattg aattaaagct tcttgagtag atcacagatg atctccaagt tttttaagtg    29640
ggaatgtaaa ccaactctat agttttagaa aactctttgg caatatctgc aaaacataca    29700
cgtatctaat aacccaggaa tttcaattct aggtatccac ctttgagaaa tgaaaaatat    29760
atgtctacac aaaagtgcac atacaaatgt tcactgcagc tttatgtatt atagccagaa    29820
aaactgtaac ccaatcaggt gtccaaaaac aggagaatag ttaaacaaat tgtgatatat    29880
ggtcaggtgt ggtggcttac acctgtaatc taagcacttg ggaggctaag gcgggcagat    29940
cagttgacca gcctggtcaa catggtgaaa ccccatctct actaaaatta caaaaatgag    30000
```

```
ctgagtgtgg tggctcacgc ctgtaatccc agctactcag gaggctaaga caggagaatg    30060
gcttgaagcc aggaggcaga agttgcagtg aggtgagatc acgcccctgc actccatcca    30120
atctgggcaa cagggcgaga ctatgtatca acaacaacaa aaaattgaca tacactattg    30180
ataacatgga attttattca gtaatagaaa ggaacaaact accagtagac atgacaacat    30240
ggatgaatct cgtagataaa aggttgagtg aaagaaacca gatggacaag aaaaagtaga    30300
tgtagcagaa ttaccgagta aaactaaact acagtgataa aggtcatatc cctacttcct    30360
ctgacaggag gtgggaggtt gtgactggaa agaggtatga gagagcctct gcagcaccga    30420
aaaggtgttt tgttttgttt tttgagactg agtcttgcta tgtcaccagg ctggagtgca    30480
gtggtgtgat ctcagctcac tgcaacctcc gcttcctggg ttcaagcaat tctcctgcct    30540
cagcttccca gtagctggga ttacagaca cgcgccacca cgcccagcta attttgtat     30600 ttttaataga cagagtttt caccatgttg gccaggatgg tctcgattgc ccaacctcat     30660
gatccgcctg cctctgcctc ccaaagtgct gggattacag gcatgagcca ccgcgcccgg    30720
cctgaaaagg ttttacatct taatgtgttc atatacatac ttttctcatg gtaaaatata    30780
tataagatta aatttatcat tttaactact tttaaagtat acaattcatt ggcattaagt    30840
acattcctgt tgtgcagcca tcaccactgt ccatctccaa aacttttca tctccccaaa     30900 ctgaaactcc atatccatta aacactaact ccccatttcc tcctccccca gctgctggca    30960
accattctac cttctgtctc tatgaatttg actataatag ttacctcgta taagtggaat    31020
catatttgtc atttgacatc tggtttgttt cacataggtt tatttcacaa aggtatcttg    31080
tttatttcac ataggatgac cttgttttca agtcatccat gttgtagcat atatcagaat    31140
ttacatttta tggttgaata atattctgtt gtatgtttat accactttat gtgtatccat    31200
tcattcactg atggacactt gggctgcttc cacctttgg ctgttgtgac taatggtgct     31260
atgaacatgg gtgtaggctg agtgtggtgg ctcacgcctg taatcccagc actttgggag    31320
gccgaggcag gcggatcact tgaggtcagg agttcaagac cagcttggac aacatggcaa    31380
aaccccattt ctaccaaaaa tgcaaaaatt agccaggcat ggtgctgcat gcctgtaatt    31440
cccagctact ggagggctg aggcaggaga atcgcttgaa cctaggaggt agaggttgca    31500
gtgagcccag atggtgctac tgcactccag cctgggtgac agagtgaggc tgtctcaatt    31560 gaaaaacaa aacaaaaac aaaaaaaac acatggatgt acaaacatct gttcgagtcc       31620
ctgcttttag ttcttttgag tatattctta gaagtaaaat tactggatca tatggtaact    31680
ccatgtttca ttttttgagg aatcaccatg ctgtttttca cagtactgca tcatttt       31737
```

<210> SEQ ID NO 21  
<211> LENGTH: 31737  
<212> TYPE: DNA  
<213> ORGANISM: H. sapiens

<400> SEQUENCE: 21

```
atattcccac cagcaatgca caagggcttc aatttcttta cattctgctt tttggtgacc      60
tccataattc taaattatat gtatatgctg tttcttctta attcttttat taataaaaaa     120
gacaacataa ttcttttgcct ctccagtgtg aaaaaatggg aatttaccctt acactatccc   180 cccattttaat atttgtatta tttcctgttc tgctgctgtt tattagtttc ctcagacttc    240
tgtaacaaaa ctccatgaac tgggtggctt aaacaataga aatttattgt ctcagagttt    300
tggaggctag aagtccttgcg ggctgtgcgg gagaatctgt tctatgatt tcttctagct     360 tctggtagcc tcaggcatcc cttacattgt agatggcatt ctctctgtat cttcagattg    420
```

```
tcttccctct atgcatatct gtctcttgtg tccaaatttc cttttcaaa ataagtgcgc      480 tagtcattgg attagggacc accctaatga gctcatctca acttgatcat atgcaaaaat      540
cctctttcta ataagttca cattcacagg aactgagtag ggggttacaa ttttaacatc      600
ttttagggga cacaattcag tctgggtgac agaacaaatc tctgtctcaa aaacaaaaca      660
aaacaaaccc ataaagtgat tacatttcta actttcggaa gtactcttca acctcctttt      720
tttaggttaa ttttcagcac tctttccttc tttcttcctt tccttttcc ttttccttt      780 tttttttttt tttttttttt acttttatt tttttgagac agagtcttgg tctgtcgctc      840
aggctggagt acagtggtgt gatcttggct cactgcaacc tctgcctcct aggctgaagt      900
gattttcctg cctcagcctc ccaagtagct gggattacag gcacccgcca ccacgcccgg      960
ctaatttttg tatttttagt agagccaggt tttcaccttg ttggccaagc tggtctcaaa     1020
cttctggcct caagtgatcc gcccgcctcg gcctcccaaa gtgctgggat tacaggcata     1080
tgccaccaca cctggctaat ttttgtattt ttagtagaga cagggtttca cctgttggat     1140
ctcctgacct catgatcgcc ctcctcagcc tcccaaagtg ctgggattac agtcgtgagt     1200
gccgcgccca cttaatattt atgttattat agctaagtaa atattgttca ctgtcaggcc     1260
aggcagcatt ttctgggttt ttatttcttt ctctgtaggt tcaatgtcat agaccctggg     1320
ctattcaaat gagaaaatga agaaaaagtg aattctctct ctgaaactat cagttgcttc     1380
caatcatgtc tttatatttt atatttgaac cgtaactttc cataaaatt ttctccctgg     1440 agtttctaat tttcttgtct atttgcctgt tattatagtt tcacttttca ccaagatctc     1500
aatcatacac tccagcctgt caaggctagt tcaaaccata cactgtggcc caaatttagg     1560
ctagtcgtac actccaatcc gagaccagtg ggcactgttt tttaggctgt ctacacagtc     1620
atattggtat tttccttact ggttttttctt tgacgggggt gcaggggagg ttgggtccac     1680
tgatcttgga tatcagtctt tcttttgtatt tgtttttttaa atcttactag aggctagggg     1740
gcatggtggc tcatgcctgt aaccccagca ctttgggagg ctgaggcagg tggatcactt     1800
gaggccagga gttcaagacc agcctggcca acacggcaaa accctgtctc tactaaaaat     1860
acaaaaatta gccaggcgtg gtggtgggtg cctgtaatcc tagctagtcg ggaggctgag     1920
gcaggagaat tgcttgaacc cgggtggtgg aggttgcagt gagccaagat cataccattg     1980
cactgcagcc taggcgacag agtgagactc catctcagtc aatcaatcag tcaatcaatc     2040
tatcttacca gagttcattc tcaagtcact tactgagaga aaaggtacct ggcagataaa     2100
ttttgactct ttctggtatc cgttttttgt tgttgttgtt gttgttgttt gtttgtttttg     2160 gagacggagt ctcgctctgt tgcccaggct ggagtgcagt ggcgcgatct tggctcactg     2220
caagcttcgc ctcccaggtt catgccattc tcctgcctca gcctcctaag tagctgggac     2280
tataggcgcc tgtcaccacg cctggctaat ttttgtatt tttagtagag atggagtttc     2340
actgtgttag ctgatctgcc ctccttggcc tcccaaagtg ctgggattac aggcgtgagc     2400
caccgtaccc agcctctggt gtctgttttt aagaccctca tgttggagtg atggtttggt     2460
tgactataga attctaggtt gcctattatt tttcctcaaa actttgaagt cattgctcca     2520
tttcttctga catcccttgt tgttcatgag aaatagaaag tttcatatag gaaattaatt     2580
tttcttcttt tctggaagct tttatgttct atatagtctg gaattccata gaggtgtact     2640
tggtgggccc cttaatagat ctgcagactc atagctctcc attttttggt tcttttctgt     2700 cagcagctt ctgatattga gcttcctggg ttgttcatat aatgttctta tctattctgt     2760 ccttttaaa aactctttgc ttttggttgt tttcctggag attgtcataa ctttatctcc     2820
```

```
taatctttt   ttctctcttt   tttttttttt   ttttgagaca   gggtctcacc   ctgtggccca    2880
gactggagtt   cagtggtgcc   atcacagctc   actgcagcct   cgagctccca   ggttcaagca    2940
atcctcccac   ctcagctttc   caagtagctg   gaactatagg   catgcgctac   tacacccagc    3000 taatttttt   tattttagt    agtgacaggg   tctcactgtg   ttgccctggc   tggtctcaaa    3060
ctcctgagct   caagtgatcc   ttctgcctct   ggggactaca   ggagtatgcc   accacacctg    3120
gctaattttt   gtatttttta   gtagagacag   ggtttcacca   tgttgccagg   ctggtcttga    3180
actcctaggc   tcaagcgatc   cacctgcctc   agcctcccaa   agtgctggga   ttacaggtgt    3240
gagccaccac   acctggcctg   ctgttttttc   ttttactgtt   tcttaaacta   gtcttctccc    3300
cgctttcttt   tcctgtatga   acgttaatag   ttgaccacag   cattggccct   gtaatactct    3360
tttgttcttt   gtatttcttc   agtttttattt  agcctctgtt   gtgtgttcac   acattccttt    3420
ttatttgctt   gatgtgtgtc   ccatcccttc   ttttgaacac   tgtgtggtca   ttaatgagag    3480
tgtggtagga   ttttatgtac   tgatatttaa   gaaaatgacc   ataaaatgtt   cttggagatg    3540
gtctttaaag   accgggcatg   gtagctcatg   tttgtaatct   tagtactttg   ggtggctgag    3600
gcaggaggat   tgcttgagct   caggagtttg   agaccagcct   gggaaacatg   gggagatccc    3660
atctctacaa   aaaatgcaca   aattacccag   gcgtggtagt   acatgcccgt   ggtcccagct    3720
attccagagc   ctgaagtggg   aggattgctt   gagcccagga   gctcgaggct   gcagtaagcc    3780
atgtttgcac   cactgcactc   cagcctgagt   aacagaacaa   gaccctgtct   caaagaaagg    3840
aaaaaaaaat   tttaagtagt   tgattaaaag   aggtctttag   ggtgggctct   aatttgatgt    3900
gactggtgtc   cttgtaagaa   aaggaaattt   gtacacgcag   acatcagaaa   caaatacaca    3960
gaggaatgac   caggtgagga   tacagtaaga   tggtggccat   ctgcaggcca   aggagagagg    4020
tctcatagga   aaccaaactt   gctgacactt   tcatcttgga   cttctagcct   gtacagctgt    4080
gagaaaataa   atttctgttg   ttgaacccac   cgagtctgtg   atacttttat   ggcagcccta    4140
ccaaatgaat   atagacattt   aagaaggctt   ggtgcattgc   agcatttggt   aaattattat    4200
gcatttcgtt   gtattgtgca   tgtagtgcca   ttactgagaa   tagcaggatg   gatgggaagc    4260
atcgagacaa   agtaaaatac   gagctggcca   ctaacatatg   gtatgatttt   gtggtaggtg    4320
aaaaaaggat   tccagaagta   gagtgcttat   gaaagaaaag   ctcagtagtg   taagaatttt    4380
acaccagttt   gactttaaca   gagagtgagt   tcaacagtga   aagatgaggt   tgcaaatgta    4440
gtttggggac   ccatattaat   ttcctggtgc   tgcccaaaca   aagtaccata   aactcggtgg    4500
ctaaagacag   cagaaatata   ttgtctggca   gttctggagg   cccaaagtca   aggtgttggc    4560
agtgttggtt   ccttcttggg   gggaatctgt   cccatgcatc   tctccttagc   ttccaagagc    4620
cccctgtgtt   atttggattg   taaatgatca   ctcaaatcct   ctttcttcaa   ttggcatttt    4680
ccctgtctgt   tttcacatga   ttatcttctt   ataaggacac   cagtcatatt   ggattagggg    4740
cccacagtac   tccagaatga   cctcatcttt   atttaactaa   ttacatcttc   aacgacccta    4800
tttccaaata   aggtcacatc   ctatggtact   ggggattagg   acttcatatc   ttttttgggg    4860
aggcatagtt   caacccataa   caggggccaa   actgtgaagc   atttcctata   tatcaatcca    4920
gatattttca   aatctattgt   ttattcagtg   ggaaaccatt   gaaaactttg   agcaggatga    4980
atctaacact   ttaggaagac   tccttgggga   tggggttgga   gagatgttag   ctgcactgga    5040
agtcagtaga   ccagagtctg   gaccactggg   agtctggacc   agatcaatgt   tatggaaaac    5100
caggattctg   gggctcccac   tcaagatatc   ccaaacccaa   atcttcagac   tggagaccca    5160
ggactgtttt   ttaaaagctc   cctctctctc   cctgtgagtc   agatgattta   gcctagcttg    5220
```

```
gatgtaacac tgggtgtgag gtgatagagg catgaaatgg gttggtggtt atgcaagtag    5280
aaagaccaga gagaacctgg gaaaagagac atttcgaaaa agtagtatgt aaactggcac    5340
cggagagtct gagacagtgg tggaatcctt aacagaaata aagatgtcta gagaataaat    5400
tgggtttaaa gggaaggtaa ttaatttggt ttacagtgta aggtgataga cagtcagcag    5460
gcacttggag aatggtgatg tatgttcaga agtgagataa tggaggtgat aatcaaaacc    5520 cttttgttttg atttgagcct ttgtgtggga gaaaggatat ggcgagaaga acagaagatc    5580
aggaagccaa tactgtagac cctcattccc tagcccctga acaaatgga tttgacttct    5640 ctgtcatgac acctggaaca aatgtggcat tgcttactta cttcctttgc catgaactca    5700
gtgaaggcag ggacgggtct tggcttgtgt gtgtgtgtgt gtgtgtgtgt gtgtaagaga    5760
ctgggtctca ttctgttacc caggcatgag tgccatggca taatcatagc tcactgcagc    5820
ctcaaacgaa cctcctccct caggcctcct gagttgctgg gactacaggc atgcaccaat    5880
ggccctggct ttttaaaggc catcatctag cacagtgcct ggcttttcaa tggaagtctg    5940
ttgaatgact gactgactga ccgacttgga aaatgaacac atcaacttga gaataagaac    6000
tttaactttt ttcttccttg catccccctaa catttaatcc aatgcctggt ccttaatagg    6060
acccaaataa aattttgatg tgtgaatggt agaagaaaag ctaaaattga gtagtcattg    6120
tgtcaaagag aaccaggaaa cagagaagct tttgagaata agttgaccat aacatgtcaa    6180
atgcaagtca aggagaatga aaactgaggg caggaattag atttaatcag gaggttattt    6240
gtagatttga gaacgaagga tttaagaaca taatgaggtt gttaagggag aatgaaggaa    6300
ttaagatcat aatgaggttg ttaagtagag gtggaaagtg aggaaatgaa agccaagtac    6360
atcttataca agtttagtag taatgaggaa aagagaagct catagagtta aagctctaaa    6420 aatctgtttta gaacatccgt gtctatttgt aaacaaggg gtatgagggt tagggatgga    6480
aaaatggaaa gtaccagaag gaaatgcata attttagggg aaagatctca aatgggatca    6540
agaacatggg cagtagcctt aaaaaggatg agggaatctc ttcctctagt ctaaaagggg    6600
agaatagagc ctctatagag gagagagagg tcatgtcctc ttgtcagcca tctgctcaga    6660
gggagcttgg gctgctgtgc tagaaactga cataggaaac tgacaaagga aggatatgtt    6720
ttctgcacag cactgaggag tgtgatactc ctaagcagta gttggcagcc tgagatagga    6780
atggtggaac cagatggtaa gtataatcca ggaatcagga tggcactttc tgtagattag    6840
ggagttgtag gctgggggtg tacttttatt cactcttctc tgattcagag gttttataat    6900
tttcactaac atcattaaaa acaatattgg atgcctacta cctgttggtt tttattttaa    6960
tcttgggaaa aaaagtaaa agctactatc ctgaggtttc tggttttatt ggggagatag    7020
atcatatatg taaaagcaa gtttagcaaa tggcacatgg cattatagac taagtcccaa    7080
atcagtagat tacataaatg tcagagagat tacaattata gcagtacact ttgaggttct    7140
tttcccctta gcttatgaac atttaaattt tgtcactttt ataaatacat gcctatttga    7200
gaggtaagaa aagtaccatg ttgctttaat ttgcttttct ttgttagcaa agatgaattt    7260
tttcagttgt ttatcattat tttactttt atgaattgcc tattcatagc ttttatccat    7320 cttttccatgg ttgtgtttgt acttactaat ttgtaaatac ctcatttaat aaggttattt    7380 aacctttttgc ctgtaacatt ttgcaaatgt ttttctagc ttgtttttg gggttctttc    7440 ttttggttgg ttggtggtt ggttggttgg ttgggttttt ttttgagac agatcatcac    7500 tctgttaccc aggctggaat gcagtggtgc catctctgct cactgcaacc tccaccttct    7560
ggggtcaaat gattcttgtg tctcagcctc ccaagtagct gggattacag gcgcacgcca    7620
```

```
ccacgcccag ctaatttta taattttgt agagatgggg tttcacgatg ttggctaggg    7680
tggtctcaaa actcctgacc tcaagtgatt tgcctccctc agcctcccaa agtgctggga   7740
ttacagatgc agccaccatg ccagcctt tctagttt ttaattaaa catttctt        7800
cagatttctt attttgattt attttcagtt tatgatgttt tgttgacaca taagagttta   7860
aatatcttat gtattagaaa ctattaaata ttctttta atatttagga aggctacctc    7920
agcctgagaa cagacaaata tttcaaatg tttctcaa attgtttat agtttattgg     7980
tacttattta cattccattg tattattgtt atttatatac ttaaactt aaaccattt    8040
ggaatattgc atgaaataga gacctaattt ttgctgagta gttcagcagt ttctagtact   8100
gtttactaaa taatctatga aaatttctg cggattccta aatgattttg tccaggctgg   8160
agtacagtgg cacaatcatg gctcactgcg gcatctacct ccccaggctc aggtgattgt   8220
cccacctcag cctctcaagt agctgggact acagaagtgc cactacccc agctaatttt    8280
tgcatttttt tgtagagact atattcacc atgttgctga gcctggtctt gaactcctgg   8340
gctcaagcga cctgcccact tcggcctccc aaagtactag gattacaagg catgagccac   8400
cgggtattt tatcatatt cccaatactt atgtatacag acttccttgt ttataaatct    8460
gtatctgtac cattgccaca tattattgta ttaatataat ctcatagtgc aaatacttgt   8520
tcattatttg ttttaaataa tgcctagact acactcacct atttgtatat gtgaactt    8580
tttaaaacat tttattttt aataattaa gactcagaaa gctgcagtag tacaggttcc   8640
caggtatgct tcacccaagg gctttcaatt agaaccttt tttttttt ttttttgag    8700
atggagtctc gctctgtcac caggctggag tgcagtggcg ccatctcagc acactgcaac   8760
ctctgactcc ctgattcgag caattctcct gtctcagcct cccgagtagc tggaattaca   8820
ggcatacgcc accacaccca gctaattttt gtattttag tcaagacggt gtttcgccat   8880
gttggtcagg ctgatctcaa actcctgacc tcaggtgatc tgcttgcctt agcctcccaa   8940
agtgctggga ttagagtggt gagccactgt gcccggcccc tgaaatcacc ttttctgtaa   9000
tgctactttg ttcaataaaa ataacatatt aatatccttt ttaaaaatac atacaatata   9060
ttgttattaa ctgtagtcac catgatgtac aatagatctc ttgaacttat tcctcctaac   9120
tgaattttgt gtcctttgtt cagtatttcc ccaattcccc tacccaccaa cctctagtaa   9180
ccaccatttt actctctatt tctatgaatt caactttta cattccacgt gtaagtgaga   9240
tcatgtgata tttgtctttc tatgtctggc ttatttcgtt taacataatg tcctccaggt   9300
ttatccatgt tatcacaaat gacagaattt attctttt taaggctgaa tagtgttcca   9360
ttgtgtatgt atgccacatt ttctttcacc attcatccat caatgaatga aaacacttag   9420
gttgatttca tatcttagct attgtgaata atgctgcaat gaacatagta gtacagatat   9480
ctcttcaaca tacccatatt agttatatcc tttagatata tatccaatag ggggaattac   9540
tgaatcatat agtagttcta tttaaatttt tttttgttt ttaattttgt ttgtttagag   9600
acagggtctc gctgtgtctc caaggctgta gcacagttct gcaatcataa ctcactgtaa   9660
gctcaagtga tctacttcag cttcgctact acaggcacat gccactatag tcagctaatt   9720
tttaaaatt gtttgtagag tccaggtgtg gtggctcacg cctgtaatcc cagcaatttg   9780
ggaggcctag gcgggtggat cacctgaagt caggagtttg acactagcct gactgccatg   9840
gtaaaacccc atctctacta aaaatacaaa aaattagcc gggcgtggct gtgcatgcct   9900
atgatcccag ctacttggga ggctgagagg caggagaatc acttgaaccc gggaggcaga  9960
ggttgcagta agccaagatc tcgccattgc actccagcct gggcgacaag agtgaaaatc   10020
```

```
caactcaaaa aaaaaaaaaa tcgtttgtag agacagggtc tcacaatatt gaccagtctg   10080
gtctcaaact cctggcttca ggcagtcttc ctgtcttggc ctcccaaagt gctgacatta   10140
tagccatgag cccctgcacc cagccttatt tttaattttt tgaggaacct ccatacatgt   10200
tttccataat ggctgtactt atttaccttc tcaccttatt gtataatggt gcatatctca   10260
gaatgtgtcc ttactgagtg acacataact atatttgaag taagtttctt atagatagca   10320
tatagttggg tcttttcttt tctttttta atagagacag ggtcttgcta tgttgcccag   10380
gctggttttg aactcctggg ctcaagcagt atgcctgcct gggcctccca aagtgttggt   10440
attataggca tgagccacca tgcctggcct aggtcttttt tttttgagac agggtctcac   10500
ttttgtcacc caagctggag tgccgtggtg caatcatggc tcactgcagc ctcaacctcc   10560
taggctcaat cagccctcca cctcagcctc ctgagtagct gggattacag atgcatgcca   10620
tcatgcctgg ctaattttg ttttgtttgg ggttttttg gtagagacag ggttttgcca   10680
tgttgcccag gctggtctcg aagtcttggg ctgaagtgat ccacctacct tggtctccca   10740
aagtgctggg attacaagcg taaaccatta cacgtggtct agttgggttc tttttaaaa   10800 gaatcagttc tactaatttc ttttcgttgg tatgtataaa ccatttatat ttaatataat   10860
tattgatact ttggatttaa atttgccatt tttgtttcat tcattatttt tgttcttctg   10920
tttcccattt cctgttttac agtgggttcc ttgaacattt tttaatattt cattttgagt   10980
gtatctcttt ataaagtttt ttgtgtgatt gctctaggaa tatatatgta gataacttat   11040
tacagtctat taatatcaac ttttaccac cttaagtaga atgtagttag ttttagtaga   11100
aggaatcttt tagttccttc taccttctt cttcttttt tttttttg agacggagtc   11160 ttgctctgtc atcaggttgg agtgcagtgg cgtgatctca gctcattgca atctccacct   11220
cccgggttca agccattctc ctgcctcagc ccctccgagt agctgggatt acaggtgcat   11280
gccaccacac ccagctaatt tttgtattt tagtagagat gaggtttcac catgttggcc   11340
aggatggtct cgatttcctg acctcgtgat ctgccggcct cagcctccca aagtgctggg   11400
attacaggca tgagccattg tgcctggcac accttcctt tttatggtac agttgtctta   11460
aatattacct ctacatacaa ggagaaccac ttcagggact gctataattt ttactttcaa   11520
ccatcaaaca taatctttaa aactcaagag aagaattgct taattagtgt atgtatgtgt   11580
gtctgtatat gaataaacat atatatatgc ataacatata tatggatata tgcatatata   11640
gacacacaca cacccttttcc attgcttttt ctttacttct atttgaggtt ttcttctgtt   11700
atcatttact tcctttctga tagagtttct ttagccattc tttttcaaagc tgatctgttg   11760 gtgacacatt tttagttttg ttcatctgcc agtatttgta tttcattttt atttctgaag   11820
gatattttca ctgtctatag aattttagct tgatagttat tttcttcag catttgaaaa   11880 atattgtatc catccttgtg gtttccatgg ttcctgatga aaatctgtt gtctttcaaa   11940 ttgttattct cctatgagtg atatgttgtt tctctctaat tgatttcagg actttctttt   12000 agttttaga agtttgattc tgtaagttta tatctaaatc tgaggctgag tgtggtggct   12060
catgcccata atcccaacac tttgagaggc caaggtaaga ggatttcgtg agtccaggag   12120
tttgagacca gcctgacaa catagtgaga ccccacctct aaaacagata gatagatagt   12180
tgattttgtt tttgttttttt cctttttttg agacggagtc ttgctgtgtc acccaggctg   12240
gagggcagtg gctcgatctt ggttcactac aacctccgcc tcctgggttc aagcaattct   12300
cctgcgtcag ccacccaagt agctgggatt acaggcaccc gccaccacac ccaactcatt   12360
ttttgtattt ttagtacaga tggggtttca ccatgttggc caagctggtc tcgaactcct   12420
```

```
gacctcaggt gatcccctg cctcagcctc ccaaaatgct gggattacag atgcgagcca   12480
ccgtacccag tagacagttt ttagccatta tttcttaaat ttttttttt catctctcca   12540 ttcattctct tactcttggg accctgatag catgaatgtt agatctttgt tattatccca   12600
caggactttg aaactgtgtt catttctttt caatctactt tctctcttgt acagactgga   12660
tgatttccat tcatttaagt ttactaattg tttcctttat cattttctt ttgctgttga    12720 gcccatccag tgggtctttt taatttcaga aattttattt ttaaaaattc catttggtac   12780
tccttatgtc ttctatatgc tgagtgttta taatgtcttg tttgagcagt ttcatgagcg   12840
ctgttttaaa ttcttttcaa ataattccaa aatctatatt atcttggtat tgtcatctgt   12900
tgattgcctt ttttcattca agttgagatt tcatgttcc tggtataatg agtaatgttg    12960
gattgcatcc tagcacttgg aatattgtgc tatgagattc tggttcctgt ttaaattttt   13020
atatttaaca gtcaacctgt ttaggtttag aacacatacc ctgtcccact tttgtcgact   13080
gtggttcagt tttcagtctt gttttactct tatggtctgt gctaccgaaa ggccagtctg   13140
aaatttaggt gttattccgg agcagtgttc agttcttatg ccttttgctg tgttgtttct   13200
ggtcattttt acacatgggt tgctcagagg cacttttagg atttcataca cagattcaga   13260
gaattcattt ctctagctct ctcctcacca taatcctttc ccaattctgt agttttgctg   13320
ggattaggac tccatctggt tattccaggg tagagaaaga tgagttcacc cacattctct   13380
gcagctgtaa catggagaag aggggaaagg cgtgccacct cattatggca gagttgtgtt   13440
ggaaggcaga atgctgttca caatttctgg gccacagtgt ctggtgagga aaaggagggg   13500
tacctcctcc cctttttag tttgcctggt caaaatgttt ttgtctgctg agctgcccct    13560
ttcccagttc tttacctaga gagggcaggc ttttcttggc actttcttgt ctgtgcttac   13620
tggatctttc agattgtggc ttcagagctt gggctaggac atattagaag ttaaaccaaa   13680
ccaaacaaaa aagtagggag cttcctgttg ggtcagtcct catgtcccct ggtccctagc   13740
caatctacct tcttttttct acttttcaga atttttctgt cacttgtgtc atgaatttca   13800
tctagaatgt tcggttataa tcggtgggaa gggctgggcg cggtggctga cgcctacaat   13860
cccagcactt tgggaggcca aggcgagcgg atcacctgag gtgaggagtt cgagaccagc   13920
ctggccaaca tggtgaaacc ccgtctctac taaaaataca aaaaaatta gccgggcatg    13980 gtgggggacg cctgtaatcc cagctacttg ggaggctcag ataggagaat cgtttgaacc   14040
caggaggtgg aggttgcagt gagctgagat cgcgccactg cgctccagcc tgggcaagaa   14100
gagcaaaact ccatctcaaa caaaaacaaa aacaaaaaca aatcagtggg aggaataggg   14160
tggaatatgc ttactccatc ttttcctgaa ctgtaaatcc ctgctgcaat tttaaattat   14220
gaactttagt tccagtagtt ttttttaacc tatgtacgta gtctttcaaa tacaaataac   14280
agttaagggg ttttccccca ataattatat cttgttttct tttctttct ttttttttt     14340 tttaaagaga ccgggtctcg ctgtatcgcc taggctggac ttgaactcct gtgctcaggc   14400
aatcctcctc cctcagcctt ccaagtatct gggactacag gcatatccc ccatacctag    14460 ctgttttctt atcccattat ctacttttag aacaaggatt ggcaaactat aatctgtttc   14520
ccatatccag ctcactgctt attttggtat ggcagacaag ctcagaatag gttttccttt   14580
tttttggaga caggtctcac tttgtcactg aggctggagt gcattggtgt aaacacagct   14640
cacttcagcc tcgacctccc aggctcatgg gatcctcctg tctcagagag aaaaagagag   14700
agagaaaaaa agaaattata tgaaattcaa atttcagcgt tttattagaa tatgccatgt   14760
tcatttgttt atatattgtc tgtggctgcc ttcatggtac gacagcagag ttgagtagtt   14820
```

```
gaagcagaga cttaattgcc agcccttttt ccagatgatt tgtaaatcct agaagtgaaa   14880
ccattgtccc tttcttgtcc tgctttagtg atactgatat ttcaagatac ataattttct   14940
tgggtgaaag tttcttttgt ttctggtttc taggtatttg tgagatattt ctctcacaaa   15000
acgtgttctt ttcttctggt ttttttttgg gggtttttt tgtttctttg gttttttgag    15060
acagtctcgc tctgtcaccc aggctggagt tcagtggcgc gatctcaact cactgcaacc   15120
tctgcctcct gggttcaagc agttctcctg cctcggcctc cctagtagct gggattacag   15180
gtgcctgcaa tcacgccagg ctaatttttg tattttagt agagatgggg tttcaccatg      15240
ttggccaggc tggtcttgaa ctcctgacct caggtgatct gccctccttg gcctcccaaa   15300
gtgctgggat tacaggcatg agccactacg ccttgtctct tttcctctgt tatctgactt   15360
actggatggc atctgttagg taaatcagaa accaaagagg agtagcattc agcactccct   15420
gtcaccccaa gagcaaatct attatcacac cctgtgcagt ttacttcctg aatatctcct   15480
tccttgtaac acttttgtgt ctccaccagt aacttctaac tggactgtcc acatccagtg   15540
ctatattctc tacacccagc taaatgaagt gttcattcca aaatgcaggg cagggaggtc   15600
actgtcatgc ttctgttctt caaaggcttc ttaatgctta tgggacaaag aaaaatcacc   15660
cttgtgtggc cctaccctgt atacatctcc agcttcctgg cacctgctcc cccttactct   15720
ttatacttca gacacggtgg cttctttcag accctgctcc tgcccttct gaggttacgg     15780 actggcatgg agttccctgc cctccttaat gcctccctga ttcctgttca tcttctactt   15840
gtcagctcag gaatcagtgc cttagggagg ccttggctga gctccctgac taggtcaaat   15900
tttcttcttc tataggctct tagagtccta taattctctt ttccatcact tctcctatt     15960 gtctgtgagg tgatttgttt aatgtcagtt ttctgctact agactgtaag cttcatgaag   16020
atagggattc tgttagaatt tgttcactat ttctagtaga aggaacaggg cctagcacat   16080
agtaaatact gagtaagcgg gttatttccc caatgattgc cttttaaag aaaaccagtt     16140 ctgtaaacca gcattcatca ggcttatcat atggcttttt atattttgaa ttatttttgt   16200
gaggattttt attaatatgt tttccaataa tggaccatgg ttaaattttt gaagtaagcc   16260
ttacttgatc aggttgtggt ataattataa catatgctgc ttttttcttg ctaggatttt   16320
aagattttgc agttaaagtt attttctttt ttgtgtgctt tgtcagattt tgacatcagt   16380
gttatactag tattttcatg gcttattta ttccattctt ttattttcaa cttttctata     16440
tccttaagct taaaaatgtc tcttttaaac agcatataat tgagggcttt tattattagg   16500
ctttataatt tttgtatttt aattggaaca tttagtttgt ttaatatagt taatatattc   16560
tttgctttct attttcctca aagatttgaa tagaacaaaa ggctgacctc ccccaagcaa   16620
gagggaattc tctggcagtc tgcctttgca cttgaaatgc aactcctccc tgaatctcca   16680
gcctgccagc ctcttctatt atgagtcaat tccttaaaat aattctatat gatatatatt   16740
taatataatt aatatataat gtggctacta cctagtagaa ttaatgtata cttaatatga   16800
catataatat aattacagta gtaccttctt atctggggga agcattatat tccaagaccc   16860
ccagtggatg cctaaaacca cagatatata ttttcctata catacatagc tgtgataaag   16920
tttaatttat aaattaggca cagtaaaaaa ttaacaataa ctaataataa aatacaatac   16980
ttataataat atgccagcat gttccttttt ctctttttc ttgctttttg gattgataga     17040
cttttttact atcctagctt ttttccctct tgccaagtta tagaccctgt tcttttagtg   17100
gttaccctac agattacaac acatagcctg catgtatagg aatgaaatac agtttacgta   17160
gggttcagta ccatctgtgg tttcaggcat ctactgggag tcttggaaca tatcccccca   17220
```

```
cccccccccc agataagggg gtagtactga aattatatta aatatatgct tattatatta   17280
aatattagtc atatattaca tacatattat atagatttat tttaagggat tgattcacag   17340
tgggggaggc tagcaggctg gagacccagg aaggaactgc acttcaagtt caagggtagt   17400
ctgctggaga attccctctt gcgtggggaa ggtcagcctt ttgtgctatt cagaccttca   17460
gttgtatgga tgaagcccac ctacattatg gagggcaacc ttctgtactc aagagtccat   17520
tgatttaaat gtaaatctca tccaaaaaaa cccctcacag aaatatccag aataacctttt  17580 aaccaaatat ctggacactg tggtgtggcc caaccaaatt aacaatcaca agtctactct   17640
ttatcaactt ggcacccata cacatctcct taaaccatta ttaatctcca aataaagaca   17700
gtaacaaagt catacttctg cttagcatga aagaactatc ttgcatgtag ccgaaaacac   17760
actattcctt tctctaaaag aggatgcaga ttatttggtt gatgtttact cttcttgata   17820
tcctgcaact taaattctaa agtttaagaa aaagttaata cttaagtatt atgatcagct   17880
gttaatctaa ttttttttga cgaaaatatt ttcgtatcca ttttctattg ctgcctagca   17940
aaacatcccc aaatttaata ttttaaagca acaaccatca aaaattggct cacaattctg   18000
tgaatatcaa tcaatgctgg gtagctgttt ggttcctcta ctggtctttt ttttttttt    18060 tttttagac agggtctcac tctgccaccc aggctggagt gcagtggcat gatctcggct    18120
cactgtaacc tccgcctccc aggctcaagc aattgtcctg tctcaaccttt ctgagtagct  18180 gggattacag acacacacca ctaccacctg gctaatttttt ttatttttag tagatatagg   18240
gtttcaccat gttggccagg ctggtctcga actcctcacc tcaaatgatc cacctgcctc   18300
ggcctcccaa agtgctggga ttacaggcgt gagccaccat gcctggcccc tctgctggtc   18360
ttgattgaag tcattcatgc aactgtaatc atctaatggt tcatctggga ctgagattgt   18420
ctcaagcaca tgtctggcag ttggtgtcac ttgttgattg ggcctctctc ttaacgtaag   18480
gaagtgagcc aaagcttctc acattatgac agcagtgttc ccatagagcc aaatgacagc   18540
tgtaagttct cttgaggtat caacttggaa gacacaccat tacttctgca ttttattggt   18600
ttaagcaagt cacagggcca actcaaatta aaggaatgga gaaataaact tcacctgttg   18660
ataggagtgg cagtgtctca ctgtaaaagg catgtgtaca aggatgggat tttacgtagc   18720
catctttgca aacagtctac cacagtgtct tttttccttt cgagtgctta aaaaaattgt   18780
ttttaaataa ttatttggtt ttcagaaatt tcactattgt gtatctagac acagatttcc   18840
tttttattta tctgtttggg gggtgtttag ggcttcttgg atctgtggtt tgatgttttt   18900
cctcagtttt ggagaatttt cagccttcgt ctgttcttcg aatatttctt ctgttccatt   18960
tctccctttc cgcttttctg aaactgaaat tacatgtagg ttagatcatt tcattgtatc   19020 ctttataccct cttaccttct ctttggtatt tttttataaa tctttttgct tctctctgct   19080
tcattctaga tacttccttt tgacctattt accagctcac taattctctc ttcaggtata   19140
ttttacctgt tcttaaattt atccattaag atcttttttt cagatctgct attacatttt   19200
tataccattc ttgactaaaa ttcttaatgc tacaggactg ttcttcttgt ctgtttctta   19260
ctgattctca tgttgccttt ttatggacta gacactgtag ttttaaaatt atttatagaa   19320
atgacctgag acctatgata tatttttcaa gagaggattt acgtttgttt ctagctttgc   19380
ctaggagtct tcaatcattt taattcagtt tcagggactg atttgctttt aagcagggct   19440
gtagtcccta caggggtggt caacttcatt tcactaccta atataccctat tatgtgtgga  19500 gtactttgct agatgttggg taggtcttgt gagcagagca gacctctctt tggtctgtat   19560
ggagcacgga gcttgattat aattggcagg tgtgtgtgtg tgtgtgtgtg tgtgtgtgta   19620
```

```
aataaataaa tatttattta tttatttatt ataggccggg tacagtggct tacacctgta   19680
atcccagcac tttatgaagt caaggcaggt ggatcacttg aggtcaggag tttgaggcca   19740
gccttgccaa catggtgaaa ccctgtctct tctgaaaata caaaaattag ccagacgtgg   19800
tggcaggtgc ctgtaatccc agctactcga gaggctgcgg catgacagtc actcaagccc   19860
gggaggtaga ggttgcagtg agctgagatt gtgccactgt aatccagcct gggtgacaga   19920
gtgagactcc atctcaatat atatatgcgt gtgtgtatat atatatatct atatctttaa   19980
gatagatata tttatatagc taagtaatta ataaatatat taagttctat gaaagcaatg   20040
agtaggctgc tatggttgtg aatatttgga ctacacaggg gataagaatg ggtctaccat   20100
aattagcagg gacaggtttt gtttaagcca aaaactaaga gggcttagaa cagaaaccgc   20160
caggcagaag cagttaccag tgtgaagact agatgacaac caaaaaagta tgtgggagga   20220
gggaggggag gttgcgcagt ggggagttga gattgactta gaactgtatt aatgagcttt   20280
ccccccaacc cccattttc tcccatttac cttcagaaaa attagtgatt tggctaccag   20340
tgaatctagg ctccaggtgt agctctgtag ttttggacta gttacctaat tcttcattca   20400
caacaaaaca gaaggagaga ggaaaaagag agcaaacatg gaattgggat gggaagtaag   20460
agagcacatg aggagagaga ctatgtcaag tttcttcgta ttcctttttt aattacagaa   20520
gaaaagatgg gataaaaata ttccatctta tttctctgtt taaaagaaag agtaggccgg   20580
gcatggtggc tcacacctgt aatcccagca ctttgggagg ctgaggcagg cggatcacaa   20640
ggtcaggagt ttgacaccag cctgaccaac atggtgaaac cccatctcta ctaaaattac   20700
aaaaattagc cgggcgtggt ggcgcatgcc tgtaatccca gctacttggg aggctgaggc   20760
aggagaatcg cttgaacccg ggaggcagag gttgcagtga ccgagatca cgccactgca   20820
ctccagcctg ggcaacagag cgagactcct tctcagaaaa aaaaaaaata ataataataa   20880
aataaataaa agaaagagta aatgaatcaa aatgaagaga agccatttta tctgcctcct   20940
ggatgaagag tttcattgat gaacctgaaa tgttttggtt aacatgagaa aggagggtga   21000
gaagatgcct gagatgtgag ctccttgagg acaggagctg ctttctctct ccagcctggc   21060
acaagacaag gaacttagtt gaatgaatga gcaaataagt ggttctctgc tttgaaggaa   21120
cttggactgt cattaccttg caaatcaggt ttaccattta tttgctttat ataagttcca   21180
gaaagaaact atttcctctc ataatattac taccctaaac ttctggtctg atctatggat   21240
tgtagagctt aaatttcctc aaaccccaac agtcagagat tgttacacca agataaaatag   21300
catatttctc agcgccttgt attttctgtc tttggccaca gaccttagga cttaggctga   21360
tatttgagaa ggaaaaactg gaatttagta gaattatact tcctgtatct taattttcca   21420
actcttatat aaggtttgct ttttctagag agagactaat ctggaatgag aatgaattct   21480
catcagtaaa ggcaaagctt taagtgggtc atctgacttt gcttttgtgc tctacattca   21540
ccctgctcat aaaaggtcct ttcatgagtt ttctaggctt tcatcactgc cagcgtctcc   21600
acaggcattg tgaaagtatt aaacttccta ccctccccca tgcttgtctc atggactctt   21660
tcgtagagtg cacagtggac tgtgtttagc tcagcaggaa ctcttttgcaa acactgaata   21720
catgaacaac cccctgaa agataagaga tttcagtatt gcttggtgtc atagccgcag   21780
aagttagtgt ctgccagtat ctgatgaata tggtgacttg cagcctaatt tttgtgaaat   21840
tatgaggcca agtttaaga agtgttcatg ttaaagttac ttatatataa aatttgccta   21900
tcgataattt ctgtcaatag gaggttgatg aatgcttcac ataacctaga tactcctaat   21960
taactgtttt ttatttcttt ttttctagga cacatgttca aagagcataa ttaacttttt   22020
```

```
aaaagaagct agtaagtact gaaatagttt tttaagtttt ttctacaaga atagaggaag   22080
aaaggaaaca tggaattctg aagggctact tagcaagctg cttatggcat aatctgggt    22140
gggggtgcat agtaaaggat ttgcatttta ctgagaccga tacatgtcaa gggaatggta   22200
tttaaaatta gtgatatgtg ttgatttttc aaggactata gcccatcaac tacaataggc   22260
tccaaaaaat tctggtgaaa ttagcttctt ggagccttcc agtttaccta ctatgttatt   22320
cccactataa aatattctca acttttgggg ttttagccac ttaagttttt tattttctct   22380
aatgtctcta gtatctgctt tagtttcctg tcaatgctag actctgtggt tcagcagttc   22440
atccattctc ttcccagtac tcaacctcgt tgcttatagt ttcattacat tcatctagca   22500
aaaccttaat tctgtatgtt tgccatacca ttagtgctta gagcattttt tcagaaaaga   22560
atcctggaaa aatggatctt atctcacctg ggccctcagg actgctgggc tgcctggtgt   22620
cagcacttcc cgccattttc tatagcacca gtattattct taatacttta aaaaaccacc   22680
aggcacggtg gctcacgcct ggaatcccag cactttggga ggccaaggtg ggcggatcac   22740
aaggtcagga gatcaagacc atcctggcta acacagtgaa accctgtctg tactaaaaat   22800
agaaaaaaat tagctgggcg tggtggcggg cacctgtagt cccagctgct ggggaggctg   22860
aggcaggaga atggcgtgaa cccgggaggc ggagcttgca gtgagccgag attgcaccac   22920
tgcactccag cctgggtgac agagcgagac tccgtctcaa aaaaaaaag taaataaaaa    22980
taaaaaacca tatcccacta tctccccctt ctctctttgc ctgtgatctt gctgcatact   23040
tatgggaaa tctttaagat gtcagatttc agttctctca cttttctaca acttctccca    23100
cttttgcctt tcttatgtac cttcccttcc ttcccatctg attccttatc agtatttaca   23160
catgattagt tcttgcctaa cctaatagac ccttttcttga gtgcaaatca gtggctattt   23220
ttgctagggt ataaaaatta cctatctaat caccttgaca aagttaccct gttatttcca   23280
ataacttact tccatatggat tcttgtagat tttcttttttt tttttttaa tttttttat   23340
ttcagatgtt ttctcgcttt gtcaccatgc ctggcctaaa ttctcgtagg ttttctatgt   23400
aaacaatcag atttttctgca agtattagtc tcctttctaa ttgttataat tttaatttct   23460
ttttctttt aaaattttttc gtagagacaa ggttttgcta tgttgtccag cctggtcttg   23520
aactcctggg ctcaagcaat cctcccatct cagcctccca aagtgccatt acagtggcat   23580
gagccactgt gcctggccaa atttcttttc ttgttgcgaa ggcagacttt tcatacaata   23640
ctgaatagaa gtgatagtag attactttat ttctgatttt caaggaatg ctttccgttt    23700
ctctctgttg aagataattg cgtattgttt ttttttttaa atagtaactt ttatcaggtt   23760
aaggaaggtt tcttctattt ctatttaaaa ggatttttta aaatcttgaa ttcatatgtt   23820
tttatctaat gcattttcta catcagttga aatggttgta tgaactcttt taatatgggt   23880
gaattatatt tatagatttt atgttaaaat atccttgtat atcttggata aactcaactg   23940
gatcatgatt tatcttttttt atatgctaga ttcaatttgt tgatactttg ttatgatttt   24000
tgaatatata ttattgtgta aaagtgagcc tgtgattttc tttcttgtaa tgtttctgtc   24060
cagttttggt gcctggtttt gctctctcct tagaatgagc tgggaactag tcactcttgt   24120
tttctcacct ataatagcat ctgggtccag tgttttttat gtgggacaaa tttgaacttg   24180
tggtcaacct ctttaattgt aagaatattc aggtcttttg ttcttcctgg ctagtttttt   24240
tattctttttt ctagagattc gttcattttt cttagtttta tttgcctata attgtggata   24300
atctgttttt tatctgctac ttctgtaatt atttccacat ttgatttata atattaactt   24360
gtgggccagg cgtcgtggct cacacctgta atcccagcac tttgggaggc cgaggcgggc   24420
```

```
ggatcacgag gtcaagagat cgagaccatc ctggccatca tggtgaaacc ccgtctctac   24480
taaaaataca aaaaaaaaaa ttagccgggc gtggtggcag gcacctgtag tcccagctac   24540
tcagaaggct gaggcaggag aatggcgtga acccaggagg cggaggttgc agtgagccga   24600
gatcgcacca ctgcactcca gcctgggcga cagagcgaga ctccatctca aaaaaaaaaa   24660
aaatttactt gtgtcttctc tttttacctg tttgttaatt tatcaaataa ctacttttgg   24720
ctttgtttca ttttttattat acaataaaat gaaattcttt tcattgtatt tcttttcatt   24780
gattattcct ataattctta aacaacttta taattgatgt aacaataacc tgtacacatt   24840
taaagtgtaa aatttattac attttgatcc atgtatatag cagggaaata tcaccacaac   24900
aagagtgtga acatataatc tctccccaaa gttttcttgt gtcttttata atcactgcct   24960
cttgcccctg cccactccct catccttaag caaccattgg tctgttttct gccactatag   25020
attagattgt attttctaga gttttataca agtgaaatca tgtagtatag tattaaccat   25080
gtgtttgttt gtttgtttgt ttctttcttt ctttcttttt tttttagacg gagtctcgct   25140
ttgtcaccca ggctaaagtg cagtggggcg atctcggctt actgccagct ccgactccgg   25200
ggttcacacc attctcctac ctctgcctcc cgagtagctg ggactccagg cgtgcccgcc   25260
accacgccca gctagttttt gtattttttag tagagacggg gtttcaccat gttagccagg   25320
atggtctcga tctcctgacc tcgtgatccg cccacctcag cctcccaaag cgctgggatt   25380
acaggcagga gccactgcgc ccagcaacta tgtgtttctg atcctttgtc agggctagcc   25440
aattcctaga gacagtgaat aactcactca taatctagct gcctccttta tgtcgctctc   25500
ataggacttt gacacctctc tgctacaatc cacctgccct gttcatttca agatcaggta   25560
ccaggaaact cgggacatcc ctatgctgca gaactcactg aaattattca aactagccag   25620
tcctaaacat gcttaccctg ccttgcccat tccttccgct gaaaccacat aaaggctctt   25680
gcccatgttt tcatcccatt ccattgacct ccttactgac cctagctagt gcttcctcat   25740
gtggcccctg catggcatgg tgtgcacctt cctcttcgga actgcgagta actgtcttgt   25800
cagcggcaat catcttgtga tctgttggcc tcatcatatt tgaataacaa taaaatctgt   25860
tttaaggctg ggcgcggtgg ctcatgcctg taatcccagc actttgggag gccaaggcag   25920
gcggatcacg aggtcaagag attgaggtga accccctct ctactaaaag tagaaaaatt   25980
agctgggcat ggtggtgcgt gcctgtaatc ccagctactc aggagactga ggcagggaat   26040
ctcttgaacc caggaggcag aggttgcggt gagccaagat tgcaccacgg cactccagcc   26100
tggtgacaga gcgagactcc atctcaaaaa aagaaaaaaa aaaaactgtc aaatgatact   26160
ccaaaatggt tgtaccattt tatatttgca acaacaatgt ctgagggtac tgattgctcc   26220
atatccttga cagcacttgg tatagctgat cttttaattt tagtcacttt agtgggcata   26280
tactggtatt ttatgtttta cttttttattt tcctaatgat taatagtttg cagcatcttt   26340
catgtgctta tttcccttc atatatcttc tttgataaaa atatctgttc aaatattttg   26400
cccattattt tgttggaata cttatttct tactgttgag ctttgagagt tctttatata   26460
tctggatacc aatcctttgt cagatatatt ttttgcaaaa ttttttccca gcctgtgatt   26520
tagtttgtta ttctcatgtc ttttaaaaaa aattgtagtt aaaatataca cataatacaa   26580
aatttaacat tttaactctt tgtaagtata cagttttgtg gtattaagca tagtcacatt   26640
gttgtgcaac catcaccgcc atccatctct ggaactttt catcctccct gactgaaatt   26700
ctgtacccat ttaaacacta acttctcatt cccccttact ccagcccctg gcaaccatcg   26760
ttctgttttc cttctctatg agtttgactg ctctaagtac ttcatataag tggagtcata   26820
```

```
caatattttc attttgtgac tggcttatta gtataatgtc ttcaagtttc atccatgtgg   26880
tagcatgtgt cagaatttcc ttcctttta aggctaacat tccatcctat gtatatacca   26940
cattttatcc attcatctgt tgatggacat ttaagttgct tcctcctttt ggctattgtg   27000
aataatgctg ctgtgaatgt tgttgtataa atatctgttc gagttcctgc tttcaattct   27060
tttgagtatg ttcccaaaag tagaattgct gggtcatatg ttaatactgt atttagtttt   27120
ttgaggaatt gccatactga tttctatagt agtggtacca tttacattcc aaccagcagt   27180
gttcagggtt ccaatttgtt aacattcttg ccaacccttg ttgttttctg gattttttt    27240 attttggggt ttttttattt atttatttat ttttttttg aggcagagtc tcactctgtc   27300
acccaggctg aagtgtagtg gcgcaatctc ggctcactgc aacctctgcc ccccgggttc   27360
aagcgattct cctgcctcag cctccgagta gctgggacta caggcgcgcg ttaccacgcc   27420
tggctaattt tttgtatttt tagtagaggg ggggtttcac tgtgttaatc aggatggtct   27480
cgatctccgg accttgtgat tcacccgcct cagcctcccg aagtgctggg attacaggcg   27540
tgagccacta tgcctggcca ttttttattt ttaaacaata gccatcctaa tgggtatgaa   27600
ataggttttt tggtgttttg tttttttttt ttgagacaga atcttgctgt gttgccctgg   27660
ctggagtgta gtgacgtgat ctcggctcac ctcaacctcc gtctcctggg ttcaagcact   27720
tctcctgcct cagacttcca agtggctggg actacaggcg cccgccacca cacccagcta   27780 gttttgtat ttttagtaga gatgggtttt cactgtgttg gccaggctgg tccacgatcc   27840
atccaccttg gcctcccaaa gtgttgggat tacaggggtg agccaccatg cacagccagg   27900
gttttgtttt gttttgtttt tactattttt tttttttttt agagacaagc tgtctcccaa   27960
gctgtagtgc agtggcacca ttcgtatctc actgtaacct caaactcctg acccaagca   28020 atcctcctgc ctcagccttc catgtagcta cgtctacagg catgtgccac catacccggc   28080 taacttttt ttttttttt ttttgagag ttttgctctt gttgcccagg ctggagtgca   28140
atggcatgat cttggctcac tgcaacctcc tcttcctggg ttcaagtgat tttcctgcct   28200
cagcctcctg agtagctggg attacaggcg cccgccacca cgcctggcta atttttgta    28260 tttttagtag agatggggtt tcaccatgtt ggccaggctg ggctcgaact cctgacctca   28320
ggtgatccac ccaccttgac ctcccaaagg gctgggatta caggcgtgcg ccaccacacc   28380
tggcccccag ctaactttta aatgtatttt gtagagatga ggtctcactg tgttggccag   28440
gctggtcttg aacttctgag ctcaagtcat tctcccacct cggcctccca aagtgctggg   28500
attacaggca tgagccacca cacctggccc ctttgcccat tttaaaaatt aggttgtttt   28560
tgttgttgtt gagttgtagg agctcttttgt atattctgca tttcggttcc ttattggata   28620
tgtgattggc atacattttt tcccatccat ggattgcttt tcattctgt tatagtatcc    28680 ttgattcaca gaagtttta atattgatga ggtcctgctt agtctgtgtt ttgttttgtt   28740
gcttgtgctt ttggtgttat atccaagaaa tttttgccaa atccaaagtc atgaagcttt   28800
gccctctgtt tccttctgag ttttatagtt ttaggactta aatttaggtt ttcgacccat   28860
ttttagttaa ttttgcaag tggtataagg gaggggtcca gcgttattgt ttcacgtgta   28920
gatatacagt tttctgagta ccatttgatg aaaaggctgt ccattgaatt gcttttgcaa   28980
cttttatttg ggcatattta tgtgagtctg ttactggttc tatatttac tccattgatc   29040 tatgtgtcta ttcctctgct aatactgtct taaatatggt agctatatag taagccttaa   29100
cactgagtag atagatttct cccctttttt tgttcttttt caaaattgtc actggttgt    29160 ttttattttt tactttatgc agataatctg tactatactt tggtttcatg tatcaagtag   29220
```

```
tttgttccaa gttgtgcttt aagcagaaca aataaatttt catattgttc tttgtgttaa   29280
tctgcaatat aaacctatac caaattctat tttgtgtatt tgtttattgt agtaatctga   29340
ctgactcttt tgcctccaga ctcatctctt tcaaggtccc caactgaatc ttgttttagg   29400
tggaacttag aagcagtaga agttaagaat ctatttcaca gccttagtag tctagtttca   29460
ttctctatat aatgttgtct atgcaagtga gctgctctcc agtgccttag tttcactaat   29520 gttgggaag gtctcttctc ttgttttgga cttctctatc acattgcctt tctcaagaga    29580
agacatataa tgaaagttga tatctggtgt tctaggactt cttcagaagc ttgccagttt   29640
ttcaagctga tttctctcac tggcaactct tcagagtgct gttcctactc caccctcccc   29700
tggtggtatg tatcagtttt ctactcatca gcacccacct actcctgcct actgtgtttc   29760
tcagatgtct gctgcctggc tagctcattg ctgcttttgt cactcataga gctgtcttct   29820 tcccttttt tggcttttctg cctgacttcc agggcagctg ctctgtcatt gcctgtctgc   29880
cattctgtct ttttccccc tacccccac agatacaaca tctactctaa taccacacat    29940
tctccatgtt caaactaacc tcatcacttt ccccaccaca ttccccaaaa ctggtcatcc   30000
tccagcttat agcattgcag ttcactgaag ttagacatct gggccttgct tacctccaac   30060
atctcattag ccttcgattc taccectata aatcctcttc tcagtctcct ttagatattc   30120
ctgccctgct gtgagatcca tctggtttat tggctagatt acttcagaaa gcttcagtca   30180
gtgaccctcc ttacttcaaa ccccaccagt tgatccttca ctctgccatc agtcattgct   30240
tctaaaatct aaattgttcc atttaacctt gctgtgataa aacctttggt agttcttcag   30300
tgtgttcagt ggtaagttaa aactttcact gtaatgtaca ggccccttca tgatatgatc   30360
gctgcctcct cgagcctcat tgtgtgcatt tccccgcccc accctttcct cacccaccct   30420
agtctttcat gtctgccatt tttacattca tttagcagat atttattgaa gccccctgtg   30480
atgtccttac ctaggtcttt cttgttgcca ggaccagaca ggcttttca agcttccaag    30540 tcatctcagt ttgaaagact atgtctgacc cttgtcttgg ccaattactc tttatccttc   30600
caagttcaat gattgtccca ctgcactcca accagagtga gagagcaaga ccctgtctca   30660
gtaaataaaa ataaataaat aaataaataa ataaataaat aaatcagcca taatttattt   30720
aatcatgtct ctctccccca ttgatagacg ttaagggtat ttccagtatt cttctcttga   30780
aaacaatgct acattgaata accttgtaca tgggtcactt tgaaagtatg gatatgtatc   30840
cgtggaataa gttccagaa gtggaattgt gtcagagggg ttgtgcattt gtaattctga    30900
tgaatattta tagattatat gagagtacct gtttactcaa actcttgcca atgcagcatt   30960
atcaaagttt tttatgttcg ccagtgtgat agattaaaaa atggtatctc agccaggcgc   31020
agtggctcac gcctgtaatc ccagcacttt gggaggctga ggcgggcaga tcacggggtc   31080
aggagatcga gaccatcctg gccaacacag tgaaaccctg tctctactaa aaatacaaaa   31140
aattatccag gcgtggtggc gggcacctgt agtcccagct actcggaagg ctgaggcagg   31200
agaatggcat gaacctggga ggcggagctt gcactgagcc gagatcgcgc cacaacattc   31260
gagcctgggc gacagagcga gactccgtct caaataataa aaaaaaaaga tggtatctca   31320
gcattgattt ctttgatcat cagtgaggtt gagcatcttt tcatagattt aagagaactg   31380 tatgttttt tgtgagttat gtttcatatc gtttacccat tttacttta ggctggaagc     31440 agctgtttta gtggaatggt ggaacaagaa gccagattgc catggagaga caactctttc   31500
tagagatttg gctatgaagc agagtagaga caatgatagc tgaaggattg atgtagatgc   31560
aaagaaattt ttcatcttct ttgaaaactt aattgtgtta aaaactggta tgaaagggag   31620
```

| | |
|---|---:|
| gggttaaagc tagagatggt ggtagaaaaa aatgcagggt tcctaaagga ctgagattcc | 31680 |
| tggatggaat ttcagggaag gggaaaattt ctggatatag tgactgggga gttaagg | 31737 |

<210> SEQ ID NO 22
<211> LENGTH: 31737
<212> TYPE: DNA
<213> ORGANISM: H. sapiens

<400> SEQUENCE: 22

| | |
|---|---:|
| gtgtctagtc caatggcttt tattttcttg gaagggtagg caaggccaac agccacatgt | 60 |
| gtgggaggag atggttagag gggagaggag gtttgaaggc accgctatgg agaattggag | 120 |
| agagctaagg aaagacagaa agactgcaga aagtgcttag ggttccactg aagcggaaat | 180 |
| agtgatttgt agtgatacaa cccttatgag ttatttgatt tttttttttt tttaagcagc | 240 |
| atctggcagt ccaagtatag ggctgacagt ttgggatttt tctttccatg ttggtgtaaa | 300 |
| agaagaacag tgtagtgaag gaagttagga caaaagaatg attgaactga caccaagttt | 360 |
| tcttgatttg gtagaaaagg aaataaagat agagcagaga tattgaaaag aattagagag | 420 |
| gggttcaaga gactgaaggc ctgggtgagg tcagagagca ggtgtggtag acataacaga | 480 |
| gagaactaca aggatagaaa gtgtggttgg agagtgggaa ggcaagattt attcagtatg | 540 |
| ggggcttttc tgggtgatga cagcatctgg agtacagcca ttgtcgtgag tggcccaagt | 600 |
| gtagcagaga taaagcgttg ttggagtgaa ggaagtcaag gaactgagag gctggcctag | 660 |
| atggggattt tggttgtcat ccatgaggat attgaagtca tccaggagaa tagcaggcct | 720 |
| gggggacagg aaggaaactg agccacttac agtgtcttca gtgataggaa agcacagggc | 780 |
| aaaaagcttt caagaacagg gactgttaag ccgggtacag tggctcacac ctataatcct | 840 |
| agcattttgg gaggccaagg cgggtggatc acttgaggtc aggagttcaa gaccagcctg | 900 |
| gccaacatgt tgaaacccca tctctactaa aaaaaaaaaa aaaaaaaaaa aaaagaaat | 960 |
| acaaaaatta gccaggcatg gtggcacgcg cctgtaatcc cagctacttg ggaggctgag | 1020 |
| gcaggagaat tgcttgaacc taggaggcgg aggtggcagt gagcctagat cacaccactg | 1080 |
| tactccagcc tgggcaacag agcgagactg tatcaaaaaa aaaaaaaaa aaaagaaca | 1140 |
| gggactgtta gagcaggctc caggagaaat gctttgcata tggcattctt gaggagtgag | 1200 |
| gaggacctca accctacttc ctgaaatgga gctctgagat gttggagtag aaatttggaa | 1260 |
| accagagaga gaagtaagga tagtgttgtt gcaaatgcat tgtatatggg gggtcgggaa | 1320 |
| gtcacaggag tttgcctcaa agtctttctc ggagacggat gaggttttca ctgtgatttt | 1380 |
| cctggtcgtg gtctatggat atagtacctg ttagtgacat ggatcttctt aacttctgat | 1440 |
| gtgtcttttc ctccctagtg tacgcatacc aattctctcc acagcttcca tcaccatgca | 1500 |
| tttgttcttt tcccttgttc ttgtattacc tttctggaaa ggaattttta ttgtaggcta | 1560 |
| attgttactc ccaccagtat ttaaccactg gatatttcat atgattgatc tcttctgatt | 1620 |
| tggaaaataa aaatgtaatc tcattatatt catttgatta gtggggacag tcaacacttc | 1680 |
| tttgtgtatt ttcttagctg ttcgtttttc tcgtctgtaa attatctgtt taggtccttc | 1740 |
| agatttttca aaattggact gttatgtttt cagtattgtt atgagttctt gtttcaatta | 1800 |
| tttatgacag ttcattttct tttttaaaat agacttttt tttcttagag aaataagaaa | 1860 |
| aaataaaaat taaatagac tttgtgtttt agagagtttc aggttcacag caaaattgat | 1920 |
| caaaagtat ggagagttcc ggccaggcgc ggtggctcac acctgtaatc ccagcacttt | 1980 |
| ggaaggccaa ggtgggcaga tcacaaggtc aggagtttaa gaccagcctg gccaatatga | 2040 |

```
tgaaacccca tgtctactaa caatacacaa attagctggg tgtggtggtg cacacctgta    2100
actgtaccta ctcaggaggc tgaggcagaa gaatctcttg aacctgggag gtggaggtta    2160
cagtgagcca cagtcatgcc cctgcactcc agcctgggca acagagtgag actccgtcct    2220
aaaaaaagaa agaaagaaaa tatagagcat tcctaaatac cacctgtccc caacacctgc    2280
acagcctcct cattatccac atcctacacc actgtggtac ctttgttgca attgatggac    2340
caacattgac tcctcattat cacccaagct ttggtgttgt acattctgta gatttggaca    2400
aatgtataat gacatgtgtc taccattgta gtatcataca gaagaatttg actgccctga    2460
cagtcctctg ctccacctgc ttactcctct ctccctttc ctaactgcac aaccactgat    2520
tttttttttt ttttttttgag acggagtctc actctgtccc ccaggccgga gtgcagtggc    2580
gccatcttgg gtcactgcaa gctccacctc ccgggttcat gccattctcc tgcctcagcc    2640
tcccgagtag ctgggactac aggtgcccgc caccacatcc ggctaatttt ttgtatttgt    2700
agtagagacg gggtttcacc atgttagcca ggatggtctc gatctcctga cctcgtgatc    2760
cgcccacctc ggcctcccaa agctgggatt acaggcatga gccaccacgc cctaccttt    2820 ttttaaaaaa caaggtcttg ctctgtcacc caggcctgag tgcagtgatg atcactcctc    2880
actgaagcgt cgacctccca ggctcaagtg atcctcccac ctcagcctcc taaatagctg    2940
agactacaca cacacaccac catgcccagc taagttttgt atttttata gaaatgtggt    3000 cttgctgtgt tgtccaggct ggtcttgaac tcctgagctc aagcaatttg cctgccttgg    3060
cctctcaagg tgttgggatt acaggcatga gtcaccgcac ctggccttt ttattttctt    3120 tttttttttt taaccagtga tcttttactg tctccatggt ttttcacatt ggcttctgtc    3180
acttagtaat atatgtttaa gtttcttcta cgtattttca tgtttttagc ttatttcttt    3240
ttagcagtga gtaatatttc attgtctgga tgtgccatca cttatttatc cattcgcctg    3300
ctgaaggata tcttgattgc tcccagtcgt ggcaattata aataaagttg ctgtaaacat    3360
ccatgtgcag gttttttta agtggcataa gttttcatct catttggtta aataccaagg    3420
agcacaattg ctggatcata tggtaagagc ttatttattt ttttgagaga ctaccaagct    3480
gccttccaaa gtggatgtac cattttgcat tcccaccagc agtgaatgag agttcctgct    3540
gctccatatt cttacaaaca tgtagtattg tcaaatgttt tggatttaa aaccaaaatc    3600 cattttcata gatgtgtagt ggtatcccgt tttaatttgc aattacctaa tgacttgatg    3660
ttctgtgtct tttcagatgc ttatttgccg tactgtttat cttctttggt gaggtgtctc    3720
ttcaggtctt ttgcccattt ttaatctggt tgttattttt cttgttgagt ttaagaattc    3780
tctgtccttt gtcagatcta tcttttgcaa atattttctc ctagtctgtg gcttatcctc    3840
tgattctctt ggcattgtct ttcacagagt agacatttta tattaatg aagtccagac    3900 tatcaattat gttctcatgg atcatgcctt tgatgttata tctaaaaagt tctcgccata    3960
cccaaagtca tctagatttt ctcctgttat cttcttggca ttttatagtc ttatgattga    4020
tatttaggtc tatgattcat ttttagttaa atttttgtga aagataataa ggtctgatat    4080
ggattaattt ttctatatgt agctgtccct ttccagtatc atttgttgaa aagactatct    4140
tgctccattt tattgccttt gctccttgt cagttgacta tatttatgtg ggtctgttta    4200
tgatctctgt tccgttccat tgatctgttt gccttttctt ttgctaatac cacagtctta    4260
attaccatag ctttaaagta agtccttgaa gtccaatagca ttaatctttg actcttcttt    4320
aatattgagt tgccccttca gaatcttaat gtctctccat gtaaacttta gaatcagcat    4380
ttttatattc acaaaataac ttgctgagat tatgattgag attgcattga atctataggc    4440
```

```
ttatttggga ataactgaca tcttgacaat attgagtctt cctgtccata aacattattt    4500
atgatgggct tcttctttat gtttaggagc ttttgttttt tctgtcagat attccacttc    4560
tacctttatg atttcttaat tgcctttat gcttagaaag ttttcctca tcctgagctc    4620 acatattcat ttattttctt ttaaaatgtg ttttcaagca tttaattttt aaacctatgt    4680
ggaatttatt ttggtatatg gaatgaggtg gtggtctaac tccctcctct caaatatgta    4740 gttattttc ccaaaaccat tttctattaa tttatcaaga atagacatgt atacatatac    4800
atatataata gtcagccttc cacttgttgt ttgacccttg tgaaggaaat tgtatgagtt    4860
tccaattttg gattaggctc aggtagtaat tgagctgggt tctgccagag atccatgtta    4920
attcactatc caaacagagt tataaaatgt aagttttatg aaaatctaac agtatatcac    4980
tggtttaatg atcacagcct aggaagaatg gggaaattgt caaaatcttc tgtggatgca    5040
cctgaaggcc actgctgaac ccatttccct gctaggcacg gctgctggta ccaggggcaa    5100
actcctggag tatatatgaa ccacctacat ctccttctct tcccccccta cccttgagat    5160
tttcatgtgt cccttaagga tgtgtgtcct acttcccttg gagagtcact accacattga    5220
acactttaga ctgtgagtcc tgtgaagatg gggctcatga gtgtattgct ccccagttgt    5280
ttctctagca ctagctcagt atagggcata aaaatctgaa tggatgaaca aaccactatt    5340
actggtgggg acatgctact atcttacatg gttcgaggtg gaataaaggt tgagaacagc    5400
tatataatgt gttccttgaa gggcagcagt acatcagtgc aatcagccta ccttctccat    5460
acttctcact ctgaaaactg taaagctgca cctagcaatc aacttgggag ctttaaaagg    5520
gactgctccc tagctctcac ccacaaagct gtagtctagc acaggtgact tttttaaaaa    5580
agttttttgg tccagatgtg atgactcacg cctgtaatcc cagcacttcg ggaggctgag    5640
gctgggaggt cacctggggt caggagtttg agaccagcgt gaccaacatg gagaaacccc    5700
atctctacta aaaatttgcc gggcatggtg gcacatgcct ctaatctcag ctactcggga    5760
ggctgaggca ggagaattgc ttgaacccgg gaggcggagg ttgccgtgag ccaagatcac    5820
accattgcac tccagcccgg gcgacagtgc aagactccgt ctcaaaaaaa aataaaaaag    5880
gagtcctatt aagacttatt tttacaggtt ggatatctct aatcccaaaa tctgaaatgc    5940
tccaaaattt gaaactttt gagcgcagac atgatgctca aaaaaatgct cactgggaca    6000
ttttggattt caaatttgg attagggact aggtgtggga gctcacacct gtaatcatag    6060
cactttggga agttgaagca agaggatcag ttgaacccaa gagtttgaga gcagcctaga    6120
caacatagtg agacgccgtc tctacagaaa attttaaaaa ttagccaggc atcgtagtac    6180
atgcctatag tcccagctac tcaggaggct gagacagaag gatcacttga gtccaggagg    6240
tagaggctgc actgagctat gatcataacc actgtctcca tcctgggcaa cagagcaaga    6300
ccctatctct taaaaaaaat ctgaaacact gctagtcctc aagataaggg atagtcagtc    6360
tttataaaga ctcaattagt tattggatat ctgaggaagc atgcatatca ggctcccaaa    6420
agatcattgg tttaggcaca cattttaata gcttggaaat ccagaatact cttctggtga    6480
ccagctcaga catagtcctg ataatatagg acctcatcta acatgactcc ctattttcca    6540
gataagcatg gattcctggt tcattcttgt tctgctcggc agtggtctga tatgtgtcag    6600
tgccaacaat gctaccacag gtaaattgtc atttgataag gctgctattt gaatgaaat    6660 tttgctttca catttaatga gccacatttg aaaccgaga tggtatttga agaaaggaat    6720
ataaaaattt tattcaaagt gatggtaaaa taggtgtctt cagaaatctt ggaattgaat    6780
gctcagcatt gttttcata catacataac tgctttaaat aaatcaaaga gattatgtgt    6840
```

```
tctttcctga aaagtaaaat aaattgttga catttacaac tctatatatg gtttctgagg    6900
aactaagtga agaatcttgt gtcttctcc  cttaaaccgt agtcctttgg aggaggtagg    6960
aaaggtccag catgagataa aaacgtaggg ggtgggtggt gttgagggg  attggtcttt    7020
gcttggtctc catatgtttg agagtttatt aaggcttgct gctttgtgtc tcacagcttt    7080
ttagcctcac attcttcatg tgctatttcc ttgttttttg gtgtttgtag ttgcaccttc    7140
tgtaggaatt acaagattaa ttaactcatc aacggcagaa ccagttaaag aagaggccaa    7200
aacttcaaat ccaacttctt cactaacttc tctttctgtg gcaccaacat tcagcccaaa    7260
tataactctg ggacccacct atttaaccac tgtcaattct tcagactctg acaatgggac    7320
cacaagaaca gcaagcacca attctatagg cattacaatt tcaccaaatg gaacgtggct    7380
tccagataac cagttcacgg atgccagaac agaaccctgg gagggaatt  ccagcaccgc    7440
agcaaccact ccagaaactt tccctccttc aggtactaga gatgattctg tttgttcttt    7500
tgctctttga gtttagtctt ccttttatta tcttgtttgt gttttctagc cttaaaattt    7560
cttcaaataa gtaaaattgc tcaagtgaag taatgaaacc tgtatgtgga attttgggt    7620
tagcatgagt gaagaggaaa gaagaaagat tctggagaat atctttctgc taggtgggat    7680
cctggttaga ttgagaggac ttaaatgtgt ttaaaggtag agaagaaggc ttaaaaagac    7740
aagagaaata gaggagctca ttgacgatgc aagagactga agatgaaaag atacagagaa    7800
tgagtaataa gattaggttt ggaaagggag ggatccgtgg agaccatgga aaggagaatg    7860
ggtattgatg tccatgacag ttagatgtga gatacagaga atgagtaata agattaggtt    7920
tggaaaggga gggatccatg gagaccatgg aaaggagaat ggacattgat gtccatgaca    7980
gttagatatg gagtggcagg ccagtggcca ggggtggcat caggctctgg gaaatggtta    8040
cattgcagtg ccagttgttc agggcctcag gttgaagcag tagtcccaag gagaaaatca    8100
gagacgtgga tctgagacca gggcaggtaa gacaagtttc tgacctcttt gaaccttagg    8160
taccttgtct gtaaaagagg attagagata ccctcaaagg gcttctatga ggagtaaagg    8220
aaataatcat tacctgattg ctatgtaact gtcatcccct ttctagcaaa aatcactctt    8280
tcctcttctg tgttcccagt tagatggtga gtgcccctaa gcagaatcac atctcgctca    8340
tgtggaacat tcaggaactg tttgctcagt tgattctcat tgttactac  agatgatatc    8400
ttttactgcg ccttataact cagacccttc acctgccagc ttttccccat attttctacc    8460
gtaaagacaa gacagcattt gcagttaaga gcacagtctt cagtgccaca ctgagtttga    8520
atcccagctc ttccataaac cagccatgtt tatggcatag ctggcttact ttatctctct    8580
acctcggttt gttcatctgt gaaacaagaa tgagtgatag taatagttct tacctcatag    8640
aggagatatt aggattaaac aagttaatat gggtaaagca cttataaagg tgcctacaca    8700
tggtaagcac tattttaag  tgtgagctgt tagtattgtt gtggttattg ctctgatagt    8760
taccagtaaa atatatgaag gtacctttaa tgcagatggc atcccactat tcttgatgag    8820
atagggact  gcagacaaat aatgtctgat acttgctttg tgcttagag  ttaatgtagt    8880
tttgtcatag ttattactgt gtgctaggca tcgtactaag agttttctag aataatccta    8940
tgaattaagt tctatttat  gttttatagg tgaaagtatt ttacaatgat gaaaccataa    9000
tttgtggaat gtttttcagt gtacaggtca tgacacaatt catgaaatca ctttagcagg    9060
ccaccactag ttgtttgttt tgttttattt taatggatga tccagttcca tgtttattct    9120
tttaatgtta catacaattt tttgaaattt tagtaacaac ataaaatgtt gggttgtggc    9180
cattgcttag ggagaaaggc aggataactt gtacaaactg tatgagtgaa tggaaaaggt    9240
```

```
ggagactgta acacaggcct gactgactga acagcccatg ttctattgtg tactgtcttt      9300
catttaacag ttctgtgaca tgaccatgga taatcatctc cttttaacag atgcttgatt      9360
tcagactgta tatagaggtt aaatgatttg ttttagatct caaggctgac aaattaggcc      9420
tatttctcac ttttgcggtc tttccactct gcttgtaggg aacttagttt tccataaact      9480
gacttaggtc caaattgtgc cacagctaag aatctagtta ttgtacattt aacacagttc      9540
acgtcatagg aggctgagac tatgtttctc tagtggcgtt tattcaagat gagtaaaaca      9600
caagaaacca ttatcgcaca tgggaatttc atagtcttaa accccacatc ccacttatca      9660
ccaccattta ccagtcctcc tgtaacagtt acaatttttt attaaatcag tatttgatgt      9720
atattattgt aattatgaaa tattcattgc tgagctataa gtataaatgg attgtttttc      9780
ttgtacagtt tttttctgg atttaatact taccttattt tttgtttatt tagttttcta       9840
tttagtcagg ccaggcacac tggctaacac ctgtaatccc agcactttgg gaggccaagg      9900
tggacagatc acttgagctc aagagtttga gaccagcctg ggaacatgg tgaaacccca       9960 tctctacaaa aaatacaaaa attagctggg catgggtgca tgtgcttgta gtcccagcta     10020
ctcaggagcc tgaggtggga ggattgctta agcccaggag gttgaggctg cagtgagctg     10080
tgttcatacc actgcactcc agcctgggtg acaaagcgag accatgtctc aaaaaagtta     10140
ttgctactca attcttacca tgctctccag agcctctcaa aacagcttc tacaaagtga      10200 gatctgttag ataatctatt tcttttttac ctctagaaat tcctcctgag ccctccattg     10260
tcttattcca gtctaggctt gtcgatctct agggctacta cacagataca tcagcctgag     10320
atttcccttc tctgtcattc tgggaattcc ccttgctgct gcttcctgac ttccatattg     10380
tcttcctttt tgtcttctca tcattcggta gattcctgag aaaagggtc catgggaggc      10440 aaattgcatc cttacatatc taaaaatatc tttagggctg tgcatagaat ttgaggaata     10500
tttttccccc agaatttta aagtaatgcc ctaactgaca cctgtttacc aggtttggag      10560
gattttactg ctatcttaat ccctaattgt ttgtatgctt tctaggatct tctctttatc     10620
atcagtatcc tgaaatttca cagagatgta tcttgatgtg ggtctttttc gttcattatt     10680
atggatactt aataggccct ttagagcctt gatcttgcat ttctgaaaat tttctcccat     10740
ttctttgaaa ccttctcccc ctcttccttt tttttttttc tcaaattctt aatatttgga     10800
tattggatgt atcctgaatt aattctttaa tctttaaaat ttttcctttc tgttgatctt     10860
tgctttgagt ctttttctcc ttttaaaaat aaacaaaggc cagctaggca cagtggctta     10920
tatctgtaat tccagcactt tgggaggctg aagcaggagg atcgcttaag cccgggagtt     10980
tgagaccagc ctaagcatcg cagcaaaacc tcatctctac aaatgattta gaaattagca     11040
gggcctaatg gctcatgcct gtggtcccag ctactcaggg ctgaggcagg aggattactt     11100
gaggcctggc agttgaggct gctgcagtga gctgtgatcg caccaccgta ctccagtctg     11160
ggcaacagag ggagacctca tctcaaaaat aaataggcct ggtgtggtgg ctcactcctg     11220
taatcccagc actttgggag gccaaggcag gtggatcact tgaagccagg agctcaagac     11280
cagcctagcc gacatggcaa aaccctctgt ctacctacta aaataaaaa attagtcaa       11340 acgtgttggc atatacttgt aatcccagct acttgggagg ctgagacatg agaattgctt     11400
gaacctggga ggtggaggtt gcagtgagtc aagtccctgc actatagcct ggggaacaga     11460
gtgagacccg agactctatc tcaaaaaaaa aaatcagtg acaagtaaaa aggtagaata     11520
cctttttttt tttctttgag acagtctcac cctgtcgccc agtctggagt gcaatggcgc     11580
agtctcggca tactgcaaac tctgccttca gggttcaaac aattctcctg cctcagcctc     11640
```

```
ctgagtagct gggattacac atgcccacca ccacacccag ctgttttttg tattttagt    11700
agagacaggt ttcaccatgt tggccatgct ggtctcgaac tcctgacctc atgatccacc    11760
tgccccggcc tcccaaagtg ctggtattac aggcgtgagc cactgcgccc agcctagaat    11820
acctttaaa aataaataaa taggccgggc gcggcggctc atgcctgtaa tcccagcact     11880
ttgggaggct gaggcgggca gatcacgagg tcaggagatc aagaccctcc tggctaacat    11940
ggtgtaaata ataggccgg gcgcggcggc tcatgcctgt aatcccagca ctttgggagg    12000
ctgaggcggg cagatcacga ggtcaggaga tcaagaccct cctggctaac atggtgaaac    12060
cccatctcta ctaaaaaata caaaaaaaaa ttagctgggc gtggtggcag gtgcctgtag    12120
tcccagctac tctggaggct gaggcaggag aatggcgtga acccaggagg tggagcttgc    12180
agtgagccga gattgcgcca ctacactcca gcctgggcaa cagagcaaga ctctctctct    12240
aaataaataa taaataaata aataactcct tttacaaaag catatatatt catttttcc     12300
atttataata taaataatag atatgctgag ttgatttctg catattgctt tttcagttac    12360
cctatcatac ttgctctttg ttttagtaaa gagctgctgt attgaaggat atacctaat     12420
ctctttatcc agtttcccca tcagtggaca ctaagattgt tttcagagta ctcttataaa    12480
caatacagtt tgtcatttca gacacatatg agaatattag caggatgaat tattttaagt    12540
ctgcattat aaatttatgg atattgccac atttacctct gctaggaagt ctattcctat     12600
taacaatatg tcaaagtgcc tatttttcta aactctcttc agtgtggtga attgttaaac    12660
ttggggatct ctgccaatct gacaggtgaa aaataacatc tcagtgtaag tttaatttgc    12720
attttgctga gattgagcaa ttttgtgtaa tttaaaagat catttatttt tctgagcatt    12780
ctctgttgat attctttacc cattttatt agagtgtcaa ggttttcctg actcgtttgt     12840
agatgttctt tgtacgtttg ggaaatgagt cctttgccta tggtaaaact gcaaatgttg    12900
ttccctaggt ggtcatctag attttctgca ttgcagaaga tatcattagc tatttttaat    12960
ttttttaatt taaatatttc tcagtttagg ttttctagga attgggtcat atctaggaag    13020
gctttccta ctccaagatt ataaaataa tttttcttctg gacttctatg gtttcgtgtg     13080
tgtgtgtgtg tgtgtacacg cacttaagtc tgtctcgaat ttattctgat gcagagtgag    13140
ctatggatct gttttttcccc aaatatctaa cttgtcccaa tacccttaa taatttattt     13200
ttcctcattg atttgaaatg ccacctatct tatatattga attcagatat ttatttacct    13260
cttcatatgt atttgagtat ttgggaacat tcattttatt ttctattaat cttttttctct    13320
gtccatgtgc aaagcctcac tgtctcaata attgtaactt tgtaaagtat ttaatatcca    13380
gtaaaatgag tcattccttg ttaatttat ttttcagaat tttgttagca attcttatta     13440
taaacattag aattaacttg tctagcagga aaaaagttt gtattgatca tgttaaatac     13500
gtagattaac agagaaaatg gcatcttaca gatgttgagt ctaactatcc aagaatgcaa    13560
tatattccat tttctgaagt cttttttttt taaatcttct gttttgtaa ttataaatgg     13620
agcattttct tccatcagat cttctaactg gctgctgttg gggatatgaa ggctactgat    13680
ttttgtagag acattttgta ctggccacct taaactctct tagtattgga agtaatttc     13740
ttcattaatt tttatggctt caagtcatct catctgcata tatcttccaa atttttagaa    13800
cttttctttt cttctgttta atcgcattga tgaatacctc cagaacaaag ttaagcagct    13860
ggtaaatgca gacagcattc tcttgtatct gacactaagg aggacacttt cagtggtttt    13920
tcattatacg tggtactgac tcttgagttg agataaacat attttattgt gttcaggatt    13980
taatgagcgt ttatgttagg aatgggtgtt aaattttgcc agttgcctgt tcaggatcaa    14040
```

```
tgagaaagat ctgaatgatt ttttttctct tttggtctgt ttctatggtg gattctattc    14100
ctaggtttgt ttgtttgttt gtttattttg agatggagtc tgttaccagg ctggagtgca    14160
gtggcgccat ctcagctcac tgcaacctcc acctcgcggg ttcaagtgat tcccctgcct    14220
cagcctccga gtagctggga ctacaggcac gcaccaccat gcccggctaa ttttttgtat    14280
tttagtagag acgtggtttc accatgttgg ccaacctggt ctcgaactcc tgaccccatg    14340
atcctgcctc agcctcccaa agtgctggga ttataggtgt gagccactgc gccctgccag    14400
tttttattta ttcattttt agagacaggg tcttgctctg aattaattct ttaatcttct    14460 taattttct tttctgttga cctttgcttt gctttaagtc ttttcctttg agtcatccag    14520
gctgaagtac agtggcacga tcatggctca ctgtaacctt gaactcccag acttaagcaa    14580
accccacctc agacttctga gtagctaagg actataggcg catgtcacca cgcccagcta    14640 attttaaat tttctcagaa acagggactc actgtgttgc ccagactggt catgaactcc    14700
tggcctcaag cagtcctcag ccttagcctt ccaaagcact gggattatag gcatgagcca    14760
aggccgccca aacatattgt atcgttcctg taacaagctg ttgcagtcta tttgatatta    14820
tttcttattt ttttcattta gaattttctc tgtctagata ttctcaaatt atctctaaat    14880
gagattgatc tatgtttttc ctttgtgtgt gtattctttt tgataagttt tagttttttag   14940 tgttttgttt tgctacatgg aaaggatttg aaagtttaca ctaaaaaata tgctttttt     15000 ttttaagaca ggcttttca ctgttgccta gtgctggagt gcagtggcat gatctcggct    15060
cattgcggcc tgcacctcct gggctcaggt gatcctctca cctcagcctc ccaagtagct   15120
gggattacag gtgtgttcca ccatgcccag ctaattttt gtatttttt gtagagatgg    15180 ggtttcgcca tgttgcccag gctggtcttg aactcctggg ctcacatgat tctcctgtct   15240
tagcctccca aagtgctagg attacaggtg tgagccacca catctggcca tttcattcat   15300
gttttcaaat gtatttgaat gaggaaaagt tctcccttgt gattatttat tataatagcc   15360
tacagagcta ttaattttta aattttgttt acttatgtc tccttttttt ttttgtttag    15420
gctgaataac catttatttc ataggtttat tgcctttttt cttccaaaga acttgctatt    15480
gtgcatttat agtcctttta tgtttacgtt ttctatttca ttgattttta ctttctacct   15540
tctttagatt tattttgttc tttttctatc ttcttgaatt gagtgtgctt taattgcatt   15600
ctttccagtt aattaacata tttagtgctg tgaattttga acaagcacag ctttagccac   15660
atcccatagg tgtttctata ggcagttgta ttaggatgcg ctataagctg ctctgacaaa   15720
gataccaaaa ttcagtgact taaataagac caaagtgtct ttctctcccc agttacattc   15780
cagaggtaga cagggccttc gtctcagtag ggaccaaatt cctttcctct tgtggccctg   15840
ccatcctaac aatattgccc ttatctgttt ggttagagat agttctcacc attgggttct   15900
agttccaacc actgcgaagg acaaacaaag ggaataggg ccatttctct tccaaaagat    15960
gtgacctgga agttactcac attgctttag ctcacatccc gttggctaga attcatcaca   16020
tgaccacacc tagcacaaag gagtctcaaa tatagtctgc caggagagct tggtgctcag   16080
ctaaaaaaca aaggttctgt atcaaggcaa gaagagaaag agactgatct gaggggagga   16140
gagttggcag gttctgtcac aaaacttctc gtcattgtta ttttttaaggt attttttccat  16200 tttgggtttt ttgtttgtct gattttttt tttttttg agatggagtc tcgctctgtt     16260
gcccaggctg gagtgcagtg gcgtgatctc tgctcaccgc aagctctgcc tcctggttca   16320
cgccattctc ctgcctcagc ctcccaagta gctgggacta caggcgtaca ccaccacgcc   16380
tggctaattt tttttttgta tttttattag agacagggtt tcactgtgtt acccaggatg   16440
```

```
gtctcattct cctgactttg tgatctgccc acttcggcct cccaaagtgt taggattaca    16500
ggcgtgagcc accgcgcccg gccgtctgtt tgattttttga gatggaatct cactctgccc   16560
cccttctgga gtacagtggt gtgatcttgg gtcactgcaa cctctaccct cccaggttta    16620
agcaattctt gtgcctcagc ctcccaaagt gctgggatta agacgtgag ccactgtgcc     16680 cagcccattt tggttttgat ttttttttt ctttgaaata gagtctcgct ctgttaccta     16740
ggctggagta cagtggcatg atctcggctc actgcaacct cccctcctg ggttcaagtg     16800 attctcgtgc ctcagcctcc caagtagctg ggattatagg cacccaccac cacgcccagc    16860
taatttgttt tgtattttta gtagagacgg ggttttacca tgttggccag gctggtctcg    16920
aactcctgac ctcaggtgat ccactgcacc cggcctcatt ttggttttga tttttatttt    16980
caaatgtttt cttactttgt caatttctaa ttttattgca ttgggacaaa agaatattgt    17040
actctttcta ctgttggggt ttataagggc tgtggatatt tcactcgcct ttgaaaagaa    17100
ggttttctct gttagtctgt agagtttggt atgtaccaat tagatttat tacttatcat    17160 tttggtcttt tgtatcctta cttaattttg tcctcttgaa ttttaatgga gcaaaagaca    17220
taaagtcctc taataacatg cgttctgttt gcattctcat acttttatg aatattgatg     17280 ctgcactatt tgtgtaccca gggagaaggc cagaccactg tccaaagttt agtgaatctg    17340
ggcagccttg tttcccagtt gttggaggat gcctcatgga ggaaagcatt cctaatcctg    17400
gagcttgttt tgttgtactc taattgaatt gtaatgtgtt tctttaaccct gaatgaatgt   17460 ttctattttt tacttattac acaggtaatt ctgactcgaa ggacagaaga ggtgagctgc    17520
tcaccttata tctgttgttc cttttacaca gtgtacagta ttcatttatt tcctctgctc    17580
acagtctgtg gtaaccgtgt gcatctgtgg ctgtgttgtt tgtttacttt cccttaagtt    17640
atttccatgt taatctcatg gagaagagca atagaaacaa gtactgtatt cagtatgttt    17700
tttaatatag actatggatt ctaacagcta tgatgtattt taacaagtaa caaaatatat    17760
cttactttga catgtcactt tgttaacatt acttttggt gatattaggt cataatttct     17820
ataccattag ttacttctga tttctaggcc acagttccct ttaaatattc tttgtgttgt    17880
ttttccccta gtgtataaaa tgtcaaccct ttgtggcttt atatggattt tatggatttt    17940
cagcccttaa atgtaaagtc tctatggcct gagatgttgt gtctgtggtt taagctggac    18000
tgctgagtcc ctggtcacta gagagtaggg ggacatgggt acttgtctgc agaagtgtgg    18060
cacattttgc ctagaatgac agtaaggctg ctatcaaaga gcatgagaga aagagaaaga    18120
gatcatctaa cattctaaga agtgattatt acatttgagt tttaaaaatg ttactattcg    18180
aagcagtgtt tttatcataa ttttctattt tatcaaatca gacttgagtt ttttttctga   18240
ttctgttatt taaccataca caattttccc tgtgtaatta agtaatggaa cacttggagg    18300
catatgaagt cccactaagt agggagcatt tgagtcagaa aagtgggtac tctcttcctt    18360
tatgtgatgt ccatctgcca ttgtatttgg taaggaatag tgaggtgtta ccatactgtg    18420
tacagatttc cctcactttt ccacctctca cttttcctaaa cttgggaact aaacattgga   18480
ttaatacagt gtctttgctg ttcagattca cttgccagat tttatcaaat gtagacttaa    18540
ataggtttta ttgtgataga tatttacttg ctccctaaaa ctgctctctt aaccagcctt    18600
acaataaagt caaaagtcaa agtggtaggc ttcaagatga aacataagat ctgttgactc    18660
cttcctctat ttagtatata ttttcataat attcagcctt tcttgcccc agatatcata     18720 tctatttac ctacccaata tttaagtagt ttccatgttg tgattaagaa aacaaaatta     18780
ccataattac ctagattatt gctaattgtg acatatgtaa agtctattaa tgtaataaat    18840
```

```
ctcctttctt aagtcaaaaa ataattttgt gtaattccaa acaggaaact gaaaaggcat   18900
aggtattctc agcagtctct aaagtcccaa aatctaatgg caattttacc agagcagatc   18960
tttagaagta ttgctataaa tttggatatc ccattctaat tttaagccaa atgcttttg    19020 agaaataagc cagctgtttg gaaatgcttg tattataatc ggtttgataa gcagttatgt   19080
cttatgcaga tgaattaggg gctacctgtt tttatgcact ggtctttggg gtgcttttga   19140
acagtagtgt ctgatgtttt aattgtcaaa gcaaaagaa atgagaggga gggcaacttt    19200
tcttcctctt ctgaagtcca ggaaactggt tattttctca tgcatattat tttaaaatat   19260
attccagcca ggtgcagtgg ctcacgcctg taatcccagc actttgggag gccaaggcgg   19320
gtggatcaca aggtcaggag ttcaagacca gcctgaccaa tatgataaaa ccccatctct   19380
actaaaaata caaaaattag ccgggcgtgg tggtgtgcgc ctgtaatccc agctactcgg   19440
gaggctgagt caggagaatt gcttgaacct gggaggcaga ggttgcagtg agccaagatc   19500
gcgctcttgg ctgcgatcca gactgcactc cagcctgggt gacagagcaa gactctgtct   19560
caaaaaaaaa aaaaaaaatc agactcttaa tatttgtaaa gaagtagtcc ttgagctact   19620
acttaagtct agaagagtt gatattcttg ttttaagagt gttagggcac tttgggaggc    19680
tgaggcaggt ggatcacttg agcccaggag ttccagacca gcctgagcaa tatggggaaa   19740
ccttgtctct actaaaaata caaaaattaa ccaggcatgt ggtacgtacc tgtagtccca   19800
gccacttggg acgctgaggt gggaggatca cctgagccca ggaaatggag gttgcagtga   19860
gccaagattg cgtgactgta ctctagcctg ggcaacagag caagactctg tctcaaaaaa   19920
aaaaagggcg gggattatca tagtgccatt attattatga gtttatgatg gctttctcta   19980
agcacctttt acattcggca tttattcagt acctattaag catcaaggag tccagaaaaa   20040
attttatata taaatatata taaaatatgt aaatatatat atgcatatgc ttccctatct   20100
caggaaggaa atatgtgaac atcaggaacc gaagtctact cagttacatg ccattggata   20160
tatcacacaa agtgctgagg gaactcagaa ggctcattat atctggggag tgggaaggag   20220
gcacagagat gtgctttggg aagtttaaat taaaatagca aatggggaaa atgaagacac   20280
accagacagg gcacaagcaa agagacatga aagagtaagt catgtgtttg aggatctgtg   20340
cgcagttgac atgtgtgagg tgtggggagt gatcagaggt ggcctcaaca gaatgggtgt   20400
ggtggtccac tgagttcagg agttggagca tctcctgaag atgatggtga gtaaggaagt   20460
aacatagtca gattttggtt ttagaaagat attccagagg acttagggga gatagatgga   20520
caatagaaat ttaggtttct gaataatttg gctcaaaaca acggtgattg ggctcaaccc   20580
agtggttaga ttctagaggc aatccaatga atattgctgt ttttagagcc aataggaaac   20640
atttaaaaca acattacaac cttgcctttg agagctgata aatacttgta ccaaaaagtg   20700
tggcaatagg taaatgggcc ataggaactg gggctatagg actatggcta ttcctttact   20760
gactagtttg tagttgacca gtgtgtgtct gaagtcctta agtcactcac ctgtttagag   20820
gtgagccctt caattaatat ggccctttgt tttcaaggaa agaagttata gcaagtaggt   20880
atctgttgtc ccgggacacc atttagtgg ttttcatttt catgcttgct ccctggcctg    20940
aatctagaaa gtaaactttt gctggaatga agttggggtt gaaacagttt cggtttgtaa   21000
ccatactgtc tctgtctcat ctactcagct ctgccttttgt aatgtaaaag cagccataga  21060
tggtatgtaa atgaatgaac atggccatgt tctgatagca ttttatttac aaaaacaggc   21120
agtgggctaa atttgggcta tagtttgccg accctcttc taggcaaaga actgcctgag    21180
cgtaggaagc tggactgagg ttctctgcta gtgtgtgaac ttgtggatgc caaagccaat   21240
```

```
ctcttccctt catgtcagac actttgcaaa tgttacctct tttagatctc ccattaactc    21300
taaaaggtgg agggtgctat tatgcttcca tttcatacat tgttctaaga gattatcaca    21360
ctactagtaa gttaggatag taggaatttg aacttcaggt ctgtcagacc ctaaaacccc    21420
atgccctgga aatggttttc taaggctggc ctgtggttcg ttggttgatt tcaattagaa    21480
tttaagaatt ttttcagaat acatctaggt gtaaagattt ttttgtcaat attactccac    21540
aaactagatt atttcttttg gcctgataac tcaggaactt tcttgtatta cttctctccc    21600
ttcttactgg tttcttcttt ggactctcct gttgcacagg tattggatct cctggaccta    21660
tccagttcct ttcttttcta tgctgtcata ttttcatct cttattgctc tgtgttctgg     21720
gagcttccag gacagttgct ctttcacaca actaatttgg ttttcagtta tatcagttct    21780
cctatttagc ctttcttttt ttggaggcag ggctggggca gactcatgct ctgtcgccca    21840
ggctggagtg cagtggcctg atcacagctc actgcagcct tgacctctgg gactcaagcg    21900
atcctccagc ctcagcctcc cgggtagctg ggactatagg catatgccac catgcccagc    21960
taatcaggtg tttgtttgtt tgtttggtag agacagacta ccagagtctc gctaagttgc    22020
ccaggctggt ctcaaactcc tggcctcaag cagtcctccc accctggcct cccaaagtgt    22080
tgggcttaca ggcatgagcc accgtgcccg gccctgttaa gcctttctat ctagattttt    22140
tccctcctaa tcatgttggt gttttttgt ttgttttcat ttttgttttg ttttgttttg     22200
agacggagtt ttgctcttgt tgcccaagct ggtgtgcaat ggcacgatct cggttcaccg    22260
caacctctgc cttccaggtt caaacgattc tcctgcctca gccccagag tagctgggat     22320 tacaggcatg tgccaccaca cctggctaat tttgtatttt tagtagagat ggggtttctc    22380
tatgttggtc aggctgctct taaactacca acctcaggtg atctgcctgc tcggcctcc    22440 caaagtgttg ggattacagg cgtgagccac catgcccggc cagttttaa agaactcctt    22500 cttactactc agattactcc tttttaaata gtggctttta aaaatatca atgtaggctg     22560 ggcacagtgg ctcacaccta taatcccagc actttgggag gctgaggcag gctgatcacc    22620
tgaggtcagg agttcaagac caggctggcc aacatagtga aaccctgtct ctactaaaaa    22680
tacaaaactt agccaggcct gcagttccag ctactaggga ggctaaggtg tgaggatcgc    22740
tcgaaccagg aggccgttgc agtgaaccaa gatcacgcca gtgcacttca gcctgggtga    22800
cggagtgaga ctccgtctcg agaaaagaaa aaaaaacgca atgcagcagt ggctcacgca    22860
cataatcata gcattttggg aggccaaggc aagaagatca cttgagacca agagttcaag    22920
accagcctgg gcaacaacaa gaccccctcc ccccatctct acaaaaaatt taagaaaaaa    22980 aatttttta aatcaatatg gcatcctgtt gcacaaattg cagtatattt tgaaagattt     23040
attctgtttc ttttgtcacc tccatttccc agggctactg ttgctctgtt tgagctatgc    23100
cctggaccat tgagtggctt agactgtgct cacaataggt gtcccttcat cccttcagaa    23160
gacaaacatg gacatacgtc ctaaaccagg aaggggttca gtgatggctc aggaaaatcg    23220
gggcagggtg cagttatcct ctaggcgagc tgccgttttc tttttccttt cctctcttgt    23280
ggttgcctag aattagcttg ggcactacta tggttttttt ctgtctgcag gccccaggag    23340
accttctgtg gacccaatat acttaacaat catatgcagt gtagacctgc tctggtgtca    23400
attctaacca aaacaaaaaa aaagcattta tgagacactc agggaaattc aagcagtaac    23460
tgaataatat tagatgatac taaggaatta gtgttacttt ttaaattgga taatagtatt    23520
atgtttatgt taagaatctt gatctcttgg tgatacatac ctaagtaatt gcatttgaaa    23580
tgctaggtct cggatttgcc ttaaaagaat tcagttagaa tggcgtgagt atagaccagt    23640
```

```
ggttccttac tgggggctat ttcccccaca aaggcattta gcaatgcttg gagatacttt    23700
tggtcatcaa aattgggaat ttgctacaga catctaataa ttagaggcta gggatattgt    23760
taaatgtcct acagtgcaca tgacagaccc acataacaga gaattgtata gcccaaaatg    23820
tcattagtgt gacgttgaga aaatatatat gcagcatatg ttttgtaaaa aagaagccct    23880
taccagtctc tgtgacaaac tctctactct gtgtagagca ctgttttcc agctgagtct    23940 agatgggaag ccccgcttgt catttgggct gtgggtgtac tggtgctggg ttggcaggcc    24000
tttgcttaag taccatcctg gtacctcaag gtccactttc aaccccagtc ccaattccct    24060
ctgagcttga ggtgtttcca ggcccaaact ggtagaacta gtacttagtt ttcagctgga    24120
ggctctttgg ctctgtttga tctcttggac atcgagtctg gtctgttttg tcttccagaa    24180
atctctcaaa gattctgatc tacatatgcc accgtttgct gcctttcaga tatgctgttg    24240
attcattagt attttatat ttcttctacc atgtcagtgt gctttggggg aagatgaagt    24300
aaattcatgg atttagccca gtgtcttaag ccaaaggtgc ctaattactt tcttcttctt    24360
cttttttttt ttttttttga ggcagagtct cgctccgtca cccaggctgg agtgcagtgg    24420
cacgatcttg gctcactgaa acctccgcct cctgggtaca gcgattctc ctgcctcagc    24480 ctcctgagta gctgggacca gaggggtgtg ccaccacacc cgctaatttt gtattttag    24540 cagagacggg gtttcaccat attggccagg ctggtcttga actcctgacc ttgtgatcca    24600
cccgcctcgg cctcccaaag tgctgggatg tgcctaatta cttctttata atacctgata    24660
tactgccccc tgttgttgga atttaacaaa gacatttagt gataaattac tatttttttt    24720
tgttctttgg ctcaacgtaa tccattgttt gttttgtgcc tgttatgtgt gagaccctgt    24780
gctaggtttt aggtgtacag tgagaatgaa gcagacatgt aatccttgct cttgtggaat    24840
ttatgctata aaggagggat attcattaat caacaaagtc aaatatgtaa ttataaagtg    24900
tgagaggtat tatcaaggaa aataataagg tccttgcctt acaaaaatag tataggaaat    24960
aacagcaatt tttttttttt ttttgagaca gagtctcgct ctattgccca ggctgaagtg    25020
cagtggcgca atctcggctc actacaacct ctgccccca ggttcaagcg attctcctgc    25080
ctcagcctcc taagtagctg agattacagg catgtgccac cacacctggc taattttttt    25140
tgtattttta gtagagatgg ggtttcacca tgttggccaa gctggtctcg aattcttgac    25200
ctcatgatct gcccacctcg gcttcccaaa gtgctgggat tgcaggcgtg agccactgtg    25260
cctggccgta acagctaaaa tgaagtacac actgtgtgct agttactgtg ccaacaactt    25320
tacatgaaag atctcattta atacgcagaa taacttattt cagaaatgag gaaactgaga    25380
cttatgatcc taatttagta ttaggaagtc agagaagacc tgtgtgggaa aagtgacaca    25440
cagagaacca gacaagtagg agataaccag gcaaagaaca gagagaggct gtgtaaagca    25500
gaaggaataa catgctcaaa ggcctgagga tgaatgaatg aaagcatgga aggacaccag    25560
tggctgaaat tgagtgagca aggaaagagt gcaagagata gggcaggtag gggctaaatc    25620 gaggggttg ttagagtcca ggataaggag attagatttc attctgaggc atgagaaact    25680
gttggagggt tttacctaag agtgggacac aacctgagtt gctttcctag agatcactct    25740
gctttgtgga gaatggattg gcaggggcag aggcttactg tgatccaggt gagagaggat    25800
ggaggttggg actacactgg tggcaataaa aaaaatgcaa aaaaaaaaa aaaaaaggc    25860 agacagattt gaagttttag atatatctcc aaaatatatt attgcagct gtgctagata    25920 tagaagataa gtgtgaggaa gaaatcaagg gggtttccac atttcttact tgagcaacag    25980
ggtgggttgg agtactagct actgaatggt gagggaaagg ttttaaacac agaaagcttg    26040
```

```
tgttgcctat gaaatttaaa gtggaggtgg caaataggca gttgagaatc tggaactcag    26100
aaaagaggtc tgatcaagca aagcaactgt gggaattgct agcatggcat ttatatttac    26160
agtcatctct ctgatcagat taactagata tagagaagag tgccaaggac agagccctga    26220
ggaattccca catttagaga tctggtgttg aagaggaac  agatagtgag ggaaactgag    26280
atgggcagac gagatagaag gaaaatcaga ggagtgtttc gttgtggaaa gctaagagag    26340
gaaagtgctt cagagaggaa ggagtgatca gccagtctga acactcattt taaggtgaga    26400
gccacatacc acagtatgtt tgaaacttac cattaacaaa gaagcgtcat gtaatgtctt    26460
ccatctctaa aaacaaaacc aaaaaaaacc catctgtcca cctcactcac atctccctcc    26520
atctgtcatt cctttcctct gcatccctta atgttaaaag tccccacgaa aggacccagt    26580
gtctcactgt cctttttcta tctttatttc actccattta ggctttctca cccatattca    26640
actgaaaata ctcttggaaa ggtcaccagt agccaccgtc ttgtcaaatc tggtttcact    26700
tctctgtctc atccttctta agtctgtagg cagtatttga ttgaattgat tgctccctcc    26760
ttgaaaaact ctgctcttgg cttctatgac actacattct tagattaacc tctcacctca    26820
tggctactgc ttatgggtca gtttagcttt taacagaatg taaatccagt tatatatctc    26880
ctctgttcaa agcccttcga tgacatagtg tttctcatca cactcagaat taaatccaca    26940
atcattacaa tggactccca agtcctaagt ctgctggctt tgcccacct  ctctggcatc    27000 ttatattgaa ctggcctttg tgctgtttct tgaacctgcc aagctcctga gagctaccat    27060
gcttgctgtt cccagtgtct agaaagctct tcacccagat ctttgcgtgg ttcacttcac    27120
gttatttaga gctctgcttg tatattactt cctcagagag accttcccag accactgtat    27180
cactgctccc caacctgtca ctttctctct ccccaccctg cttttattc  ctcatagcac    27240 ttgtccctgt ctaaaattaa gtattgactt gtttataaac agtgtcttcc ttcctcccca    27300
cagaatggaa gctttctatc acttgtctcc ttgaacactt ctctgttcct agtgtctcaa    27360
acaatggcat gcaattgctg gcccacagat atttgaatga atgctgctaa aaggttgaat    27420
cagatgagga tgggaatgtt cctgttggat ttggcaatat gccatttgtt ggtgttctgg    27480
ctgagcagtt taaacagagc actgagggtg ggagtcaggg caaatagatt aaggagaacc    27540
tgaaggtaag gaattagaca agacgaatta gacaactgtg tttcggaaag tcagctgaga    27600
agagagacgc gaggctggtg gtagctgggg gagggtaaat gaggtcaaga agacaagtct    27660
ttgagttgac agcagtggat gtaatccaga gcacacatga caggatggaa gagacttgtc    27720
ttccctttta gcaggtagga aaatggtgaa gatagttacc aagccactct gatggtgtag    27780
ttcatggagt cgggtggagg gtgagagtgg aggcggatga gtcagtgcct ggccagctgc    27840
atgagaaaac aaggctaggt attgggtgaa agggagccag gccctgtgga atgaggtggg    27900
attgccatgt cttcaaacca gatgttgcca tggttggggt cctggcaaaa ggtgactaag    27960
ggagcagggt gtggaaagag gaaaaaagaa gcaaccagca gttttgttac atggtggctg    28020
aggatctaat aatgtctcct tgttttattt tatttttatt tagctggtct caaattcctg    28080
gcctcaagca atccttctac ctcagcctcc caaagtgctg ggataggcat gagccgccac    28140
acccagctgt ctccttgttt gtttgtttgt tgtttgtttt gtttgtttgt tgttttgag    28200 acagggtctt gctctgttgc ccagggtgga gtgtagtgta caggcccggc tcactgtaat    28260
ctccatctcc taagctccag tgatcctcct acctcagcct cctgagtagc tgggactata    28320
ggcgcacatc accacaccgg ctattttttt aatttttagt agagatggag ttttacccctg   28380 ttgccaggct ggtctcgaat accttggctc aagcaatcca cccgctttgt cctcctaaaa    28440
```

```
tgctaggatt acaggcatga gccattgtgc cctacttgtc tccttgtttt aattaggaac   28500
agtattctct gtgcccggaa accatttggg tttatgatag gaaaactgtc tttttccctt   28560
cctctcccat cttcctctag atggaaccca ttgaggctga gagagtgtac agtgttggcc   28620
ctgcatacct aacttgccat cagaattgaa tgtgttcatg cctccagata ttccagtgct   28680
ttttatgtgc taagtactgt tttaggctca aaggatatag cagtgagtaa aacaaagtgt   28740
ctgcctttaa acagctttta ttctaatgca gggagacaga gtaaataaat gtatgatagt   28800
cagagatggg gtgagcatgt catcctgggc cccatgctct ctccccacct cacctcaata   28860
gccctggcat ggcagtggga ggtgcacact catactttct tctctgtttc catttcctgg   28920
catctgcaga aggactgaat gagctcttcc tcttcagggt gttgccctga atggctgact   28980
taagccctcc attgcacaac acagtaatga cttgttctgt tgtcttgatt tcagatgaga   29040
caccaattat tgcggtgatg gtggccctgt cctctctgct agtgatcgtg tttattatca   29100
tagttttgta catgttaagg tgagcctact aacacttcac attctcttag attctgtttc   29160
aatatcccag tgtcccaatg aacccacaca gtccagtaga cagtaggata tacacaatga   29220
ataggataga gggggaatga cccatgatag tgctaaaatt gaagttctac ttagaaatta   29280
tttaaaagct ctacatagtc ttccttaagt cctaagccct ccctctttct tccatctgtc   29340
caagcccagt ctcccaactc cagtgcaagc taaagcccag aatggtagtt tggaggttga   29400
ggtaagaaac cgcagtttgt tattagtgac aggtgttaca ggatctctag gtctagccct   29460
gctgaagcaa cccctaaaag ggccccagta agattacatg ctcaacaaaa gcctactgta   29520
tttctggctg gggctttgtc cccagaccct tctgggaccc ctggccctgg catgttgagt   29580
tgagccatgt gagttgtgag ttacaggatc cctctttcta accttctttc agggtcctct   29640
agacgttacc actcaagcag aagcaaggaa ggggaaccca agggagagaa gagggtggtg   29700
catttattct cttcctgcta aagctactgc cctgactaat tggatttagc cctgccttat   29760
ctttggccta accaaagatg ttctgtgctc cctctgttct tctgcaggga taaagagaga   29820
ggaatcatgt gcccctata atttgtcatg tgtctctatc attctgcagg agacttgtgg   29880
ccaggactgt gtccacccaa tccaaagctc tgggcttctc cctgggtctc ccaggctaca   29940
ctgaggaaat accaagattt ttgtttgata tatattgtct gtctccccca gctgtattcc   30000
acccactcac cctctctcta cctggtgtgg ctgtgctctg cagtgagcca catgagcctg   30060
aatatactgt tgggggttccc tggttggatt ccagtgtgcc aagggtaaac aggagtatcc   30120
cgaggtactc ggtcacccca gcatgctgct gcctcagggt gtgcatgacc tgtctctaaa   30180
aaagcccgat tatttttaaa ggcgatttag aaaggctgaa ttgatgagca ggaatacaga   30240
ggtgtgattt gcctctccca cctctgtgct ccattcttca ctgtgatcat tttctcatta   30300
ggtttaagaa atacaagcaa gctgggagcc attccaattc tttccgctta tccaacggcc   30360
gcactgagga tgtgggtaag gcattcctta atgtcatggg gaaccttcac aaggaaggaa   30420
atcaagaaat taggagtttc tccatccttt taaaagaata agacaataaa aagaggaaaa   30480 aagattttg aagaaaacag tcctagttct tacaggcttg gtccatgagg tagaaccccg   30540
tttagcctcc agaagagggg ctaggttctc agggtacctg actgaccttc tcccttgtgt   30600
actgcagagc cccagagtgt gccacttctg gccagatccc caagcaccaa caggaaatac   30660 ccaccctgc ccgtggacaa gctggaagag gaaattaacc ggagaatggc agacgacaat   30720
aagctcttca gggaggaatt caacgtgagt actttgttga ggctggtgta tcagcaggga   30780
agaaggcaga cctaaagtca gacctttcag atctttggag tcatgaagta aaaaatgggc   30840
```

```
ttttaatgtt taagaggtga gaaatgtttt accaagttta tctgactccc tgtatgatca    30900
tggataggaa atgaagtgag atttgcctca cctccctaat ctacccatcc attcagtcat    30960
catcacatct cttacttctt ttgtttaata aatacttagc aagcatctaa tatttgtcag    31020
gtaatattct agttgccagt gatatgatga ggagcagaaa cagatccaat ccctattctc    31080
aaggaactca ctgtccagga gggaaacctc acaaacaaga acaaatataa ctgtgtaagt    31140
tcaaacagca gtacagcaca tgaaggactg gtgcatattt gtaggcatcc atattaagag    31200
gttgcctttt tgagtctaga gcaggggtgt cagtgtttaa agtagacagt gggatagatc    31260
agtgtgggaa atgacgacca tgggagactg cagagcacag gtctcatctt gagtatttag    31320
attcacattt tttataattc ccacaaggaa gcagaatatg tttttaatcc accagttggt    31380
gatcctagcc taccagttct gatcccagat cagaagagct tctggccagc acggtgactc    31440
acgcctgtaa tcccaacact tgggaggct gaggcgggca catcacgagg tcaagagata    31500
gagaccatcc tggctgactt ggtgaaaccc tgtctctact aaaaatacaa aaattagctg    31560
ggcgtggtgg catgtgcctg tagtcccagc tactcaggag gctgaggcag gagaatcgct    31620
tgaacccagg aggcggaggt tgcagtgagc caaggtcacg ccactgcact ctgacctggc    31680
gacagagcga gactccatct caaaaaaaca agagcttcct cgaataaatg atatttt       31737

<210> SEQ ID NO 23
<211> LENGTH: 31737
<212> TYPE: DNA
<213> ORGANISM: H. sapiens

<400> SEQUENCE: 23
aattgatacc taatcatagg caagggtggt ggggacaggg gattggggag ccttccagcc      60
actggaaata gcaggagaat tgtcaggagt gagtgtgctg aaggagggca cacccagaac     120
atgacagggc tgtgtgcagc tgaagaccag agcttcaaag gaggataaga ggtgaaacta     180
gtgtggccag accacagacc ttgcagatag tcatgagaga agtggcaagc catagagcag     240
ccagatttac atcttgaaaa aatgactcag ctgggcacgg tggctcacgc ctgtaatccc     300
agcactttgg gaggccaagg cgggcggatc acaaggtcag gagatcgaga ccatcctggc     360
taacacagtg aaaccctgtc tctactaaaa atacaaaaaa ttagctgggc atggtggtgg     420
gcacctatag ttgcagctac tctggaggct gaggcaggag aatggtcaga acccgggagg     480
cggagcttgc agtgagccga gatcatgcta ctgcactgca gcctgggcaa cagagggaga     540
ccccatctca aaaaaagaa aaaatgactc tggcttctgt aaggagaata gcccatgggc     600
agaccagaat agttgcggga atacagttag gggttacagg tgttaatatc agaagtgcta     660
gtagattgac ctaatgtcat gactaggaaa tgggggatgg atttaaggac acagaggagc     720
agttccagag ttggtaaata catcagctgg ggcattgcta aaccatcagt ttccttcaca     780
actttccact aagccatgtg tcagctttgc cttataggct ggctcctttt ttatcagtgg     840
gaaaaatttt cccaaaagct tctggagact tctcttgtca catgctcctt cttaaaccgg     900
tcgtgagcaa gggagaaaat aaggttactg tggttggctg agactagtcc agattactcc     960
tgggtcaagg ccaggcatgc tagctcacac ctataatccc aacactttga gaggctgagg    1020
caggcagatt gccttgatca caggagttcg aaaccagcct gagcaacatg gtgaaacccc    1080
atctctacaa caacaacaac aacaaaatac aaaaattagc tgagcatagt ggtacatgcc    1140
tgcagtctca gctacttggg agatgaggtg ggagtatcgc ttgagcctgc ggggtggagg    1200
ttgcagtgag tcagattcac tccactgcac cccagcctgg acaacagagc cagatcctgt    1260
```

```
ctcaagaaaa aatttttttt agatattcat gtgggatatg gatggataac ctcacagaat   1320
aggaggtctg gtaaaggagg aatggttatt gggtcagtgg gtcaccattc atatctgctc   1380
catgacagaa gggcttaggg ggagtggtga gtgatgtcag atttgcattt tgagaaaata   1440
actaactaca atatagagaa tagataaaag ggagaggcaa gagttgaagt gggagaccat   1500
ttaccaggca agagttaaca gaatagcttg gacccttttt gggggctatt ggaaaaatag   1560
caccatttaa tgttcattat tgattgataa gatttaccac atcctgccag gcacagtggc   1620
tcacacctgt aatcccagca ctttgggagg ccaagccagg cagatcacct gaagccagga   1680
gttcaagact agcctggcta acatggggca atcccatccc atctctacta aaaatacaaa   1740
aattagccag gcgtggtggc acgtgcctgt aatcccagct acttggaagt ctgaggctga   1800
ggcaggagaa ttgcttgaac ctgggaggcg gaggttgcag tgagccaagg tcgtgccatt   1860
gcactccagc ctgggcgaca agagtgaaac tccatctcaa aaaaaaaaaa aaaaaattta   1920
ccacatctca caagacagca ctccagcctc agtaccatag ctggatctgt gctaggcatt   1980
gtactgtttt gtaatctata atgccaactg cttctgggtg atggggtatg tgatcccatt   2040
actatacttt ttttctgaca aattagttct tttcttttc cataacatta aatttacata    2100
agcatgaaac gaattatttg tttggaggta atattccctg agactccatg gtaaggtatt   2160
tcagtaaatc cctggatggt gatggtattc ctggaggcat gacaggtaaa ttcggataga   2220
tattgtggtg agagccattt gctgtgctac catggcaacc gtgttcacga gctcattggg   2280
ccagcactag ggtagtgagg gaaagggctg accatcatca cctgggtttc tagcaatgag   2340
tgccatcttg tgagcattca catggaacat aaatattttc tttcttgtgc tagttatcca   2400
ctacccagcg attggtttag atcctgactt ccagtgagat aagtggtgtg ataatttgct   2460
tgaagttctc ttcactagga gaatttctct tttatacaca ttcaaagcca tcacttaagt   2520
agtatacccc atagcagtct acttccagcc cagcatgggc cagcatgttt caccaagcag   2580
tttatatacc aggccggact ttttcttctt cagttaactg ttgatgtcaa taggaagtca   2640
gaagtatcta ttgcggcagt gggttgtgtg gtaggcattt tatagagatc acttccagct   2700
gataatggga ttctgctggg catgtccaaa tctatggcta attgaatctc ataataccta   2760
gtttacgaga ccggcccggt ggctcatgcc tgtaatccct gcactttgag aggctgagtt   2820
ggacagatca cctgaggtca gaagttcaag accagcctgg ccaacatggt gaaacccgt    2880 ctctactaaa aatacaaaaa ttagccaggc atggtggcaa atgcctgtaa tcccagctac   2940
tcgggaggtt gaggcaggag aatcgcttga acccgggagg cagaggttgc attgagccga   3000
gaccacgcca ttgcactgta gcctgggcga caagagcgaa actccatctc aaaaaaacaa   3060
aacaaacaaa aaaccccta gtttacgatg gggagttgaa gtcatttgga tacctgtctg    3120
tgatcaggct tgcagtctct accctagagc ccagtactag gctaggagca tggtcttacc   3180
aataggatca tggtcttata tccatatcca aatattcga ttcttctgtt taccttacta    3240
caaacactct agagctccat acaatctacc agagcttatt tctctgtggc ctggatcagc   3300
aggagcactt tctcttttca gatcactcaa taaattggtc agaggctggg cacagtggct   3360
catgccttta atcctcgcac tttgggagat gaggcaggca gattgctttg agtccaggag   3420
ctcaagacca gcctgggcaa catggcgaaa gcctgcctct tcaaaaaatt agctgggcat   3480
ggtggtatgc acccgtagtt ccagctactg ggaggctgag gtggggtat gcttgagcc     3540 taggagtttg aggctgcagt gagctgtgat tgcaccactg cactgcagcc tgtgtgacag   3600
agcaagatct tgtctctatg taggtaggta ggtagattga ttgattgatc agatggatta   3660
```

```
gatggattaa attgagagat cagagttgga tgcaaggata aggtatctgc tgtctccaaa    3720
actcaaaatg gcccagcaag cattgctcct ctttgttagc aggagagggg tggtggggca    3780
aggggcaaca agttgtcttt tatgttggag gagatacccct gacgtgctgc aggcctttga   3840 cttcagaaa atttggctga ggtggcaggc cactgtattt ttatgtctga catgtacatc     3900
taagatacat aacttcctgc ttttcatgtc tcacattgat gtcattagca tagttgtcaa    3960
ggtaatgtcc tgtgaaacag acaaaatctt gatgaaccag atcacaacac agaaaggtca    4020
agatgattta tcactgaggc tgctcttgcc atgagcaaga aaaactgctt caagtagtcc    4080
acacaactta aaagaacac acacttaccc ctagcagtag tctaggtacc aggagttata    4140
tgttaatctg cagaaagtag agtacgtctg gaaaagtaac tgcaaatctg caaagtcttc    4200
tgtagcactt aagatcctgc ggttcacatg gagacttcgc cttttgctaa agagatcact    4260
gctctaggag cttacatttg ctctttctgt gatggttctt atccagtggg ctagggaatc    4320
tgtgtgtctt tgggcattac ctaatggcca atgttattga aaatcaaggt ggcacagagg    4380
gaggtctagc caacttcaca gagccgggag catctagttt cttcccctcc cttttggagg    4440
ccctgacaga caggcaggca ggcagacaga cagatcgaca gacaggtaag atagattaga    4500
tagattaata ggtcctaatg tgaagccacc tcaggccaaa attccttcca tcagctggcc    4560
tgcaaaggct ccgttctaac tagcatatct tagcgacatt ctgagttcct agcaagtagc    4620
tacctcaagg ccaggaccta gcagaccca aaagatgcat ttcccttttac ctagtacagt    4680 tgccatggca aatatctgca gattattaag aaaagatgag gagggaggtt tataatatat    4740
gtgtgttaat gcgctgtggc agggttcctc cttacagatg cctggcctcc ctgttattga    4800
agggttctgg gtctgaaatg acccaggcct acgagttgga tgaggggggcc ccctctctag    4860 catggtggtc tagtaggctg cctaaactga cctggaaagc tactttccgt ttccattact    4920
gggagcttca caatgaatta ttcacagcca taaacgtctg atcatggtct ccaacagtct    4980
ttctagccca cttagatcag gaatcccatt ttgaaatagt cccttccact agcatctcac    5040
gctgctgagg acagccagga aagcacttct gaaagattcc agtgctttcc tcaccagtgt    5100
atagcctcag caaggcatgt gatgtggatc ccatcaaggg catactgaag gtgtcagtag    5160
aaggctgagc cttagagtc catatgccac tctggtctcc tctactttgt gcccaggttt    5220
ttctggcttt tcattatcac ctcactaaat ccagcattca gtccaggttt ccactggcga    5280
gcctagctca acattaaaac catggccagt tacctgagct gttacactac ctgcagaagt    5340
tcttttgacc ataccataat tagaaatttg gctttatcca ggctgggcac aatggctcat    5400
gcctgtaatc ccagaacttt gggaggctga ggcaggcaga tcacttgagg tcaggagttt    5460
gagaccagcc tgaccaacat gctgaaaccc tgtctctact aaaaatacaa aaattagccg    5520
ggcatggtgg tgagtgcctg taatcccagc tactcgggag gctgaggcag gagaatcgct    5580
tgaacccggg aggcagaggt tgcagtgagc caagattgca ccactgctct ccagcctggg    5640
ggacagaaca agactccatc tcaaaaaaga aagaaattt ggctttaacc aagtcatact     5700
ctcccttcct tgttataacg tctccaaaat ctatatcaac aattgttcct atcatttgta    5760
atgatccagc tcagtgaatt cctgtagttt cttctggata tttattagct ctttacttttt   5820 tttcccccgc tgtagagacg gggtcttgtt gtgttgccca ggctggtctt gaactcctga    5880
tctcaagcag tcctcccacc ttggtctccc agagtgctgg gattacaggc atgagctact    5940
gtgcctggcc agcattttac ttttctacct tatttatgca ttttaccctc aggtcatgtt    6000
atgcttgcat tctggtaatg tgtgggcaat gcaggctggg ttgtggggca gttttcatca    6060
```

```
tgacagcaag atgcagtaga gagcataata gagattttg  gaaattaact ttctttgggt   6120
cctctctttt atcatcattt ctgttgtctc acttaaagcc ttatctttct catgagcaac   6180
ccaggaaaga tgtgaattct gtggcattaa aattcagcaa ctcgcaaaat ttggaaacct   6240
taacatttca cttagcaaaa tacatatata gtaatgtaaa ggccctgagt cttgggtttt   6300
catttcaagg tgagcatttg atattggagc tgggttattt cttgttttgt tctctaatat   6360
tgtcagaagt aatcctactc cttggtttca acatttcccc tctccttta  attgggacac    6420 ccctactcgt ttaccaccag cttgaacaca tcacaggtaa ttgcaagcaa taactaaaat   6480
agtagttgtg cagctatgaa ctgtgagcag cttgctcttt cccatcctgg caattggttg   6540
tcagtttctt tccttccatc tgaacccagt aacatcaccc acgtttcccc tagcagtctc   6600
tcaactacaa cccactctga tagtaattgc taaatcagtt aaggtcctct agttaaaagc   6660
aagagaagtc acctcaacta aattaagcaa aaacaaacag aactattgat ttgggaagac   6720
actggaggag ctggcagaat cagaaggtaa gttggagtac caagtctcag gtagagccga   6780
ccttggtggc tttggggccc ttctagggaa gcccctgctt cttcctagtt ttcaaaatcc   6840 tgggagaaa  tctgattggc tcagtatcag tcaggtatga ctgtgtttgg atcagtcagc   6900
cctgggagag aagaggagaa ataacacata gggcaaacaa accaatttgt gtctactgtc   6960
atagaataat attttagta  accatcagat ggggaaggcc tttctaagct acttagaaga   7020
tttagatgcc agaatggaaa agtttgaaag atagcaaata tattaaaatg tgaaacatct   7080
ttgtgacaaa tgatgtcgta aaaagtggc  caactgggag aatctatttg ccataggtag   7140
acaaagaatg ttccagaata tacaaacctg tgagtaaaag gtaaacaatc cagtcaagaa   7200
actggcaatt tacagaagaa atacagatgg tctataaaga tatgaaaaga agatcaacta   7260
tatctagtaa tcagggaaat acagattaaa gctaaccatt attttggacc tatcagattt   7320 gaaaattta  aaagctttat atcaaatgtg gacaaaagta tggggctgca gagacttaca   7380
ggtgggggag tttaaattgg tattgcattg gagggatgat tctggcagta ccaatcatta   7440
tttaaatgtt tgagttttct gaccaagctt ctgagattct taacagaaaa agccatgtac   7500
aaagatgttt atgacagcat tatttataat agcaaagaag ataaaaacgc aaatatctgt   7560
caaatagaat ggccagatga tttcttatat ccattatgat attctatact atcattaaaa   7620
taaatgtgtt cacatagatc tctaagttat attgttatgt gagaaaacat atgtgggata   7680
atttcatttt tgttttcaaa aatatgtata tctgtgtgtg tttgggtatg ttaatgcttt   7740 ttttttaag  tctgaaagac tacaaattgt caacagtggc tgcctacaag ggggctggaa   7800
gagaggagag acataatagg gaactttgtt ttctactaaa ttatttgact taaaacaagc   7860
atattctttt tataatattt ttaaagcaga ttttttgaa  tatgggaaat aaatctaatg   7920
gacttagttt gcttcgatgg atatataaca tctagaataa agaagttcct atgcctagtt   7980
tgaactgtgt caggagtctt gtggtcaggt ctctataaaa agggatatca ccaaatggga   8040
tgttgttctg gagagaaact ggaccatggg ggtgaataac taaaggaaca acactcatag   8100
gacatgacag ctgttttcag atatgtgaca ggctaaaagg agactgtagc atttccgtga   8160
atgcccacct gattagaagt tctaggctgt ggctttcatc ctaattacaa gctggagctt   8220
ttttgttcac cagcatttgt ctttctagga atcattgaat ttattcaaaa gaaatacttt   8280
gaaaaaccac tcagaagccc ccattttcag ggaaaattga ggtctttaag gcattatcaa   8340
ggtttaaaaa gaaacaaaaa gataaaattg tgttagcttc tggctgggtg cagttgttca   8400
tgcctgtaat ctagcacttt gggaagccaa tgcgggaaga ttgaggccag gagtttaaga   8460
```

```
ccagcctagg caatgtagca agaccttatc tctacaaaac aatttttttt aattagccag   8520
gcgtgatggc acatgcctgt agttctagct actcaggggg ctgaggtggg agaatcattt   8580
gagcccaaca cttggaggct acagtgtgag ctatagtgct aactttatag agctgcagga   8640
gctacagtga gctacagtga tcaccgcact gccctccagc ctcctggcta ccagagtgag   8700
actctgtctc aaaaaaaaaa aaaaaaaaag gcttagctcc tgagaggaat gggataggag   8760
agaaagaaaa gagggaaaga ggtgaagcca gtgaaatagt cagaatctgt gcgatgtgag   8820
atgtgacctt cctcaggacc tcacatctct tagattgcca ggtgaagaag gcatgtgtgt   8880
gtcactagtg atgggactga gtgtggcatc tgagttgaga tgggtgaaat cgcctctaca   8940
ttgatgagtt gtcccaaaat aagtgaatca gagtcacagt cctgtgggaa ttagcaggaa   9000
ctgtgacaag ggctttggaa ttccactgtc cagagagttg ggagtttgcg ttttgcaagg   9060
ggcagaaaag atgcccgctg acatctgggt tttacattgc ttagtacgag ggaaatgcaa   9120
aagaaattgt gtgtctgggt gttgggtcgt tttaaacaga actgttccaa gacctacctt   9180
ggaaggtagt aaatttccca tcactctagt gttcagtcac tggtgactat tgggtgagag   9240
tattgaaagg agattcagac ttaaaagtga atgagattca gacctgtact ggagatctag   9300
gcaagaaaag aaaggtataa ggattgcaaa ggaagggaca aaatataaat ttttcacaga   9360
ccaaatactg tcttcagaaa aacccacaga ttcatcagac atattataga attaatatga   9420
catattatat tatagaatta ataaatatga catatttata atttattata tatgacatat   9480
ttataattaa taaatatgac attatagaat taatatgaca tattatagaa ttaatattca   9540
tcagacatat tatggaatta gcaaggttgc tagatacaga agcagcataa aaatttaatg   9600
catttctata cataggccac aaacagaaaa cctaataata ccttttaaaa ggtgccaatt   9660
acaatagcat ccaaatgtaa agtacctagg aatggattta acaatttaga gaaaattatt   9720
aaaatgtttg aagacattaa aggaaaatag cttaaattag tgaagagata ggatcaatgg   9780
attaggaggc tcaattttgt aaagatgtca attctccccc aagatatata gattcaatgc   9840
aattccaata aaaatcccaa caggttttttt tgtggaactt gacaagctga ttctaaaatt   9900
tatatggagg agaaaagatt caagaatagc caagacattc ctgaagaaga gaacaaggt   9960
gaggagacct gccttaccag atataaagag attataaaat tttagtaatt aagacagttg  10020
tgtattggca ctgggataga cagatcgacc agtggaatga aataaagagc ccagaagcag  10080
atccatttgt aagtgaaaac ctatttatga cagaaatgct cttgcagttt gggtggggaa  10140
aagatggtct tcacaataaa tagtgcctgg gaccattggt aaccctgtgg gaataaatga  10200
aattgaatgc ttgtcacata tcaaacacaa aaaccaattc cagttgctgt aaacactgaa  10260
atttaaagga caaaatgat aaaatgtaga gatcataatg tagtaaaata tacttctgat  10320
ctcacagtag gaaaggattt cttaagactt aaaatgttga taaaagggaa gattgatgaa  10380
tttacatgaa aatgcaaaac ctctgttcat aaatgatacc ataagaaga tgaaagggaa   10440
ggccacaacc ttggtaaaag ataacacagg taactgataa aggaagagta tccagaatat  10500
ataaagaact tctacaaatt gttaagaaaa taagtaggct gggcgcagtg gttcatgcct  10560
gtaatcccag cactttggga ggctgaggta ggcggatcac aaggtcagga gttcgagacc  10620
agcctggcca acacggtgag accctgtctc tacaaaaaaa tacaaaaaaa attagccagg  10680
tgtggtggcg ggcgcctgta atcccagcta caggggaggc tgaggaagga gaattgcttg  10740
aacacaggag gtggaggctg cagtgagcca agattgcgcc actgcactcc agtctgggtg  10800
acagaacaag actccatttt gaaaaaaata atccagtagg acaacgggga aaccacttga  10860
```

```
ctaggtactt cacggaagag gaaactctttt tgaccagtat gctatggaaa gatgatgaac   10920
ctcattaata atcagagaaa tgtaaatcag ttaacacaaa gtctgacagt agcaaatgtt   10980
gataagcata cggaactgga acactacatt gctggtggga gtataaatta gtacaacttc   11040
tttgaaaaac aatttggcct tatctggtaa ggttaaagat acctatacct gaaattcttg   11100
cacatatgca caagaaagat acaaaaatgt gtctcaaagc aggacctttta actgtaaaca   11160 acccaaatat tcatcagtag tagaatggat aagtaaattt taacaccgtc tcaaatggag   11220
cactacaaag tagctgaagt tagcagccag gatgaatctt aggaacgtaa tgttgagcca   11280
aagaaaaaag caactcacca cttaatcatg attccatttt cctcaaaaac tagactagca   11340
ataataatac attgttttgg atgtaaaaaa tatgagatac aaataaagga atgtaatgat   11400
aattataaaa cttcaggttt accagtgaga ggggaaggaa gaggatataa ggagaggagc   11460
ccaaagagag cttctaagtt aaattatgtg atggatactt tttaaaaaat aaatatcaac   11520
aaatgtgaaa aaaaaatttt ttttttaaccg acatgtcttt aaaaaatgaa tgagtactta   11580
gccttggttc cagttaaggc ttaaacaaga gatgaaacgg tcttcgatgc cacctagtgt   11640
ttctagagag tttaacattt tatagacttc tgctctagct gctccttcct agctctgtga   11700
gctaggtttt tcagagtaga aaccaaaagg agtaggattc accttgtttt catccgtgac   11760
gcaggctctt cattctgaac cttttgcatct agcgctgtgt tctccagggc aagccctttc   11820
ttctctcttg ttaaacaatg gctcctgttt cttcctgact cttttttagga gccttagtcc   11880 acctggagac ctagtttttc tttatcatga ctgagggagc tagggatgct gatagggctg   11940
tgagatgtag tctttgttat tcctgacatt tttgtattga agactgtttt caagagtctt   12000
gctgtcccta cgtctgttct acattttaga gaagggatgc acaggaaaac tagtgcctct   12060
ggattagcca tcagggctta aaaaactgac atctcatcct gccctgtact tgggtggaaa   12120
cctgtggaaa tcttatgtga aggaagagaa tgcaaactgt gggtgaactg agaaattctg   12180
atctaaaata atggtctcta ctgcgtgtgt aagagtccag cccaggaaaa tcttttcttc   12240
cttttgtggt attcacagca tagggtcagg ggtaattgcc tctgttagta aaataacatg   12300
cagaacctcc agggttttaa tctgaaagga aatctcttga gtaggtgagg gcagatggat   12360
tttgaggtcc taatttccct atctttgggt cttttcacttt aatttctcct atcactgtca   12420
tgctggtttc cagtaaatat atttgctcct ttcttaaagc tcttgcttcc cagcctgggc   12480
aacatagcaa gatccacctc tacaaaaata aaaattaaaa aattagccag gcatggtggt   12540
gctgtgcctg tagtcccagt tactcaggag gctgaggcag taggataccct ccagcccagg   12600 agttcaaggc tgcaatgagc tatgatggcg ccactgcact ccagcctggg tgacagagcg   12660
agaccctgtc tccaaaaaaa aacaacaaaa aactcttgct tccatctgac aaaaaattgg   12720 ttcccttttgg gttggcattt ccttattca gtcttttttt aaaattattat caaagacaga   12780 aacgttcatt cttcatttct gcctcttgct cttcccagtc cacttttgcc ttcattccat   12840
ctccaaatgt agtaattttt tttttttttt ttttttgaga cagagttttg ctctttctgc   12900
ccaggctgga gtgcaatggc gcagtcttgg ctcactgcaa cctccatctc ccgggttcaa   12960
gcagttctcc tacctcagcc tcccaagtag ctgggggttac aggcatgtgc caccatacct   13020
ggctaatttt ttgtattttt agtagagatg gggtttcacc atgttggtca gctggtctcg   13080
aacaccagac ctcaaatgat ccacccgcct cggcctccca aagtgctggg attacaggcg   13140
tgagccaccg cgcctggccc aaatgtagta attctaattc cagaatatgt ctcaaatgca   13200
tccatttcct tgtatcatca ttttttccatg cttctcttct tgctcctctc tagtccattt   13260
```

```
tccatacaat aacaagtaat tctttaacat ggaaaatgga tcacacttta aaaaccttca  13320
atgatttcct tatgcactta acataaaatt tgaactccct attcaaggac ctacctggaa  13380
atggatgatc tgactttgcc aggctcatct cttcctactt cctcctgcca tccccatcaa  13440
cctcaccttc tgcgtgatac ctgcactgat tttcggttcc tcacacaacc aagccttctt  13500
ccacctctgg gttaccacag atgctgttct ctgtgtctgg aatactattt tctatactca  13560
tccttcctca gagagaccca cctgtaatcc aaatttggtg cttttctgata cttcatctct  13620
agtagcattc tgttctttga ttgcattcat catggtatat aattatatat gtatttgttt  13680
tatttgttta atgtctgctt ttcacccaca agtttatatt gtccttgagg gcgagaactg  13740
cacttatatt tgattcccca ctctttgctc tgtatctagc ccagtgcctg gtaggtacaa  13800
aatatatatt tgttgaaaga atgaatgaaa agtaatgcat gaattgttcc tctactgctg  13860
aatactacgg ttgttctcag ttttgggtca ttctaaataa tgatgaagta aataattagg  13920
acataaagat ttttatttcc taagggtatg ttctcaaaat tgaagttgct aggccaaaaa  13980
gtattttttga aaagttttttt taaggctcat aaaatgtaat ttccaagtca cttactcgga  14040
attagtgttg gaatttttaaa gtgcctccct ttttgctttc ttgtttgttt ttatagtgtc  14100
agagtctcac tgtgtcactc aggctggagt gcagtggtat aatcatggcc ttgaactcct  14160
gggctgaagt gttcctccca cctcagcctt ctgagtagct gggactacag gcatgcacca  14220
ccatacctgg ctattttttt tttttttttt tttttaatg tagagacgag gtcttgctgt  14280
gttgcccagg ctggtctcaa acttctggcc tcaagtagtc ctcccacctc tacctcccaa  14340
agtgctggga ttacaggcat gagccaccac acccagctcc tttttcatc cttaattttg  14400
aatatatgaa acatacaaga ggagaacaga tcaaataata aaatttagct tcccactctg  14460
ataaaactca tttatttgaa tacttattct ttgctacaca tgagattatt tccttatgtg  14520
gcagatgttg ttgttccaat tttatgtatt tatttattat ttattttttga gacggagtct  14580
cgctctgtcg cctaggctgg agtacaatgg cgtgatcttg gctcactgca acctccacct  14640
cccaggttca gcgattctc ctgcctcagc ctcctgagta gctggggtta caggtgtgca  14700
ccaccatacc cagctaattg ttgtcttttt agtagagaca gggtttcgcc ttgttagcca  14760
ggctggtctc gaactcctga cctcaggtga tccacccgcc tcagcctccc aaagtgctgg  14820
gattacaggc gtgagccact tcacccggcc ccaatttttac agatgaggaa actggaccta  14880
gaaatttttaa cagatgtgct caagttcata caaacacaga ctatctcatg tcagatcatt  14940
gtgtgataac ctccctgcac taactaatct acatttgctc cagaactgct gcaaatttaa  15000
tgtcacctca cccaaatctt ctgcttctta actgctgcat ctatatgaat gccctcccac  15060
ccacccacca gtccttgctt ccttgccaca tgatgctaga ggctggggtg ccatgccccc  15120
ttagatccct aggaagagat taaatcagct ggccatccag aaccttcctg tgtggttcac  15180
tctgagatgc atgtcatctt tgtgtggtgg taattagcat gaggataaat ggcccattcc  15240
ttcaggtatg tccccattcc aatttacaag ggtaggccct tttggcccag tatcataaca  15300
acaggctgct aaccacatag taatcatgga aagagcatgc tatacttaca taacagaaag  15360
ggcattctgc ccctgaggaa ttcttgtgtt gttgaactct aaggagcttg tggctgtttc  15420
gggggagagg agcattctct gtgttaggct gcaggtattc acctgggccc atgttttttcc  15480
ccccaggaaa aggtagaaca tgctaccagg tcagggtttg gtgcagcagt ttgcatgttt  15540
gatgtttatc cctgctaata attcctctaa tttctcttaa cctttcaggc tctccctgca  15600
tgtcctatcc aggccaccctg tgaggctgct tccaaggagg aaaacaagga aaaaaatcga  15660
```

```
tatgtaaaca tcttgccttg tgagtgtctt tagtgtttct tgggatgtaa cctgaaatta   15720
catctctgga gggattttct gaagatggaa agaatcttgc aattgggcac agcagggtga   15780
ataacaagag tgcgttcatg gcagtactca gtggctcata cctgtaatcc cagaactttg   15840
gaaggccaag gtgggagaat ctcttgagcc caggagtttg aaactagcct gggcaatata   15900
gtgagacctc atctctacaa aaaccttaaa aaattagcca ggcatggtgg tgtgtgtctg   15960
tcgtcccagc tactcaggag gctgaggtag gaggatccct tgagcccagg ggggcagagg   16020
ttgcagtgac ccaagatcgt gtcactgcat tctagcctgg gtgacagggc aagaccgtgt   16080
ctcaaaaaaa taaagtaaaa gaaatgaaat aaataataat aaataagata aataaataag   16140
agtaggttga agactttggg ctgaaagagc ctttatggat cccacatact cagagtcaat   16200
taggatgatc caggaggatt tttgtgtcag gcctaaagtt tctaggaggt cctggagaac   16260
agcttcacta ggatcaggca ggaagcaggg ggtaatggtg gtggtagaga tggttttttg   16320
tggtattcat tgaaagaaat tctaatgcag agttctctgt ataaacccct cccagagtta   16380
gccattgcta atcagttgat ccataagcta acagacattt ttctagtcca ttggtatcca   16440
gaatgggata tgcataattt aatgagatat gagaggaaga tgtttgaacc tcacttgatt   16500
tttatatttg cttttcaaaa aaaaaaaatt cctaatcctc agaacctgtg aaaatgtttt   16560
ttttttaatt ttttgtagag atggtcttgc tgtgttgcct tggctgatct caaactcctg   16620
gcctcaaaca gtcctcctgc tttggtctcc caagtgttgg gattacaagc atgagccagt   16680
gagcccagcc agtatatttg cctttttaaaa attcatcctt ttaaatttttt tatttcattt   16740 atttttttag agacagggcc acccaagctg gggtgcaatg atgtgatcat agatatgtat   16800
cctcgaattc ctgggctcaa gtaatcctcc tgccacagcc tgctgagtaa ctagaactac   16860
aggtgcatct accatgcctg gctgattatt ttttagacac agggtcttgc tgtgttaccc   16920
agcctggtct caaactcttg gcctcaagca gtcctcccac tttgacctcc caagaattg   16980 ggattacgtg catgagccac cacatctaga ccctaaaaat tttatatttc agggtatatc   17040
atacattagc atatgtgcat aatttatcaa taaatgagca tgtattagag atgcctgctc   17100
acatttttat aagtgaagta tggaaccaaa aaattaggac cactcacta tgcatttaca   17160 gatacttttg tctttttctt ttttctttct cgctctgtca cccaggctgg agtgcagtgg   17220
cacgatcttg gctcactgca ggctctacct cctgggttca agccatttc ctgcttcagc   17280 ctcccaagta gctgggacta cctataggca catgccacca cacccagcta attttgtatt   17340
tttagtagag acggagtttc accatgttgg ccaggctggt ctggaactcc tgacctcaag   17400
tgatgcaccg cctctgcctc ctgaagtgct aggattatag gcgtgaccca ccatgctcgg   17460
ccttgtcttc ttatttatgt gcacatgttg gaggagggg atgtgtgtat gtgtgtgggt   17520
gtgggtatgt gtatatataa tacatatttt ttaatatgat tggtatactg tacacatttc   17580
tctcttttaa tagtatatat tgtcagttca tctgtcaaga aactttcttt tttctcaact   17640
acttagtatt ccacattgta gatgcatctt aatttattta actagtcccc taatgatact   17700
taaggtattc ccaattttt gctgttatac tgttggagtt atattgttgg agtggcatct   17760
ttatacaagc gtgagtctgt gcacataggc acagatgtct caactgtcct ggttgcgtca   17820
ggttctgtga gaaataaatt ttgattttac tgaaatattg ttggtttgtt tcctagatga   17880
ccactctaga gtccacctga caccggttga aggggttcca gattctgatt acatcaatgc   17940
ttcattcatc aacgtaagga tcgggtgctt tccctgtcac ttccctgcct gaccattgcc   18000
actatctgtt ggctcctccc cagctgtgtg ttaggagaaa tatttgtcat ttcatgtttt   18060
```

```
ccctgacaag tctggttttt ttaagtgact gaattttttt ttaaggtcag tcaaatagtt   18120
ttaatcattt tctatattta ccctgtcgtc attccctatg gtttcccatg tagaaatctg   18180
tgtctaaata tgtattttgt gataagagtc agtgaatcct ttattgagct gattctaatt   18240
acaaacaaaa gcaggccttg ccctcaacag taaaaataag ggagaacagg acaagaatac   18300
ctgacatgac accagctata ttatatatgt gtgtgtatgt atatatgtgt gtgtgtgtgt   18360
ctgtgtgtgt gtatatatat atatatatga ctatctggtt agccatatat gaaccaaggc   18420
ctgagggaag agctgatact aagaggaggt ttttaaagat gatttagaga atgtttatag   18480
aacagtctgt atgagagatt tgaggttttt gtttggttgg ttttgtcttt ggcagtagcc   18540
tgaaaaaaca cataaagagt taagaatatg ttttataggt ttgggggaag catcctgtag   18600
agagagtgaa tttgaacaga aaaagagag agggaaagct ggcaaaagca agtctgactc   18660
ctgatgcaaa atgcatgaga agactggata aaatttccac ttgcatgttt atagcagcat   18720
taatcctaaa agccaggtgg gagcactcca agtgtccatt gacggatgag tgaataaatt   18780
aaatgtggta catgcataca gtggaatgtt attcagcctt taaaggaag gaaattctaa    18840 tacatgctac aacatggatg aacctggaag acatcatggt aagtgaaata agccagtcac   18900
aaaaggacaa atattgtatg attctacata tagaatataa actatatata catatgtaga   18960
gtagtcaaat tcacagggac agaaagtaga atagtggttg ctgggggagg gaggaatgag   19020
gagtgggtac agagtttcat ctggggaaga tgaaaaagtt ctgtagacgg atggtggtga   19080
tggttgcacg acagcgtgaa tatacttaat gctacagaac tgtacactta aaatggctaa   19140
aatcagccgg gcacggtggc acacctgtaa tctcagcact ttgggaggcc aaggcggtgg   19200
atcacttgag gtcagaagtt tgagaccagc ctgaccaaga tggtgaaacc tcatctctac   19260
taaaaaaaaa aaaaaacaa aaaaaaaaaa aacaacttag ccgggcgtgg tggcaggcgc    19320
ctgtaatccc agctacttgg gagattgagg cagagaattg cttgaacccg ggaggcggag   19380
gttgcagtga gccgagatgg cgccactgca ctccagcctg ggcgacaggg tgagactgtc   19440
tcaaaaaaaa agaagagtca aaatggctaa aatcgtaaat tttatgttgt attttaccac   19500
aagaaaaaaa aaggacactg atggagagat tagtgtgaac ataagaaggg ctgtttcttc   19560
ctctgagagt gaagataaag gagaggacag aatggataga gacgactcgt aggtgtgggt   19620
aaagcaagtt gaggcaactc acccgtgtgc tcatggttgt gtactgaaca aatgagatgg   19680
gactgtgaca tgagagcttc gaaagtttag aacagcttct gaggtccctg agaaaaggat   19740
accaaagaga gaaagcaaag gacatgtcta gtgggatgtc attgatgggg gtgggggtg    19800 ctgagttgtg tgattttttt tttcttcatc tgcaccctgg gattggtggt aaatgcagag   19860
gacatgtggt actcagacaa aagggaaggt cagtggctgc ttcaagtagt cagccaaggg   19920
cttcagtttc agtagaaaag aaaagcgtta ggaagttgtt aggaataaac aactattcct   19980
aaggtggtag gattgaggaa ctggagatct tgagaaagtg aaagaacagg aggttgtgtc   20040
caaaaaatag gctattagat ggacttcaaa aatggggcag tccgggcatt ctcactggag   20100
tgaatttgct gaagttcctg tatgtatgtt taacattaat ggttacatgt ttgtagtttt   20160
aaggaaaggg accctgacta gacaaataat tgttgtagtc gataaggaaa atggagaaag   20220
gctagtaatc agcaggaatt cctagaactt acatcgaaga tcatgatgaa gagattaggt   20280
ggaataggtt gactttaatg ttatgcagaa gagaagagca agatcagtta gtgtgtccag   20340
ctgcgggtaa gagaatactc aactaaaagt tgtctagatg ggaacatttt ttttttttct   20400
ggagacagtc tcaccccgac acccaggctg gattgcactg gtacgatctt ggcttactac   20460
```

```
gacctctgcc tcccgggctc aagcgattct catgccttag cctccctagt agccaggatt  20520
acagacatgt gccaccatgc ccagctaatt ttttgtattt ttagtagaga cggtgttttg  20580
ctatgctggc caggctggtc ttgaactctg agcctcaagt gatccacctg cctctgcctc  20640
ccaaagtgct gggattacag gcgtgagcca ccgtgcccag ctggaacatt tatttgtctc  20700
atatactgtg aaagcaaatg agaccagtt cttgagttgg ctgattccat gggtcagtga  20760
catacttaca aaccaggtg cttccatctt tctactcagt tatccttagc cctgtcaaca  20820
gtctcatggc cacaagatgg ctgcagcagt cccaagcatt cctcataaac acagcatcca  20880
gccgggtgcg gtggctcacg cctgtaatcc cagcactttg ggaggccgag gcgggcggat  20940
cacaaggtca ggagatcgag accatcctgg ctaacacggt gaaacccgt ctctactaaa  21000
aatacaaaaa attagtcggg cgtggtggcg ggcacctgta gtcccagcta cttgggaggc  21060
tgaggcagga acggcgtg aacctgggag gcggagcttg cagtgagccg agatcacgcc  21120
accgcactcc agcctgggcg acagagcgag actctgtctc aaaaaaaata aataaataaa  21180
aaataaaaaa aataaacaca gcatccagca cagaagagga acatatctgc ctatgctttt  21240
ctctctgtta gggagcaagg cttttcacgg aatcctcccc accaccctgt cctcaggacc  21300
agcaggccag gattggatca catgttcaca tccctctcta atcactggct aggacattga  21360
gaatgatcat gatttacccc tctgagcctg ggaatgggc accttccaag ccagtgaaag  21420
gttaatgtcc aaacaaaatt gtggctctaa tggcaaagaa gaaagggagg aatggatttg  21480
agttagtaac cagcagcatc tgccaccgta accagtttgg tcccttccca cattgaaggt  21540
gaaaactgac aaaagttaat tgtatgttaa ggctgttaag cagctgagat ggggatctct  21600
tcatggtaat ggcacagtag aaagaaacag ccttatccct tgaccatgtt tatttagagc  21660
ttacactagg gcattccata atgccttgat ggttattaga cagttattag taggcagagt  21720
ttacatgaag agggttaaat gggggacctt atgaactcag tgaaggaaca aaagcaggga  21780
aaacctgtg gttaaccata agtgggaagc agggattaaa gatttggatt tcacagttta  21840
ttaaactcag tcaacatttt ttgagcacct gctgtgtgcc aagcactgtg ggtaggctta  21900
aaggttacag aggtaagatg taatccctca tatactacac aggtagttag gttgttttcct  21960
gtaatgtgct acgtgtgcaa aggaggtatt gccaggttct gtggagttat gagaaaaaac  22020
attcagccca gcctggtaac ccagtagagc tcattattga agagtgagtc agagttcagg  22080
agaagaaagt tgggcagaaa cttcaaagca aaggagaaac atgagcaaag tcacagagac  22140
tagaaacagc agtcttaggt tataaggtat aagatgggaa gtggtgggaa atgagacttg  22200
atcttgaaag gtagtggatg tcaagtgtgt ccattggagt tcttacttgc agactataga  22260
gtgtactttt catccactct tttaagcaga aaggggttta ttataagata ctgggtacct  22320
taacaaaacc tggggaagag ccagtgagcc aagctcagat gctgctcagc aaagagcaga  22380
gcagctatag atctatgcag catgtgactg tcatagtgaa acctctgcac agtgctgcag  22440
aagaactgga tgcttctact accgtgcttg cccaaagacc agatttctag cacagtcgtt  22500
atctcatgtt gctcatttct accccaagtc ttgtgtggga gcatctgcta ggaagaagct  22560
aggtctcgtg gattgctgag ctgctaggga gtctgggaaa tgtagctgta agatagtcaa  22620
gctagaaggg agcaggagtg ggtactaagt gaaccaccta atagtgtctg ccagttttca  22680
gtacagctga gcggttttga tgaatttatc taggccgtgg ggtaccattg aaaagtgttc  22740
aaggcaggga gtagtgtgac cacatttaca tattgatcac tggggctatc atgtacaaca  22800
tggatttagg aggggccaat tgggggctat tgcaatagca ggtagatcac aaatgatgag  22860
```

```
ggttgacaag gaagcggcga caaagtgaaa actacgtgga ggtagaattt agcaggaatt    22920
ggtggttgat ttatatatga gagagtagag ggtgatatat ccatgtagat gtatccagca    22980
tacagttggt catatctaga gctgtggact tggaagtaat aaaggagtgg gccaagaaca    23040
gagcccttgg gcccacagcc cctgccaggc acattgaaca ggtgctcatg ggtgagatgg    23100
aaggagacca agagaagaga gcatctgaga aggcaaagat aaagcatggc tcaggaagtg    23160
tttggcagtg aagagggtta tgtgcagatt agagatcagt gggaaagagg aacagatttt    23220 cttggactt agtgtgtagg gcagcatcct ttgctgaagc aaattcagag gccgtttgtt    23280
gcatcctttt tgtgggctgc tagttaacac ttatcaaacc cttttttcc cctaacattg    23340 aggtataata tatataacat aaaattcacc cattttaagt gagaattcag tgattttttg    23400
gtaagtttac caagttatgc agccatcacc ataaatgtct tagaacattt tctaacaact    23460
ttattgagat gtaattcaaa taccatgtat ttcacccaga gtttacaatt cagtgttttt    23520
ttaagtatat tcacatataa ctgcagccca tcaccaattt tagaacattg tcatcccctc    23580
aaaagaagaa ccttacactc tagctgttgc ccccttagtt ttagaacaca ttgctcaccc    23640 caaaagaac ctcagtgtct aaatacaatt aatctccatt ctcacccccc ggccatcact    23700 taacttttg cgtagagaac tgagaccaca cacatggatc ttgaagggaa ctaggcacca    23760
tggagtagtg gtgaaaggcc taggaaagtg gggtctgtag tttgggaaac acataggtca    23820
gctaacctaa cactgttcac aggaggagat gaaacagagg cagtggcaca gttggcaggt    23880
gggcttccag cctagagcct taggagaaac cagtttcctt actcattttt agatgtctaa    23940
gaatatatag gattttttt tttttttgag acggaatttc actcttgttg cccaggctgg    24000
agtgcaatgg cgcgatctca ctacaacctc tgcatccggg gttcaagcaa ttctcctgcc    24060
tcagcctccc aagtagctga gattacaggc atgcaccacc acacctgcta attttgtatt    24120
tttagtagag atggggtttc tccatgttgg tcatgctggc ctcaaactcc ctacctcagg    24180
tgatctgccc acctcggcct cccaaagtgt tgggattaga ggcatgagcc accgcgccca    24240
gcctagaata tataggatct ttagacgtgt ttcttttag aggtaggaat gtagctacca    24300
cctagagccc actgagattc agctttcaga atctagagac atctcaggag ccagggagcc    24360
acatttcatc tttcccttga acagaacaca agatcagtgg ctttgcttca ttctcattac    24420
tctgtattag ttaagcagtg ccgccacatc actgtacaag catgttttca ggaaggcata    24480
tgacgcactc ctggtaagat ggggcaggaa gcactttggg gctgggcctt ccaaccaggt    24540
gttcaggctg ttcagggccc gcatgctgca atgagaattt agcagtgact cctcatggag    24600
caggaatatg atgcgcttaa cgtattctta aggacttctc agttttaatt ataagtttag    24660
taatataagc agaatttaac atccagaatt aaggctattt ccatttccat tctctaataa    24720
ataaaaacat ttgttgaaac ttaaattgct cttctcaatg aaaactttaa caagtctttt    24780
gttgctgact aaacatatcc atctctgagg cctaaagctt tctccttctg tgttgggcag    24840
caaccctgcc ctgcccttgt ttgaactgaa attgaaagtg gctcctcaga ccaggcacgg    24900
tggctcacac ctgtaatccc agtactttgg gaggccaagg tgggcggatc atctgagttc    24960
aggaattcga gagcagcgtg gccaacatgg tgaaacccca tctctaattt ttgtaaaaat    25020
acaaaaatta gccggcgtg atggctcatg cttgtgatcc cagctccttg ggaagctgag    25080
gcaggagaat cacttgaacc cgggagcaga aggttgccgt gagccaagat cgcaccactg    25140
cactccagcc tgggtgacag agcaagactc cgtctcaaaa aaaaaagaa agtggctcct    25200 cagatttagg ccacttctta tatttggcca ctgccttgca gccttgtagt tcacattgcc    25260
```

```
accctggtgt tggtgtgaca tggtgtccca tccctgaagc tgcctccctt gttactcacc   25320
ttattgctgt ctgagaaagg aaatgggtga ttcacaatcc ttaaatcaag tggctttctc   25380
ttacctagaa cttctgaatt gaacatacat ttaaacaatg acgttgaaaa gatgtataac   25440
tggagcaata aagactgaaa aagaaagctg cggccagttg ttagttttc cgaggctcct    25500 tatctgttga gtggcacccc aggctccctt gctcttgtcc cccactgcct gtgatagaga   25560
agcctcttgt taaacactgg gagctacttc accacactca caggctattc ccagaaagat   25620
tttgcacctg ggtaaagcat ccttgagaaa ataacctgtt ttctttccca gagtgaaccc   25680
agcttcatcc ctggaaccac cacatatgct tttcccctgg tgggttctta acctgttaac   25740
actgaaatct acattgttag ctgctgataa agcatcagaa acatggtcta atctgggagt   25800
cagtatttgg atttcttttt tctttcttc tttttctttt ttttttttt ttggagatgg      25860 agtcttgctc tgtcaccaag gctggagtgc agtggcgcaa tcttggcttg gctcagtgca   25920
acctccacct cccaggttca agcaattctc ttgccttagc caccctagta gctggaatta   25980
caggagtgca ccaccacgcc cggctaattt ttgtatttta gtagagatgg ggtttcacca   26040
tgttggccca atgctctcac actcttgacc ttagatgatc cgcccacctt ggcctctcaa   26100
agttctggga ttacaggtgt gagctaccac gcctggcctg gatttcttat tctagtattt   26160
attaataatt caatttgaga agactaccta gactatttga gttttgtaat ctctaattcc   26220
tagctctaaa gctaatccct tgtgaatatc tagactggaa atccccgtta agtacctgca   26280
cattttcagg ttttgttaac tggttggagt cagactggag aatttcattt ctattcattt   26340
ttggttttct ctttcttttt ctttccttcc ccacacccca gggctaccaa gaaaagaaca   26400
aattcattgc tgcacaaggt aaagtaatga caactttttt ctgttagatt taaccatgat   26460
cacataatgg gtttggtttt tttctcccaa atgctgagtg gattaaccag aatgctgtag   26520
cttttctgta cttttttacca cctgaaagaa ttataatcca ttatacaggt ttacagctaa   26580
cagccttcat cttgatgact tagtatccag ggatccatta aaagaagtct ttttgtgtat   26640
gtatattaaa aagactggaa aaggctgtat acacaaaaca cagtctaata aggccctctg   26700 tccttgggc tagttaacct taggttccag ccaggctgct cagagtttga attaggaatc     26760
agtttccaga gaggatcagc cacctcacag ggtccaggct ggttctcccc cagctcatgg   26820
gcctgagcct caccattatt cacagatagt tggtctagga accctcagat cagggaccca   26880
gcaccatgtc ctttatgtgt tctacacaca tttccaggcc tgctgttcta caactgtct    26940 tcactcttg aaccctagca aaaatatctg gatgtttgca gcattaaaaa gtaattgagg    27000
ccgggcaggg tggctcatgc ctgtaatcct aacactttgg gaggccaaga caggaggatc   27060
gtttgagccc aggagttcaa gatcagcctg ggcaacatag tgaaacccg tctctactaa    27120 aaattagcca ggcgtggtgg cacacacctg tgatcccagc tactgggag ctgaggcac     27180 aagaatcaca tgaacccggg agccagaggt tgcagtgagc tgagattgca ctactgtact   27240
ccagcctggg tgacagagtg agactttgtc tcaagaaaaa gagtcattag ggactacaag   27300
atttataaaa acaaagttct cctcccttt cttttcactt ttttagtcta atgcccctgg    27360
ggcaaccatt tttatctatt ggcttcttat gatagatgac atcatctgat cccttacag    27420 agcacctccc cctcagtcag acagacgtgt acccacatat cctcccccatt ctcccagaag  27480 agtcaaatca caatttgggg ttaaggtatt tattattatt atgagtttac aaatattcac   27540
agccgaaaca cacagtatta tgttattttt tgtatagttt ttttcccct tcttttttag    27600 tcattgtgtt ttttatatac ctactactga ttttcctccc aaactcttta ccagaagtat   27660
```

```
atatcttctc tcagtacctt tagatacatg aggtttaatt tttttatctt gggatccttc   27720
tagaatcttc tttcttcagt tgcattgtgg attggttgct ctctatcctc tggcagagtt   27780
atcattctaa gaccagtacc ctgggaattc cgttagcctc tctgctgtgt tggatctcat   27840
ttattttcct ctgtttgcct ctcattttg tttagaattt tctagtgact ttccgaaaaa   27900
ggttatatgg gaggtaaatt ttgaattcta gcctgaacaa gtcatccaac ctttctgggg   27960
ctgatgacac ccacctcaga gcataatagg aaggagtaaa tgccatatga agcacttagc   28020
tcactgtcag gtccataatg taggtattct gtgagcagtc atgatttcta attcccaact   28080
gtaatatcct tgggagacat cattcgtgtt ctgtttatat ttttgacagc cttccaccca   28140
gccccatcct tgtgcagtgc ctggcacata catggtagaa acatggaaaa tactcaatta   28200
gtaacggggt ggatggatac atgggttaga tatttagctg gggacatttg ggcacaagct   28260
tccaaaagtc aggaatggat gttcccagcc tcccagcatc tttcttcttg gtgtatattc   28320
tcttcatttt tgctgttggc tactttagga ccaaaagaag aaacggtgaa tgatttctgg   28380
cggatgatct gggaacaaaa cacagccacc atcgtcatgg ttaccaacct gaaggagaga   28440
aaggaggtaa gtgaaaaaat tggatgtgaa cagcagaagg atcactctgc atataagctc   28500
tgagtttaag cctggctgtc tatcctttgt gggtgctgta ccagtagttc atccagaaag   28560
acacaggctg aagtctatca gactttgcta tggcctggaa gccccagata tgaacctcag   28620
gtgtgtgcct agagcacatt ccctgtattt ggtagtcaaa caactcaccc tggttccaga   28680
acagcctgaa agagactgac ttgggccatc agctaaggaa aagccacaga ggggttttt   28740
ttgttgttgt tttgttttgt tttgttttgt ttttttattg atcattcttg ggtgtttctc   28800
atagaggggg atttggcagg gtcacaggac aatagtggag ggaaggtcag cagataaaca   28860
agtgaacaaa ggtctctggt tttcctaggc agaggaccct gcggccttct gcagtgtttg   28920
tgtccctggg tacttgagat tagggagtgg tgatgactct taacgagcct gctgccttca   28980
agcatctgtt taacaaagca catcttgcac cgcccttaat ccattcaacc ctgagtggat   29040
acagcacatg tttcagagag cacagggttg ggggtaaggt cacagatcta caggatccca   29100
aggcagaaga ttttttctta gtatagaaca aaatgaaaag tctcccatgt ctacttcttt   29160
ccacacagac acggcaacca tccgatttct caatctttc cccacctttc ccccttttct   29220
attccacaaa accgccattg tcatcatggc ccgttctcaa tgagctgctg ggcacacctc   29280
ccagacgggg tggtggccgg gcagaggggc tcctcacttc ccagtagggg cggccgggca   29340
gaggcgcccc tcacctcccg gacagggcgg ctggccgggc gggggctga tccccccacc   29400
tccctcccgg acggggtggc tggccggca gagggctcc tcacttccca gtagggcgg   29460
ccgggcagag gcgcccctca cctcccggac ggggcggctg gccgggcagg gggctgatcc   29520
cccaacctcc ctcccggaca gggcagctgg ccggcgggg gggctgaccc cccacctcc   29580
cggacggggc ggctggccgg gcagaggggc tcctcacttc ccagtagggg cggccgggca   29640
gaggcgcccc tcacctcctg acggggcgg ctggccgggc gggggctga tccccccaacc   29700
tccctcccgg acggggcggc cggccgggcg tggggctgac cccccacct ccctcccgga   29760
cggggcggct ggccgggcgg ggggctgacc ccccacctc cctcccggac gaggtggctg   29820
ccgggcagag acgctcctca cttcccgac ggggtggctg ctgggcggag gggctcctca   29880
cttctcagac cggcggctg ctgggcggag gggctcctca cttctcagac ggggcggttg   29940
ccaggcagag ggtctcctca cttctcagac ggggcggcca ggcagagatg ctcctcacat   30000
cccggacggg gcggcagggc agaggtgctc cccacatctc agacgatggg cggccgggca   30060
```

```
gagacgctcc tcacttccta gatgggatgg cggccgggca gagactctcc tcactttcca    30120
gactgggcag ccaggcagag gggctcctca catcccagac gatgggcggc cgggcagaga    30180
cgctcctcac ttcccagacg gggtggcggc tgggcagagg ctgcaatctc ggcgctttgg    30240
gaggccaaag caggctgctg ggaggtggag gttgtagcga gccaagatca cgccactgca    30300
ctccagcctg gcaccattg agcactgagt gaacgagact ccgtctgcaa tcccggcacc    30360
tcgggaggcc gaggctggca gatcacttgc ggttaggagc tggagaccag cccggccaac    30420
acagcgaaac cccgtctcca ccaaaaaaat acgaaaacca gtcaggcgtg gcggcgcgcg    30480
cctgcaatcg caggcactcg gcaggctgag gcaggagaat caggcaggga ggttgcagtg    30540
agccgagatg gcagcagtac cgtccagctt cggctcggca tcggagggag accgtggaaa    30600
gagagggaga gggagaccgt ggggagaggg agagggagag ctgttttgtt ttgtttttg    30660 agacggagtc tcgctctgtc gcccaggctg aagggcagtg gtgccatctc ggctcactgc    30720
aagctccgcc tcccgggttc acaccattct tctgcctcag cctcccgagt accacccgcc    30780
accacgccca gctaattttt tgtgtttttt ttagtagaga cggggtttca ctgtgttagg    30840
caggatggtc tcgatctcct gacctcgtga tccacccacc tcggcctccc aaagtgctgg    30900
gattataggc gtgagccacc acgcccggcc cacagaggag cttttttccc ctggtttctc    30960
tagttcctta tttccctggt tttctgcccc acctgctgag gcctttggta tatcctggat    31020
cagcagaggg agctttatga actgagaccc tgcaagccaa agggaatttg aggccttggc    31080
ctaatcctgg aggcagcctc ctaactgggc cttttccttt tgtggctacc aagtgcatgc    31140
ctggcctaac cagctctatc actgggccac agccagagcc aattctgggt cctggggtcg    31200
agccccagcg aggaatacct atttgttacc gtgtttctca aggatggccc ttgagtcacc    31260
ttgatcctag ggtatcgggt gtcatgatca acagctccac agtggcatgg aagacagtg    31320 ctagggctgg gctttaggtt agtttcctcc aaccaaacct cttgctcttg gaagctatcc    31380
aaagctcagg caacagaaaa agctctaggc ctctcatggc aggtttacag tctgcatcag    31440
tctaccctgg tggcccccctc atagcagact gctggttcga ggggttcaaa caggctttct    31500
cctagagcat gacctgaaat gttgtgaaag tgcagatttt gtaggtaaga tggcttcaga    31560
ttcgccctga accaagggag tgtgggtggg aaacattgag aagtatgggg ctagggctgt    31620
gtgtaagtta ggagactgtg ctcaatagga tggcggctaa ggaacttgag aaaagggcaa    31680
atttgaataa gtaagtgtgc aactgactga gatagagaag aggtcaaagg gccttct      31737

<210> SEQ ID NO 24
<211> LENGTH: 28054
<212> TYPE: DNA
<213> ORGANISM: H. sapiens

<400> SEQUENCE: 24
ggggactttt aatctgggct ttgtgggctc ttccttccag gcccttgca tctgccatgg        60 gcaggaggtc taaggtcagg gaatgtatgt ctttttcttt ccagtgcaag tgcgcccagt       120
actggccaga ccaaggctgc tggacctatg ggaatattcg ggtgtctgta gaggatgtga       180
ctgtcctggt ggactacaca gtacggaagt tctgcatcca gcaggtagtg tctcctctgt       240
cctttctcag ttcttatgtt ggatctgctg accagtaaga gggaacaggc tggatcatcc       300
cgctgtggtc aggagttgct gagtatgcag tatgtgaatt ctgaaaccag atatccgggc       360
tcaggggaac ttgtctgtca aagctaaagg agcagtattt tcatgactgg tgaaaaatta       420
cctgttgaga tgaagtctga tcatttagat atgaccaagc actgtggaaa gggagcatgg       480
```

```
ggaggcagtg cagtctccta ggtgcttgac tcacctttct cctcctttcc tactccaaag    540
actcctgaca tcaaggatgt gatgggcctg cccctggccc tccaggcaac cctggagacc    600
tgagcaaagg tcaccttcag ccaaggggca gtgtggtact gcgaaaagag gacttagctg    660
ggagcactgc attttagttc tgaccctgcc actgactagt tgtgagacct tgtgtctgtg    720
gttaactaac tcccctgggt acacttactt ttccattgtc actgacaacc acagctgtca    780
ccttccctcc cctggtactg cccacccttg ggtatcaggg ccaacacaca ggatctcctc    840
acttcacagg tgggcgacat gaccaacaga aagccacagc gcctcatcac tcagttccac    900
tttaccagct ggccagactt tggggtgcct tttaccccga tcggcatgct caagttcctc    960
aagaaggtga aggcctgtaa ccctcagtat gcaggggcca tcgtggtcca ctgcaggtca   1020
gtgtggcctg acccttgtac ccccaccccc acatttcgcc cccatggcca gagcagggga   1080
acagcacaag ggccctggct gaggaggctg gcacagagta gatgacctac tggggcacca   1140
gcgcaacagc cagagactcc aagttctagt gcaggtgtgga gaatatgact tgaggaagga   1200
gggtagggca gtcctccaag attaggagtt gggagaccct gctatgaagc caaaagactg   1260
ggtcaagtgc tggccatgta tttttgcagc cttcggaccc ttctagctgg aggtcaggat   1320
tcaggacata ctggagttgt tggctcctgg agagccccag ctctacccca ttcagaatta   1380
ggatttagac cctgaaggaa gagccctgc ctgtgttgcc cctccctatc tgctcccaca   1440
aggcaggctg gccatcccta taacccctg ctctctggct acagtgcagg tgtagggcgt   1500
acaggtacct ttgtcgtcat tgatgccatg ctggacatga tgcatacaga acggaaggtg   1560
gacgtgtatg gctttgtgag ccggatccgg gcacagcgct gccagatggt gcaaaccgat   1620
gtgagtgatc tgtgggtcag gtgagggtgg ggggttccag gactaaaaca tctgcccaca   1680
ttgaggattc actcagtctc acaggttatt gtaaatgatt actatagagt gtgattgtgg   1740
gggaaagaaa gatagatcac actgttaccg tgtctatgta gaaaaaggaa gacacgagaa   1800
actccatttt gttctgtact aagaaaaatt cttctgcctt gagatgctgt taatctgtaa   1860
ccctagcccc aaccctgtgc tcgcagaaac atgtgctgta ttgactcaag gtttaatgga   1920
tttagggctg tgcaggatgt gctttgttaa aaatgtgttt gcaggcagta tgcttggtaa   1980
aagtcatcgc cgttctccag tctcaagcac ccagggacac aatgcactgc ggaaggccgc   2040
agggacctct gcccaagaaa gcctgggtgt tgtccaaagt ttctcccac tgagatagcc   2100 tgagatatgc cctcgtggga agggaagggt ctgtgctgag gaggattagt gaaagaggaa   2160
ggcttctttg gagttaagat aagaggaagg catctgtctc ctgctcgtcc ctgggaatgg   2220
aatgtcttgg tgtaaaaccc gatcgtacat tctatttact gagataggag aaaaccgcct   2280
tatggctgga ggtgagatat gctggcggca atactgctct ttactgcact gagatgtttg   2340
tgtaaagtca gacataaatc tggcctacgt gcacatcaag gcacagcacc tttccttaaa   2400
cttatttatg acacagagtc ctttgctcac atgttttct gctgaccctc tgcccaccat   2460
taccctatag tcctgccaca tccccttagc cgagatagta gagatagtga tcaataaata   2520
ctgagggaac tcagagacga gtgctggcgc atgtcctccg tatgctgagc accggtcccc   2580
tggcccactg ttctttctct atactttgtc tctgtgtctt ctttctttcc tcagtctctc   2640
gtcccacctg acgagaaaca tccacaggtg tggagggget agcccctttc atgtgatgaa   2700
gggctcttat aaaattatgta ttcaaagaaa tcgagcacag aggaggttgt ggtttcatgc   2760
ctgggagagt caggaaggca gatgacaggt tactggactt caaagattag ggaacaggca   2820
gctgaaagag ccagtgccca gagacatgat gaagctcggc cacatctggg agcagcagtg   2880
```

```
agattggctc tgcagttggg gcatagcacc aggagggagg cagggaccag actatcacgg   2940
gctttgggtg tctccagttt ctgacagccc cttcagacta ttaaatctgc actctcagaa   3000
tgaacaggaa ttgagtttgt ccttctctcc aggcgtccac cacccccaag atagacctgg   3060
acccttcttc ccaagtaaag cacccccaca gggactcctg catttcaagt cccacttcac   3120
taaattggga taataagagg gagtcctttt attcctgcta ggatcaaagg agaaatggac   3180
tggagtgaag tggggtggg aacaggtgat ctggcatgag aactatgttg tatgtaacca   3240
agaacttctg tgtcattcat gtttcagatg cagtatgtct tcatatacca agcccttctg   3300
gagcattatc tctatggaga tacagaactg gaagtgacct ctctagaaac ccacctgcag   3360
aaaatttaca acaaaatccc agggaccagc aacaatggat tagaggagga gtttaaggtg   3420
agttggagct ggataacctc cttcagattg aaggatcctt gtaatctggg aacatggga   3480
tgcctgactg tgcatttgcc aacagtaaat ccccttgtga ggcatgccag tggttaagga   3540
gatggtcctt tcctcgtact ctggtaactc tcaactcatc ctgcacgttg gaatcacttt   3600
ggttgtgtta gagtagggag aagcaggcaa cagtatttta aggcccctag ccctccgagg   3660
tgattatgat acacagcaag agcagttttt tctgtaagag ccagataata aatattttag   3720
gctttgcagc ccacatggtt tctatccagc tacttagtgc tgtctttgta acacaaaggc   3780
agccataacc aataggtaaa tataatgagt gtggctgttt tataaaactt tatttgcagg   3840
cagcaggcag caggccagat ttggcctctg gaccttagat cactgatagc tcctatatgc   3900
cactagacaa tggttctcaa cacacctaag gcatatgtca cactgtcatc agtaaaagtg   3960
ctctcccagg ctgggcacag tggctcacgc ctgtaatcac agcactttgg gaggctgaga   4020
caggtggatc atgaggtcag gagttccaga ccagcctggc caatatggtg aaacccgtc    4080
tctactaaaa atacaaaaag tagccaggca tgatggcaca tgcctgtagt cccagctact   4140
caggaggctg aggcgagaga attgcttgaa cccggaaggc agaggttgca gtgagccgaa   4200
atcatgccac tgcactccag cctgggcgac agagcgagac tccatctcaa aaaaaaaaa    4260
aaaaaagtg ctttctcaga agcaggagat tctgggttgg ggtggggagg accacttaga    4320
gaagttcttc tcaaatatag catgtgcaca gatttctttg ggatcctgtc aagatgtggg   4380
ttctgccagg cacggtggct aatgcctgta atcccagcac tttgggaggc caagtcaggc   4440
agatcacctg agctcaggag ttcaagacca gcctgaccaa cacggagaaa ctctgtctct   4500
attaaaaata caaaattagc caggcatggt ggcacatgcc tgtaatccca gctacttggg   4560
aggctgaggc aggagaatca cttgaaccca ggaggcagag attgcagtga gctgagattg   4620
tgccactgca ctccagcctg ggtgacagag caagactctg tctcaaaaaa aaaaaaaaa    4680
aagatattag gttctgattc agcaggtatg agttagagct tgagattctg catttctttt   4740
tttcttttct ttttttttga gatggagttt cactcttgtc acccgggctg gggtgcaatg   4800
gcgcgatctc agctcactgc aacctctgcc tcccgggttc aagggattct tctgtctcag   4860
cctcctaagt agctgggtct acaggcacgt gccactaccc ccggctaatt tttagtagag   4920
acagggtttc accatgttgg ccatgcgggt ctcaaactcc taacctcagt tgattgccca   4980
ccttggcctc ccaaagtgct gggattacag gcatgagcca ccacgcccgg cttgagattc   5040
tgcatttcta ataaggtgaa gccaacgctg ctggtgtatg ggctacactt tgagtagcaa   5100
atgtcaagaa ggagcctcaa tcgggaaggg aggatgcaat tctgaataag ttttttttgaa 5160
gagccttagg cagcctctgg gggtggaact gcagagtgga cacactccct cctacgatgc   5220
tggaatccct tgctccagga tcacaaaatt ccaagccagg agaatctcaa gagagtccac   5280
```

```
aggagcctgg aaggtagcat ttcccaaaca gtctcttggc ttcagggttc cagctgaaca    5340
tatgggaaca gaggtcaggg ccctggtgag aagagcagta tggagccaga gtggcctgga    5400
ggtgcaggcc aagggacagg cataatcttg tcaagttcag ttactgggat cagtaatgtt    5460
tcccctcccc ttcccaattc agaagttaac atcaatcaaa atccagaatg acaagatgcg    5520
gactggaaac cttccagcca acatgaagaa gaaccgtgtt ttacagatca ttccatgtaa    5580
gagccctccc gccactccaa agccttattg ccccatccct caattccctc cacccctttcc   5640 atttctcagg tactagttaa tgattggcgt atagacaaga atcatggcat tgcctcttgt    5700
tgcacccact taacaacatg gcgttgcctt ttgttgcacc ttagtggctt ctggaaataa    5760
cgtaaaagcc aaaggctttc tccctaatga gctaggaaca gacatgtcct tgcccagctg    5820
ggattctgtc tgcccagggc ctgaggtggg agcaatgcaa ggagagggag aggacaaatg    5880
atattggcta gccataagcc gctattcttc ttacagatga attcaacaga gtgatcattc    5940
cagttaagcg gggcgaagag aatacagact atgtgaacgc atcctttatt gatgtaagtg    6000
gtgggtgtga cccctgagcc cccaacaccc cgtggagatt cagccagcac ttgcagtgcc    6060
tccctcccat acctgctggg gaggatcatg tttgaatcag tcaacaaata gtgaattgat    6120
actcacccac ccactcaccc tgtgcattag gtctgtccag ctccatagag cagaaggtgg    6180
gggaaaacag atggcatgca gtagtataat acctggaaga aaaagttcac agagcagacc    6240
acagccaaga ggaacctggc tgccccctga tctttcccat tcctgccctc ttcatcctag    6300
ctctaatccc tgttccactt ccctgtctct tacagaaagc aaccagcttg tcagataggg    6360
tttcgtcctt ggccacaggg gagctctgca tgggctgagt ttgcctccga gcagtcccca    6420
ttcccttcta gtggtctgtc ttctccacta gtccctctgt gattaaacca tctcacccct   6480
gcaattaacc tggcctgtgc agggctaccg gcagaaggac tcctatatcg ccagccaggg    6540
ccctcttctc cacacaattg aggacttctg gcgaatgatc tgggagtgga atcctgctc    6600 tatcgtgatg ctaacagaac tggaggagag aggccaggtg agttcaaaag gtcctgggtg    6660
gtgagagaca gagacagcat gaaaagatgt gtgtgtaaat ggggacgttg ggaaggcaag    6720
aaggtgtttg gaccttgtct ttgacttata cggtccaaag agtacgtttg catagtataa    6780
gtacatactt aaaggtatat aaatacatat gcatttccag gattgcccag cccgttggtg    6840
tctaagcagt cattagcttc tcccaagact agaaaagcaa tgtgatctga gcctccatgt    6900
tattcccaga cagctcacac ccttgcactt tctcctgaat acagtccccc tagcctagcc    6960
tttgcacagt gccccaggcg ggggggggcac cctctccttc ccagtgcccc aggcagggca    7020
gataggtcaa ggttctgagg tggacccaat atgagtgtcc ctaagaaggg attgcctcat    7080
tgctgactac ataaaataaa gcagtagaat ttgagaaatt atacaaacaa gaaacttaca    7140
gtctaatatt cagtaataag gaaatctttt aaagaaaaaa gccctcaggt ctattaaaaa    7200
gcagagctgt ccggaaactc atactaaaaa gggacactag cagtccccta ggtcaacttc    7260
ctctcagtat aggaaacctc ctaatattgt tcctgagtca gaatcataca gcctctacta    7320
agcacattca atctcaggga tatctccctc acccccaca ttatggggggg acccagtctg     7380 tgttctgaca atgcttattc ttttaaaaat tatttctgtt gaggttgcac attgcagcaa    7440
atgagcggtt cactatgtct ggggtgtcac ttagcaggga tgagaatcta gagaatgggc    7500
ctggagagaa gctagcaagg cctggtgaga aaattccttc taagccacag tgaagagttt    7560
ggtcttccta aagcaattga agagcccttg acaacatccc atttgtgttt tttaaaaaat    7620
ccctctggca gcagtgagaa ggactcatta gaaatgcgaa agctgtggca gtaatgctgg    7680
```

-continued

```
tggcctggac tcgggtggtg agagggtgct gtcccagaaa gggtgaagtg aggaggaatt     7740
aaggatggca cccactcatg actcattgaa tttatagtca aacatttaaa atacaaagta     7800
tgttttacat tagttgtctc aagtcactag ttgttcccca tctgtacttg tgttaacttt     7860
ggtacaaggc tttacacata ttttctcacc ctgatgtttc attacatcag gattttttt      7920 ttttttttgg ttttgtttgt tgtttgttt  gtttgagaga gggtctcact tgtcaccca      7980 ggctggagtg cagtggcacg atcttggctc actgcagcct caacctccca ggttcaagtg     8040
atcctcccac atagccctcc aagtagctag gactaaaggc acgtgccacc atgcccagct     8100 agttttgta  ttttttgta  gagacagggt ttcaccatgt tgcccaggct ggtcttgaac     8160
tcctgggctc aattgatcca cccacctggt tgacccaaag tgctaggatt acaggtttga     8220
accaccttgc ccggcatttt tttcaatttt gatcagtcat ttaactcatt agctattctt     8280
cctagacttg tatcatgtac ctaatcaaca gacatacttt gtaggtcttc atcatctttt     8340 tttttttt   ttttgagacg gagtctctgt cacccaggct ggagtgcagt ggcacaatat     8400
gggctcattg caacctctgc ctcccaggtt ctggcaattc tcctgccaca gcctccctag     8460
taactgggat taaagacacc caccatcatg cctggctaat ttttgtaggc acggggtttc     8520
accatgttgg ccaggcttgt ctcaaactcc tgacctcagg ttatctgcct gactcagcct     8580
cccaaagtgc tgggattaca ggcgtgagcc actgcgccca gtgtcttcat catcattaat     8640
aacaatactg atgaggtggg aggttcggtt aaggtgcttg gctttgcact caaggaagca     8700
cacacctgag taacaaaagc tgtttaggaa atgagccact gtgttctcag gagctaggtg     8760
cctgttcctg ccgtctctga tcagtcgtga tggaacctgc agatcagacc agggccctac     8820
ctgtggttcc ttctgcaccc ctgcccttca gatctgtgat gggcaggacc aaagagcagg     8880
ccgaagagct ggaaccacga gcacaaggac catctcggcc cactgccctg tgataaaatg     8940
tggcccagtg aacatctccg cctctgtcca gtcagatgca ggctcttcca tccttgaaaa     9000
ggacctagtg agagtaaagg gcaggggggca ggaagcattt catgtgtgtg gcggtgggga     9060
gaagagtcgt gcgcacacaa attctgctgc ctgttgagtg aggcctctcc ctctgccttc     9120
cactgtagct tatgctctgt cttcctaggc cagtgaagca gacagtagtg cttgccctca     9180
aaagcttctg agtggattgg aacaggatgt tagtgatgtt ctttacaagg cctcactggc     9240
ccccaagttc actttctgtt ccattcatgt tgtcaagtgt agctcccaga agtaattaac     9300
gcactaagcc taaatgatgc aatgaaaggt gcctacactt atacagtgac actaccatcc     9360
tcacctacaa tattaagttc ccagagaaaa aaattcgatc ccataatata aattctgtac     9420
ttacaaatta aaatctcgaa ggaattaaaa attttaatt  atctccctct gctttttttt     9480
tttttttttt ttttttttg  agatggagtc tcactctgtc caccagactg gagtgcagtg     9540
gcacaatctc agctcgctgc aacctccacc tccagggttc aagtgattct cccacctcag     9600
cctcccgagt agctgggatt acaggcatgc actaccatgc ccagctaatt tccatagtag     9660 agacaggggtt tcgtcatgtt ggccatgctg gtctcaaact cctgacccca agtgatccgc     9720
ccgccttagc ctcccagagt gctaagatta caggcatgag ccattgcgcc tggcctcctt     9780
ctgctctatt ttaatcaaaa gggtccacca ggatgcctgg gttccctcag cagctgcagc     9840
ttggaccatc atcagcctgg gcagacagag cagtgccagg aactcccatg ctgggtcaac     9900
cctaggccta gcccaacccct aggcctcatc ctgcttctct aaagcatagt gaaacctgat     9960
agcattagtc ttcacaaagc tgtgtgtccc catcaccatg tccgccttag acctcataag    10020
agacataaga cataagagac ttcatgctat ctggtggaaa gacaaagtag gagaaaagac    10080
```

```
agaaaacctt ccctgtttca cttctttaag atgctattat ctagaggccg taacgtgaac    10140
acacaaatct gagatgaaac tccagtcccc agcttttctt ctactggtct tgaatcccca    10200
ttccccatct tctgtccctc acccactgat gactttaaca cctggcttac tgctcctttt    10260
gagcccctgt tcctgactct gcttttggag gcatcagtca ccatgtggat gatccatcta    10320
tcctcaatct ttctattcct cagcttcctc agccacctga tcccatggtc aagtcaccat    10380
ctgccctgta tctgcactgc ccttggaatc tcaacaaggc atccgccctg tttactgcct    10440
ccttcctccc acctcagtat tctctttat tccagtcatt tttgtcttca tcaagtcctt    10500
agagttattg atgcctccac tttctcaaca tcagtcacac cgaacatgtc ctcaccttcc    10560
tccttactct gtgtgttttt gagttctgtt tttgagcgtt tgagttttct gatttgagtt    10620
tttgtggtat gtcattatta cctttcctta ttccctcatg ctttcttact ttcatagcaa    10680
actctctagt aaaacccagt tatatgcctc tatctgatat agcaaacatc actgggcaaa    10740
aacacaaaac agtgccaaat gctctcacac tgaactcatg accacaaatc tcatagaggt    10800
aattggtgcc acctagcaat gctattgctc tttcttttct tcctgaaacc tccagcatct    10860
gctcttgcct gtcccatcat actcacacct tagcttgtga cctggcctca ttcttctcca    10920
agaaatcaga caagaacact gtcatcctcc caccccaaa caaccagcct cttcaaatct    10980
gtaccaactc tattctctct tgttacagtg aaaagggtt tctgcatctc tcaatccacc    11040
tgtccactgt gctcttggcc ccattccgtc ctgcctgctc agggatgttg ctgctataac    11100
catcttctct cccacctcca tcagcagttc ccctctttaa ccactactct catcagccta    11160
tacatgttac atttcctatc ttttaaaaac aaaaaatctg ctaatctcac tttcccttcc    11220
acctactatc ctatttctct gcacccttc ccagcaaaac tcctttaaag agttggcttt    11280
cggccgggcg cggtggctca cgcctgtaat cccagcactt gggaggcca aggtgggcgg    11340
atcacaaagt caggagatcg agaccagcct ggccaacatg gcaaaaccc atctctacta    11400
aaaatacaaa aattagctgg gcgcgatggt gcatgcctgt gatcccagct actcgggagg    11460
ctgaggcagg agaatcgttt gaaccaggga gctgaaggtt gcaatgagcc aagatcgcgc    11520
cactgcattc cagcctggtg gcagagtgag actccatctc aaaaaaaaaa aaaaaagagt    11580
tggcttctc cctgcaagtt ctctgttcgc tctgttcctt ccaggcttgg ccccactggg    11640
actgctttag tcaagatcac cagtgactgt cctcttgcca aatccaaagg tcatttctct    11700
tttctgattt tttttttttt gtccttacag cagcatttga aagagtcagt acctccctcc    11760
tcttcctcag aacacttact tccgtagcat caccccactc actaacctgg cagctccttt    11820
gttatttctt tgtgacctcc tcctctaaaa cattggagta tactagactc gggcgctagc    11880
ccactctgtt ttcttttgac acactagccc ttcaggatct cagccagtcc tatggcttta    11940
agtacaaccc atatgccagg gatcctcaat ctgcgtctct aggccagtca cctgtccccc    12000
ttcccaatgt gggctcctga tttcctcctt ccccgacac cagtccaccc cactcttagc    12060
catctaaata aatagtacca ccttctgccc agttgctcat gtctaaaatc cgggagttac    12120
cttccttcct cccctctcct cacccctcac atccagtctg ccactgagtc ctgatacagg    12180
cagagcctcc ccactttct ccagcgtaac tgctgtcatc tgaacaagcc ctcgtctctc    12240
actgcttgcc cgtgggactg tgggcatgac tcatatgcgc agcctcgtct gcagtggcct    12300
ggcaactggt cctcctgctc tcatcctaac ccacttttag ttttttcaaat ggcagctgct    12360
ggtccttttg aaaatataaa tcattgtcac tccttgtctt acaaatcctg tttgaggcca    12420
ggtgcggcag ctcacgcctg taatcccagc actttgggag gccgaggcgg gtggatcacc    12480
```

```
tgaggtcggg agttcgagac cagcctgacc aacatggaga acccccgtct ctactaaaaa    12540
tacaaaatta gcgggcatgg tgatgcatgc ctgtaatctc agctactggg gaggctgagg    12600
caggagaatc acttgaaccc gggagccgga ggttgcagtg agccaagatc gcgccattgc    12660
actccagcgt gggcaataag agtgaagctc catctcaaaa aaaaaaaaaa aaaaaatcct    12720
ctttggtctt ccagagatct tgagagaaaa tccgcccatg tatacaaaat ttagagactt    12780
ttgatcagat gtggtggctc acgcctgtgt aatcctacca ctttgggagg ctgaggcagg    12840
tggatcacct gaggtcaaga gtttgagacc agcctggccg acatggtgaa accctgtctc    12900
tactaaaaat acaaaaatta gctaggcatg gtggcgcaca cttgtagtcc cagctacttg    12960
ggagtctggg gtgggagaat cacttgaaac tgggaggcgg aggctgcagt aagtcaagat    13020
catgccactg cactccagcc tgggcgacag agcaagactc tctcaaaaaa gaaaaaaaaa    13080
atgagactct tagtgttgat acctagtccc tagacttgat atgtatttct gtctgagaga    13140
tcatgctcaa ttcctccagc acacacacac tgtggctcac acccatgggg accttatggt    13200
tctgatggtt ttaaaggccc agtcttcatc ccagctgaga cactgtgtaa agcagtgttg    13260
agaaggcact gtggtagcaa aatccattcc acccaccagt gccataaaaa ctaatataat    13320
gcctgatcga ggtgagcctt aatgagaatt ttttttttt tttggctgtt ctggttgaag     13380
agaggcccag ggcaccgatc cctgaggcat ccccagggct tctagagaac atgggtggaa    13440
aagcactagt ccagggcatg ttcttgattc aacactttaa taatcatgat tttatttgga    13500
ctgtgagact attcacaatt tcttttttcta cttaattttt ttccaaatct ttcaatgaca    13560
ttatatgtat ggttgagaat ttttcaattg ccagtagtga agaatctcag atcttacccc    13620
caaattctct aaagaaatgg gcagcataac tgtgtgatgt tatatttatg tatttatgcc    13680
ttggcttgtt ctgcagacat tgaacaaatt catttaccag atactgagag cctaccatgt    13740
gccaggcatt gtgcaaggtg tggggaatac agagatgaaa agagacgcag ccactcccac    13800
aaggagctgt agagggaagt gagccaggtg caagcaaaga cagacagtag accacctcct    13860
gctcactagc aaggacagaa aggcgagtgc tagcaacttg aaggtaccct gcagatcaaa    13920
gagataaagg taaagggag aaaggatact gtggcctggg cggtggtgaa gcccatggct     13980
gtgtgggaat gtgaattggt tctgattttc tgaattagca gtctggcgga tgtaagcagc    14040
attaaatatg aaaacacccc atgggagaaa aagaaaggaa ttggaacaaa gattttcact    14100
cgtcctcctc tccctgcagc caccaagtat tggatacccct gtgagcctgt agtcagagtc    14160
ctttacagac cccggcagtg ttttagatgg tctctggtga ggatcggagg ttaattggaa    14220
tgatgtgata taatgatcct gcaagttttc aataccttgg ggacgaagcg tatcagcgta    14280
agaggtggct gtactgagag gggtcaggct gctcgtgggc agtgctgctt ctacacatgt    14340
ggtactctga gctcctcacc tctccaacct gtctctccag gagaagtgtg cccagtactg    14400
gccatctgat ggactggtgt cctatggaga tattacagtg gaactgaaga aggaggagga    14460
atgtgagagc tacaccgtcc gagacctcct ggtcaccaac accagggtaa gatgggtcgt    14520
gggtggactc tgcccacagg aaaagcaggg ttacccctgc ctccctgatc cccttttttc    14580
caaaggagaa taagagccgg cagatccggc agttccactt ccatggctgg cctgaagtgg    14640
gcatccccag tgacgaaaag ggcatgatca gcatcatcgc cgccgtgcag aagcagcagc    14700
agcagtcagg gaaccacccc atcaccgtgc actgcaggta tggctcaccc ttgccctcag    14760
cgggagagag aaagcgagga ggggcagata ggggaagctg atgaccatgg gtcagactga    14820
agaaagccat acaagagcaa gatattggtg agcacatagt agttgagatt gatgccaaga    14880
```

```
caggattgga tgctaagaga gaggaccttg gagcttgaac ttggcacaat aagtgctagg   14940
ggactaatgt tcagatagtg ggcaggagag cagcagggga gactggcagt ggagaccccg   15000
gttgtgctat gaacagaggg tgaaagagaa gaggagtcaa gggtgtctcc caggtttgag   15060
cctgggttgg tgtgaccagc agaagagaga cagtaaagag gtttgtttga ggggaaaagt   15120
tgaattttgt atggggcatg ttgctggagg ttacgtttta gaaaaaatgc actcctttac   15180
ttagaatcct aacaacagct tacaaggccc aatatgttct gaggggtccc tggccagggc   15240
cgggagagga tggtgtgcac catgggctgg ctctgagcac actcctgcca tgggcctgag   15300
atgccagttt cccaggcagc cacagggctt tgcccaagcc ttccctgagt accctgccag   15360
aactcccact cctcttttct ctttccttac cacacatctt cttgtctggg gacattgcta   15420
aaccccacag tccctgcctc agagtaggca ctcagtgtct ggtgagtgaa tcagctgatg   15480
acattgaata gggggatatt gtcaaggtca gagtctggat tccgtggatt tgggaagaaa   15540
gtgaaagaca tggaaaggaa tcagcagata cacaccagtg tagggagtgg ggtttgtcag   15600
aaaaagggaa agacaggact agagctagtt ctaactgagc gaacagcagg tcagaacaac   15660
ctaggccagc atgtgcaggt ggacagcaat ggctctgtgc tggtggggtg tgagtgaagg   15720
tcgtccccca cggtccaaca ggtgagtccc tccacagcac atggggccat gcaggaaggg   15780
cacagggtac actgcctccc gacccagaac ccctccaggc tggtgggtcc acagggcaaa   15840
ggcgagcacc agctgcctgc ccccacctct tctgccactc accactgtca ctcaccccct   15900
tgcacagagg gccatcacag gtgtggtaaa tgtgtctgct ctgttgcagc gccggggcag   15960
gaaggacggg gaccttctgt gccctgagca ccgtcctgga gcgtgtgaaa gcagagggga   16020
ttttggatgt cttccagact gtcaagagcc tgcggctaca gaggccacac atggtccaga   16080
cactggtatg ctgcccacat atttgtccct gccaccacac cacctgcagc ccttctctca   16140
gggaggaggc tcttcagagg ggcccaccca gtagtcagaa gactgtctaa acacagacct   16200
gcccttgccc tcccaaggtg ccccaaatac acaggaaaca ttgggaggca ggatggcagc   16260
aatgggagca tagcccctgt tgccagaggt tgggccaggt tagaaggggt gtctgggtgc   16320
cccacagggc tcatctgtac ttctctgtgg gtcttgggta aggaagatcc atgaagagta   16380
cctgcctttg ggcttgggct ccctgttaag aggtctgact ttaataagcc gcacatccac   16440
agaggttttc ctgaatccca tggagctaga aatgtttggg gggtaaagaa aagtgaatgt   16500
taggaggttt gggagacgag gttctgagag ccagggtgca tgctagcctg gcagccatgg   16560
taagcgtggg ccatgctcag ctgcactgtc tcccagccca gcacatgcct gtctgacctc   16620 tgtgggcct gggtcagctc tggtcagctc tgcttgtaga aggtctgctg cattcagccc   16680 ggaagggaa tgctgtcaga actctggcag gcagatcaga gctcaggtga aagttcaaaa   16740
acattcagtt cctcttgatt ttccatcttc aacaaaaaaa tgagtctgtt aggaattaca   16800
ggtactgtgt gttcttcagt aaccctgact tttttccctac ctttcactct ccaggaacag   16860
tatgagttct gctacaaggt ggtgcaggag tatattgatg cattctcaga ttatgccaac   16920
ttcaagtaag cggcaacaag ggtccgtgga ccaggaggat tgcctttaat attttgtaat   16980
attctgtttt gttaatatac cccaaattgt gtatatatct tataactgtt ttagaaattg   17040
gtacataggc ttctattacc tattaggtgg aaattttata tgtaaatgtg ttagcactga   17100 tagtccttt tccaatgttt tattgggaa ttaaatagtg tgatgtttgg attgatatcg   17160
tgaaatcctc agccgagaaa ttgggctgga ttgtgctttg gttaatacat ctttccctaa   17220
agaagataaa cacaaaatcc attccaggta gctcggcacc aactaagaaa aaaagcacaa   17280
```

```
agttctcaga gctctcgagg aaagtggttg tccccgtacc accatgcact gtaaatatcc    17340
ctcccctctc tccctggtcc cctcccccat ccccaccact gatatcatgg ggagtaatag    17400
gaccagagcg gtatctctgg caccacacta gggactatca ggtaataaaa gctttgactc    17460
cctgaggaaa tgtctctccc tttgtctggg ggtggggcag ccatacaggc tggggctctc    17520
ctcggctgtt catggccctc ctgttgctgt tctctctgag ttatctgaga gaggccacag    17580
tcccccagct cctcctgtcc accaaacaca gcccttccag ttcttaggtg atctccagga    17640
ccctcctttc attcccagca catctttggt ttagtggtcc tggccagcct ccctccctag    17700
gaaggtggcc aggtcctcac tgagtctcct taaggacagg ggcacagggg agactagagc    17760
tggctcagct ttgggctgag gccagtctga cctctccagt ctgtggtgct ttgctacaaa    17820
actgtctgga ttgtgtcacc ctatctagga taaatcttta tgtccacata tattgtgttg    17880
aattgttccc attttctttc atacgtgtcc tcatttctgg gacagtgtga atgtttctca    17940
gatctagaag tcagatggtg ggagtcttag atccgaactt ggttttgagt gacatgttag    18000
acaaaagtgt tgaacttttg tttcttaaag aagctggatg ttcatttatg tctcccgtaa    18060
cagtctgtgc tgtccagaga cccagtatcc ttaggatatt attctcatcc tcatggttga    18120
agctgggtca ctgccatgtc cataatccac cctgaggaaa gagcatggag agccagcagc    18180
ttcatttcta aggacaggaa gccaaatctg cacttttcac ttccactcat aatccacccc    18240
gcattccact catcagcttc acaagtaggt tttcacctgg tcatagctat gcctaactac    18300
agggagtgct ggggaagtgt gatcttttgt tgggggcaca ctgggagagt gggtctgtcc    18360
actgcctccc agcctcagag cagctcacca caggagcagg agagtgaact cgtggctgtg    18420
gctgtcaggc agggcctttc ttgagagcca gcgcaggcct gggctcctca gaggcttctg    18480
gagtgagaga tggcacctca gcctggccca tggaggcatg ttcagggatc agcactactg    18540
tgcttcttgg aggaggtggg acttgagctg gacccatggg aggctggaaa tttagatgag    18600
tgaaaaggag gaaaggcgaa gtagagccac attacagagg gcctcagagt ccagataaag    18660
cagttaacat gtagtggctc caggagggaa gcctgtctgt gcaccacata cccaggatgt    18720
ttgtgggaag gaaggagatg tgcggaaggg acccaggaga cctgcaggag gcaagggctg    18780
caacagaccc cctctggaag tttacaggag gtgagtgtga gtcattagag acattcagtt    18840
ctgtaggaac taacgaactc ccaagaggca gtaaacttaa aactcagcag tctcgataag    18900
tatggataaa ttaggcaaag acagattctg aggaatttct ggtgaggggt gccaagtttg    18960
gggagcagcc cctggctcct tgcaagctac ccttcagtgc tctgtgtgac caagtccaag    19020
tcgatgcagg agggcaggca ctgggtcagc aagccactca gtgaatgtgc aggtgaggcc    19080
gttcataggc gcttgtgtgc ctcccagcag gctgcctgcc attgcagggg ctggccttca    19140
gcagggtgcg ccaccatggc ctgagtggtt ttctgctgaa gtccgtgctg atttggccag    19200
tggataggca tcacctgggt gcaaaaccat tgtctccagg taggaatgac ctcagctgtt    19260
tgctccgtgt ctcgctcagc ctgtagatgt gtccctcatc ccttcatgcc tccctcttca    19320
ctcctctttt actttctact cggggcttgc atgtttacaa gagaggtgaa cccaacagaa    19380
actagtatag gccaaaagga aaatgtgctg aagctcacac agcacagtcg tgtggaaaag    19440
gcagcagtga ctgcttcatc cagtgccctt cccacagcca gtcagttgcg acccaagggg    19500
cttagggtag gagtgtttct ccataggga agagtaacag cctgcaccca ccacacaccc    19560
aaagccctac atcctgccac actgagacct cacttcattt gggcgggtcc ctcctggntt    19620
gcagtttcct tcattgctcc cctgtcccaa atactcaagt ctctctcatt aaaaataaag    19680
```

```
agcaggccag gtgcagtggc tcacacctgt aatcccacac tttggggaggc caaggcgggt   19740 ggatcacttg agcccaggat tcgagaccaa cctgggcaac atgacaagat cctgtctcta   19800
caaaaaataa caaaaatcat ctgggcatgg aggcacacgc ctgtagtccc agctacttgg   19860
gaggctgagg tggaaggatc acctgagccc atgaggtgga ggctacagtg agctgtgatc   19920
atgccactgc actccagcct gggtcaaaga gtgagaccct gtctcaaaaa aaaaaaaaaa   19980
taggccgggc acagtggcta atgcctataa tcccagcact ttgggaggcc aaggcggacg   20040
gatcacctga ggtcaggagt tcgagaccag cctggccaac atggtgaaac catctctact   20100
aaaaatacaa aaattagccg ggcgtggtgg cacgtgcctg taatcccagc taccggggag   20160
gctgaggcaa gagaattgct ggaacctggg aggcagaaac tgcagtgagc tgagatcacg   20220
ccactgcact ccagcctgga tgacagcgag actccatctc aaaaaaaaaa aaagaaaaag   20280
aaaaagaatt aattaattaa ttaaataaag agcatgtctc ccacccccagg cctaagttct   20340 tccctctatg agagactact tgcagaaacc tgtgttctca ctcttccccc ttcctcactt   20400
cattcccaca catttctttt ccatccctgc gcaccaaggt caccttggtg ctaaacacca   20460
gggacccatg gtctcttccc ctttgtgtca caggctgtcc tctgcctctt atcctcaccc   20520
tttagctgct cctccactgt ctcctctctc agaggtcagg attctggatc tgtctctgtg   20580
gaccctcagc tctcctccaa tcccaagtcc cccgcatcct ggtcgcatgt cagggtggtc   20640
cagagatgcc tgcctcccac tgcccacacc caggggcccg cctcctttc ctctaacctt   20700 cccacatact ctggcccat ggatccacgg cagttcctgc tggcccttct ccatttttgtt   20760 ccttatgctg caccctctg ctgccactcc ctgcgtccgt gactccagct cactcgtctc   20820
tgtccttcac ccaggccgcc tgctcagggt ttgtgcctct ctgtgctcct gcagcacctg   20880
agtgtttatt cacctctgaa cctctgcttt cccacctgag tacacgcagc tcctggctgc   20940
agtgacttca tatcctgagg actggagctc cgtggtgaac agatggcttt ctatgttcta   21000
atgagaggga tacaagagtt ccacagttct agtctggaaa ggaccaaaca tttcttaaaa   21060
gctaagtatg ttgccggaaa aaaaagggag cagagctttc cccaggaagc ttggctctgg   21120
tttagatttt tcaggaaaag ccggaatcaa attacagaat aaataaaggc aaccatcccc   21180
cttttaaagg tacaccagcc ttggtgcatc tttgaagaaa gcattctgta aaccccaacc   21240
agaactaaac tagtacgtcg aactcagatt cattttcact aaaccacaag caaatgtttc   21300
cctaaaaatc acccagttaa caaagtccgc atatttaagc caaaacaatt taactgaaca   21360
aatgggccac acgttgattt ccggtccctg ctaataagtc agtctggaag ttcacaggtg   21420
tgcccatcct gccttggctg ctgaagtcca ggtgtctagg gctgactgat gcccattatg   21480
cctcccctcc cccatctttg tcacaggatt tgacgcacca gctctccaaa tgaccctggc   21540
cctcccattt gctgttcagc ccaagtgcgg agattggcta tgaaccctgt aaacaggcct   21600
ctgaccccca gaggctgatg gctggccaag gaaagctgag ctgctgacgc agactgggaa   21660
gcaagagccc acttccagca gcccaggcta gctgtgtcca aatccatgac tggggagggg   21720
ttagagcctt gagggacaaa attattctac ctacctaggg agactgcact ggcccaacag   21780
ctgggcccca tctcatgggc ccgcttcttc gccaggagag aagccactcc ggggtaggta   21840
ctgccccacc caaacccagc catctggagt gacccagccc tggttcccag gtgtgtggat   21900
gtgaattgtc ccacccaacc cactctacag tgagcaaacg gaagccctct gggagagtgg   21960
tcacagcctc ccctgtacct ctgaacagcc tgccaggctc cctactctta ggcttccact   22020
gtccaccagg gaaagccctg agctgggagt tggggagccc ccaggcattg ccctgccca   22080
```

```
ggacacaatt ctcttttggg atcagggaag gctgtgaggg ctttctaggt ctcaagatca    22140
ggagcttgaa gatgcagcct gggaagtggg aaggtgagac caggacatag gccagcctaa    22200
agcaagagtc ctgggcctga aggctcctgg gaaggtggtg gggagggagc atgtgtcggt    22260
ggcctcaggg cagcagctgc ctggtgaatg ttcatggact ggatgctctg ggaagcgggt    22320
tgggtggtga gcttctctct tcccctctga agacgtcact ggagtctggg ggtggagctg    22380
cctggtctat aaatcctggg gccatcaggc tagggtcctg cagctgcctg aaggagccat    22440
ctcatccaca gctcttcctt ggtgagtggg gagccttccc taagggctag gacacctgga    22500
ccaagtttca tcctgggcgt atggtgtgct gctcctcttc cccattccca ggtgcctcca    22560
cccctgaacc atgccagaga agtcccctt tcctctcctc tccccaacag ctctaccatc    22620
tattcttgtg cttgttgccc ctggcatggg agggataagg ggtagaagca cttgcccca    22680 tcaataccac tcatccattc cacatcccca actactatgg aagagataca gcaggccacg    22740 gagaaaggg cagaaggcct gcaactctgg ttccctagca ctggtgctcc aaacacgcct    22800
acattgagaa ctcccctgac catccatcta tcctcccatc cattggcctg aattcaggtc    22860
tctgttcccc tccaactttc ttccacttct ggaaactcct tgaaggaaag atggatggac    22920
ctggacaagt gggagggccc tcagagctgg caaggcaggt agcctctgtg ccccaggctc    22980
agggagaagg ctcgtcccct ggagcatcat ccctgctgg gccaggatcc cccaggatct    23040 ggaccctgt atgcttggga tgaggagcgg tggcagagag ggaagggcat aaggagatac    23100
caaagctgcc cctgagatgc cagtttccca aagtggccct ggaggaagta gggggatgtg    23160
ggggtgaggt aagtctcctt gaatgctgta ccctgtccat tagagcagcc atggccagct    23220
ccaggcgagg cctcctgctc ctgctgctgc tgactgccca ccttggaccc tcagaggctc    23280
agcactggtc ccatggctgg taccctggag gaaagcgagc cctcagctca gcccaggatc    23340
cccagaatgc ccttaggccc ccaggtgggt gtctcccagc ctcatgggga ggaagaaagt    23400
gatggccggg ggctccccca ccctcctgga gcctgaggtc ggggtaggga ggacagcatc    23460
agttcccttc taaggaaggg ccctggacac tgcagcaggc agcccagtcc agactgccca    23520
tggcctccca agtgatgccc tggctcccct ggacgacagc atgccctggg agggcaggac    23580
cacggcccag tggtccccttc acaggaagcg acacctggca cggacactgc tggtgagtag    23640
ggtgagaggt ccccagcatc aagaccagcc actggtcatc agaggccatt gtggcttagg    23700
gttgggtgct gggagggtgg ggagaatgaa acaccactga gatgcccct gccacagcac    23760 ccccagccat ttctcagtgc ccctactgca cacagcaggg tgctgtctgc tatccttcct    23820
atttcccagg aggattctag acaatttaca aagcacttgg gttaaagacc aaagtcacta    23880
gtagactaga aggagataat tgttctataa gacagtggtg gccatgggat cccacaggca    23940
tcctgacaag ccaatgactg tcttgaggtg gacagacccc aggccagtgg aaagaggtga    24000
gggatgcaac ctcactcaaa cagacaacag ggccaagagg accaggtggt gactgacatg    24060
tgcactagga acatctcagg gactgcagag ctccccaaga ccatagcaga agacaggcgt    24120
ggggaaatgg tttgctactg ttttgcaaat caaacattta cagtgcatca ggagagcccg    24180
gtaactaaag aagaaagtgg ttagttccta tgaggcaatg tcttaccgcc tgatttgtgt    24240
gtatgtgctg aggtttctat gcgtcaggct tgtttagggt ggacaagagg gcatgcccaa    24300
gggagctgga gatccccaca ctagctggat cctcaggctt ctacgggagg cggggggcgt    24360
cctgctgtgg gaggccacat ggggactggg ggggacgaga gggggagagaa ccaggaagat    24420 ggcagctcgg cggttacgag accagtgtcc tgagacatga ccgccacctc tccctccgca    24480
```

```
gaccgcagcc cgagagcccc gccccgcccc gccatcctcc aataaagtgt gaggttctcc    24540
gaagctgttg cgtcgagttc tgtccttcgt cccctccctg tcttcccgc tgagacccct      24600 ccctgcgtgg gggctggagg gacgcgggtc cggccccgcg ggcggagta actaagggat     24660 ggccccgggc cctggcggga aggccgggcc agagcctggg ggcgggatgc ggacgtccgc    24720
agggtcgccg cttcggttcc agaggccaca cggccgggcg gggcgtgagg gacagcccga   24780
ggactacagg tcccaaggtt ccccgcgccg cttccggggc acggtggcgt cccggcaccg    24840
cggccgcagt gaggagactc ggccatgcta cgcgcgctga gccgcctggg cgcggggacc   24900
ccgtgcaggc cccgggcccc tctggtgctg ccagcgcgcg gccgcaagac ccgccacgac    24960
ccgctggcca aatccaagat cgagcgagtg aacatgccgc ccgcggtgga ccctgcggag    25020
ttcttcgtgc tgatggagcg ttaccagcac taccgccaga ccgtgcgcgc cctcaggtgt    25080
gcggccgggg ggaggtggcc gcccgcgcgc gctggtgacg gtgggagtgg gcggagaggg   25140
tgctgattcc tggcgcgtct gcacccagga tggagttcgt gtccgagtg cagaggaagg    25200 tgcacgaggc ccgagccggg gttctggcgg agcgcaaggc cctgaaggac gccgccgagc   25260
accgcgagct gatggcctgg aaccaggcgg agaaccggcg gctgcacgag ctgcggtgcg   25320
tggggcggga ggcggggcgg ggcggcgcgg cctggccggc ctgggagaag cccgggcccc    25380
gctcagcctc ggcccttga ccctcacagg atagcgaggc tgcggcagga ggagcgggag    25440
caggagcagc ggcaggcgtt ggagcaggcc cgcaaggccg aagaggtgca ggcctgggcg    25500
cagcgcaagg agcgggaagt gctgcagctg caggtgggca acgtctccgg agggtgggac    25560
tccagccggg gacgcggctt gcggggcact gggaattctg ggcaccgcga cgcgggcgct    25620
ggctatgtgc agagacttac agttggcagg tccggatttg gagaggagag tgccagtcag    25680
gcgcaaagac ccggaggtga gcggagtaat tggacagtgt tcaggtacct agcaggtctg    25740
tgggagggac cctgcgttcc acaaagaggt tgtattttgc ataacaggtg atgaagccat    25800
gaagggttaa gtatttcagg ctaggattag caggtgtgcg acttaaaagc agggagacca    25860
cttaggagta atgcagtgag aatggatgag gcttgattta agtatagaa gggtggctgg    25920 gagcggtggt tcacgcctgt aatcccagta ctatgggagg ccgaagcggg cgtatcactt    25980
gaggtcggga gttcgagtcc agcctggcca agcccgtct ctcctaaaaa tacaaaaatt     26040
agccgggcgt ggtgtgcgcc agtaatcgca gctactcggg aggctgaggc atgagaatcg   26100
cttgaaccca ggaggcagag gttgcagtga gccgagatgg cgccactgca ctccatcctg   26160
ggcgacagtg agactccgtc tcaaaataaa taaataaata aataaataaa gtaatggggg    26220
gaaggatgag ttagagtgat tcagagggga ccactgaggg acggatttca cctaccagga   26280
cgtgagattt tcatagctgg cactcggggc tatggctgaa gtgtctgaga aaagaggaac    26340
gtggaaaagc aacctgatat cactccactg ggaggccaga ggggctctca aataggacct   26400
gggttccagg catgcttccc cagggagagc aggagctgct ttctcagtgg ggtgagaggc   26460
cagcaggctg ggtgggctgg ctggcatgtg cccaaggctc ctgttcagct gggcttttct    26520
ctcccgatag gaagaggtga aaaacttcat caccccgagag aacctggagg cacggggtgga  26580 agcagcattg gactcccgga agaactacaa ctgggccatc accagagagg gctggtggt   26640 caggccacaa cgcagggact cctagggggcc cagtaaggac agtgcccgcc agggaccatg    26700
tatgtatcat ggcggaagag ttggcccctga cctggaataa agcagttggt gttgcttatg   26760
aggaaggttc agccttatcc agcacagcct tcacgttttg ccctctgctg tcaccacttg   26820 gtcagaaaact tccaaacgca gtgccctgtt ctgccggtgt gtacagcctc agcgcaccag   26880
```

```
gagaccctag agtggtttcc atctcacaga gaatcagaca gggccacagc cccctcaggc    26940
agccaggtca tctgagtatc attaagagta gtgatgggaa gattacagtc tgagggccaa    27000
acgtgcctgc ttcctgtttt tgtaaataaa gttttgttgg aacacagcca cacccactca    27060
ttgacttctt tttactacag tggcaaaggt gagtagttgc aacagagacc atatgaatcc    27120
caaagactaa aatctttaac tttttacagg aaaagtgtag tgatctctca tctggagctt    27180
taggactcta gcctgtgtca cccaggacct gagccacaag ctaaccattg gccaggcgcc    27240
tgcctctgct ctatactgtg ctttgctggc cagagtctgg tgtatccaag acccagaagg    27300
caaagaggag accccatttt tttctgggtt ccacaaagag gttgtatttt gccttacagg    27360
taatgaagcc atgaagaatt aaatattcta ggctaggatt agcaggtgtg tgacttaaaa    27420
gcagggaggc cattaggagt gggtctctcc acccatggcc tcagtgacct acatttgccc    27480
tggcattgcc attgcccttg gccacccag cagatggctg ctggcagggg agacatggtt     27540
gaccaagatt ttatgaggtt agtgtggctt agcaagcact tggaccaacc tctatgggta    27600
ctgggactac ctgtgatgat gaagagagta tatagatcca tagtccctgt tcagatgcag    27660
gccctcaagc agtgtctggg atgagctgga ggaatgtttc tcaaccagag cagcttccgt    27720
ttgctgccat gcacatgaac tccagcttct ctccatgtct cccacttctt tgcagggaag    27780 gcctaggac ccccaagaaa tgaaaacctt tttttttctt tctttttttt ttgagacaga     27840
gtctcactat gttgcccagg ctggagtgca gtggcacgat cttgctcact gcaagctctg    27900
cctcccgggt tcacgccatt ctcctgcctc agcctcccaa gtagctggga ctacaggcgt    27960
ctgccaacac gcctggctaa ttttttatat ttttagtaga cgtagtttt cactgtgtta     28020 gtcaggatgg tctcgatctc ctgacctcgt gatc                                 28054

<210> SEQ ID NO 25
<211> LENGTH: 222
<212> TYPE: DNA
<213> ORGANISM: H. sapiens

<400> SEQUENCE: 25
accaactaag aaaaaaagca caaagttctc agagctctcg aggaaagtgg ttgtccccgt     60
accaccatgc actgtaaata tccctcccct ctctccctgg tccctcccc catccccacc    120 actgatatca tggggagtaa taggaccaga gcggtatctc tggcaccaca ctagggacta    180
tcaggtaata aaagctttga ctccctgaga aaaaaaaaa aa                        222

<210> SEQ ID NO 26
<211> LENGTH: 407
<212> TYPE: DNA
<213> ORGANISM: H. sapiens

<400> SEQUENCE: 26
atgacctgtc tctaaaaaag cccgattatt tttaaaggcg atttagaaag gctgaattga     60
tgagcaggaa tacagaggtg tgatttgcct ctcccacctc tgtgctccat tcttcactgt    120
gatcattttc tcattaggtt taagaaatac aagcaagctg ggagccattc caattctttc    180
cgcttatcca acggccgcac tgaggatgtg gagcccagaa gtgtgccact tctggccaga    240
tccccaagca ccaacaggaa ataccccacc ctgcccgtgg acaagctgga agaggaaatt    300
aaccggagaa tggcagacga caataagctc ttcagggagg aattcaacgc tctccctgca    360
tgtcctatcc aggccacctg tgaggctact aaaaaaaaaa aaaaaac                  407
```

-continued

```
<210> SEQ ID NO 27
<211> LENGTH: 31737
<212> TYPE: DNA
<213> ORGANISM: H. sapiens

<400> SEQUENCE: 27
tcctgaagta cagggcgtca gcaggatcct ggcccactgg gcctgctaca aggcaaggat      60
gtgggatggg gtccaagggc atttagagga ttccaggccc tggtgaggtg gaggaaatag     120
aaagtgtaga actgcgctgg gcacggtggc tcatgcctgt aatcccaaca ctttgggagg     180
ctgaggcggg cgaatcacct gaggtcaggt attcgagact agcctggcta acatggtgaa     240
accccgtctc tactaaaaat acaaaattag ccgggcacgg tggcgcatgc ctgtaatccc     300
agctacccgg gaggctgagg caggagaatt gctttcacct gggaggcaga ggttgcagtg     360
agctgagatt gcactgctgc actccagcct gggcgacaga gcaagactct gtctcaaaaa     420
aaaagaaaga agtggcgggg gcggaggagg agggaaagag agagaaagaa gaaagagaga     480
aagaaagaaa gaagaaggaa gggagggagg aagggaactg aaggggtggg tcctaagggc     540
ttgcaggagt ggagagtgag gaatggcatc cagatgtttg tgacaccccg catcccttgc     600
aggtgcaaca gaaggatgtc tcagatgagg atgtggctcg agccattaac cagaagctgg     660
gggacacgcc tggtgtctct tactccgaca ttgctgcacg agcctatggt tgtggccgca     720
cggagctggc catcaaggtg tgggtgccca gccctccaca gacactctga tgtggttgtt     780
cagggccccc atgccagctc cttctctctg tgccttcctt ctcacctcac agctgctgga     840
gtatgagcca cgctcagggg agcaggtacc ccttctccta aagatgaaga ggagcaaact     900
ggcactaagc aaggccatcg agagcgggga cactgacctg ggtgagggca aggctggggg     960
gcccctgggc taagtgggag cctggctgga attcccactc caccttactc tcctgcagtg    1020
ttcacggtgt tgctgcacct gaagaacgag ctgaaccgag gagatttttt catgacccct    1080
cggaatcagc ccatggccct cagtttgtac cgacaggtgt gtgtagtggg cagggttgtg    1140
gtgtagcctt ctgagcactt gagttggcct tgctgactga ttgcctgcct gtggcccag    1200 ttctgtaagc atcaggagct agagacgctg aaggaccttt acaatcagga tgacaatcac    1260
caggaattgg gcagcttcca catccgagcc agctatgctg cagaagaggt ctgagatcca    1320
tggggcgtgt ggggcgtgtg gggcatgtgg gctgggggctg ttggtccggt tccttcagga    1380
atctaggcct tcgtgttggg tgcacactcc atctggtcct cactgtgagg gagactctga    1440
cgtgaggcca ggatgggggt tagtgtcaga ggagctagcc atccctctag gacatcagag    1500
tggtgcacct agcaggcaag gctgaccctg gcgaccctgg gcacagggat gggggagaag    1560
actgtagcct gggtgaggag ggcgagggtc ctgcatgctg tgagttcagg ccttccttct    1620
tgtctttata gcgtattgag gggcgagtag cagctctgca gacagccgcc gatgccttct    1680
acaaggccaa gaatgagttt gcagccaagg tttggcccac cttttttccaa gagcctcctc    1740 gtctcctggt cttccctcct ggtccctcat ccccatcatg cctcattatc cgggtcccca    1800
ggctacagag gatcaaatgc ggctcctacg gctgcagcgg cgcctagaag acgagctggg    1860
gggccagttc ctagacctgt ctctacatga cacagttacc accctcattc ttggcggtca    1920
caacaagcgt gcagagcagc tggcacgtga cttccgcatc cctgacaaga ggtaggtgag    1980
ggcccaggct gcatgtgggt cccaggacca cctgcctctc ctgcaacacc tccaagccca    2040 gcttttcctgc aggctctggt ggctgaagct gactgccctg gcagatttgg aagattggga    2100
agagctagag aagttttcca agagcaagaa atcacccatt ggctacctgg tgaggcaggg    2160
tcctccctcc agcccacttc cagtgagggt agtcttcggg agagagggct aggcagggag    2220
```

```
acagatagga tggcccgttc atgctcctgt tcagctgccc gcatagttag cgagtgcttc    2280
ctgtatacac atttgtgggc aggcatcatc tgctgtgttg ggtgcactgg aggatgggtc    2340 caagttttgcc tgcagatgtt acggggagag agaatgagct gctttcccca gggagggcca   2400 caggggggcac tatgtgctag agggaaagtc ttgtctgagg agggtggagg gggcacaggg   2460
agggtgcata tgggaggcag tggagatact gagggctgtt ttctgtggtg ggtagttcag    2520
aggtgtatag ggcaggtttg agaatgtcaa tcacaagaga acacaggaaa tgtgagggct    2580
ggtggcagga acgcctgttg caaggggtaa tggtgggtgg tagagcagaa gcgtggaaat    2640
aattggtctc aagtctctga cagagctttg gtttaggtga tttctgccct aagaatgttg    2700
agatcacaac tgtctgtgca tgggggttgg gggattatat gtactgacgg gtgtatacat    2760
atagaatata tatggacgat gtatgcattg cgcctctgct cgtaagagag aggacaggag    2820
ggctgtgcat tacctcctcc ctccacccgc ttcctctcct ccaagccttt tgtggagatc    2880
tgcatgaaac aacataacaa atacgaagcc aagaagtatg cttcccgcgt gggtcccgag    2940
cagaaggtca aggctttgct tcttgttggg tgcgtcaact gagggcctgt gggtgctggg   3000
tggctgagct gtgggctggt gagaggcagg gtttgtgccc ttgagcagcc ccaacaccac    3060
ctcctctctt gctcaaacca cagcgatgtg gctcaggctg cagatgtggc catcgaacac    3120
cggaatgagg ctgagctgag cctcgtattg tcccactgca cggagccac agatggggcc     3180 acagctgaca agattcaacg ggccagggca caagcccaga agaagtgagg agtccatcct    3240
gtacatctca gcaagggggt tcctccccta gcacctgggc ttggcagaag ggccatagtt    3300
catccagctc ctcccctaga gcaatgctga ggagcggggg catggtagca gggctgtctg    3360
gttttaaata aagttggaac acttcacagt gcttgtctta cacagtccag cctaagcaaa    3420
ggcaagctca agacaggatc ctccagacac cacagcaaaa ctccatgtgt tccgttgtgt    3480
tgggaccgga ggtgggggct tctccagcca tactcgcaag aaacgtgtcc tctccacagt    3540
taccaaggaa agctttctct atctcacagc tcctaggaag attatagggga gagatggcac    3600 aaaacttaag caccagctca ccaagaacat actgtaaagc attctgtgtg tgtgcgtgta    3660
aacacgcaag aaccacgcta aacactttttg ctgcctgtac ttcctttatt cctcgtgaca   3720
gccctgtgag gtaacatcac cccactttac agaaaggaga ttgaggacca gggagttcga    3780
taataacaaa tatgtggcaa aacagggatt tgaaacccccg ggccaagtgc aagctggaac   3840
tggaatcggg ccctctgtga gaagggagcc tgaggcaagg ccccaatttg cactgcagtg    3900
gtgattggag gactaatgag aagtgtgtgg cctgcgggcc atagggtca ggggggtggtg     3960 gcctttggaa ctcttgccca ctgaactgtg gtgagcaatt ccaagttgtc tctgggccaa    4020
atagagaagg aggatggaag atttcaattc tgccaaaaag aaccatgaac accagacccg    4080
caatcagtag gagtacccgc ggggccctct gctctctcta tctagccttc cgttggcact    4140
ccagtgcacc ccctctgctc tccctgtcta gcccctccgtt ggcactccag tgcaccccct   4200
ctgctctccc tgtctagccc tccgttggca ctccagtgca ccccctctgc tctccctatc    4260
tagccttccc ttggcactcc agtgcacctt ggcttcatgc ccagggcccc acccaacact    4320
gagggcattg cctttttcctt tgtcgccccc actttgtcta caaggaggaa accacagcca    4380
gagggagtgc aggcctcact ggagcttcag gcctctccct atttaacacc ctagggccg    4440 accatgcttt tagaaagaca gtgagagact cagggcctga gaaggtattt cttttttttcc   4500 ttttcctacc tgacttgtaa atgaaagttt gtgaaagtcc ttcaaggaga tataagtcaa    4560
atggtaaaat aactatcatg ctcgccattc attatgtggg tcaagaattt ggacaggttg    4620
```

```
taacagggat ggtttgtgtc tgtttcatag tgtctgaggc atcagctgga agactaaaag    4680
gttgatagct aggggctgaa atcatgtgaa agcttgctaa ctcacacact tggtgagtga    4740
cgctggttct tcactgggac cttagctggg gtggtctgcc agaacacctg caacatggtg    4800
gctgggtccc aaggacaagc atcccaagag ggtgccaggt agaatctgga ctgccttcct    4860
aacctagatt tggaagttac gtggtgtcac atctgctaga gtatttgtca cagcagtaat    4920
acaggcccac cccaccaatt tcaaggggaa atagactcca cctcttttt tttttttttt      4980 ttttgcgtgg tagagatggg gtctcggggg tctccttatg ttgcccaagc tggttttaaa    5040
ctcctgagct caagcagtcc tccctcctca gcatctcaaa gtgctgggt tacagcatga     5100 accactgaac ctggcctgga ctccacctcc tgatagggag tagcaaagtt ctggaaatac    5160
tgtggctagg ttttggaatc acaatctggc acagcccatc agctttccct tttggaatca    5220
gcagacaaga ggaaaggaaa taatcccaa tgctgggctc atcattctgg gctttttttt      5280
tttttttttt tttttttttt ttgtcccag tcttggcccc acaattcctc actgccctgg      5340
tagctctttg atgcctttaa aaaatgtttt cccagctttt cgagttctca atgaaaaagg    5400
attgctatca acaacccag ttttcctctc tggaaaggga ggcttgacca gtgcttttag      5460
aatgtacaca atacaaaacc cacatctcca agtaacata cagtatattt actcataggc      5520
tatgtaaaca aacactgtac atatgaagtt ttagaaatat gtgagaaata acttttaact    5580
gatgacaaat gtatatcaac agtgatttca actttataaa aggtgtgtgt gcatgtagag    5640
aagcattgga attgtctatg gggagagttg ctttaaaaag gcagttttgt atactttttt    5700
gtaaagttaa tcactgattt gccccccacc tccacagttt attataaaaa ctttcaaaca    5760
tacagccagg tagaaataat tttacagtga acatttgtgt aactaccact ggattctacc    5820
attagcatct tactatatca cacatctgtt catctatcca ttcctctatg tcaatccatc     5880
gtatttttca tatatttcaa agtaagttgc agacatcagt acacctcccc ctaaatactt    5940
cagtatgcat ttcaataact agagttcatt tttggtttgc aatttttttt ttcttttcag    6000
gcaaaatcta catacattgc aatccacaga tcttaaatgt aattttctaa gttttgacag    6060
atgtataagc ctatgaattg tgacatttaa aaaccagaac tgggattttc ttttttcaaa     6120
tccttgctta ctcaattgaa attagtgtga gatgccttct gccctgagca gtttgtacag    6180
caggcctatg cctacatggg tgggcagggc caagtttcgt ccaatgtatg acgctaggat    6240
tggggctagg aactaggact gtgtagctgg aggcaaagaa tctgggaaca tttcttcttg    6300
tatcagtggt agccagtgca gggagaatca gggcaaaggc tgggcgcagt ggctcatgcc    6360
tgtaattcca gcactttggg aggcttaggt gggtggatca cctggggtca ggagtttgag    6420
accagcctgg ccaacatggt gaaaccctgt ctctagtaaa aatacaaaaa aattagctgg    6480
gggtggtggc gggtcctgta atcccagcta cttgggaggc tgaggcagga gaatcgcttg    6540
attgcttgaa cccaggaggt ggaggttgca gtgagctgaa atggcgccat tgcactccag    6600
cctgggcaat gagtgaaact ctgtcttaaa aatatatata tatatatcga gcaaaggctc    6660
ctacaactca ccttctcagg gtaagggggct gtatgtccag tctcttagat acaaagttcc    6720
agtgaaagac tcttgggggtt ggccaggcgc agtggttcac ccctgtaatc ccagcatttt    6780
gggaggctga ggcaggcaga tcgcctgagg tcaggagttc aagaccagcc tggccaacat    6840
ggtgaaaccc tgtctctact aaaaatacaa aattagccag gcgtggtggc gcatgcctgt    6900
aatcccagct actcgggagg ctgaggcagg agaatcgctt gaacccggga ggcagaggtt    6960
gcagtgagcc gagatcgtgc cattgcactc aagcctgggc aacaagagca aaaactccgt    7020
```

```
ctcaaaaaaa agaaaaaaaa aactcgggtt tgaacagtgt ggcctgcaaa gggacttggc    7080
tctcatttac ttcaccttc tatcttattg ccttgcttta ttttcatttc agcatttagg    7140
aaattttctt gttcttttgt ttattgtctg tgttcctatc cagaatgtaa gctcctgaga    7200
gcagaggcct cttctgtcct cttctgtctt attccctgct gtgtccagca catggtctgc    7260
actcaataag tatttgttgc gagaatgact cattgttcca tttactagaa ggggaaagga    7320
ggccccgaga ggggaaatga cttgcctaaa gaaacaggag tcctttcccc ccatcctcca    7380
gctctcctga tcctctcctt tgctcataaa ccctgtgact gttggggcac ctgtggggtg    7440
gctgcgaaat gcctacctgt aggtatgtgc tcctgtgggt tgggactaat gcaggactag    7500
gagtaggagg gctctgcagt cccccatttg ggtaggcttg ggcacaggaa actgcctcct    7560
ttcccttcct cagttctctt ctcttccagg ataacccttt actctgtgat gatgatgggc    7620
gagggagctc aggacactct gggagccaag taggatggag ggctgggcag gtctctacag    7680
gcaggcagct gaggagggg ctctgtcttc ttccaatgga aacagcatct gtgtggttgc    7740
tgagctgaac cctccttccc agggtctcca gggtctgtag ttctccttgg tctgtagttc    7800
tgtcacccct gtgcacaccc cacaaatgct ttgaccatag tgcagctgtc tcatggggag    7860
agaaagaact ttcatttcct gagaatgggt tacttgccaa gctgaacatg cctaattctc    7920
aatacagccc tgggaagttc caggaagagt tgcagaggga ggctcaggtc acccagcaca    7980
tggtggggct ggaaccccg ggctctttga ctaccacgcc caacaacaat ttttccaagt    8040
gtggtcatat ccaaaagggg tccttcagat aatctcaaag atgaacactt actgcaatca    8100
ctatttcagt tatattaaaa atataagtag catgtcaacc ccttctaggg taatacaaat    8160
aaaaagtaaa aaaaaactaa tcaacaaaaa gaaacatatt aagaaataat agtgtaaatt    8220
agatataagg caaagtaag ctggtgggt ttggttctag agcatagggc tgctatccca    8280
gctactgagg tacctcctgc gtttgcagtc attacttgtt aggggttttc acactttgac    8340
ttcctgctttt tcacttttcc attcggtgtt gcgggataga ttgagtttgg acttaagggg    8400
atatgtgaat gttgggcgtg gggaaggatc caccctcact ggggtctgag cgttaggaga    8460
gtaggcgtgt ggactctggg cctttgggct ggagtgtcta ttggtcagag gtgtcgggtt    8520
cggccatttc accctcacct ctaggctggc cctgctgaga gggagagaga gtcacaactc    8580
ccactcaagg agagacttcc ctgctgggga ggggacggcc tgaggcccgc cccacccata    8640
ttcccaggcc ctggctctgg ttagcatgga ctaacttatt ccacaatacg gaggagtggg    8700
gcacagagtc cctaactggc gccccaacag aaggcggtgg tggggaccgg agatggtagg    8760
actggagatg gtaggggctg ctgatgtgag cccacaatac ggaggagtgg ggcacagagt    8820
ccctaactgg cgccccaaca aaggcggtg gtggggaccg gagatggtag gactggagat    8880
ggtgggggct gctgggagcc ccttttgcgc gcagtgttt cctgccatga agagttgccg    8940
ccggtcacaa cccttccccg ggggcgcccc gaatgtggga ctccttccgg cctgggtgc    9000
gtgaggggga ctcagggggtt gcccggtctg gaggagagac tcgccgccac ctaccccggg    9060
aaccgcagac tctgggtctg ggataaagcg tcccctaccc gcaagctcgg tttgtgcgct    9120
actgtgcaat ctgtcttttg cctgcagacg cccagccgct cgccctgcgc gggtctcgga    9180
atgtccaggg gtccctactg gggatcacaa cccggcgaaa tgtcgcattt gccaccacct    9240
atctcgactg cgtaatcggc tttcagccgc agacgctcag gtcctgcagc acccgcgggg    9300
atccgtgtag gaacctgctg ccgctggatg gactgagcga ttgcttcgcg ggtgtcacgc    9360
accagacgcc gtgccgggag cgccgggaag ggggtacgcg ccccaacccc ggccggggga    9420
```

```
gggcgcactc tggctcctct ctgcgttttg agcctcccct cccccgccag gcgtatcgca    9480
aaaggcacct ccatcgcaga gcaccatgtg ttgtgcttct actcagctcg gtggcgagcg    9540
gggccccagc atgcgcatct ggaaagcggg ggagattacc ctggagctcg ggtggggacg    9600
gcgtgggctg acttgatata agacgacacc cacggagcca gatccgttct agggacttgg    9660
caggttcctc tccctcccca gtgagatccg tcgttctttg cagcaattag gggagggaaa    9720
aaaaagaccc acagtatcac gtttggagag ggttaggaag atggctctcg agttgcaggc    9780
cgccctggtg gctagacatt ggtgtagttt gtgcctggcc tcggtttcct gatctgtaaa    9840
ctgggaagaa ggcccaagtc atgaggcctg tgactgtaga atggctgaag gcactggtgc    9900
actcgcagcc ggtccttccg gggtccagct tcccgaagga ctgggcagcc ccggggcgaa    9960
cccctctgga gctaccagga gaacgtgcga ccgggttcgg cgcccagcc ggcaagtgag    10020
cgcccagcgg agcgcaaggg cggggcccgc gcgggccgga gacgcccgtt cgctgtcggc    10080
caaccagcgc ctgtctctga acagccaatg aacacgcgtc ttacagccaa ggccgggtcg    10140
ggagcgaggc tgcggcgagt gcggcgctga cagagacgcg cgcgcgcgcg atcgcgctcg    10200
gacccccggc gctgccgcca tcactgtcgc ccgcccagtc gccccctcagc cgcttcccct    10260
cgccatggag gcgaggccgc cgccgccgcc gcggggctcg gagccgcggg ccgggcggcg    10320
gccctgaggg ctagtggcgg cccgaaacgc cgccgcggag ccgaggcgga gccgctgtcc    10380
tcgtccccag cggtcccgcc caacgcccga ctctgtgagt gttcgcggcc gctgcgcccg    10440
ggtgggctcc ggaaggggga gcggctcccg ggggcggtgg gagggtcccc gggccacagc    10500
ccagagcccg gagcccgaag ccctaagcca tcttttccgg gtagaagcct gcgggcgcct    10560
gcaggttgat tgtgcatcct tgcgggtccg tcgcggggag gggtccccg gaaacgtgcc    10620
ggcccgagtg ccgacccctc gcgactgccc aggaactttg catgcgtcct tctgggacca    10680
ggccagggca ctgccagagt tgattctcag agaagaaact tagaacggcg agaacagaat    10740
ttgctcaggt ccatttaatg ggaggaaaga ggaaaactct tggcatgaga aaatttgctt    10800
ttgcagtgac caacttttct ttcccttcaa gtccacctcc ctcggtcccc cggcccgtct    10860
cccaggcccc tctccttgcc gccctctccc aactgttgag gctgtttaag aagggaaata    10920
agggctgaga gctgcccaga attcagaata ggccaattga gaacgcaggt cccctccctt    10980
tttactttcg gtaaataaaa aattttttt gaaaaaatta gttactaatt atatctcctg    11040
aagattaaaa aaaaaaaata gcagagcaga gtcctgtctt gagggtttcg ttttattttt    11100
tgagatcact gatgatattt gtaagacagg aaaagaagaa tgtgcaaatc caccctctgc    11160
agggtgaacg ccatcagaag cctttgctca ggagagggat tccggctcta gaaccagtcc    11220
acatcaccct ggagatggct tcgtttgcca cctgctagct gtgcaggcag cctgagaaac    11280
agaagatggt gggcgagagg aggactgact aggaaagggc gaacatcttc ctgcctggcc    11340
actcctttca gaaacagatc tgatgctgtc acttgtttac ttaaaaactc cctcgctttt    11400
cttttttccca tgggatgaat gaagcctaaa atgccttatc aggtcataca aagcccttga    11460
caatcttgcc tcaatttact cctttacttt tagcctaatc ggatcctcca attctccttc    11520
ccctcatccc gcttgctggc tagtattcag agctgcttga ctgcccctc acatgttggg    11580
atgttttgt tttatgtgat cctctttctt ccccacctt acctgccaag ctccacttt    11640
tcttttaaag ttcttctcat ttgagaagct tcttgcgggc aggagctgtg tcttgcccac    11700
cttctatct cccgtggtgg gagaatcctc caagttgtct tgtagattct ttccaatctc    11760
ttctctctta tgcctaggct ctgtttattt cccggtatcc acttcccaag agatttttc    11820
```

```
gtgttttgaa ggcctgcttg gagtacatgc ccaggacttt tagtatttct gattcccggc   11880
ttccccatgt ccatcccacc cagcccccat aagcagtcag caggtgggaa ctggtaggtc   11940
ccatatccca ctggcctcca aaaaactgtc tctgaaagac taaaagccct tcagtctctt   12000
ttcacctctg cctgctcaaa gtgacctggc tgataccgtg cattgtaagg catggtggga   12060
tcccggggcc tgttctctgt ttagccactt aacatctggg tgaaatacag aaccagaaaa   12120
accacccctc tgacttcagt acattcatgt gtcttccctt tgccaggtga attgcttggg   12180
atacaaaagt gaggaagtca gtccttaacc tttgaggaac tcagagtcta atgtaggaca   12240
ggtggatata aatacatcac aggtgctata agattgtgat aataataata gctatttttt   12300
atttgccttg tgacaagcta tgtaatgttt tccatgaatt ccctcagtct tttcaacagt   12360
cataaaaggg cttattccta ctctacaggg ttggaaactg aggccaaaca gtgggcaaat   12420
gagggaatag tcaagatttg aattttggcc gtgtatttgc agagcctctg ccaggctgtg   12480
tagggagcat cccctgcctg ggtgatttgg gaaagctttc ctgggacggg ggggccttcg   12540
gatcatgaag gatgcatagg agtttgcgcg tggtggactg cacacatagg caagagggag   12600
cagcacaagc aaacttggtg gtggaaggaa tccactgtcc ttggggagga gggaagaggt   12660
taatcatagc tggatcaggt aaggacaatg gagagctact agaggattta aaggaggtca   12720
gggacttggg ctgaaagaat tttggaaaga tcatttgggg gcaatatagg gccaaatgca   12780
gatgcccctg caatatagga ggcactggtt gggtctgaca gaggtagagt cacagcctct   12840
tagacccaga ggaaggtgta gagagaatcc tgctcaattt tgggaaaaga taattaatgc   12900
agatgagaga aaaattcaaa agttctagca atacaaaaga gtatatagag aaaaatgtcc   12960
ctcctaccct ggccccaagt ctcctgtctc cctaacctcc tccccagaga tggctgaagt   13020
tttcagttta tatggccttc catagacact gttgctttat aaatatgtgc ctgcttatcc   13080
atactcctcc caccatggga cgtaccactc acaccttact gggtttttt acttaacata   13140 tttaggaaat cattctatta tcaacatata tagagagtta tttgttcttt ctgttgacat   13200
gcttttactt atttagttgt atggctgtac tgtaacatct ttgggttaaa tatttgtttc   13260
caggttcttc tcttacagca atgaatgtcc ttgtacatac tgtgttatgt gctcatttgc   13320
aaagttatct gaacaatatg cttttagaag tagaattact gggtcaaggg atatgtctgc   13380
atttttgatt tgcagacatg gagccaaact gccacccgtt tctgggggt tgtaccaatt   13440 tatcctctcc cccaaagtgt atagctggat agatgatctt tggagaattc aggaggatca   13500
actacgatgc ttttttcagct attatatgcc tactttcct ccacaaatcc tcccccaccc   13560
tatgcgattc tagccagttt ctttgaattt acagagggag atgttgaggc tcagaaggat   13620
aaaagtaact tgtgcaggat gatcagtgcg ggtggtggtg ggtgtttgt tttgtatttt   13680 tgcacccctc atgtttgtat ttgccagcac cttcattgg aggtgctcag tgtcagtttg   13740
taaacattat tgcattattt ttctccattt tcacatgaa aaaaatgaga tgcagggaa   13800 gtttgagtta tgagagggaa actggccaaa tatagaatct tgtcatttta cttccagtgc   13860
aataataaat gtttccaaat gacaaagctg aagagatgtt ttttgtttgt ttgtttgttt   13920
gtttgttttt tgagatggag ttttgctctt gttgcccagg ctggaatgca atggcgctat   13980
cttggctcac gcaactttg cctcctgggt tcaagcgatt ctcctgcctc agcctcccga   14040
gtagctggga ttacaggcat gtgtcactgt acctggctaa ttttgtattt ttagtaaaga   14100
cggggtttct ccatgttggt aaggctggtc ttgaactcct gacctcaggt gatccgctga   14160
tcttggcctc ccaaagtcct gggattacaa gcatgagcca ccgtgcccgg tgaagaaatg   14220
```

```
gtttttagt gagtctgagt acaacaaaaa tagcaataat ataacactaa cttaataaaa    14280
ctgaacagca ggcccaaaaa tagcccaaca ttaaaattta ttttaatgta ttctctatgg    14340
aaaagagaat ccattaaatg taaaactatt tattttactc taaattcaca tccatttgtg    14400
tcagtgtaca agacataatt tttatagtag cagtcagtac atatagaata tgattttttga   14460 attcttcaat agcataaaat attttatatt tactcattta agtatttgtt catttaaaat    14520
cacaggctgg gtgcggtggc tcacgcctgt aatcccagca ctttgggagg ctgaggcagg    14580
tggatcatga ggtcaagaga tcaagaccat cctggccaac atggtgaaac cccatctcta    14640
ctaaaaatac aaaaattagc tgggtgtggt ggcgcgtgcc tgtaatccca gctactcggg    14700
aggctgaggc atgagaatca cttgaaccca ggaggcggaa gttgcagtga gccaagatct    14760
tgccactgta ctccagcctg gcgacagagc gagactccgt ctcaaaaaaa agaaaaaaaa    14820
aatcacagta tagtattcca tgcatcgaca gctgtagttt tttttaaatt tgttttttgtt   14880 tttttgagac agggtctcac tctgccaccc tggctggagt gcagtggcat gatcacagct    14940
cactgcagcc ttgacctcct gggctaaatg atcttcccat ctcagccacc tgaatagctg    15000
ggactgcaca ggtctgtgcc accacgacca gctaattttt ttatttttg tagagacatt    15060 tttatgttgc ccaggctagt cttgaactcc tggactcaag tgatccaccc gccttggcct    15120
cccaaagtgc tgggattaca ggtgtgagcc accactctca gccaacagct gtagttggtg    15180
caatcctttt tattcttta tttttttcta cctttttgct attataaatg gtacttttat     15240
accccttgtt caaatacttc ttttggatta tttccttgga ctcttactcc caacctgggc    15300
tcaccaagtc agaggataca gtttcggtgc ctaattgcaa tctggaaagg ttgaactagt    15360
ttccagcact atcagcaatt tatggggcca tttcttgaca acccatctag tgctattaca    15420
aagaaatgta atgataccct gaattaggtt taatttacat tgctttggaa aaagagacca    15480
gtagctgatt tagatttttt gaaagaagta cagtgctgtg atatagatta tctccaagat    15540
ttatgtaact gaagccaact tgtggttgaa gaaagatttg gttgatgaga ttgaaatatt    15600
gtggaagttt agaataggat catagcagta taaaatataa ggctagatgc tgttcagttg    15660
gaaataccag gcattgtgcc ggaagctggg gacaccccag agtaacatag atgtgatgtc    15720
tgtcctcatg acacttttag gttagtgcag tagacagaca ttaaaatcac ctatggtaat    15780
tatagatgtg atgaaagggg aagaataggg tgtcgggagt gtcagagaag ttcagcagct    15840
aaacaacatt tgcagttaaa catttgtgaa ggccctgagc tgagaaggga tttggtagct    15900
cagggcagcg cttcgctaac ttgaatgtgc tcatgaacca tctgggaatc ttgttaaaat    15960
gccaagtcct gaatcagtag gtttggggtg ggacttggga ttctgtgtta ctaaccagct    16020
cctgggtgag gcagatgctg ctggtgggtg gatcacactt ggtgtagcaa ggcctaattg    16080
agagcttggt gagcacctaa aactggctga ccatggtgag caggaagggg caggtggctt    16140
gcagtgacag agtaattctc tgcctaggct gcactttaga ttcacctggg aacttagaa     16200 aaatcagggt tgcaaatgcc ccacccgcag ccattttaat ttaattggtc tcagttgggg    16260
cctgagaatg tgtatacagt catgcacagt ataacgatgt ttccatcaag agagactgc     16320 atatgccaca gtggtcccat aagattataa tccataattt tactataccc tttctatttt    16380
tagatatgtt taaatacaca aatactcact gtgttagtta cttacagtat tcagtacagt    16440
aacatgctgt acaggtttgt agcctaggag cagtaggcta tacaatatag cctagatacg    16500
tagcaagctg taccatctca ttttgtgtaa gtaccttta tgatgtttgc agaattatga    16560
aatcacatca ggactcatcc tcagaatgtg ttccattgtt aagtgatgca tacctgtata    16620
```

```
tatattttaa ctccccaggt gattctaatg tgtagccagg cttgagaact agagactaag  16680
gacagtgttg agactagaga atggcaagga gcagagttga gggtcctgta tggcatgcaa  16740
ggattttgga ctctatcctg aaggcagagc taaatctttg aaggattttt aagcaggaga  16800
gtgaactgat ctgatttgca attgttaaaa agttcactgt ggctgtagtc cagagcagta  16860
gttttcaaat tgaggtagat aagatgatcc aggggaactg gaagaaaatt tagaactttt  16920
tattgttttt atctaaaaga taagataaaa catttaattt aggaattgtc tctggcatct  16980
tcttgggtct ataggtcaaa cagttaatgt gttaactgta gaactttggg tgtcctgaag  17040
gaagagactg aattctgcag tgagcagaga catatttata catttgttct ccatgtattg  17100
caacatgttg ttaacagttt atattaacca gttctcattg aactagcctt tacaaaatgg  17160
acatgcagag aaaccagtga tcaaagaaaa tactaataat acaagcacaa gcaaacaagt  17220
tgtcagagct gacacttgtc caactcctgt gatgaattct tggtgagcta ttcaaataag  17280
tcagctctta ctaaattgga aagtatcagg aaatttataa gaaacatgaa ctttcgtgct  17340
ctgtcattaa taggaatctt gctttaagat tcctttttaat cgtatgtaga acccagctgc  17400
acggtggctc acacccataa tcccactgtt ttgggagcct gaggtgcagg aggccaggag  17460
ctcaagacaa acctgggcaa catagcgaga ccccatctct accaaaaata aaaaattagc  17520
cgtgtggtgt cacgtgcctg tagtcccact tacttgggag gctgaggcag aggattgctt  17580
gaacccagga gttcaaggct gcattgagcc atgattgcac cactgtactc cagcctgggg  17640
gacagaggga gactctgtgt ctcaaaaaaa aaagaggag gaccgggcat agtgggtcac  17700
acctgtaatc ccagcacttt gggaggtcag ggtgggtgga tcacaaggtc aagagatcga  17760
gaccatcctg gccaacacag tgaaacccca tctctactaa aaatacaaga attcgccggg  17820
cgtggtggcg tgtgcctctg ggtaatttca gctactcggg aggctgaggc aggagaatcc  17880
tctgagccca ggaggcggag tttgcagtga gccgagatct cgccactgca ctcaagcctg  17940
ggtgacagag caagactctg tctccaaaaa aaaaaaagta tgtaaaacct tgagatatta  18000
aataataaaa tatgaggctg tcaccagtat gaagacattt gaaaaccaaa aatttggaac  18060 ataaaagaa cctctacatt ttttttgcag tgatgtttaa agataaagga tattccatca  18120
gatgctttac aaaattttgc taacttcaat tattaaaatt tatattttga gggttttttg  18180
cttttaagag acagggtctc actctgttgc ccaggctgga gtacagtggc acaatgatag  18240
ctcactgcag cattgaactc ctgggctcaa gcgatcttcc caccttggcc ttccaaagct  18300
ctgggactac acatgtgaac caccatgcct ggccagtttt taagtttatt gttcttataa  18360
aagacaaaat ggggccgggt gcagtggctc atgcatgtaa tcccagcact tgggaggcc  18420 gaagtggacg gatcacttga ggtcaggagt ttgaaaccag cctggccaac atggcaaaac  18480
cctgtctcta ctaaaaacac agaaattagc caggtatggt gggcacacct gtagtcccag  18540
ctactcggga ggctgaggca ggagaatcgc ttgaacctgg gaggcggaga ttgcagtgag  18600
ctgaggttgc gccgctgtac tccagcctgg gagacagagc gagactgttt caggggaaaa  18660
aaagaaaaaa gacaaaaaaa cacataccct tggcagattc ttcctgcccc acccccaaaa  18720
ggcccactta aacaaaaaat ggactgatgt actacatgga aaataatttt gtcaggaaat  18780
caaaatactg ttggaagatg tatagaaaac attgctgaat atgtgaacaa acaatattag  18840
aacaaatttt gcagtgtggg aagtttggta tacggttata aaagtacaga agcttctagc  18900
atgtctcagt atcgctagat actctttttt ttcttttctt tctttctttc ttttttttt  18960 tttgagacag ttttgttctg tcacccaggc tggagtgcag tggcaccatc atggttcact  19020
```

```
gcagcattga cctcccagtc tcaagtgatc atcctacctc agcctctcaa gtagccagga    19080
ccacaggcat gcaccaccat acctatttt tttattttt atttttagga gagatgaggt      19140
ctcactatgt ttcccaggct ggccttgaac tcctggctca agcaatccac ctgccaaaag    19200
accttccaaa gtgctgggat tacaggcatg agccaccgtg ccaactgtgc caggcctaga   19260 ttaccttta atagttacat ccaagaataa ggaccactc ttttgtgagc tactggaaga     19320
aagttgtact ggagaagaca tatttttaat agtaaatgat tgccttcata agaacattac   19380
tatatggaat aatagactga atgtaaatta atggaacagc tgctttgact gaacaaaaga   19440
atgaaattca ttcattactt ctctatgggc aggctgttga gtccacttat ttgttaatta   19500
tcttgtggta gagttgttga tgagttttgc attttctttt tttaaaaaaa tgccaacttt    19560
ttgttatggt aagtggctac agtttgagta atcctaatat gaaatccaaa aggcttccaa   19620
atccaacact ttttttttt ttttttttt ttgagacagg ttctcactct gtatgtagcc      19680
caggctggag cgcagtggca tgatcatggc tcattgcagc cttgacctcc tgggctcggg   19740
tgatcctccc acctcagcct cctgagtagc tgggactaca ggcatgcacc accatgccca   19800
gctaattttg caaccagtag gaataatgca aatagtacaa aatctgaaaa atacctaaat   19860
ctgaaacact tctggtccca agcatttcag ataaggaata ctcaacctga acctagcaaa   19920
tatcatttga aaaataata tcttaatctg tctcttcaag taaaagtatt atttaaatag    19980
tgagtgaaaa aggaactact tcttttctta gaaagaaatg tgcaggccgg gcgcggtggc   20040
tcacgcctgt aatcccagca ctttgggagg ccgaggcggg cggatcacga ggtcaggaga   20100
tcgagaccat cctggctaac acggtgaaac cccgtctcca ctaaaaatac aaaaaattag   20160
ccgggcgtgg tggcgggcgc ctgtagtccc agctactcgg gaggctgagg caggagaatg   20220
gcgtgaaccc gggaggcgga gcttgcagtg agccgagatc gcgccactgc actccagcct   20280
gggcgacaga gcgagactcc gtctcaaaaa aaaaaaaaa aaaaaaaaa aagaaagaaa     20340 tgtgcaatgg tagagcgttt tcctcgttgg aattttttt acatgtaatc attataagct    20400
ataacttaca tattataaaa ttctccttt taaaatgtac agttctgtgg tttttttgtat    20460 atgcatagag ttgtgcagct tttgccactg tctagtttaa gaacatttca tcaccccaaa   20520
agagaccctg cacccattag cctcacttcc cattctctcc tccctccagt ccctggcaac   20580
tactaatctt cctgttctt tggatttgcc tattctggac atttcatata aatgaaatca    20640
tacaatatgt gaccttttgt agctggcttc ttttacttag cataatgttt ctggggttca   20700
ttcatgttgt atcatgtatc agtacttcat tccttcttat ggctgaataa taatccatta   20760
tattgatata cgacatttgg ctaactggtt catcaattga tgaacattta tttgtttcta   20820 cttttttggct ttatgaataa tgctgctgtg aacattcatg tataaatttt tgtgtagtca  20880
taggttttaa tttctcttgg gtatatatat ataccctagga gtaggattgc tgggttaaac  20940
ggtgactaac tttgagggc tgtcaaactg ttttgtaaag tgactaccca ttcccagtag    21000
caactcacaa aggttccagc agcaatacaa taggggtcca gtttctccca gcaatgctta   21060
ggggtcccaa tgtctcccat cttgtccaac atttgttact ctctttttga ttatagccat   21120
cttagtgggt gtgaagttgt atctcattgt ggtttttatt tgcatttcca tgatgattta   21180
tgatgtgcat cttttcatgt gctgttggcc gtttatgtat gttctttggg gaaatgtctg   21240
ttcagatact tggctcattt taaaatttag ttattgctct ttttattatt aagttactta   21300 tatatttta gatataagtc ccatatcaga tatacgatct gtaaatatt ttcccatct      21360 gtgggttgtg tgttcagctg tttgcgtgga catatccttt tgggtagatc taggagtgga   21420
```

```
actgctgagt caaatggtaa ctctctggtt tttttgttt ttttgtttt tttttttttt    21480 tgagacggag tctcgctctg tcgcccaggc tggagtgcag tgacacgatt ttggctcact    21540
gcaagctctg cctcccaggt tcatgccatt ctcctgcctc agcctcccga gtagctggga    21600
ctacaggcgc cccccaccac atccagctaa ttttttgtat ttttagtaga gatgggattt    21660
cacagtgtta gccaggatgg tctcgacctc gtgatccgcc cgcctcggcc tcccaaagtg    21720
ctgggattac aggcacaagc cactgcgccc ggtttgagga accactgact tgttgagga    21780 acagaaagaa cgcctgcacc tttttacaat cccagcagca gtgtatgagt gtatcagttt    21840
ctccatatcc ttgtcaacac ttgttgtttt ttttaactgt agccatccta gtaggtgtaa    21900
agtggtattg cattatgttt taatttgcat ttccttaatg actcatgatc tgactgtgat    21960
tttgttgcat ctataaaatt ctcataattt gacacatgaa aaccttagaa acaattttgt    22020
aacctaataa aaatctccaa atgtgtttct aaaaacattt ccagatgatc taatgaagta    22080
aagaatctag gcattggtca ccagtggctg ttaaaaccat tagggaactt tataataaag    22140
ggatcagtgt gacaatcttc tgatcaatca taacatctct aaaattggga caaccaaatc    22200
ttatattctt tctatgtgat actaggaaga acatatcatt catgaaatag tcttgcttgc    22260
cccaacaaac agagtcaaac cttcctctga ttagtgtaga tctgattact ggtttatagg    22320
atataattgg caaatttaga atgtgaaaaa tattatagga caaatgaacc catttacttc    22380
aaatgaatgg caagaaaaaa aaagtacacg aactgctaca gattaaaaaa gacttgaggc    22440
tgggcgtggt ggcccacgcc tgtaatccca gcactttggg aggccaaggt gggtggatca    22500
tgaggtcagg agttcgagaa cagcctgacc aacatggtga aaccccgtct ctactaaaaa    22560
tacaaaaatt agctgggcgt ggtggcacgc acctataatc ccagctactc gggaggctga    22620
ggcaggagaa ttgcttgaac ccaggaggcg gaggttgcag tgagatcatg ccaccacact    22680
ccagtgtggg cgacagagca agactctgtc ttggaaaaaa taaaaagac ttgaatgaaa    22740 catattaatt gaacataagt atagatcttg tttagatcct gtttcatgca aaccaactgt    22800
aaaaagttat ttatgagccc attgggagta atttaaattt gaaaaccact tgtatattag    22860
atgattttta aacaatttta atttttttaaa ggttattata gtagtatggt tacattaaaa    22920
agaaagactc ctttctctta cagataggta ctgaagtatt ttggatgaaa tgatgttgat    22980
atctggaatt tgctttaaaa taattcagca tgtttggagg attacagacg agacaagaat    23040
tgccatacgt tgataattat tgaagctgga taataggtat ataagggttt attatagtat    23100
tttctctact gttgtatatg tttgagaatt cccatagtaa aaaattaaaa gagaaaccac    23160
tgtaagggaa gagttttagt ggatttcatg tccatttgtt agaaatagaa aaatgtggcc    23220
aggcacggtg actcacacct gtaatcccag cactttggga ggccgaggcg gcggatcac    23280 ctgaggttgg gagttcgaga ccagcctgac caacatggag aaacccccgt ctctactaaa    23340
aaaaaaaaaa aaatacaaaa ttagcctggc atggtggtgc atacctgtaa tcccagctac    23400
tcgggaggct gaggcaggag acttgcttta acctgggagg tggaggttgc cctgagccga    23460
gatcgcacca ttgtactcca gcctgggcaa caagagtgaa actctgtctc aaaaaaaaaa    23520
aaggaaaaga aaaaaagaa aagaaataa aaaaatgtag tatctttgat taattttcaa    23580
aagtatatca cagaagatag atatttgcta gccatattta aaaggaaata tttgtataat    23640 ggggggtgaaa aaatgattat cacagtttag taaacacagc catagtgctt cttcctttgg    23700
attcatgttt cttttggtt atgatagcat taaaacttgg aatcaggctt ttaaattgct    23760
ctataatata ttaaaatgag attttcaaa cataatgaga aatatttaat catatggatt    23820
```

```
gcactaaaat attttttaaga tgggttttac attactattt taattgatgg aagtaccatt   23880
attgtgatca ttatgtattt catttgaaat gttttgtagt atttataggt attagtacct   23940
gtgttctgtt tataaatgaa catgtgttgg ggatgtatac tcttatttat tggtggatgt   24000
gcagtaaaag gtttgtttgt ggagaacgga ctgggcaggg tatagagact tatttgatgt   24060
ttattagagc aaatgtggcc agtgatgatg gtgttctgga ttggcttagg gtgggaggag   24120
tggtgatagg gatggagata catggacaag tatgatttaa gcagtagagg cattagggtt   24180
ctagatttct ggcttttttgg aagagatgat tgctagttaa tgaactgagc ttttgtgtgt   24240
gggaagaagt tgaaacctgg cccctgtgaa ttgtgcaagt agttcttaaa tattgattga   24300
caaatagctt aacgagcaac taattttcaa atattggttg acaagtggct tattacaata   24360
ttgtaaatgc attgatacta ccattagtaa agagaatgtc ttcctttgat aatgttagca   24420
gcactgttac cagagcagtg tgggatagtt ccaggactttt cactgtctaa aaggaactgg   24480
aggcccaagc ttttacgggg atacttctgc tctcctggtt cccatgtccc cagtgatgtg   24540
aatgtccctg actcagtgcc tctgctcacg ctgtctgtga gatcactgcc ttccagtgcc   24600
tcttacctct tgggcctgcc cactttgtta acagggacag atttcacagt gatttccagc   24660
cagtatttct ctctccccag tttggggtgt tagctagaat ggtccctcaa agccctcaaa   24720
cacggatgag aaatagaaga agctcaggga gactatacct gggctaggtt cttgctacca   24780
gctggtggaa gacaagaaa accccttttc ttcctgtatt tcatgcccag tgagcagtag   24840
tgccatcagc agcagttgtg aaccctaaa tcagtgattc tcaatatgac tgacatggtg   24900
gggaagacgt aagtttgaaa atgcatttc aggctaggtg tggtggctca cacctgtaat   24960
cctagcactt tcggaggcca acatgggagg atcacttgag cccaggagtt cgagaccagc   25020
ctgggcaaca tagtgagacc ctgcttctac agaaaaataa aagctagcca ggtgtaatgg   25080
catgcaccca tagtcctagc tacttgggag gctgaggtgg gaggattgct taagcccagg   25140
agatcaaggc tgcagtgaac ataccacagc actccagcct gggcagcaga gtgagacccc   25200
tgtctcaaaa agaaaaagca tttaaaaaaa aaaaaggttt gttagtgttt gtctcaaaat   25260
tttgcttaat ttaaaattat gtatatattt gaataatatg tgtccatgtt aatagttcta   25320
aaagtatata tagtatatat agtaaaaggt agttttctct cccctgcct ttcagctttc   25380
cctttccata ggcatccaca agtactatga gcaatacttg tgaaaccatg ctgaaatact   25440
acatgctcat aaaatgtaag ttacttaagt ttggtatttc aagtaacaat aagggaagat   25500
aggagagttt tatgtttatc aaaagggtg aatgttatag cagattgaga tgagatgttc   25560
ttacctttgg gtgggatctt aagtggagct caattcggtt tccccaatgt tagtgggaga   25620
gattacttaa accatccata cttatccagt tgtacttggt aagttttcaa aggttctact   25680
ttgaagaggg cttttgttga gcaagtagtg gttaatagag cagctcagtt acatgtgtaa   25740
gttttttgat gtgggaaaag ggcttttgta tacagaagga ctattttaaa attatttggg   25800
ctttaaatta acatgtatta aagtggtaaa tttaaaaccc agttttcttt tagtcttgtt   25860
attgtacttg taagcatagg cattttgtat agaaataaga atagtaattt tcacctgctt   25920
gtcaattaag ttaatataaa tttaacagat ttaattgctc caggccccctt acttagtgaa   25980
ttaaattttcc ttagatgttt aaaatacatt tacacagtca gtctgtcagg cacagtcagt   26040
ccttgacagg tcagagttac caccttaaac agaaacttct taagctcttg ggcaatctgt   26100
gatactaaga aattaaattt gtaaatgtag taaaacaggt tttggttaag acttccagtg   26160
cttttcatta gctgaatctg aattaccaac atttaaaaaa cacataccct aaacttaacg   26220
```

```
caaaagtact actagtacca tgagtttgat ataccatacc tcattttatt gctcatgtct  26280
tttctttctg ggattgtgat gccacttacc caattaagga ggacagtttt atcatctcag  26340
aaagccatgg ttatcagatt aaaaatacag aatcatgata cagttattat tggtcagaga  26400
tttgagactg ggaagggaa ctaaggggtc tgtgtttcca ggataattct actcaagaga  26460
tgctgtgcct ttccttatgt taagagtcct gaatgtggca tcaaaggggg aatccatgtt  26520
cagagtttgt tttgcaaccc cccatacctt tttttgagac aggatcttgg taggttgccc  26580
atgctggtgt gcagtggtgc aatcatggct cactgcagcc ttgacctcct gggctcaagt  26640
gatcctcccg cctcagcctc ctgagtaagt agctgggacc acagatgtac gtcatcatgc  26700
ccagctaatt ttttgatttt ttttttttt ttgtagagat gaggcctcac tatgagccta  26760
ggatgatctc aaattcctgg cctcaaacag tcctcccgcc tcagcctgcc caagtgctgg  26820
gattacaggc ataagccacc atgcctggcc ttttcttcaa aaataaccct tcaatcaatt  26880 tttttttcc tggtcaaatt ggattttgtg tttcttttat atattccttg tcaggcccta  26940
cagttatttt aattttgggt gttggataga ctagggttca tattccatgc ctgccatgct  27000
ttttgtgaac ttgggcaaaa tagttagctc ttctgagact cacttttgtc acctagtaaa  27060
tgggttcagc tgtagtactc tatgtatttg tttgttttaa gcattagata gtgcgtggta  27120
aatgcttagc acagttctta gcacatagta aatctttaat aaatgttaga aaatataatg  27180
atcttgattc tctgtcttcc ctcccctagta gttgatttgg ggcacagtgt agcattattt  27240
gaattatcac agaataactt tttacctttc tgattttaac aggggagagt gtgtaaagga  27300
tgggagaggg aagagagaaa aaagctgagt aaatgtgatc aactttacag tcttattcc  27360 ctgaactatc tttccctgag ttatgtgaca cattctcctt gttttcctct ttctatctt  27420 gtggccactc ctcagttccc taggccctc ttctttgacc actccttgtt tgagttacca  27480
aagattccat ctctggcctt cttgtgttga ttctacacgt tcttcctgga agcacatgtc  27540
catggtttca gcttccttgc taattaggag aaactttgtc ctcagaaccc atctggatta  27600
cagccaacag cctactggtc tccattgggc tatctcccag gtacctataa cagtctcaga  27660
actgactcat cttccttttc agcgtgttat ttttataatc tctatcttga tgaatggcac  27720
aacacagtga cccaaactgg aaacttgaat gttgttcatc tggttggtga tctgttccta  27780
actgttttac atctgtaaca tttctcaaat ttgcctattt tccaccattt ctcctatccc  27840
ttaattcagg ctgcttctca cctagatgac tgctgcaggt tcccttgttg tctactcatt  27900
attagtttct cattccaagt cattgattag atggctgcca aaagtgatct ctttaacttc  27960
ccaactttag attctgtgaa taaaatccaa actccttaac agagcaggcc tcatgatcc   28020 aactcctctt aacgttggta gccttatctt ttctctgagc ccactgccgc ttgatccttg  28080
gtggtgctgt gctcttcttt gctctctgtc tttggttgga ctgcccacct ccctccttct  28140
tacttgacat tataatttat cagatagaga tcagctcctc cagtcagcat ttccttactg  28200
actactccaa gtctgaccca gtgtagattc tgtgcttata tctgtcaagt cacttattgt  28260
atgataattc atacacttat atgataattc acacattggc atgtgtagat taaacattta  28320
tagtctcaga aggatcctga tagtccaaaa ggtatagtaa tgcagttgtc tcttagtatc  28380
ttcaggtgat tgattccagg atccccccca tggagatcaa aatccaggga tactcaggtg  28440
ccttatataa aatggcatat ttgcatgtaa cctatgcaca tcctcctgtg tactttatag  28500
gccctaaata atctccagat tacctatatg gctaaaacaa tgcaaatact atgtaaatag  28560
ctgttatact gtattttaa gtttgtttct tattttatgg ttttatttgt ttatttttt   28620
```

```
gatctgtgga tgtgcaaccc acagatagag agggtcaact gggccgggcg cggtggctca   28680
cacccgtaat cccagcactt tgggaggctg gggtgggagg attgcctgag gttaggagct   28740
cgagaccagc ctggccaata tggtgaaacc gtgtctctac taaaaataca aaaattagcc   28800
aggcatggtg gcaggtgcct gtaatcctag ctactctgga ggctgaggca ggacaattgc   28860
ttgaacctgg gagttgaagg ttgcagtgag ccaagatcct gccatagcac tccagcctgg   28920
gcaacagaat gagactctgt ctcaaaaaaa aaaaaaaaa aaaagaagag agggccaact   28980
gtatgtaatt tactgaagca tggattcaca ttatagatgg tccctgattt atgatggttc   29040
aacttatgat ttttatacta tgatggtggg aaagctggtg tgatatacgt attcagtaga   29100
aattgtactt ccaattttga aatttgatct tttcccaggc tagtgatatg cagtgtgaca   29160
atttctcatg gtgctgggca gaagcattga cccacacctc ccagtcagcc atgtgatcag   29220
gagggtaaat gagtatactc catggtgtac tgtgttgcca ggtgattctg ctcaactgta   29280
tgctaatgtg agtgttctga acacatttaa ggtaggctag gctaactatg gcattcggta   29340
ggtaaagtgt gttaaatgca tttcctactt aaacgatatt ttcagtttat ggtgggtata   29400
ttggaatata gccccattgt agggcaagga gcatctttat ttacccagtt gagtttagtg   29460
gcagcagaac taagttcggt ttagctgttc agtgagccaa gcctcactta gcatctaatt   29520
ctgtctttat tttctgcttt agataggcca cagctctcct gaagggatta agactttctg   29580
tgtgaaaaat ggtattcaga aggaagccag cattaattct gtttttatac atttatgaag   29640
atttgaagga atttcactgt caattctgtc ttaattgtat tctgtataat aaatcataat   29700
ggtatccaac ggctcttgaa aggtttggtt tttgtgaaca tttctttgaa tgtcaaagtt   29760
gtattagttt gtttctcaat taaactgggt gctctttgag ggcagggatt tatgggactt   29820
gtttgttttg cagttttata tctccagctg ctaatgcagt gcctggtttg tagtaggaat   29880
gagagattta ctccaataga accatactaa agatcttaca cttatggatt acagttgata   29940
gctttgtaga gtgaactggt attcccttta aatgagacga catgacctga gtataaagta   30000
taatcaacta catgactcca gcaagaatac catgtgtccc tcagatagca tagctggcag   30060
atggagttat gcacatcaac tggacattta agacagctgg agatttctta catttagatg   30120
acagtttaga ttagaaatat ttaatcttag ctgtacttaa tatattatgt agctatatga   30180
tacatcatgt atatatggta tatcatatat atcatatatt taatcacatt taatccttag   30240
ctatattttc atccccaaaa tggtatatgg atctgttttt attgtcagct ggttatttat   30300
tgttgcttat ccatggctca tgaaaatctt catgttactt gggaaatctt tcactctgcc   30360
ttttgaagga cagcccagaa ccatttcctt cttggcacat gaccttctaa cccagtgacc   30420
aaagagtatg taaaagcatg gtacacactg cttttgaaga ttacgtgtgt ctattctaga   30480
tgtgtcttat ttcttgcaga tatattgcct acaaagattt tgatatatat atatacagta   30540
gactatacta taattaat atttataccga gatattaaat atataagcat tctactagaa   30600
ctaaagttaa gaatttgaaa tagtctcatg tgagtaatta aaataacaat agcatctttt   30660
tcaagaaagt tttttttaat atggtggaga taatgacatg gaaaaaagta gttaattatt   30720
tttggtattc ccgtatttca tcagtaggtt gccatagaac ataatagtta tataatcaaa   30780
cagcagaata atttatatg aggttattg atacagaaat gtttggttca gtgtttgtct   30840
tccagttttg cagattttct tttcgatttt aaaactggag aatacattaa aaccagaaac   30900
tttcagcctc tataatgccc tcaaaactca gcaggttttg aaaatgcctc ttccttctct   30960
tctcctcccc ataatcctgc ttatttttgg cattaagtga gtcagggggtt ccaaacccaa   31020
```

-continued

```
atacgttttt caaggctatg tagtcagtgt gaatgagaga agtaaatctg ttgggtcctg    31080
tgccacactg gagtttccaa ggctggtcta aatgagttca acttcagttt ttttgtgttt    31140
ttttagagat ggagtcttgc tgtgttgctt gagctggtct tgaactcccg ggctcaagtg    31200
atcttccagc cttggcctcc caaggtgcta gaattatagg catgagccac tgtgctggcc    31260
aatttttttt ttttagaccc actgtgctac cagtttgtga tcttcacttt aactgtgaaa    31320
ggactgtcaa agattgtacg tataagattt agtttgagag ccaggcctgg tggctcatgc    31380
ctgtaatccc agcactttgg gaggctgagg cgggtggatc acgaggtcag gagatcaaga    31440
ccatcttggc taacacggtg aaaccccgtc tctactaaaa atacaaataa attggccagg    31500
cgtggtgacg ggcgcctgta gtcccagcta ctcgggaggc tgagacagga gaatggggtg    31560
aacccgggag gcggagcttg cagtgagcag agatcacgtc actgcactcc agcctgggcg    31620
acagagcgag actccttcac ccaaaaaaaa aaaaaaaaag tagtttgtct ttctctttga    31680
aactgaattc attaaacaaa agcctaaata actatactat tacttgttat ttattta       31737
```

<210> SEQ ID NO 28
<211> LENGTH: 20
<212> TYPE: DNA
<213> ORGANISM: Artificial Sequence
<220> FEATURE:
<223> OTHER INFORMATION: Antisense Compound

<400> SEQUENCE: 28
ttggtgccac agaaagagaa                                                20

<210> SEQ ID NO 29
<211> LENGTH: 20
<212> TYPE: DNA
<213> ORGANISM: Artificial Sequence
<220> FEATURE:
<223> OTHER INFORMATION: Antisense Compound

<400> SEQUENCE: 29
ggctgaatgt tggtgccaca                                                20

<210> SEQ ID NO 30
<211> LENGTH: 20
<212> TYPE: DNA
<213> ORGANISM: Artificial Sequence
<220> FEATURE:
<223> OTHER INFORMATION: Antisense Compound

<400> SEQUENCE: 30
agggccacca tcaccgcaat                                                20

<210> SEQ ID NO 31
<211> LENGTH: 20
<212> TYPE: DNA
<213> ORGANISM: Artificial Sequence
<220> FEATURE:
<223> OTHER INFORMATION: Antisense Compound

<400> SEQUENCE: 31
actagcagag aggacagggc                                                20

<210> SEQ ID NO 32
<211> LENGTH: 20
<212> TYPE: DNA
<213> ORGANISM: Artificial Sequence
<220> FEATURE:
<223> OTHER INFORMATION: Antisense Compound

<400> SEQUENCE: 32
cttaaacctt aacatgtaca                                          20

<210> SEQ ID NO 33
<211> LENGTH: 20
<212> TYPE: DNA
<213> ORGANISM: Artificial Sequence
<220> FEATURE:
<223> OTHER INFORMATION: Antisense Compound

<400> SEQUENCE: 33
acaggtggcc tggataggac                                          20

<210> SEQ ID NO 34
<211> LENGTH: 20
<212> TYPE: DNA
<213> ORGANISM: Artificial Sequence
<220> FEATURE:
<223> OTHER INFORMATION: Antisense Compound

<400> SEQUENCE: 34
gcctcacagg tggcctggat                                          20

<210> SEQ ID NO 35
<211> LENGTH: 20
<212> TYPE: DNA
<213> ORGANISM: Artificial Sequence
<220> FEATURE:
<223> OTHER INFORMATION: Antisense Compound

<400> SEQUENCE: 35
ttgatgtaat cagaatctgg                                          20

<210> SEQ ID NO 36
<211> LENGTH: 20
<212> TYPE: DNA
<213> ORGANISM: Artificial Sequence
<220> FEATURE:
<223> OTHER INFORMATION: Antisense Compound

<400> SEQUENCE: 36
cgtactgtgt agtccaccag                                          20

<210> SEQ ID NO 37
<211> LENGTH: 20
<212> TYPE: DNA
<213> ORGANISM: Artificial Sequence
<220> FEATURE:
<223> OTHER INFORMATION: Antisense Compound

<400> SEQUENCE: 37
cccacctgct ggatgcagaa                                          20

<210> SEQ ID NO 38
<211> LENGTH: 20
<212> TYPE: DNA
<213> ORGANISM: Artificial Sequence
<220> FEATURE:
<223> OTHER INFORMATION: Antisense Compound

<400> SEQUENCE: 38
ggaactgagt gatgaggcgc                                          20

<210> SEQ ID NO 39
<211> LENGTH: 20

```
<212> TYPE: DNA
<213> ORGANISM: Artificial Sequence
<220> FEATURE:
<223> OTHER INFORMATION: Antisense Compound

<400> SEQUENCE: 39
aggccttcac cttcttgagg                                               20

<210> SEQ ID NO 40
<211> LENGTH: 20
<212> TYPE: DNA
<213> ORGANISM: Artificial Sequence
<220> FEATURE:
<223> OTHER INFORMATION: Antisense Compound

<400> SEQUENCE: 40
agataatgct ccagaagggc                                               20

<210> SEQ ID NO 41
<211> LENGTH: 20
<212> TYPE: DNA
<213> ORGANISM: Artificial Sequence
<220> FEATURE:
<223> OTHER INFORMATION: Antisense Compound

<400> SEQUENCE: 41
cgcatcttgt cattctggat                                               20

<210> SEQ ID NO 42
<211> LENGTH: 20
<212> TYPE: DNA
<213> ORGANISM: Artificial Sequence
<220> FEATURE:
<223> OTHER INFORMATION: Antisense Compound

<400> SEQUENCE: 42
actggaatga tcactctgtt                                               20

<210> SEQ ID NO 43
<211> LENGTH: 20
<212> TYPE: DNA
<213> ORGANISM: Artificial Sequence
<220> FEATURE:
<223> OTHER INFORMATION: Antisense Compound

<400> SEQUENCE: 43
tggagaagag ggccctggct                                               20

<210> SEQ ID NO 44
<211> LENGTH: 20
<212> TYPE: DNA
<213> ORGANISM: Artificial Sequence
<220> FEATURE:
<223> OTHER INFORMATION: Antisense Compound

<400> SEQUENCE: 44
tccactccca gatcattcgc                                               20

<210> SEQ ID NO 45
<211> LENGTH: 20
<212> TYPE: DNA
<213> ORGANISM: Artificial Sequence
<220> FEATURE:
<223> OTHER INFORMATION: Antisense Compound

<400> SEQUENCE: 45
ggcacacttc tcctggcctc                                               20
```

<210> SEQ ID NO 46
<211> LENGTH: 20
<212> TYPE: DNA
<213> ORGANISM: Artificial Sequence
<220> FEATURE:
<223> OTHER INFORMATION: Antisense Compound

<400> SEQUENCE: 46
tactgggcac acttctcctg						20

<210> SEQ ID NO 47
<211> LENGTH: 20
<212> TYPE: DNA
<213> ORGANISM: Artificial Sequence
<220> FEATURE:
<223> OTHER INFORMATION: Antisense Compound

<400> SEQUENCE: 47
agatggccag tactgggcac						20

<210> SEQ ID NO 48
<211> LENGTH: 20
<212> TYPE: DNA
<213> ORGANISM: Artificial Sequence
<220> FEATURE:
<223> OTHER INFORMATION: Antisense Compound

<400> SEQUENCE: 48
cattcctcct ccttcttcag						20

<210> SEQ ID NO 49
<211> LENGTH: 20
<212> TYPE: DNA
<213> ORGANISM: Artificial Sequence
<220> FEATURE:
<223> OTHER INFORMATION: Antisense Compound

<400> SEQUENCE: 49
ggtgaccagg aggtctcgga						20

<210> SEQ ID NO 50
<211> LENGTH: 20
<212> TYPE: DNA
<213> ORGANISM: Artificial Sequence
<220> FEATURE:
<223> OTHER INFORMATION: Antisense Compound

<400> SEQUENCE: 50
gtgttggtga ccaggaggtc						20

<210> SEQ ID NO 51
<211> LENGTH: 20
<212> TYPE: DNA
<213> ORGANISM: Artificial Sequence
<220> FEATURE:
<223> OTHER INFORMATION: Antisense Compound

<400> SEQUENCE: 51
ttctccctgg tgttggtgac						20

<210> SEQ ID NO 52
<211> LENGTH: 20
<212> TYPE: DNA
<213> ORGANISM: Artificial Sequence
<220> FEATURE:
<223> OTHER INFORMATION: Antisense Compound

```
<400> SEQUENCE: 52
tggaagtgga actgccggat                                          20

<210> SEQ ID NO 53
<211> LENGTH: 20
<212> TYPE: DNA
<213> ORGANISM: Artificial Sequence
<220> FEATURE:
<223> OTHER INFORMATION: Antisense Compound

<400> SEQUENCE: 53
agccgcaggc tcttgacagt                                          20

<210> SEQ ID NO 54
<211> LENGTH: 20
<212> TYPE: DNA
<213> ORGANISM: Artificial Sequence
<220> FEATURE:
<223> OTHER INFORMATION: Antisense Compound

<400> SEQUENCE: 54
acttgaagtt ggcataatct                                          20

<210> SEQ ID NO 55
<211> LENGTH: 20
<212> TYPE: DNA
<213> ORGANISM: Artificial Sequence
<220> FEATURE:
<223> OTHER INFORMATION: Antisense Compound

<400> SEQUENCE: 55
ttctaaaaca gttataagat                                          20

<210> SEQ ID NO 56
<211> LENGTH: 20
<212> TYPE: DNA
<213> ORGANISM: Artificial Sequence
<220> FEATURE:
<223> OTHER INFORMATION: Antisense Compound

<400> SEQUENCE: 56
agtgctaaca catttacata                                          20

<210> SEQ ID NO 57
<211> LENGTH: 20
<212> TYPE: DNA
<213> ORGANISM: Artificial Sequence
<220> FEATURE:
<223> OTHER INFORMATION: Antisense Compound

<400> SEQUENCE: 57
agagctctga gaactttgtg                                          20

<210> SEQ ID NO 58
<211> LENGTH: 20
<212> TYPE: DNA
<213> ORGANISM: Artificial Sequence
<220> FEATURE:
<223> OTHER INFORMATION: Antisense Compound

<400> SEQUENCE: 58
acctgctccc ctgagcgtgt                                          20

<210> SEQ ID NO 59
<211> LENGTH: 20
```

```
<212> TYPE: DNA
<213> ORGANISM: Artificial Sequence
<220> FEATURE:
<223> OTHER INFORMATION: Antisense Compound

<400> SEQUENCE: 59
gtgtcatgta gagacaggtc                                               20

<210> SEQ ID NO 60
<211> LENGTH: 20
<212> TYPE: DNA
<213> ORGANISM: Artificial Sequence
<220> FEATURE:
<223> OTHER INFORMATION: Antisense Compound

<400> SEQUENCE: 60
ggaatccatg cttgttagct                                               20

<210> SEQ ID NO 61
<211> LENGTH: 20
<212> TYPE: DNA
<213> ORGANISM: Artificial Sequence
<220> FEATURE:
<223> OTHER INFORMATION: Antisense Compound

<400> SEQUENCE: 61
gaccactgcc gagcagaaca                                               20

<210> SEQ ID NO 62
<211> LENGTH: 20
<212> TYPE: DNA
<213> ORGANISM: Artificial Sequence
<220> FEATURE:
<223> OTHER INFORMATION: Antisense Compound

<400> SEQUENCE: 62
tgctgcggtg ctggaattcc                                               20

<210> SEQ ID NO 63
<211> LENGTH: 20
<212> TYPE: DNA
<213> ORGANISM: Artificial Sequence
<220> FEATURE:
<223> OTHER INFORMATION: Antisense Compound

<400> SEQUENCE: 63
acctgtacgc cctacacctg                                               20

<210> SEQ ID NO 64
<211> LENGTH: 20
<212> TYPE: DNA
<213> ORGANISM: Artificial Sequence
<220> FEATURE:
<223> OTHER INFORMATION: Antisense Compound

<400> SEQUENCE: 64
tgttgccgct tacttgaagt                                               20

<210> SEQ ID NO 65
<211> LENGTH: 20
<212> TYPE: DNA
<213> ORGANISM: Artificial Sequence
<220> FEATURE:
<223> OTHER INFORMATION: Antisense Compound

<400> SEQUENCE: 65
aatttctcgg ctgaggattt                                               20
```

<210> SEQ ID NO 66
<211> LENGTH: 20
<212> TYPE: DNA
<213> ORGANISM: Artificial Sequence
<220> FEATURE:
<223> OTHER INFORMATION: Antisense Compound

<400> SEQUENCE: 66
tgggccaaac cttggctgca                                             20

<210> SEQ ID NO 67
<211> LENGTH: 20
<212> TYPE: DNA
<213> ORGANISM: Artificial Sequence
<220> FEATURE:
<223> OTHER INFORMATION: Antisense Compound

<400> SEQUENCE: 67
gaacactcac agagtcgggc                                             20

<210> SEQ ID NO 68
<211> LENGTH: 20
<212> TYPE: DNA
<213> ORGANISM: Artificial Sequence
<220> FEATURE:
<223> OTHER INFORMATION: Antisense Compound

<400> SEQUENCE: 68
cataatatat taagtacagc                                             20

<210> SEQ ID NO 69
<211> LENGTH: 20
<212> TYPE: DNA
<213> ORGANISM: Artificial Sequence
<220> FEATURE:
<223> OTHER INFORMATION: Antisense Compound

<400> SEQUENCE: 69
gttgtgtcac ctgcaacaaa                                             20

<210> SEQ ID NO 70
<211> LENGTH: 20
<212> TYPE: DNA
<213> ORGANISM: Artificial Sequence
<220> FEATURE:
<223> OTHER INFORMATION: Antisense Compound

<400> SEQUENCE: 70
cagtacttac tagcttcttt                                             20

<210> SEQ ID NO 71
<211> LENGTH: 20
<212> TYPE: DNA
<213> ORGANISM: Artificial Sequence
<220> FEATURE:
<223> OTHER INFORMATION: Antisense Compound

<400> SEQUENCE: 71
tgaagaagtc ctagaacacc                                             20

<210> SEQ ID NO 72
<211> LENGTH: 20
<212> TYPE: DNA
<213> ORGANISM: Artificial Sequence
<220> FEATURE:
<223> OTHER INFORMATION: Antisense Compound

```
<400> SEQUENCE: 72
ccatgcttat ctggaaaata                                           20

<210> SEQ ID NO 73
<211> LENGTH: 20
<212> TYPE: DNA
<213> ORGANISM: Artificial Sequence
<220> FEATURE:
<223> OTHER INFORMATION: Antisense Compound

<400> SEQUENCE: 73
gtaggctcac cttaacatgt                                           20

<210> SEQ ID NO 74
<211> LENGTH: 20
<212> TYPE: DNA
<213> ORGANISM: Artificial Sequence
<220> FEATURE:
<223> OTHER INFORMATION: Antisense Compound

<400> SEQUENCE: 74
gacaggtcat gcacaccctg                                           20

<210> SEQ ID NO 75
<211> LENGTH: 20
<212> TYPE: DNA
<213> ORGANISM: Artificial Sequence
<220> FEATURE:
<223> OTHER INFORMATION: Antisense Compound

<400> SEQUENCE: 75
tttcttaaac ctaatgagaa                                           20

<210> SEQ ID NO 76
<211> LENGTH: 20
<212> TYPE: DNA
<213> ORGANISM: Artificial Sequence
<220> FEATURE:
<223> OTHER INFORMATION: Antisense Compound

<400> SEQUENCE: 76
aatgccttac ccacatcctc                                           20

<210> SEQ ID NO 77
<211> LENGTH: 20
<212> TYPE: DNA
<213> ORGANISM: Artificial Sequence
<220> FEATURE:
<223> OTHER INFORMATION: Antisense Compound

<400> SEQUENCE: 77
caggctggtt tcgaactcct                                           20

<210> SEQ ID NO 78
<211> LENGTH: 20
<212> TYPE: DNA
<213> ORGANISM: Artificial Sequence
<220> FEATURE:
<223> OTHER INFORMATION: Antisense Compound

<400> SEQUENCE: 78
ttaaagccaa atttcttttc                                           20

<210> SEQ ID NO 79
<211> LENGTH: 20
```

```
<212> TYPE: DNA
<213> ORGANISM: Artificial Sequence
<220> FEATURE:
<223> OTHER INFORMATION: Antisense Compound

<400> SEQUENCE: 79
gcccagcccc aaagtgcttc                                              20

<210> SEQ ID NO 80
<211> LENGTH: 20
<212> TYPE: DNA
<213> ORGANISM: Artificial Sequence
<220> FEATURE:
<223> OTHER INFORMATION: Antisense Compound

<400> SEQUENCE: 80
gttgtgtcac agagtcgggc                                              20

<210> SEQ ID NO 81
<211> LENGTH: 20
<212> TYPE: DNA
<213> ORGANISM: Artificial Sequence
<220> FEATURE:
<223> OTHER INFORMATION: Antisense Compound

<400> SEQUENCE: 81
ggtgtctcat ctgaaggagg                                              20

<210> SEQ ID NO 82
<211> LENGTH: 20
<212> TYPE: DNA
<213> ORGANISM: Artificial Sequence
<220> FEATURE:
<223> OTHER INFORMATION: Antisense Compound

<400> SEQUENCE: 82
tgaagaagtc tagcttcttt                                              20

<210> SEQ ID NO 83
<211> LENGTH: 20
<212> TYPE: DNA
<213> ORGANISM: Artificial Sequence
<220> FEATURE:
<223> OTHER INFORMATION: Antisense Compound

<400> SEQUENCE: 83
atccatgctt atcaccaggg                                              20

<210> SEQ ID NO 84
<211> LENGTH: 20
<212> TYPE: DNA
<213> ORGANISM: Artificial Sequence
<220> FEATURE:
<223> OTHER INFORMATION: Antisense Compound

<400> SEQUENCE: 84
ggctcgagcc acatccccat                                              20

<210> SEQ ID NO 85
<211> LENGTH: 20
<212> TYPE: DNA
<213> ORGANISM: Artificial Sequence
<220> FEATURE:
<223> OTHER INFORMATION: Antisense Compound

<400> SEQUENCE: 85
acaccttgat ggccagctcc                                              20
```

```
<210> SEQ ID NO 86
<211> LENGTH: 20
<212> TYPE: DNA
<213> ORGANISM: Artificial Sequence
<220> FEATURE:
<223> OTHER INFORMATION: Antisense Compound

<400> SEQUENCE: 86
agcagcacct ggatggtgag                                          20

<210> SEQ ID NO 87
<211> LENGTH: 20
<212> TYPE: DNA
<213> ORGANISM: Artificial Sequence
<220> FEATURE:
<223> OTHER INFORMATION: Antisense Compound

<400> SEQUENCE: 87
ccagtgggcc aggatcctgc                                          20

<210> SEQ ID NO 88
<211> LENGTH: 20
<212> TYPE: DNA
<213> ORGANISM: Artificial Sequence
<220> FEATURE:
<223> OTHER INFORMATION: Antisense Compound

<400> SEQUENCE: 88
gttcattgct gttcagagac                                          20

<210> SEQ ID NO 89
<211> LENGTH: 20
<212> TYPE: DNA
<213> ORGANISM: Artificial Sequence
<220> FEATURE:
<223> OTHER INFORMATION: Antisense Compound

<400> SEQUENCE: 89
cctcgcctcc atggcgaggg                                          20

<210> SEQ ID NO 90
<211> LENGTH: 20
<212> TYPE: DNA
<213> ORGANISM: Artificial Sequence
<220> FEATURE:
<223> OTHER INFORMATION: Antisense Compound

<400> SEQUENCE: 90
cccatgatat cagtggtggg                                          20

<210> SEQ ID NO 91
<211> LENGTH: 20
<212> TYPE: DNA
<213> ORGANISM: Artificial Sequence
<220> FEATURE:
<223> OTHER INFORMATION: Antisense Compound

<400> SEQUENCE: 91
ctcagggagt caaagctttt                                          20

<210> SEQ ID NO 92
<211> LENGTH: 20
<212> TYPE: DNA
<213> ORGANISM: Artificial Sequence
<220> FEATURE:
<223> OTHER INFORMATION: Antisense Compound
```

<400> SEQUENCE: 92

```
gggctccaca tcctcagtgc                                                 20
```

<210> SEQ ID NO 93
<211> LENGTH: 625
<212> TYPE: DNA
<213> ORGANISM: M. musculus

<400> SEQUENCE: 93

```
acgcgtccgg cggcgagtga ggcgctgaca gggactcgcg ggggcatctt gcacagaccc    60
ctggaccacg ccgccatcgc agcctccagc ccagtcctct ctctgccgct tctcctcgcc   120
atggaggcga ggccgccgcc gccgccgcgg ggcttcgagc agcggaccgg gcggcggccc   180
tgagggagc ggcgggccga gacgccgccg cggtcctgag gcggagctgc cgtgcgcgtc    240
ccccgcggtc ccgcccagcg ccgggctcgg tcagcatgga ttcctggttc attcttgtcc   300
tgtttggcag tggtctaata catgttagtg ccaacaatgc tactacagtt tcaccttctt   360
taggaacgac aagattaatt aaaacatcaa caacagaatt ggctaaggaa gagaataaaa   420
cctcaaattc aacctcttca gtaatttctc tgtctgtggc accaacattc aggccagacc   480
tgactctgga gcccacctat gtgactactg ttaattcttc acactctgac aatgggacca   540
ggaaggcagc cagcactgaa tctgatgca ctacccttgc ccggacggaa gcttgcttat    600
tgagaaccag tcacggatgg ccata                                         625
```

<210> SEQ ID NO 94
<211> LENGTH: 97
<212> TYPE: DNA
<213> ORGANISM: M. musculus

<400> SEQUENCE: 94

```
ttgtttgcag atgaccactc tagagtgcac ctgacacctg ttgaaggggt cccagattct    60
gattacatca acgcttcatt cattaatgta agggatc                             97
```

<210> SEQ ID NO 95
<211> LENGTH: 140
<212> TYPE: DNA
<213> ORGANISM: M. musculus

<400> SEQUENCE: 95

```
ttcattgtag tgtaaatgtg cccaatactg gccagaccaa ggctgctgga cctatgggaa    60
tgtccgtgtg tctgtcgagg atgtgactgt tctggtggac tacacagtac ggaaattctg   120
catccagcag gtacagtctt                                               140
```

<210> SEQ ID NO 96
<211> LENGTH: 156
<212> TYPE: DNA
<213> ORGANISM: M. musculus

<400> SEQUENCE: 96

```
ctggctacag tgcaggtgta gggcgcactg gcacctttgt tgtcatcgat gccatgctgg    60
acatgatgca ttcggaacgc aaagtggatg tatacgggtt tgtgagccgg atccgggccc   120
agcgctgcca gatggtacag acagacgtga gtgacc                             156
```

<210> SEQ ID NO 97
<211> LENGTH: 114
<212> TYPE: DNA
<213> ORGANISM: M. musculus

```
<400> SEQUENCE: 97
cttcattcag aaattaactt caatcaaaat ccagaatgac aagatgcgca cgggaaacct      60
tccagccaac atgaagaaga accgggtttt acagatcatt ccatgtaagt tctc           114

<210> SEQ ID NO 98
<211> LENGTH: 155
<212> TYPE: DNA
<213> ORGANISM: M. musculus

<400> SEQUENCE: 98
acccatacag ggataccggc agaaagactc ctacattgcc agccagggcc ctcttctcca     60
cacgattgag gacttctggc gaatgatctg ggagtggaag tcctgttcta tcgtaatgct    120
gacagaactg gaagagagag gccaggtgag ttcaa                              155

<210> SEQ ID NO 99
<211> LENGTH: 146
<212> TYPE: DNA
<213> ORGANISM: M. musculus

<400> SEQUENCE: 99
gttcctccag gagaagtgtg cccagtactg gccatctgat ggcctggtgt cctatggaga    60
catcacagtt gagctgaaga aggaggagga atgtgaaagc tacactgtcc gagacctcct   120
ggtcaccaac accagggtga ggtggg                                        146

<210> SEQ ID NO 100
<211> LENGTH: 172
<212> TYPE: DNA
<213> ORGANISM: M. musculus

<400> SEQUENCE: 100
tcttccaaag gagaacaaga gtcggcaaat ccggcagttc cacttccacg gctggcctga    60
ggtgggcatc cccagcgacg gcaagggcat gatcaacatc attgcagcag tgcagaagca   120
gcagcagcag tcggggaacc atcccatcac tgtgcactgc aggtacgcga cc           172

<210> SEQ ID NO 101
<211> LENGTH: 191
<212> TYPE: DNA
<213> ORGANISM: M. musculus

<400> SEQUENCE: 101
caccctcatc tccctaccaa gatcagccac ctcaggcatg gggagtaatg agaccagagc    60
ggcctctctg gcaccacagc agggatcgtc aggtaataaa cactcttgat tccctgagga   120
aatgtcggtc cctttgtctt gggcagagca gtcttatgaa gctggggctc tcctgggttg   180
ttcctagccc c                                                        191

<210> SEQ ID NO 102
<211> LENGTH: 913
<212> TYPE: DNA
<213> ORGANISM: M. musculus

<400> SEQUENCE: 102
cttcagtaat ttctctttct gtggcaccaa cattcagccc aaacctgact ctggagccca    60
cctatgtgac tactgttaat tcttcacact ctgacaatgg gaccaggagg gcagccagca   120
cggaatctgg aggcactacc atttccccga acgaagctg gcttattgag aaccagttca    180
cggatgccat aacagaaccc tgggaggga actccagcac tgcagcaacc actccagaaa   240
```

```
ccttccccc  ggcagatgag  acaccaatta  ttgcggtgat  ggtggccctg  tcctctctgc    300
tagtaatcgt  gtttattatc  atagttctgt  acatgttaag  gtttaagaaa  tacaagcaag    360
ctgggagtca  ttccaactct  ttccgcctgt  caaatggccg  cacggaggat  gtggagcccc    420
aaagtgtacc  acttctggcc  aggtccccaa  gcaccaacag  gaagtaccca  ccactgcctg    480
tggacaagct  ggaagaggag  attaaccgga  gaatggctga  tgacaataag  ctcttcagag    540
aagaattcaa  cgctctccct  gcttgtccta  tccaggccac  ctgtgaggct  gctccaggaa    600
gaaaacagga  aaaagaccgc  tatgtaaaac  atcctgccct  aagaacactc  tagagtgcac    660
ctgacacctg  ttgaggggtt  cccaaattct  gatacattca  cgcttcttct  ttagggtacc    720
ggacagaaca  atcctcgctg  ccggaccaag  aaaaaccggc  aggcttcggg  acggtcggac    780
cacccgctcc  ttgctgggcc  ccgagagaaa  ggggtggccc  aatgccacac  ggctgcacga    840
gagcggtccg  acatagggc  accagaagct  cccgggggc  acgagcagaa  cccccggagg    900
gcaagcccag  agc                                                          913

<210> SEQ ID NO 103
<211> LENGTH: 20
<212> TYPE: DNA
<213> ORGANISM: Artificial Sequence
<220> FEATURE:
<223> OTHER INFORMATION: Antisense Compound

<400> SEQUENCE: 103
caggaatcca tgctgaccga                                                     20

<210> SEQ ID NO 104
<211> LENGTH: 20
<212> TYPE: DNA
<213> ORGANISM: Artificial Sequence
<220> FEATURE:
<223> OTHER INFORMATION: Antisense Compound

<400> SEQUENCE: 104
gaatgaacca ggaatccatg                                                     20

<210> SEQ ID NO 105
<211> LENGTH: 20
<212> TYPE: DNA
<213> ORGANISM: Artificial Sequence
<220> FEATURE:
<223> OTHER INFORMATION: Antisense Compound

<400> SEQUENCE: 105
tcccctccca gggttctgtt                                                     20

<210> SEQ ID NO 106
<211> LENGTH: 20
<212> TYPE: DNA
<213> ORGANISM: Artificial Sequence
<220> FEATURE:
<223> OTHER INFORMATION: Antisense Compound

<400> SEQUENCE: 106
gtttctggag tggttgctgc                                                     20

<210> SEQ ID NO 107
<211> LENGTH: 20
<212> TYPE: DNA
<213> ORGANISM: Artificial Sequence
<220> FEATURE:
<223> OTHER INFORMATION: Antisense Compound
```

```
<400> SEQUENCE: 107
tcaccgcaat aattggtgtc                                               20

<210> SEQ ID NO 108
<211> LENGTH: 20
<212> TYPE: DNA
<213> ORGANISM: Artificial Sequence
<220> FEATURE:
<223> OTHER INFORMATION: Antisense Compound

<400> SEQUENCE: 108
aggacagggc caccatcacc                                               20

<210> SEQ ID NO 109
<211> LENGTH: 20
<212> TYPE: DNA
<213> ORGANISM: Artificial Sequence
<220> FEATURE:
<223> OTHER INFORMATION: Antisense Compound

<400> SEQUENCE: 109
gtatttctta aaccttaaca                                               20

<210> SEQ ID NO 110
<211> LENGTH: 20
<212> TYPE: DNA
<213> ORGANISM: Artificial Sequence
<220> FEATURE:
<223> OTHER INFORMATION: Antisense Compound

<400> SEQUENCE: 110
cccagcttgc ttgtatttct                                               20

<210> SEQ ID NO 111
<211> LENGTH: 20
<212> TYPE: DNA
<213> ORGANISM: Artificial Sequence
<220> FEATURE:
<223> OTHER INFORMATION: Antisense Compound

<400> SEQUENCE: 111
tcctcttcca gcttgtccac                                               20

<210> SEQ ID NO 112
<211> LENGTH: 20
<212> TYPE: DNA
<213> ORGANISM: Artificial Sequence
<220> FEATURE:
<223> OTHER INFORMATION: Antisense Compound

<400> SEQUENCE: 112
aggacaagca gggagagcgt                                               20

<210> SEQ ID NO 113
<211> LENGTH: 20
<212> TYPE: DNA
<213> ORGANISM: Artificial Sequence
<220> FEATURE:
<223> OTHER INFORMATION: Antisense Compound

<400> SEQUENCE: 113
tctttctaac aatggagtgg                                               20

<210> SEQ ID NO 114
<211> LENGTH: 20
```

```
<212> TYPE: DNA
<213> ORGANISM: Artificial Sequence
<220> FEATURE:
<223> OTHER INFORMATION: Antisense Compound

<400> SEQUENCE: 114
gagtggtcat ctgagagaca                                                   20

<210> SEQ ID NO 115
<211> LENGTH: 20
<212> TYPE: DNA
<213> ORGANISM: Artificial Sequence
<220> FEATURE:
<223> OTHER INFORMATION: Antisense Compound

<400> SEQUENCE: 115
tcttttggtc cttgtgcagc                                                   20

<210> SEQ ID NO 116
<211> LENGTH: 20
<212> TYPE: DNA
<213> ORGANISM: Artificial Sequence
<220> FEATURE:
<223> OTHER INFORMATION: Antisense Compound

<400> SEQUENCE: 116
tcccataggt ccagcagcct                                                   20

<210> SEQ ID NO 117
<211> LENGTH: 20
<212> TYPE: DNA
<213> ORGANISM: Artificial Sequence
<220> FEATURE:
<223> OTHER INFORMATION: Antisense Compound

<400> SEQUENCE: 117
cgtcgcccac ctgctggatg                                                   20

<210> SEQ ID NO 118
<211> LENGTH: 20
<212> TYPE: DNA
<213> ORGANISM: Artificial Sequence
<220> FEATURE:
<223> OTHER INFORMATION: Antisense Compound

<400> SEQUENCE: 118
tgagggttac aggccttcac                                                   20

<210> SEQ ID NO 119
<211> LENGTH: 20
<212> TYPE: DNA
<213> ORGANISM: Artificial Sequence
<220> FEATURE:
<223> OTHER INFORMATION: Antisense Compound

<400> SEQUENCE: 119
ctttgcgttc cgaatgcatc                                                   20

<210> SEQ ID NO 120
<211> LENGTH: 20
<212> TYPE: DNA
<213> ORGANISM: Artificial Sequence
<220> FEATURE:
<223> OTHER INFORMATION: Antisense Compound

<400> SEQUENCE: 120
gcccggatcc ggctcacaaa                                                   20
```

<210> SEQ ID NO 121
<211> LENGTH: 20
<212> TYPE: DNA
<213> ORGANISM: Artificial Sequence
<220> FEATURE:
<223> OTHER INFORMATION: Antisense Compound

<400> SEQUENCE: 121
aagttaattt cttaaactcc                                              20

<210> SEQ ID NO 122
<211> LENGTH: 20
<212> TYPE: DNA
<213> ORGANISM: Artificial Sequence
<220> FEATURE:
<223> OTHER INFORMATION: Antisense Compound

<400> SEQUENCE: 122
tggcaatgta ggagtctttc                                              20

<210> SEQ ID NO 123
<211> LENGTH: 20
<212> TYPE: DNA
<213> ORGANISM: Artificial Sequence
<220> FEATURE:
<223> OTHER INFORMATION: Antisense Compound

<400> SEQUENCE: 123
ccatcagatg gccagtactg                                              20

<210> SEQ ID NO 124
<211> LENGTH: 20
<212> TYPE: DNA
<213> ORGANISM: Artificial Sequence
<220> FEATURE:
<223> OTHER INFORMATION: Antisense Compound

<400> SEQUENCE: 124
atactgttcc agtgtctgga                                              20

<210> SEQ ID NO 125
<211> LENGTH: 20
<212> TYPE: DNA
<213> ORGANISM: Artificial Sequence
<220> FEATURE:
<223> OTHER INFORMATION: Antisense Compound

<400> SEQUENCE: 125
gtcacctgtc acttgaagtt                                              20

<210> SEQ ID NO 126
<211> LENGTH: 20
<212> TYPE: DNA
<213> ORGANISM: Artificial Sequence
<220> FEATURE:
<223> OTHER INFORMATION: Antisense Compound

<400> SEQUENCE: 126
aagatatata caattttggg                                              20

<210> SEQ ID NO 127
<211> LENGTH: 20
<212> TYPE: DNA
<213> ORGANISM: Artificial Sequence
<220> FEATURE:
<223> OTHER INFORMATION: Antisense Compound

```
<400> SEQUENCE: 127
tgccatttct aaaacagtta                                              20

<210> SEQ ID NO 128
<211> LENGTH: 20
<212> TYPE: DNA
<213> ORGANISM: Artificial Sequence
<220> FEATURE:
<223> OTHER INFORMATION: Antisense Compound

<400> SEQUENCE: 128
aacaggtaat agaagcctat                                              20

<210> SEQ ID NO 129
<211> LENGTH: 20
<212> TYPE: DNA
<213> ORGANISM: Artificial Sequence
<220> FEATURE:
<223> OTHER INFORMATION: Antisense Compound

<400> SEQUENCE: 129
aggactatca gtgctaacac                                              20

<210> SEQ ID NO 130
<211> LENGTH: 20
<212> TYPE: DNA
<213> ORGANISM: Artificial Sequence
<220> FEATURE:
<223> OTHER INFORMATION: Antisense Compound

<400> SEQUENCE: 130
gcaaggaaca atctggccca                                              20

<210> SEQ ID NO 131
<211> LENGTH: 20
<212> TYPE: DNA
<213> ORGANISM: Artificial Sequence
<220> FEATURE:
<223> OTHER INFORMATION: Antisense Compound

<400> SEQUENCE: 131
tcttctttag gaaaagatat                                              20

<210> SEQ ID NO 132
<211> LENGTH: 20
<212> TYPE: DNA
<213> ORGANISM: Artificial Sequence
<220> FEATURE:
<223> OTHER INFORMATION: Antisense Compound

<400> SEQUENCE: 132
aatgagtctt aggtttatct                                              20

<210> SEQ ID NO 133
<211> LENGTH: 20
<212> TYPE: DNA
<213> ORGANISM: Artificial Sequence
<220> FEATURE:
<223> OTHER INFORMATION: Antisense Compound

<400> SEQUENCE: 133
ttttagttgg cactgagcta                                              20

<210> SEQ ID NO 134
<211> LENGTH: 20
```

```
<212> TYPE: DNA
<213> ORGANISM: Artificial Sequence
<220> FEATURE:
<223> OTHER INFORMATION: Antisense Compound

<400> SEQUENCE: 134
cctcaagagc tctgagaact                                          20

<210> SEQ ID NO 135
<211> LENGTH: 20
<212> TYPE: DNA
<213> ORGANISM: Artificial Sequence
<220> FEATURE:
<223> OTHER INFORMATION: Antisense Compound

<400> SEQUENCE: 135
accatttcct caagagctct                                          20

<210> SEQ ID NO 136
<211> LENGTH: 20
<212> TYPE: DNA
<213> ORGANISM: Artificial Sequence
<220> FEATURE:
<223> OTHER INFORMATION: Antisense Compound

<400> SEQUENCE: 136
tgcctgaggt ggctgatctt                                          20

<210> SEQ ID NO 137
<211> LENGTH: 20
<212> TYPE: DNA
<213> ORGANISM: Artificial Sequence
<220> FEATURE:
<223> OTHER INFORMATION: Antisense Compound

<400> SEQUENCE: 137
ctgacgatcc ctgctgtggt                                          20

<210> SEQ ID NO 138
<211> LENGTH: 20
<212> TYPE: DNA
<213> ORGANISM: Artificial Sequence
<220> FEATURE:
<223> OTHER INFORMATION: Antisense Compound

<400> SEQUENCE: 138
aagagtgttt attacctgac                                          20

<210> SEQ ID NO 139
<211> LENGTH: 20
<212> TYPE: DNA
<213> ORGANISM: Artificial Sequence
<220> FEATURE:
<223> OTHER INFORMATION: Antisense Compound

<400> SEQUENCE: 139
atgcccccgc gagtccctgt                                          20

<210> SEQ ID NO 140
<211> LENGTH: 20
<212> TYPE: DNA
<213> ORGANISM: Artificial Sequence
<220> FEATURE:
<223> OTHER INFORMATION: Antisense Compound

<400> SEQUENCE: 140
gaagcggcag agagaggact                                          20
```

<210> SEQ ID NO 141
<211> LENGTH: 20
<212> TYPE: DNA
<213> ORGANISM: Artificial Sequence
<220> FEATURE:
<223> OTHER INFORMATION: Antisense Compound

<400> SEQUENCE: 141
agagtggtca tctgcaaaca                                               20

<210> SEQ ID NO 142
<211> LENGTH: 20
<212> TYPE: DNA
<213> ORGANISM: Artificial Sequence
<220> FEATURE:
<223> OTHER INFORMATION: Antisense Compound

<400> SEQUENCE: 142
cacatttaca ctacaatgaa                                               20

<210> SEQ ID NO 143
<211> LENGTH: 20
<212> TYPE: DNA
<213> ORGANISM: Artificial Sequence
<220> FEATURE:
<223> OTHER INFORMATION: Antisense Compound

<400> SEQUENCE: 143
tacacctgca ctgtagccag                                               20

<210> SEQ ID NO 144
<211> LENGTH: 20
<212> TYPE: DNA
<213> ORGANISM: Artificial Sequence
<220> FEATURE:
<223> OTHER INFORMATION: Antisense Compound

<400> SEQUENCE: 144
tgaagttaat ttctgaatga                                               20

<210> SEQ ID NO 145
<211> LENGTH: 20
<212> TYPE: DNA
<213> ORGANISM: Artificial Sequence
<220> FEATURE:
<223> OTHER INFORMATION: Antisense Compound

<400> SEQUENCE: 145
ttgaactcac ctggcctctc                                               20

<210> SEQ ID NO 146
<211> LENGTH: 20
<212> TYPE: DNA
<213> ORGANISM: Artificial Sequence
<220> FEATURE:
<223> OTHER INFORMATION: Antisense Compound

<400> SEQUENCE: 146
ctcaccctgg tgttggtgac                                               20

<210> SEQ ID NO 147
<211> LENGTH: 20
<212> TYPE: DNA
<213> ORGANISM: Artificial Sequence
<220> FEATURE:
<223> OTHER INFORMATION: Antisense Compound

<400> SEQUENCE: 147
tcttgttctc ctttggaaga                                              20

<210> SEQ ID NO 148
<211> LENGTH: 20
<212> TYPE: DNA
<213> ORGANISM: Artificial Sequence
<220> FEATURE:
<223> OTHER INFORMATION: Antisense Compound

<400> SEQUENCE: 148
ataagactgc tctgcccaag                                              20

<210> SEQ ID NO 149
<211> LENGTH: 20
<212> TYPE: DNA
<213> ORGANISM: Artificial Sequence
<220> FEATURE:
<223> OTHER INFORMATION: Antisense Compound

<400> SEQUENCE: 149
taggaacaac ccaggagagc                                              20

<210> SEQ ID NO 150
<211> LENGTH: 20
<212> TYPE: DNA
<213> ORGANISM: Artificial Sequence
<220> FEATURE:
<223> OTHER INFORMATION: Antisense Compound

<400> SEQUENCE: 150
tagagtgttc ttagggcagg                                              20

<210> SEQ ID NO 151
<211> LENGTH: 20
<212> TYPE: DNA
<213> ORGANISM: Artificial Sequence
<220> FEATURE:
<223> OTHER INFORMATION: Antisense Compound

<400> SEQUENCE: 151
ttctctttct gtggcaccaa                                              20

<210> SEQ ID NO 152
<211> LENGTH: 20
<212> TYPE: DNA
<213> ORGANISM: Artificial Sequence
<220> FEATURE:
<223> OTHER INFORMATION: Antisense Compound

<400> SEQUENCE: 152
tgtggcacca acattcagcc                                              20

<210> SEQ ID NO 153
<211> LENGTH: 20
<212> TYPE: DNA
<213> ORGANISM: Artificial Sequence
<220> FEATURE:
<223> OTHER INFORMATION: Antisense Compound

<400> SEQUENCE: 153
attgcggtga tggtggccct                                              20

<210> SEQ ID NO 154
<211> LENGTH: 20

```
<212> TYPE: DNA
<213> ORGANISM: Artificial Sequence
<220> FEATURE:
<223> OTHER INFORMATION: Antisense Compound

<400> SEQUENCE: 154
gccctgtcct ctctgctagt                                          20

<210> SEQ ID NO 155
<211> LENGTH: 20
<212> TYPE: DNA
<213> ORGANISM: Artificial Sequence
<220> FEATURE:
<223> OTHER INFORMATION: Antisense Compound

<400> SEQUENCE: 155
tgtacatgtt aaggtttaag                                          20

<210> SEQ ID NO 156
<211> LENGTH: 20
<212> TYPE: DNA
<213> ORGANISM: Artificial Sequence
<220> FEATURE:
<223> OTHER INFORMATION: Antisense Compound

<400> SEQUENCE: 156
gtcctatcca ggccacctgt                                          20

<210> SEQ ID NO 157
<211> LENGTH: 20
<212> TYPE: DNA
<213> ORGANISM: Artificial Sequence
<220> FEATURE:
<223> OTHER INFORMATION: Antisense Compound

<400> SEQUENCE: 157
atccaggcca cctgtgaggc                                          20

<210> SEQ ID NO 158
<211> LENGTH: 20
<212> TYPE: DNA
<213> ORGANISM: Artificial Sequence
<220> FEATURE:
<223> OTHER INFORMATION: Antisense Compound

<400> SEQUENCE: 158
ccagattctg attacatcaa                                          20

<210> SEQ ID NO 159
<211> LENGTH: 20
<212> TYPE: DNA
<213> ORGANISM: Artificial Sequence
<220> FEATURE:
<223> OTHER INFORMATION: Antisense Compound

<400> SEQUENCE: 159
ctggtggact acacagtacg                                          20

<210> SEQ ID NO 160
<211> LENGTH: 20
<212> TYPE: DNA
<213> ORGANISM: Artificial Sequence
<220> FEATURE:
<223> OTHER INFORMATION: Antisense Compound

<400> SEQUENCE: 160
ttctgcatcc agcaggtggg                                          20
```

<210> SEQ ID NO 161
<211> LENGTH: 20
<212> TYPE: DNA
<213> ORGANISM: Artificial Sequence
<220> FEATURE:
<223> OTHER INFORMATION: Antisense Compound

<400> SEQUENCE: 161
gcgcctcatc actcagttcc                                              20

<210> SEQ ID NO 162
<211> LENGTH: 20
<212> TYPE: DNA
<213> ORGANISM: Artificial Sequence
<220> FEATURE:
<223> OTHER INFORMATION: Antisense Compound

<400> SEQUENCE: 162
cctcaagaag gtgaaggcct                                              20

<210> SEQ ID NO 163
<211> LENGTH: 20
<212> TYPE: DNA
<213> ORGANISM: Artificial Sequence
<220> FEATURE:
<223> OTHER INFORMATION: Antisense Compound

<400> SEQUENCE: 163
gcccttctgg agcattatct                                              20

<210> SEQ ID NO 164
<211> LENGTH: 20
<212> TYPE: DNA
<213> ORGANISM: Artificial Sequence
<220> FEATURE:
<223> OTHER INFORMATION: Antisense Compound

<400> SEQUENCE: 164
atccagaatg acaagatgcg                                              20

<210> SEQ ID NO 165
<211> LENGTH: 20
<212> TYPE: DNA
<213> ORGANISM: Artificial Sequence
<220> FEATURE:
<223> OTHER INFORMATION: Antisense Compound

<400> SEQUENCE: 165
aacagagtga tcattccagt                                              20

<210> SEQ ID NO 166
<211> LENGTH: 20
<212> TYPE: DNA
<213> ORGANISM: Artificial Sequence
<220> FEATURE:
<223> OTHER INFORMATION: Antisense Compound

<400> SEQUENCE: 166
agccagggcc ctcttctcca                                              20

<210> SEQ ID NO 167
<211> LENGTH: 20
<212> TYPE: DNA
<213> ORGANISM: Artificial Sequence
<220> FEATURE:
<223> OTHER INFORMATION: Antisense Compound

```
<400> SEQUENCE: 167
gcgaatgatc tgggagtgga                                               20

<210> SEQ ID NO 168
<211> LENGTH: 20
<212> TYPE: DNA
<213> ORGANISM: Artificial Sequence
<220> FEATURE:
<223> OTHER INFORMATION: Antisense Compound

<400> SEQUENCE: 168
gaggccagga gaagtgtgcc                                               20

<210> SEQ ID NO 169
<211> LENGTH: 20
<212> TYPE: DNA
<213> ORGANISM: Artificial Sequence
<220> FEATURE:
<223> OTHER INFORMATION: Antisense Compound

<400> SEQUENCE: 169
caggagaagt gtgcccagta                                               20

<210> SEQ ID NO 170
<211> LENGTH: 20
<212> TYPE: DNA
<213> ORGANISM: Artificial Sequence
<220> FEATURE:
<223> OTHER INFORMATION: Antisense Compound

<400> SEQUENCE: 170
gtgcccagta ctggccatct                                               20

<210> SEQ ID NO 171
<211> LENGTH: 20
<212> TYPE: DNA
<213> ORGANISM: Artificial Sequence
<220> FEATURE:
<223> OTHER INFORMATION: Antisense Compound

<400> SEQUENCE: 171
ctgaagaagg aggaggaatg                                               20

<210> SEQ ID NO 172
<211> LENGTH: 20
<212> TYPE: DNA
<213> ORGANISM: Artificial Sequence
<220> FEATURE:
<223> OTHER INFORMATION: Antisense Compound

<400> SEQUENCE: 172
tccgagacct cctggtcacc                                               20

<210> SEQ ID NO 173
<211> LENGTH: 20
<212> TYPE: DNA
<213> ORGANISM: Artificial Sequence
<220> FEATURE:
<223> OTHER INFORMATION: Antisense Compound

<400> SEQUENCE: 173
gacctcctgg tcaccaacac                                               20

<210> SEQ ID NO 174
<211> LENGTH: 20
```

```
<212> TYPE: DNA
<213> ORGANISM: Artificial Sequence
<220> FEATURE:
<223> OTHER INFORMATION: Antisense Compound

<400> SEQUENCE: 174
gtcaccaaca ccagggagaa                                              20

<210> SEQ ID NO 175
<211> LENGTH: 20
<212> TYPE: DNA
<213> ORGANISM: Artificial Sequence
<220> FEATURE:
<223> OTHER INFORMATION: Antisense Compound

<400> SEQUENCE: 175
atccggcagt tccacttcca                                              20

<210> SEQ ID NO 176
<211> LENGTH: 20
<212> TYPE: DNA
<213> ORGANISM: Artificial Sequence
<220> FEATURE:
<223> OTHER INFORMATION: Antisense Compound

<400> SEQUENCE: 176
actgtcaaga gcctgcggct                                              20

<210> SEQ ID NO 177
<211> LENGTH: 20
<212> TYPE: DNA
<213> ORGANISM: Artificial Sequence
<220> FEATURE:
<223> OTHER INFORMATION: Antisense Compound

<400> SEQUENCE: 177
agattatgcc aacttcaagt                                              20

<210> SEQ ID NO 178
<211> LENGTH: 20
<212> TYPE: DNA
<213> ORGANISM: Artificial Sequence
<220> FEATURE:
<223> OTHER INFORMATION: Antisense Compound

<400> SEQUENCE: 178
atcttataac tgttttagaa                                              20

<210> SEQ ID NO 179
<211> LENGTH: 20
<212> TYPE: DNA
<213> ORGANISM: Artificial Sequence
<220> FEATURE:
<223> OTHER INFORMATION: Antisense Compound

<400> SEQUENCE: 179
cacaaagttc tcagagctct                                              20

<210> SEQ ID NO 180
<211> LENGTH: 20
<212> TYPE: DNA
<213> ORGANISM: Artificial Sequence
<220> FEATURE:
<223> OTHER INFORMATION: Antisense Compound

<400> SEQUENCE: 180
agctaacaag catggattcc                                              20
```

<210> SEQ ID NO 181
<211> LENGTH: 20
<212> TYPE: DNA
<213> ORGANISM: Artificial Sequence
<220> FEATURE:
<223> OTHER INFORMATION: Antisense Compound

<400> SEQUENCE: 181
tgttctgctc ggcagtggtc                                            20

<210> SEQ ID NO 182
<211> LENGTH: 20
<212> TYPE: DNA
<213> ORGANISM: Artificial Sequence
<220> FEATURE:
<223> OTHER INFORMATION: Antisense Compound

<400> SEQUENCE: 182
ggaattccag caccgcagca                                            20

<210> SEQ ID NO 183
<211> LENGTH: 20
<212> TYPE: DNA
<213> ORGANISM: Artificial Sequence
<220> FEATURE:
<223> OTHER INFORMATION: Antisense Compound

<400> SEQUENCE: 183
caggtgtagg gcgtacaggt                                            20

<210> SEQ ID NO 184
<211> LENGTH: 20
<212> TYPE: DNA
<213> ORGANISM: Artificial Sequence
<220> FEATURE:
<223> OTHER INFORMATION: Antisense Compound

<400> SEQUENCE: 184
acttcaagta agcggcaaca                                            20

<210> SEQ ID NO 185
<211> LENGTH: 20
<212> TYPE: DNA
<213> ORGANISM: Artificial Sequence
<220> FEATURE:
<223> OTHER INFORMATION: Antisense Compound

<400> SEQUENCE: 185
aaatcctcag ccgagaaatt                                            20

<210> SEQ ID NO 186
<211> LENGTH: 20
<212> TYPE: DNA
<213> ORGANISM: Artificial Sequence
<220> FEATURE:
<223> OTHER INFORMATION: Antisense Compound

<400> SEQUENCE: 186
gcccgactct gtgagtgttc                                            20

<210> SEQ ID NO 187
<211> LENGTH: 20
<212> TYPE: DNA
<213> ORGANISM: Artificial Sequence
<220> FEATURE:
<223> OTHER INFORMATION: Antisense Compound

```
<400> SEQUENCE: 187
tttgttgcag gtgacacaac                                               20

<210> SEQ ID NO 188
<211> LENGTH: 20
<212> TYPE: DNA
<213> ORGANISM: Artificial Sequence
<220> FEATURE:
<223> OTHER INFORMATION: Antisense Compound

<400> SEQUENCE: 188
aaagaagcta gtaagtactg                                               20

<210> SEQ ID NO 189
<211> LENGTH: 20
<212> TYPE: DNA
<213> ORGANISM: Artificial Sequence
<220> FEATURE:
<223> OTHER INFORMATION: Antisense Compound

<400> SEQUENCE: 189
ggtgttctag gacttcttca                                               20

<210> SEQ ID NO 190
<211> LENGTH: 20
<212> TYPE: DNA
<213> ORGANISM: Artificial Sequence
<220> FEATURE:
<223> OTHER INFORMATION: Antisense Compound

<400> SEQUENCE: 190
tattttccag ataagcatgg                                               20

<210> SEQ ID NO 191
<211> LENGTH: 20
<212> TYPE: DNA
<213> ORGANISM: Artificial Sequence
<220> FEATURE:
<223> OTHER INFORMATION: Antisense Compound

<400> SEQUENCE: 191
acatgttaag gtgagcctac                                               20

<210> SEQ ID NO 192
<211> LENGTH: 20
<212> TYPE: DNA
<213> ORGANISM: Artificial Sequence
<220> FEATURE:
<223> OTHER INFORMATION: Antisense Compound

<400> SEQUENCE: 192
cagggtgtgc atgacctgtc                                               20

<210> SEQ ID NO 193
<211> LENGTH: 20
<212> TYPE: DNA
<213> ORGANISM: Artificial Sequence
<220> FEATURE:
<223> OTHER INFORMATION: Antisense Compound

<400> SEQUENCE: 193
ttctcattag gtttaagaaa                                               20

<210> SEQ ID NO 194
<211> LENGTH: 20
```

```
<212> TYPE: DNA
<213> ORGANISM: Artificial Sequence
<220> FEATURE:
<223> OTHER INFORMATION: Antisense Compound

<400> SEQUENCE: 194
gaggatgtgg gtaaggcatt                                              20

<210> SEQ ID NO 195
<211> LENGTH: 20
<212> TYPE: DNA
<213> ORGANISM: Artificial Sequence
<220> FEATURE:
<223> OTHER INFORMATION: Antisense Compound

<400> SEQUENCE: 195
aggagttcga aaccagcctg                                              20

<210> SEQ ID NO 196
<211> LENGTH: 20
<212> TYPE: DNA
<213> ORGANISM: Artificial Sequence
<220> FEATURE:
<223> OTHER INFORMATION: Antisense Compound

<400> SEQUENCE: 196
gaaaagaaat ttggctttaa                                              20

<210> SEQ ID NO 197
<211> LENGTH: 20
<212> TYPE: DNA
<213> ORGANISM: Artificial Sequence
<220> FEATURE:
<223> OTHER INFORMATION: Antisense Compound

<400> SEQUENCE: 197
gaagcacttt ggggctgggc                                              20

<210> SEQ ID NO 198
<211> LENGTH: 20
<212> TYPE: DNA
<213> ORGANISM: Artificial Sequence
<220> FEATURE:
<223> OTHER INFORMATION: Antisense Compound

<400> SEQUENCE: 198
cctccttcag atgagacacc                                              20

<210> SEQ ID NO 199
<211> LENGTH: 20
<212> TYPE: DNA
<213> ORGANISM: Artificial Sequence
<220> FEATURE:
<223> OTHER INFORMATION: Antisense Compound

<400> SEQUENCE: 199
cccaccactg atatcatggg                                              20

<210> SEQ ID NO 200
<211> LENGTH: 20
<212> TYPE: DNA
<213> ORGANISM: Artificial Sequence
<220> FEATURE:
<223> OTHER INFORMATION: Antisense Compound

<400> SEQUENCE: 200
gcactgagga tgtggagccc                                              20
```

<210> SEQ ID NO 201
<211> LENGTH: 20
<212> TYPE: DNA
<213> ORGANISM: Artificial Sequence
<220> FEATURE:
<223> OTHER INFORMATION: Antisense Compound

<400> SEQUENCE: 201
tcggtcagca tggattcctg                                              20

<210> SEQ ID NO 202
<211> LENGTH: 20
<212> TYPE: DNA
<213> ORGANISM: Artificial Sequence
<220> FEATURE:
<223> OTHER INFORMATION: Antisense Compound

<400> SEQUENCE: 202
gcagcaacca ctccagaaac                                              20

<210> SEQ ID NO 203
<211> LENGTH: 20
<212> TYPE: DNA
<213> ORGANISM: Artificial Sequence
<220> FEATURE:
<223> OTHER INFORMATION: Antisense Compound

<400> SEQUENCE: 203
ggtgatggtg gccctgtcct                                              20

<210> SEQ ID NO 204
<211> LENGTH: 20
<212> TYPE: DNA
<213> ORGANISM: Artificial Sequence
<220> FEATURE:
<223> OTHER INFORMATION: Antisense Compound

<400> SEQUENCE: 204
agaaatacaa gcaagctggg                                              20

<210> SEQ ID NO 205
<211> LENGTH: 20
<212> TYPE: DNA
<213> ORGANISM: Artificial Sequence
<220> FEATURE:
<223> OTHER INFORMATION: Antisense Compound

<400> SEQUENCE: 205
gtggacaagc tggaagagga                                              20

<210> SEQ ID NO 206
<211> LENGTH: 20
<212> TYPE: DNA
<213> ORGANISM: Artificial Sequence
<220> FEATURE:
<223> OTHER INFORMATION: Antisense Compound

<400> SEQUENCE: 206
acgctctccc tgcttgtcct                                              20

<210> SEQ ID NO 207
<211> LENGTH: 20
<212> TYPE: DNA
<213> ORGANISM: Artificial Sequence
<220> FEATURE:
<223> OTHER INFORMATION: Antisense Compound

```
<400> SEQUENCE: 207
aggctgctgg acctatggga                                        20

<210> SEQ ID NO 208
<211> LENGTH: 20
<212> TYPE: DNA
<213> ORGANISM: Artificial Sequence
<220> FEATURE:
<223> OTHER INFORMATION: Antisense Compound

<400> SEQUENCE: 208
catccagcag gtgggcgacg                                        20

<210> SEQ ID NO 209
<211> LENGTH: 20
<212> TYPE: DNA
<213> ORGANISM: Artificial Sequence
<220> FEATURE:
<223> OTHER INFORMATION: Antisense Compound

<400> SEQUENCE: 209
gtgaaggcct gtaaccctca                                        20

<210> SEQ ID NO 210
<211> LENGTH: 20
<212> TYPE: DNA
<213> ORGANISM: Artificial Sequence
<220> FEATURE:
<223> OTHER INFORMATION: Antisense Compound

<400> SEQUENCE: 210
gatgcattcg gaacgcaaag                                        20

<210> SEQ ID NO 211
<211> LENGTH: 20
<212> TYPE: DNA
<213> ORGANISM: Artificial Sequence
<220> FEATURE:
<223> OTHER INFORMATION: Antisense Compound

<400> SEQUENCE: 211
gaaagactcc tacattgcca                                        20

<210> SEQ ID NO 212
<211> LENGTH: 20
<212> TYPE: DNA
<213> ORGANISM: Artificial Sequence
<220> FEATURE:
<223> OTHER INFORMATION: Antisense Compound

<400> SEQUENCE: 212
aacttcaagt gacaggtgac                                        20

<210> SEQ ID NO 213
<211> LENGTH: 20
<212> TYPE: DNA
<213> ORGANISM: Artificial Sequence
<220> FEATURE:
<223> OTHER INFORMATION: Antisense Compound

<400> SEQUENCE: 213
taactgtttt agaaatggca                                        20

<210> SEQ ID NO 214
<211> LENGTH: 20
```

```
<212> TYPE: DNA
<213> ORGANISM: Artificial Sequence
<220> FEATURE:
<223> OTHER INFORMATION: Antisense Compound

<400> SEQUENCE: 214
ataggcttct attacctgtt                                           20

<210> SEQ ID NO 215
<211> LENGTH: 20
<212> TYPE: DNA
<213> ORGANISM: Artificial Sequence
<220> FEATURE:
<223> OTHER INFORMATION: Antisense Compound

<400> SEQUENCE: 215
gtgttagcac tgatagtcct                                           20

<210> SEQ ID NO 216
<211> LENGTH: 20
<212> TYPE: DNA
<213> ORGANISM: Artificial Sequence
<220> FEATURE:
<223> OTHER INFORMATION: Antisense Compound

<400> SEQUENCE: 216
tgggccagat tgttccttgc                                           20

<210> SEQ ID NO 217
<211> LENGTH: 20
<212> TYPE: DNA
<213> ORGANISM: Artificial Sequence
<220> FEATURE:
<223> OTHER INFORMATION: Antisense Compound

<400> SEQUENCE: 217
agttctcaga gctcttgagg                                           20

<210> SEQ ID NO 218
<211> LENGTH: 20
<212> TYPE: DNA
<213> ORGANISM: Artificial Sequence
<220> FEATURE:
<223> OTHER INFORMATION: Antisense Compound

<400> SEQUENCE: 218
agagctcttg aggaaatggt                                           20

<210> SEQ ID NO 219
<211> LENGTH: 20
<212> TYPE: DNA
<213> ORGANISM: Artificial Sequence
<220> FEATURE:
<223> OTHER INFORMATION: Antisense Compound

<400> SEQUENCE: 219
aagatcagcc acctcaggca                                           20

<210> SEQ ID NO 220
<211> LENGTH: 20
<212> TYPE: DNA
<213> ORGANISM: Artificial Sequence
<220> FEATURE:
<223> OTHER INFORMATION: Antisense Compound

<400> SEQUENCE: 220
accacagcag ggatcgtcag                                           20
```

<210> SEQ ID NO 221
<211> LENGTH: 20
<212> TYPE: DNA
<213> ORGANISM: Artificial Sequence
<220> FEATURE:
<223> OTHER INFORMATION: Antisense Compound

<400> SEQUENCE: 221
acagggactc gcggggcat                                                   20

<210> SEQ ID NO 222
<211> LENGTH: 20
<212> TYPE: DNA
<213> ORGANISM: Artificial Sequence
<220> FEATURE:
<223> OTHER INFORMATION: Antisense Compound

<400> SEQUENCE: 222
gagaggccag gtgagttcaa                                                  20

<210> SEQ ID NO 223
<211> LENGTH: 20
<212> TYPE: DNA
<213> ORGANISM: Artificial Sequence
<220> FEATURE:
<223> OTHER INFORMATION: Antisense Compound

<400> SEQUENCE: 223
cttgggcaga gcagtcttat                                                  20

<210> SEQ ID NO 224
<211> LENGTH: 20
<212> TYPE: DNA
<213> ORGANISM: Artificial Sequence
<220> FEATURE:
<223> OTHER INFORMATION: Antisense Compound

<400> SEQUENCE: 224
gctctcctgg gttgttccta                                                  20

<210> SEQ ID NO 225
<211> LENGTH: 3643
<212> TYPE: DNA
<213> ORGANISM: H. sapiens

<400> SEQUENCE: 225
ggagtatgag tcacgctcag gggagcaggt acccttctc ctaaagatga agaggagcaa        60
actggcacta agcaaggcca tcgagagcgg ggacactgac ctggtgttca cggtgttgct      120
gcacctgaag aacgagctga accgaggaga ttttttcatg acccttcgga atcagcccat      180
ggccctcagt ttgtaccgac agttctgtaa gcatcaggag ctagacgc tgaaggacct       240 ttacaatcag gatgacaatc accaggaatt gggcagcttc cacatccgag ccagctatgc      300
tgcagaagag cgtattgagg ggcgagtagc agctctgcag acagccgccg atgccttcta      360
caaggccaag aatgagtttg cagccaaggc tacagaggat caaatgcggc tcctacggct      420
gcagcggcgc ctagaagacg agctgggggg ccagttccta gacctgtctc tacatgacac      480
agttaccacc ctcattcttg gcggtcacaa caagcgtgca gagcagctgg cacgtgactt      540
ccgcatccct gacaagaggt gacacaacta aaaaaaaaca aaggtattta tggaattcca      600
ctgagtggta atggatgatg cagttcaaat aactaaggac acatgttcaa agagcataat      660
taacttttta aaagaagcta ataagcatgg attcctggtt cattcttgtt ctgctcggca      720

```
gtggtctgat atgtgtcagt gccaacaatg ctaccacagt tgcaccttct gtaggaatta    780
caagattaat taactcatca acggcagaac cagttaaaga agaggccaaa acttcaaatc    840
caacttcttc actaacttct ctttctgtgg caccaacatt cagcccaaat ataactctgg    900
gacccaccta tttaaccact gtcaattctt cagactctga caatgggacc acaagaacag    960
caagcaccaa ttctataggc attacaattt caccaaatgg aacgtggctt ccagataacc   1020
agttcacgga tgccagaaca gaaccctggg aggggaattc cagcaccgca gcaaccactc   1080
cagaaacttt ccctccttca ggtaattctg actcgaagga cagaagagat gagacaccaa   1140
ttattgcggt gatggtggcc ctgtcctctc tgctagtgat cgtgtttatt atcatagttt   1200
tgtacatgtt aaggtttaag aaatacaagc aagctgggag ccattccaat tctttccgct   1260
tatccaacgg ccgcactgag gatgtggagc cccagagtgt gccacttctg ccagatccc    1320 caagcaccaa caggaaatac ccaccccctgc ccgtggacaa gctggaagag gaaattaacc   1380
ggagaatggc agacgacaat aagctcttca gggaggaatt caacgctctc cctgcatgtc   1440
ctatccaggc cacctgtgag gctgcttcca aggaggaaaa caaggaaaaa aatcgatatg   1500
taaacatctt gccttatgac cactctagag tccacctgac accggttgaa ggggttccag   1560
attctgatta catcaatgct tcattcatca acggttacca agaaaagaac aaattcattg   1620
ctgcacaagg accaaagaa gaaacggtga atgatttctg gcggatgatc tgggaacaaa    1680
acacagccac catcgtcatg gttaccaacc tgaaggagag aaaggagtgc aagtgcgccc   1740
agtactggcc agaccaaggc tgctggacct atgggaatat tcgggtgtct gtagaggatg   1800
tgactgtcct ggtggactac acagtacgga agttctgcat ccagcaggtg ggcgacatga   1860
ccaacagaaa gccacagcgc ctcatcactc agttccactt taccagctgg ccagactttg   1920
gggtgccttt taccccgatc ggcatgctca agttcctcaa gaaggtgaag gcctgtaacc   1980
ctcagtatgc aggggccatc gtggtccact gcagtgcagg tgtagggcgt acaggtacct   2040
ttgtcgtcat tgatgccatg ctggacatga tgcatacaga acggaaggtg gacgtgtatg   2100
gctttgtgag ccggatccgg gcacagcgct gccagatggt gcaaaccgat atgcagtatg   2160
tcttcatata ccaagcccctt ctggagcatt atctctatgg agatacagaa ctggaagtga   2220
cctctctaga aacccacctg cagaaaattt acaacaaaat cccagggacc agcaacaatg   2280
gattagagga ggagtttaag aagttaacat caatcaaaat ccagaatgac aagatgcgga   2340
ctggaaacct tccagccaac atgaagaaga accgtgtttt acagatcatt ccatatgaat   2400
tcaacagagt gatcattcca gttaagcggg gcgaagagaa tacagactat gtgaacgcat   2460
cctttattga tggctaccgg cagaaggact cctatatcgc cagccagggc cctcttctcc   2520
acacaattga ggacttctgg cgaatgatct gggagtggaa atcctgctct atcgtgatgc   2580
taacagaact ggaggagaga ggccaggaga agtgtgccca gtactggcca tctgatggac   2640
tggtgtccta tggagatatt acagtggaac tgaagaagga ggaggaatgt gagagctaca   2700
ccgtccgaga cctcctggtc accaacacca gggagaataa gagccggcag atccggcagt   2760
tccacttcca tggctggcct gaagtgggca tccccagtga cggaaagggc atgatcagca   2820
tcatcgccgc cgtgcagaag cagcagcagc agtcagggaa ccaccccatc accgtgcact   2880
gcagcgccgg ggcaggaagg acggggacct tctgtgccct gagcaccgtc ctggagcgtg   2940
tgaaagcaga ggggattttg gatgtcttcc agactgtcaa gagcctgcgg ctacagaggc   3000
cacacatggt ccagacactg gaacagtatg agttctgcta caaggtggtg caggagtata   3060
ttgatgcatt ctcagattat gccaacttca gtaagcggc aacaagggtc cgtggaccag   3120
```

```
gaggattgcc tttaatattt tgtaatattc tgttttgtta atatacccca aattgtgtat    3180
atatcttata actgttttag aaattggtac ataggcttct attacctatt aggtggaaat    3240
tttatatgta aatgtgttag cactgatagt ccttttttcca atgttttatt ggggaattaa   3300
atagtgtgat gtttggattg atatcgtgaa atcctcagcc gagaaattgg gctggattgt    3360
gctttggtta atacatcttt ccctaaagaa gataaacaca aaatccattc caggtagctc    3420
ggcaccaact aagaaaaaaa gcacaaagtt ctcagagctc tcgaggaaag tggttgtccc    3480
cgtaccacca tgcactgtaa atatccctcc cctctctccc tggtcccctc ccccatcccc    3540
accactgata tcatggggag taataggacc agagcggtat ctctggcacc acactaggga   3600
ctatcaggta ataaaagctt tgactccctg aaaaaaaaaa aaa                      3643
```

<210> SEQ ID NO 226
<211> LENGTH: 3279
<212> TYPE: DNA
<213> ORGANISM: H. sapiens

<400> SEQUENCE: 226

```
gcgctcggac cccggccgct gccgccatca ctgtcgcccg cccagtcgcc cctcagccgc     60
ttcccctcgc catggaggcg aggccgccgc cgccgccgcg gggctcggag ccgcgggccg    120
ggcggcggcc ctgagggcta gtggcggccc gaaacgccgc cgcggagccg aggcggagcc    180
gctgtcctcg tccccagcgg tcccgcccaa cgcccgactc tgtgacacaa ctaaaaaaaa    240
acaaaggtat ttatggaatt ccactgagtg gtaatggatg atgcagttca ataactaag     300 gacacatgtt caaagagcat aattaacttt ttaaaagaag ctaataagca tggattcctg    360
gttcattctt gttctgctcg gcagtggtct gatatgtgtc agtgccaaca atgctaccac    420
agttgcacct tctgtaggaa ttacaagatt aattaactca tcaacggcag aaccagttaa    480
agaagaggcc aaaacttcaa atccaacttc ttcactaact tctctttctg tggcaccaac    540
attcagccca aatataactc tgggacccac ctatttaacc actgtcaatt cttcagactc    600
tgacaatggg accacaagaa cagcaagcac caattctata ggcattacaa tttcaccaaa    660
tggaacgtgg cttccagata accagttcac ggatgccaga acagaaccct gggagggaa     720 ttccagcacc gcagcaacca ctccagaaac tttccctcct tcagatgaga caccaattat    780
tgcggtgatg gtggccctgt cctctctgct agtgatcgtg tttattatca gtttttgta    840 catgttaagg tttaagaaat acaagcaagc tgggagccat tccaattctt tccgcttatc    900
caacggccgc actgaggatg tggagcccca gagtgtgcca cttctggcca gatccccaag    960
caccaacagg aaatacccac ccctgcccgt ggacaagctg gaagaggaaa ttaaccggag   1020
aatggcagac gacaataagc tcttcaggga ggaattcaac gctctccctg catgtcctat   1080
ccaggccacc tgtgaggctg cttccaagga ggaaaacaag gaaaaaaatc gatatgtaaa   1140
catcttgcct tatgaccact ctagagtcca cctgacaccg gttgaagggg ttccagattc   1200 tgattcatc aatgcttcat tcatcaacgg ttaccaagaa aagaacaaat tcattgctgc    1260
acaaggacca aaagaagaaa cggtgaatga tttctggcgg atgatctggg aacaaaacac   1320
agccaccatc gtcatggtta ccaacctgaa ggagagaaag gagtgcaagt gcgcccagta   1380
ctggccagac caaggctgct ggaccatatgg gaatattcgg gtgtctgtag aggatgtgac   1440
tgtcctggtg gactacacag tacggaagtt ctgcatccag caggtgggcg acatgaccaa   1500
cagaaagcca cagcgcctca tcactcagtt ccacttcacc agctggcag actttgggt    1560 gccttttacc ccgatcggca tgctcaagtt cctcaagaag gtgaaggcct gtaaccctca   1620
```

```
gtatgcaggg gccatcgtgg tccactgcag tgcaggtgta gggcgtacag gtacctttgt   1680
cgtcattgat gccatgctgg acatgatgca tacagaacgg aaggtggacg tgtatggctt   1740
tgtgagccgg atccgggcac agcgctgcca gatggtgcaa accgatatgc agtatgtctt   1800
catataccaa gcccttctgg agcattatct ctatggagat acagaactgg aagtgacctc   1860
tctagaaacc cacctgcaga aaatttacaa caaaatccca gggaccagca acaatggatt   1920
agaggaggag tttaagaagt taacatcaat caaaatccag aatgacaaga tgcggactgg   1980
aaaccttcca gccaacatga agaagaaccg tgttttacag atcattccat atgaattcaa   2040
cagagtgatc attccagtta gcggggcga agagaataca gactatgtga acgcatcctt   2100
tattgatggc taccggcaga aggactccta tatcgccagc cagggccctc ttctccacac   2160
aattgaggac ttctggcgaa tgatctggga gtggaaatcc tgctctatcg tgatgctaac   2220
agaactggag gagagaggcc aggagaagtg tgcccagtac tggccatctg atggactggt   2280
gtcctatgga gatattacag tggaactgaa gaaggaggag gaatgtgaga gctacaccgt   2340
ccgagacctc ctggtcacca acaccaggga gaataagagc cggcagatcc ggcagttcca   2400
cttccatggc tggcctgaag tgggcatccc cagtgacgaa aagggcatga tcagcatcat   2460
cgccgccgtg cagaagcagc agcagcagtc agggaaccac ccatcaccg tgcactgcag   2520 cgccggggca ggaaggacgg ggaccttctg tgccctgagc accgtcctgg agcgtgtgaa   2580
agcagagggg attttggatg tcttccagac tgtcaagagc ctgcggctac agaggccaca   2640
catggtccag acactggaac agtatgagtt ctgctacaag gtggtgcagg agtatattga   2700
tgcattctca gattatgcca acttcaagta agcggcaaca agggtccgtg gaccaggagg   2760
attgccttta atattttgta atattctgtt ttgttaatat accccaaatt gtgtatatat   2820
cttataactg tttagaaat tggtacatag gcttctatta cctattaggt ggaaattta    2880 tatgtaaatg tgttagcact gatagtcctt tttccaatgt tttattgggg aattaaatag   2940
tgtgatgttt ggattgatat cgtgaaatcc tcagccgaga aattgggctg gattgtgctt   3000
tggttaatac atctttccct aaagaagata aacacaaaat ccattccagg tagctcggca   3060
ccaactaaga aaaaagcac aaagttctca gagctctcga ggaaagtggt tgtccccgta    3120
ccaccatgca ctgtaaatat ccctcccctc tctccctggt cccctccccc atccccacca   3180
ctgatatcat ggggagtaat aggaccagag cggtatctct ggcaccacac tagggactat   3240
caggtaataa aagctttgac tccctgaaaa aaaaaaaaa                          3279
```

<210> SEQ ID NO 227
<211> LENGTH: 2430
<212> TYPE: DNA
<213> ORGANISM: H. sapiens

<400> SEQUENCE: 227

```
taattaactt tttaaaagaa gctaataagc atggattcct ggttcattct tgttctgctc    60
ggcagtggtc tgatatgtgt cagtgccaac aatgctacca cagttgcacc ttctgtagga   120
attacaagat taattaactc atcaacggca gaaccagtta agaagaggc caaaacttca    180 aatccaactt cttcactaac ttctctttct gtggcaccaa cattcagccc aaatataact   240
ctgggaccca cctatttaac cactgtcaat tcttcagact ctgacaatgg accacaagaa   300
acagcaagca ccaattctat aggcattaca atttcaccaa atggaacgtg gcttccagat   360
aaccagttca cggatgccag aacagaaccc tgggagggga ttccagcac cgcagcaacc   420 actccagaaa ctttccctcc ttcagatgag acaccaatta ttgcggtgat ggtggccctg   480
```

```
tcctctctgc tagtgatcgt gtttattatc atagttttgt acatgttaag gtttaagaaa      540
tacaagcaag ctgggagcca ttccaattct ttccgcttat ccaacggccg cactgaggat      600
gtggagcccc agagtgtgcc acttctggcc agatccccaa gcaccaacag gaaatacccca     660 cccctgcccg tggacaagct ggaagaggaa attaaccgga gaatggcaga cgacaataag      720
ctcttcaggg aggaattcaa cgctctccct gcatgtccta tccaggccac ctgtgaggct      780
gcttccaagg aggaaaacaa ggaaaaaaat cgatatgtaa acatcttgcc ttatgaccac      840
tctagagtcc acctgacacc ggttgaaggg gttccagatt ctgattacat caatgcttca      900
ttcatcaacg gttaccaaga aaagaacaaa ttcattgctg cacaaggacc aaaagaagaa      960
acggtgaatg atttctggcg gatgatctgg aacaaaaaca cagccaccat cgtcatggtt     1020
accaacctga aggagagaaa ggagtgcaag tgcgcccagt actggccaga ccaaggctgc     1080
tggacctatg ggaatattcg ggtgtctgta gaggatgtga ctgtcctggt ggactacaca     1140
gtacggaagt tctgcatcca gcaggtgggc gacatgacca cagaaagcc acagcgcctc      1200 atcactcagt tccactttac cagctggcca gactttgggg tgccttttac cccgatcggc     1260
atgctcaagt tcctcaagaa ggtgaaggcc tgtaaccctc agtatgcagg ggccatcgtg     1320
gtccactgca gtgcaggtgt agggcgtaca ggtacctttg tcgtcattga tgccatgctg     1380
gacatgatgc atacagaacg gaaggtggac gtgtatggct ttgtgagccg gatccgggca     1440
cagcgctgcc agatggtgca aaccgatatg cagtatgtct tcatatacca gcccttctg      1500 gagcattatc tctatggaga tacagaactg gaagtgacct ctctagaaac ccacctgcag     1560
aaaatttaca acaaaatccc agggaccagc aacaatggat tagaggagga gtttaagaag     1620
ttaacatcaa tcaaaatcca gaatgacaag atgcggactg gaaaccttcc agccaacatg     1680
aagaagaacc gtgttttaca gatcattcca tatgaattca acagagtgat cattccagtt     1740
aagcggggcg aagagaatac agactatgtg aacgcatcct ttattgatgg ctaccggcag     1800
aaggactcct atatcgccag ccagggccct cttctccaca caattgagga cttctggcga     1860
atgatctggg agtggaaatc ctgctctatc gtgatgctaa cagaactgga ggagagaggc     1920
caggagaagt gtgcccagta ctggccatct gatggactgg tgtcctatgg agatattaca     1980
gtggaactga gaaggagga ggaatgtgag agctacaccg tccgagacct cctggtcacc     2040
aacaccaggg agaataagag ccggcagatc cggcagttcc acttccatgg ctggcctgaa     2100
gtgggcatcc ccagtgacgg aaagggcatg atcagcatca tcgccgccgt gcagaagcag     2160
cagcagcagt cagggaacca ccccatcacc gtgcactgca gcgccggggc aggaaggacg     2220
gggaccttct gtgccctgag caccgtcctg gagcgtgtga agcagaggg gatttggat      2280 gtcttccaga ctgtcaagag cctgcggcta cagaggccac acatggtcca gacactggaa     2340
cagtatgagt tctgctacaa ggtggtgcag gagtatattg atgcattctc agattatgcc     2400
aacttcaagt aagcggcaac aagggtccgt                                      2430
```

<210> SEQ ID NO 228  
<211> LENGTH: 20  
<212> TYPE: DNA  
<213> ORGANISM: Artificial Sequence  
<220> FEATURE:  
<223> OTHER INFORMATION: Antisense Compound

<400> SEQUENCE: 228

```
ccttccctga aggttcctcc                                                    20
```